US012435060B2

(12) United States Patent
Zhang et al.

(10) Patent No.: US 12,435,060 B2
(45) Date of Patent: Oct. 7, 2025

(54) ACYLAMINO BRIDGED HETEROCYCLIC COMPOUND, AND COMPOSITION AND APPLICATION THEREOF

(71) Applicant: BEIJING SCITECH-MQ PHARMACEUTICALS LIMITED, Beijing (CN)

(72) Inventors: Qiang Zhang, Beijing (CN); Yansheng Liu, Beijing (CN); Xingfu Li, Beijing (CN); Shaohua Zhang, Beijing (CN); Chenming Hu, Beijing (CN)

(73) Assignee: BEIJING SCITECH-MQ PHARMACEUTICALS LIMITED, Beijing (CN)

( * ) Notice: Subject to any disclaimer, the term of this patent is extended or adjusted under 35 U.S.C. 154(b) by 1111 days.

(21) Appl. No.: 17/425,496

(22) PCT Filed: Jan. 17, 2020

(86) PCT No.: PCT/CN2020/072738

§ 371 (c)(1),
(2) Date: Jul. 23, 2021

(87) PCT Pub. No.: WO2020/151589

PCT Pub. Date: Jul. 30, 2020

(65) Prior Publication Data

US 2023/0026425 A1 Jan. 26, 2023

(30) Foreign Application Priority Data

Jan. 25, 2019 (CN) ......................... 201910071476.7
Jan. 10, 2020 (CN) ......................... 202010027582.8

(51) Int. Cl.

*C07D 401/12* (2006.01)
*C07D 401/14* (2006.01)
*C07D 405/14* (2006.01)
*C07D 413/12* (2006.01)
*C07D 413/14* (2006.01)
*C07D 417/12* (2006.01)

(52) U.S. Cl.

CPC ......... *C07D 401/12* (2013.01); *C07D 401/14* (2013.01); *C07D 405/14* (2013.01); *C07D 413/12* (2013.01); *C07D 413/14* (2013.01); *C07D 417/12* (2013.01)

(58) Field of Classification Search

CPC .. C07D 401/12; C07D 401/14; C07D 405/14; C07D 413/12; C07D 413/14; C07D 417/12

See application file for complete search history.

(56) References Cited

U.S. PATENT DOCUMENTS 6,297,258 B1 * 10/2001 Wissner ............... C07D 215/44
546/171

FOREIGN PATENT DOCUMENTS

| | | |
|---|---|---|
| NO | 2005/040152 A1 | 5/2005 |
| WO | 2006/018725 A1 | 2/2006 |
| WO | 2011/025706 A2 | 3/2011 |
| WO | 2014/125444 A1 | 8/2014 |
| WO | 2017/109724 A1 | 6/2017 |
| WO | 2017/136727 A2 | 8/2017 |
| WO | 2018/044783 A1 | 3/2018 |
| WO | 2018/109097 A1 | 6/2018 |

OTHER PUBLICATIONS

International Search Report and Written Opinion for Application No. PCT/CN2020/072738, dated Apr. 15, 2020, 17 pages.

* cited by examiner

*Primary Examiner* — Rebecca L Anderson

(74) *Attorney, Agent, or Firm* — McCarter & English, LLP; Xin Zhang

(57) ABSTRACT

Provided are an acylamino bridged heterocyclic compound of formula (I) or a pharmaceutically acceptable salt, an isomer, a solvate, a crystal, or a prodrug thereof, and a pharmaceutical composition comprising the compound, and an application of the compound or composition in drug preparation. The compound and the pharmaceutically acceptable salt, the isomer, the solvate, the crystal, or the prodrug thereof and the like can be used for treatment or prevention of autoimmune diseases, tumors, and neurodegenerative diseases related to receptor-interacting protein kinase-1 (RIPK1).

(I)

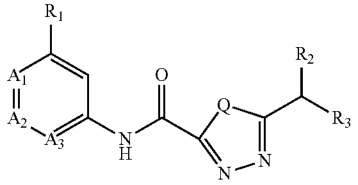

23 Claims, 1 Drawing Sheet

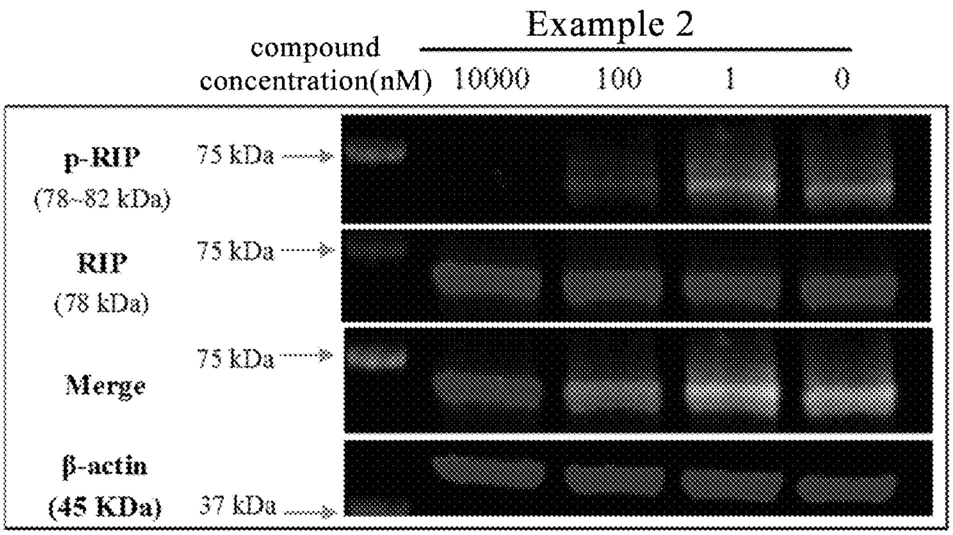
Figure 1
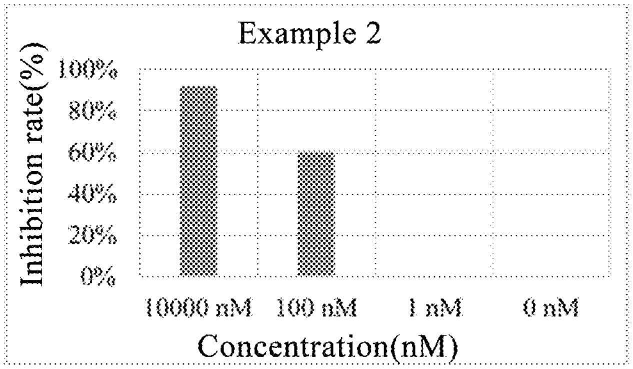
Figure 2
Compound concentration
4-fold dilution of compounds in DMSO( 15 μLcompound+ 45 μLDMSO)
| | | | | | | | | | | |
|---|---|---|---|---|---|---|---|---|---|---|
| 400× (μM) (DMSO:100%) | 10000 | 2500 | 625 | 156.25 | 39.0625 | 9.76563 | 2.44141 | 0.61035 | 0.15259 | 0 |
40-fold dilution (5 μLcompound+195 μL medium )
| | | | | | | | | | | |
|---|---|---|---|---|---|---|---|---|---|---|
| 10× (nM) (DMSO:2.5%) | 250000 | 62500 | 15625 | 3906.25 | 976.563 | 244.141 | 61.0352 | 15.2588 | 3.8147 | 0 |
10-fold dilution (10 μLcompound +90 μL medium )
| | | | | | | | | | | |
|---|---|---|---|---|---|---|---|---|---|---|
| 1× (nM) (DMSO:0.25%) | 25000 | 6250.000 | 1562.500 | 390.625 | 97.656 | 24.414 | 6.104 | 1.526 | 0.381 | 0 |
Figure 3

ACYLAMINO BRIDGED HETEROCYCLIC COMPOUND, AND COMPOSITION AND APPLICATION THEREOF

CROSS REFERENCE TO RELATED APPLICATIONS

The present application is a 35 U.S.C. § 371 national stage filing of International Application No. PCT/CN2020/072738, filed on Jan. 17, 2020, which claims the priority of the Chinese Patent Application No. 201910071476.7 filed on Jan. 25, 2019, and the Chinese Patent Application No. 202010027582.8 filed on Jan. 10, 2020.

TECHNICAL FIELD

The present disclosure belongs to the field of medicinal chemistry, and particularly relates to acylamino bridged heterocyclic compounds, or isomers, solvates, pharmaceutically acceptable salts or prodrugs thereof, and to pharmaceutical compositions thereof, and their use in the preparation of medicaments for the treatment of autoimmune diseases, tumors and neurodegenerative diseases related to receptor-interacting protein 1 kinase (RIPK1).

BACKGROUND OF THE INVENTION

In the early days, it was thought that there are two main ways of cell death, i.e., apoptosis and necrosis. Apoptosis is the autonomous and orderly death of cells controlled by genes in order to maintain the stability of the body's internal environment. It plays an important role in the evolution of the organism, the stability of the internal environment, and the development of the system. Cell necrosis is a pathological process in which cells are affected by physical, chemical and other environmental factors, such as mechanical damage, poisons, microorganisms, radiation, etc., causing cell death. In 2005, Degterev A et al. first discovered and reported an orderly cell necrosis process regulated by a series of biochemical molecules, and named it Necroptosis (also known as programmed necrosis). This process is a kind of programmed cell necrosis produced by stimulating death receptors with TNF-α, FasL or TRAIL. Morphologically, it is manifested as cell swelling, cell volume increasing, organelle dysfunction, damage to cell membrane integrity, release of cell contents, and mass production of ROS.

Receptor-interacting protein 1 kinase (RIPK1) belongs to the TKL family of serine/threonine protein kinases. Members of the RIPK serine/threonine kinase family have the same N-terminal kinase domain, but different binding domains. Studies have shown that receptor-interacting protein 1 can regulate the process of cell apoptosis. The death domain of RIPK-1 binds to death receptors such as TNFR1, Fas, TRAILR1, TRAILR2, etc., and they can also bind to other proteins containing death domains, such as TRADD, FADD, etc. Binding with the latter is a necessary condition for activating caspase-8 and inducing apoptosis. The intermediate structure of RIPK-1 is the RIPK isotype interaction target, through which RIPK-1 can interact with RIPK-3. Kelliher et al. found that mice with congenital defects of RIPK-1 died less than 3 days after birth due to a large number of cell apoptosis, which indicates that RIPK-1 is also involved in regulating cell apoptosis. In addition, cells with congenital RIPK-1 deficiency are quite sensitive to TNF-induced cell death, perhaps because such cells cannot effectively activate NF-kB.

On the other hand, studies have also shown that RIPK-1 and RIPK-3 are also involved in the process of cell necroptosis. In most cell types, death receptors TNFR1, Fas and TRAILR mediate cell apoptosis. Activating TNFR1 can trigger the ubiquitination of RIPK-1 through cIAP1 and cIAP2, and the ubiquitinated RIPK-1 determines whether the cell will continue to survive or die. When the apoptosis pathway is blocked by the pan-caspase inhibitor z-VAD-fmk, cell death will move toward to necroptosis. In this process, the activity of RIPK-1 is a key factor, which is regulated by FasL, TNF and TRAIL death receptors.

Recent studies have shown that the process of necroptosis is related to a variety of diseases, including tumors, autoimmune diseases, degenerative diseases, inflammatory diseases and the like. Based on this, it can be known that RIP family kinases are closely related to the occurrence of tumors, autoimmune diseases, degenerative diseases, inflammatory diseases and other diseases.

For example, in the study of Alzheimer's disease, Claudia Balducci et al. found that activated microglia plays an important role in the evolution of Alzheimer's disease (Pharmacological Research. 2018; 130: 402-413). At the same time, microglias highly expresses RIPK-1, and RIPK-1 inhibitors can protect from Aβ-induced neuronal death in vitro and reduce the proliferation of microglias. Moreover, in Alzheimer-like mouse brains, RIPK-1 inhibitors can improve their learning and memory abilities. In addition to Alzheimer's disease, RIPK-1 inhibitors are expected to be used in a variety of other neurodegenerative diseases including Parkinson's disease, amyotrophic lateral sclerosis, Huntington disease, etc.

At present, there are not many studies on RIPK-1 inhibitors, and only a small number of studies have entered the clinical stage. There is an urgent need for more research and development of drugs based on RIPK-1 inhibitors.

The present disclosure provides a class of acylamino bridged heterocyclic compounds, which exhibit good RIPK-1 inhibitory activity and can be used as RIPK-1 inhibitors in the preparation of a medicament for the treatment of tumors, autoimmune diseases, degenerative diseases, and inflammatory diseases.

SUMMARY OF THE INVENTION

The compound represented by formula (I) provided by the present disclosure, or pharmaceutically acceptable salts, isomers, hydrates, solvates, or prodrugs thereof, can be used to prepare medicaments for the treatment or prevention of diseases related to RIPK1.

formula (I)

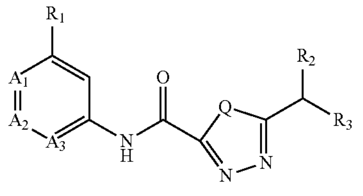

In formula (I),

Q is NH, O or S;

$A_1$, $A_2$, and $A_3$ are each independently selected from N or $CR_4$ and at least one of $A_1$, $A_2$, and $A_3$ is N, $R_4$ is H, F, Cl or methyl;

$R_1$ is $C_3$-$C_8$ cycloalkyl, which is unsubstituted or substituted with 1 to 3 substituents selected from the group consisting of $C_1$-$C_6$ alkyl, $C_1$-$C_6$ alkoxy, $C_1$-$C_6$ alkylthio, $C_1$-$C_3$ acyl, hydroxyl, halogen, trifluoromethyl, cyano, —$CONH_2$, oxo (=O) and —$NR^aR^b$, or 4- to 8-membered heteroalicyclic group, which is unsubstituted or substituted with 1 to 3 substituents selected from the group consisting of $C_1$-$C_6$ alkyl, $C_1$-$C_6$ alkoxy, $C_1$-$C_6$ alkylthio, $C_1$-$C_3$ acyl, hydroxyl, halogen, trifluoromethyl, cyano, —$CONH_2$, oxo (=O) and —$NR^aR^b$, or aryl or heteroaryl, which is unsubstituted or substituted with 1 to 3 substituents selected from the group consisting of $C_1$-$C_{10}$ alkyl, halogen, $C_3$-$C_8$ cycloalkyl, halogenated $C_1$-$C_{10}$ alkyl, cyano, hydroxyl, $C_1$-$C_6$ alkylthio, —$SO_2$—$R_5$, —SO—$R_5$, —CO—$R_5$, —CONH—$R_5$, —NHCO—$R_5$, —R'—COO—R", —$NR^aR^b$, 4- to 8-membered heteroalicyclic group, $C_2$-$C_6$ alkynyl, $C_2$-$C_6$ alkenyl, $C_1$-$C_3$ alkoxy $C_1$-$C_6$ alkylthio, $C_1$-$C_{10}$ alkyl substituted with hydroxyl and/or $C_1$-$C_6$ alkoxy, $C_3$-$C_8$cycloalkyl $C_1$-$C_6$ alkyl, ($C_3$-$C_8$ cycloalkyl)-O—($C_1$-$C_6$ alkyl), $C_1$-$C_6$ alkyl substituted with 4- to 8-membered heteroalicyclic group, and —O—$R_6$, the aryl group is a monocyclic or bicyclic group containing 6 to 12 carbon ring atoms and having at least one aromatic ring, the heteroaryl is a monocyclic or bicyclic group having 5 to 10 ring atoms and containing 1 to 3 heteroatoms selected from N, O, or S as ring atoms, the 4- to 8-membered heteroalicyclic group is a 4- to 8-membered heteroalicyclic group containing 1-2 atoms selected from N, O, or S as ring atoms, $R_5$ is hydrogen, hydroxyl, $C_1$-$C_6$ alkyl, $C_1$-$C_6$ alkoxy $C_1$-$C_6$ alkyl, $C_1$-$C_6$ alkyl substituted with hydroxyl, $C_3$-$C_8$ cycloalkyl, or $C_1$-$C_6$ alkyl substituted with 4- to 8-membered heteroalicyclic group, $R_6$ is $C_1$-$C_{10}$ alkyl, $C_3$-$C_8$ cycloalkyl, 4- to 8-membered heteroalicyclic group, or $C_1$-$C_{10}$ alkyl which is substituted with 1 to 3 substituents selected from the group consisting of hydroxyl, $C_1$-$C_6$ alkoxy, cyano, —$NR^aR^b$, $C_3$-$C_8$ cycloalkyloxy, —CONH—$R_5$, $C_3$-$C_8$ cycloalkyl, $C_3$-$C_8$ cycloalkyl substituted with hydroxyl and/or $C_1$-$C_4$ alkyl, carboxylic, halogen, halogenated $C_1$-$C_6$ alkoxy, —$SO_2$—$R_5$, —SO—$R_5$, —CO—$R_5$, $C_2$-$C_6$ alkynyl, $C_2$-$C_6$ alkenyl, $C_1$-$C_4$ alkoxy $C_1$-$C_6$ alkoxy, 4- to 8-membered heteroalicyclic group, 4- to 8-membered heteroalicyclic group substituted with oxo, 4- to 8-membered heteroalicyclic group substituted with hydroxyl and/or $C_1$-$C_4$ alkyl, and $C_1$-$C_6$ alkylthio, R' is $C_2$-$C_6$ alkenylene, or $C_1$-$C_6$ alkylene, R" is hydrogen, $C_1$-$C_6$ alkyl, $C_1$-$C_6$ alkoxy $C_1$-$C_6$ alkyl, $C_1$-$C_6$ alkyl substituted with hydroxyl, $C_3$-$C_8$ cycloalkyl, or $C_1$-$C_6$ alkyl substituted with 4- to 8-membered heteroalicyclic group, $R^a$ and $R^b$ are each independently selected from hydrogen, $C_1$-$C_6$ alkyl, $C_3$-$C_8$ cycloalkyl, $C_1$-$C_6$ alkyl substituted with $C_1$-$C_6$ alkoxy, $C_1$-$C_6$ alkyl substituted with hydroxyl, $C_3$-$C_8$ cycloalkyl $C_1$-$C_6$ alkyl, $C_1$-$C_6$ alkyl substituted with 4- to 8-membered heteroalicyclic group, $C_1$-$C_6$ alkyl substituted with $C_1$-$C_3$ alkylthio, or $C_1$-$C_6$ alkyl substituted with substituted amino or unsubstituted amino, wherein the substituted amino is substituted with mono- or di-$C_1$-$C_3$ alkyl;

$R_2$ is $C_3$-$C_8$ cycloalkyl, which is unsubstituted or substituted with 1 to 3 substituents selected from the group consisting of $C_1$-$C_6$ alkyl, $C_1$-$C_6$ alkoxy, $C_1$-$C_6$ alkylthio, $C_1$-$C_3$ acyl, hydroxyl, halogen, trifluoromethyl, cyano, —$CONH_2$, oxo (=O) and —$NR^cR^d$, or $C_7$-$C_{12}$ bridged cyclyl, which is unsubstituted or substituted with 1 to 3 substituents selected from the group consisting of $C_1$-$C_6$ alkyl, $C_1$-$C_6$ alkoxy, $C_1$-$C_6$ alkylthio, $C_1$-$C_3$ acyl, hydroxyl, halogen, trifluoromethyl, cyano, —$CONH_2$, oxo (=O) and —$NR^cR^d$, or $C_1$-$C_{10}$ alkyl, which is unsubstituted or substituted with 1 to 3 substituents selected from the group consisting of $C_1$-$C_6$ alkoxy, $C_1$-$C_6$ alkylthio, $C_1$-$C_3$ acyl, hydroxyl, halogen, cyano, —$CONH_2$, $C_3$-$C_8$ cycloalkyl, and —$NR^cR_d$, or —$(CH_2)$n-$R^e$, wherein $R^e$ is aryl or heteroaryl, which is unsubstituted or substituted with 1 to 3 substituents selected from the group consisting of $C_1$-$C_6$ alkyl, $C_1$-$C_6$ alkoxy, $C_1$-$C_6$ alkylthio, $C_1$-$C_3$ acyl, hydroxyl, halogen, trifluoromethyl, cyano, —$CONH_2$, $C_3$-$C_6$ cycloalkyl, phenyl, naphthyl, $C_2$-$C_6$ alkynyl, $C_2$-$C_6$ alkenyl, and —$NR^cR^d$, wherein n is an integer from 0 to 3, or —$(CH_2)$m-$R^f$, wherein $R^f$ is 4- to 8-membered heteroalicyclic group, which is unsubstituted or substituted with 1 to 3 substituents selected from the group consisting of $C_1$-$C_6$ alkyl, $C_1$-$C_6$ alkoxy, $C_1$-$C_6$ alkylthio, $C_1$-$C_3$ acyl, hydroxyl, halogen, trifluoromethyl, cyano, —$CONH_2$, oxo (=O) and —$NR^cR^d$, m is an integer from 0 to 3, the 4- to 8-membered heteroalicyclic group is a 4- to 8-membered heteroalicyclic group containing 1 to 2 atoms selected from N, O, or S as ring atoms, the aryl group is a monocyclic or bicyclic group containing 6 to 12 carbon ring atoms and having at least one aromatic ring, the heteroaryl is a monocyclic or bicyclic group having 5 to 10 ring atoms and containing 1 to 3 heteroatoms selected from N, O, or S as ring atoms, $R^c$ and $R^d$ are each independently selected from hydrogen, $C_1$-$C_6$ alkyl, $C_3$-$C_8$ cycloalkyl, $C_1$-$C_6$ alkyl substituted with $C_1$-$C_6$ alkoxy, $C_1$-$C_6$ alkyl substituted with hydroxyl, $C_3$-$C_8$ cycloalkyl $C_1$-$C_6$ alkyl, $C_1$-$C_6$ alkyl substituted with 4- to 8-membered heteroalicyclic group, $C_1$-$C_6$ alkyl substituted with $C_1$-$C_3$ alkylthio, or $C_1$-$C_6$ alkyl substituted with substituted amino or unsubstituted amino, wherein the substituted amino is substituted with mono- or di-$C_1$-$C_3$ alkyl;

$R_3$ is hydrogen, $C_1$-$C_3$ alkyl, hydroxyl, halogen, trifluoromethyl, or cyano.

In some embodiments, alternatively, Q is NH, O or S;

$A_1$, $A_2$, and $A_3$ are each independently selected from N or $CR_4$ and at least one of $A_1$, $A_2$, and $A_3$ is N, $R_4$ is H, F, Cl or methyl;

$R_1$ is $C_3$-$C_8$ cycloalkyl, which is unsubstituted or substituted with 1 to 3 substituents selected from the group consisting of $C_1$-$C_6$ alkyl, $C_1$-$C_6$ alkoxy, $C_1$-$C_6$ alkylthio, $C_1$-$C_3$ acyl, hydroxyl, halogen, trifluoromethyl, cyano, —$CONH_2$, oxo (=O) and —$NR^aR^b$, or 4- to 8-membered heteroalicyclic group, which is unsubstituted or substituted with 1 to 3 substituents selected from the group consisting of $C_1$-$C_6$ alkyl, $C_1$-$C_6$ alkoxy, $C_1$-$C_6$ alkylthio, $C_1$-$C_3$ acyl, hydroxyl, halogen, trifluoromethyl, cyano, —$CONH_2$, oxo (=O) and —$NR^aR^b$, or aryl or heteroaryl, which is unsubstituted or substituted with 1 to 3 substituents selected from the group consisting of $C_1$-$C_{10}$ alkyl, halogen, $C_3$-$C_8$ cycloalkyl, halogenated $C_1$-$C_{10}$ alkyl, cyano, hydroxyl, $C_1$-$C_6$ alkylthio, —$SO_2$—$R_5$, —SO—$R_5$, —CO—$R_5$, —CONH—$R_5$, —$NR^aR^b$, 4- to 8-membered heteroalicyclic group, $C_2$-$C_6$ alkynyl, $C_2$-$C_6$ alkenyl, $C_1$-$C_3$ alkoxy $C_1$-$C_6$ alkylthio, $C_1$-$C_{10}$ alkyl substituted with hydroxyl, $C_1$-$C_6$ alkoxy $C_1$-$C_{10}$ alkyl, $C_3$-$C_8$ cycloalkyl $C_1$-$C_6$ alkyl, ($C_3$-$C_8$ cycloalkyl)-O—($C_1$-$C_6$ alkyl), $C_1$-$C_6$ alkyl substituted with 4- to 8-membered heteroalicyclic group, and —O—$R_6$, the aryl group is a monocyclic or bicyclic group containing 6 to 12 carbon ring atoms and having at least one aromatic ring, the heteroaryl is a monocyclic or bicyclic group having 5 to 10 ring atoms and containing 1 to 3 heteroatoms selected from N, O, or S as ring atoms, the 4- to 8-membered heteroalicyclic group is a 4- to 8-membered heteroalicyclic group containing 1 to 2 atoms selected from N, O, or S as ring atoms, $R_5$ is hydrogen, hydroxyl, $C_1$-$C_6$ alkyl, $C_1$-$C_6$ alkoxy $C_1$-$C_6$ alkyl, $C_1$-$C_6$ alkyl substituted with hydroxyl, $C_3$-$C_8$ cycloalkyl, or $C_1$-$C_6$ alkyl substituted with 4- to 8-membered heteroalicyclic group, $R_6$ is $C_1$-$C_{10}$ alkyl, $C_3$-$C_8$ cycloalkyl, 4- to 8-membered heteroalicyclic group, or $C_1$-$C_{10}$ alkyl which is substituted with 1 to 3 substituents selected from the group consisting of hydroxyl, $C_1$-$C_6$ alkoxy, cyano, —$NR^aR^b$, $C_3$-$C_8$ cycloalkyloxy, —CONH—$R_5$, $C_3$-$C_8$ cycloalkyl, $C_3$-$C_8$ cycloalkyl substituted with hydroxyl and/or $C_1$-$C_4$ alkyl, carboxylic, halogen, halogenated $C_1$-$C_6$ alkoxy, —$SO_2$—$R_5$, —SO—$R_5$, —CO—$R_5$, $C_2$-$C_6$ alkynyl, $C_2$-$C_6$ alkenyl, $C_1$-$C_4$ alkoxy $C_1$-$C_6$ alkoxy, 4- to 8-membered heteroalicyclic group, 4- to 8-membered heteroalicyclic group substituted with oxo, 4- to 8-membered heteroalicyclic group substituted with hydroxyl and/or $C_1$-$C_4$ alkyl, and $C_1$-$C_6$ alkylthio, $R^a$ and $R^b$ are each independently selected from hydrogen, $C_1$-$C_6$ alkyl, $C_3$-$C_8$ cycloalkyl, $C_1$-$C_6$ alkyl substituted with $C_1$-$C_6$ alkoxy, $C_1$-$C_6$ alkyl substituted with hydroxyl, $C_3$-$C_8$ cycloalkyl $C_1$-$C_6$ alkyl, $C_1$-$C_6$ alkyl substituted with 4- to 8-membered heteroalicyclic group, $C_1$-$C_6$ alkyl substituted with $C_1$-$C_3$ alkylthio, or $C_1$-$C_6$ alkyl substituted with substituted amino or unsubstituted amino, wherein the substituted amino is substituted with mono- or di-$C_1$-$C_3$ alkyl;

$R_2$ is $C_3$-$C_8$ cycloalkyl, which is unsubstituted or substituted with 1 to 3 substituents selected from the group consisting of $C_1$-$C_6$ alkyl, $C_1$-$C_6$ alkoxy, $C_1$-$C_6$ alkylthio, $C_1$-$C_3$ acyl, hydroxyl, halogen, trifluoromethyl, cyano, —$CONH_2$, oxo (═O) and —$NR^cR^d$, or $C_7$-$C_{12}$ bridged cyclyl, which is unsubstituted or substituted with 1 to 3 substituents selected from the group consisting of $C_1$-$C_6$ alkyl, $C_1$-$C_6$ alkoxy, $C_1$-$C_6$ alkylthio, $C_1$-$C_3$ acyl, hydroxyl, halogen, trifluoromethyl, cyano, —$CONH_2$, oxo (═O) and —$NR^cR^d$, or $C_1$-$C_{10}$ alkyl, which is unsubstituted or substituted with 1 to 3 substituents selected from the group consisting of $C_1$-$C_6$ alkoxy, $C_1$-$C_6$ alkylthio, $C_1$-$C_3$ acyl, hydroxyl, halogen, cyano, —$CONH_2$, $C_3$-$C_8$ cycloalkyl, and —$NR^cR_d$, or —$(CH_2)$n-$R^e$, wherein $R^e$ is aryl or heteroaryl, which is unsubstituted or substituted with 1 to 3 substituents selected from the group consisting of $C_1$-$C_6$ alkyl, $C_1$-$C_6$ alkoxy, $C_1$-$C_6$ alkylthio, $C_1$-$C_3$ acyl, hydroxyl, halogen, trifluoromethyl, cyano, —$CONH_2$, $C_2$-$C_6$ alkynyl, $C_2$-$C_6$ alkenyl, and —$NR^cR^d$, wherein n is an integer from 0 to 3, or —$(CH_2)$m-$R^f$, wherein $R^f$ is 4- to 8-membered heteroalicyclic group, which is unsubstituted or substituted with 1 to 3 substituents selected from the group consisting of $C_1$-$C_6$ alkyl, $C_1$-$C_6$ alkoxy, $C_1$-$C_6$ alkylthio, $C_1$-$C_3$ acyl, hydroxyl, halogen, trifluoromethyl, cyano, —$CONH_2$, oxo (═O) and —$NR^cR^d$, m is an integer from 0 to 3, the 4- to 8-membered heteroalicyclic group is a 4- to 8-membered heteroalicyclic group containing 1 to 2 atoms selected from N, O, or S as ring atoms, the aryl group is a monocyclic or bicyclic group containing 6 to 12 carbon ring atoms and having at least one aromatic ring, the heteroaryl is a monocyclic or bicyclic group having 5 to 10 ring atoms and containing 1 to 3 heteroatoms selected from N, O, or S as ring atoms, $R^c$ and $R^d$ are each independently selected from hydrogen, $C_1$-$C_6$ alkyl, $C_3$-$C_8$ cycloalkyl, $C_1$-$C_6$ alkyl substituted with $C_1$-$C_6$ alkoxy, $C_1$-$C_6$ alkyl substituted with hydroxyl, $C_3$-$C_8$ cycloalkyl $C_1$-$C_6$ alkyl, $C_1$-$C_6$ alkyl substituted with 4- to 8-membered heteroalicyclic group, $C_1$-$C_6$ alkyl substituted with $C_1$-$C_3$ alkylthio, or $C_1$-$C_6$ alkyl substituted with substituted amino or unsubstituted amino, wherein the substituted amino is substituted with mono- or di-$C_1$-$C_3$ alkyl;

$R_3$ is hydrogen, $C_1$-$C_3$ alkyl, hydroxyl, halogen, trifluoromethyl, or cyano.

In some embodiments, alternatively, $A_3$ is N, $A_1$, and $A_2$ are each independently selected from N or $CR_4$, $R_4$ is H, F, Cl or methyl; still alternatively, $A_3$ is N, $A_1$, and $A_2$ are each independently CH.

In some embodiments, alternatively, $A_3$ is N, $A_1$, $A_2$ are each independently selected from N or $CR_4$, $R_4$ is H or F.

In some embodiments, still alternatively, Q is NH.

In some embodiments, alternatively, $R_1$ is $C_3$-$C_8$ cycloalkyl, 4- to 8-membered heteroalicyclic group, or aryl or heteroaryl which is unsubstituted or substituted with 1 to 3 substituents selected from the group consisting of $C_1$-$C_{10}$ alkyl, halogen, $C_3$-$C_8$ cycloalkyl, halogenated $C_1$-$C_{10}$ alkyl, cyano, hydroxyl, $C_1$-$C_6$ alkylthio, —CO—$R_5$, —$SO_2$—$R_5$, —SO—$R_5$, —CONH—$R_5$, —$NR^aR^b$, 4- to 8-membered heteroalicyclic group, $C_2$-$C_6$ alkynyl, $C_2$-$C_6$ alkenyl, $C_1$-$C_3$ alkoxy $C_1$-$C_6$ alkylthio, $C_1$-$C_{10}$ alkyl substituted with hydroxyl, $C_1$-$C_6$ alkoxy $C_1$-$C_{10}$ alkyl, $C_3$-$C_8$ cycloalkyl $C_1$-$C_6$ alkyl, ($C_3$-$C_8$ cycloalkyl)-O—($C_1$-$C_6$ alkyl), $C_1$-$C_6$ alkyl substituted with 4- to 8-membered heteroalicyclic group, and —O—$R_6$, the aryl group is phenyl, naphthyl,

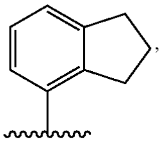,
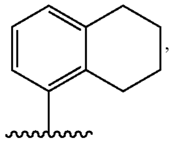, the heteroaryl group is pyrrolyl, furyl, pyridyl, thienyl, imidazolyl, thiazolyl, isothiazolyl, indazolyl, indolyl, indazolyl, isoindolyl, indolinyl, isoindolinyl, isoquinolinyl, indolizinyl, isoxazolyl, 1,5-naphthyridinyl, 1,6-naphthyridinonyl, oxadiazolyl, oxazolyl, 1-phenyl-1H-pyrrolyl, phenazinyl, phenothiazinyl, phenoxazinyl, phthalazinyl, pteridinyl, purinyl, pyranyl, pyrazolyl, pyrazolo[3,4-d]pyrimidinyl, pyridyl, pyrido[3,2-d]pyrimidinyl, pyrido[3,4-d]pyrimidinyl, pyrazinyl, pyrimidinyl, pyridazinyl, quinazolinyl, quinoxalinyl, quinolinyl, isoquinolinyl,

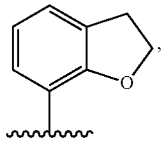,
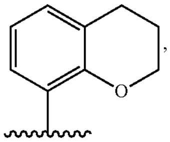,
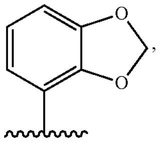,

-continued

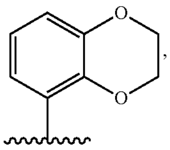, 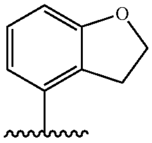, 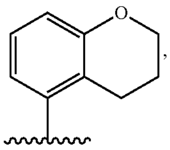, the 4- to 8-membered heteroalicyclic group is a 4-to 8-membered heteroalicyclic group containing 1 to 2 atoms selected from N, O, or S as ring atoms, $R_5$ is hydrogen, hydroxyl, $C_1$-$C_6$ alkyl, $C_1$-$C_6$ alkoxy $C_1$-$C_6$ alkyl, $C_1$-$C_6$ alkyl substituted with hydroxyl, $C_3$-$C_8$ cycloalkyl, or $C_1$-$C_6$ alkyl substituted with 4- to 8-membered heteroalicyclic group, $R_6$ is $C_1$-$C_{10}$ alkyl, $C_3$-$C_8$ cycloalkyl, 4- to 8-membered heteroalicyclic group, or $C_1$-$C_{10}$ alkyl which is unsubstituted or substituted with 1 to 3 substituents selected from the group consisting of hydroxyl, $C_1$-$C_6$ alkoxy, cyano, —NR$^a$R$^b$, $C_3$-$C_8$ cycloalkyloxy, —CONH—$R_5$, $C_3$-$C_8$ cycloalkyl, $C_3$-$C_8$ cycloalkyl substituted with hydroxyl and/or $C_1$-$C_4$ alkyl, carboxylic, halogen, halogenated $C_1$-$C_6$ alkoxy, —CO—$R_5$, —$SO_2$—$R_5$, —SO—$R_5$, $C_2$-$C_6$ alkynyl, $C_2$-$C_6$ alkenyl, $C_1$-$C_4$ alkoxy $C_1$-$C_6$ alkoxy, 4- to 8-membered heteroalicyclic group, 4- to 8-membered heteroalicyclic group substituted with oxo, 4- to 8-membered heteroalicyclic group substituted with hydroxyl and/or $C_1$-$C_4$ alkyl, or $C_1$-$C_6$ alkylthio, R$^a$ and R$^b$ are each independently selected from hydrogen, $C_1$-$C_6$ alkyl, $C_3$-$C_8$ cycloalkyl, $C_1$-$C_6$ alkyl substituted with $C_1$-$C_6$ alkoxy, $C_1$-$C_6$ alkyl substituted with hydroxyl, $C_3$-$C_8$ cycloalkyl $C_1$-$C_6$ alkyl, $C_1$-$C_6$ alkyl substituted with 4- to 8-membered heteroalicyclic group, $C_1$-$C_6$ alkyl substituted with $C_1$-$C_3$ alkylthio, or $C_1$-$C_6$ alkyl substituted with substituted amino or unsubstituted amino, wherein the substituted amino is substituted with mono- or di-$C_1$-$C_3$ alkyl.

In some embodiments, alternatively, $R_1$ is cyclopropyl, cyclobutyl, cyclopentyl, cyclohexyl, oxetan-3-yl, tetrahydrofuran-3-yl, tetrahydropyran-4-yl, tetrahydropyran-3-yl, pyrrolidinyl, piperidinyl, piperazinyl, morpholinyl, thiomorpholinyl, or aryl or heteroaryl which is unsubstituted or substituted with 1 to 3 substituents selected from the group consisting of $C_1$-$C_{10}$ alkyl, halogen, $C_3$-$C_8$ cycloalkyl, halogenated $C_1$-$C_{10}$ alkyl, cyano, hydroxyl, $C_1$-$C_6$ alkylthio, —$SO_2$—$R_5$, —SO—$R_5$, —CO—$R_5$, —CONH—$R_5$, —NR$^a$R$^b$, 4- to 8-membered heteroalicyclic group, $C_2$-$C_6$ alkynyl, $C_2$-$C_6$ alkenyl, $C_1$-$C_3$ alkoxy $C_1$-$C_6$ alkylthio, $C_1$-$C_{10}$ alkyl substituted with hydroxyl, $C_1$-$C_6$ alkoxy $C_1$-$C_{10}$ alkyl, $C_3$-$C_8$ cycloalkyl $C_1$-$C_6$ alkyl, ($C_3$-$C_8$ cycloalkyl)-O—($C_1$-$C_6$ alkyl), $C_1$-$C_6$ alkyl substituted with 4- to 8-membered heteroalicyclic group, and —O—$R_6$, the aryl group is phenyl,

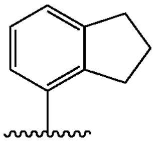, 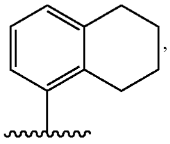, the heteroaryl group is pyrazolyl, pyridyl, pyrimidinyl, thiazolyl, oxazolyl,

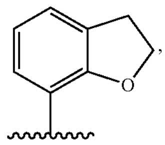, 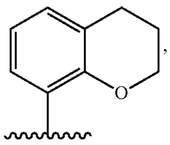, 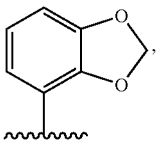,

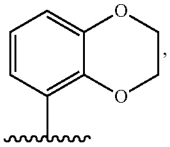, 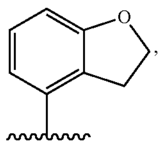, 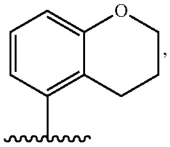, the 4- to 8-membered heteroalicyclic group is a 4- to 8-membered heteroalicyclic group containing 1 to 2 atoms selected from N, O, or S as ring atoms, $R_5$ is hydrogen, $C_1$-$C_6$ alkyl, $C_1$-$C_6$ alkoxy $C_1$-$C_6$ alkyl, $C_1$-$C_6$ alkyl substituted with hydroxyl, $C_3$-$C_8$ cycloalkyl, or $C_1$-$C_6$ alkyl substituted with 4- to 8-membered heteroalicyclic group, $R_6$ is $C_1$-$C_{10}$ alkyl, $C_3$-$C_8$ cycloalkyl, 4- to 8-membered heteroalicyclic group, or $C_1$-$C_{10}$ alkyl which is unsubstituted or substituted with 1 to 3 substituents selected from the group consisting of hydroxyl, $C_1$-$C_6$ alkoxy, cyano, —NR$^a$R$^b$, $C_3$-$C_8$ cycloalkyloxy, —CONH—$R_5$, $C_3$-$C_8$ cycloalkyl, $C_3$-$C_8$ cycloalkyl substituted with hydroxyl and/or $C_1$-$C_4$ alkyl, carboxylic, halogen, halogenated $C_1$-$C_6$ alkoxy, —$SO_2$—$R_5$, —SO—$R_5$, —CO—$R_5$, $C_2$-$C_6$ alkynyl, $C_2$-$C_6$ alkenyl, $C_1$-$C_4$ alkoxy $C_1$-$C_6$ alkoxy, 4- to 8-membered heteroalicyclic group, 4- to 8-membered heteroalicyclic group substituted with oxo, 4- to 8-membered heteroalicyclic group substituted with hydroxyl and/or $C_1$-$C_4$ alkyl, or $C_1$-$C_6$ alkylthio, R$^a$ and R$^b$ are each independently selected from hydrogen, $C_1$-$C_6$ alkyl, $C_3$-$C_8$ cycloalkyl, $C_1$-$C_6$ alkyl substituted with $C_1$-$C_6$ alkoxy, $C_1$-$C_6$ alkyl substituted with hydroxyl, $C_3$-$C_8$ cycloalkyl $C_1$-$C_6$ alkyl, $C_1$-$C_6$ alkyl substituted with 4- to 8-membered heteroalicyclic group, $C_1$-$C_6$ alkyl substituted with $C_1$-$C_3$ alkylthio, or $C_1$-$C_6$ alkyl substituted with substituted amino or unsubstituted amino, wherein the substituted amino is substituted with mono- or di-$C_1$-$C_3$ alkyl.

In some embodiments, alternatively, $R_1$ is

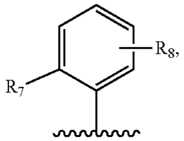 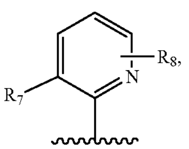

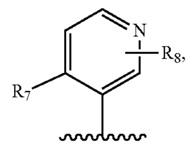 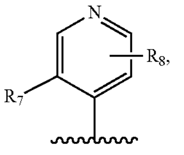

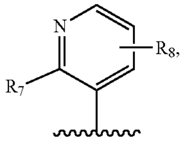 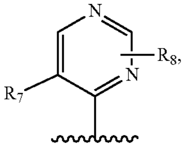

-continued

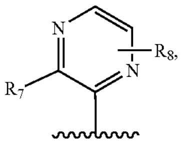

or

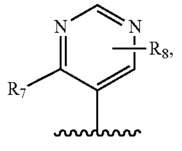

$R_7$ is hydrogen, $C_1$-$C_4$ alkyl, $C_1$-$C_3$ alkoxy, halogen, hydroxyl, trifluoromethyl, trifluoromethoxy, cyano, $C_2$-$C_4$ alkynyl, $C_2$-$C_4$ alkenyl, $C_3$-$C_4$ cycloalkyl, or $C_1$-$C_3$ acyl;

$R_5$ is hydrogen, $C_1$-$C_{10}$ alkyl, halogen, $C_3$-$C_8$ cycloalkyl, halogenated $C_1$-$C_{10}$ alkyl, cyano, hydroxyl, $C_1$-$C_6$ alkylthio, —CO—$R_5$, —$SO_2$—$R_5$, —SO—$R_5$, —CONH—$R_5$, —$NR^aR^b$, 4- to 8-membered heteroalicyclic group, $C_2$-$C_6$ alkynyl, $C_2$-$C_6$ alkenyl, $C_1$-$C_3$ alkoxy $C_1$-$C_6$ alkylthio, hydroxyl $C_1$-$C_{10}$ alkyl, $C_1$-$C_6$ alkoxy $C_1$-$C_{10}$ alkyl, $C_3$-$C_8$ cycloalkyl $C_1$-$C_6$ alkyl, ($C_3$-$C_8$ cycloalkyl)-O—($C_1$-$C_6$ alkyl), $C_1$-$C_6$ alkyl substituted with 4- to 8-membered heteroalicyclic group, or —O—$R_6$, the 4- to 8-membered heteroalicyclic group is a 4- to 8-membered heteroalicyclic group containing 1 to 2 atoms selected from N, O, or S as ring atoms, $R_5$ is hydrogen, hydroxyl, $C_1$-$C_6$ alkyl, $C_1$-$C_6$ alkoxy $C_1$-$C_6$ alkyl, $C_1$-$C_6$ alkyl substituted with hydroxyl, $C_3$-$C_8$ cycloalkyl, or $C_1$-$C_6$ alkyl substituted with 4- to 8-membered heteroalicyclic group, $R_6$ is $C_1$-$C_{10}$ alkyl, $C_3$-$C_8$ cycloalkyl, 4- to 8-membered heteroalicyclic group, or $C_1$-$C_{10}$ alkyl which is unsubstituted or substituted with 1 to 3 substituents selected from the group consisting of hydroxyl, $C_1$-$C_6$ alkoxy, cyano, —$NR^aR^b$, $C_3$-$C_8$ cycloalkyloxy, —CONH—$R_5$, $C_3$-$C_8$ cycloalkyl, $C_3$-$C_8$ cycloalkyl substituted with hydroxyl and/or $C_1$-$C_4$ alkyl, carboxylic, halogen, halogenated $C_1$-$C_6$ alkoxy, —$SO_2$—$R_5$, —SO—$R_5$, —CO—$R_5$, $C_2$-$C_6$ alkynyl, $C_2$-$C_6$ alkenyl, $C_1$-$C_4$ alkoxy $C_1$-$C_6$ alkoxy, 4- to 8-membered heteroalicyclic group, 4- to 8-membered heteroalicyclic group substituted with oxo, 4- to 8-membered heteroalicyclic group substituted with hydroxyl and/or $C_1$-$C_4$ alkyl, and $C_1$-$C_6$ alkylthio, $R^a$ and $R^b$ are each independently selected from hydrogen, $C_1$-$C_6$ alkyl, $C_3$-$C_8$ cycloalkyl, $C_1$-$C_6$ alkyl substituted with $C_1$-$C_6$ alkoxy, $C_1$-$C_6$ alkyl substituted with hydroxyl, $C_3$-$C_8$ cycloalkyl $C_1$-$C_6$ alkyl, $C_1$-$C_6$ alkyl substituted with 4- to 8-membered heteroalicyclic group, $C_1$-$C_6$ alkyl substituted with $C_1$-$C_3$ alkylthio, or $C_1$-$C_6$ alkyl substituted with substituted amino or unsubstituted amino, wherein the substituted amino is substituted with mono- or di-$C_1$-$C_3$ alkyl.

In some embodiments, alternatively, $R_1$ is:

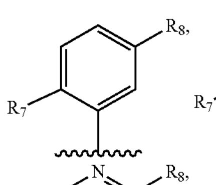

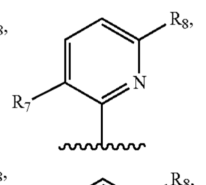

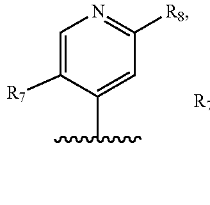

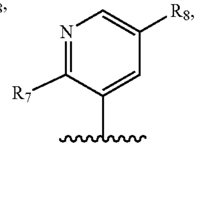

-continued

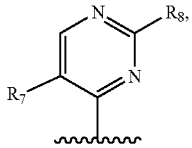

or

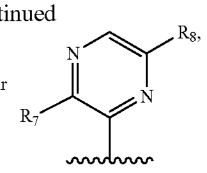

$R_7$ is hydrogen, methyl, ethyl, propyl, isopropyl, methoxy, ethoxy, propoxy, isopropoxy, fluorine, chlorine, hydroxyl, trifluoromethyl, trifluoromethoxy, cyano, ethynyl, propynyl, vinyl, propenyl, cyclopropyl, cyclobutyl, formyl, or acetyl;

$R_5$ is hydrogen, $C_1$-$C_{10}$ alkyl, halogen, $C_3$-$C_8$ cycloalkyl, halogenated $C_1$-$C_{10}$ alkyl, cyano, hydroxyl, $C_1$-$C_6$ alkylthio, —CO—$R_5$, —$SO_2$—$R_5$, —SO—$R_5$, —CONH—$R_5$, —$NR^aR^b$, 4- to 8-membered heteroalicyclic group, $C_2$-$C_6$ alkynyl, $C_2$-$C_6$ alkenyl, $C_1$-$C_3$ alkoxy $C_1$-$C_6$ alkylthio, $C_1$-$C_{10}$ alkyl substituted with hydroxyl, $C_1$-$C_6$ alkoxy $C_1$-$C_{10}$ alkyl, $C_3$-$C_8$ cycloalkyl $C_1$-$C_6$ alkyl, ($C_3$-$C_8$ cycloalkyl)-O—($C_1$-$C_6$ alkyl), $C_1$-$C_6$ alkyl substituted with 4- to 8-membered heteroalicyclic group, or —O—$R_6$, the 4- to 8-membered heteroalicyclic group is heteroalicyclic group containing 1 to 2 atoms selected from N, O, or S as ring atoms, $R_5$ is hydrogen, hydroxyl, $C_1$-$C_6$ alkyl, $C_1$-$C_6$ alkoxy $C_1$-$C_6$ alkyl, $C_1$-$C_6$ alkyl substituted with hydroxyl, $C_3$-$C_8$ cycloalkyl, or $C_1$-$C_6$ alkyl substituted with 4- to 8-membered heteroalicyclic group, $R_6$ is $C_1$-$C_{10}$ alkyl, $C_3$-$C_8$ cycloalkyl, 4- to 8-membered heteroalicyclic group, or $C_1$-$C_{10}$ alkyl which is unsubstituted or substituted with 1 to 3 substituents selected from the group consisting of hydroxyl, $C_1$-$C_6$ alkoxy, cyano, —$NR^aR^b$, $C_3$-$C_8$ cycloalkyloxy, —CONH—$R_5$, $C_3$-$C_8$ cycloalkyl, $C_3$-$C_8$ cycloalkyl substituted with hydroxyl and/or $C_1$-$C_4$ alkyl, carboxylic, halogen, halogenated $C_1$-$C_6$ alkoxy, —$SO_2$—$R_5$, —SO—$R_5$, —CO—$R_5$, $C_2$-$C_6$ alkynyl, $C_2$-$C_6$ alkenyl, $C_1$-$C_4$ alkoxy $C_1$-$C_6$ alkoxy, 4- to 8-membered heteroalicyclic group, 4- to 8-membered heteroalicyclic group substituted with oxo, 4- to 8-membered heteroalicyclic group substituted with hydroxyl and/or $C_1$-$C_4$ alkyl, and $C_1$-$C_6$ alkylthio, $R^a$ and $R^b$ are each independently selected from hydrogen, $C_1$-$C_6$ alkyl, $C_3$-$C_8$ cycloalkyl, $C_1$-$C_6$ alkyl substituted with $C_1$-$C_6$ alkoxy, $C_1$-$C_6$ alkyl substituted with hydroxyl, $C_3$-$C_8$ cycloalkyl $C_1$-$C_6$ alkyl, $C_1$-$C_6$ alkyl substituted with 4- to 8-membered heteroalicyclic group, $C_1$-$C_6$ alkyl substituted with $C_1$-$C_3$ alkylthio, or $C_1$-$C_6$ alkyl substituted with substituted amino or unsubstituted amino, wherein the substituted amino is substituted with mono- or di-$C_1$-$C_3$ alkyl.

In some embodiments, alternatively, $R_5$ is hydrogen, hydroxyl, $C_1$-$C_4$ alkyl, $C_1$-$C_3$ alkoxy $C_1$-$C_3$ alkyl, $C_1$-$C_3$ alkyl substituted with hydroxyl, cyclopropyl, cyclobutyl, cyclopentyl, cyclohexyl, or $C_1$-$C_3$ alkyl which is substituted with 4-6 membered heteroalicyclic group selected from oxetanyl, azetidinyl, tetrahydrofuranyl, tetrahydro-2H-pyranyl, tetrahydropyrrolyl, piperidinyl, piperazinyl, morpholinyl, or thiomorpholinyl, In some embodiments, alternatively, $R_6$ is $C_1$-$C_8$ alkyl, $C_3$-$C_6$ cycloalkyl, 4-6 membered heteroalicyclic group, or $C_1$-$C_{10}$ alkyl which is unsubstituted or substituted with 1 to 3 substituents selected from the group consisting of hydroxyl, methoxy, ethoxy, propoxy, isopropoxy, butoxy, tert-butoxy, pentoxy, neopentoxy, cyano, amino, dimethylamino, diethylamino, cyclopropyloxy, cyclobutyloxy, cyclopentyloxy, cyclohexyloxy, —CONH—$R_5$, cyclopropyl, cyclobutyl, cyclopentyl, cyclohexyl, cycloheptyl, cyclooctyl, $C_3$-$C_8$ cycloalkyl substituted with hydroxyl and/or $C_1$-$C_4$ alkyl, carboxyl, fluorine, chlorine, trifluoromethoxy, trichloromethoxy, methylsulfone, ethylsulfone, —SO—$R_5$, —CO—$R_5$, ethynyl, vinyl, methoxyethoxy, methoxypropoxy, ethoxyethoxy, ethoxypropoxy, 4- to 8-membered heteroalicyclic group, 4- to 8-membered heteroalicyclic group substituted with oxo, 4- to 8-membered heteroalicyclic group substituted with hydroxyl and/or $C_1$-$C_4$ alkyl, methylthio, ethylthio, and propylthio. Still alternatively, 4- to 8-membered heteroalicyclic group described herein is oxetanyl, azetidinyl, tetrahydrofuranyl, tetrahydro-2H-pyranyl, tetrahydropyrrolyl, piperidinyl, piperazinyl, morpholinyl, thiomorpholinyl, 1,3-dioxolan-2-yl, etc.

In some embodiments, still alternatively, $R_6$ is 4-ethyl-4-hydroxyhexyl, 4-methyl-4-hydroxypentyl, 5-methyl-5-hydroxyhexyl, 2-methyl-2-hydroxypropyl, tetrahydro-2H-pyran-4-ylethyl, tetrahydro-2H-pyran-4-ylmethyl, tetrahydro-2H-pyran-2-ylmethyl, tetrahydro-2H-pyran-2-ylethyl, tetrahydrofuran-2-ylmethyl, tetrahydrofuran-3-ylmethyl, tetrahydrofuran-2-ylethyl, tetrahydrofuran-3-ylethyl, methoxypropyl, ethoxypropyl, tert-butoxypropyl, isobutoxypropyl, isopropoxypropyl, ethoxyethyl, tert-butoxyethyl, isobutoxyethyl, isopropoxyethyl, methoxyethyl, methoxybutyl, ethoxybutyl, tert-butoxybutyl, isobutoxybutyl, isopropoxybutyl, methoxyethoxyethyl, piperidin-1-ylethyl, piperidin-1-ylpropyl, 1-methylpiperidin-4-ylmethyl, 1-methylpiperidin-4-ylethyl, 1-methylpiperidin-4-ylpropyl, 1-methylpiperazin-4-ylethyl, 1-methylpiperazin-4-ylpropyl, methyl, ethyl, propyl, isopropyl, butyl, isobutyl, tert-butyl, pentyl, isopentyl, neopentyl, hexyl, heptyl, 3,3-dimethylbutyl, octyl, hydroxymethyl, hydroxyethyl, hydroxypropyl, hydroxybutyl, hydroxypentyl, hydroxyoctyl, hydroxyheptyl, cyanomethyl, cyanoethyl, cyanopropyl, cyanobutyl, 4-cyanopentyl, 4,4,4-trifluorobutyl, N,N-dimethylpropyl, N,N-dimethylethyl, N,N-diethylpropyl, N,N-diethylethyl, methylthiobutyl, methylthiomethyl, methylthioethyl, methylthiopropyl, methylsulfonylbutyl, methylsulfonylmethyl, methylsulfonylethyl, methylsulfonylpropyl, cycloheptylethyl, cycloheptylpropyl, cyclohexylethyl, cyclohexylpropyl, cyclopentylethyl, cyclopentylpropyl, allyl, penten-1-yl, oxetan-3-yl, tetrahydro-2H-pyran-4-yl, oxetan-3-ylmethyl, oxetan-3-ylethyl, fluoroethyl, fluoropropyl, fluorobutyl, cyclopropylethyl, cyclopropylpropyl, cyclopropylbutyl, cyclobutoxypropyl, cyclobutoxyethyl, cyclobutoxymethyl, cyclopropyl, cyclobutyl, cyclopentyl, cyclohexyl, cycloheptyl, cyclooctyl, —$CH_2CONH_2$, —$(CH_2)_2CONH_2$, —$(CH_2)_3CONH_2$,

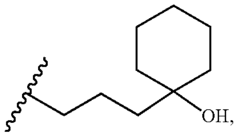, 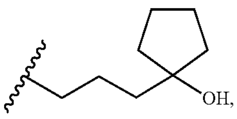, 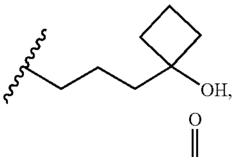, 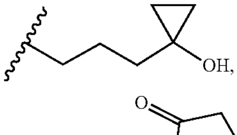, 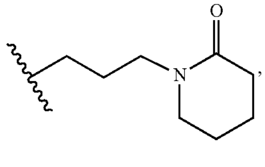, or 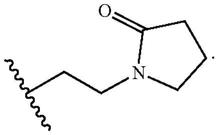.

In some embodiments, alternatively, $R^a$ and $R^b$ are each independently selected from hydrogen, $C_1$-$C_3$ alkyl, $C_3$-$C_6$ cycloalkyl, $C_1$-$C_3$ alkyl substituted with $C_1$-$C_3$ alkoxy, $C_1$-$C_3$ alkyl substituted with hydroxyl, $C_3$-$C_6$ cycloalkyl $C_1$-$C_3$ alkyl, $C_1$-$C_3$ alkyl substituted with 4-6 membered heteroalicyclic group, $C_1$-$C_3$ alkyl substituted with $C_1$-$C_3$ alkylthio, or $C_1$-$C_3$ alkyl substituted with substituted amino or unsubstituted amino, wherein the substituted amino is substituted with mono- or di-$C_1$-$C_3$ alkyl.

In some embodiments, still alternatively, $R_7$ is hydrogen, fluorine, chlorine, methyl, or trifluoromethyl.

In some embodiments, alternatively, $R_1$ is

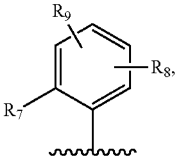 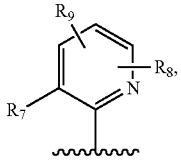 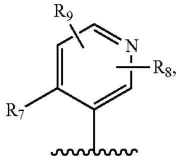 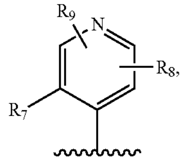 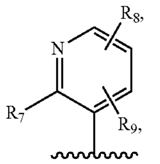 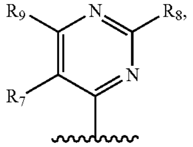 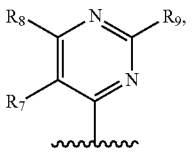 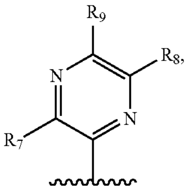 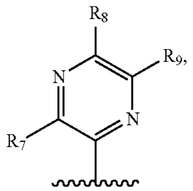 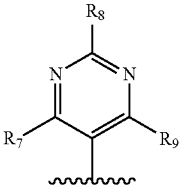 or 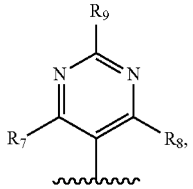

$R_7$ is hydrogen, $C_1$-$C_4$ alkyl, $C_1$-$C_3$ alkoxy, halogen, hydroxyl, trifluoromethyl, trifluoromethoxy, cyano, $C_2$-$C_4$ alkynyl, $C_2$-$C_4$ alkenyl, $C_3$-$C_4$ cycloalkyl, or $C_1$-$C_3$ acyl; still alternatively, $R_7$ is hydrogen, fluorine, chlorine, methyl, or trifluoromethyl.

$R_8$ is hydrogen, $C_1$-$C_{10}$ alkyl, halogen, $C_3$-$C_8$ cycloalkyl, halogenated $C_1$-$C_{10}$ alkyl, cyano, hydroxyl, $C_1$-$C_6$ alkylthio, —CO—$R_5$, —$SO_2$—$R_5$, —SO—$R_5$, —CONH—$R_5$, —$NR^aR^b$, 4- to 8-membered heteroalicyclic group, $C_2$-$C_6$ alkynyl, $C_2$-$C_6$ alkenyl, $C_1$-$C_3$ alkoxy $C_1$-$C_6$ alkylthio, $C_1$-$C_{10}$ alkyl substituted with hydroxyl, $C_1$-$C_6$ alkoxy $C_1$-$C_{10}$ alkyl, $C_3$-$C_8$ cycloalkyl $C_1$-$C_6$ alkyl, ($C_3$-$C_8$ cycloalkyl)-O—($C_1$-$C_6$ alkyl), $C_1$-$C_6$ alkyl substituted with 4- to 8-membered heteroalicyclic group, or —O—$R_6$, the 4- to 8-membered heteroalicyclic group is a 4- to 8-membered heteroalicyclic group containing 1 to 2 atoms selected from N, O, or S as ring atoms, $R_5$ is hydrogen, hydroxyl, $C_1$-$C_6$ alkyl, $C_1$-$C_6$ alkoxy $C_1$-$C_6$ alkyl, $C_1$-$C_6$ alkyl substituted with hydroxyl, $C_3$-$C_8$ cycloalkyl, or $C_1$-$C_6$ alkyl substituted with 4- to 8-membered heteroalicyclic group, $R_6$ is $C_1$-$C_{10}$ alkyl, $C_3$-$C_8$ cycloalkyl, 4- to 8-membered heteroalicyclic group, or $C_1$-$C_{10}$ alkyl which is unsubstituted or substituted with 1 to 3 substituents selected from the group consisting of hydroxyl, $C_1$-$C_6$ alkoxy, cyano, —$NR^aR^b$, $C_3$-$C_8$ cycloalkyloxy, —CONH—$R_5$, $C_3$-$C_8$ cycloalkyl, $C_3$-$C_8$ cycloalkyl substituted with hydroxyl and/or $C_1$-$C_4$ alkyl, carboxylic, halogen, halogenated $C_1$-$C_6$ alkoxy, —$SO_2$—$R_5$, —SO—$R_5$, —CO—$R_5$, $C_2$-$C_6$ alkynyl, $C_2$-$C_6$ alkenyl, $C_1$-$C_4$ alkoxy $C_1$-$C_6$ alkoxy, 4- to 8-membered heteroalicyclic group, 4- to 8-membered heteroalicyclic group substituted with oxo, 4- to 8-membered heteroalicyclic group substituted with hydroxyl and/or $C_1$-$C_4$ alkyl, and $C_1$-$C_6$ alkylthio, $R^a$ and $R^b$ are each independently selected from hydrogen, $C_1$-$C_6$ alkyl, $C_3$-$C_8$ cycloalkyl, $C_1$-$C_6$ alkyl substituted with $C_1$-$C_6$ alkoxy, $C_1$-$C_6$ alkyl substituted with hydroxyl, $C_3$-$C_8$ cycloalkyl $C_1$-$C_6$ alkyl, $C_1$-$C_6$ alkyl substituted with 4- to 8-membered heteroalicyclic group, $C_1$-$C_6$ alkyl substituted with $C_1$-$C_3$ alkylthio, or $C_1$-$C_6$ alkyl substituted with substituted amino or unsubstituted amino, wherein the substituted amino is substituted with mono- or di-$C_1$-$C_3$ alkyl;

$R_9$ is hydrogen, $C_1$-$C_4$ alkyl, $C_1$-$C_3$ alkoxy, halogen, hydroxy, trifluoromethyl, trifluoromethoxy, cyano, $C_2$-$C_4$ alkynyl, $C_2$-$C_4$ alkenyl, $C_3$-$C_4$ Cycloalkyl, or $C_1$-$C_3$ acyl.

In some embodiments, alternatively, $R_2$ is $C_3$-$C_8$ cycloalkyl, which is unsubstituted or substituted with 1 to 3 substituents selected from the group consisting of methyl, ethyl, propyl, isopropyl, methoxy, ethoxy, propoxy, isopropoxy, methylthio, ethylthio, propylthio, formyl, acetyl, hydroxyl, fluorine, chlorine, trifluoromethyl, cyano, —$CONH_2$, oxo (=O), amino, dimethylamino, and diethylamino, or $C_7$-$C_{10}$ bridged cyclyl, which is unsubstituted or substituted with 1 to 3 substituents selected from the group consisting of methyl, ethyl, propyl, isopropyl, methoxy, ethoxy, propoxy, isopropoxy, methylthio, ethylthio, propylthio, formyl, acetyl, hydroxyl, fluorine, chlorine, trifluoromethyl, cyano, —$CONH_2$, oxo (=O), amino, dimethylamino, and diethylamino, or $C_1$-$C_{10}$ alkyl which is unsubstituted or substituted with 1 to 3 substituents selected from the group consisting of methoxy, ethoxy, propoxy, isopropoxy, methylthio, ethylthio, propylthio, formyl, acetyl, hydroxyl, fluorine, chlorine, cyano, —$CONH_2$, cyclopropyl, cyclobutyl, cyclopentyl, cyclohexyl, amino, dimethylamino, and diethylamino, or —$(CH_2)$n-$R^e$, wherein $R^e$ is aryl or heteroaryl, which is unsubstituted or substituted with 1 to 3 substituents selected from the group consisting of methyl, ethyl, propyl, isopropyl, methoxy, ethoxy, propoxy, isopropoxy, methylthio, ethylthio, propylthio, formyl, acetyl, hydroxyl, fluorine, chlorine, trifluoromethyl, cyano, —$CONH_2$, ethynyl, vinyl, amino, dimethylamino, and diethylamino, n is an integer from 0 to 3, or —$(CH_2)$m-$R^f$, wherein $R^f$ is 4- to 8-membered heteroalicyclic group, which is unsubstituted or substituted with 1 to 3 substituents selected from the group consisting of methyl, ethyl, propyl, isopropyl, methoxy, ethoxy, propoxy, isopropoxy, methylthio, ethylthio, propylthio, formyl, acetyl, hydroxyl, fluorine, chlorine, trifluoromethyl, cyano, —$CONH_2$, oxo (=O), amino, dimethylamino, and diethylamino, m is an integer from 0 to 3, the 4- to 8-membered heteroalicyclic group contains 1 to 2 atoms selected from N, O, or S as ring atoms, the aryl group is phenyl, and the heteroaryl group is pyridyl, pyrimidinyl, pyrazolyl, oxazolyl, isoxazolyl, or thiazolyl.

In some embodiments, alternatively, $R_2$ is cyclopropyl, cyclobutyl, cyclopentyl, cyclohexyl, cycloheptyl, cyclooctyl, 4,4-difluorocyclohexyl, bicyclo[2.2.1]heptyl, adamantyl, methyl, ethyl, propyl, isopropyl, butyl, isobutyl, sec-butyl, tert-butyl, pentyl, neopentyl, hexyl, 2-hydroxy-2-methylpropyl, 3,3-dimethylbutyl, 3-hydroxy-3-methylbutyl, cyclopropylmethyl, cyclopropylethyl, cyclopropylpropyl, cyclobutylmethyl, cyclobutylethyl, cyclobutylpropyl, cyclopentylmethyl, cyclopentylethyl, cyclopentylpropyl, cyclohexylmethyl, cyclohexylethyl, cyclohexylpropyl, benzyl, phenethyl, phenyl, 2-fluorophenyl, 2-chlorophenyl, 2-methoxyphenyl, 2-cyanophenyl, 2-ethynylphenyl, 3-fluorophenyl, 3-chlorophenyl, 3-methoxyphenyl, 3-cyanophenyl, 3-ethynylphenyl, 4-fluorophenyl, 4-chlorophenyl, 4-methoxyphenyl, 4-cyanophenyl, 4-ethynylphenyl, 3,4-difluorophenyl, 3-cyano-4-methylphenyl, pyridin-2-yl, pyridin-3-yl, pyridine-4-yl, pyrimidin-2-yl, pyrimidin-4-yl, pyrimidin-5-yl, pyrazinyl, pyrazolyl, oxazolyl, isoxazolyl, thiazolyl, oxetan-3-yl, tetrahydrofuran-3-yl, tetrahydro-2H-pyran-4-yl, tetrahydropyrrolyl, piperidin-1-yl, piperazin-1-yl, morpholin-4-yl, methylpiperazin-4-yl, 1-methylpiperidin-4-yl, 1-acetylpiperidin-4-yl, 4-hydroxypiperidin-1-yl, 4-methyl-4-hydroxypiperidin-1-yl,

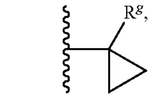
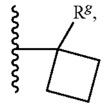
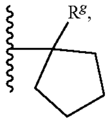
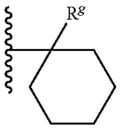
,
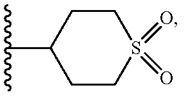
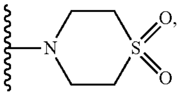
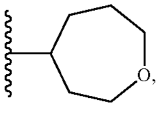
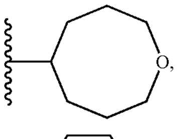
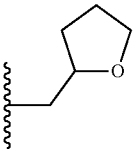
,
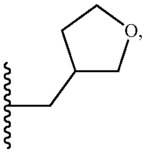
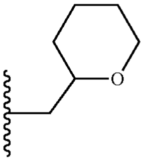
,
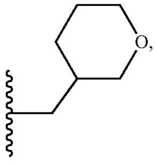
or
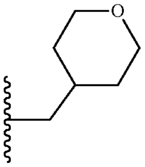
, $R^g$ is —$CH_3$ or —OH, In some embodiments, alternatively, $R_2$ is 2,3-difluorophenyl, 3,5-difluorophenyl, 2,5-difluorophenyl, 2,4-difluorophenyl, 2,3,4-trifluorophenyl, 2,3,5-trifluorophenyl, 2,3,6-trifluorophenyl, 3,4,5-trifluorophenyl, 2,4,5-trifluorophenyl, 3-chloro-2-fluorophenyl, 2-chloro-3-fluorophenyl, 5-chloro-2-fluorophenyl, 2-chloro-5-fluorophenyl, 5-chloro-3-fluorophenyl, 3-chloro-5-fluorophenyl, 3-chloro-4-fluorophenyl, 4-chloro-3-fluorophenyl, 2-chloro-4-fluorophenyl, 4-chloro-2-fluorophenyl, 3-chloro-2,4-difluorophenyl, 5-chloro-2,4-difluorophenyl, 3-chloro-2,5-difluorophenyl, 3-chloro-2,6-difluorophenyl, 3-chloro-4,5-difluorophenyl, 2-chloro-4,5-difluorophenyl, 2-chloro-3,4-difluorophenyl, 2-chloro-3,5-difluorophenyl, 2-chloro-3,6-difluorophenyl, 4-chloro-2,3-difluorophenyl, 4-chloro-3,5-difluorophenyl, 4-chloro-2,5-difluorophenyl, 5-chloro-2,3-difluorophenyl, 5-chloro-3,4-difluorophenyl, 6-chloro-2,3-difluorophenyl, 3-fluoro-5-methylphenyl, 4-fluoro-3-methylphenyl, 2-fluoro-3-methylphenyl, 2-fluoro-4-methylphenyl, 2-fluoro-5-methylphenyl, 3-fluoro-4-methylphenyl, 3-fluoro-2-methylphenyl, 3-fluoro-5-methoxyphenyl, 4-fluoro-3-methoxyphenyl, 2-fluoro-3-methoxyphenyl, 2-fluoro-4-methoxyphenyl, 2-fluoro-5-methoxyphenyl, 3-fluoro-4-methoxyphenyl, 3-fluoro-2-methoxyphenyl, 2-fluoro-3-trifluoromethylphenyl, 2-fluoro-4-trifluoromethylphenyl, 2-fluoro-5-trifluoromethylphenyl, 3-fluoro-2-trifluoromethylphenyl, 4-fluoro-2-trifluoromethylphenyl, 5-fluoro-2-trifluoromethylphenyl, 4-fluoro-3-trifluoromethylphenyl, 3-fluoro-4-trifluoromethylphenyl, 3-fluoro-5-trifluoromethylphenyl, 2-fluoro-5-ethylphenyl, 2-fluoro-5-cyclopropylphenyl, or 2-fluoro-5-phenylphenyl.

In some embodiments, alternatively, $R_3$ is hydrogen, methyl, ethyl, hydroxyl, cyano, trifluoromethyl, fluorine, or chlorine.

Disclosed is a compound represented by formula (I), pharmaceutically acceptable salts, isomer, solvate or prodrug thereof, formula (I)

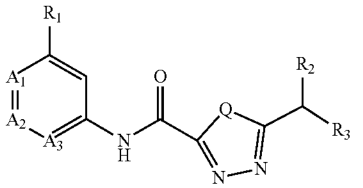

wherein, Q is NH;

$A_3$ is N, $A_1$, and $A_2$ are each independently selected from N or $CR_4$, $R_4$ is H, F, Cl or methyl, alternatively H or F;

$R_1$ is

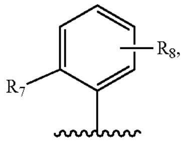

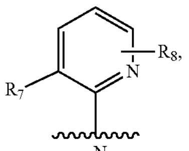

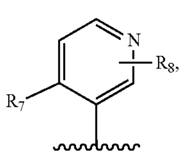

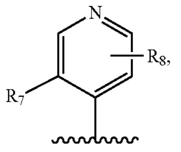

-continued

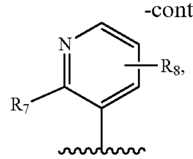

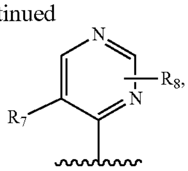

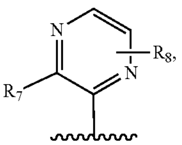

or

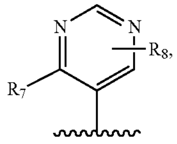

$R_7$ is hydrogen, $C_1$-$C_4$ alkyl, $C_1$-$C_3$ alkoxy, halogen, hydroxyl, trifluoromethyl, trifluoromethoxy, cyano, $C_2$-$C_4$ alkynyl, $C_2$-$C_4$ alkenyl, $C_3$-$C_4$ cycloalkyl, or $C_1$-$C_3$ acyl;

$R_8$ is hydrogen, $C_1$-$C_{10}$ alkyl, halogen, $C_3$-$C_8$ cycloalkyl, halogenated $C_1$-$C_{10}$ alkyl, cyano, hydroxyl, $C_1$-$C_6$ alkylthio, —CO—$R_5$, —$SO_2$—$R_5$, —SO—$R_5$, —CONH—$R_5$, —$NR^aR^b$, 4- to 8-membered heteroalicyclic group, $C_2$-$C_6$ alkynyl, $C_2$-$C_6$ alkenyl, $C_1$-$C_3$ alkoxy $C_1$-$C_6$ alkylthio, hydroxyl $C_1$-$C_{10}$ alkyl, $C_1$-$C_6$ alkoxy $C_1$-$C_{10}$ alkyl, $C_3$-$C_8$ cycloalkyl $C_1$-$C_6$ alkyl, ($C_3$-$C_8$ cycloalkyl)-O—($C_1$-$C_6$ alkyl), $C_1$-$C_6$ alkyl substituted with 4- to 8-membered heteroalicyclic group, or —O—$R_6$, the 4- to 8-membered heteroalicyclic group is a 4- to 8-membered heteroalicyclic group containing 1 to 2 atoms selected from N, O, or S as ring atoms, $R_5$ is hydrogen, hydroxyl, $C_1$-$C_6$ alkyl, $C_1$-$C_6$ alkoxy $C_1$-$C_6$ alkyl, $C_1$-$C_6$ alkyl substituted with hydroxyl, $C_3$-$C_8$ cycloalkyl, or $C_1$-$C_6$ alkyl substituted with 4- to 8-membered heteroalicyclic group, $R_6$ is $C_1$-$C_{10}$ alkyl, $C_3$-$C_8$ cycloalkyl, 4- to 8-membered heteroalicyclic group, or $C_1$-$C_{10}$ alkyl which is unsubstituted or substituted with 1 to 3 substituents selected from the group consisting of hydroxyl, $C_1$-$C_6$ alkoxy, cyano, —$NR^aR^b$, $C_3$-$C_8$ cycloalkyloxy, —CONH—$R_5$, $C_3$-$C_8$ cycloalkyl, $C_3$-$C_8$ cycloalkyl substituted with hydroxyl and/or $C_1$-$C_4$ alkyl, carboxylic, halogen, halogenated $C_1$-$C_6$ alkoxy, —$SO_2$—$R_5$, —SO—$R_5$, —CO—$R_5$, $C_2$-$C_6$ alkynyl, $C_2$-$C_6$ alkenyl, $C_1$-$C_4$ alkoxy $C_1$-$C_6$ alkoxy, 4- to 8-membered heteroalicyclic group, 4- to 8-membered heteroalicyclic group substituted with oxo, 4- to 8-membered heteroalicyclic group substituted with hydroxyl and/or $C_1$-$C_4$ alkyl, or $C_1$-$C_6$ alkylthio, $R^a$ and $R^b$ are each independently selected from hydrogen, $C_1$-$C_6$ alkyl, $C_3$-$C_8$ cycloalkyl, $C_1$-$C_6$ alkyl substituted with $C_1$-$C_6$ alkoxy, $C_1$-$C_6$ alkyl substituted with hydroxyl, $C_3$-$C_8$ cycloalkyl $C_1$-$C_6$ alkyl, $C_1$-$C_6$ alkyl substituted with 4- to 8-membered heteroalicyclic group, $C_1$-$C_6$ alkyl substituted with $C_1$-$C_3$ alkylthio, or $C_1$-$C_6$ alkyl substituted with substituted amino or unsubstituted amino, wherein the substituted amino is substituted with mono- or di-$C_1$-$C_3$ alkyl, still alternatively, $R_1$ is

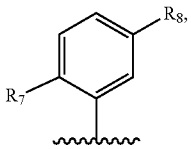

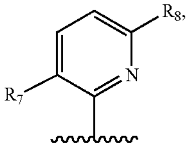

-continued

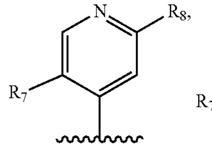 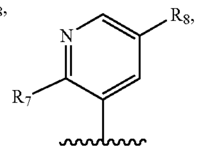

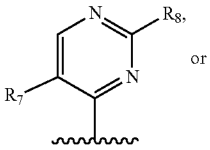 or 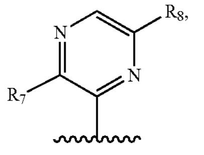

$R_7$ is hydrogen, methyl, ethyl, propyl, isopropyl, methoxy, ethoxy, propoxy, isopropoxy, fluorine, chlorine, hydroxyl, trifluoromethyl, trifluoromethoxy, cyano, ethynyl, propynyl, vinyl, propenyl, cyclopropyl, cyclobutyl, formyl, or acetyl; alternatively $R_7$ is hydrogen, fluorine, chlorine, methyl, or trifluoromethyl;

$R_8$ is hydrogen, $C_1$-$C_{10}$ alkyl, halogen, $C_3$-$C_8$ cycloalkyl, halogenated $C_1$-$C_{10}$ alkyl, cyano, hydroxyl, $C_1$-$C_6$ alkylthio, —CO—$R_5$, —$SO_2$—$R_5$, —SO—$R_5$, —CONH—$R_5$, —$NR^aR^b$, 4- to 8-membered heteroalicyclic group, $C_2$-$C_6$ alkynyl, $C_2$-$C_6$ alkenyl, $C_1$-$C_3$ alkoxy $C_1$-$C_6$ alkylthio, $C_1$-$C_{10}$ alkyl substituted with hydroxyl, $C_1$-$C_6$ alkoxy $C_1$-$C_{10}$ alkyl, $C_3$-$C_8$ cycloalkyl $C_1$-$C_6$ alkyl, ($C_3$-$C_8$ cycloalkyl)-O—($C_1$-$C_6$ alkyl), $C_1$-$C_6$ alkyl substituted with 4- to 8-membered heteroalicyclic group, or —O—$R_6$, the 4- to 8-membered heteroalicyclic group is heteroalicyclic group containing 1 to 2 atoms selected from N, O, or S as ring atoms, $R_5$ is hydrogen, hydroxyl, $C_1$-$C_4$ alkyl, $C_1$-$C_3$ alkoxy $C_1$-$C_3$ alkyl, $C_1$-$C_3$ alkyl substituted with hydroxyl, cyclopropyl, cyclobutyl, cyclopentyl, cyclohexyl, or $C_1$-$C_3$ alkyl which is substituted with 4-6 membered heteroalicyclic group selected from oxetanyl, azetidinyl, tetrahydrofuranyl, tetrahydro-2H-pyranyl, tetrahydropyrrolyl, piperidinyl, piperazinyl, morpholinyl, or thiomorpholinyl, $R_6$ is $C_1$-$C_5$ alkyl, $C_3$-$C_6$ cycloalkyl, 4-6 membered heteroalicyclic group, or $C_1$-$C_{10}$ alkyl which is unsubstituted or substituted with 1 to 3 substituents selected from the group consisting of hydroxyl, methoxy, ethoxy, propoxy, isopropoxy, butoxy, tert-butoxy, pentoxy, neopentoxy, cyano, amino, dimethylamino, diethylamino, cyclopropyloxy, cyclobutyloxy, cyclopentyloxy, cyclohexyloxy, —CONH—$R_5$, cyclopropyl, cyclobutyl, cyclopentyl, cyclohexyl, cycloheptyl, cyclooctyl, $C_3$-$C_8$ cycloalkyl substituted with hydroxyl and/or $C_1$-$C_4$ alkyl, carboxyl, fluorine, chlorine, trifluoromethoxy, trichloromethoxy, methylsulfone, ethylsulfone, —SO—$R_5$, —CO—$R_5$, ethynyl, vinyl, methoxyethoxy, methoxypropoxy, ethoxyethoxy, ethoxypropoxy, 4- to 8-membered heteroalicyclic group, 4- to 8-membered heteroalicyclic group substituted with oxo, 4- to 8-membered heteroalicyclic group substituted with hydroxyl and/or $C_1$-$C_4$ alkyl, methylthio, ethylthio, and propylthio. Still alternatively, 4- to 8-membered heteroalicyclic group described herein is oxetanyl, azetidinyl, tetrahydrofuranyl, tetrahydro-2H-pyranyl, tetrahydropyrrolyl, piperidinyl, piperazinyl, morpholinyl, thiomorpholinyl, 1,3-dioxolan-2-yl, etc., still alternatively, $R_6$ is 4-ethyl-4-hydroxyhexyl, 4-methyl-4-hydroxypentyl, 5-methyl-5-hydroxyhexyl, 2-methyl-2-hydroxypropyl, tetrahydro-2H-pyran-4-ylethyl, tetrahydro-2H-pyran-4-ylmethyl, tetrahydro-2H-pyran-2-ylmethyl, tetrahydro-2H-pyran-2-ylethyl, tetrahydrofuran-2-ylmethyl, tetrahydrofuran-3-ylmethyl, tetrahydrofuran-2-ylethyl, tetrahydrofuran-3-ylethyl, methoxypropyl, ethoxypropyl, tert-butoxypropyl, isobutoxypropyl, isopropoxypropyl, ethoxyethyl, tert-butoxyethyl, isobutoxyethyl, isopropoxyethyl, methoxyethyl, methoxybutyl, ethoxybutyl, tert-butoxybutyl, isobutoxybutyl, isopropoxybutyl, methoxyethoxyethyl, piperidin-1-ylethyl, piperidin-1-ylpropyl, 1-methylpiperidin-4-ylmethyl, 1-methylpiperidin-4-ylethyl, 1-methylpiperidin-4-ylpropyl, 1-methylpiperazin-4-ylethyl, 1-methylpiperazin-4-ylpropyl, methyl, ethyl, propyl, isopropyl, butyl, isobutyl, tert-butyl, pentyl, isopentyl, neopentyl, hexyl, heptyl, 3,3-dimethylbutyl, octyl, hydroxymethyl, hydroxyethyl, hydroxypropyl, hydroxybutyl, hydroxypentyl, hydroxyoctyl, hydroxyheptyl, cyanomethyl, cyanoethyl, cyanopropyl, cyanobutyl, 4-cyanopentyl, 4,4,4-trifluorobutyl, N,N-dimethylpropyl, N,N-dimethylethyl, N,N-diethylpropyl, N,N-diethylethyl, methylthiobutyl, methylthiomethyl, methylthioethyl, methylthiopropyl, methylsulfonylbutyl, methylsulfonylmethyl, methylsulfonylethyl, methylsulfonylpropyl, cycloheptylethyl, cycloheptylpropyl, cyclohexylethyl, cyclohexylpropyl, cyclopentylethyl, cyclopentylpropyl, allyl, penten-1-yl, oxetan-3-yl, tetrahydro-2H-pyran-4-yl, oxetan-3-ylmethyl, oxetan-3-ylethyl, fluoroethyl, fluoropropyl, fluorobutyl, cyclopropylethyl, cyclopropylpropyl, cyclopropylbutyl, cyclobutoxypropyl, cyclobutoxyethyl, cyclobutoxymethyl, cyclopropyl, cyclobutyl, cyclopentyl, cyclohexyl, cycloheptyl, cyclooctyl, —$CH_2CONH_2$, —$(CH_2)_2CONH_2$, —$(CH_2)_3CONH_2$,

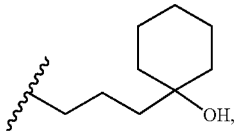 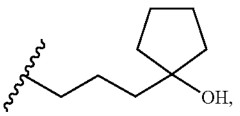

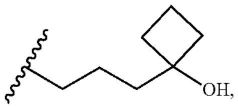 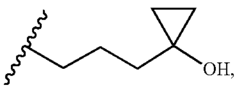

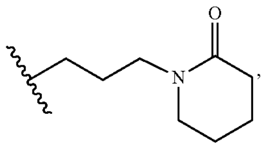, or 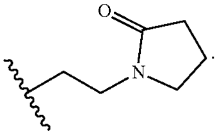.

$R^a$ and $R^b$ are each independently selected from hydrogen, $C_1$-$C_3$ alkyl, $C_3$-$C_6$ cycloalkyl, $C_1$-$C_3$ alkyl substituted with $C_1$-$C_3$ alkoxy, $C_1$-$C_3$ alkyl substituted with hydroxyl, $C_3$-$C_6$ cycloalkyl $C_1$-$C_3$ alkyl, $C_1$-$C_3$ alkyl substituted with 4-6 membered heteroalicyclic group, $C_1$-$C_3$ alkyl substituted with $C_1$-$C_3$ alkylthio, or $C_1$-$C_3$ alkyl substituted with substituted amino or unsubstituted amino, wherein the substituted amino is substituted with mono- or di-$C_1$-$C_3$ alkyl;

$R_2$ is $C_3$-$C_8$ cycloalkyl, which is unsubstituted or substituted with 1 to 3 substituents selected from the group consisting of methyl, ethyl, propyl, isopropyl, methoxy, ethoxy, propoxy, isopropoxy, methylthio, ethylthio, propylthio, formyl, acetyl, hydroxyl, fluorine, chlorine, trifluoromethyl, cyano, —$CONH_2$, oxo (=O), amino, dimethylamino, and diethylamino, or $C_7$-$C_{10}$ bridged cyclyl, which is unsubstituted or substituted with 1 to 3 substituents selected from the group consisting of methyl, ethyl, propyl, isopropyl, methoxy, ethoxy, propoxy, isopropoxy, methylthio, ethylthio, propylthio, formyl, acetyl, hydroxyl, fluorine, chlorine, trifluoromethyl, cyano, —$CONH_2$, oxo (=O), amino, dimethylamino, and diethylamino, or $C_1$-$C_{10}$ alkyl which is unsubstituted or substituted with 1 to 3 substituents selected from the group consisting of methoxy, ethoxy, propoxy, isopropoxy, methylthio, ethylthio, propylthio, formyl, acetyl, hydroxyl, fluorine, chlorine, cyano, —$CONH_2$, cyclopropyl, cyclobutyl, cyclopentyl, cyclohexyl, amino, dimethylamino, and diethylamino, or —$(CH_2)$n-$R^e$, wherein $R^e$ is aryl or heteroaryl, which is unsubstituted or substituted with 1 to 3 substituents selected from the group consisting of methyl, ethyl, propyl, isopropyl, methoxy, ethoxy, propoxy, isopropoxy, methylthio, ethylthio, propylthio, formyl, acetyl, hydroxyl, fluorine, chlorine, trifluoromethyl, cyano, —$CONH_2$, ethynyl, vinyl, amino, dimethylamino, and diethylamino, n is an integer from 0 to 3, or —$(CH_2)$m-$R^f$, wherein $R^f$ is 4- to 8-membered heteroalicyclic group, which is unsubstituted or substituted with 1 to 3 substituents selected from the group consisting of methyl, ethyl, propyl, isopropyl, methoxy, ethoxy, propoxy, isopropoxy, methylthio, ethylthio, propylthio, formyl, acetyl, hydroxyl, fluorine, chlorine, trifluoromethyl, cyano, —$CONH_2$, oxo (=O), amino, dimethylamino, and diethylamino, m is an integer from 0 to 3, the 4- to 8-membered heteroalicyclic group contains 1 to 2 atoms selected from N, O, or S as ring atoms, the aryl group is phenyl, and the heteroaryl group is pyridyl, pyrimidinyl, pyrazolyl, oxazolyl, isoxazolyl, or thiazolyl;

still alternatively, $R_2$ is cyclopropyl, cyclobutyl, cyclopentyl, cyclohexyl, cycloheptyl, cyclooctyl, 4,4-difluorocyclohexyl, bicyclo[2.2.1]heptyl, adamantyl, methyl, ethyl, propyl, isopropyl, butyl, isobutyl, sec-butyl, tert-butyl, pentyl, neopentyl, hexyl, 2-hydroxy-2-methylpropyl, 3,3-dimethylbutyl, 3-hydroxy-3-methylbutyl, cyclopropylmethyl, cyclopropylethyl, cyclopropylpropyl, cyclobutylmethyl, cyclobutylethyl, cyclobutylpropyl, cyclopentylmethyl, cyclopentylethyl, cyclopentylpropyl, cyclohexylmethyl, cyclohexylethyl, cyclohexylpropyl, benzyl, phenethyl, phenyl, 2-fluorophenyl, 2-chlorophenyl, 2-methoxyphenyl, 2-cyanophenyl, 2-ethynylphenyl, 3-fluorophenyl, 3-chlorophenyl, 3-methoxyphenyl, 3-cyanophenyl, 3-ethynylphenyl, 4-fluorophenyl, 4-chlorophenyl, 4-methoxyphenyl, 4-cyanophenyl, 4-ethynylphenyl, 3,4-difluorophenyl, 3-cyano-4-methylphenyl, pyridin-2-yl, pyridin-3-yl, pyridine-4-yl, pyrimidin-2-yl, pyrimidin-4-yl, pyrimidin-5-yl, pyrazinyl, pyrazolyl, oxazolyl, isoxazolyl, thiazolyl, oxetan-3-yl, tetrahydrofuran-3-yl, tetrahydro-2H-pyran-4-yl, tetrahydropyrrolyl, piperidin-1-yl, piperazin-1-yl, morpholin-4-yl, methylpiperazin-4-yl, 1-methylpiperidin-4-yl, 1-acetylpiperidin-4-yl, 4-hydroxypiperidin-1-yl, 4-methyl-4-hydroxypiperidin-1-yl, 2,3-difluorophenyl, 3,5-difluorophenyl, 2,5-difluorophenyl, 2,4-difluorophenyl, 2,3,4-trifluorophenyl, 2,3,5-trifluorophenyl, 2,3,6-trifluorophenyl, 3,4,5-trifluorophenyl, 2,4,5-trifluorophenyl, 3-chloro-2-fluorophenyl, 2-chloro-3-fluorophenyl, 5-chloro-2-fluorophenyl, 2-chloro-5-fluorophenyl, 5-chloro-3-fluorophenyl, 3-chloro-5-fluorophenyl, 3-chloro-4-fluorophenyl, 4-chloro-3-fluorophenyl, 2-chloro-4-fluorophenyl, 4-chloro-2-fluorophenyl, 3-chloro-2,4-difluorophenyl, 5-chloro-2,4-difluorophenyl, 3-chloro-2,5-difluorophenyl, 3-chloro-2,6-difluorophenyl, 3-chloro-4,5-difluorophenyl, 2-chloro-4,5-difluorophenyl, 2-chloro-3,4-difluorophenyl, 2-chloro-3,5-difluorophenyl, 2-chloro-3,6-difluorophenyl, 4-chloro-2,3-difluorophenyl, 4-chloro-3,5-difluorophenyl, 4-chloro-2,5-difluorophenyl, 5-chloro-2,3-difluorophenyl, 5-chloro-3,4-difluorophenyl, 6-chloro-2,3-difluorophenyl, 3-fluoro-5-methylphenyl, 4-fluoro-3-methylphenyl, 2-fluoro-3-methylphenyl, 2-fluoro-4-methylphenyl, 2-fluoro-5-methylphenyl, 3-fluoro-4-methylphenyl, 3-fluoro-2-methylphenyl, 3-fluoro-5-methoxyphenyl, 4-fluoro-3-methoxyphenyl, 2-fluoro-3-methoxyphenyl, 2-fluoro-4-methoxyphenyl, 2-fluoro-5-methoxyphenyl, 3-fluoro-4-methoxyphenyl, 3-fluoro-2-methoxyphenyl, 2-fluoro-3-trifluoromethylphenyl, 2-fluoro-4-trifluoromethylphenyl, 2-fluoro-5-trifluoromethylphenyl, 3-fluoro-2-trifluoromethylphenyl, 4-fluoro-2-trifluoromethylphenyl, 5-fluoro-2-trifluoromethylphenyl, 4-fluoro-3-trifluoromethylphenyl, 3-fluoro-4-trifluoromethylphenyl, 3-fluoro-5-trifluoromethylphenyl, 2-fluoro-5-ethylphenyl, 2-fluoro-5-cyclopropylphenyl, 2-fluoro-5-phenylphenyl,

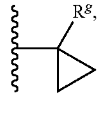 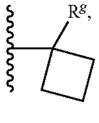 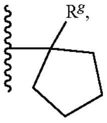

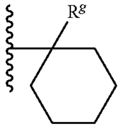, 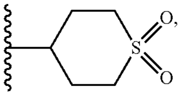 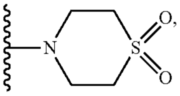

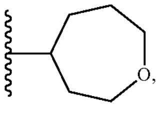 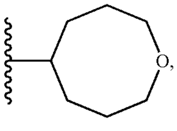 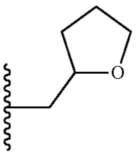,

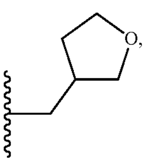 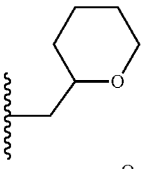, 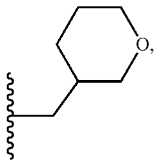 or

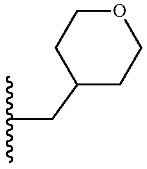, $R^g$ is —$CH_3$ or —OH.

$R_3$ is hydrogen, methyl, ethyl, hydroxyl, cyano, trifluoromethyl, fluorine, or chlorine, still alternatively hydrogen, fluorine, hydroxyl, or chlorine.

According to some embodiments of the present disclosure, the pharmaceutically acceptable salt of the compound is selected from the group consisting of one or more of the following salts: hydrochloride, hydrobromide, hydroiodide, perchlorate, sulfate, nitrate, phosphate, formate, acetate, propionate, glycolate, lactate, succinate, maleate, tartrate, malate, citrate, fumarate, gluconate, benzoate, mandelate, methanesulfonate, isethionate, benzenesulfonate, oxalate, palmitate, 2-naphthalenesulfonate, p-toluenesulfonate, cyclohexylsulfamate, salicylate, hexonate, trifluoroacetate, aluminum salt, calcium salt, chloroprocaine salt, choline salt, diethanolamine salt, ethylenediamine salt, lithium salt, magnesium salt, potassium salt, sodium salt and zinc salt.

Another aspect of the present disclosure relates to the application of the compound, pharmaceutically acceptable salt(s), isomer(s), solvate(s), or prodrug(s) thereof in the preparation of a medicament for the treatment of RIP1 related diseases, Wherein, the RIP1 related disease include ocular fundus disease, xerophthalmia, psoriasis, leucoderma, dermatitis, alopecia areata, rheumatoid arthritis, colitis, multiple sclerosis, systemic lupus erythematosus, Crohn's disease, atherosclerosis, pulmonary fibrosis, liver fibrosis, myelofibrosis, non-small cell lung cancer, small cell lung cancer, breast cancer, pancreatic cancer, glioma, glioblastoma, ovarian cancer, cervical cancer, colorectal cancer, melanoma, endometrial cancer, prostate cancer, bladder cancer, leukemia, gastric cancer, liver cancer, gastrointestinal stromal tumor, thyroid cancer, chronic myeloid leukemia, acute myeloid leukemia, non-Hodgkin's lymphoma, nasopharyngeal cancer, esophageal cancer, brain tumor, B-cell and T-cell lymphoma, lymphoma, multiple myeloma, biliary cancer and sarcoma, cholangiocarcinoma, inflammatory bowel disease, ulcerative colitis, retinal detachment, retinitis pigmentosa, macular degeneration, pancreatitis, atopic dermatitis, spondyloarthritis, gout, SoJIA, Sjogren's syndrome, systemic scleroderma, antiphospholipid syndrome, vasculitis, osteoarthritis, non-alcoholic steatohepatitis, alcoholic steatohepatitis, autoimmune hepatitis, autoimmune hepatobiliary disease, primary sclerosing cholangitis, nephritis, celiac disease, autoimmune ITP, transplant rejection, ischemia-reperfusion injury of solid organs, sepsis, systemic inflammatory response syndrome, cerebrovascular accident, myocardial infarction, Huntington's disease, Alzheimer's disease, Parkinson's disease, allergic diseases, asthma, atopic dermatitis, multiple sclerosis, type I diabetes, Wegener's granulomatosis, pulmonary sarcoidosis, Behcet's disease, interleukin-1 converzyme-related fever syndrome, chronic obstructive pulmonary disease, tumor necrosis factor receptor related periodic syndrome and periodontitis.

Another aspect of the present disclosure provides a pharmaceutical composition, which includes the acylamino bridged heterocyclic compounds of the present disclosure, or isomers, solvates, pharmaceutically acceptable salts or prodrugs thereof, and one or more pharmaceutically acceptable carriers or excipients.

According to some embodiments of the application, the pharmaceutical composition may also include one or more other therapeutic agents.

The present disclosure also relates to a method for treating diseases or disorders mediated by RIP1 kinase, which comprises administering a therapeutically effective amount of a compound of formula (I) or a salt thereof to a patient (human or other mammals, especially human) in need thereof. The RIP1 kinase-mediated diseases or disorders include those mentioned above.

DESCRIPTION OF THE FIGURES

FIG. 1 shows a Western Blot picture of the inhibition of RIPK1 phosphorylation by the compound of Example 2;

FIG. 2 shows the inhibitory rate of the compound of Example 2 on the inhibition of RIPK1 phosphorylation;

FIG. 3 shows the dilution flow chart for the compound of Assay Example 2.

DETAILED DESCRIPTION OF THE EMBODIMENTS

Unless otherwise stated, the following terms used in this application (including the description and claims) have the definitions given below. In this application, the use of "or" or "and" means "and/or" unless stated otherwise. In addition, the use of the term "comprising" and other forms such as "including", "containing" and "having" is not limiting. The chapter headings used herein are for organizational purposes only and should not be interpreted as limitations on the topics described.

DETAILED DESCRIPTION

Unless otherwise specified, alkyl represents a saturated straight-chain, or branched-chain hydrocarbon group with the specified number of carbon atoms. The term $C_1$-$C_{10}$ alkyl represents an alkyl moiety containing 1 to 10 carbon atoms, similarly $C_1$-$C_3$ alkyl represents an alkyl moiety containing 1 to 3 carbon atoms, such as, $C_1$-$C_6$ alkyl including methyl, ethyl, propyl, isopropyl, n-butyl, isobutyl, sec-butyl, tert-butyl, n-pentyl, 3-(2-methyl)butyl, 2-pentyl, 2-methylbutyl, neopentyl, n-hexyl, 2-hexyl and 2-methylpentyl etc.

When substituent terms such as "alkyl" are used in combination with other substituent terms, for example in the term "$C_1$-$C_3$ alkoxy $C_1$-$C_6$ alkylthio" or "$C_1$-$C_{10}$ alkyl substituted with hydroxyl", this linking substituent term (e.g. alkyl or alkylthio) is intended to include a divalent moiety, wherein the connection point is through the connection substituent. Examples of "$C_1$-$C_3$ alkoxy $C_1$-$C_6$ alkylthio" include, but are not limited to, methoxymethylthio, methoxyethylthio and ethoxypropylthio, etc. Examples of "$C_1$-$C_{10}$ alkyl substituted with hydroxyl" include, but are not limited to, hydroxymethyl, hydroxyethyl, and hydroxyisopropyl.

Alkoxy is an alkyl-O— group formed by the previously described linear or branched alkyl group and —O—, for example, methoxy, ethoxy, etc. Similarly, alkylthio is an alkyl-S— group formed by the previously described linear or branched alkyl group and —S—, for example, methylthio, ethylthio, etc.

Alkenyl and alkynyl include straight chain, or branched alkenyl or alkynyl, the term $C_2$-$C_6$ alkenyl or $C_2$-$C_6$ alkynyl means a straight or branched chain hydrocarbon group having at least one alkenyl or alkynyl group.

The term "halogenated $C_1$-$C_{10}$ alkyl" represents a group having one or more halogen atoms, which may be the same or different, on one or more carbon atoms of the alkyl moiety comprising 1 to 10 carbon atoms. Examples of "halogenated $C_1$-$C_{10}$ alkyl" may include, but are not limited to, —$CF_3$ (trifluoromethyl), —$CCl_3$ (trichloromethyl), 1,1-difluoroethyl, 2,2,2-trifluoroethyl and hexafluoroisopropyl, etc. Similarly, the term "halogenated $C_1$-$C_{10}$ alkoxy" represents a haloalkyl-O— group formed by the halogenated $C_1$-$C_{10}$ alkyl group and —O—, for example, trifluoromethoxy, trichloromethoxy, etc.

The term "$C_1$-$C_3$ acyl" includes formyl (—CHO), acetyl ($CH_3CO$—), propionyl ($C_2H_5CO$—).

The terms "—CO—$R_5$, —$SO_2$—$R_5$, —SO—$R_5$, —CONH—$R_5$" represent

“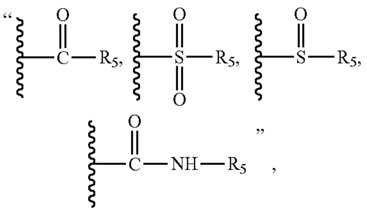”, respectively.

“Cycloalkyl” represents a non-aromatic, saturated, cyclic hydrocarbon group containing the specified number of carbon atoms. For example, the term “($C_3$-$C_6$) cycloalkyl” refers to a non-aromatic cyclic hydrocarbon ring with 3-6 ring carbon atoms. Exemplary “($C_3$-$C_6$) cycloalkyl” includes cyclopropyl, cyclobutyl, cyclopentyl and cyclohexyl.

The term “aryl” represents a group or moiety containing an aromatic monocyclic or bicyclic hydrocarbon atom group, which contains 6 to 12 carbon ring atoms and has at least one aromatic ring. Examples of “aryl” are phenyl, naphthyl, indenyl and indanyl. Generally, in the compounds of the present disclosure, the aryl group is a phenyl group.

The term “heteroalicyclic group” as used herein, unless otherwise specified, represents an unsubstituted or substituted stable 4- to 8-membered non-aromatic monocyclic saturated ring system, which consists of carbon atoms and 1 to 3 heteroatoms selected from N, O, or S, wherein, N and S heteroatoms can be arbitrarily oxidized, and N heteroatoms can also be arbitrarily quaternized. Examples of such heterocycles include, but are not limited to, azetidinyl, oxetanyl, thietanyl, pyrrolidinyl, pyrrolinyl, pyrazolidinyl, pyrazolinyl, imidazolidinyl, imidazolinyl, oxazolinyl, thiazolinyl, tetrahydrofuranyl, dihydrofuranyl, tetrahydrothienyl, 1,3-dioxolanyl, piperidinyl, piperazinyl, tetrahydropyranyl, dihydropyranyl, tetrahydrothiopyranyl, 1,3-dioxanyl, 1,4-dioxanyl, 1,3-oxathiolanyl, 1,3-oxathianyl, 1,3-dithianyl, 1,4-oxathiolanyl, 1,4-oxathianyl, 1,4-dithianyl, morpholinyl, and thiomorpholinyl.

The term “heteroaryl” as used herein represents a group or moiety containing an aromatic monocyclic or bicyclic group (which contains 5 to 10 ring atoms), which includes 1 to 3 heteroatoms independently selected from nitrogen, oxygen and sulfur. The term also includes bicyclic heterocyclic aryl, which contains an aryl ring moiety fused to a heterocycloalkyl ring moiety, or a heteroaryl ring moiety fused to a cycloalkyl ring moiety. Unless otherwise specified, it represents an unsubstituted or substituted stable 5- or 6-membered monocyclic aromatic ring system, and can also represents an unsubstituted or substituted benzene fused heteroaromatic ring system or bicyclic heteroaromatic ring system with 9 or 10 ring atoms, which are composed of carbon atoms and 1 to 3 heteroatoms selected from N, O, or S, where N, S heteroatoms can be oxidized, and N heteroatoms can also be quaternized. Heteroaryl groups can be connected to any heteroatom or carbon atom to form a stable structure. Illustrative examples of heteroaryl groups include, but are not limited to, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridyl, oxopyridyl (pyridyl-N-oxide), pyridazinyl, pyrazinyl, pyrimidinyl, triazinyl, benzofuranyl, isobenzofuranyl, 2,3-dihydrobenzofuranyl, 1,3-benzodioxolyl, dihydrobenzodioxinyl, benzothienyl, indazinyl, indolyl, isoindolyl, indolinyl, benzimidazolyl, dihydrobenzimidazolyl, benzoxazolyl, dihydrobenzoxazolyl, benzothiazolyl, benzoisothiazolyl, dihydrobenzisothiazolyl, indazolyl, imidazopyridyl, pyrazolopyridyl, benzotriazolyl, triazolopyridyl, purinyl, quinolinyl, tetrahydroquinolinyl, isoquinolinyl, tetrahydroisoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridyl.

The term “carbonyl” refers to the —C(O)— group. The terms “halogen” and “halo” represent chlorine, fluorine, bromine or iodine substituents. “Oxo” represents the oxygen moiety with double bond; for example, it forms a carbonyl moiety (C═O) when it is directly attached to a carbon atom. “Hydroxy” is intended to mean the —OH group. As used herein, the term “cyano” refers to the group —CN.

The term “each independently” means that when more than one substituents are selected from a number of possible substituents, those substituents may be the same or different.

It is clear that the compounds of formula I, or isomers, crystal forms or prodrugs and pharmaceutically acceptable salts thereof may exist in solvated and unsolvated forms. For example, the solvated form can be a hydrate form. The present disclosure includes all these solvated forms and unsolvated forms.

The compounds of the present disclosure may have asymmetric carbon atoms. According to their physical and chemical differences, such diastereomeric mixtures can be separated into single diastereomers by known, technically mature methods, such as chromatography or fractional crystallization. The separation of enantiomers can be carried out by first reacting with a suitable optically active compound, converting the enantiomeric mixture into a diastereomeric mixture, separating the diastereoisomers, and then the single diastereomers are transformed (hydrolyzed) into the corresponding pure enantiomers. All such isomers, including diastereomeric mixtures and pure enantiomers, are considered as part of the invention.

The compound of the present disclosure as an active ingredient, and the method of preparing the same, are both included in the present disclosure. Moreover, the crystalline form of some of the compounds may exist as polymorphs, and such forms may also be included in the present disclosure. Additionally, some of the compounds may form solvates with water (i.e., hydrates) or common organic solvents, and such solvates are also included within the scope of the disclosure.

The compounds of the disclosure may be used in the free form for treatment or, when appropriate, in the form of a pharmaceutically acceptable salt or other derivative for treatment. As used herein, the term “pharmaceutically acceptable salt” refers to organic and inorganic salts of the compounds of the present disclosure which are suitable for use in human and lower animals without undue toxicity, irritation, allergic response, etc., and have reasonable benefit/risk ratio. Pharmaceutically acceptable salts of amines, carboxylic acids, phosphonates, and other types of compounds are well known in the art. The salt can be formed by reacting a compound of the disclosure with a suitable free base or acid, including, but not limited to, salts with inorganic acids such as hydrochloric acid, hydrobromic acid, phosphoric acid, sulfuric acid, perchloric acid or with organic acids such as acetic acid, oxalic acid, maleic acid, tartaric acid, citric acid, succinic acid, malonic acid. Or the salts may be obtained by methods well known in the art, such as ion exchange. Other pharmaceutically acceptable salts include adipate, alginate, ascorbate, aspartate, besylate, benzoate, bisulfate, borate, butanoate, camphorate, camphorsulfonate, citrate, digluconate, lauryl sulfate, ethanesulfonate, formate, fumarate, glucoheptonate, glycerol phosphate, glyconate, hemisulfate, hexanoate, hydroiodide, 2-hydroxyethanesulfonate, lactobionate, lactate, laurate, lauryl sulfate, malate, maleate, mesylate, 2-naphthalenesulfonate, nicotinate, nitrate, oleate, palmitate, pamoate, pectate, persulphate, per-3-phenylpropionate, phosphate, picrate, propionate, stearate, sulfate, thiocyanate, p-toluenesulfonate, undecanoate, and the like. Representative alkali or alkaline earth metal salts include salts of sodium, lithium, potassium, calcium, magnesium, and the like. Other pharmaceutically acceptable salts include suitable non-toxic salts of ammonium, quaternary ammonium, and amine cations formed from halides, hydroxides, carboxylates, sulfates, phosphates, nitrates, lower alkyl sulfonates and aryl sulfonates.

Further, the term "prodrug" as used herein means that a compound can be converted into the compound of the present disclosure represented by formula (I) in vivo. Such transformation is affected by hydrolysis of the prodrug in the blood or enzymatic conversion to the parent compound in the blood or tissue.

Pharmaceutical compositions of this disclosure comprise the compound of formula (I) described herein or a pharmaceutically acceptable salt thereof; an additional agent selected from a kinase inhibitory agent (small molecule, polypeptide, antibody, etc.), an immunosuppressant, an anticancer agent, an anti-viral agent, anti-inflammatory agent, antifungal agent, antibiotic, or an anti-vascular hyperproliferation compound; and any pharmaceutically acceptable carrier, adjuvant or vehicle.

The compounds of the present disclosure may be used alone or in combination with one or more of other compounds of the present disclosure or with one or more of other agents. When administered in combination, the therapeutic agents can be formulated for simultaneous or sequential administration at different times, or the therapeutic agents can be administered as a single composition. By "combination therapy", it refers to the use of a compound of the disclosure in combination with another agent in the form of co-administration of each agent or sequential administration of each agent, in either case, for the purpose of achieving the optimal results. Co-administration includes dosage form for simultaneous delivery, as well as separate dosage forms for each compound. Thus, administration of the compounds of the disclosure can be combined with other therapies known in the art, for example, radiation therapy or cytostatic agents, cytotoxic agents, other anticancer agents, and the like as used in the treatment of cancer, in order to improve the symptoms of cancer. The administration sequence is not limited in the present disclosure. The compounds of the present disclosure may be administered before, simultaneously, or after other anticancer or cytotoxic agents.

To prepare the pharmaceutical ingredient of the present disclosure, one or more compounds of formula (I) or salts thereof as an active ingredient can be intimately mixed with a pharmaceutical carrier, which is carried out according to a conventional pharmaceutical formulation technique. The carrier can be used in a wide variety of forms depending on the form of preparation which is designed for different administration modes (for example, oral or parenteral administration). Suitable pharmaceutically acceptable carriers are well known in the art. A description of some of these pharmaceutically acceptable carriers can be found in the Handbook of Pharmaceutical Excipients, published jointly by the American Pharmaceutical Association and the Pharmaceutical Society of Great Britain.

The pharmaceutical composition of the present disclosure may have the following forms, for example, those suitable for oral administration, such as tablets, capsules, pills, powders, sustained release forms, solutions or suspensions; those for parenteral injections such as clear solutions, suspensions, emulsion; or those for topical use such as ointments, creams; or as a suppository for rectal administration. The pharmaceutical ingredients may also be presented in unit dosage form for single administration in a precise dosage. The pharmaceutical ingredient will include a conventional pharmaceutical carrier or excipient and a compound as an active ingredient prepared according to the present disclosure, and may also include other medical or pharmaceutical preparations, carriers, adjuvants, and the like.

Therapeutic compounds can also be administered to mammals other than humans. The drug dosage for a mammal will depend on the species of the animal and its disease condition or its disordered condition. The therapeutic compound can be administered to the animal in the form of a capsule, a bolus, or a tablet or liquid. The therapeutic compound can also be introduced into the animal by injection or infusion. These drug forms are prepared in a traditional manner complying with standard veterinary practice. As an alternative, the therapeutic compounds can be mixed with the animal feed and fed to the animal, so that the concentrated feed additive or premix can be prepared by mixing ordinary animal feed.

It is a further object of the present disclosure to provide a method for treating cancer in a subject in need thereof, comprising a method for administering to the subject a therapeutically effective amount of a composition containing the compound of the present disclosure.

The present disclosure also includes the use of the compound of the present disclosure or a pharmaceutically acceptable derivative thereof, in the manufacture of medicaments for treating RIP1 related diseases, including ocular fundus disease, xerophthalmia, psoriasis, leucoderma, dermatitis, alopecia areata, rheumatoid arthritis, colitis, multiple sclerosis, systemic lupus erythematosus, Crohn's disease, atherosclerosis, pulmonary fibrosis, liver fibrosis, myelofibrosis, non-small cell lung cancer, small cell lung cancer, breast cancer, pancreatic cancer, glioma, glioblastoma, ovarian cancer, cervical cancer, colorectal cancer, melanoma, endometrial cancer, prostate cancer, bladder cancer, leukemia, gastric cancer, liver cancer, gastrointestinal stromal tumor, thyroid cancer, chronic myeloid leukemia, acute myeloid leukemia, non-Hodgkin's lymphoma, nasopharyngeal cancer, esophageal cancer, brain tumor, B-cell and T-cell lymphoma, lymphoma, multiple myeloma, biliary cancer and sarcoma, cholangiocarcinoma, inflammatory bowel disease, ulcerative colitis, retinal detachment, retinitis pigmentosa, macular degeneration, pancreatitis, atopic dermatitis, spondyloarthritis, gout, SoJIA, Sjogren's syndrome, systemic scleroderma, antiphospholipid syndrome, vasculitis, osteoarthritis, non-alcoholic steatohepatitis, alcoholic steatohepatitis, autoimmune hepatitis, autoimmune hepatobiliary disease, primary sclerosing cholangitis, nephritis, celiac disease, autoimmune ITP, transplant rejection, ischemia-reperfusion injury of solid organs, sepsis, systemic inflammatory response syndrome, cerebrovascular accident, myocardial infarction, Huntington's disease, Alzheimer's disease, Parkinson's disease, allergic diseases, asthma, atopic dermatitis, multiple sclerosis, type I diabetes, Wegener's granulomatosis, pulmonary sarcoidosis, Behget's disease, interleukin-1 converzyme-related fever syndrome, chronic obstructive pulmonary disease, tumor necrosis factor receptor related periodic syndrome and periodontitis.

The present disclosure also provides a method for preparing the corresponding compounds. A variety of synthetic methods can be used to prepare the compounds described herein, including the method involved in the following examples. The compounds of the present disclosure, or pharmaceutically acceptable salts, isomers or hydrates thereof, can be synthesized using the following methods, synthetic methods known in the field of organic chemical synthesis, or variations of these methods understood by those skilled in the art. Preferred methods include, but are not limited to, the following methods.

In order to make the objectives, technical solutions and advantages of the present disclosure more clear, the present disclosure will be further described in detail below in conjunction with specific examples. It should be understood that the specific examples described here are only used to explain the present disclosure and are not intended to limit the present disclosure. If no specific technology or conditions are indicated in examples, the technology or conditions described in the literature in the art or the product specification shall be followed. If reagents or instruments used do not indicate manufacturers, they are all conventional products that are commercially available. The term "and/or" as used herein includes any and all combinations of one or more related listed items. The Example provided below can better illustrate the present disclosure, unless otherwise specified, all temperatures are in ° C. The names of some compounds in this disclosure are generated by Chemdraw and translated into Chinese.

Preparation of Some Intermediates

I. Preparation of a Series Intermediates

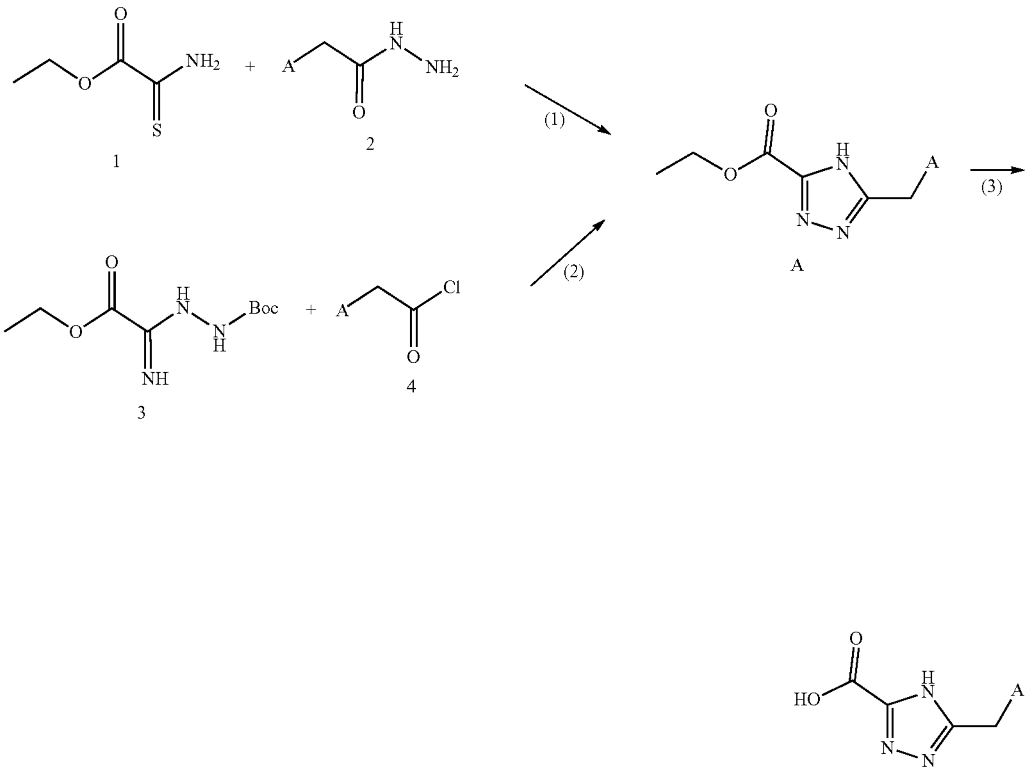

1
2
3
4
A
A'

A series intermediates may include A and A', where A' can be further formed by hydrolysis of A. A can be prepared by the above two routes. In Route 2, Intermediate A is generated by the reaction of compound 3 and acid chloride 4 in a pyridine solvent at 110 degrees, and in Route 1, Intermediate A is synthesized by refluxing compound 1 and hydrazide 2.

Synthesis of Intermediate A-1 (ethyl 5-benzyl-4H-1,2,4-triazole-3-carboxylate) and A-2 (5-benzyl-4H-1,2,4-triazole-3-carboxylic acid)

The synthetic method refers to WO2014125444A1.

A-1

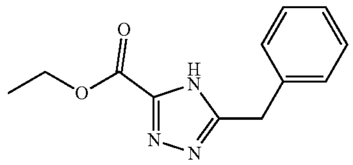

A-2

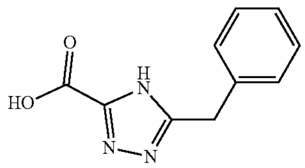

Synthesis of Intermediate A-3 (ethyl 5-(1-phenylethyl)-4H-1,2,4-triazole-3-carboxylate) and A-4 (ethyl 5-(1-phenylethyl)-1,3,4-oxadiazole-2-carboxylate)

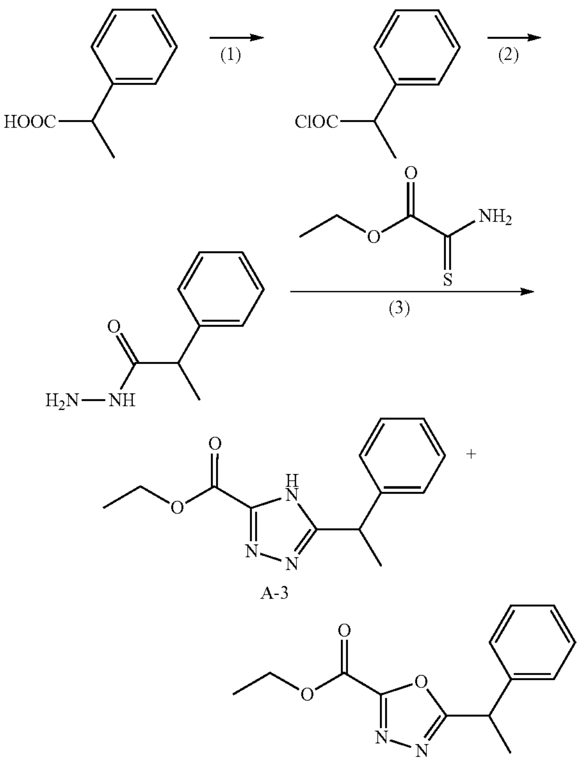

A-3
A-4

Step 1: Synthesis of 2-phenylpropionyl chloride 2-phenylpropionic acid (1 g, 6.66 mmol) was dissolved in thionyl chloride (10 mL), and reacted at 85° C. for 1 hour. The reaction solution was diluted with toluene and spin dried. The crude product was used directly in the next step.

Step 2: Synthesis of 2-phenylpropionyl hydrazide 2-phenylpropionyl chloride was dissolved in methanol (20 mL), and reacted at 25° C. for 2 hours. Hydrazine hydrate (10 mL) was then added, and reacted at 80° C. for 16 hours. The reaction solution was cooled, extracted with ethyl acetate, washed with saturated brine, dried over anhydrous sodium sulfate, filtered and evaporated to dryness, to afford 900 mg of colorless oil. MS: 165 $[M+H]^+$

Step 3: Synthesis of A-3 and A-4

2-phenylpropionyl hydrazide (900 mg, 5.5 mmol) was dissolved in ethanol (15 mL), ethyl thiooxamate (805 mg, 6 mmol) was adde, and reacted at 70° C. for 3 hours. The reaction solution was cooled and filtered to afford 800 mg of white solid. Xylene (20 mL) was added to the solid, and reacted at 160° C. under refluxing to remove water for 24 hours. The reaction solution was cooled and concentrated, the crude product was rinsed with mixture of petroleum ether/ethyl acetate (10:1), to afford 300 mg of ethyl 5-(1-phenylethyl)-4H-1,2,4-triazol-3-carboxylate as white solid. MS: 246 $[M+H]^+$. The mother liquor was evaporated to dryness to afford 200 mg of ethyl 5-(1-phenylethyl)-1,3,4-oxadiazol-2-carboxylate as yellow solid. MS: 247 $[M+H]^+$.

Synthesis of Intermediate A-5 (ethyl 5-(cyclopentylmethyl)-4H-1,2,4-triazole-3-carboxylate) and A-6 (ethyl 5-(cyclopentylmethyl)-1,3,4-oxadiazol-2-carboxylate)

A-5

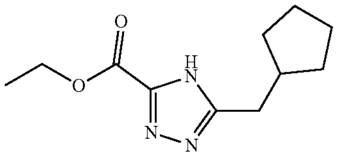

A-6

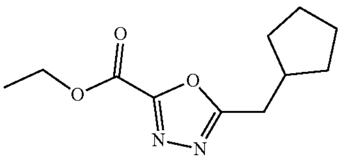

The preparation was carried out in a similar manner to intermediate A-3 and A-4 (step 2 to step 3), except that in step 2, cyclopentylacetyl chloride was used in place of 2-phenylpropionyl chloride.

Synthesis of Intermediate A-7 ethyl 5-(morpholinomethyl)-4H-1,2,4-triazole-3-carboxylate

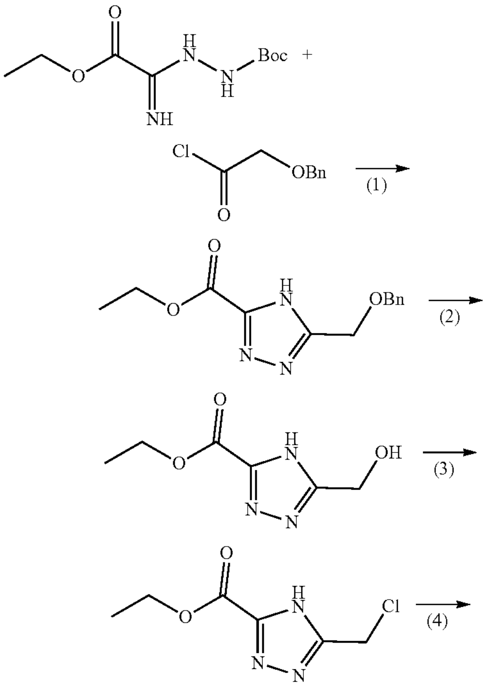

-continued

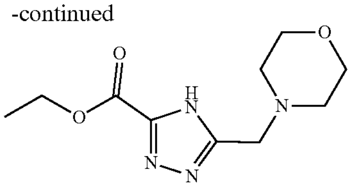

Step 1: Tert-butyl 2-(2-ethoxy-1-imino-2-oxoethyl)hydrazine-1-carboxylate and 2-(benzyloxy)acetyl chloride in pyridine were reacted at 110° C. to afford ethyl 5-((benzyloxy)methyl)-4H-1,2,4-triazol-3-carboxylate (see M. V Chudinov et al./Bioorg. Med. Chem. Lett. 26(2016) 3223-3225 for detailed operations)

Step 2: Synthesis of Ethyl 5-(hydroxymethyl)-4H-1,2,4-triazol-3-carboxylate

Ethyl 5-((benzyloxy)methyl)-4H-1,2,4-triazole-3-carboxylate (250 mg, 11 mmol) was dissolved in a mixture of ethanol and ethyl acetate (2:1, 3 mL), palladium on carbon (10%, 25 mg) was added, and was reacted for 5 hours under hydrogen atmosphere. The reaction was filtered through diatomaceous earth and the filtrate was evaporated to get 150 mg of yellow solid. MS: 172 $[M+H]^+$

Step 3: Synthesis of ethyl 5-(chloromethyl)-4H-1,2,4-triazole-3-carboxylate

Ethyl 5-(hydroxymethyl)-4H-1,2,4-triazole-3-carboxylate (150 mg, 0.9 mmol) was dissolved in thionyl chloride (2 mL), and reacted at 85° C. for 7 hours. The reaction was cooled and diluted with toluene, and the resultant was spin dried to afford 160 mg of a yellow oil. MS: 190 $[M+H]^+$

Step 4: Synthesis of ethyl 5-(morpholinomethyl)-4H-1,2,4-triazole-3-carboxylate Ethyl 5-(chloromethyl)-4H-1,2,4-triazole-3-carboxylate (160 mg, 0.9 mmol) was dissolved in tetrahydrofuran (2 mL), diisopropylethylamine (220 mg, 1.7 mmol) and morpholine (150 mg, 1.7 mmol) were added, and reacted at 25° C. for 5 hours. The reaction solution was evaporated to dryness, and purified by column chromatography to get 180 mg of 2 yellow solid. MS: 241 $[M+H]^+$ Table 1 below shows the structure and synthesis of intermediates A-8 to A-28 and mass spectral data thereof, wherein intermediates A-8 to A-12 were prepared in a similar manner to intermediate A-3, without collecting the oxadiazole by-product, and the synthesis of intermediates A-i13 and A-28 were carried out in a similar manner to the first step of synthesis of intermediate A-7.

TABLE 1

Structures and synthesis of intermediates A-8 to A-28 and mass spectral data thereof

| Intermediate | Structure | Name | Synthesis | MS: $[M + H]^+$ |
|---|---|---|---|---|
| A-8 | 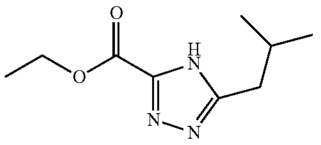 | Ethyl 5-isobutyl-4H-1,2,4-triazol-5-carboxylate | The operation was the same as the steps 2 to 3 of the preparation of interemediate A-3, but 3-methylbutyryl chloride was used in place of 2-phenylpropionyl chloride | 198 |
| A-9 | 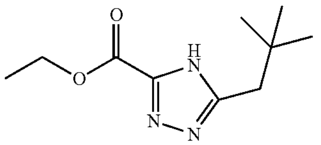 | Ethyl 5-neopentyl-4H-1,2,4-triazol-5-carboxylate | The operation was the same as the steps 2 to 3 of the preparation of intermediate A-3, but 3,3-dimethylbutyryl chloride was used in place of 2-phenylpropionyl chloride | 212 |
| A-10 | 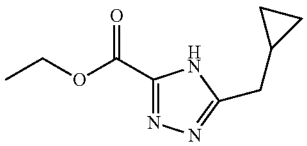 | Ethyl 5-(cyclopropylmethyl)-4H-1,2,4-triazol-5-carboxylate | The operation was the same as the steps 1 to 3 of the preparation of intermediate A-3, but 2-cyclopropylacetic acid was used in place of 2-phenylpropionic acid | 196 |
| A-11 | 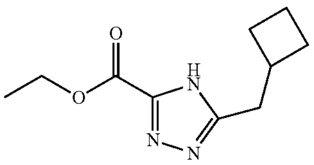 | Ethyl 5-(cyclobutylmethyl)-4H-1,2,4-triazol-5-carboxylate | The operation was the same as the steps 1 to 3 of the preparation of intermediate A-3, but 2-cyclobutylacetic acid was used in place of 2-phenylpropionic acid | 210 |
| A-12 | 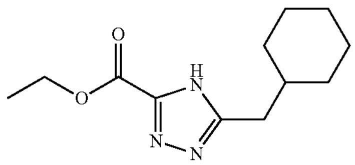 [SMILES: CCOC(=O)c1nnc(CC2CCCCC2)[nH]1] | Ethyl 5-(cyclohexylmethyl)-4H-1,2,4-triazol-3-carboxylate | The operation was the same as the steps 1 to 3 of the preparation of intermediate A-3, but cyclohexylacetic acid was used in place of 2-phenylpropionic acid | 238 |

TABLE 1-continued

| Structures and synthesis of intermediates A-8 to A-28 and mass spectral data thereof | | | | |
|---|---|---|---|---|
| Intermediate | Structure | Name | Synthesis | MS: [M + H]+ |
| A-13 | 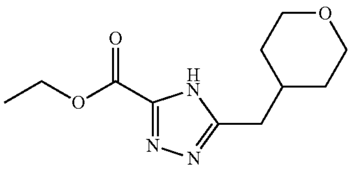 [SMILES: CCOC(=O)c1nnc(CC2CCOCC2)[nH]1] | Ethyl 5-((tetrahydro-2H-pyran-4-yl)methyl)-4H-1,2,4-triazol-3-carboxylate | The operation was the same as the step 1 of the preparation of intermediate A-7, but 2-(tetrahydro-2H-pyran-4-yl)acetyl chloride was used in place of 2-(benzyloxy)acetyl chloride | 240 |
| A-14 | 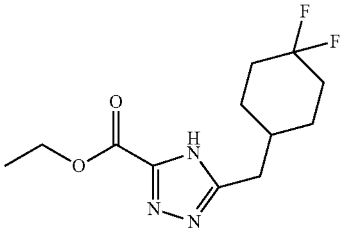 [SMILES: CCOC(=O)c1nnc(CC2CCC(F)(F)CC2)[nH]1] | Ethyl 5-((4,4-difluorocyclohexyl)methyl)-4H-1,2,4-triazol-3-carboxylate | The operation was the same as the step 1 of the preparation of intermediate A-7, but 2-(4,4-difluorocyclohexyl)acetyl chloride was used in place of 2-(benzyloxy)acetyl chloride | 274 |
| A-15 | 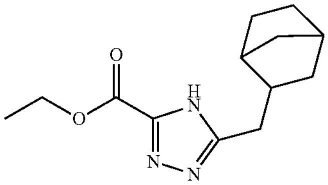 [SMILES: CCOC(=O)c1nnc(CC2CC3CCC2C3)[nH]1] | Ethyl 5-(bicyclo[2.2.1]heptan-2-ylmethyl)-4H-1,2,4-triazol-3-carboxylate | The operation was the same as the step 1 of the preparation of intermediate A-7, but 2-(bicyclo[2.2.1]heptan-2-yl)acetyl chloride was used in place of 2-(benzyloxy)acetyl chloride | 250 |
| A-16 | 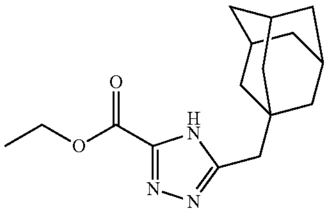 [SMILES: CCOC(=O)c1nnc(CC23CC4CC(CC(C4)C2)C3)[nH]1] | Ethyl 5-(adamantan-1-yl)methyl)-4H-1,2,4-triazol-3-carboxylate | The operation was the same as the step 1 of the preparation of intermediate A-7, but 2-(adamantan-1-yl)acetyl chloride was used in place of 2-(benzyloxy)acetyl chloride | 290 |
| A-17 | 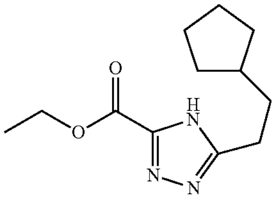 [SMILES: CCOC(=O)c1nnc(CCC2CCCC2)[nH]1] | Ethyl 5-(2-cyclopentylethyl)-4H-1,2,4-triazol-3-carboxylate | The operation was the same as the step 1 of the preparation of intermediate A-7, but 3-cyclopentylpropionyl chloride was used in place of 2-(benzyloxy)acetyl chloride | 238 |
| A-18 | 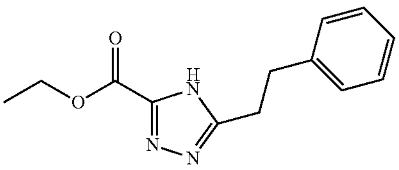 [SMILES: CCOC(=O)c1nnc(CCc2ccccc2)[nH]1] | Ethyl 5-(phenethyl)-4H-1,2,4-triazol-3-carboxylate | The operation was the same as the step 1 of the preparation of intermediate A-7, but 3-phenylpropionyl chloride was used in place of 2-(benzyloxy)acetyl chloride | 246 |
| A-19 | 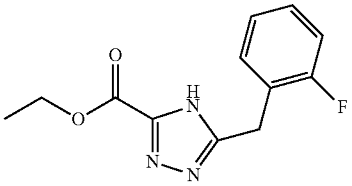 [SMILES: CCOC(=O)c1nnc(Cc2ccccc2F)[nH]1] | Ethyl 5-(2-fluorobenzyl)-4H-1,2,4-triazol-3-carboxylate | The operation was the same as the step 1 of the preparation of intermediate A-7, but 2-(2-fluorophenyl)acetyl chloride was used in place of 2-(benzyloxy)acetyl chloride | 250 |

TABLE 1-continued

Structures and synthesis of intermediates A-8 to A-28 and mass spectral data thereof

| Intermediate | Structure | Name | Synthesis | MS: [M + H]+ |
| --- | --- | --- | --- | --- |
| A-20 | 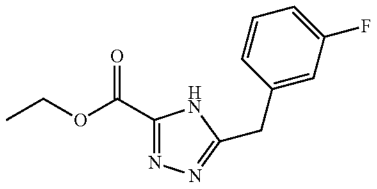 [SMILES: CCOC(=O)c1nnc(Cc2cccc(F)c2)[nH]1] | Ethyl 5-(3-fluorobenzyl)-4H-1,2,4-triazol-3-carboxylate | The operation was the same as the step 1 of the preparation of intermediate A-7, but 2-(3-fluorophenyl)acetyl chloride was used in place of 2-(benzyloxy)acetyl chloride | 250 |
| A-21 | 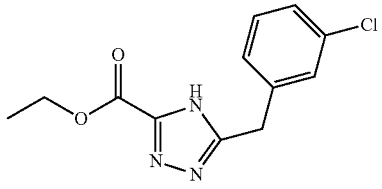 [SMILES: CCOC(=O)c1nnc(Cc2cccc(Cl)c2)[nH]1] | Ethyl 5-(3-chlorobenzyl)-4H-1,2,4-triazol-3-carboxylate | The operation was the same as the step 1 of the preparation of intermediate A-7, but 2-(3-chlorophenyl)acetyl chloride was used in place of 2-(benzyloxy)acetyl chloride | 266 |
| A-22 | 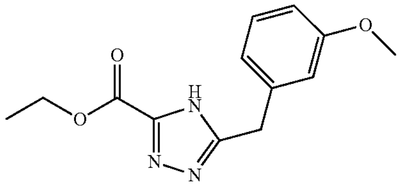 [SMILES: CCOC(=O)c1nnc(Cc2cccc(OC)c2)[nH]1] | Ethyl 5-(3-methoxybenzyl)-4H-1,2,4-triazol-3-carboxylate | The operation was the same as the step 1 of the preparation of intermediate A-7, but 2-(3-methoxyphenyl)acetyl chloride was used in place of 2-(benzyloxy)acetyl chloride | 262 |
| A-23 | 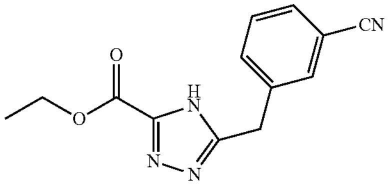 [SMILES: CCOC(=O)c1nnc(Cc2cccc(C#N)c2)[nH]1] | Ethyl 5-(3-cyanobenzyl)-4H-1,2,4-triazol-3-carboxylate | The operation was the same as the step 1 of the preparation of intermediate A-7, but 2-(3-cyanophenyl)acetyl chloride was used in place of 2-(benzyloxy)acetyl chloride | 257 |
| A-24 | 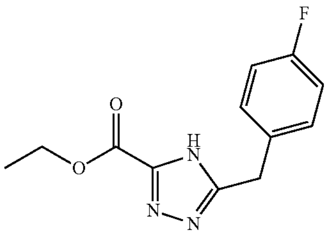 [SMILES: CCOC(=O)c1nnc(Cc2ccc(F)cc2)[nH]1] | Ethyl 5-(4-fluorobenzyl)-4H-1,2,4-triazol-3-carboxylate | The operation was the same as the step 1 of the preparation of intermediate A-7, but 2-(4-fluorophenyl)acetyl chloride was used in place of 2-(benzyloxy)acetyl chloride | 250 |
| A-25 | 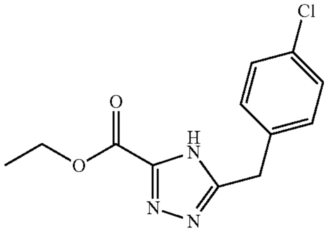 [SMILES: CCOC(=O)c1nnc(Cc2ccc(Cl)cc2)[nH]1] | Ethyl 5-(4-chlorobenzyl)-4H-1,2,4-triazol-3-carboxylate | The operation was the same as the step 1 of the preparation of intermediate A-7, but 2-(4-chlorophenyl)acetyl chloride was used in place of 2-(benzyloxy)acetyl chloride | 266 |

TABLE 1-continued

Structures and synthesis of intermediates A-8 to A-28 and mass spectral data thereof

| Intermediate | Structure | Name | Synthesis | MS: [M + H]+ |
|---|---|---|---|---|
| A-26 | 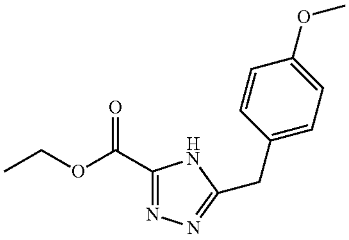 [SMILES: CCOC(=O)c1nnc(Cc2ccc(OC)cc2)[nH]1] | Ethyl 5-(4-methoxybenzyl)-4H-1,2,4-triazol-3-carboxylate | The operation was the same as the step 1 of the preparation of intermediate A-7, but 2-(4-methoxyphenyl)acetyl chloride was used in place of 2-(benzyloxy)acetyl chloride | 262 |
| A-27 | 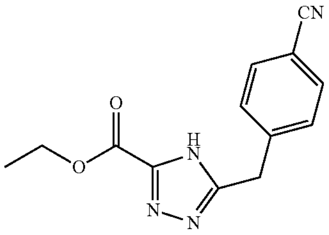 [SMILES: CCOC(=O)c1nnc(Cc2ccc(C#N)cc2)[nH]1] | Ethyl 5-(4-cyanobenzyl)-4H-1,2,4-triazol-3-carboxylate | The operation was the same as the step 1 of the preparation of intermediate A-7, but 2-(4-cyanophenyl)acetyl chloride was used in place of 2-(benzyloxy)acetyl chloride | 257 |
| A-28 | 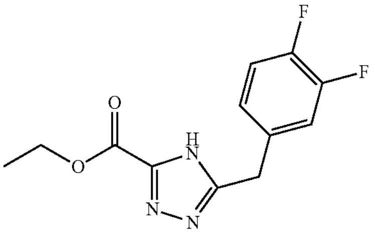 [SMILES: CCOC(=O)c1nnc(Cc2ccc(F)c(F)c2)[nH]1] | Ethyl 5-(3,4-difluorobenzyl)-4H-1,2,4-triazol-3-carboxylate | The operation was the same as the step 1 of the preparation of intermediate A-7, but 2-(3,4-difluorobenzyl)acetyl chloride was used in place of 2-(benzyloxy)acetyl chloride | 268 |

Synthesis of Intermediate A-29 methyl 5-benzyl-1,3,4-thiadiazole-2-carboxylate

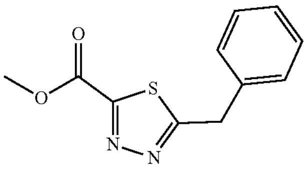 [SMILES: COC(=O)c1nnc(Cc2ccccc2)s1]

Phenylacetylhydrazine (5 g, 33.3 mmol) was dissolved in anhydrous dichloromethane (100 mL), triethylamine (6.74 g, 66.7 mmol) was added, and under argon protection, methyl oxalyl chloride (4.1 g, 33.5 mmol) was added dropwise at 0° C. The reaction solution was slowly warmed to 25° C. After 16 hours reaction, the solvent was evaporated to dryness, rinsed with mixture of petroleum ether/ethyl acetate, filtered, and the filter cake was re-dissolved in toluene (100 mL), Lawson's reagent (26.9 g, 66.5 mmol) was added, heated to 110° C. and reacted for 6 hours. The reaction was cooled and diluted with ethyl acetate, washed with water, saturated aqueous solution of sodium bicarbonate and brine, the organic phase was dried over anhydrous sodium sulfate, filtered and evaporated to dryness, and purified by column chromatography to get 4 g product. MS: 235 $[M+H]^+$.

EXAMPLES

Example 1: 5-benzyl-N-(4-phenylpyridin-2-yl)-4H-1,2,4-triazole-3-carboxamide

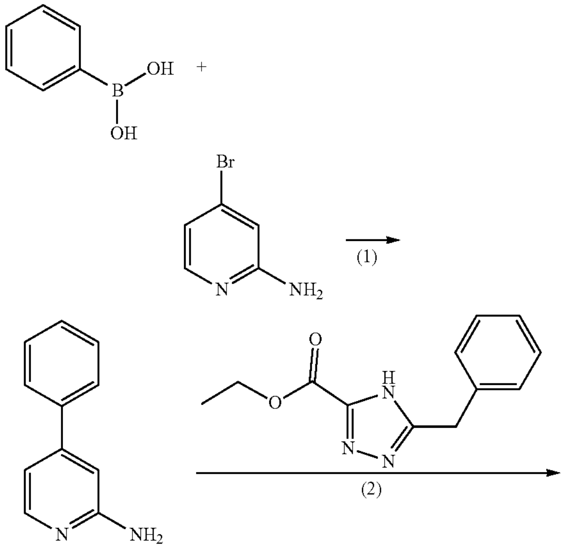

-continued

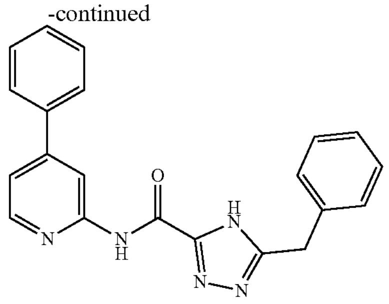

Step 1: Synthesis of 4-phenylpyridin-2-amine

4-Bromopyridin-2-amine (173 mg, 1 mmol), phenylboronic acid (146 mg, 1.2 mmol), Pd(dppf)$Cl_2$ (73 mg, 0.1 mmol) and sodium carbonate (160 mg, 1.5 mmol) were placed in a mixture of dioxane (4 mL) and water (0.8 mL), which was reacted at 100° C. for 16 hours under argon protection. After cooling, the reaction solution was evaporated to dryness and subjected to column chromatography to afford 120 mg of brown solid. MS: 171 $[M+H]^+$.

Step 2: Synthesis of 5-benzyl-N-(4-phenylpyridin-2-yl)-4H-1,2,4-triazole-3-carboxamide 4-Phenylpyridin-2-amine (120 mg, 0.7 mmol) was placed in dry xylene (3 mL), to which trimethyl aluminum (3M, 0.7 mL) was slowly added under argon protection, and reacted at 25° C. for 1 hour. Then, intermediate 1 (197 mg, 0.9 mmol) was added, and reacted at 100° C. for 16 hours. The reaction solution was cooled and diluted with methanol, evaporated to dryness and subjected to column chromatography and preparative liquid chromatography to afford 50 mg of white solid. $^1$H NMR (400 MHz, DMSO-$d_6$) δ 14.65 (s, 1H), 9.90 (s, 1H), 8.49-8.38 (m, 2H), 7.82-7.71 (m, 2H), 7.62-7.45 (m, 4H), 7.40-7.30 (m, 4H), 7.30-7.18 (m, 1H), 4.18 (s, 2H). MS: 356 $[M+H]^+$.

Example 2: 5-benzyl-N-(4-(o-methylphenyl)pyridin-2-yl)-4H-1,2,4-triazole-3-carboxamide The preparation was carried out in a similar manner to Example 1, except that in step 1, o-methylphenylboronic acid was used in place of phenylboronic acid. $^1$H NMR (400 MHz, DMSO-$d_6$) δ 14.55 (s, 1H), 9.86 (s, 1H), 8.42 (d, J=5.1 Hz, 1H), 8.13 (s, 1H), 7.51-7.34 (m, 3H), 7.34-7.30 (m, 4H), 7.30-7.23 (m, 2H), 7.21 (d, J=5.1 Hz, 1H), 4.19 (s, 2H), 2.28 (s, 3H). MS: 370 $[M+H]^+$.

Example 2

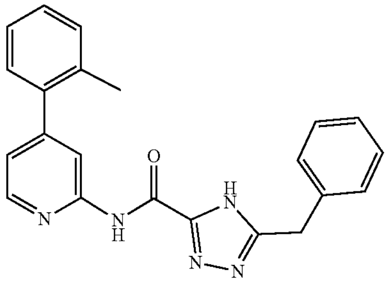

-continued

Example 3

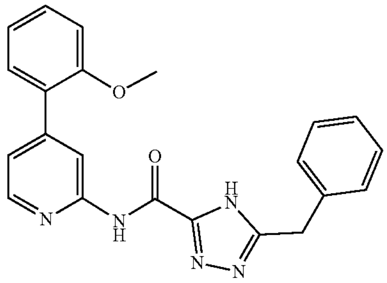

Example 3: 5-benzyl-N-(4-(2-methoxyphenyl)pyridin-2-yl)-4H-1,2,4-triazole-3-carboxamide The preparation was carried out in a similar manner to Example 1, except that in step 1, o-methoxyphenylboronic acid was used in place of phenylboronic acid. $^1$H NMR (400 MHz, DMSO-$d_6$) δ 14.58 (s, 1H), 9.82 (s, 1H), 8.37 (d, J=5.2 Hz, 1H), 8.33-8.17 (m, 1H), 7.60-6.91 (m, 10H), 4.18 (s, 2H), 3.81 (s, 3H). MS: 386 $[M+H]^+$.

Example 4: 5-benzyl-N-(4-(2-ethoxyphenyl)pyridin-2-yl)-4H-1,2,4-triazole-3-carboxamide The preparation was carried out in a similar manner to Example 1, except that in step 1, o-ethoxyphenylboronic acid was used in place of phenylboronic acid. $^1$H NMR (400 MHz, DMSO-$d_6$) δ 14.60 (s, 1H), 9.80 (s, 1H), 8.62-8.40 (m, 1H), 8.38 (d, J=5.2 Hz, 1H), 7.60-6.94 (m, 10H), 4.18 (s, 2H), 4.10 (q, J=7.0 Hz, 2H), 1.32 (t, J=6.9 Hz, 3H). MS: 400 $[M+H]^+$.

Example 4

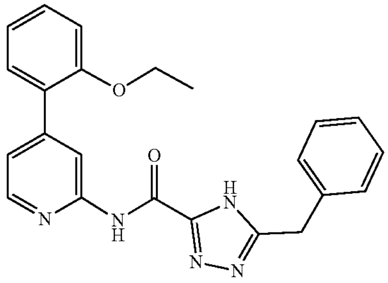

Example 5

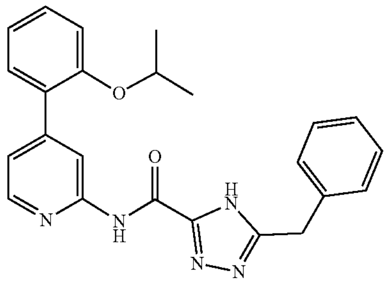

Example 5: 5-benzyl-N-(4-(2-isopropyloxyphenyl)pyridin-2-yl)-4H-1,2,4-triazole-3-carboxamide The preparation was carried out in a similar manner to Example 1, except that in step 1, 2-isopropyloxyphenylboronic acid was used in place of phenylboronic acid. $^1$H NMR (400 MHz, DMSO-$d_6$) δ 14.55 (s, 1H), 9.74 (s, 1H), 8.56-8.26 (m, 2H), 7.45-7.38 (m, 2H), 7.38-7.29 (m, 5H), 7.27 (d, J=7.3 Hz, 1H), 7.19 (d, J=8.6 Hz, 1H), 7.09-7.02 (m, 1H), 4.69 (p, J=6.0 Hz, 1H), 4.19 (s, 2H), 1.27 (d, J=6.0 Hz, 6H). MS: 414 $[M+H]^+$.

Example 6: 5-benzyl-N-(4-(2-(trifluoromethoxy)phenyl)pyridin-2-yl)-4H-1,2,4-triazole-3-carboxamide The preparation was carried out in a similar manner to Example 1, except that in step 1, 2-(trifluoromethoxy)phenylboronic acid was used in place of phenylboronic acid. $^1$H NMR (400 MHz, DMSO-$d_6$) δ 14.64 (s, 1H), 9.96 (s, 1H), 8.47 (d, J=5.2 Hz, 1H), 8.30 (d, J=1.5 Hz, 1H), 7.70-7.51 (m, 4H), 7.41-7.18 (m, 6H), 4.18 (s, 2H). MS: 440 $[M+H]^+$.

Example 6

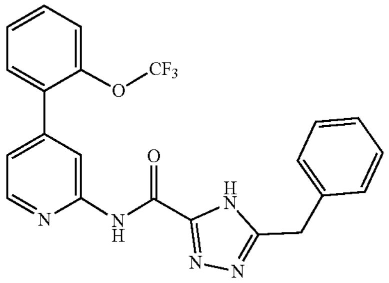

Example 7

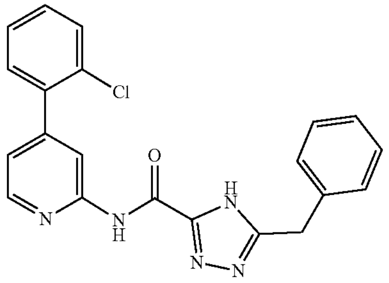

Example 7: 5-benzyl-N-(4-(2-chlorophenyl)pyridin-2-yl)-4H-1,2,4-triazole-3-carboxamide The preparation was carried out in a similar manner to Example 1, except that in step 1, 2-chlorophenylboronic acid was used in place of phenylboronic acid. $^1$H NMR (600 MHz, DMSO-$d_6$) δ 14.65 (s, 1H), 9.95 (s, 1H), 8.46 (d, J=5.1 Hz, 1H), 8.23 (d, J=1.5 Hz, 1H), 7.68-7.60 (m, 1H), 7.56-7.46 (m, 3H), 7.39-7.30 (m, 4H), 7.30-7.21 (m, 2H), 4.18 (s, 2H). MS: 390 $[M+H]^+$.

Example 8: 5-benzyl-N-(4-(2-cyclopropylphenyl)pyridin-2-yl)-4H-1,2,4-triazole-3-carboxamide The preparation was carried out in a similar manner to Example 1, except that in step 1, 2-cyclopropylphenylboronic acid was used in place of phenylboronic acid. $^1$H NMR (400 MHz, DMSO-$d_6$) δ 14.56 (s, 1H), 9.87 (s, 1H), 8.43 (d, J=5.1 Hz, 1H), 8.27 (s, 1H), 7.42-7.30 (m, 5H), 7.30-7.20 (m, 4H), 7.10-7.01 (m, 1H), 4.18 (s, 2H), 1.91-1.77 (m, 1H), 0.95-0.81 (m, 2H), 0.79-0.63 (m, 2H). MS: 396 $[M+H]^+$.

Example 8

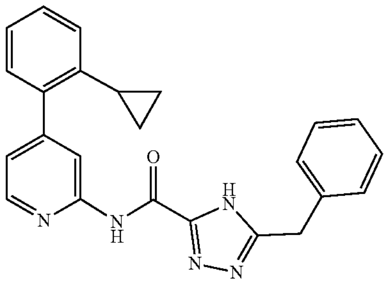

Example 9

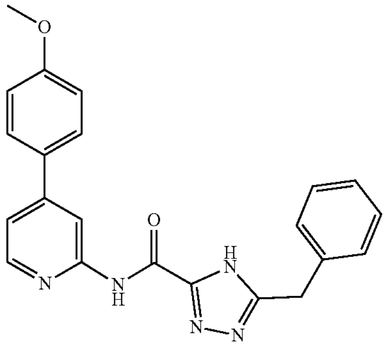

Example 9: 5-benzyl-N-(4-(4-methoxyphenyl)pyridin-2-yl)-4H-1,2,4-triazole-3-carboxamide The preparation was carried out in a similar manner to Example 1, except that in step 1, 4-methoxyphenylboronic acid was used in place of phenylboronic acid. $^1$H NMR (400 MHz, DMSO-$d_6$) δ 14.60 (s, 1H), 9.82 (s, 1H), 8.48-8.29 (m, 2H), 7.80-7.66 (m, 2H), 7.47 (dd, J=5.2, 1.8 Hz, 1H), 7.42-7.18 (m, 5H), 7.18-6.98 (m, 2H), 4.18 (s, 2H), 3.83 (s, 3H). MS: 386 $[M+H]^+$.

Example 10: 5-benzyl-N-(4-(4-methoxy-2-methylphenyl)pyridin-2-yl)-4H-1,2,4-triazole-3-carboxamide The preparation was carried out in a similar manner to Example 1, except that in step 1, 4-methoxy-2-methylphenylboronic acid was used in place of phenylboronic acid. $^1$H NMR (400 MHz, DMSO-$d_6$) δ 14.59 (s, 1H), 9.85 (s, 1H), 8.38 (d, J=5.1 Hz, 1H), 8.10 (s, 1H), 7.47-7.02 (m, 7H), 7.04-6.76 (m, 2H), 4.18 (s, 2H), 3.80 (s, 3H), 2.29 (s, 3H). MS: 400 $[M+H]^+$.

Example 10

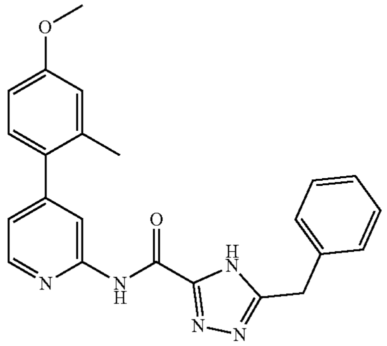

-continued

Example 11

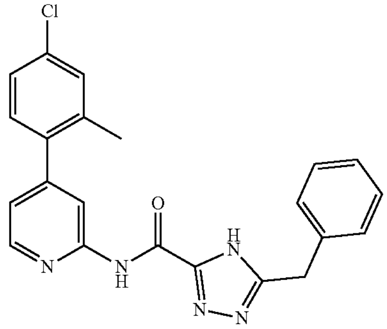

Example 11: 5-benzyl-N-(4-(4-chloro-2-methylphenyl)pyridin-2-yl)-4H-1,2,4-triazole-3-carboxamide The preparation was carried out in a similar manner to Example 1, except that in step 1, 4-chloro-2-methylphenylboronic acid was used in place of phenylboronic acid. $^1$H NMR (400 MHz, DMSO-$d_6$) δ 14.59 (s, 1H), 9.93 (s, 1H), 8.43 (d, J=5.1 Hz, 1H), 8.10 (s, 1H), 7.48 (d, J=2.1 Hz, 1H), 7.43-7.11 (m, 8H), 4.18 (s, 2H), 2.28 (s, 3H). MS: 404 $[M+H]^+$.

Example 12: 5-benzyl-N-(4-(4-cyano-2-methylphenyl)pyridin-2-yl)-4H-1,2,4-triazole-3-carboxamide The preparation was carried out in a similar manner to Example 1, except that in step 1, 4-cyano-2-methylphenylboronic acid was used in place of phenylboronic acid. $^1$H NMR (400 MHz, DMSO-$d_6$) δ 14.60 (s, 1H), 10.00 (s, 1H), 8.47 (d, J=5.1 Hz, 1H), 8.12 (s, 1H), 7.89 (s, 1H), 7.81 (d, J=7.8 Hz, 1H), 7.49 (d, J=7.9 Hz, 1H), 7.41-7.29 (m, 4H), 7.29-7.15 (m, 2H), 4.18 (s, 2H), 2.30 (s, 3H). MS: 395 $[M+H]^+$.

Example 12

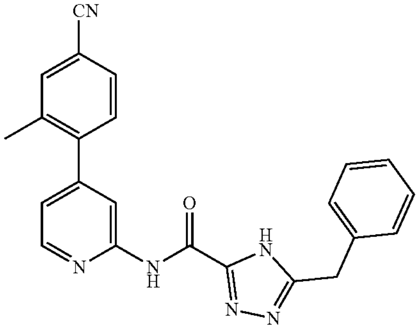

Example 13

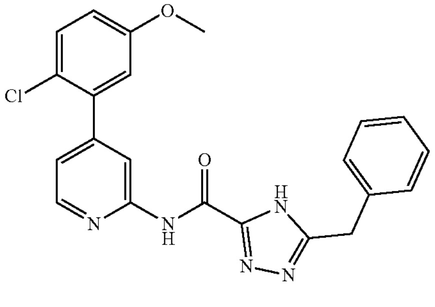

Example 13: Synthesis of 5-benzyl-N-(4-(2-chloro-5-methoxyphenyl)pyridin-2-yl)-4H-1,2,4-triazole-3-carboxamide The preparation was carried out in a similar manner to Example 1, except that in step 1, 2-chloro-5-methoxyphenylboronic acid was used in place of phenylboronic acid. $^1$H NMR (600 MHz, DMSO-$d_6$) δ 14.56 (s, 1H), 9.91 (s, 1H), 8.46 (d, J=5.1 Hz, 1H), 8.23 (s, 1H), 7.53 (d, J=8.8 Hz, 1H), 7.45-7.30 (m, 4H), 7.30-7.19 (m, 2H), 7.08 (dd, J=8.8, 3.1 Hz, 1H), 7.03 (d, J=3.0 Hz, 1H), 4.18 (s, 2H), 3.81 (s, 3H). MS: 420 $[M+H]^+$.

Example 14: 5-benzyl-N-(4-(5-fluoro-2-methoxyphenyl)pyridin-2-yl)-4H-1,2,4-triazole-3-carboxamide The preparation was carried out in a similar manner to Example 1, except that in step 1, 5-fluoro-2-methoxyphenylboronic acid was used in place of phenylboronic acid. $^1$H NMR (400 MHz, DMSO-$d_6$) δ 14.60 (s, 1H), 9.87 (s, 1H), 8.40 (d, J=5.2 Hz, 1H), 8.32 (s, 1H), 7.51-7.03 (m, 9H), 4.18 (s, 2H), 3.80 (s, 3H). MS: 404 $[M+H]^+$.

Example 14

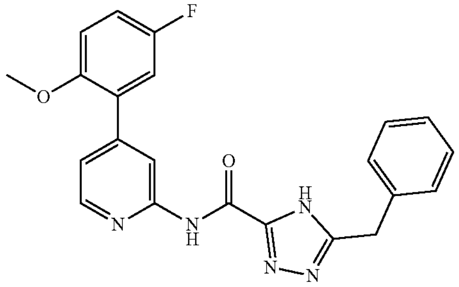

Example 15

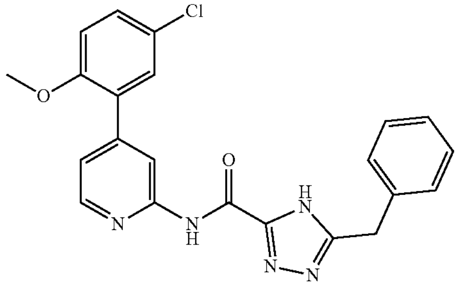

Example 15: 5-benzyl-N-(4-(5-chloro-2-methoxyphenyl)pyridin-2-yl)-4H-1,2,4-triazole-3-carboxamide The preparation was carried out in a similar manner to Example 1, except that in step 1, 5-chloro-2-methoxyphenylboronic acid was used in place of phenylboronic acid. $^1$H NMR (400 MHz, DMSO-$d_6$) δ 14.57 (s, 1H), 9.86 (s, 1H), 8.39 (d, J=5.2 Hz, 1H), 8.28 (s, 1H), 7.50 (dd, J=8.8, 2.7 Hz, 1H), 7.43 (d, J=2.7 Hz, 1H), 7.40-7.29 (m, 5H), 7.29-7.15 (m, 2H), 4.18 (s, 2H), 3.81 (s, 3H). MS: 420 $[M+H]^+$.

Example 16: 5-benzyl-N-(4-(2-methoxy-5-methylphenyl)pyridin-2-yl)-4H-1,2,4-triazole-3-carboxamide The preparation was carried out in a similar manner to Example 1, except that in step 1, 2-methoxy-5-methylphenylboronic acid was used in place of phenylboronic acid. $^1$H NMR (400 MHz, DMSO-$d_6$) δ 14.55 (s, 1H), 9.79 (s, 1H), 8.36 (d, J=5.2 Hz, 1H), 8.28 (s, 1H), 7.38-7.29 (m, 5H), 7.29-7.21 (m, 2H), 7.20 (d, J=2.2 Hz, 1H), 7.07 (d, J=8.4 Hz, 1H), 4.18 (s, 2H), 3.77 (s, 3H), 2.31 (s, 3H). MS: 400 [M+H]$^+$.

Example 16

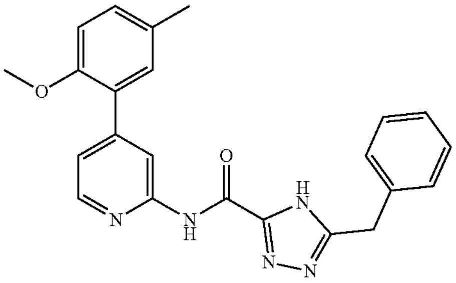

Example 17

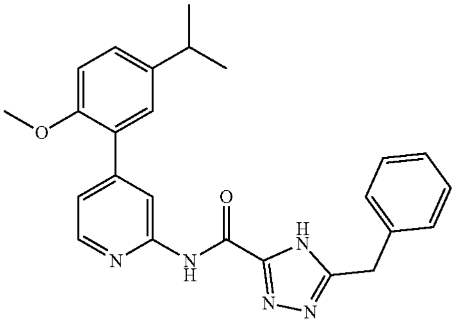

Example 17: 5-benzyl-N-(4-(5-isopropyl-2-methoxyphenyl)pyridin-2-yl)-4H-1,2,4-triazole-3-carboxamide The preparation was carried out in a similar manner to Example 1, except that in step 1, 5-isopropyl-2-methoxyphenylboronic acid was used in place of phenylboronic acid. $^1$H NMR (400 MHz, DMSO-$d_6$) δ 14.62 (s, 1H), 9.84 (s, 1H), 8.37 (d, J=5.2 Hz, 1H), 8.29 (d, J=1.5 Hz, 1H), 7.41-7.19 (m, 8H), 7.09 (d, J=8.5 Hz, 1H), 4.18 (s, 2H), 3.78 (s, 3H), 2.91 (p, J=6.9 Hz, 1H), 1.21 (d, J=6.9 Hz, 6H). MS: 428 [M+H]$^+$.

Example 18: 5-benzyl-N-(4-(2,5-dimethoxyphenyl)pyridin-2-yl)-4H-1,2,4-triazole-3-carboxamide The preparation was carried out in a similar manner to Example 1, except that in step 1, 2,5-dimethoxyphenylboronic acid was used in place of phenylboronic acid. $^1$H NMR (400 MHz, DMSO-$d_6$) δ 14.62 (s, 1H), 9.83 (s, 1H), 8.38 (d, J=5.2 Hz, 1H), 8.29 (d, J=1.5 Hz, 1H), 7.45-7.29 (m, 5H), 7.29-7.22 (m, 1H), 7.12 (d, J=9.0 Hz, 1H), 7.02 (dd, J=9.0, 3.1 Hz, 1H), 6.95 (d, J=3.1 Hz, 1H), 4.18 (s, 2H), 3.76 (s, 3H), 3.75 (s, 3H). MS: 416 [M+H]$^+$.

Example 18

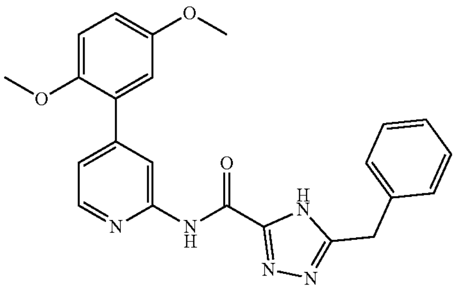

Example 19

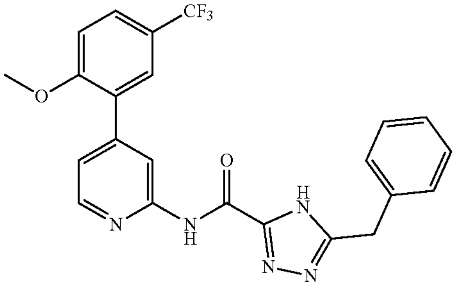

Example 19: 5-benzyl-N-(4-(2-methoxy-5-(trifluoromethyl)phenyl)pyridin-2-yl)-4H-1,2,4-triazole-3-carboxamide The preparation was carried out in a similar manner to Example 1, except that in step 1, 2-methoxy-5-(trifluoromethyl)phenylboronic acid was used in place of phenylboronic acid. $^1$H NMR (400 MHz, DMSO-$d_6$) δ 14.55 (s, 1H), 9.86 (s, 1H), 8.42 (d, J=5.2 Hz, 1H), 8.29 (s, 1H), 7.83 (dd, J=8.9, 2.3 Hz, 1H), 7.69 (d, J=2.3 Hz, 1H), 7.46-7.18 (m, 7H), 4.19 (s, 2H), 3.90 (s, 3H). MS: 454 [M+H]$^+$.

Example 20: 5-benzyl-N-(2-methyl-[3,4'-bipyridin]-2'-yl)-4H-1,2,4-triazole-3-carboxamide The preparation was carried out in a similar manner to Example 1, except that in step 1, 2-methyl-3-(4,4,5,5-tetramethyl-1,3,2-dioxaborolan-2-yl)pyridine was used in place of phenylboronic acid. $^1$H NMR (400 MHz, DMSO-$d_6$) δ 14.63 (s, 1H), 9.99 (s, 1H), 8.57 (dd, J=4.9, 1.7 Hz, 1H), 8.48 (d, J=5.1 Hz, 1H), 8.18 (d, J=1.5 Hz, 1H), 7.73 (dd, J=7.7, 1.8 Hz, 1H), 7.44-7.32 (m, 5H), 7.32-7.24 (m, 2H), 4.21 (s, 2H), 2.50 (s, 3H). MS: 371 [M+H]$^+$.

Example 20

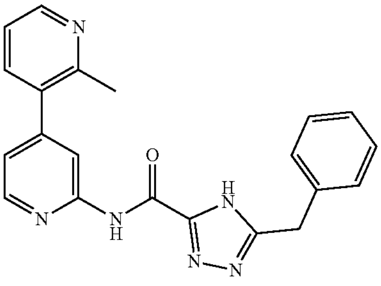

-continued

Example 21

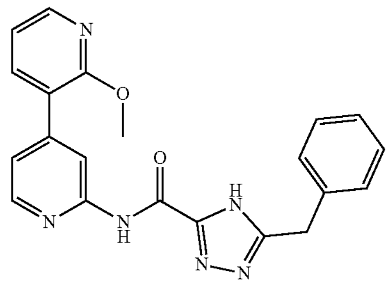

Example 21: 5-benzyl-N-(2-methoxy-[3,4'-bipyridin]-2'-yl)-4H-1,2,4-triazole-3-carboxamide The preparation was carried out in a similar manner to Example 1, except that in step 1, (2-methoxypyridin-3-yl) boronic acid was used in place of phenylboronic acid. $^{1}H$ NMR (400 MHz, DMSO-$d_6$) δ 14.61 (s, 1H), 9.88 (s, 1H), 8.41 (d, J=5.2 Hz, 1H), 8.37 (d, J=1.5 Hz, 1H), 8.28 (dd, J=5.0, 1.9 Hz, 1H), 7.88 (dd, J=7.4, 1.9 Hz, 1H), 7.40 (dd, J=5.2, 1.6 Hz, 1H), 7.38-7.29 (m, 4H), 7.29-7.21 (m, 1H), 7.17 (dd, J=7.4, 4.9 Hz, 1H), 4.18 (s, 2H), 3.92 (s, 3H). MS: 387 $[M+H]^+$.

Example 22: 5-benzyl-N-(2-ethoxy-[3,4'-bipyridin]-2'-yl)-4H-1,2,4-triazole-3-carboxamide The preparation was carried out in a similar manner to Example 1, except that in step 1, (2-ethoxypyridin-3-yl) boronic acid was used in place of phenylboronic acid. $^{1}H$ NMR (400 MHz, DMSO-$d_6$) δ 14.58 (s, 1H), 9.83 (s, 1H), 8.48 (s, 1H), 8.42 (d, J=5.2 Hz, 1H), 8.26 (dd, J=4.9, 1.9 Hz, 1H), 7.90 (dd, J=7.4, 1.9 Hz, 1H), 7.42 (dd, J=5.2, 1.6 Hz, 1H), 7.39-7.30 (m, 4H), 7.30-7.21 (m, 1H), 7.15 (dd, J=7.4, 4.9 Hz, 1H), 4.41 (q, J=7.0 Hz, 2H), 4.18 (s, 2H), 1.34 (t, J=7.0 Hz, 3H). MS: 401 $[M+H]^+$.

Example 22

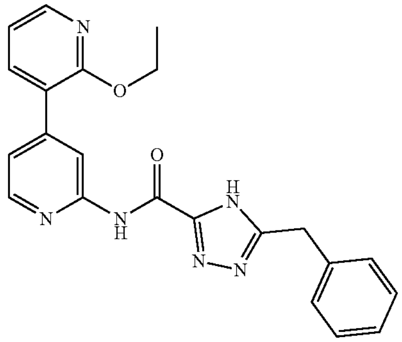

-continued

Example 23

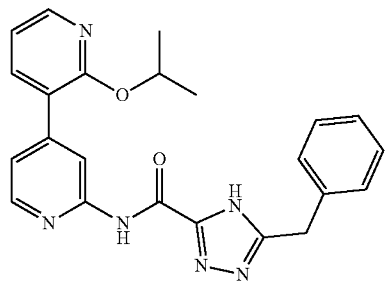

Example 23: 5-benzyl-N-(2-isopropyloxy-[3,4'-bipyridin]-2'-yl)-4H-1,2,4-triazole-3-carboxamide The preparation was carried out in a similar manner to Example 1, except that in step 1, (2-isopropyloxypyridin-3-yl)boronic acid was used in place of phenylboronic acid. $^{1}H$ NMR (400 MHz, DMSO-$d_6$) δ 14.59 (s, 1H), 9.81 (s, 1H), 8.52 (s, 1H), 8.41 (d, J=5.2 Hz, 1H), 8.25 (dd, J=4.9, 1.9 Hz, 1H), 7.89 (dd, J=7.4, 1.9 Hz, 1H), 7.40 (dd, J=5.2, 1.6 Hz, 1H), 7.38-7.30 (m, 4H), 7.29-7.21 (m, 1H), 7.12 (dd, J=7.4, 4.9 Hz, 1H), 5.39 (p, J=6.2 Hz, 1H), 4.18 (s, 2H), 1.33 (d, J=6.2 Hz, 6H). MS: 415 $[M+H]^+$.

Example 24: 5-benzyl-N-(3'-methyl-[4,4'-bipyridin]-2-yl)-4H-1,2,4-triazole-3-carboxamide The preparation was carried out in a similar manner to Example 1, except that in step 1, (3-methylpyridin-4-yl) boronic acid was used in place of phenylboronic acid. $^{1}H$ NMR (400 MHz, DMSO-$d_6$) δ 14.58 (s, 1H), 9.97 (s, 1H), 8.58 (s, 1H), 8.53 (d, J=5.0 Hz, 1H), 8.49 (d, J=5.1 Hz, 1H), 8.15 (s, 1H), 7.39-7.30 (m, 5H), 7.30-7.22 (m, 2H), 4.18 (s, 2H), 2.28 (s, 3H). MS: 371 $[M+H]^+$.

Example 24

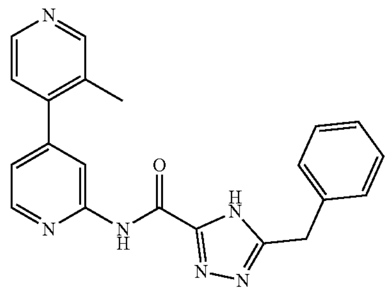

Example 25

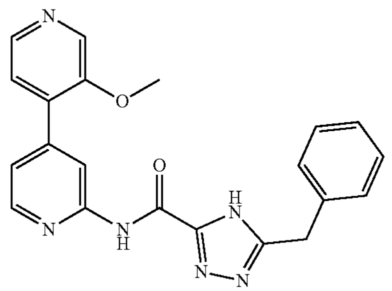

Example 25: 5-benzyl-N-(3'-methoxy-[4,4'-bipyridin]-2-yl)-4H-1,2,4-triazole-3-carboxamide The preparation was carried out in a similar manner to Example 1, except that in step 1, (3-methoxypyridin-4-yl) boronic acid was used in place of phenylboronic acid. $^1$H NMR (400 MHz, DMSO-$d_6$) δ 14.56 (s, 1H), 9.91 (s, 1H), 8.56 (s, 1H), 8.45 (d, J=5.2 Hz, 1H), 8.38-8.33 (m, 2H), 7.44 (d, J=4.8 Hz, 1H), 7.39 (dd, J=5.2, 1.6 Hz, 1H), 7.37-7.29 (m, 4H), 7.29-7.21 (m, 1H), 4.18 (s, 2H), 3.94 (s, 3H). MS: 387 $[M+H]^+$.

Example 26: 5-benzyl-N-(4-(1-methyl-1H-pyrazol-5-yl)pyridin-2-yl)-4H-1,2,4-triazole-3-carboxamide The preparation was carried out in a similar manner to Example 1, except that in step 1, 1-methyl-5-(4,4,5,5-tetramethyl-1,3,2-dioxaborolan-2-yl)-1H-pyrazole was used in place of phenylboronic acid. $^1$H NMR (400 MHz, DMSO-$d_6$) δ 14.66 (s, 1H), 10.00 (s, 1H), 8.47 (d, J=5.2 Hz, 1H), 8.28 (d, J=1.4 Hz, 1H), 7.55 (d, J=1.9 Hz, 1H), 7.40 (dd, J=5.2, 1.5 Hz, 1H), 7.38-7.29 (m, 4H), 7.29-7.21 (m, 1H), 6.63 (d, J=1.9 Hz, 1H), 4.18 (s, 2H), 3.96 (s, 3H). MS: 360 $[M+H]^+$.

Example 26

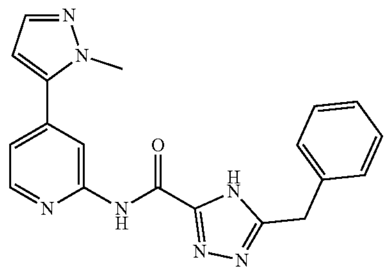

Example 27

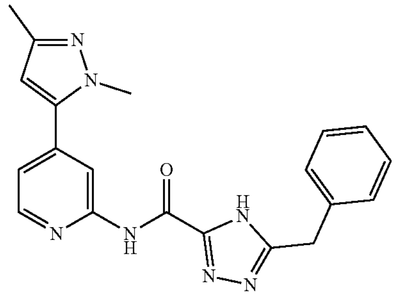

Example 27: 5-benzyl-N-(4-(1,3-dimethyl-1H-pyrazol-5-yl)pyridin-2-yl)-4H-1,2,4-triazole-3-carboxamide The preparation was carried out in a similar manner to Example 1, except that in step 1, 1,3-dimethyl-5-(4,4,5,5-tetramethyl-1,3,2-dioxaborolan-2-yl)-1H-pyrazole was used in place of phenylboronic acid. $^1$H NMR (400 MHz, DMSO-$d_6$) δ 14.62 (s, 1H), 9.97 (s, 1H), 8.45 (d, J=5.2 Hz, 1H), 8.25 (s, 1H), 7.42-7.29 (m, 5H), 7.29-7.20 (m, 1H), 6.40 (s, 1H), 4.18 (s, 2H), 3.87 (s, 3H), 2.19 (s, 3H). MS: 374 $[M+H]^+$.

Example 28: 5-benzyl-N-(4-(1-methyl-3-(trifluoromethyl)-1H-pyrazol-5-yl)pyridin-2-yl)-4H-1,2,4-triazole-3-carboxamide The preparation was carried out in a similar manner to Example 1, except that in step 1, 1-methyl-5-(4,4,5,5-tetramethyl-1,3,2-dioxaborolan-2-yl)-3-(trifluoromethyl)-1H-pyrazole was used in place of phenylboronic acid. $^1$H NMR (400 MHz, DMSO-$d_6$) δ 14.59 (s, 1H), 10.08 (s, 1H), 8.65-8.41 (m, 1H), 8.31 (d, J=3.7 Hz, 1H), 7.63-7.41 (m, 1H), 7.41-7.19 (m, 5H), 7.15 (d, J=3.8 Hz, 1H), 4.19 (s, 2H), 4.04 (s, 3H). MS: 428 $[M+H]^+$ Example 28

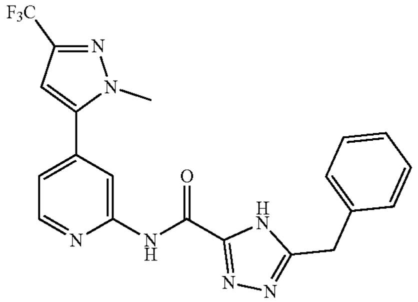

Example 29

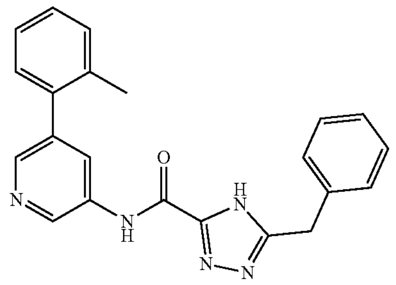

Example 29: 5-benzyl-N-(5-(o-methylphenyl)pyridin-3-yl)-4H-1,2,4-triazole-3-carboxamide The preparation was carried out in a similar manner to Example 1, except that in step 1, o-methylphenylboronic acid was used in place of phenylboronic acid, and 5-bromopyridin-3-amine was used in place of 4-bromopyridin-2-amine. $^1$H NMR (600 MHz, DMSO-$d_6$) δ 14.61 (s, 1H), 10.80 (s, 1H), 9.02 (d, J=2.4 Hz, 1H), 8.31 (d, J=2.0 Hz, 1H), 8.27-8.11 (m, 1H), 7.57-7.12 (m, 9H), 4.17 (s, 2H), 2.27 (s, 3H). MS: 370 $[M+H]^+$.

Example 30: 5-benzyl-N-(5-(2-chlorophenyl)pyridin-3-yl)-4H-1,2,4-triazole-3-carboxamide The preparation was carried out in a similar manner to Example 1, except that in step 1, 2-chlorophenylboronic acid was used in place of phenylboronic acid, 5-bromopyridin-3-amine was used in place of 4-bromopyridin-2-amine. $^1$H NMR (600 MHz, DMSO-$d_6$) δ 14.59 (s, 1H), 10.84 (s, 1H), 9.04 (s, 1H), 8.53-8.23 (m, 2H), 7.66-7.58 (m, 1H), 7.54-7.45 (m, 3H), 7.37-7.31 (m, 2H), 7.31-7.28 (m, 2H), 7.28-7.22 (m, 1H), 4.18 (s, 2H). MS: 390 $[M+H]^+$.

Example 30

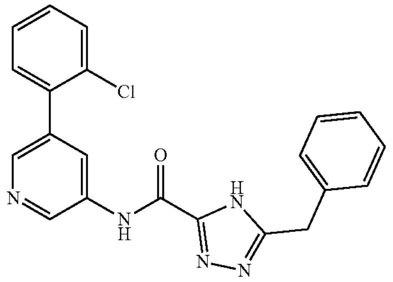

Example 31

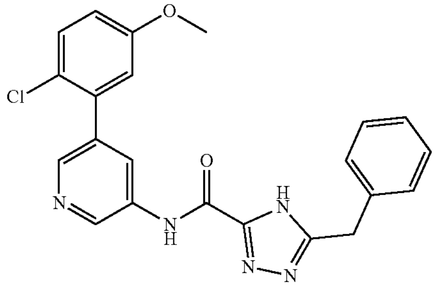

Example 31: 5-benzyl-N-(5-(2-chloro-5-methoxyphenyl)pyridin-3-yl)-4H-1,2,4-triazole-3-carboxamide The preparation was carried out in a similar manner to Example 1, except that in step 1, 2-chloro-5-methoxyphenylboronic acid was used in place of phenylboronic acid, 5-bromopyridin-3-amine was used in place of 4-bromopyridin-2-amine. $^1$H NMR (600 MHz, DMSO-$d_6$) δ 14.59 (s, 1H), 10.82 (s, 1H), 9.04 (d, J=2.4 Hz, 1H), 8.49-8.23 (m, 2H), 7.59-7.44 (m, 1H), 7.37-7.31 (m, 2H), 7.31-7.27 (m, 2H), 7.27-7.22 (m, 1H), 7.07-7.02 (m, 2H), 4.18 (s, 2H), 3.81 (s, 3H). MS: 420 $[M+H]^+$.

Example 32: 5-benzyl-N-(4-(1-isopropyl-3-(trifluoromethyl)-1H-pyrazol-5-yl)pyridin-2-yl)-4H-1,2,4-triazole-3-carboxamide

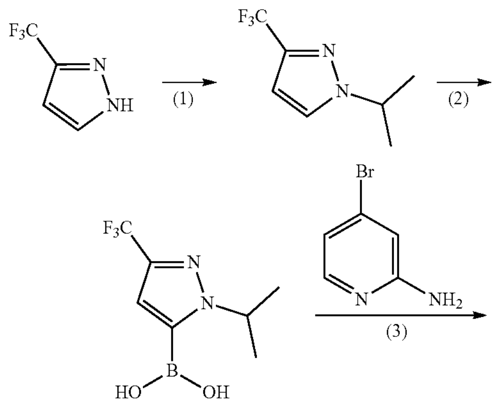

-continued

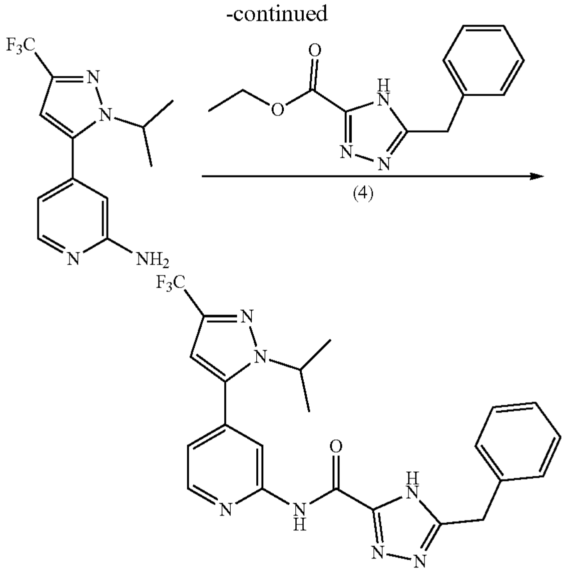

Step 1: Synthesis of 1-isopropyl-3-(trifluoromethyl)-1H-pyrazole 3-(Trifluoromethyl)-1H-pyrazole (1.09 g, 8 mmol) was dissolved in anhydrous tetrahydrofuran (24 mL), and under argon protection at 0° C., sodium hydride was added in batches (60%, 385 mg, 9.6 mmol). After reacting for 40 minutes, 2-bromopropane (1.28 g, 10.4 mmol) was added dropwise, and the reaction was warmed to 25° C. and reacted for 16 hours. The reaction solution was quenched with saturated aqueous solution of ammonium chloride, and extracted with ethyl acetate. The organic phase was washed with saturated brine, dried over anhydrous sodium sulfate, filtered and evaporated to dryness, and purified by column chromatography to afford 300 mg of product, MS: 179 $[M+H]^+$.

Step 2: Synthesis of (1-isopropyl-3-(trifluoromethyl)-1H-pyrazol-5-yl)boronic acid 1-Isopropyl-3-(trifluoromethyl)-1H-pyrazole (300 mg, 1.7 mmol) was dissolved in anhydrous tetrahydrofuran (6 mL), and under argon protection at −78° C., n-butyllithium (2.5M, 1 mL, 2.5 mmol) was added dropwise. After reacting at this temperature for 1 hour, trimethyl borate (351 mg, 3.4 mmol) was added, and slowly warmed up overnight. The reaction solution was quenched with saturated aqueous solution of ammonium chloride, and extracted with ethyl acetate. The organic phase was washed with saturated brine, dried over anhydrous sodium sulfate, filtered and evaporated to dryness, and purified by column chromatography to afford 70 mg of product, MS: 223 $[M+H]^+$.

Step 3 to Step 4: 5-benzyl-N-(4-(1-isopropyl-3-(trifluoromethyl)-1H-pyrazol-5-yl)pyridin-2-yl)-4H-1,2,4-triazole-3-carboxamide The preparation was carried out in a similar manner to Example 1, except that in step 1, (1-isopropyl-3-(trifluoromethyl)-1H-pyrazol-5-yl)boronic acid was used in place of phenylboronic acid. $^1$H NMR (400 MHz, DMSO-$d_6$) δ 14.61 (s, 1H), 10.08 (s, 1H), 8.54 (d, J=5.1 Hz, 1H), 8.26 (s, 1H), 7.41-7.29 (m, 5H), 7.29-7.21 (m, 1H), 7.04 (s, 1H), 4.86-4.60 (m, 1H), 4.18 (s, 2H), 1.45 (d, J=6.5 Hz, 6H). MS: 456 $[M+H]^+$.

Example 33: 5-benzyl-N-(4-(5-fluoro-2-methylphenyl)pyridin-2-yl)-4H-1,2,4-triazole-3-carboxamide

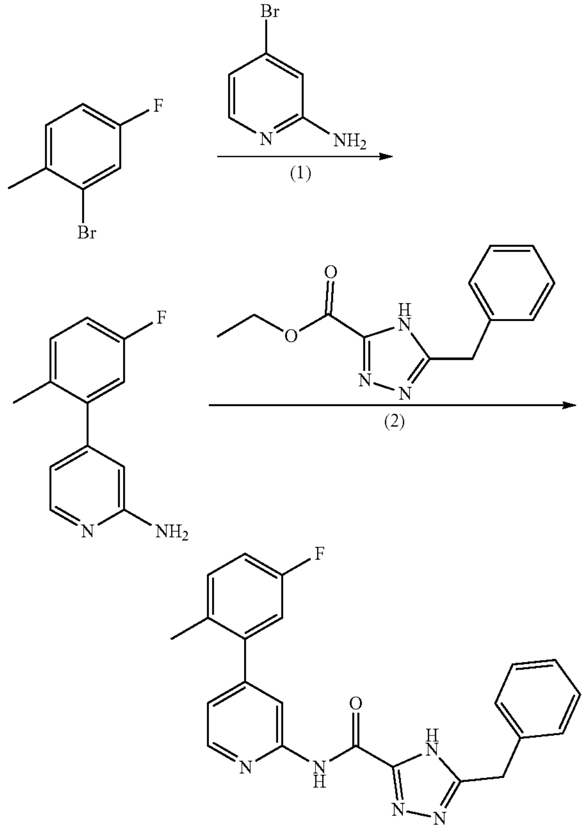

Step 1: Synthesis of 4-(5-fluoro-2-methylphenyl)pyridin-2-amine

4-Bromopyridin-2-amine (400 mg, 2.3 mmol), pinacol diborate (645 mg, 2.5 mmol), Pd(dppf)$Cl_2$ (170 mg, 0.2 mmol) and potassium acetate (564 mg, 5.8 mmol) were placed in dioxane (12 mL), and reacted at 85° C. for 16 hours under argon protection. The reaction solution was cooled to 25° C., and 2-bromo-4-fluoro-1-methylbenzene (321 mg, 1.7 mmol), Pd(dppf)$Cl_2$ (150 mg, 0.2 mmol) and an aqueous solution (1 mL) of sodium carbonate (360 mg, 3.4 mmol) was added, and continued to react under argon protection at 100° C. for 5 hours. The reaction solution was cooled and evaporated to dryness, and subjected to column chromatography to afford 240 mg of brown solid. MS: 203 $[M+H]^+$.

Step 2: Synthesis of 5-benzyl-N-(4-(5-fluoro-2-methylphenyl)pyridin-2-yl)-4H-1,2,4-triazole-3-carboxamide 4-(5-Fluoro-2-methylphenyl)pyridin-2-amine (0.7 mmol) was placed in dry xylene (3 mL), and trimethyl aluminum (3M, 0.7 mL) was slowly added under argon protection. After reacting at 25° C. for 1 hour, intermediate 1 (197 mg, 0.9 mmol) was added, and reacted at 100° C. for 16 hours. The reaction solution was cooled and diluted with methanol, evaporated to dryness and subjected to column chromatography and preparative liquid chromatography to prepare the product. $^1$H NMR (400 MHz, DMSO-$d_6$) δ 14.62 (s, 1H), 9.96 (s, 1H), 8.44 (d, J=5.1 Hz, 1H), 8.12 (d, J=1.5 Hz, 1H), 7.54-7.00 (m, 9H), 4.18 (s, 2H), 2.24 (s, 3H). MS: 388 $[M+H]^+$.

Example 34: 5-benzyl-N-(4-(5-chloro-2-methylphenyl)pyridin-2-yl)-4H-1,2,4-triazole-3-carboxamide The preparation was carried out in a similar manner to Example 33, except that in step 1, 2-bromo-4-chloro-1-methylbenzene was used in place of 2-bromo-4-fluoro-1-methylbenzene. $^1$H NMR (400 MHz, DMSO-$d_6$) δ 14.50 (s, 1H), 9.96 (s, 1H), 8.44 (d, J=5.1 Hz, 1H), 8.11 (s, 1H), 7.57-7.06 (m, 9H), 4.17 (s, 2H), 2.24 (s, 3H). MS: 404 $[M+H]^+$.

Example 34

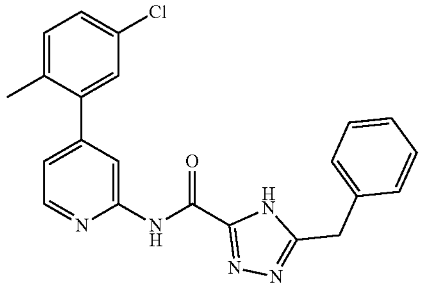

Example 35

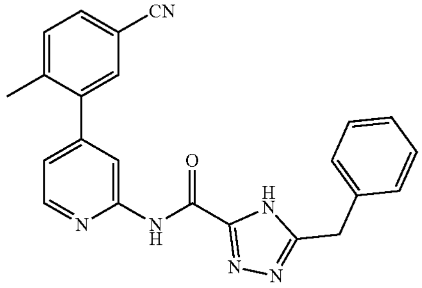

Example 35: 5-benzyl-N-(4-(5-cyano-2-methylphenyl)pyridin-2-yl)-4H-1,2,4-triazole-3-carboxamide The preparation was carried out in a similar manner to Example 33, except that in step 1, 2-bromo-4-cyano-1-methylbenzene was used in place of 2-bromo-4-fluoro-1-methylbenzene. $^1$H NMR (400 MHz, DMSO-$d_6$) δ 14.56 (s, 1H), 9.93 (s, 1H), 8.46 (d, J=5.1 Hz, 1H), 8.14 (s, 1H), 7.74 (dd, J=8.1, 2.0 Hz, 1H), 7.68-7.53 (m, 2H), 7.38-7.30 (m, 4H), 7.30-7.23 (m, 2H), 4.20 (s, 2H), 2.35 (s, 3H). MS: 395 $[M+H]^+$.

Example 36: 5-benzyl-N-(4-(2-methyl-5-(trifluoromethyl)phenyl)pyridin-2-yl)-4H-1,2,4-triazole-3-carboxamide The preparation was carried out in a similar manner to Example 33, except that in step 1, 2-bromo-4-trifluoromethyl-1-methylbenzene was used in place of 2-bromo-4-fluoro-1-methylbenzene. $^1$H NMR (400 MHz, DMSO-$d_6$) δ 14.56 (s, 1H), 9.93 (s, 1H), 8.46 (d, J=5.1 Hz, 1H), 8.14 (s, 1H), 7.74 (dd, J=8.1, 2.0 Hz, 1H), 7.65-7.57 (m, 2H), 7.39-7.23 (m, 6H), 4.20 (s, 2H), 2.35 (s, 3H). MS: 438 $[M+H]^+$.

Example 36

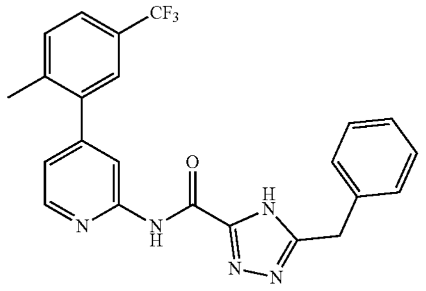

Example 37

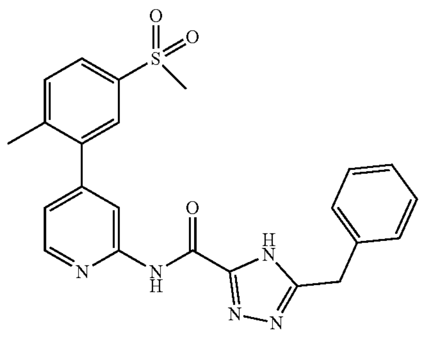

Example 37: 5-benzyl-N-(4-(2-methyl-5-(methylsulfonyl)phenyl)pyridin-2-yl)-4H-1,2,4-triazole-3-carboxamide The preparation was carried out in a similar manner to Example 33, except that in step 1, 2-bromo-4-methylsulfonyl-1-methylbenzene was used in place of 2-bromo-4-fluoro-1-methylbenzene. $^1$H NMR (400 MHz, DMSO-$d_6$) δ 14.61 (s, 1H), 10.00 (s, 1H), 8.48 (d, J=5.1 Hz, 1H), 8.15 (s, 1H), 7.91 (dd, J=8.0, 2.1 Hz, 1H), 7.79 (d, J=2.0 Hz, 1H), 7.66 (d, J=8.1 Hz, 1H), 7.40-7.21 (m, 6H), 4.18 (s, 2H), 3.26 (s, 3H), 2.37 (s, 3H). MS: 448 $[M+H]^+$.

Example 38: 5-benzyl-N-(4-(2,3-dihydrobenzofuran-7-yl)pyridin-2-yl)-4H-1,2,4-triazole-3-carboxamide The preparation was carried out in a similar manner to Example 33, except that in step 1, 7-bromo-2,3-dihydrobenzofuran was used in place of 2-bromo-4-fluoro-1-methylbenzene. $^1$H NMR (600 MHz, DMSO-$d_6$) δ 14.55 (s, 1H), 9.78 (s, 1H), 8.53 (s, 1H), 8.39 (d, J=5.3 Hz, 1H), 7.52 (d, J=5.3 Hz, 1H), 7.41 (d, J=7.8 Hz, 1H), 7.38-7.30 (m, 5H), 7.27 (d, J=7.2 Hz, 1H), 7.03-6.98 (m, 1H), 4.63 (t, J=8.7 Hz, 2H), 4.18 (s, 2H), 3.27 (t, J=8.7 Hz, 2H). MS: 398 $[M+H]^+$.

Example 38

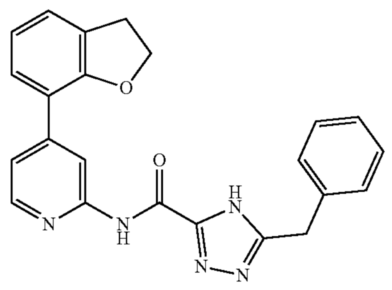

Example 39

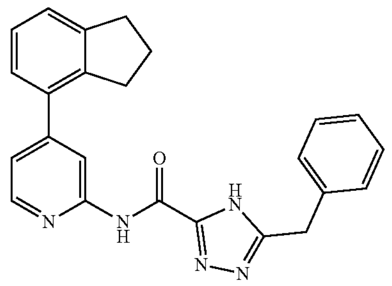

Example 39: 5-benzyl-N-(4-(2,3-dihydro-1H-inden-4-yl)pyridin-2-yl)-4H-1,2,4-triazole-3-carboxamide The preparation was carried out in a similar manner to Example 33, except that in step 1, 4-bromo-2,3-dihydro-1H-indene was used in place of 2-bromo-4-fluoro-1-methylbenzene. $^1$H NMR (400 MHz, DMSO-$d_6$) δ 14.62 (s, 1H), 9.89 (s, 1H), 8.42 (d, J=5.1 Hz, 1H), 8.27 (d, J=1.5 Hz, 1H), 7.60-7.12 (m, 9H), 4.18 (s, 2H), 3.04-2.88 (m, 4H), 2.11-1.95 (m, 2H). MS: 396 $[M+H]^+$.

Example 40: 5-benzyl-N-(4-(chroman-5-yl)pyridin-2-yl)-4H-1,2,4-triazole-3-carboxamide The preparation was carried out in a similar manner to Example 33, except that in step 1, 5-bromochroman was used in place of 2-bromo-4-fluoro-1-methylbenzene. $^1$H NMR (400 MHz, DMSO-$d_6$) δ 14.60 (s, 1H), 9.90 (s, 1H), 8.41 (d, J=5.1 Hz, 1H), 8.11 (s, 1H), 7.44-7.30 (m, 4H), 7.30-7.14 (m, 3H), 6.91-6.76 (m, 2H), 4.27-4.09 (m, 4H), 2.61 (t, J=6.5 Hz, 2H), 1.95-1.78 (m, 2H). MS: 412 $[M+H]^+$.

Example 40

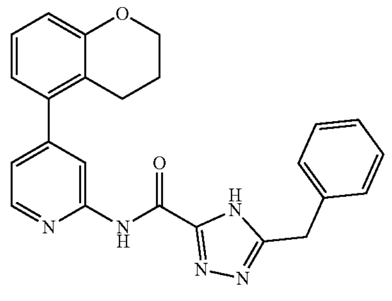

-continued

Example 41

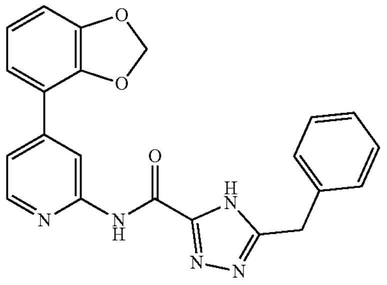

Example 41: N-(4-(benzo[d][1,3]dioxol-4-yl)pyridin-2-yl)-5-benzyl-4H-1,2,4-triazole-3-carboxamide The preparation was carried out in a similar manner to Example 33, except that in step 1, 4-bromobenzo[d][1,3]dioxole was used in place of 2-bromo-4-fluoro-1-methylbenzene. $^1$H NMR (600 MHz, DMSO-$d_6$) δ 14.55 (s, 1H), 9.85 (s, 1H), 8.57 (s, 1H), 8.44 (d, J=5.3 Hz, 1H), 7.55 (d, J=5.3 Hz, 1H), 7.38-7.29 (m, 4H), 7.29-7.19 (m, 2H), 7.08-6.97 (m, 2H), 6.15 (s, 2H), 4.18 (s, 2H). MS: 400 $[M+H]^+$.

Example 42: 5-benzyl-N-(4-(2,3-dihydrobenzo[b][1,4]dioxin-5-yl)pyridin-2-yl)-4H-1,2,4-triazole-3-carboxamide

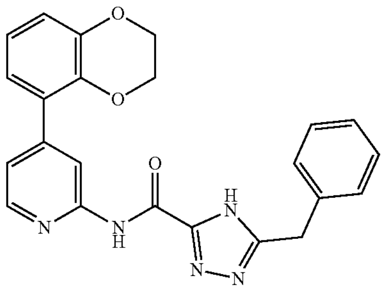 [SMILES: O=C(Nc1cc(-c2cccc3c2OCCO3)ccn1)c1nnc(Cc2ccccc2)[nH]1]

The preparation was carried out in a similar manner to Example 33, except that in step 1, 5-bromo-2,3-dihydrobenzo[b][1,4]dioxine was used in place of 2-bromo-4-fluoro-1-methylbenzene. $^1$H NMR (600 MHz, DMSO-$d_6$) δ 14.59 (s, 1H), 9.84 (s, 1H), 8.38 (d, J=5.2 Hz, 1H), 8.29 (s, 1H), 7.39-7.29 (m, 5H), 7.29-7.21 (m, 1H), 7.02-6.92 (m, 3H), 4.34-4.25 (m, 4H), 4.17 (s, 2H). MS: 414 $[M+H]^+$.

Example 43: 5-benzyl-N-(4-(5,6,7,8-tetrahydronaphthalen-1-yl)pyridin-2-yl)-4H-1,2,4-triazole-3-carboxamide

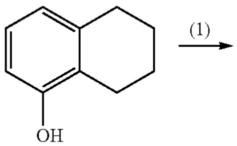

-continued

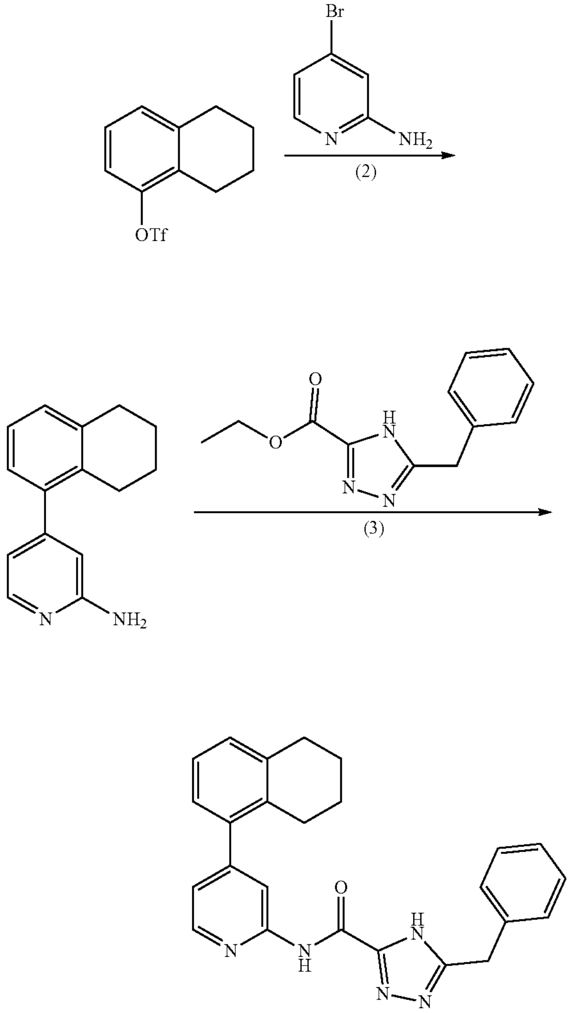

Step 1: Synthesis of 5,6,7,8-tetrahydronaphthalen-1-yl trifluoromethanesulfonate 5,6,7,8-tetrahydronaphthalen-1-ol was dissolved in dichloromethane (600 mg, 4 mmol) and pyridine (480 mg, 6.1 mmol), trifluoromethanesulfonic anhydride (1.37 g, 4.8 mmol) was added dropwise under argon protection at 0° C., and the reaction was warmed to 25° C. and reacted for 5 hours. The reaction solution was diluted with dichloromethane, washed with 1M HCl, washed with saturated brine, dried over anhydrous sodium sulfate, filtered and evaporated to dryness to afford 444 mg of colorless oil. MS: 281 $[M+H]^+$.

Step 2 to Step 3: The preparation was carried out in a similar manner to Example 33, except that in step 1, 5,6,7,8-tetrahydronaphthalen-1-yl trifluoromethanesulfonate was used in place of 2-bromo-4-fluoro-1-methylbenzene. $^1$H NMR (400 MHz, DMSO-$d_6$) δ 14.59 (s, 1H), 9.88 (s, 1H), 8.40 (d, J=5.1 Hz, 1H), 8.07 (s, 1H), 7.40-7.29 (m, 4H), 7.29-7.12 (m, 4H), 7.03 (dd, J=7.3, 1.6 Hz, 1H), 4.17 (s, 2H), 2.81 (t, J=6.4 Hz, 2H), 2.56 (t, J=6.2 Hz, 2H), 1.81-1.71 (m, 2H), 1.71-1.59 (m, 2H). MS: 410 $[M+H]^+$.

Example 44: 5-benzyl-N-(5-cyclopropyl-2-methoxy-[3,4'-bipyridin]-2'-yl)-4H-1,2,4-triazole-3-carboxamide

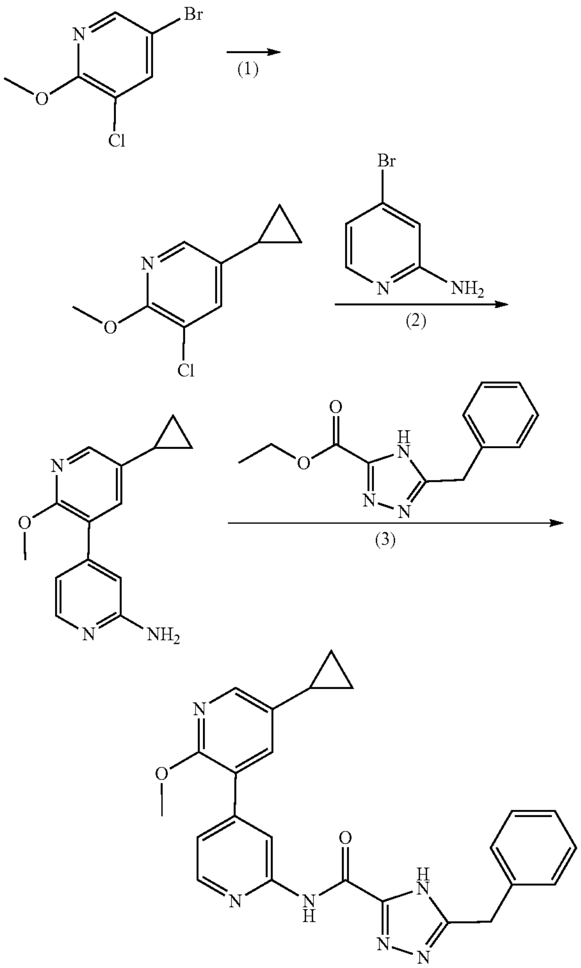

Step 1: Synthesis of 3-chloro-5-cyclopropyl-2-methoxypyridine 5-bromo-3-chloro-2-methoxypyridine (500 mg, 2.2 mmol), cyclopropylboronic acid (212 mg, 2.5 mmol), $Pd(dppf)Cl_2$ (145 mg, 0.2 mmol) and potassium carbonate (930 mg, 6.7 mmol) were placed in a mixture of dioxane (8 mL) and water (2 mL), and reacted for 16 hours under argon protection at 80° C. The reaction solution was evaporated to dryness and subjected to column chromatography to afford 165 mg of product, MS: 184 $[M+H]^+$.

Step 2 to Step 3: The preparation was carried out in a similar manner to Example 33, except that in step 1, 3-chloro-5-cyclopropyl-2-methoxypyridine was used in place of 2-bromo-4-fluoro-1-methylbenzene, and reacted at 120° C. $^1H$ NMR (400 MHz, DMSO-$d_6$) δ 14.59 (s, 1H), 9.87 (s, 1H), 8.40 (d, J=5.2 Hz, 1H), 8.34 (s, 1H), 8.09 (d, J=2.4 Hz, 1H), 7.51 (d, J=2.4 Hz, 1H), 7.43-7.30 (m, 5H), 7.30-7.21 (m, 1H), 4.18 (s, 2H), 3.88 (s, 3H), 2.05-1.90 (m, 1H), 1.04-0.88 (m, 2H), 0.82-0.67 (m, 2H). MS: 427 $[M+H]^+$.

Example 45: 5-benzyl-N-(4-(5-cyclopropyl-2-methylphenyl)pyridin-2-yl)-4H-1,2,4-triazole-3-carboxamide

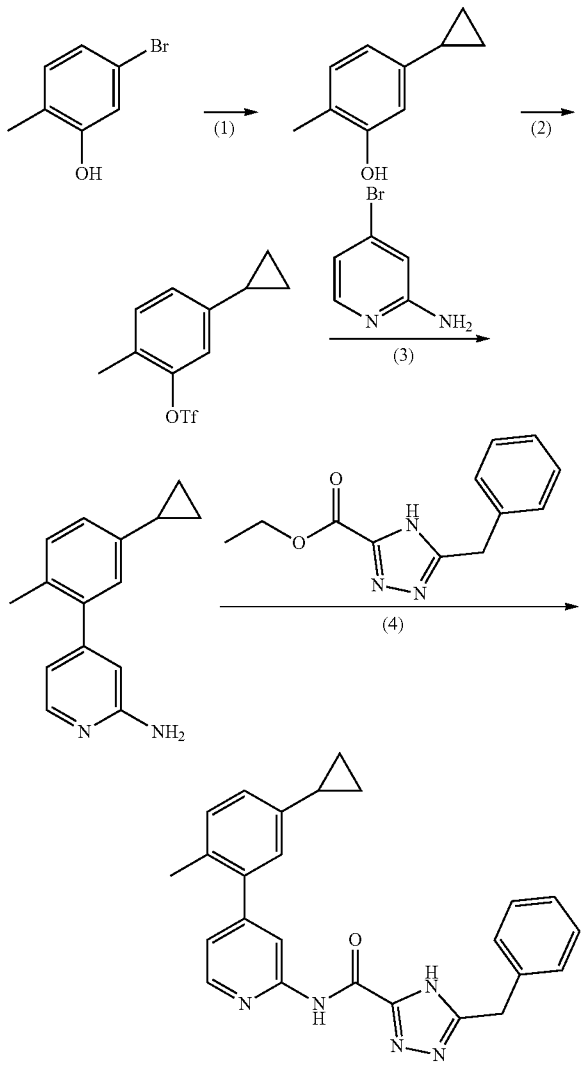

Step 1: Synthesis of 5-cyclopropyl-2-methylphenol

The operation is the same as step 1 of Example 44, but 5-bromo-2-methylphenol was used in place of 5-bromo-3-chloro-2-methoxypyridine. MS: 149 $[M+H]^+$.

Step 2 to Step 4

The preparation was carried out in a similar manner to Example 43, except that in step 1, but 5-cyclopropyl-2-methylphenol was used in place of 5,6,7,8-tetrahydronaphthalen-1-ol. $^1H$ NMR (400 MHz, DMSO-$d_6$) δ 14.58 (s, 1H), 9.90 (s, 1H), 8.41 (d, J=5.1 Hz, 1H), 8.10 (s, 1H), 7.46-7.11 (m, 7H), 7.11-6.87 (m, 2H), 4.17 (s, 2H), 2.21 (s, 3H), 2.02-1.84 (m, 1H), 1.00-0.87 (m, 2H), 0.76-0.56 (m, 2H). MS: 410 $[M+H]^+$.

Example 46: 5-benzyl-N-(4-(5-cyclopropyl-2-methoxyphenyl)pyridin-2-yl)-4H-1,2,4-triazole-3-carboxamide

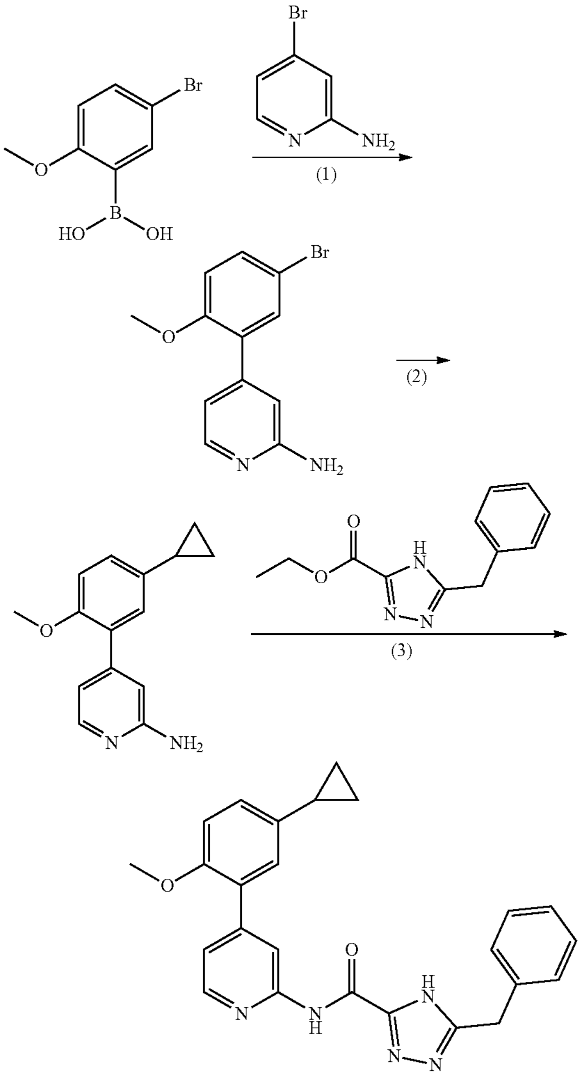

Step 1: Synthesis of 4-(5-bromo-2-methoxyphenyl)pyridin-2-amine

The operation is the same as step 1 of Example 1, but (5-bromo-2-methoxyphenyl)boronic acid was used in place of phenylboronic acid. MS: 279 $[M+H]^+$.

Step 2: Synthesis of 4-(5-cyclopropyl-2-methoxyphenyl)pyridin-2-amine

The operation is the same as step 1 of Example 44, but 4-(5-bromo-2-methoxyphenyl)pyridin-2-amine was used in place of 5-bromo-3-chloro-2-methoxypyridine. MS: 241 $[M+H]^+$.

Step 3: Synthesis of 5-benzyl-N-(4-(5-cyclopropyl-2-methoxyphenyl)pyridin-2-yl)-4H-1,2,4-triazole-3-carboxamide The operation is the same as step 2 of Example 1, but 4-(5-cyclopropyl-2-methoxyphenyl)pyridin-2-amine was used in place of 4-phenylpyridin-2-amine. $^1H$ NMR (400 MHz, DMSO-$d_6$) δ 14.54 (s, 1H), 9.79 (s, 1H), 8.36 (d, J=5.2 Hz, 1H), 8.27 (s, 1H), 7.40-7.29 (m, 5H), 7.29-7.21 (m, 1H), 7.14 (dd, J=8.5, 2.3 Hz, 1H), 7.11-7.03 (m, 2H), 4.18 (s, 2H), 3.76 (s, 3H), 2.00-1.88 (m, 1H), 0.97-0.86 (m, 2H), 0.70-0.58 (m, 2H). MS: 426 $[M+H]^+$.

Example 47: 5-benzyl-N-(4-cyclopentylpyridin-2-yl)-4H-1,2,4-triazole-3-carboxamide

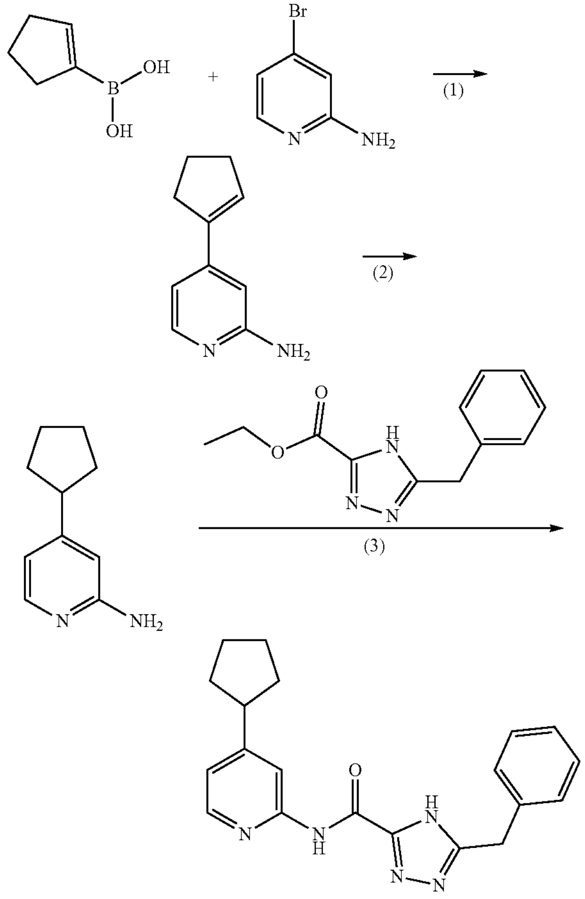

Step 1: Synthesis of 4-(cyclopent-1-en-1-yl)pyridin-2-amine

The operation is the same as step 1 of Example 1, but cyclopent-1-en-1-ylboronic acid was used in place of phenylboronic acid. MS: 161 $[M+H]^+$.

Step 2: Synthesis of 4-cyclopentylpyridin-2-amine 4-(Cyclopent-1-en-1-yl)pyridin-2-amine (160 mg, 1 mmol) was dissolved in a mixture of ethanol (2 mL) and ethyl acetate (1 mL), to which a drop of hydrochloric acid and palladium on carbon (10%, 10 mg) was added, and reacted for 16 hours under hydrogen atmosphere. The reaction solution was filtered through diatomaceous earth. The filtrate was evaporated to dryness, diluted with dichloromethane, washed with saturated aqueous solution of sodium carbonate, dried over anhydrous sodium sulfate, filtered and evaporated to dryness to afford 140 mg of yellow oil. MS: 163 $[M+H]^+$.

Step 3: Synthesis of 5-benzyl-N-(4-cyclopentylpyridin-2-yl)-4H-1,2,4-triazole-3-carboxamide The operation is the same as step 2 of Example 1, but 4-cyclopentylpyridin-2-amine was used in place of 4-phenylpyridin-2-amine. $^1H$ NMR (400 MHz, DMSO-$d_6$) δ 14.61 (s, 1H), 9.70 (s, 1H), 8.23 (d, J=5.1 Hz, 1H), 8.06 (d, J=1.5 Hz, 1H), 7.42-7.29 (m, 4H), 7.29-7.18 (m, 1H), 7.09 (dd, J=5.1, 1.5 Hz, 1H), 4.16 (s, 2H), 3.11-2.95 (m, 1H), 2.15-1.97 (m, 2H), 1.86-1.73 (m, 2H), 1.73-1.60 (m, 2H), 1.60-1.44 (m, 2H). MS: 348 $[M+H]^+$.

Example 48: 5-benzyl-N-(4-cyclohexylpyridin-2-yl)-4H-1,2,4-triazole-3-carboxamide The preparation was carried out in a similar manner to Example 47, except that in step 1, cyclohex-1-en-1-ylboronic acid was used in place of cyclopent-1-en-1-ylboronic acid. $^1H$ NMR (400 MHz, DMSO-$d_6$) δ 14.58 (s, 1H), 9.68 (s, 1H), 8.23 (d, J=5.2 Hz, 1H), 8.04 (s, 1H), 7.39-7.28 (m, 4H), 7.28-7.19 (m, 1H), 7.12-7.03 (m, 1H), 4.15 (s, 2H), 2.64-2.53 (m, 1H), 1.89-1.74 (m, 4H), 1.75-1.64 (m, 1H), 1.48-1.31 (m, 4H), 1.30-1.18 (m, 1H). MS: 362 $[M+H]^+$.

Example 48

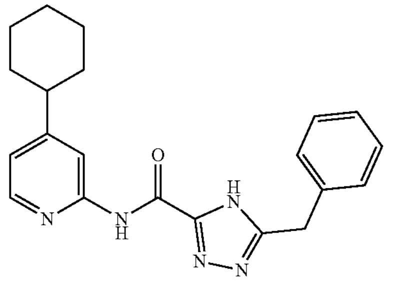

Example 49

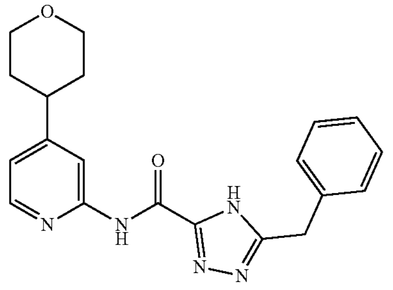

Example 49: 5-benzyl-N-(4-(tetrahydro-2H-pyran-4-yl)pyridin-2-yl)-4H-1,2,4-triazole-3-carboxamide The preparation was carried out in a similar manner to Example 47, except that in step 1, (3,6-dihydro-2H-pyran-4-yl)boronic acid was used in place of cyclopent-1-en-1-ylboronic acid. $^1H$ NMR (400 MHz, DMSO-$d_6$) δ 14.53 (s, 1H), 9.69 (s, 1H), 8.27 (d, J=5.2 Hz, 1H), 8.08 (s, 1H), 7.42-7.18 (m, 5H), 7.12 (d, J=5.3 Hz, 1H), 4.19 (s, 2H), 4.02-3.86 (m, 2H), 3.53-3.37 (m, 2H), 2.95-2.78 (m, 1H), 1.81-1.52 (m, 4H). MS: 364 $[M+H]^+$.

Example 50: 5-benzyl-N-(2-methoxy-5-methyl-[3,4'-bipyridin]-2'-yl)-4H-1,2,4-triazole-3-carboxamide

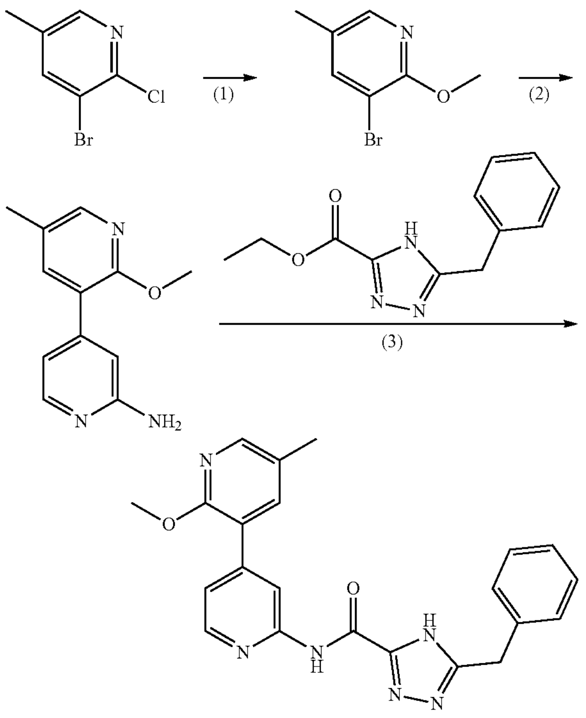

Step 1: Synthesis of 3-bromo-2-methoxy-5-methylpyridine

Anhydrous methanol (100 mg, 3.1 mmol) was dissolved in anhydrous DMF (3 mL), and sodium hydride (60%, 115 mg, 2.9 mmol) was added under argon protection at 0° C. After reacting for 1 hour, 3-bromo-2-chloro-5-methylpyridine (400 mg, 1.9 mmol) in DMF (1 mL) was added dropwise, and reacted at 60° C. for 16 hours. MS: 202 $[M+H]^+$.

Step 2 to Step 3: The preparation was carried out in a similar manner to Example 33, except that in step 1, 3-bromo-2-methoxy-5-methylpyridine was used in place of 2-bromo-4-fluoro-1-methylbenzene. $^1H$ NMR (400 MHz, DMSO-$d_6$) δ 14.58 (s, 1H), 9.86 (s, 1H), 8.41 (d, J=5.2 Hz, 1H), 8.36 (d, J=1.5 Hz, 1H), 8.09 (d, J=2.2 Hz, 1H), 7.72 (d, J=2.3 Hz, 1H), 7.39 (dd, J=5.2, 1.6 Hz, 1H), 7.38-7.29 (m, 4H), 7.29-7.21 (m, 1H), 4.18 (s, 2H), 3.88 (s, 3H), 2.30 (s, 3H). MS: 401 $[M+H]^+$.

Example 51: 5-benzyl-N-(2-ethoxy-5-methyl-[3,4'-bipyridin]-2'-yl)-4H-1,2,4-triazole-3-carboxamide The preparation was carried out in a similar manner to Example 50, except that in step 1, anhydrous ethanol was used in place of anhydrous methanol. $^1H$ NMR (400 MHz, DMSO-$d_6$) δ 14.55 (s, 1H), 9.80 (s, 1H), 8.47 (s, 1H), 8.40 (d, J=5.2 Hz, 1H), 8.07 (dd, J=2.3, 1.0 Hz, 1H), 7.73 (d, J=2.3 Hz, 1H), 7.41 (dd, J=5.2, 1.6 Hz, 1H), 7.38-7.29 (m, 4H), 7.29-7.21 (m, 1H), 4.37 (q, J=7.1 Hz, 2H), 4.18 (s, 2H), 2.29 (s, 3H), 1.32 (t, J=7.0 Hz, 3H). MS: 415 $[M+H]^+$.

Example 51

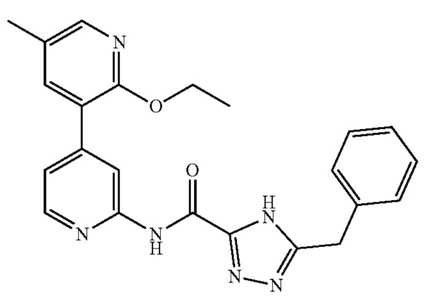

Example 52

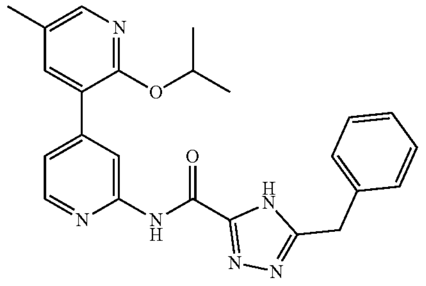

Example 52: 5-benzyl-N-(2-isopropoxy-5-methyl-[3,4'-bipyridin]-2'-yl)-4H-1,2,4-triazole-3-carboxamide The preparation was carried out in a similar manner to Example 50, except that in step 1, anhydrous isopropanol was used in place of anhydrous methanol. $^1H$ NMR (400 MHz, DMSO-$d_6$) δ 14.63 (s, 1H), 9.91-9.71 (m, 1H), 8.51 (s, 1H), 8.40 (d, J=5.2 Hz, 1H), 8.06 (d, J=2.3 Hz, 1H), 7.73 (d, J=2.4 Hz, 1H), 7.44-7.18 (m, 6H), 5.34 (p, J=6.2 Hz, 1H), 4.18 (s, 2H), 2.28 (s, 3H), 1.31 (d, J=6.2 Hz, 6H). MS: 429 $[M+H]^+$.

Example 53: 5-benzyl-N-(6-ethoxy-5-methyl-[2,4'-bipyridin]-2'-yl)-4H-1,2,4-triazole-3-carboxamide

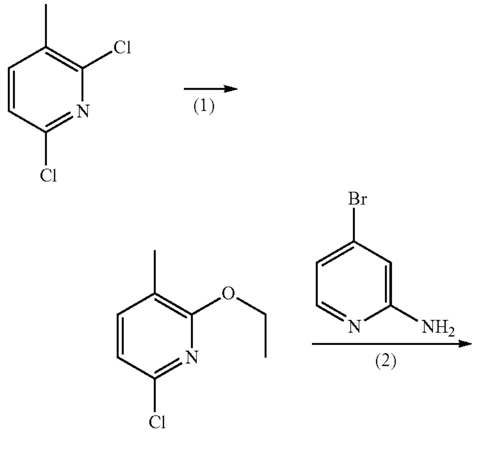

-continued

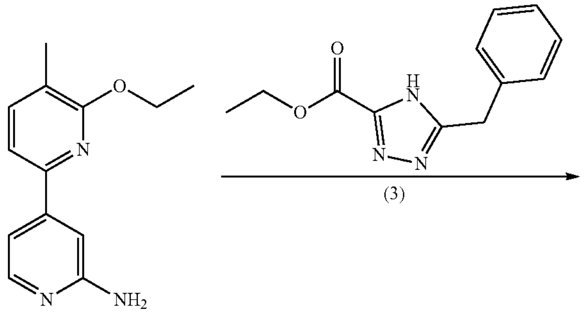

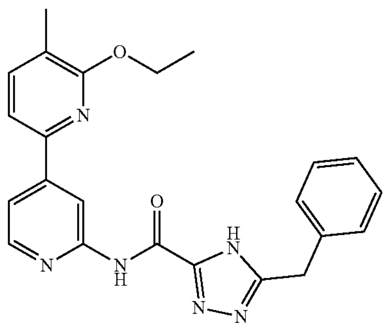

Step 1: Synthesis of 6-chloro-2-ethoxy-3-methylpyridine

Anhydrous ethanol (830 mg, 18 mmol) was dissolved in anhydrous tetrahydrofuran (10 mL), and sodium hydride (60%, 600 mg, 15 mmol) was added at 0° C. After reacting for 30 minutes, 2,6-dichloro-3-methylpyridine (810 mg, 5 mmol) in tetrahydrofuran (5 mL) was added, and reacted at 40° C. for 24 hours. The reaction solution was quenched with saturated ammonium chloride, extracted with ethyl acetate, washed with saturated brine, dried over anhydrous sodium sulfate, filtered and evaporated to dryness, and purified by column chromatography to afford 300 mg of product. MS: 172 $[M+H]^+$.

Step 2 to Step 3: The preparation was carried out in a similar manner to Example 33, except that in step 1, 6-chloro-2-ethoxy-3-methylpyridine was used in place of 2-bromo-4-fluoro-1-methylbenzene, and reacted at 120° C. $^1H$ NMR (400 MHz, DMSO-$d_6$) δ 14.21 (s, 1H), 9.86 (s, 1H), 8.86 (d, J=3.6 Hz, 1H), 8.53-8.32 (m, 1H), 7.84-7.77 (m, 1H), 7.71 (dd, J=7.8, 3.6 Hz, 1H), 7.59 (dd, J=7.8, 3.8 Hz, 1H), 7.40-7.30 (m, 4H), 7.27 (d, J=7.0 Hz, 1H), 4.56-4.43 (m, 2H), 4.18 (s, 2H), 2.21 (s, 3H), 1.52-1.36 (m, 3H). MS: 415 $[M+H]^+$.

Example 54: 5-benzyl-N-(6-(2-methoxyethoxy)-5-methyl-[2,4'-bipyridin]-2'-yl)-4H-1,2,4-triazole-3-carboxamide

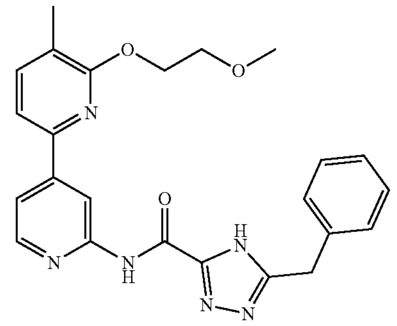 [SMILES: COCCOc1nc(-c2ccnc(NC(=O)c3nnc(Cc4ccccc4)[nH]3)c2)ccc1C]

The preparation was carried out in a similar manner to Example 53, except that in step 1, 2-methoxyethanol was used in place of anhydrous ethanol. $^1$H NMR (400 MHz, DMSO-$d_6$) δ 14.54 (s, 1H), 9.87 (s, 1H), 8.85 (d, J=1.3 Hz, 1H), 8.44 (d, J=5.3 Hz, 1H), 7.81 (dd, J=5.3, 1.6 Hz, 1H), 7.76-7.69 (m, 1H), 7.61 (d, J=7.4 Hz, 1H), 7.40-7.29 (m, 4H), 7.29-7.20 (m, 1H), 4.64-4.51 (m, 2H), 4.18 (s, 2H), 3.82-3.73 (m, 2H), 3.45 (s, 3H), 2.22 (s, 3H). MS: 445 $[M+H]^+$.

Example 55: 5-benzyl-N-(4-(5-((2-methoxyethyl)(methyl)amino)-2-methylphenyl)pyridin-2-yl)-4H-1,2,4-triazole-3-carboxamide

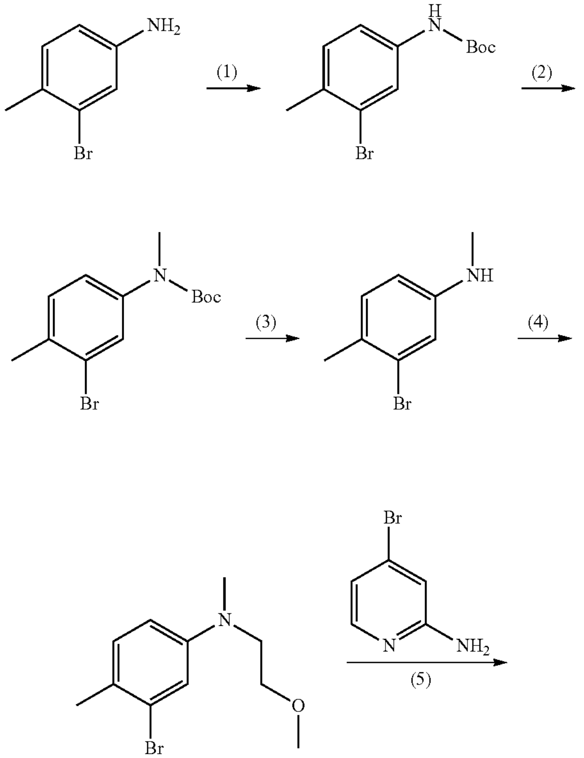

-continued

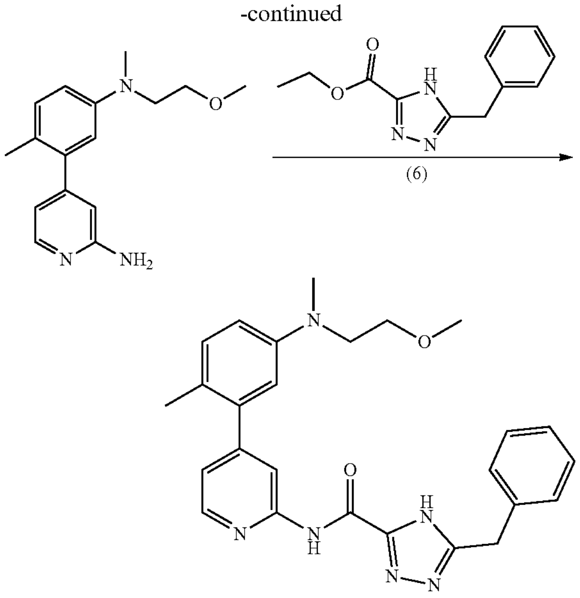

Step 1: Synthesis of tert-butyl (3-bromo-4-methylphenyl)carbamate

3-Bromo-4-methylaniline (1.86 g, 10 mmol) was placed in dichloromethane (25 mL), 4-dimethylaminopyridine (120 mg, 1 mmol) and triethylamine (2 g, 20 mmol) were added, a solution of di-tert-butyl dicarbonate (2.4 g, 11 mmol) in dichloromethane (5 mL) was added dropwise under argon protection at 0° C., and reacted at 25° C. for 4 hours after the addition. The reaction solution was diluted with dichloromethane, washed with saturated aqueous solution of ammonium chloride, washed with brine, dried over anhydrous sodium sulfate, evaporated to dryness and filtered to afford 2.84 g crude product.

Step 2: Synthesis of tert-butyl (3-bromo-4-methylphenyl)(methyl)carbamate

Tert-butyl (3-bromo-4-methylphenyl)carbamate (2.84 g, 9.9 mmol) was dissolved in DMF, and sodium hydride (60%, 475 mg, 11.9 mmol) was added in batches at 0° C. After reacting at 0° C. for 30 minutes, iodomethane (2.1 g, 14.8 mmol) was added dropwise, and reacted at 25° C. for 3 hours. The reaction solution was quenched with saturated aqueous solution of ammonium chloride, diluted with ethyl acetate, washed with saturated aqueous solution of ammonium chloride and brine, dried over anhydrous sodium sulfate, filtered and evaporated to dryness, purified by column chromatography to afford 2.5 g.

Step 3: Synthesis of 3-bromo-N,4-dimethylaniline

Tert-butyl (3-bromo-4-methylphenyl)(methyl)carbamate (2.5 g, 8.3 mmol) was dissolved in dichloromethane (25 mL), trifluoroacetic acid (10 mL) was added dropwise at 0° C., and reacted at 25° C. for 3 hours. The reaction solution was concentrated, an aqueous solution of sodium carbonate was added dropwise to adjust the pH to 9, extracted with dichloromethane, dried over anhydrous sodium sulfate, filtered and evaporated to dryness to afford 1.5 g of crude product. MS: 200 $[M+H]^+$.

Step 4: Synthesis of 3-bromo-N-(2-methoxyethyl)-N,4-dimethylaniline

3-Bromo-N,4-dimethylaniline (200 mg, 1 mmol) was dissolved in DMF, potassium carbonate (275 mg, 1.5 mmol) and 1-bromo-2-methoxyethane (180 mg, 1.3 mmol) were added, and reacted for 24 hours at 70° C. in sealed tube. The reaction solution was cooled, diluted with ethyl acetate, washed with saturated ammonium chloride and brine, dried over anhydrous sodium sulfate, filtered and evaporated to dryness to afford 180 mg of the product. MS: 258 $[M+H]^+$.

Step 5 to Step 6: The preparation was carried out in a similar manner to Example 33, except that in step 1, 3-bromo-N-(2-methoxyethyl)-N,4-dimethylaniline was used in place of 2-bromo-4-fluoro-1-methylbenzene. $^1$H NMR (400 MHz, DMSO-$d_6$) δ 14.58 (s, 1H), 9.86 (s, 1H), 8.40 (d, J=5.1 Hz, 1H), 8.11 (s, 1H), 7.38-7.29 (m, 4H), 7.27 (dd, J=6.1, 2.5 Hz, 1H), 7.19 (dd, J=5.1, 1.5 Hz, 1H), 7.12 (d, J=8.5 Hz, 1H), 6.72 (dd, J=8.5, 2.8 Hz, 1H), 6.55 (d, J=2.8 Hz, 1H), 4.17 (s, 2H), 3.54-3.43 (m, 4H), 3.24 (s, 3H), 2.90 (s, 3H), 2.13 (s, 3H). MS: 457 $[M+H]^+$.

Example 56: 5-benzyl-N-(4-(5-((2-ethoxyethyl)(methyl)amino)-2-methylphenyl)pyridin-2-yl)-4H-1,2,4-triazole-3-carboxamide The operation is the same as Example 55, but 1-bromo-2-ethoxyethane was used in place of 1-bromo-2-methoxyethane in step 4. $^1$H NMR (400 MHz, DMSO-$d_6$) δ 14.56 (s, 1H), 9.85 (s, 1H), 8.40 (d, J=5.1 Hz, 1H), 8.11 (s, 1H), 7.46-7.29 (m, 4H), 7.27 (d, J=6.5 Hz, 1H), 7.19 (dd, J=5.2, 1.5 Hz, 1H), 7.12 (d, J=8.5 Hz, 1H), 6.72 (dd, J=8.5, 2.8 Hz, 1H), 6.55 (d, J=2.8 Hz, 1H), 4.18 (s, 2H), 3.56-3.45 (m, 4H), 3.41 (q, J=7.0 Hz, 2H), 2.90 (s, 3H), 2.13 (s, 3H), 1.07 (t, J=7.0 Hz, 3H). MS: 471 $[M+H]^+$.

Example 56

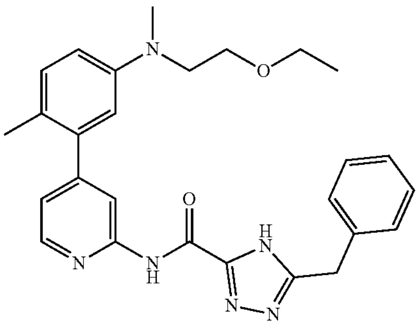

Example 57

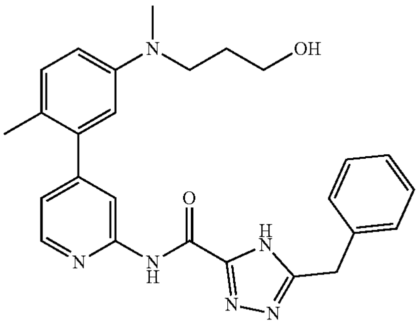

Example 57: 5-benzyl-N-(4-(5-((3-hydroxypropyl)(methyl)amino)-2-methylphenyl)pyridin-2-yl)-4H-1,2,4-triazole-3-carboxamide The operation is the same as Example 55, but 3-bromo-1-propanol was used in place of 1-bromo-2-methoxyethane in step 4. $^1$H NMR (400 MHz, DMSO-$d_6$) δ 14.58 (s, 1H), 9.88 (s, 1H), 8.40 (d, J=5.1 Hz, 1H), 8.11 (s, 1H), 7.42-7.29 (m, 4H), 7.29-7.22 (m, 1H), 7.19 (dd, J=5.1, 1.5 Hz, 1H), 7.12 (d, J=8.5 Hz, 1H), 6.72 (dd, J=8.5, 2.7 Hz, 1H), 6.54 (d, J=2.7 Hz, 1H), 4.49 (t, J=5.0 Hz, 1H), 4.17 (s, 2H), 3.51-3.36 (m, 4H), 2.86 (s, 3H), 2.13 (s, 3H), 1.73-1.55 (m, 2H). MS: 457 $[M+H]^+$.

Example 58: 5-benzyl-N-(4-(5-((3-methoxypropyl)(methyl)amino)-2-methylphenyl)pyridin-2-yl)-4H-1,2,4-triazole-3-carboxamide

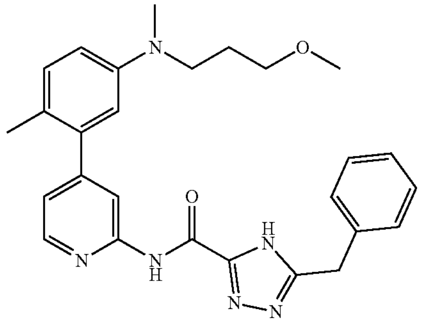 [SMILES: COCCCN(C)c1ccc(C)c(-c2ccnc(NC(=O)c3nnc(Cc4ccccc4)[nH]3)c2)c1]

The operation is the same as Example 55, but 1-bromo-3-methoxypropane was used in place of 1-bromo-2-methoxyethane in step 4. $^1$H NMR (400 MHz, DMSO-$d_6$) δ 14.56 (s, 1H), 9.88 (s, 1H), 8.40 (d, J=5.1 Hz, 1H), 8.11 (s, 1H), 7.43-7.29 (m, 4H), 7.29-7.22 (m, 1H), 7.19 (dd, J=5.1, 1.6 Hz, 1H), 7.13 (d, J=8.5 Hz, 1H), 6.70 (dd, J=8.5, 2.8 Hz, 1H), 6.54 (d, J=2.8 Hz, 1H), 4.17 (s, 2H), 3.40-3.34 (m, 4H), 3.19 (s, 3H), 2.86 (s, 3H), 2.13 (s, 3H), 1.77-1.63 (m, 2H). MS: 471 $[M+H]^+$.

Example 59: 5-benzyl-N-(4-(5-(3-methoxypropylthio)-2-methylphenyl)pyridin-2-yl)-4H-1,2,4-triazole-3-carboxamide

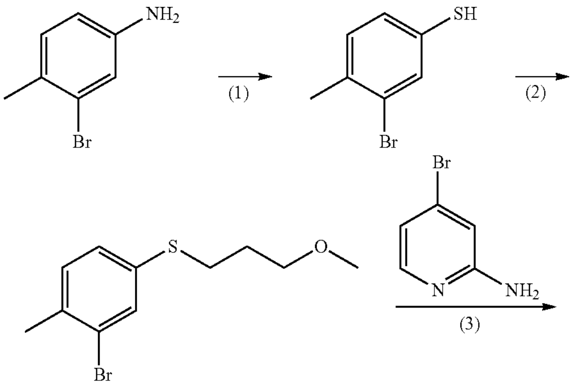

-continued

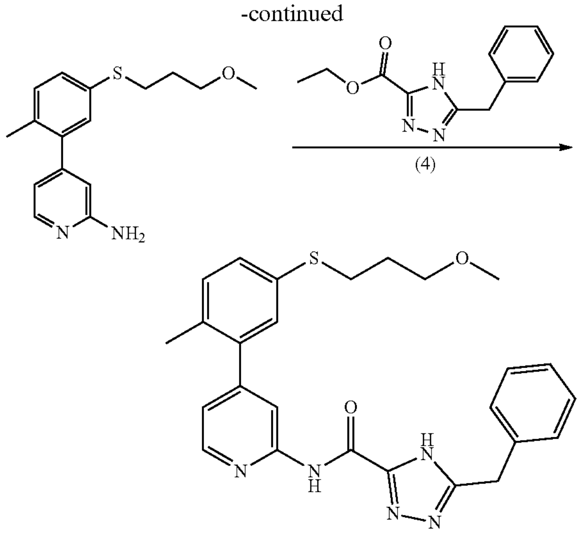

Step 1: Synthesis of 3-bromo-4-methylbenzenethiol 3-bromo-4-methylaniline (1.12 g, 6 mmol) was dissolved in 6M hydrochloric acid solution, and at −10° C., an aqueous solution (6 mL) of sodium nitrite (1.04 g, 15 mmol) was slowly added dropwise. After reacting for 30 minutes, this mixture was added dropwise to an aqueous solution (15 mL) of potassium ethylxanthate (3.36 g, 21 mmol), reacted at 80° C. for 20 minutes, and then cooled. The reaction solution was diluted with water, extracted with ether, the organic phase was dried over anhydrous sodium sulfate, filtered and evaporated to dryness. The crude product was dissolved in ethanol (30 mL), and potassium hydroxide (3.36 g, 60 mmol) in water (10 mL) was added dropwise at 0° C., and reacted at 50° C. for 3 hours. The reaction solution was concentrated, diluted with water, adjusted to pH 4 with 6M hydrochloric acid, and extracted with ether. The organic phase was dried over anhydrous sodium sulfate, filtered and evaporated to dryness to afford 1 g of crude product. MS: 203 $[M+H]^+$.

Step 2 to Step 4: Synthesis of 5-benzyl-N-(4-(5-((3-methoxypropyl)thio)-2-methylphenyl)pyridin-2-yl)-4H-1,2,4-triazole-3-carboxamide The operation is the same as steps 4 to 6 of Example 55, but 3-bromo-4-methylbenzenethiol was used in place of 3-bromo-N,4-dimethylaniline in the fourth step, and 1-bromo-3-methoxypropane was used in place of 1-bromo-2-methoxyethane in the fourth step. $^1$H NMR (400 MHz, DMSO-$d_6$) δ 14.59 (s, 1H), 9.92 (s, 1H), 8.43 (d, J=5.1 Hz, 1H), 8.10 (s, 1H), 7.41-7.29 (m, 6H), 7.29-7.13 (m, 3H), 4.18 (s, 2H), 3.40 (t, J=6.1 Hz, 2H), 3.19 (s, 3H), 3.00 (t, J=7.2 Hz, 2H), 2.23 (s, 3H), 1.84-1.72 (m, 2H). MS: 474 $[M+H]^+$.

Example 60: 5-benzyl-N-(3-methoxy-6-methyl-[2,4'-bipyridin]-2'-yl)-4H-1,2,4-triazole-3-carboxamide

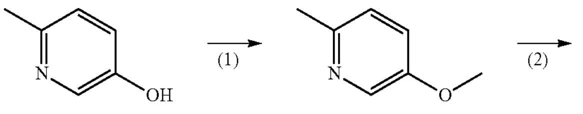

-continued

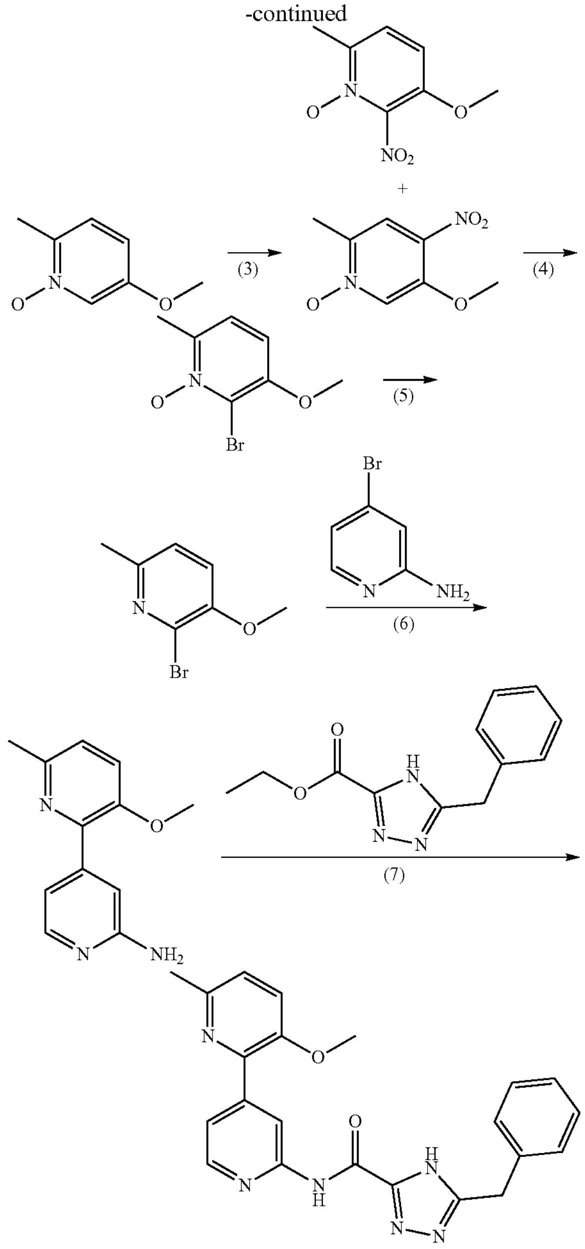

Step 1: Synthesis of 5-methoxy-2-methylpyridine

The operation is the same as step 4 of Example 55, but iodomethane was used in place of 1-bromo-2-methoxyethane, and reacted at 50° C. in sealed tube. MS: 124 $[M+H]^+$.

Step 2 to Step 5: Synthesis of 2-bromo-3-methoxy-6-methylpyridine

Synthesis was made with reference to the method in Gonzalez, Javier et al/PCT Int. Appl., 2006018725, 23 Feb. 2006. In the third step, the separated 3-methoxy-6-methyl-2-nitropyridine N-oxide was used for the subsequent reaction.

Step 6 and 7: The preparation was carried out in a similar manner to Example 33, except that in step 1, 2-bromo-3-methoxy-6-methylpyridine was used in place of 2-bromo-4-fluoro-1-methylbenzene. $^1$H NMR (400 MHz, DMSO-$d_6$) δ 14.62 (s, 1H), 9.82 (s, 1H), 8.71 (s, 1H), 8.41 (d, J=5.3 Hz, 1H), 7.68 (dd, J=5.3, 1.5 Hz, 1H), 7.58 (d, J=8.5 Hz, 1H), 7.40-7.29 (m, 5H), 7.29-7.22 (m, 1H), 4.18 (s, 2H), 3.87 (s, 3H), 3.33 (s, 3H). MS: 401 [M+H]$^+$.

Example 61: 5-benzyl-N-(5'-methoxy-2'-methyl-[4,4'-bipyridin]-2-yl)-4H-1,2,4-triazole-3-carboxamide The operation is the same as step of Example 60, but 5-methoxy-2-methyl-4-nitropyridine N-oxide separated in the third step was used for the subsequent reaction. $^1$H NMR (400 MHz, DMSO-$d_6$) δ 14.61 (s, 1H), 9.93 (s, 1H), 8.46 (d, J=5.2 Hz, 1H), 8.41 (s, 1H), 8.36 (s, 1H), 7.43-7.33 (m, 5H), 7.33-7.26 (m, 2H), 4.21 (s, 2H), 3.92 (s, 3H), 2.50 (s, 3H). MS: 401 [M+H]$^+$.

Example 61

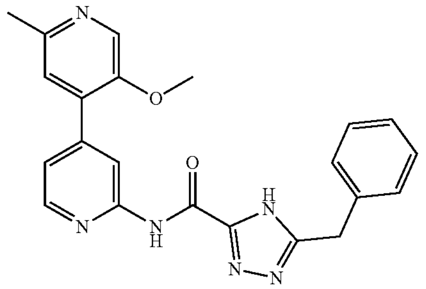

Example 62

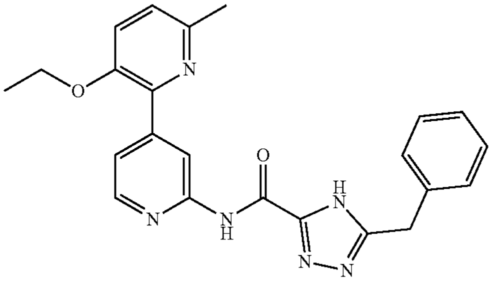

Example 62: 5-benzyl-N-(3-ethoxy-6-methyl-[2,4'-bipyridin]-2'-yl)-4H-1,2,4-triazole-3-carboxamide The operation is the same as Example 60, but bromoethane was used in place of iodomethane in the first step, and in the third step, the nitration process only gets 3-ethoxy-6-methyl-2-nitropyridine N-oxide. $^1$H NMR (400 MHz, DMSO-$d_6$) δ 14.70 (s, 1H), 9.80 (s, 1H), 8.84 (s, 1H), 8.41 (d, J=5.3 Hz, 1H), 7.74 (dd, J=5.3, 1.5 Hz, 1H), 7.55 (d, J=8.5 Hz, 1H), 7.39-7.29 (m, 5H), 7.29-7.22 (m, 1H), 4.25-4.08 (m, 4H), 2.48 (s, 3H), 1.39 (t, J=6.9 Hz, 3H). MS: 415 [M+H]$^+$.

Example 63: 5-benzyl-N-(2'-ethyl-5'-methoxy-[4,4'-bipyridin]-2-yl)-4H-1,2,4-triazole-3-carboxamide

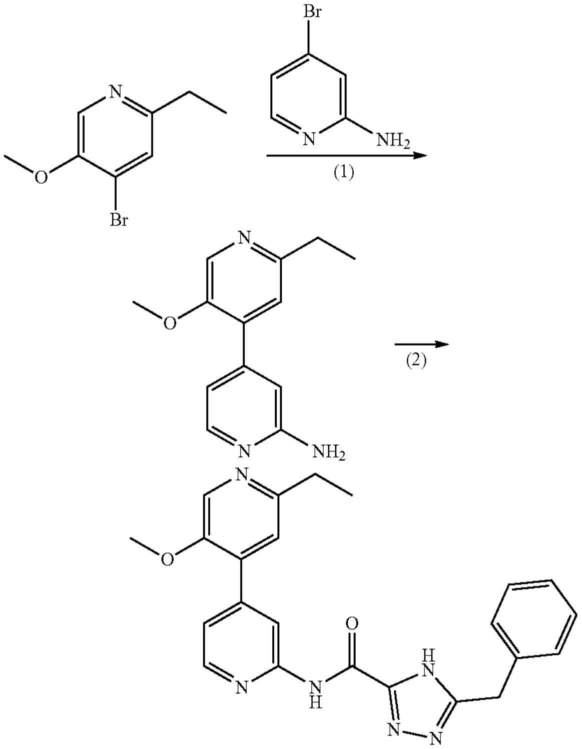

The preparation was carried out in a similar manner to Example 33, except that in step 1, 4-bromo-2-ethyl-5-methoxypyridine (see Gonzalez, Javier et al/PCT Int. Appl., 2006018725, 23 Feb. 2006 for its synthetic method) was used in place of 2-bromo-4-fluoro-1-methylbenzene. $^1$H NMR (400 MHz, DMSO-$d_6$) δ 14.66 (s, 1H), 9.93 (s, 1H), 8.50-8.38 (m, 2H), 8.33 (d, J=1.4 Hz, 1H), 7.43-7.30 (m, 5H), 7.30-7.21 (m, 2H), 4.18 (s, 2H), 3.90 (s, 3H), 2.76 (q, J=7.6 Hz, 2H), 1.24 (t, J=7.6 Hz, 3H). MS: 415 [M+H]$^+$.

Example 64: 5-benzyl-N-(4-(5-(2-(tert-butoxy)ethoxy)-2-methylphenyl)pyridin-2-yl)-4H-1,2,4-triazole-3-carboxamide

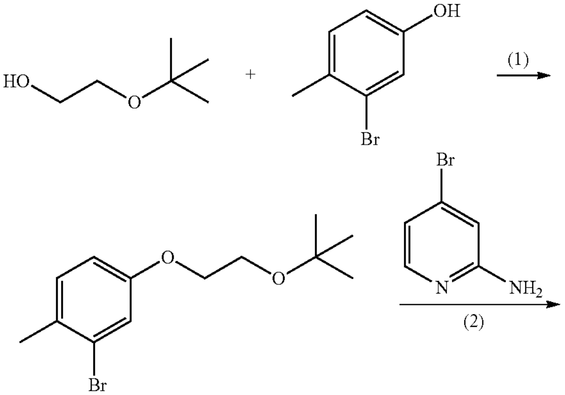

-continued

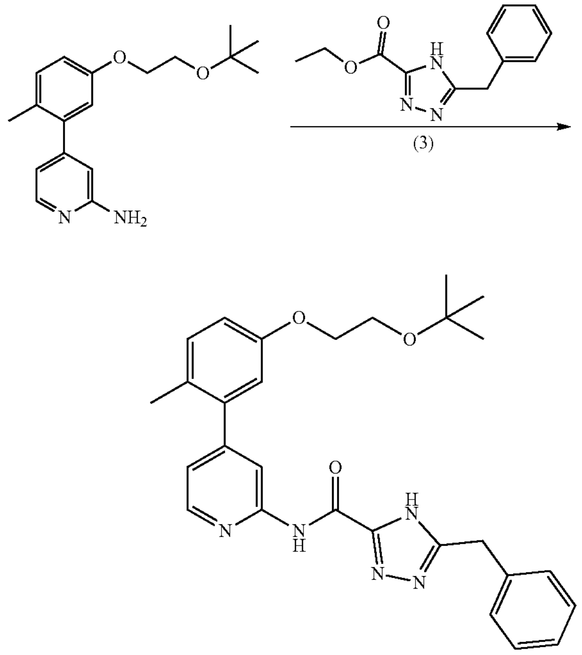

Step 1: Synthesis of 2-bromo-4-(2-(tert-butoxy) ethoxy)-1-methylbenzene

3-Bromo-4-methylphenol (187 mg, 1 mmol), 2-(tert-butoxy)ethan-1-ol (142 mg, 1.2 mmol) and triphenylphosphine (393 mg, 1.5 mmol) were placed in anhydrous tetrahydrofuran (3 mL), diisopropyl azodicarboxylate (303 mg, 1.5 mmol) was added dropwise under argon protection at 0° C., and after the addition, reacted at 25° C. for 16 hours. The reaction solution was evaporated to dryness and purified by column chromatography to afford 230 mg of colorless oil. MS: 287 $[M+H]^+$.

Step 2 to Step 3: The preparation was carried out in a similar manner to Example 33, except that in step 1, 2-bromo-4-(2-(tert-butoxy)ethoxy)-1-methylbenzene was used in place of 2-bromo-4-fluoro-1-methylbenzene. $^1$H NMR (400 MHz, DMSO-$d_6$) δ 14.59 (s, 1H), 9.90 (s, 1H), 8.48-8.37 (m, 1H), 8.12 (s, 1H), 7.41-7.29 (m, 4H), 7.29-7.18 (m, 3H), 6.94 (dd, J=8.4, 2.7 Hz, 1H), 6.83 (d, J=2.7 Hz, 1H), 4.18 (s, 2H), 4.12-3.99 (m, 2H), 3.69-3.58 (m, 2H), 2.19 (s, 3H), 1.15 (s, 9H). MS: 486 $[M+H]^+$.

Example 65: 5-benzyl-N-(4-(2-methyl-5-((tetrahydro-2H-pyran-4-yl)oxy)phenyl)pyridin-2-yl)-4H-1,2,4-triazole-3-carboxamide The preparation was carried out in a similar manner to Example 64, except that in step 1, tetrahydro-2H-pyran-4-ol was used in place of 2-(tert-butoxy)ethan-1-ol. $^1$H NMR (400 MHz, DMSO-$d_6$) δ 14.58 (s, 1H), 9.89 (s, 1H), 8.42 (d, J=5.1 Hz, 1H), 8.11 (s, 1H), 7.40-7.29 (m, 4H), 7.29-7.14 (m, 3H), 6.99 (dd, J=8.5, 2.7 Hz, 1H), 6.87 (d, J=2.6 Hz, 1H), 4.65-4.54 (m, 1H), 4.20 (s, 2H), 3.89-3.76 (m, 2H), 3.52-3.41 (m, 2H), 2.18 (s, 3H), 2.02-1.88 (m, 2H), 1.66-1.50 (m, 2H). MS: 470 $[M+H]^+$.

Example 65

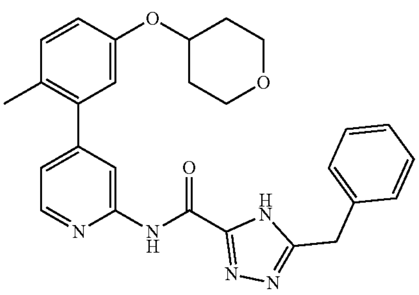

Example 66

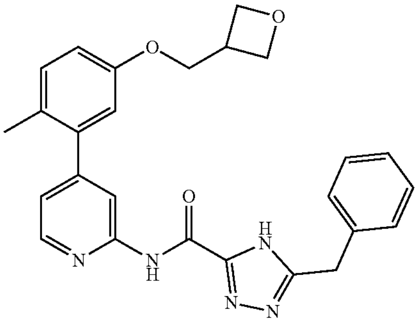

Example 66: 5-benzyl-N-(4-(2-methyl-5-(oxetan-3-ylmethoxy)phenyl)pyridin-2-yl)-4H-1,2,4-triazole-3-carboxamide The preparation was carried out in a similar manner to Example 64, except that in step 1, oxetan-3-yl methanol was used in place of 2-(tert-butoxy)ethan-1-ol. $^1$H NMR (400 MHz, DMSO-$d_6$) δ 14.58 (s, 1H), 9.89 (s, 1H), 8.42 (d, J=5.1 Hz, 1H), 8.12 (s, 1H), 7.45-7.14 (m, 7H), 6.97 (dd, J=8.4, 2.8 Hz, 1H), 6.86 (d, J=2.7 Hz, 1H), 4.78-4.64 (m, 2H), 4.48-4.36 (m, 2H), 4.22 (d, J=6.8 Hz, 2H), 4.18 (s, 2H), 3.46-3.34 (m, 1H), 2.20 (s, 3H). MS: 456 $[M+H]^+$.

Example 67: 5-benzyl-N-(4-(2-methyl-5-((tetrahydro-2H-pyran-4-yl)methoxy)phenyl)pyridin-2-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol. $^1$H NMR (400 MHz, DMSO-$d_6$) δ 14.59 (s, 1H), 9.91 (s, 1H), 8.42 (d, J=5.1 Hz, 1H), 8.11 (s, 1H), 7.42-7.29 (m, 4H), 7.29-7.12 (m, 3H), 6.94 (dd, J=8.4, 2.7 Hz, 1H), 6.82 (d, J=2.7 Hz, 1H), 4.18 (s, 2H), 3.92-3.79 (m, 4H), 3.33-3.27 (m, 2H), 2.19 (s, 3H), 2.05-1.90 (m, 1H), 1.72-1.62 (m, 2H), 1.38-1.23 (m, 2H). MS: 484 $[M+H]^+$.

Example 67

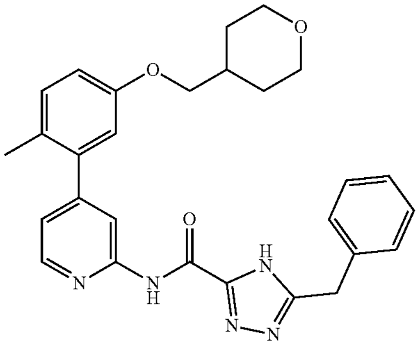

Example 68

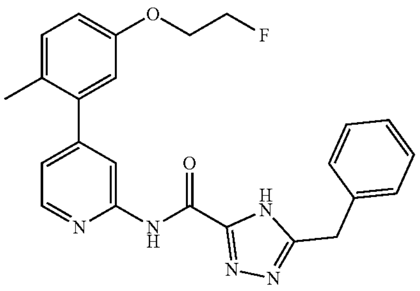

Example 68: 5-benzyl-N-(4-(5-(2-fluoroethoxy)-2-methylphenyl)pyridin-2-yl)-4H-1,2,4-triazole-3-carboxamide The preparation was carried out in a similar manner to Example 64, except that in step 1, 2-fluoro-1-ethanol was used in place of 2-(tert-butoxy)ethan-1-ol. $^{1}H$ NMR (400 MHz, DMSO-$d_6$) δ 14.64 (s, 1H), 9.93 (s, 1H), 8.42 (d, J=5.1 Hz, 1H), 8.12 (d, J=1.5 Hz, 1H), 7.44-7.14 (m, 7H), 6.98 (dd, J=8.4, 2.8 Hz, 1H), 6.87 (d, J=2.7 Hz, 1H), 4.84-4.75 (m, 1H), 4.72-4.61 (m, 1H), 4.33-4.26 (m, 1H), 4.26-4.20 (m, 1H), 4.18 (s, 2H), 2.20 (s, 3H). MS: 432 $[M+H]^+$.

Example 69: 5-benzyl-N-(4-(5-(2-cyclopropyl-ethoxy)-2-methylphenyl)pyridin-2-yl)-4H-1,2,4-triazole-3-carboxamide The preparation was carried out in a similar manner to Example 64, except that in step 1, 2-cyclopropyl-1-ethanol was used in place of 2-(tert-butoxy)ethan-1-ol. $^{1}H$ NMR (400 MHz, DMSO-$d_6$) δ 14.60 (s, 1H), 9.90 (s, 1H), 8.42 (d, J=5.0 Hz, 1H), 8.12 (s, 1H), 7.39-7.30 (m, 4H), 7.30-7.19 (m, 3H), 6.94 (dd, J=8.4, 2.7 Hz, 1H), 6.82 (d, J=2.7 Hz, 1H), 4.18 (s, 2H), 4.03 (t, J=6.6 Hz, 2H), 2.19 (s, 3H), 1.69-1.55 (m, 2H), 0.89-0.75 (m, 1H), 0.50-0.37 (m, 2H), 0.20-0.06 (m, 2H). MS: 454 $[M+H]^+$.

Example 69

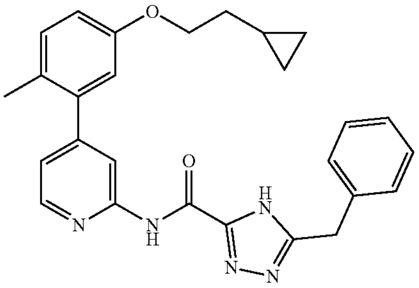

Example 70

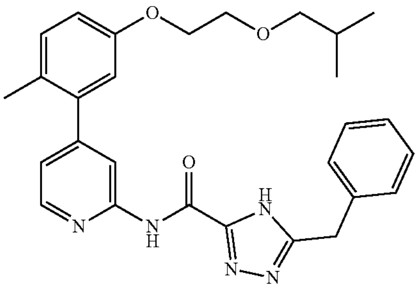

Example 70: 5-benzyl-N-(4-(5-(2-isobutoxyethoxy)-2-methylphenyl)pyridin-2-yl)-4H-1,2,4-triazole-3-carboxamide The preparation was carried out in a similar manner to Example 64, except that in step 1, 2-isobutoxy-1-ethanol was used in place of 2-(tert-butoxy)ethan-1-ol. $^{1}H$ NMR (400 MHz, DMSO-$d_6$) δ 14.57 (s, 1H), 9.89 (s, 1H), 8.42 (d, J=5.1 Hz, 1H), 8.12 (s, 1H), 7.45-7.15 (m, 7H), 6.95 (dd, J=8.4, 2.8 Hz, 1H), 6.84 (d, J=2.7 Hz, 1H), 4.18 (s, 2H), 4.15-4.06 (m, 2H), 3.74-3.61 (m, 2H), 3.21 (d, J=6.6 Hz, 2H), 2.19 (s, 3H), 1.88-1.68 (m, 1H), 0.84 (d, J=6.7, 2.5 Hz, 6H). MS: 486 $[M+H]^+$.

Example 71: 5-benzyl-N-(4-(2-methyl-5-(2-(2-oxopyrrolidin-1-yl)ethoxy)phenyl)pyridin-2-yl)-4H-1,2,4-triazole-3-carboxamide The preparation was carried out in a similar manner to Example 64, except that in step 1, 1-(2-hydroxyethyl)pyrrolidin-2-one was used in place of 2-(tert-butoxy)ethan-1-ol. $^{1}H$ NMR (400 MHz, DMSO-$d_6$) δ 14.54 (s, 1H), 9.91 (s, 1H), 8.42 (d, J=5.1 Hz, 1H), 8.11 (s, 1H), 7.41-7.29 (m, 4H), 7.29-7.23 (m, 2H), 7.21 (dd, J=5.0, 1.6 Hz, 1H), 6.95 (dd, J=8.4, 2.7 Hz, 1H), 6.84 (d, J=2.7 Hz, 1H), 4.17 (s, 2H), 4.09 (t, J=5.5 Hz, 2H), 3.53 (t, J=5.5 Hz, 2H), 3.45 (t, J=7.0 Hz, 2H), 2.26-2.13 (m, 5H), 1.95-1.83 (m, 2H). MS: 497 $[M+H]^+$.

Example 71

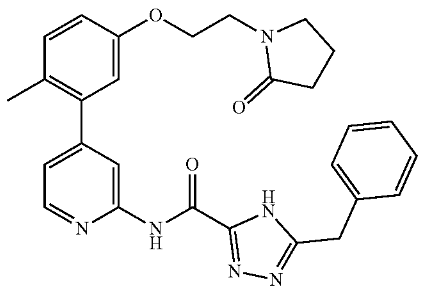

Example 72

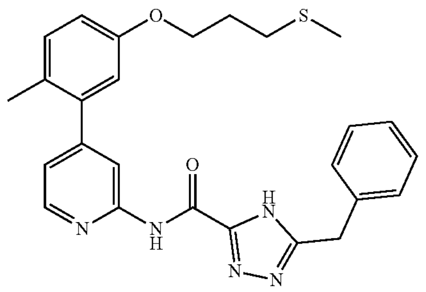

Example 72: 5-benzyl-N-(4-(2-methyl-5-(3-(methylthio)propoxy)phenyl)pyridin-2-yl)-4H-1,2,4-triazole-3-carboxamide The preparation was carried out in a similar manner to Example 64, except that in step 1, 3-(methylthio)-1-propanol was used in place of 2-(tert-butoxy)ethan-1-ol. $^1$H NMR (400 MHz, DMSO-$d_6$) δ 14.58 (s, 1H), 9.90 (s, 1H), 8.42 (d, J=5.0 Hz, 1H), 8.11 (s, 1H), 7.42-7.29 (m, 4H), 7.29-7.23 (m, 2H), 7.21 (dd, J=5.1, 1.6 Hz, 1H), 6.95 (dd, J=8.4, 2.7 Hz, 1H), 6.83 (d, J=2.7 Hz, 1H), 4.18 (s, 2H), 4.06 (t, J=6.2 Hz, 2H), 2.61 (t, J=7.2 Hz, 2H), 2.19 (s, 3H), 2.05 (s, 3H), 2.02-1.90 (m, 2H). MS: 474 $[M+H]^+$.

Example 73: 5-benzyl-N-(4-(2-methyl-5-(3-(methylsulfonyl)propoxy)phenyl)pyridin-2-yl)-4H-1,2,4-triazole-3-carboxamide The preparation was carried out in a similar manner to Example 64, except that in step 1, 3-(methylsulfonyl)-1-propanol was used in place of 2-(tert-butoxy)ethan-1-ol. $^1$H NMR (400 MHz, DMSO-$d_6$) δ 14.56 (s, 1H), 9.88 (s, 1H), 8.42 (d, J=5.1 Hz, 1H), 8.12 (s, 1H), 7.41-7.15 (m, 7H), 6.96 (dd, J=8.4, 2.7 Hz, 1H), 6.85 (d, J=2.7 Hz, 1H), 4.18 (s, 2H), 4.11 (t, J=6.2 Hz, 2H), 3.31-3.23 (m, 2H), 3.01 (s, 3H), 2.20 (s, 3H), 2.17-2.05 (m, 2H). MS: 506 $[M+H]^+$.

Example 73

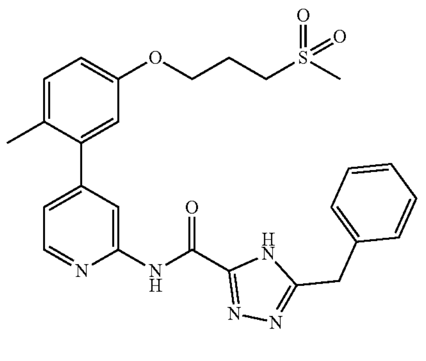

Example 74

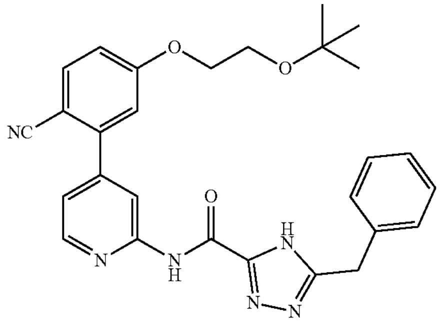

Example 74: 5-benzyl-N-(4-(5-(2-(tert-butoxy)ethoxy-2-cyanophenyl)pyridin-2-yl)-4H-1,2,4-triazole-3-carboxamide The preparation was carried out in a similar manner to Example 64, except that in step 1, 2-chloro-4-hydroxybenzonitrile was used in place of 3-bromo-4-methylphenol. $^1$H NMR (400 MHz, DMSO-$d_6$) δ 14.65 (s, 1H), 10.02 (s, 1H), 8.52 (d, J=5.1 Hz, 1H), 8.34 (s, 1H), 7.94 (d, J=9.2 Hz, 1H), 7.42 (d, J=4.9 Hz, 1H), 7.39-7.30 (m, 4H), 7.30-7.18 (m, 3H), 4.23 (t, J=4.6 Hz, 2H), 4.18 (s, 2H), 3.67 (t, J=4.7 Hz, 2H), 1.15 (s, 9H). MS: 497 $[M+H]^+$.

Example 75: N-(4-(5-(2-(tert-butoxy)ethoxy)-2-methylphenyl)pyridin-2-yl)-5-(cyclopentylmethyl)-4H-1,2,4-triazole-3-carboxamide The preparation was carried out in a similar manner to Example 64, except that in step 3, ethyl 5-(cyclopentylmethyl)-4H-1,2,4-triazole-3-carboxylate was used in place of ethyl 5-benzyl-4H-1,2,4-triazol-3-carboxylate. $^1$H NMR (400 MHz, DMSO-$d_6$) δ 14.40 (s, 1H), 9.86 (s, 1H), 8.42 (d, J=5.1 Hz, 1H), 8.14 (s, 1H), 7.32-7.13 (m, 2H), 6.95 (dd, J=8.4, 2.8 Hz, 1H), 6.84 (d, J=2.7 Hz, 1H), 4.09-4.00 (m, 2H), 3.67-3.57 (m, 2H), 2.78 (d, J=7.5 Hz, 2H), 2.39-2.22 (m, 1H), 2.20 (s, 3H), 1.80-1.66 (m, 2H), 1.66-1.44 (m, 4H), 1.29-1.17 (m, 2H), 1.15 (s, 9H). MS: 478 $[M+H]^+$.

Example 75

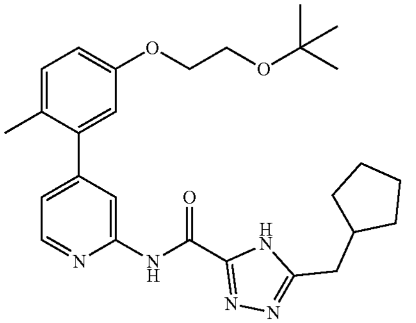

Example 76

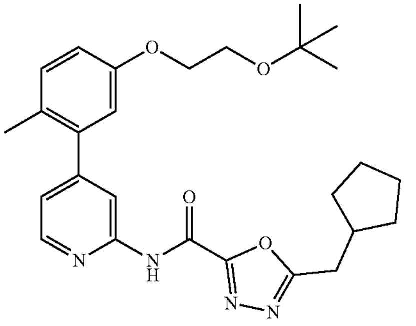

Example 76: N-(4-(5-(2-(tert-butoxy)ethoxy)-2-methylphenyl)pyridin-2-yl)-5-(cyclohexylmethyl)-1,3,4-oxadiazol-2-carboxamide The preparation was carried out in a similar manner to Example 64, except that in step 3, ethyl 5-(cyclopentylmethyl)-1,3,4-oxadiazol-2-carboxylate was used in place of ethyl 5-benzyl-4H-1,2,4-triazol-3-carboxylate. $^1$H NMR (400 MHz, DMSO-$d_6$) δ 11.24 (s, 1H), 8.48 (d, J=5.0 Hz, 1H), 7.99 (s, 1H), 7.33-7.20 (m, 2H), 6.95 (dd, J=8.4, 2.7 Hz, 1H), 6.83 (d, J=2.7 Hz, 1H), 4.10-3.99 (m, 2H), 3.67-3.58 (m, 2H), 2.97 (d, J=7.4 Hz, 2H), 2.37-2.24 (m, 1H), 2.20 (s, 3H), 1.86-1.73 (m, 2H), 1.70-1.44 (m, 4H), 1.33-1.18 (m, 2H), 1.15 (s, 9H). MS: 479 [M+H]$^+$.

Example 77: N-(4-(5-(2-(tert-butoxy)ethoxy)-2-methylphenyl)pyridin-2-yl)-5-(cyclohexylmethyl)-4H-1,2,4-triazole-3-carboxamide

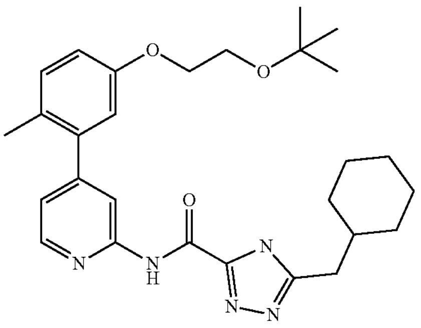

The preparation was carried out in a similar manner to Example 64, except that in step 3, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.38 (s, 1H), 9.93-9.76 (m, 1H), 8.42 (d, J=5.1 Hz, 1H), 8.14 (s, 1H), 7.32-7.15 (m, 2H), 6.94 (dd, J=8.5, 2.7 Hz, 1H), 6.83 (d, J=2.7 Hz, 1H), 4.04 (t, J=4.8 Hz, 2H), 3.63 (t, J=4.9 Hz, 2H), 2.66 (d, J=7.0 Hz, 2H), 2.20 (s, 3H), 1.83-1.53 (m, 6H), 1.30-1.06 (m, 12H), 1.06-0.88 (m, 2H). MS: 492 [M+H]$^+$.

Example 78: 5-benzyl-N-(4-(5-(2-(tert-butoxy)ethoxy)-2-vinylphenyl)pyridin-2-yl)-4H-1,2,4-triazole-3-carboxamide

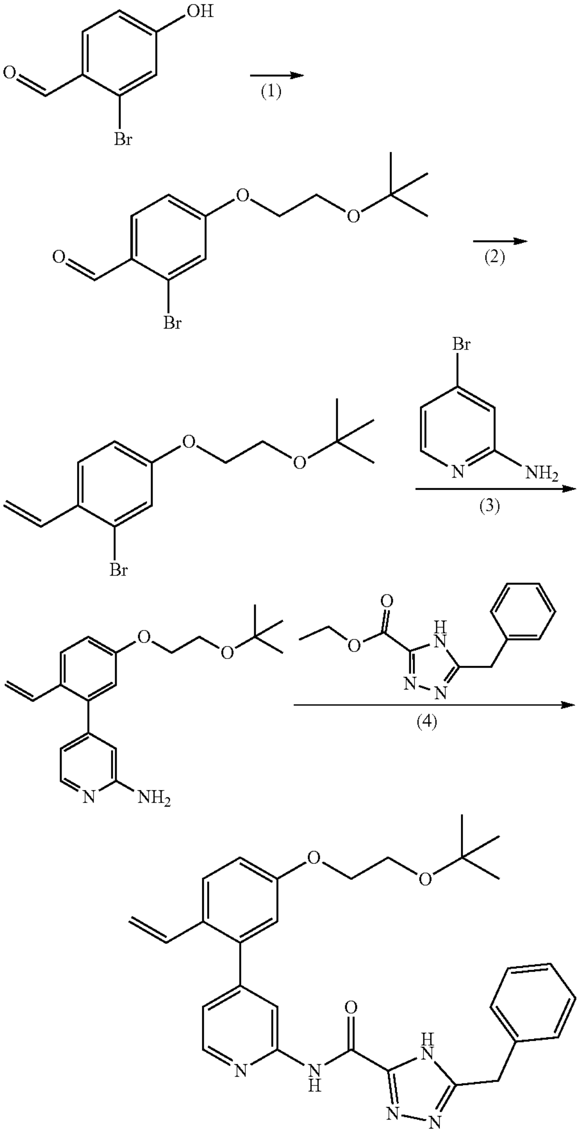

Step 1: Synthesis of 2-bromo-4-(2-(tert-butoxy)ethoxy)benzaldehyde

The operation is the same as step 1 of Example 64, but 2-bromo-4-hydroxybenzaldehyde was used in place of 2-bromo-3-methylphenol in step 1.

Step 2: Synthesis of 2-bromo-4-(2-(tert-butoxy)ethoxy)-1-vinylbenzene

Methyltriphenylphosphonium bromide (1.25 g, 3.5 mmol) was placed in anhydrous tetrahydrofuran (7 mL), and n-butyl lithium was added dropwise at −20° C. under argon protection. After reacting at 0° C. for 1 hour, 2-bromo-4-(2-(tert-butoxy)ethoxy)benzaldehyde (700 mg, 2.3 mmol) in anhydrous tetrahydrofuran (2.5 mL) solution was added, heated to 25° C. and reacted for 5 hours. The reaction solution was quenched with saturated ammonium chloride, extracted with ethyl acetate, dried over anhydrous sodium sulfate, filtered and evaporated to dryness, and the crude product was directly used in the next step.

Step 3 to Step 4: The preparation was carried out in a similar manner to Example 33, except that in step 1, 2-bromo-4-(2-(tert-butoxy)ethoxy)-1-vinylbenzene was used in place of 2-bromo-4-fluoro-1-methylbenzene. $^1$H NMR (400 MHz, DMSO-$d_6$) δ 14.54 (s, 1H), 9.92 (s, 1H), 8.43 (d, J=5.1 Hz, 1H), 8.11 (s, 1H), 7.69 (d, J=8.7 Hz, 1H), 7.38-7.30 (m, 4H), 7.29-7.22 (m, 1H), 7.17 (dd, J=5.0, 1.5 Hz, 1H), 7.06 (dd, J=8.7, 2.6 Hz, 1H), 6.88 (d, J=2.6 Hz, 1H), 6.55 (dd, J=17.4, 11.0 Hz, 1H), 5.71 (d, J=17.4 Hz, 1H), 5.15 (d, J=11.1 Hz, 1H), 4.17 (s, 2H), 4.10 (t, J=4.8 Hz, 2H), 3.64 (dd, J=5.6, 4.0 Hz, 2H), 1.15 (s, 9H). MS: 498 [M+H]$^+$.

Example 79: 5-(cyclopentylmethyl)-N-(4-(2-methyl-5-((tetrahydro-2H-pyran-4-yl)methoxy)phenyl)pyridin-2-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, and in step 3, ethyl 5-(cyclopentylmethyl)-4H-1,2,4-triazole-3-carboxylate was used in place of ethyl 5-benzyl-4H-1,2,4-triazol-3-carboxylate. $^1$H NMR (400 MHz, DMSO-$d_6$) δ 14.41 (s, 1H), 9.86 (s, 1H), 8.42 (d, J=5.1 Hz, 1H), 8.13 (s, 1H), 7.25 (d, J=8.5 Hz, 1H), 7.21 (dd, J=5.1, 1.6 Hz, 1H), 6.95 (dd, J=8.4, 2.7 Hz, 1H), 6.82 (d, J=2.7 Hz, 1H), 3.93-3.86 (m, 1H), 3.86-3.78 (m, 3H), 3.32-3.23 (m, 2H), 2.77 (d, J=7.4 Hz, 2H), 2.35-2.22 (m, 1H), 2.19 (s, 3H), 2.06-1.92 (m, 1H), 1.79-1.44 (m, 8H), 1.40-1.12 (m, 4H). MS: 476 [M+H]$^+$.

Example 79

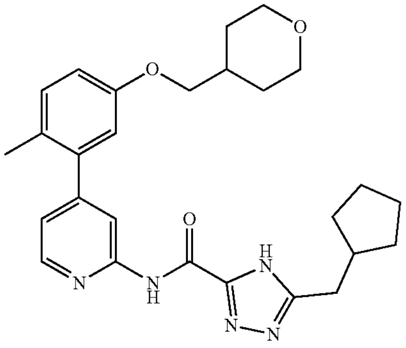

-continued

Example 80

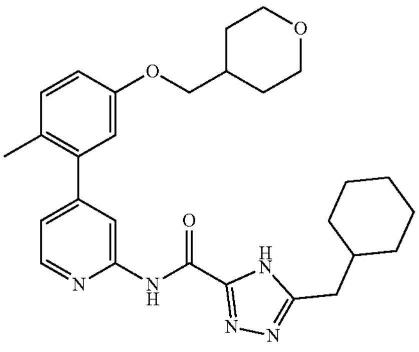

Example 80: 5-(cyclohexylmethyl)-N-(4-(2-methyl-5-((tetrahydro-2H-pyran-4-yl)methoxy)phenyl)pyridin-2-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, and in step 3, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.36 (s, 1H), 9.84 (s, 1H), 8.42 (d, J=5.1 Hz, 1H), 8.13 (s, 1H), 7.34-7.12 (m, 2H), 6.94 (dd, J=8.4, 2.7 Hz, 1H), 6.82 (d, J=2.7 Hz, 1H), 3.93-3.79 (m, 4H), 3.40-3.31 (m, 3H), 2.72-2.62 (m, 2H), 2.19 (s, 3H), 2.07-1.92 (m, 1H), 1.84-1.70 (m, 1H), 1.70-1.53 (m, 6H), 1.41-1.05 (m, 5H), 1.05-0.90 (m, 2H). MS: 490 [M+H]$^+$.

Example 81: 5-benzyl-N-(4-(5-(3-cyclobutoxypropoxy)-2-methylphenyl)pyridin-2-yl)-4H-1,2,4-triazole-3-carboxamide

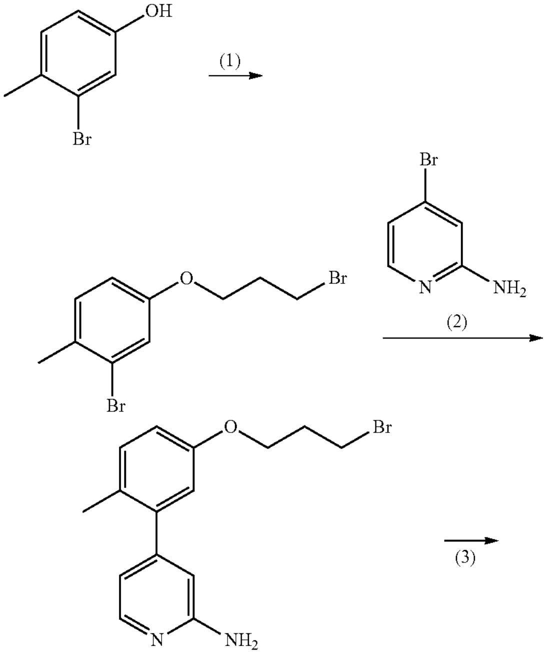

-continued

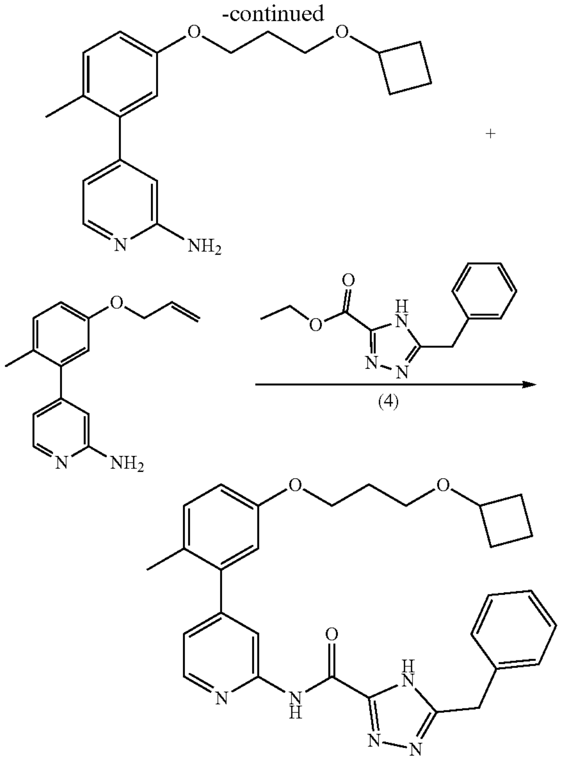

Step 1 to Step 2: Synthesis of 4-(5-(3-bromopropoxy)-2-methylphenyl)pyridin-2-amine The operation is the same as steps 1 to 2 of Example 64, but 3-bromopropyl-1-ol was used in place of 2-(tert-butoxy) ethan-1-ol in step 1.

Step 3: Synthesis of 4-(5-(3-cyclobutoxypropoxy)-2-methylphenyl)pyridin-2-amine

Cyclobutanol (115 mg, 1.6 mmol) was dissolved in anhydrous tetrahydrofuran (3 mL), and sodium hydride (60%, 65 mg, 1.6 mmol) was added under argon protection at 0° C. After 30 minutes of reaction, 4-(5-(3-bromopropoxy)-2-methylphenyl)pyridin-2-amine (200 mg, 0.6 mmol) in tetrahydrofuran was added dropwise, and reacted at 50° C. for 4 hours. The reaction was cooled, quenched with saturated ammonium chloride, the reaction solution was evaporated, and purified by column chromatography to afford 40 mg of product and 20 mg of by-product 4-(5-allyloxy)-2-methylphenyl)pyridin-2-amine. MS: 313 $[M+H]^+$ and MS: 241 $[M+H]^+$ Step 4: Synthesis of 5-benzyl-N-(4-(5-(3-cyclobutoxypropoxy)-2-methylphenyl)pyridin-2-yl)-4H-1,2,4-triazole-3-carboxamide The operation is the same as step 2 of Example 1, but 4-(5-(3-cyclobutoxypropoxy)-2-methylphenyl)pyridin-2-amine was used in place of 4-phenylpyridin-2-amine. $^1H$ NMR (400 MHz, DMSO-$d_6$) δ 14.58 (s, 1H), 9.88 (s, 1H), 8.42 (d, J=5.1 Hz, 1H), 8.11 (s, 1H), 7.49-7.30 (m, 4H), 7.30-7.17 (m, 3H), 6.94 (dd, J=8.4, 2.7 Hz, 1H), 6.82 (d, J=2.7 Hz, 1H), 4.18 (s, 2H), 4.03 (t, J=6.3 Hz, 2H), 3.93-3.81 (m, 1H), 3.42-3.39 (m, 2H), 2.19 (s, 3H), 2.16-2.06 (m, 2H), 1.96-1.85 (m, 2H), 1.85-1.71 (m, 2H), 1.66-1.53 (m, 1H), 1.50-1.36 (m, 1H). MS: 498 $[M+H]^+$.

Example 82: N-(4-(5-(allyloxy)-2-methylphenyl)pyridin-2-yl)-5-benzyl-4H-1,2,4-triazole-3-carboxamide The operation is the same as Example 81, but the by-product 4-(5-allyloxy)-2-methylphenyl)pyridin-2-amine obtained in the third step was used for the subsequent reaction. $^1H$ NMR (400 MHz, DMSO-$d_6$) δ 14.38 (s, 1H), 9.92 (s, 1H), 8.42 (d, J=5.1 Hz, 1H), 8.11 (d, J=1.5 Hz, 1H), 7.39-7.29 (m, 4H), 7.29-7.23 (m, 2H), 7.21 (dd, J=5.1, 1.6 Hz, 1H), 6.96 (dd, J=8.4, 2.8 Hz, 1H), 6.85 (d, J=2.8 Hz, 1H), 6.11-5.96 (m, 1H), 5.45-5.32 (m, 1H), 5.32-5.19 (m 1H), 4.64-4.53 (m, 2H), 4.17 (s, 2H), 2.19 (s, 3H). MS: 426 $[M+H]^+$.

Example 82

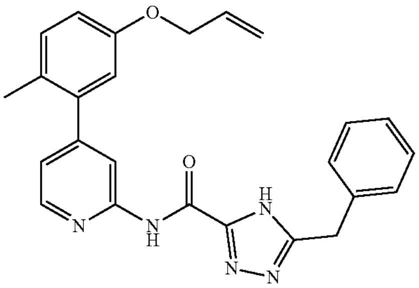

Example 83

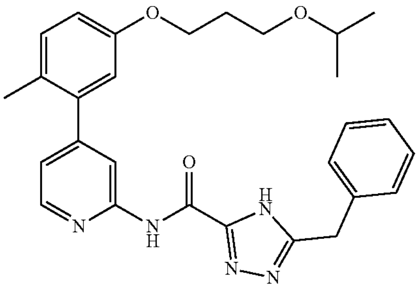

Example 83: 5-benzyl-N-(4-(5-(3-isopropoxypropoxy)-2-methylphenyl)pyridin-2-yl)-4H-1,2,4-triazole-3-carboxamide The operation is the same as Example 81, but isopropanol was used in place of cyclobutanol in the third step. $^1H$ NMR (400 MHz, DMSO-$d_6$) δ 14.57 (s, 1H), 9.89 (s, 1H), 8.41 (d, J=5.1 Hz, 1H), 8.11 (s, 1H), 7.48-7.10 (m, 7H), 6.94 (dd, J=8.4, 2.7 Hz, 1H), 6.82 (d, J=2.7 Hz, 1H), 4.18 (s, 2H), 4.03 (t, J=6.3 Hz, 2H), 3.58-3.44 (m, 3H), 2.19 (s, 3H), 1.95-1.80 (m, 2H), 1.06 (d, J=6.1 Hz, 6H). MS: 486 $[M+H]^+$.

Example 84: 5-benzyl-N-(4-(5-(2-methyl-5-(3-(2-oxopiperidin-1-yl)propoxy)phenyl)pyridin-2-yl)-4H-1,2,4-triazole-3-carboxamide

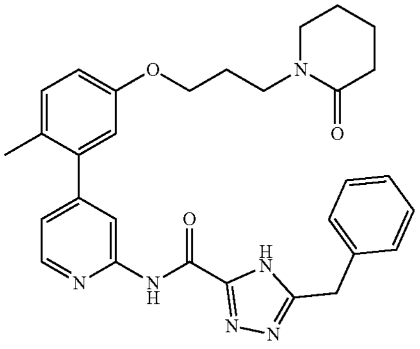 [SMILES: Cc1ccc(OCCCN2CCCCC2=O)cc1-c1ccnc(NC(=O)c2nnc(Cc3ccccc3)[nH]2)c1]

The operation is the same as Example 81, but piperidin-2-one was used in place of cyclobutanol in the third step. $^1$H NMR (400 MHz, DMSO-$d_6$) δ 14.56 (s, 1H), 9.91 (s, 1H), 8.41 (d, J=5.1 Hz, 1H), 8.11 (s, 1H), 7.46-7.11 (m, 7H), 6.93 (dd, J=8.4, 2.7 Hz, 1H), 6.81 (d, J=2.7 Hz, 1H), 4.17 (s, 2H), 3.98 (t, J=6.3 Hz, 2H), 3.28-3.20 (m, 4H), 2.26-2.13 (m, 5H), 1.91 (t, J=6.8 Hz, 2H), 1.77-1.61 (m, 4H). MS: 525 $[M+H]^+$.

Example 85: 5-benzyl-N-(4-(5-(2-(2-methoxyethoxy)ethoxy)-2-methylphenyl)pyridin-2-yl)-4H-1,2,4-triazole-3-carboxamide

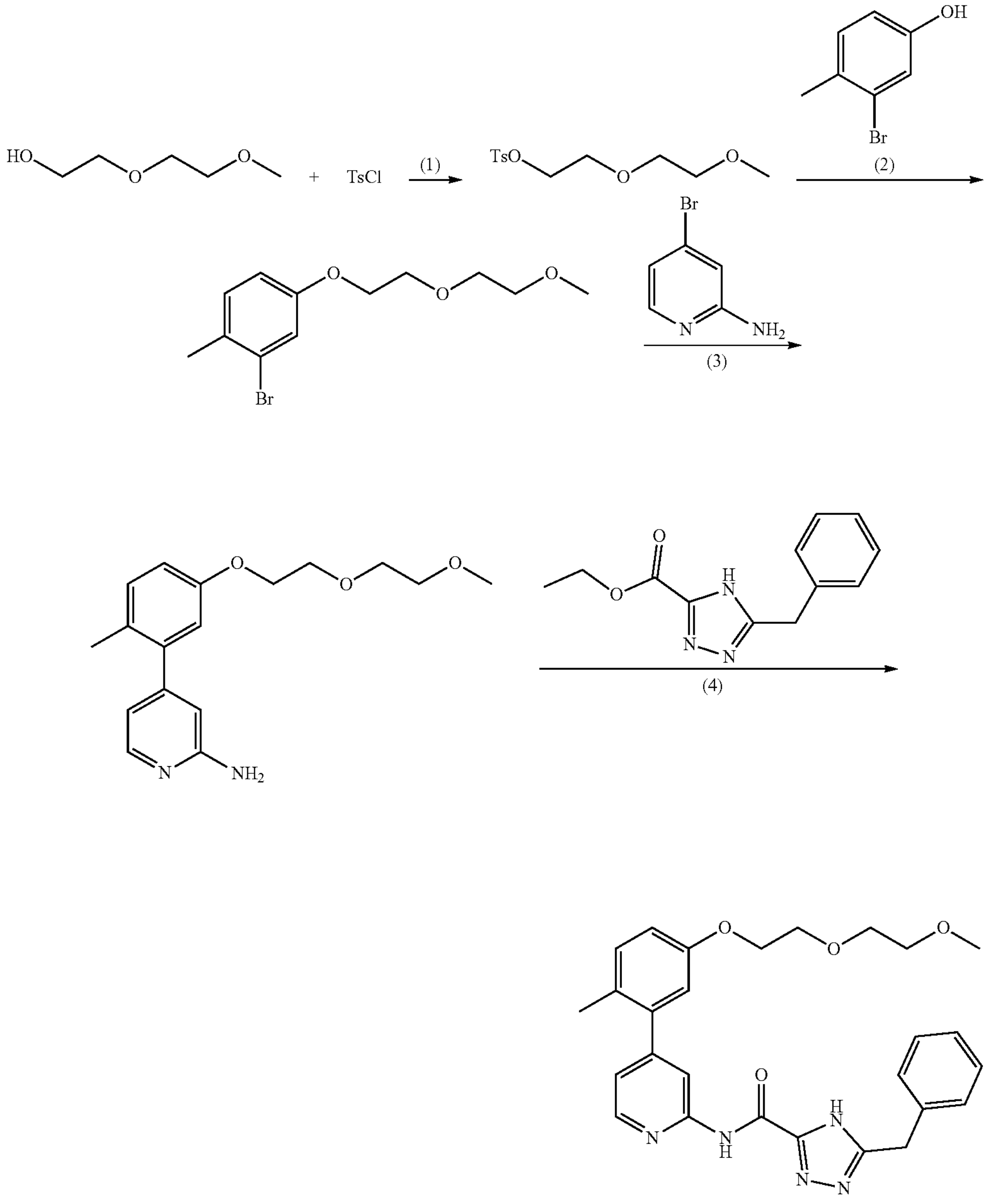

Step 1: Synthesis of 2-(2-methoxyethoxy)ethyl 4-methylbenzenesulfonate 2-(2-methoxyethoxy)ethan-1-ol (1 g, 8.3 mmol) and triethylamine (2.1 g, 20.8 mmol) were dissolved in dichloromethane (30 mL), p-toluenesulfonyl chloride (1.75 g, 9.2 mmol) was added at 0° C., and reacted at 25° C. for 2 hours. Saturated aqueous solution of sodium bicarbonate was added, extracted with dichloromethane, dried over anhydrous sodium sulfate, filtered and evaporated to dryness to afford 1.8 g of yellow oil.

Step 2 to Step 4: 5-benzyl-N-(4-(5-(2-(2-methoxyethoxy)ethoxy)-2-methylphenyl)pyridin-2-yl)-4H-1,2,4-triazole-3-carboxamide The operation is the same as steps 4 to 6 of Example 55, but 3-bromo-4-methylphenol was used in place of 3-bromo-N,4-dimethylaniline in the fourth step, 2-(2-methoxyethoxy)ethyl 4-methylbenzenesulfonate was used in place of 1-bromo-2-methoxyethane in the fourth step. $^1$H NMR (400 MHz, DMSO-$d_6$) δ 14.59 (s, 1H), 9.91 (s, 1H), 8.42 (d, J=5.1 Hz, 1H), 8.12 (d, J=1.4 Hz, 1H), 7.37-7.29 (m, 4H), 7.29-7.23 (m, 2H), 7.21 (dd, J=5.1, 1.6 Hz, 1H), 6.95 (dd, J=8.4, 2.8 Hz, 1H), 6.84 (d, J=2.7 Hz, 1H), 4.17 (s, 2H), 4.14-4.05 (m, 2H), 3.76-3.67 (m, 2H), 3.61-3.53 (m, 2H), 3.47-3.41 (m, 2H), 3.23 (s, 3H), 2.19 (s, 3H). MS: 488 $[M+H]^+$.

Example 86: 5-benzyl-N-(4-(2-methyl-5-(oxetan-3-yloxy)phenyl)pyridin-2-yl)-4H-1,2,4-triazole-3-carboxamide The preparation was carried out in a similar manner to Example 85, except that in step 1, oxetan-3-ol was used in place of 2-(2-methoxyethoxy)ethan-1-ol. $^1$H NMR (400 MHz, DMSO-$d_6$) δ 14.61 (s, 1H), 9.92 (s, 1H), 8.42 (d, J=5.1 Hz, 1H), 8.10 (s, 1H), 7.43-7.30 (m, 4H), 7.30-7.23 (m, 2H), 7.20 (dd, J=5.1, 1.5 Hz, 1H), 6.80 (dd, J=8.4, 2.7 Hz, 1H), 6.69 (d, J=2.7 Hz, 1H), 5.36-5.26 (m, 1H), 4.96-4.86 (m, 2H), 4.61-4.50 (m, 2H), 4.18 (s, 2H), 2.19 (s, 3H). MS: 442 $[M+H]^+$.

Example 86

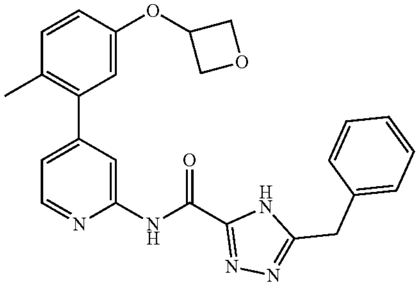

Example 87

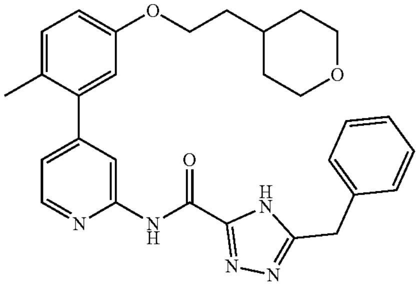

Example 87: 5-benzyl-N-(4-(2-methyl-5-(2-(tetrahydro-2H-pyran-4-yl)ethoxy)phenyl)pyridin-2-yl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol. $^1$H NMR (400 MHz, DMSO-$d_6$) δ 14.58 (s, 1H), 9.89 (s, 1H), 8.41 (d, J=5.1 Hz, 1H), 8.11 (s, 1H), 7.49-7.14 (m, 7H), 6.94 (dd, J=8.4, 2.7 Hz, 1H), 6.82 (d, J=2.7 Hz, 1H), 4.18 (s, 2H), 4.02 (t, J=6.3 Hz, 2H), 3.89-3.75 (m, 2H), 3.30-3.19 (m, 2H), 2.19 (s, 3H), 1.77-1.55 (m, 5H), 1.26-1.12 (m, 2H). MS: 498 $[M+H]^+$.

Example 88: 5-(cyclopentylmethyl)-N-(4-(2-methyl-5-(2-(tetrahydro-2H-pyran-4-yl)ethoxy)phenyl)pyridin-2-yl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, and in step 3, ethyl 5-(cyclopentylmethyl)-4H-1,2,4-triazole-3-carboxylate was used in place of ethyl 5-benzyl-4H-1,2,4-triazol-3-carboxylate. $^1$H NMR (400 MHz, DMSO-$d_6$) δ 14.37 (s, 1H), 9.84 (s, 1H), 8.42 (d, J=5.1 Hz, 1H), 8.13 (s, 1H), 7.30-7.16 (m, 2H), 6.94 (dd, J=8.4, 2.7 Hz, 1H), 6.83 (d, J=2.7 Hz, 1H), 4.09-3.98 (m, 2H), 3.88-3.76 (m, 2H), 3.32-3.21 (m, 2H), 2.85-2.72 (m, 2H), 2.36-2.22 (m, 1H), 2.19 (s, 3H), 1.79-1.45 (m, 11H), 1.31-1.14 (m, 4H). MS: 490 $[M+H]^+$.

Example 88

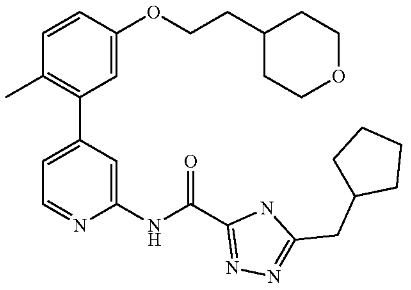

Example 89

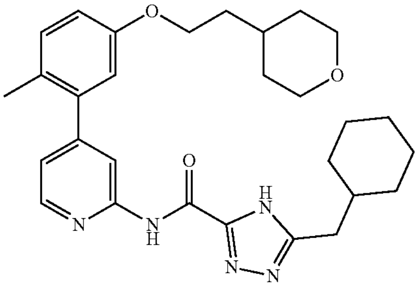

Example 89: 5-(cyclohexylmethyl)-N-(4-(2-methyl-5-(2-(tetrahydro-2H-pyran-4-yl)ethoxy)phenyl)pyridin-2-yl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, and in step 3, ethyl 5-(cyclohexylmethyl)-4H-1, 2,4-triazol-3-carboxylate was used in place of ethyl 5-benzyl-4H-1,2,4-triazol-3-carboxylate. $^1$H NMR (400 MHz, DMSO-$d_6$) δ 14.37 (s, 1H), 9.85 (s, 1H), 8.42 (d, J=5.1 Hz, 1H), 8.13 (s, 1H), 7.31-7.15 (m, 2H), 6.94 (dd, J=8.4, 2.7 Hz, 1H), 6.83 (d, J=2.7 Hz, 1H), 4.03 (t, J=6.3 Hz, 2H), 3.87-3.75 (m, 2H), 3.32-3.21 (m, 2H), 2.67 (d, J=7.0 Hz, 2H), 2.19 (s, 3H), 1.83-1.72 (m, 1H), 1.71-1.54 (m, 9H), 1.31-1.09 (m, 6H), 1.05-0.88 (m, 2H). MS: 504 $[M+H]^+$.

Example 90: 5-benzyl-N-(4-(5-((4-cyanopentyl)oxy)-2-methylphenyl)pyridin-2-yl)-4H-1,2,4-triazole-3-carboxamide

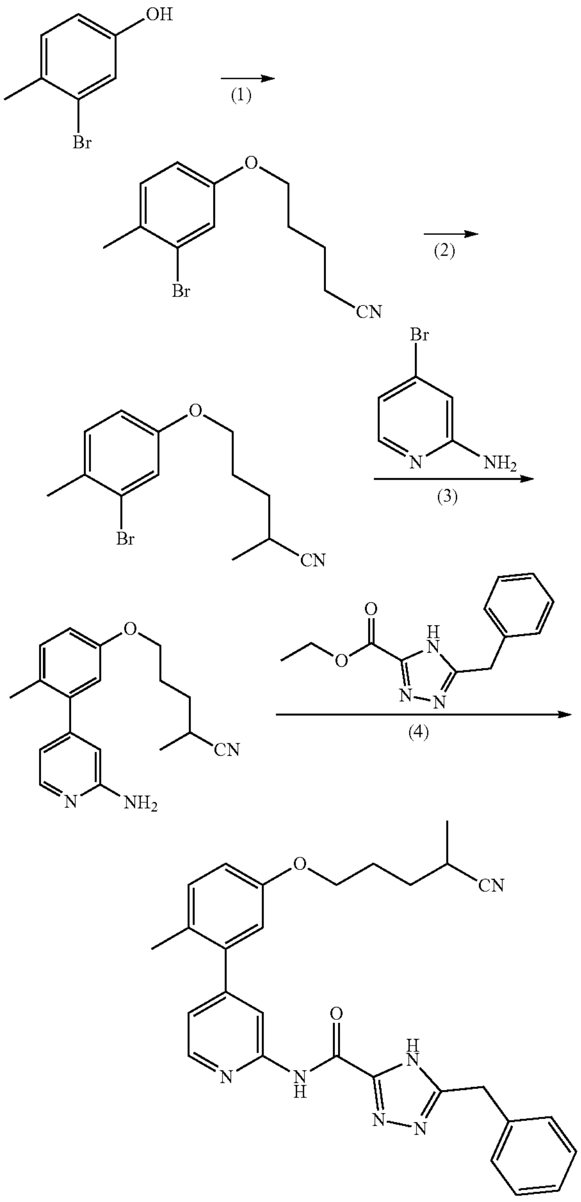

Step 1: Synthesis of 5-(3-bromo-4-methylphenoxy)valeronitrile

The operation is the same as step 4 of Example 55, but 3-bromo-4-methylphenol was used in place of 3-bromo-N,N-dimethylaniline in the fourth step, and 5-chlorovaleronitrile was used in place of 1-bromo-2-methoxyethane in the fourth step.

Step 2: Synthesis of 5-(3-bromo-4-methylphenoxy)-2-methylvaleronitrile 5-(3-Bromo-4-methylphenoxy)valeronitrile (268 mg, 1 mmol) was dissolved in anhydrous tetrahydrofuran (2 mL), and LDA (2M, 0.8 mL, 1.6 mmol) was added dropwise at −78° C. under argon protection. After reacting for 1 hour, iodomethane (215 mg, 1.5 mmol) was added dropwise at the same temperature, the reaction was gradually warmed to 25° C., and reacted for 16 hours. The reaction was quenched with saturated ammonium chloride, extracted with ethyl acetate, washed with saturated brine, dried over anhydrous sodium sulfate, filtered and dried, and purified by column chromatography to afford 210 mg of product.

Step 3 to Step 4: The preparation was carried out in a similar manner to Example 33, except that in step 1, 5-(3-bromo-4-methylphenoxy)-2-methylvaleronitrile was used in place of 2-bromo-4-fluoro-1-methylbenzene. $^1$H NMR (400 MHz, DMSO-$d_6$) δ 14.63 (s, 1H), 9.91 (s, 1H), 8.42 (d, J=5.1 Hz, 1H), 8.11 (s, 1H), 7.47-7.16 (m, 7H), 6.95 (dd, J=8.4, 2.7 Hz, 1H), 6.83 (d, J=2.7 Hz, 1H), 4.18 (s, 2H), 4.02 (t, J=6.2 Hz, 2H), 2.99-2.84 (m, 1H), 2.19 (s, 3H), 1.93-1.74 (m, 2H), 1.74-1.60 (m, 2H), 1.24 (d, J=7.0 Hz, 3H). MS: 481 $[M+H]^+$.

Example 91: 5-benzyl-N-(4-(5-(4-cyanobutoxy)-2-methylphenyl)pyridin-2-yl)-4H-1,2,4-triazole-3-carboxamide

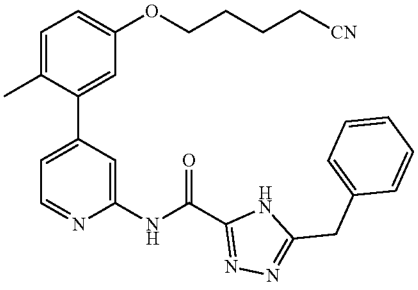 [SMILES: Cc1ccc(OCCCCC#N)cc1-c1ccnc(NC(=O)c2nnc(Cc3ccccc3)[nH]2)c1]

The operation is the same as step of Example 90, but the product of the first step 5-(3-bromo-4-methylphenoxy)valeronitrile was used directly to carry out the third to fourth step reaction. $^1$H NMR (400 MHz, DMSO-$d_6$) δ 14.47 (s, 1H), 9.91 (s, 1H), 8.42 (d, J=5.0 Hz, 1H), 8.11 (d, J=1.4 Hz, 1H), 7.41-7.30 (m, 4H), 7.29-7.18 (m, 3H), 6.94 (dd, J=8.4, 2.7 Hz, 1H), 6.83 (d, J=2.7 Hz, 1H), 4.17 (s, 2H), 4.02 (t, J=6.1 Hz, 2H), 2.57 (t, J=7.0 Hz, 2H), 2.19 (s, 3H), 1.93-1.59 (m, 4H). MS: 467 $[M+H]^+$.

Example 92: 5-benzyl-N-(4-(2-methoxy-6-methylphenyl)pyridin-2-yl)-4H-1,2,4-triazole-3-carboxamide

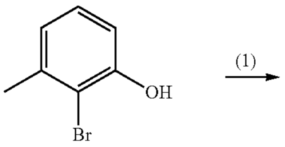

-continued

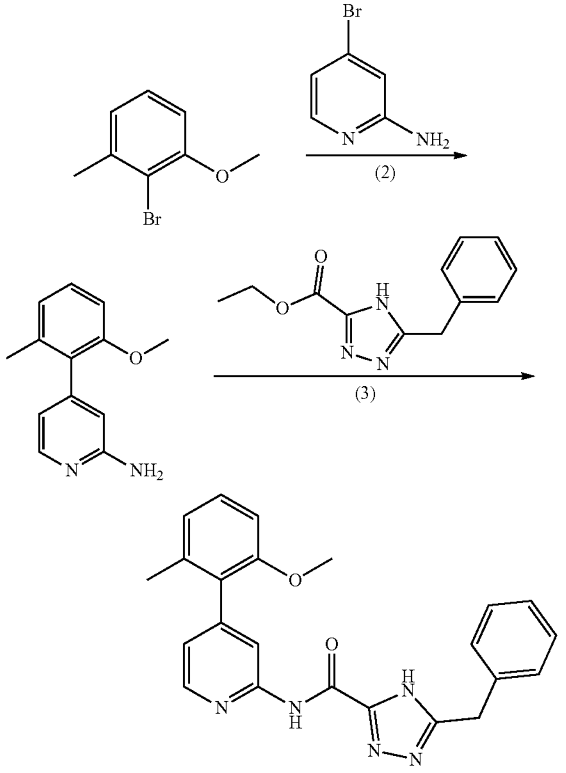

Step 1: Synthesis of 2-bromo-1-methoxy-3-methylbenzene

2-Bromo-3-methylphenol (374 mg, 2 mmol) was placed in acetonitrile (6 mL), potassium carbonate (553 mg, 4 mmol) was added and stirred at 25° C. for 1 hour. Iodomethane (426 mg, 3 mmol) was added, and reacted at 80° C. for 16 hours in sealed tube. The reaction solution was diluted with ethyl acetate, and filtered. The filtrate was evaporated to dryness, and subjected to column chromatography to afford 340 mg of yellow oil. MS: 201 $[M+H]^+$ Step 2 to Step 3: The preparation was carried out in a similar manner to Example 33, except that in step 1, 2-bromo-1-methoxy-3-methylbenzene was used in place of 2-bromo-4-fluoro-1-methylbenzene. $^1H$ NMR (400 MHz, DMSO-$d_6$) δ 14.56 (s, 1H), 9.84 (s, 1H), 8.40 (dd, J=5.0, 0.8 Hz, 1H), 7.96 (s, 1H), 7.46-7.30 (m, 5H), 7.30-7.17 (m, 1H), 7.04 (dd, J=5.1, 1.5 Hz, 1H), 7.01-6.85 (m, 2H), 4.18 (s, 2H), 3.67 (s, 3H), 2.04 (s, 3H). MS: 400 $[M+H]^+$.

Example 93: 5-benzyl-N-(4-(2-ethoxy-6-methylphenyl)pyridin-2-yl)-4H-1,2,4-triazole-3-carboxamide The preparation was carried out in a similar manner to Example 92, except that in step 1, bromoethane was used in place of iodomethane. $^1H$ NMR (400 MHz, DMSO-$d_6$) δ 14.56 (s, 1H), 9.83 (s, 1H), 8.39 (d, J=5.1 Hz, 1H), 7.99 (s, 1H), 7.43-7.29 (m, 4H), 7.29-7.16 (m, 2H), 7.05 (dd, J=5.1, 1.5 Hz, 1H), 7.01-6.89 (m, 2H), 4.18 (s, 2H), 3.98 (q, J=7.0 Hz, 2H), 2.05 (s, 3H), 1.13 (t, J=7.0 Hz, 3H). MS: 414 $[M+H]^+$.

Example 93

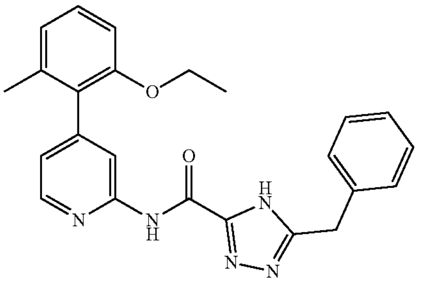

Example 94

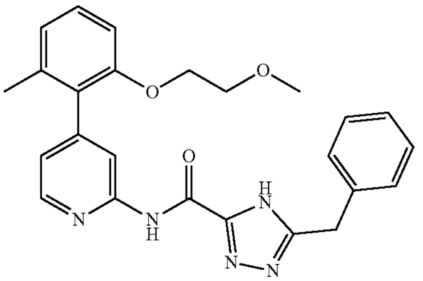

Example 94: 5-benzyl-N-(4-(2-(2-methoxyethoxy)-6-methylphenyl)pyridin-2-yl)-4H-1,2,4-triazole-3-carboxamide The preparation was carried out in a similar manner to Example 92, except that in step 1, 1-bromo-2-methoxyethane was used in place of iodomethane. $^1H$ NMR (400 MHz, DMSO-$d_6$) δ 14.52 (s, 1H), 9.80 (s, 1H), 8.39 (d, J=5.1 Hz, 1H), 8.00 (s, 1H), 7.39-7.30 (m, 4H), 7.30-7.20 (m, 2H), 7.06 (d, J=5.1 Hz, 1H), 7.01-6.87 (m, 2H), 4.19 (s, 2H), 4.09-3.98 (m, 2H), 3.52-3.41 (m, 2H), 3.10 (s, 3H), 2.07 (s, 3H). MS: 444 $[M+H]^+$.

Example 95: 5-benzyl-N-(4-(3-(2-hydroxyethoxy)-2-methylphenyl)pyridin-2-yl)-4H-1,2,4-triazole-3-carboxamide The preparation was carried out in a similar manner to Example 92, except that in step 1, 2-bromo-1-ethanol was used in place of iodomethane, and 3-bromo-2-methylphenol was used in place of 2-bromo-3-methylphenol. $^1H$ NMR (400 MHz, DMSO-$d_6$) δ 14.60 (s, 1H), 9.93 (s, 1H), 8.41 (d, J=5.0 Hz, 1H), 8.10 (d, J=1.4 Hz, 1H), 7.50-7.21 (m, 6H), 7.16 (dd, J=5.1, 1.6 Hz, 1H), 7.05 (d, J=8.2 Hz, 1H), 6.85 (d, J=7.5 Hz, 1H), 5.16-4.62 (m, 1H), 4.18 (s, 2H), 4.05 (t, J=5.0 Hz, 2H), 3.76 (t, J=5.0 Hz, 2H), 2.11 (s, 3H). MS: 430 $[M+H]^+$.

Example 95

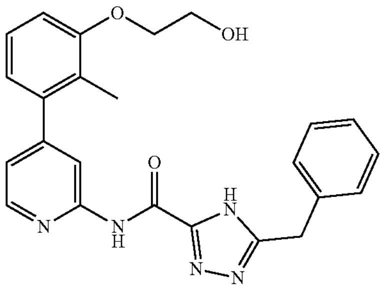

-continued

Example 96

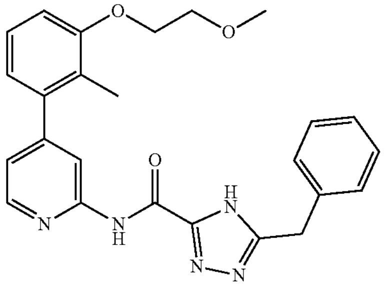

Example 96: 5-benzyl-N-(4-(3-(2-methoxyethoxy)-2-methylphenyl)pyridin-2-yl)-4H-1,2,4-triazole-3-carboxamide The preparation was carried out in a similar manner to Example 92, except that in step 1, 1-bromo-2-methoxyethane was used in place of iodomethane, and 3-bromo-2-methylphenol was used in place of 2-bromo-3-methylphenol. $^1$H NMR (400 MHz, DMSO-$d_6$) δ 14.21 (s, 1H), 9.93 (s, 1H), 8.41 (d, J=5.1 Hz, 1H), 8.10 (s, 1H), 7.54-7.20 (m, 6H), 7.16 (dd, J=5.0, 1.5 Hz, 1H), 7.05 (d, J=8.2 Hz, 1H), 6.86 (d, J=7.6 Hz, 1H), 4.28-4.06 (m, 4H), 3.75-3.66 (m, 2H), 3.33 (s, 3H), 2.09 (s, 3H). MS: 444 $[M+H]^+$.

Example 97: 5-benzyl-N-(4-(3-(3-hydroxylpropoxy)-2-methylphenyl)pyridin-2-yl)-4H-1,2,4-triazole-3-carboxamide The preparation was carried out in a similar manner to Example 92, except that in step 1, 3-bromo-1-propanol was used in place of iodomethane, and 3-bromo-2-methylphenol was used in place of 2-bromo-3-methylphenol. $^1$H NMR (400 MHz, DMSO-$d_6$) δ 14.59 (s, 1H), 9.91 (s, 1H), 8.41 (d, J=5.1 Hz, 1H), 8.08 (d, J=1.4 Hz, 1H), 7.44-7.21 (m, 6H), 7.17 (dd, J=5.1, 1.5 Hz, 1H), 7.05 (d, J=8.2 Hz, 1H), 6.85 (d, J=7.6 Hz, 1H), 4.58 (t, J=5.0 Hz, 1H), 4.17 (s, 2H), 4.09 (t, J=6.2 Hz, 2H), 3.64-3.56 (m, 2H), 2.08 (s, 3H), 1.95-1.84 (m, 2H). MS: 444 $[M+H]^+$.

Example 97

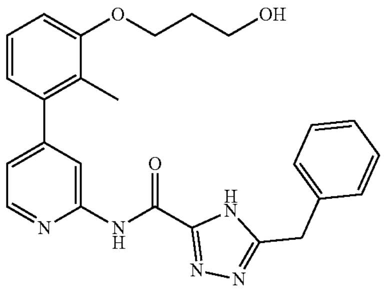

-continued

Example 98

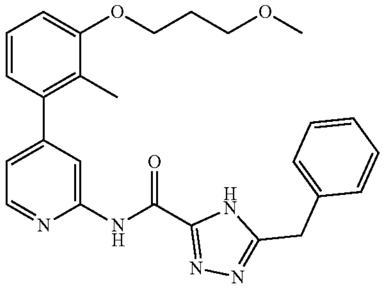

Example 98: 5-benzyl-N-(4-(3-(3-methoxypropoxy)-2-methylphenyl)pyridin-2-yl)-4H-1,2,4-triazole-3-carboxamide The preparation was carried out in a similar manner to Example 92, except that in step 1, 1-bromo-3-methoxypropane was used in place of iodomethane, and 3-bromo-2-methylphenol was used in place of 2-bromo-3-methylphenol. $^1$H NMR (400 MHz, DMSO-$d_6$) δ 14.65 (s, 1H), 9.92 (s, 1H), 8.51-8.31 (m, 1H), 8.20-7.99 (m, 1H), 7.42-7.30 (m, 4H), 7.30-7.20 (m, 2H), 7.16 (dd, J=5.1, 1.6 Hz, 1H), 7.04 (dd, J=8.4, 1.1 Hz, 1H), 6.85 (dd, J=7.7, 1.1 Hz, 1H), 4.17 (s, 2H), 4.07 (t, J=6.2 Hz, 2H), 3.51 (t, J=6.3 Hz, 2H), 3.25 (s, 3H), 2.08 (s, 3H), 2.04-1.91 (m, 2H). MS: 458 $[M+H]^+$.

Example 99: 5-benzyl-N-(4-(3-(4-hydroxybutoxy)-2-methylphenyl)pyridin-2-yl)-4H-1,2,4-triazole-3-carboxamide

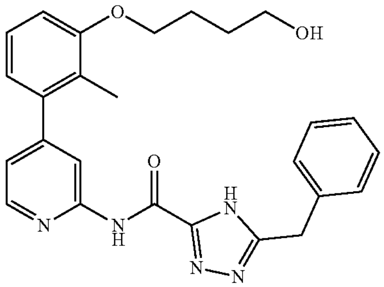 [SMILES: Cc1c(OCCCCO)cccc1-c1ccnc(NC(=O)c2nnc(Cc3ccccc3)[nH]2)c1]

The preparation was carried out in a similar manner to Example 92, except that in step 1, 4-bromo-1-butanol was used in place of iodomethane, and 3-bromo-2-methylphenol was used in place of 2-bromo-3-methylphenol. $^1$H NMR (400 MHz, DMSO-$d_6$) δ 14.59 (s, 1H), 9.90 (s, 1H), 8.41 (d, J=5.0 Hz, 1H), 8.09 (s, 1H), 7.40-7.21 (m, 6H), 7.17 (d, J=5.1 Hz, 1H), 7.04 (d, J=8.2 Hz, 1H), 6.85 (d, J=7.6 Hz, 1H), 4.53-4.41 (m, 1H), 4.17 (s, 2H), 4.04 (t, J=6.3 Hz, 2H), 3.51-3.44 (m, 2H), 2.09 (s, 3H), 1.87-1.73 (m, 2H), 1.68-1.55 (m, 2H). MS: 458 $[M+H]^+$.

Example 100: 5-benzyl-N-(4-(2-methyl-5-(octyloxy)phenyl)pyridin-2-yl)-4H-1,2,4-triazole-3-carboxamide

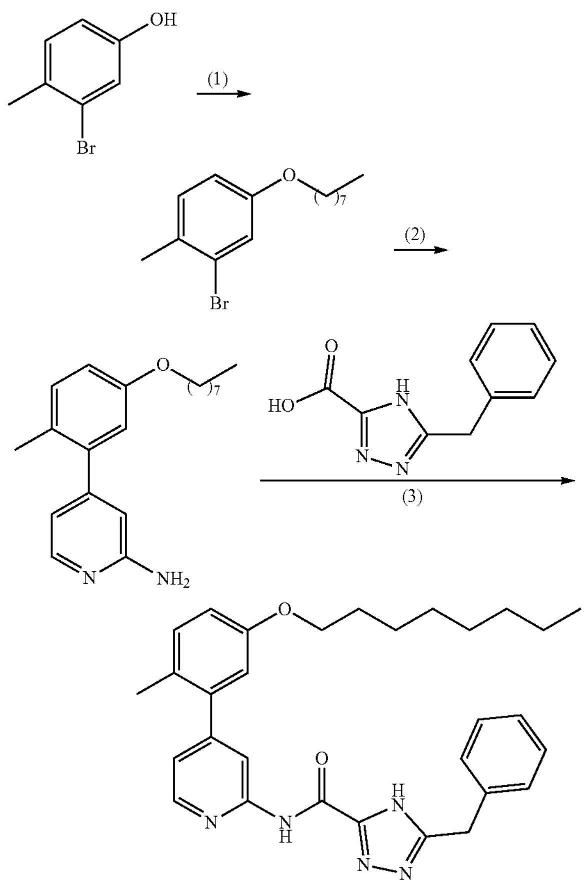

Step 1 to Step 2: Synthesis of 4-(2-methyl-5-(octyloxy)phenyl)pyridin-2-amine

The operation is the same as steps 1 to 2 of Example 92, but 3-bromo-2-methylphenol was used in place of 2-bromo-3-methylphenol in step 1, and 1-bromooctane was used in place of iodomethane in step 1. MS: 313 $[M+H]^+$.

Step 3: Intermediate 2 (98 mg, 0.48 mmol) was dissolved in DMF (3 mL), 1-propanephosphonic acid cyclic anhydride (50%, 305 mg, 0.48 mmol), diisopropylethylamine (124 mg, 0.96 mmol) and 4-(2-methyl-5-(octyloxy)phenyl)pyridin-2-amine (100 mg, 0.3 mmol) were added, and reacted at 25° C. for 16 hours. The reaction solution was diluted with water, extracted with dichloromethane, dried over anhydrous sodium sulfate, filtered, evaporated to dryness, and subjected to column chromatography and preparative liquid chromatography to afford 30 mg of white solid. $^1$H NMR (400 MHz, DMSO-$d_6$) δ 14.74 (s, 1H), 9.92 (s, 1H), 8.41 (d, J=5.1 Hz, 1H), 8.12 (d, J=1.4 Hz, 1H), 7.41-7.29 (m, 4H), 7.29-7.13 (m, 3H), 6.91 (dd, J=8.4, 2.7 Hz, 1H), 6.80 (d, J=2.6 Hz, 1H), 4.17 (s, 2H), 3.95 (t, J=6.5 Hz, 2H), 2.18 (s, 3H), 1.76-1.57 (m, 2H), 1.45-1.33 (m, 2H), 1.33-1.14 (m, 8H), 0.91-0.76 (m, 3H). MS: 498 $[M+H]^+$.

Example 101: 5-benzyl-N-(4-(5-methoxy-2-methylphenyl)pyridin-2-yl)-4H-1,2,4-triazole-3-carboxamide The preparation was carried out in a similar manner to Example 92, except that in step 1, 3-bromo-4-methylphenol was used in place of 2-bromo-3-methylphenol. $^1$H NMR (600 MHz, DMSO-$d_6$) δ 14.60 (s, 1H), 9.89 (s, 1H), 8.42 (d, J=5.1 Hz, 1H), 8.12 (s, 1H), 7.42-7.31 (m, 4H), 7.31-7.23 (m, 2H), 7.21 (dd, J=5.0, 1.5 Hz, 1H), 6.94 (dd, J=8.4, 2.8 Hz, 1H), 6.82 (d, J=2.8 Hz, 1H), 4.18 (s, 2H), 3.77 (s, 3H), 2.19 (s, 3H). MS: 400 $[M+H]^+$.

Example 101

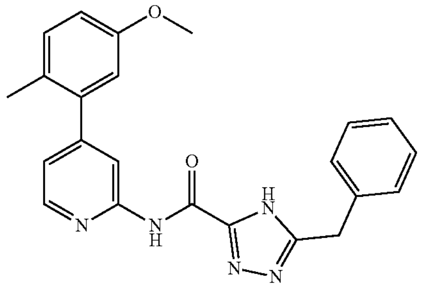

Example 102

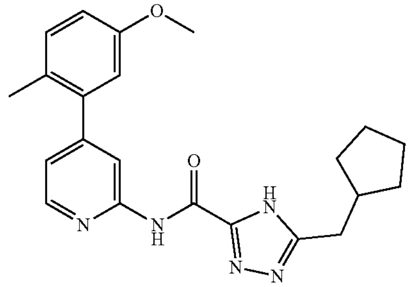

Example 102: 5-(cyclopentylmethyl)-N-(4-(5-methoxy-2-methylphenyl)pyridin-2-yl)-4H-1,2,4-triazole-3-carboxamide The preparation was carried out in a similar manner to Example 92, except that in step 1, 3-bromo-4-methylphenol was used in place of 2-bromo-3-methylphenol, and in step 3, ethyl 5-(cyclopentylmethyl)-4H-1,2,4-triazole-3-carboxylate was used in place of ethyl 5-benzyl-4H-1,2,4-triazol-3-carboxylate. $^1$H NMR (400 MHz, DMSO-$d_6$) δ 14.37 (s, 1H), 9.85 (s, 1H), 8.42 (d, J=5.1 Hz, 1H), 8.14 (s, 1H), 7.27 (d, J=8.4 Hz, 1H), 7.21 (d, J=5.1 Hz, 1H), 6.95 (dd, J=8.5, 2.8 Hz, 1H), 6.83 (d, J=2.8 Hz, 1H), 3.77 (s, 3H), 2.78 (d, J=7.5 Hz, 2H), 2.34-2.22 (m, 1H), 2.20 (s, 3H), 1.80-1.66 (m, 2H), 1.66-1.43 (m, 4H), 1.30-1.13 (m, 2H). MS: 392 $[M+H]^+$.

Example 103: 5-(cyclohexylmethyl)-N-(4-(5-methoxy-2-methylphenyl)pyridin-2-yl)-4H-1,2,4-triazole-3-carboxamide The preparation was carried out in a similar manner to Example 92, except that in step 1, 3-bromo-4-methylphenol was used in place of 2-bromo-3-methylphenol, and in step 3, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.38 (s, 1H), 9.86 (s, 1H), 8.42 (d, J=5.1 Hz, 1H), 8.14 (s, 1H), 7.34-7.16 (m, 2H), 7.03-6.88 (m, 1H), 6.83 (d, J=2.9 Hz, 1H), 3.77 (s, 3H), 2.66 (d, J=7.0 Hz, 2H), 2.19 (s, 3H), 1.83-1.52 (m, 6H), 1.30-1.06 (m, 3H), 1.06-0.86 (m, 2H). MS: 406 [M+H]$^+$.

Example 103

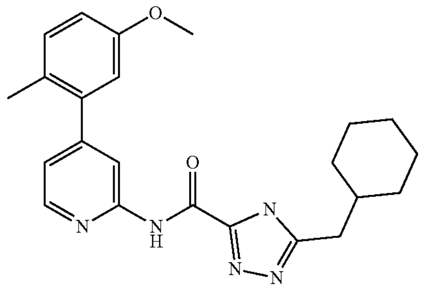

Example 104

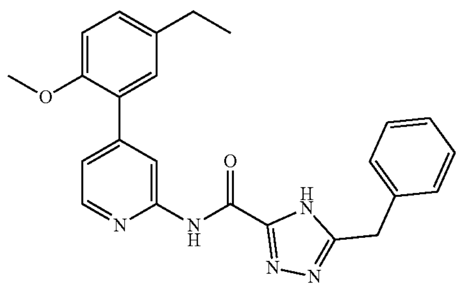

Example 104: 5-benzyl-N-(4-(5-ethyl-2-methoxyphenyl)pyridin-2-yl)-4H-1,2,4-triazole-3-carboxamide The preparation was carried out in a similar manner to Example 92, except that in step 1, 2-bromo-4-ethylphenol was used in place of 2-bromo-3-methylphenol. $^1$H NMR (400 MHz, DMSO-$d_6$) δ 14.59 (s, 1H), 9.83 (s, 1H), 8.36 (d, J=5.2 Hz, 1H), 8.29 (d, J=1.4 Hz, 1H), 7.54-7.16 (m, 8H), 7.09 (d, J=8.4 Hz, 1H), 4.17 (s, 2H), 3.78 (s, 3H), 2.61 (q, J=7.6 Hz, 2H), 1.19 (t, J=7.5 Hz, 3H). MS: 414 [M+H]$^+$.

Example 105: 5-benzyl-N-(5-(2-chloro-5-ethoxyphenyl)pyridin-3-yl)-4H-1,2,4-triazole-3-carboxamide The preparation was carried out in a similar manner to Example 92, except that in step 1, bromoethane was used in place of iodomethane, 3-bromo-4-chlorophenol was used in place of 2-bromo-3-methylphenol, and in step 2, 5-bromopyridin-3-amine was used in place of 4-bromopyridin-2-amine. $^1$H NMR (400 MHz, DMSO-$d_6$) δ 14.60 (s, 1H), 10.82 (s, 1H), 9.03 (d, J=2.3 Hz, 1H), 8.44-8.29 (m, 2H), 7.49 (d, J=8.7 Hz, 1H), 7.39-7.20 (m, 5H), 7.08-6.97 (m, 2H), 4.17 (s, 2H), 4.08 (q, J=7.0 Hz, 2H), 1.33 (t, J=6.9 Hz, 3H). MS: 434 [M+H]$^+$.

Example 105

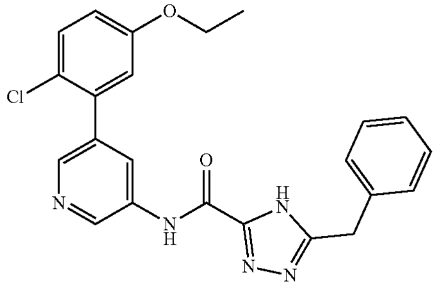

Example 106

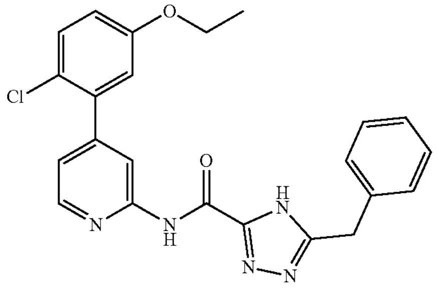

Example 106: 5-benzyl-N-(4-(2-chloro-5-ethoxyphenyl)pyridin-2-yl)-4H-1,2,4-triazole-3-carboxamide The preparation was carried out in a similar manner to Example 92, except that in step 1, bromoethane was used in place of iodomethane, and 3-bromo-4-chlorophenol was used in place of 2-bromo-3-methylphenol. $^1$H NMR (400 MHz, DMSO-$d_6$) δ 14.65 (s, 1H), 9.94 (s, 1H), 8.45 (d, J=5.2 Hz, 1H), 8.23 (d, J=1.5 Hz, 1H), 7.51 (d, J=8.8 Hz, 1H), 7.40-7.30 (m, 4H), 7.30-7.20 (m, 2H), 7.06 (dd, J=8.8, 3.1 Hz, 1H), 7.01 (d, J=3.0 Hz, 1H), 4.18 (s, 2H), 4.08 (q, J=7.0 Hz, 2H), 1.33 (t, J=7.0 Hz, 3H). MS: 434 [M+H]$^+$.

Example 107: 5-benzyl-N-(4-(5-ethoxy-2-methoxyphenyl)pyridin-2-yl)-4H-1,2,4-triazole-3-carboxamide The preparation was carried out in a similar manner to Example 92, except that in step 1, bromoethane was used in place of iodomethane, and 3-bromo-4-methoxyphenol was used in place of 2-bromo-3-methylphenol. $^1$H NMR (600 MHz, DMSO-$d_6$) δ 14.54 (s, 1H), 9.79 (s, 1H), 8.43-8.24 (m, 2H), 7.47-7.29 (m, 5H), 7.27 (d, J=6.5 Hz, 1H), 7.10 (d, J=9.0 Hz, 1H), 7.01 (dd, J=9.0, 3.1 Hz, 1H), 6.94 (d, J=3.1 Hz, 1H), 4.19 (s, 2H), 4.03 (q, J=6.9 Hz, 2H), 3.75 (s, 3H), 1.32 (t, J=6.9 Hz, 3H). MS: 430 [M+H]$^+$.

Example 107

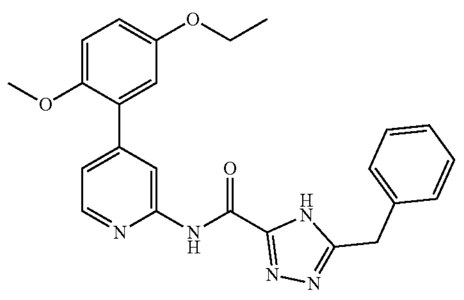

Example 108

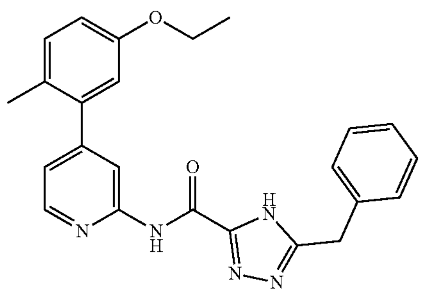

Example 108: 5-benzyl-N-(4-(5-ethoxy-2-methylphenyl)pyridin-2-yl)-4H-1,2,4-triazole-3-carboxamide The preparation was carried out in a similar manner to Example 92, except that in step 1, bromoethane was used in place of iodomethane, and 3-bromo-4-methylphenol was used in place of 2-bromo-3-methylphenol. $^1$H NMR (600 MHz, DMSO-$d_6$) δ 14.62 (s, 1H), 9.90 (s, 1H), 8.41 (d, J=5.1 Hz, 1H), 8.11 (s, 1H), 7.41-7.30 (m, 4H), 7.30-7.22 (m, 2H), 7.20 (dd, J=5.1, 1.5 Hz, 1H), 6.93 (dd, J=8.4, 2.7 Hz, 1H), 6.80 (d, J=2.7 Hz, 1H), 4.17 (s, 2H), 4.04 (q, J=7.0 Hz, 2H), 2.19 (s, 3H), 1.32 (t, J=7.0 Hz, 3H). MS: 414 $[M+H]^+$.

Example 109: 5-benzyl-N-(4-(1-ethyl-3-methyl-1H-pyrazol-5-yl)pyridin-2-yl)-4H-1,2,4-triazole-3-carboxamide The preparation was carried out in a similar manner to Example 92, except that in step 1, bromoethane was used in place of iodomethane, and 5-bromo-3-methyl-1H-pyrazole was used in place of 2-bromo-3-methylphenol. $^1$H NMR (400 MHz, DMSO-$d_6$) δ 14.63 (s, 1H), 9.98 (s, 1H), 8.46 (d, J=5.1 Hz, 1H), 8.35-8.14 (m, 1H), 7.51-7.15 (m, 6H), 6.35 (s, 1H), 4.29-3.95 (m, 4H), 2.21 (s, 3H), 1.36 (t, J=7.2 Hz, 3H). MS: 388 $[M+H]^+$.

Example 109

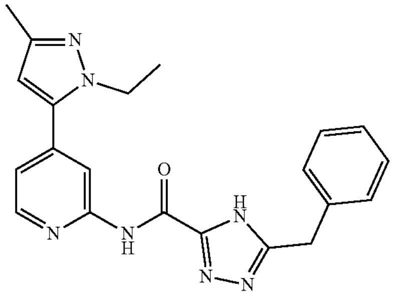

Example 110

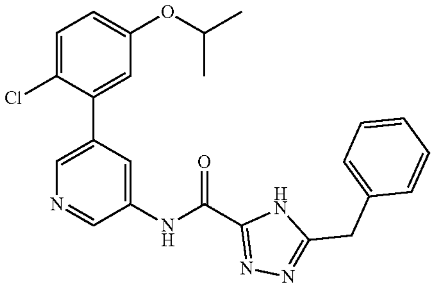

Example 110: 5-benzyl-N-(5-(2-chloro-5-isopropoxyphenyl)pyridin-3-yl)-4H-1,2,4-triazole-3-carboxamide The preparation was carried out in a similar manner to Example 92, except that in step 1, 2-bromopropane was used in place of iodomethane, 3-bromo-4-chlorophenol was used in place of 2-bromo-3-methylphenol, and in step 2, 5-bromopyridin-3-amine was used in place of 4-bromopyridin-2-amine. $^1$H NMR (600 MHz, DMSO-$d_6$) δ 14.64 (s, 1H), 10.83 (s, 1H), 9.04 (d, J=2.2 Hz, 1H), 8.49-8.20 (m, 2H), 7.48 (dd, J=8.6, 1.9 Hz, 1H), 7.41-7.31 (m, 2H), 7.31-7.28 (m, 2H), 7.28-7.22 (m, 1H), 7.07-6.98 (m, 2H), 4.74-4.64 (m, 1H), 4.18 (s, 2H), 1.28 (dd, J=6.1, 1.9 Hz, 6H). MS: 448 $[M+H]^+$.

Example 111: 5-benzyl-N-(4-(2-chloro-5-isopropoxyphenyl)pyridin-2-yl)-4H-1,2,4-triazole-3-carboxamide The preparation was carried out in a similar manner to Example 92, except that in step 1, 2-bromopropane was used in place of iodomethane, and 3-bromo-4-chlorophenol was used in place of 2-bromo-3-methylphenol. $^1$H NMR (400 MHz, DMSO-$d_6$) δ 14.66 (s, 1H), 9.94 (s, 1H), 8.45 (d, J=5.1 Hz, 1H), 8.22 (s, 1H), 7.50 (dd, J=8.8, 2.8 Hz, 1H), 7.41-7.30 (m, 4H), 7.30-7.22 (m, 2H), 7.09-7.02 (m, 1H), 6.99 (d, J=3.0 Hz, 1H), 4.69 (p, J=6.0 Hz, 1H), 4.17 (s, 2H), 1.28 (d, J=6.1, 2.7 Hz, 6H). MS: 448 $[M+H]^+$.

Example 111

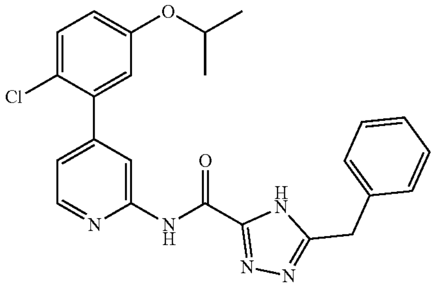

Example 112

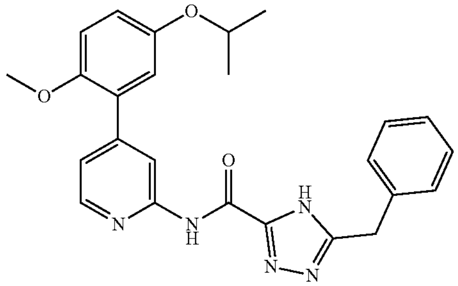

Example 112: 5-benzyl-N-(4-(5-isopropoxy-2-methoxyphenyl)pyridin-2-yl)-4H-1,2,4-triazole-3-carboxamide The preparation was carried out in a similar manner to Example 92, except that in step 1, 2-bromopropane was used in place of iodomethane, and 3-bromo-4-methoxyphenol was used in place of 2-bromo-3-methylphenol. $^1$H NMR (600 MHz, DMSO-$d_6$) δ 14.59 (s, 1H), 9.84 (s, 1H), 8.37 (d, J=5.2 Hz, 1H), 8.30 (s, 1H), 7.40-7.29 (m, 5H), 7.29-7.22 (m, 1H), 7.09 (d, J=9.0 Hz, 1H), 7.00 (dd, J=8.9, 3.0 Hz, 1H), 6.93 (d, J=3.0 Hz, 1H), 4.56 (p, J=6.0 Hz, 1H), 4.18 (s, 2H), 3.75 (s, 3H), 1.25 (d, J=6.0 Hz, 6H). MS: 444 [M+H]$^+$.

Example 113: 5-benzyl-N-(5-(5-isopropoxy-2-methylphenyl)pyridin-3-yl)-4H-1,2,4-triazole-3-carboxamide The preparation was carried out in a similar manner to Example 92, except that in step 1, 2-bromopropane was used in place of iodomethane, 3-bromo-4-methylphenol was used in place of 2-bromo-3-methylphenol, and in step 2, 5-bromopyridin-3-amine was used in place of 4-bromopyridin-2-amine. $^1$H NMR (400 MHz, DMSO-$d_6$) δ 14.62 (s, 1H), 10.79 (s, 1H), 9.02 (d, J=2.3 Hz, 1H), 8.31 (d, J=2.0 Hz, 1H), 8.25-8.08 (m, 1H), 7.42-7.16 (m, 6H), 6.88 (dd, J=8.4, 2.7 Hz, 1H), 6.79 (d, J=2.7 Hz, 1H), 4.62 (p, J=6.0 Hz, 1H), 4.17 (s, 2H), 2.17 (s, 3H), 1.26 (d, J=6.0 Hz, 6H). MS: 428 [M+H]$^+$.

Example 113

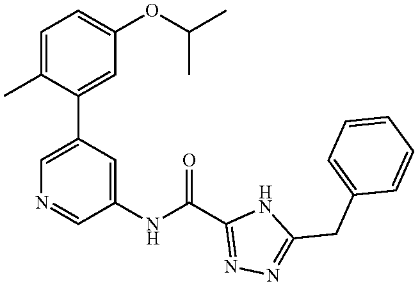

Example 114

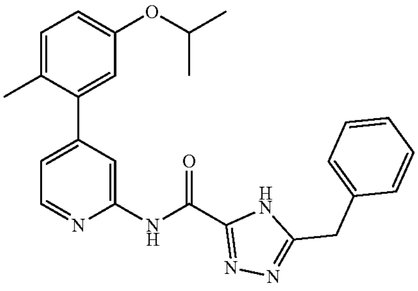

Example 114: 5-benzyl-N-(4-(5-isopropoxy-2-methylphenyl)pyridin-2-yl)-4H-1,2,4-triazole-3-carboxamide The preparation was carried out in a similar manner to Example 92, except that in step 1, 2-bromopropane was used in place of iodomethane, and 3-bromo-4-methylphenol was used in place of 2-bromo-3-methylphenol. $^1$H NMR (600 MHz, DMSO-$d_6$) δ 14.57 (s, 1H), 9.90 (s, 1H), 8.58-8.29 (m, 1H), 8.11 (s, 1H), 7.63-7.29 (m, 4H), 7.29-7.06 (m, 3H), 6.92 (d, J=8.0 Hz, 1H), 6.78 (d, J=3.5 Hz, 1H), 4.67-4.54 (m, 1H), 4.17 (s, 2H), 2.18 (s, 3H), 1.26 (d, J=6.3, 3.3 Hz, 6H). MS: 428 [M+H]$^+$.

Example 115: 5-benzyl-N-(4-(5-(3,3-dimethylbutoxy)-2-methylphenyl)pyridin-2-yl)-4H-1,2,4-triazole-3-carboxamide The preparation was carried out in a similar manner to Example 92, except that in step 1, 1-bromo-3,3-dimethylbutane was used in place of iodomethane, and 3-bromo-4-methylphenol was used in place of 2-bromo-3-methylphenol. $^1$H NMR (400 MHz, DMSO-$d_6$) δ 14.62 (s, 1H), 9.91 (s, 1H), 8.41 (d, J=5.1 Hz, 1H), 8.11 (s, 1H), 7.48-7.13 (m, 7H), 6.94 (dd, J=8.4, 2.7 Hz, 1H), 6.82 (d, J=2.7 Hz, 1H), 4.17 (s, 2H), 4.02 (t, J=7.2 Hz, 2H), 2.18 (s, 3H), 1.65 (t, J=7.2 Hz, 2H), 0.95 (s, 9H). MS: 470 [M+H]$^+$.

Example 115

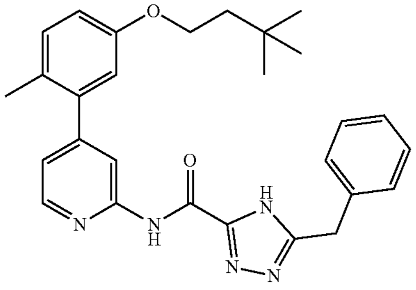

Example 116

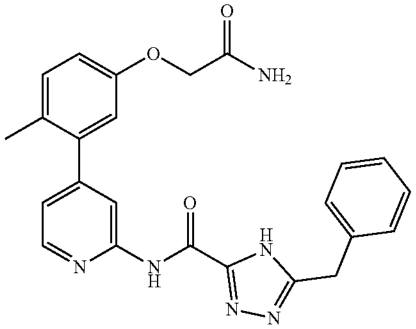

Example 116: N-(4-(5-(2-amino-2-oxoethoxy)-2-methylphenyl)pyridin-2-yl)-5-benzyl-4H-1,2,4-triazole-3-carboxamide The preparation was carried out in a similar manner to Example 92, except that in step 1, 2-chloroacetamide was used in place of iodomethane, and 3-bromo-4-methylphenol was used in place of 2-bromo-3-methylphenol. $^1$H NMR (400 MHz, DMSO-$d_6$) δ 14.61 (s, 1H), 9.91 (s, 1H), 8.43 (d, J=5.1 Hz, 1H), 8.12 (s, 1H), 7.54 (s, 1H), 7.42-7.30 (m, 5H), 7.30-7.22 (m, 2H), 7.20 (dd, J=5.1, 1.6 Hz, 1H), 6.96 (dd, J=8.4, 2.8 Hz, 1H), 6.88 (d, J=2.8 Hz, 1H), 4.44 (s, 2H), 4.18 (s, 2H), 2.20 (s, 3H). MS: 443 $[M+H]^+$.

Example 117: 5-benzyl-N-(4-(5-(2-hydroxyl-2-methylpropoxy)-2-methylphenyl)pyridin-2-yl)-4H-1,2,4-triazole-3-carboxamide The preparation was carried out in a similar manner to Example 92, except that in step 1, 1-chloro-2-methylpropyl-2-ol was used in place of iodomethane, and 3-bromo-4-methylphenol was used in place of 2-bromo-3-methylphenol. $^1$H NMR (400 MHz, DMSO-$d_6$) δ 14.91-14.25 (m, 1H), 9.90 (s, 1H), 8.42 (d, J=5.1 Hz, 1H), 8.12 (s, 1H), 7.45-7.13 (m, 7H), 6.95 (dd, J=8.4, 2.7 Hz, 1H), 6.82 (d, J=2.7 Hz, 1H), 4.61 (s, 1H), 4.18 (s, 2H), 3.73 (s, 2H), 2.19 (s, 3H), 1.19 (s, 6H). MS: 458 $[M+H]^+$ Example 117

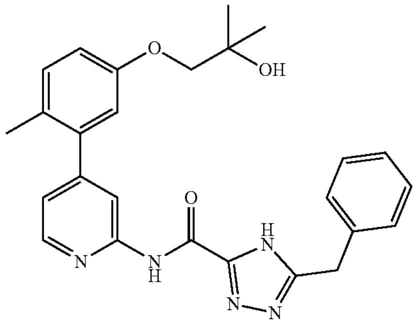

Example 118

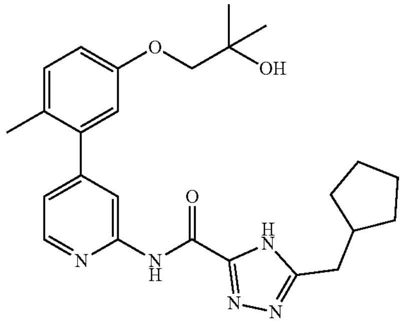

Example 118: 5-(cyclopentylmethyl)-N-(4-(5-(2-hydroxyl-2-methylpropoxy)-2-methylphenyl)pyridin-2-yl)-4H-1,2,4-triazole-3-carboxamide The preparation was carried out in a similar manner to Example 92, except that in step 1, 1-chloro-2-methylpropyl-2-ol was used in place of iodomethane, 3-bromo-4-methylphenol was used in place of 2-bromo-3-methylphenol, and in step 3, ethyl 5-(cyclopentylmethyl)-4H-1,2,4-triazole-3-carboxylate was used in place of ethyl 5-benzyl-4H-1,2,4-triazol-3-carboxylate. $^1$H NMR (400 MHz, DMSO-$d_6$) δ 14.42 (s, 1H), 9.87 (s, 1H), 8.42 (d, J=5.1 Hz, 1H), 8.14 (d, J=1.4 Hz, 1H), 7.32-7.17 (m, 2H), 6.95 (dd, J=8.4, 2.7 Hz, 1H), 6.83 (d, J=2.7 Hz, 1H), 4.63 (s, 1H), 3.73 (s, 2H), 2.78 (d, J=7.5 Hz, 2H), 2.33-2.22 (m, 1H), 2.20 (s, 3H), 1.80-1.66 (m, 2H), 1.66-1.42 (m, 4H), 1.30-1.10 (m, 8H). MS: 450 $[M+H]^+$.

Example 119: 5-(cyclohexylmethyl)-N-(4-(5-(2-hydroxyl-2-methylpropoxy)-2-methylphenyl)pyridin-2-yl)-4H-1,2,4-triazole-3-carboxamide The preparation was carried out in a similar manner to Example 92, except that in step 1, 1-chloro-2-methylpropyl-2-ol was used in place of iodomethane, 3-bromo-4-methylphenol was used in place of 2-bromo-3-methylphenol, and in step 3, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.37 (s, 1H), 9.85 (s, 1H), 8.42 (d, J=5.1 Hz, 1H), 8.14 (s, 1H), 7.34-7.14 (m, 2H), 6.95 (dd, J=8.5, 2.7 Hz, 1H), 6.83 (d, J=2.8 Hz, 1H), 4.63 (s, 1H), 3.73 (s, 2H), 2.67 (d, J=7.0 Hz, 2H), 2.20 (s, 3H), 1.84-1.53 (m, 6H), 1.31-1.05 (m, 9H), 1.05-0.88 (m, 2H). MS: 464 $[M+H]^+$.

Example 119

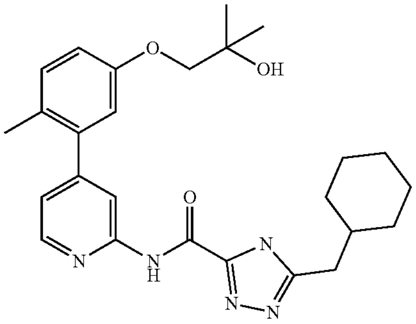

Example 120

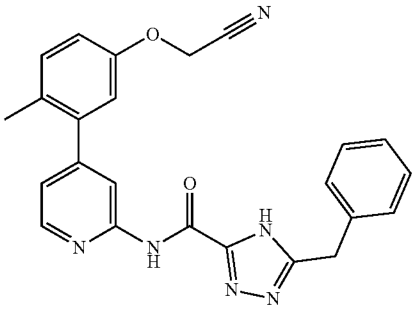

Example 120: 5-benzyl-N-(4-(5-(cyanomethoxy)-2-methylphenyl)pyridin-2-yl)-4H-1,2,4-triazole-3-carboxamide The preparation was carried out in a similar manner to Example 92, except that in step 1, bromoacetonitrile was used in place of iodomethane, and 3-bromo-4-methylphenol was used in place of 2-bromo-3-methylphenol. $^1H$ NMR (400 MHz, DMSO-$d_6$) δ 14.57 (s, 1H), 9.91 (s, 1H), 8.44 (d, J=5.1 Hz, 1H), 8.13 (s, 1H), 7.41-7.29 (m, 5H), 7.29-7.18 (m, 2H), 7.08 (dd, J=8.4, 2.8 Hz, 1H), 6.99 (d, J=2.8 Hz, 1H), 5.20 (s, 2H), 4.18 (s, 2H), 2.22 (s, 3H). MS: 425 $[M+H]^+$.

Example 121: 5-benzyl-N-(4-(2-methyl-5-((tetrahydrofuran-2-yl)methoxy)phenyl)pyridin-2-yl)-4H-1,2,4-triazole-3-carboxamide The preparation was carried out in a similar manner to Example 92, except that in step 1, 2-(bromomethyl)tetrahydrofuran was used in place of iodomethane, and 3-bromo-4-methylphenol was used in place of 2-bromo-3-methylphenol. $^1H$ NMR (400 MHz, DMSO-$d_6$) δ 14.60 (s, 1H), 9.91 (s, 1H), 8.42 (d, J=5.1 Hz, 1H), 8.11 (s, 1H), 7.44-7.29 (m, 4H), 7.29-7.12 (m, 3H), 6.94 (dd, J=8.4, 2.7 Hz, 1H), 6.83 (d, J=2.7 Hz, 1H), 4.26-4.07 (m, 3H), 4.02-3.86 (m, 2H), 3.82-3.72 (m, 1H), 3.72-3.61 (m, 1H), 2.19 (s, 3H), 2.06-1.92 (m, 1H), 1.92-1.73 (m, 2H), 1.73-1.58 (m, 1H). MS: 470 $[M+H]^+$.

Example 121

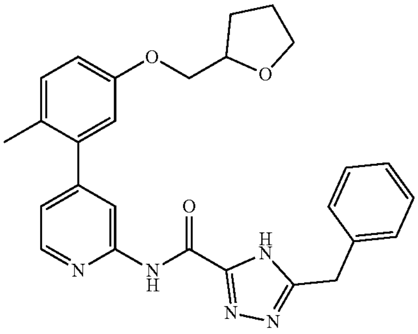

Example 122

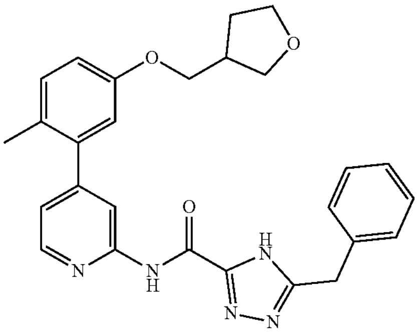

Example 122: 5-benzyl-N-(4-(2-methyl-5-((tetrahydrofuran-3-yl)methoxy)phenyl)pyridin-2-yl)-4H-1,2,4-triazole-3-carboxamide The preparation was carried out in a similar manner to Example 92, except that in step 1, 3-(bromomethyl)tetrahydrofuran was used in place of iodomethane, and 3-bromo-4-methylphenol was used in place of 2-bromo-3-methylphenol. $^1H$ NMR (400 MHz, DMSO-$d_6$) δ 14.58 (s, 1H), 9.89 (s, 1H), 8.42 (d, J=5.1 Hz, 1H), 8.11 (s, 1H), 7.41-7.30 (m, 4H), 7.30-7.23 (m, 2H), 7.21 (dd, J=5.1, 1.6 Hz, 1H), 6.95 (dd, J=8.4, 2.7 Hz, 1H), 6.84 (d, J=2.7 Hz, 1H), 4.18 (s, 2H), 4.00-3.84 (m, 2H), 3.83-3.70 (m, 2H), 3.70-3.58 (m, 1H), 3.57-3.47 (m, 1H), 2.71-2.57 (m, 1H), 2.19 (s, 3H), 2.07-1.92 (m, 1H), 1.72-1.57 (m, 1H). MS: 470 $[M+H]^+$.

Example 123: 5-benzyl-N-(4-(2-methyl-5-((tetrahydro-2H-pyran-2-yl)methoxy)phenyl)pyridin-2-yl)-4H-1,2,4-triazole-3-carboxamide The preparation was carried out in a similar manner to Example 92, except that in step 1, 2-(bromomethyl)tetrahydro-2H-pyran was used in place of iodomethane, and 3-bromo-4-methylphenol was used in place of 2-bromo-3-methylphenol. $^1H$ NMR (400 MHz, DMSO-$d_6$) δ 14.57 (s, 1H), 9.94 (s, 1H), 8.41 (d, J=5.2 Hz, 1H), 8.11 (s, 1H), 7.41-7.29 (m, 4H), 7.29-7.15 (m, 3H), 6.93 (dd, J=8.6, 2.7 Hz, 1H), 6.81 (d, J=2.7 Hz, 1H), 4.17 (s, 2H), 3.97-3.81 (m, 3H), 3.63-3.56 (m, 2H), 2.18 (s, 3H), 1.85-1.73 (m, 1H), 1.68-1.57 (m, 1H), 1.55-1.39 (m, 3H), 1.37-1.16 (m, 1H). MS: 484 $[M+H]^+$.

Example 123

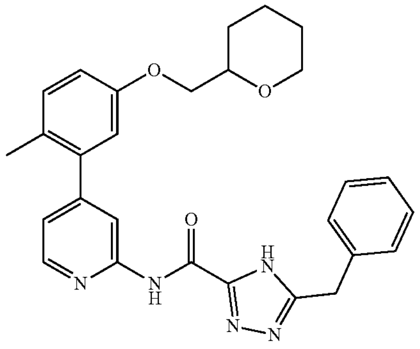

Example 124

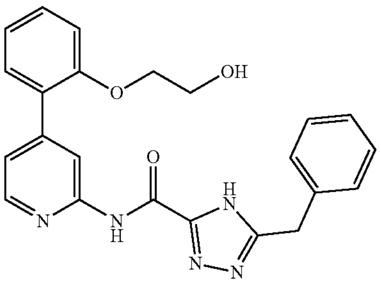

Example 124: 5-benzyl-N-(4-(2-(2-hydroxyethoxy)phenyl)pyridin-2-yl)-4H-1,2,4-triazole-3-carboxamide The preparation was carried out in a similar manner to Example 92, except that in step 1, 2-bromo-1-ethanol was used in place of iodomethane, and 2-bromophenol was used in place of 2-bromo-3-methylphenol. $^1$H NMR (600 MHz, DMSO-$d_6$) δ 14.54 (s, 1H), 9.78 (s, 1H), 8.47-8.26 (m, 2H), 7.46-7.39 (m, 3H), 7.37-7.31 (m, 4H), 7.26 (d, J=7.3 Hz, 1H), 7.19 (d, J=8.4 Hz, 1H), 7.12-7.07 (m, 1H), 4.76 (t, J=5.5 Hz, 1H), 4.18 (s, 2H), 4.08 (t, J=5.2 Hz, 2H), 3.78-3.67 (m, 2H). MS: 416 $[M+H]^+$.

Example 125: 5-benzyl-N-(4-(5-(2-hydroxyethoxy)-2-methylphenyl)pyridin-2-yl)-4H-1,2,4-triazole-3-carboxamide The preparation was carried out in a similar manner to Example 92, except that in step 1, 2-bromo-1-ethanol was used in place of iodomethane, and 3-bromo-4-methylphenol was used in place of 2-bromo-3-methylphenol. $^1$H NMR (400 MHz, DMSO-$d_6$) δ 14.55 (s, 1H), 9.85 (s, 1H), 8.41 (d, J=5.1 Hz, 1H), 8.13 (s, 1H), 7.44-7.14 (m, 7H), 6.95 (dd, J=8.4, 2.7 Hz, 1H), 6.83 (d, J=2.7 Hz, 1H), 4.85 (t, J=5.5 Hz, 1H), 4.19 (s, 2H), 4.00 (t, J=5.0 Hz, 2H), 3.77-3.62 (m, 2H), 2.19 (s, 3H). MS: 430 $[M+H]^+$.

Example 125

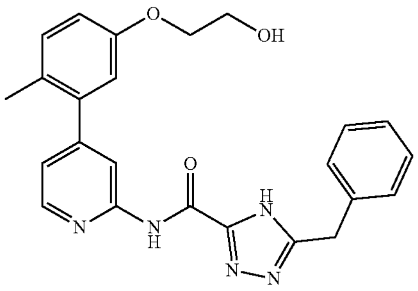

Example 126

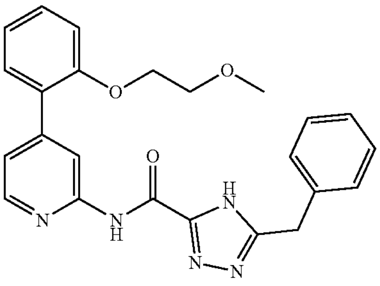

Example 126: 5-benzyl-N-(4-(2-(2-methoxyethoxy)phenyl)pyridin-2-yl)-4H-1,2,4-triazole-3-carboxamide The preparation was carried out in a similar manner to Example 92, except that in step 1, 1-bromo-2-methoxyethane was used in place of iodomethane, and 2-bromophenol was used in place of 2-bromo-3-methylphenol. $^1$H NMR (600 MHz, DMSO-$d_6$) δ 14.61 (s, 1H), 9.81 (s, 1H), 8.42-8.32 (m, 2H), 7.46-7.40 (m, 2H), 7.39 (dd, J=5.1, 1.6 Hz, 1H), 7.37-7.30 (m, 4H), 7.29-7.23 (m, 1H), 7.19 (d, J=8.4 Hz, 1H), 7.12-7.08 (m, 1H), 4.22-4.14 (m, 4H), 3.69-3.63 (m, 2H), 3.22 (s, 3H). MS: 430 $[M+H]^+$.

Example 127: 5-benzyl-N-(5-(5-(2-methoxyethoxy)-2-methylphenyl)pyridin-3-yl)-4H-1,2,4-triazole-3-carboxamide The preparation was carried out in a similar manner to Example 92, except that in step 1, 1-bromo-2-methoxyethane was used in place of iodomethane, 3-bromo-4-methylphenol was used in place of 2-bromo-3-methylphenol, and in step 2, 5-bromopyridin-3-amine was used in place of 4-bromopyridin-2-amine. $^1$H NMR (400 MHz, DMSO-$d_6$) δ 14.49 (s, 1H), 10.72 (s, 1H), 9.02 (d, J=2.3 Hz, 1H), 8.31 (d, J=1.9 Hz, 1H), 8.25-8.16 (m, 1H), 7.39-7.19 (m, 6H), 6.92 (dd, J=8.4, 2.7 Hz, 1H), 6.83 (d, J=2.7 Hz, 1H), 4.17 (s, 2H), 4.13-4.05 (m, 2H), 3.69-3.61 (m, 2H), 3.30 (s, 3H), 2.18 (s, 3H). MS: 444 $[M+H]^+$.

Example 127

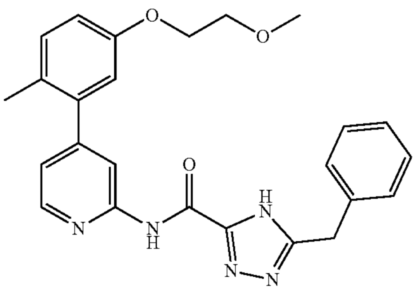

Example 128

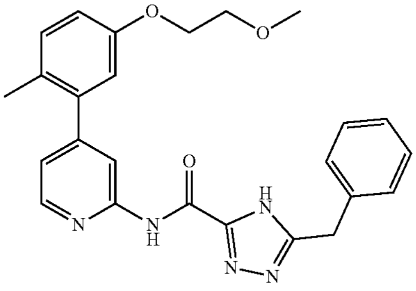

Example 128: 5-benzyl-N-(4-(5-(2-methoxyethoxy)-2-methylphenyl)pyridin-2-yl)-4H-1,2,4-triazole-3-carboxamide The preparation was carried out in a similar manner to Example 92, except that in step 1, 1-bromo-2-methoxyethane was used in place of iodomethane, and 3-bromo-4-methylphenol was used in place of 2-bromo-3-methylphenol. $^1$H NMR (400 MHz, DMSO-$d_6$) δ 14.55 (s, 1H), 9.85 (s, 1H), 8.41 (d, J=5.1 Hz, 1H), 8.13 (s, 1H), 7.41-7.29 (m, 4H), 7.29-7.16 (m, 3H), 6.95 (dd, J=8.4, 2.8 Hz, 1H), 6.83 (d, J=2.8 Hz, 1H), 4.19 (s, 2H), 4.11 (t, J=4.6 Hz, 2H), 3.65 (t, J=4.6 Hz, 2H), 3.30 (s, 3H), 2.19 (s, 3H). MS: 444 $[M+H]^+$.

Example 129: 5-benzyl-N-(5-(2-methoxyethoxy)-2-methyl-[3,4'-bipyridin]-2'-yl)-4H-1,2,4-triazole-3-carboxamide The preparation was carried out in a similar manner to Example 92, except that in step 1, 1-bromo-2-methoxyethane was used in place of iodomethane, and 5-bromo-6-methylpyridin-3-ol (for the synthetic method refers to Lin, Nan-Horng et al/U.S., 6437138, 20 Aug. 2002) was used in place of 2-bromo-3-methylphenol. $^1$H NMR (400 MHz, DMSO-$d_6$) δ 14.62 (s, 1H), 9.97 (s, 1H), 8.46 (d, J=5.1 Hz, 1H), 8.28 (d, J=2.9 Hz, 1H), 8.16 (s, 1H), 7.42-7.20 (m, 7H), 4.28-4.11 (m, 4H), 3.66 (s, 2H), 3.30 (s, 3H), 2.39 (s, 3H). MS: 445 $[M+H]^+$.

Example 129

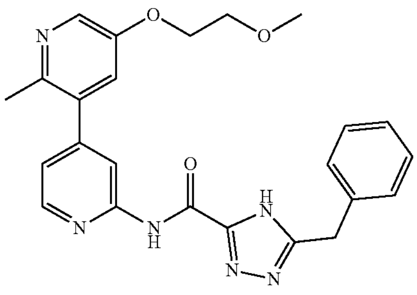

Example 130

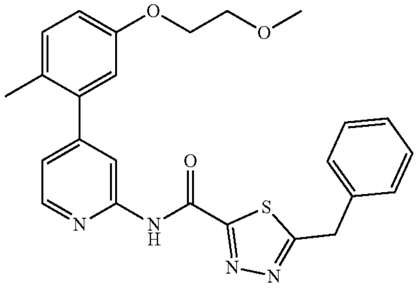

Example 130: 5-benzyl-N-(4-(5-(2-methoxyethoxy)-2-methylphenyl)pyridin-2-yl)-1,3,4-thiodiazol-2-carboxamide The preparation was carried out in a similar manner to Example 92, except that in step 1, 1-bromo-2-methoxyethane was used in place of iodomethane, 3-bromo-4-methylphenol was used in place of 2-bromo-3-methylphenol, and in step 3, methyl 5-benzyl-1,3,4-thiodiazol-2-carboxylate was used in place of ethyl 5-benzyl-4H-1,2,4-triazol-3-carboxylate. $^1$H NMR (400 MHz, DMSO-$d_6$) δ 10.84 (s, 1H), 8.47 (dd, J=5.1, 0.7 Hz, 1H), 8.00 (dd, J=1.6, 0.8 Hz, 1H), 7.44-7.20 (m, 7H), 6.94 (dd, J=8.4, 2.7 Hz, 1H), 6.83 (d, J=2.8 Hz, 1H), 4.58 (s, 2H), 4.14-4.05 (m, 2H), 3.69-3.60 (m, 2H), 3.30 (s, 3H), 2.19 (s, 3H). MS: 461 $[M+H]^+$.

Example 131: 5-benzyl-N-(4-(5-(2-ethoxyethoxy)-2-methylphenyl)pyridin-2-yl)-4H-1,2,4-triazole-3-carboxamide The preparation was carried out in a similar manner to Example 92, except that in step 1, 1-bromo-2-ethoxyethane was used in place of iodomethane, and 3-bromo-4-methylphenol was used in place of 2-bromo-3-methylphenol. $^1$H NMR (400 MHz, DMSO-$d_6$) δ 14.62 (s, 1H), 9.91 (s, 1H), 8.42 (d, J=5.1 Hz, 1H), 8.12 (s, 1H), 7.45-7.13 (m, 7H), 6.95 (dd, J=8.4, 2.7 Hz, 1H), 6.84 (d, J=2.7 Hz, 1H), 4.18 (s, 2H), 4.14-4.02 (m, 2H), 3.76-3.64 (m, 2H), 3.49 (q, J=7.0 Hz, 2H), 2.19 (s, 3H), 1.12 (t, J=7.0 Hz, 3H). MS: 458 $[M+H]^+$.

Example 131

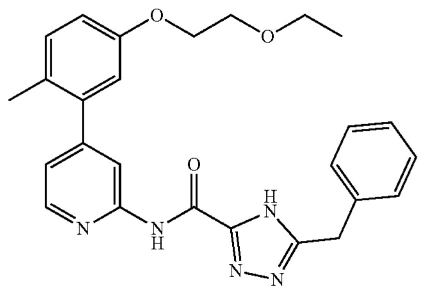

Example 133

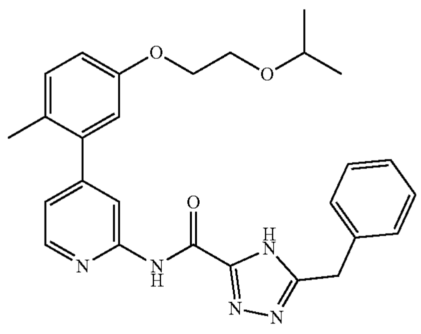

Example 132

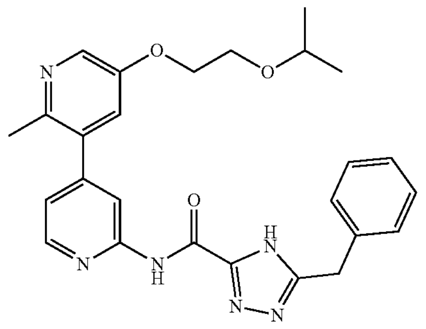

Example 134

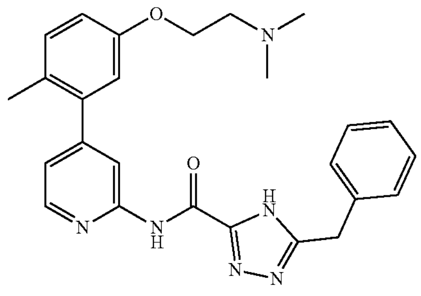

Example 132: 5-benzyl-N-(5-(2-isopropoxyethoxy)-2-methyl-[3,4'-dipyridine]-2'-yl)-4H-1,2,4-triazole-3-carboxamide The preparation was carried out in a similar manner to Example 92, except that in step 1, 1-bromo-2-isopropoxyethane was used in place of iodomethane, and 5-bromo-6-methylpyridin-3-ol (for the synthetic method refers to Lin, Nan-Horng et al/U.S., 6437138, 20 Aug. 2002) was used in place of 2-bromo-3-methylphenol. $^1$H NMR (400 MHz, DMSO-$d_6$) δ 14.64 (s, 1H), 9.98 (s, 1H), 8.46 (d, J=5.1 Hz, 1H), 8.27 (d, J=2.9 Hz, 1H), 8.16 (s, 1H), 7.41-7.18 (m, 7H), 4.26-4.07 (m, 4H), 3.69 (s, 2H), 3.61 (p, J=6.1 Hz, 1H), 2.39 (s, 3H), 1.09 (d, J=6.0 Hz, 6H). MS: 473 $[M+H]^+$.

Example 133: 5-benzyl-N-(4-(5-(2-isopropoxyethoxy)-2-methylphenyl)pyridin-2-yl)-4H-1,2,4-triazole-3-carboxamide The preparation was carried out in a similar manner to Example 92, except that in step 1, 1-bromo-2-isopropoxyethane was used in place of iodomethane, and 3-bromo-4-methylphenol was used in place of 2-bromo-3-methylphenol. $^1$H NMR (400 MHz, DMSO-$d_6$) δ 14.62 (s, 1H), 9.90 (s, 1H), 8.42 (dd, J=5.1, 0.8 Hz, 1H), 8.12 (s, 1H), 7.39-7.29 (m, 4H), 7.29-7.18 (m, 3H), 6.95 (dd, J=8.4, 2.7 Hz, 1H), 6.83 (d, J=2.8 Hz, 1H), 4.17 (s, 2H), 4.12-4.01 (m, 2H), 3.74-3.65 (m, 2H), 3.61 (p, J=6.1 Hz, 1H), 2.19 (s, 3H), 1.10 (d, J=6.1 Hz, 6H). MS: 472 $[M+H]^+$ Example 134: 5-benzyl-N-(4-(5-(2-(dimethylamino)ethoxy)-2-methylphenyl)pyridin-2-yl)-4H-1,2,4-triazole-3-carboxamide The preparation was carried out in a similar manner to Example 92, except that in step 1, 2-bromo-N,N-dimethyl-1-ethylamine hydrochloride was used in place of iodomethane, and 3-bromo-4-methylphenol was used in place of 2-bromo-3-methylphenol. $^1$H NMR (400 MHz, DMSO-$d_6$) δ 14.89-14.02 (m, 1H), 9.90 (s, 1H), 8.42 (dd, J=5.1, 0.8 Hz, 1H), 8.15-8.07 (m, 1H), 7.39-7.30 (m, 4H), 7.30-7.17 (m, 3H), 6.95 (dd, J=8.4, 2.7 Hz, 1H), 6.83 (d, J=2.7 Hz, 1H), 4.17 (s, 2H), 4.06 (t, J=5.8 Hz, 2H), 2.62 (t, J=5.8 Hz, 2H), 2.21 (s, 6H), 2.19 (s, 3H). MS: 457 $[M+H]^+$.

Example 135: 5-benzyl-N-(4-(5-(2-(diethylamino)ethoxy)-2-methylphenyl)pyridin-2-yl)-4H-1,2,4-triazole-3-carboxamide The preparation was carried out in a similar manner to Example 92, except that in step 1, 2-bromo-N,N-dimethyl-1-ethylamine hydrochloride was used in place of iodomethane, and 3-bromo-4-methylphenol was used in place of 2-bromo-3-methylphenol. $^1$H NMR (400 MHz, DMSO-$d_6$) δ 14.20 (s, 1H), 9.91 (s, 1H), 8.42 (d, J=5.1 Hz, 1H), 8.11 (d, J=1.5 Hz, 1H), 7.41-7.29 (m, 4H), 7.29-7.18 (m, 3H), 6.94 (dd, J=8.4, 2.7 Hz, 1H), 6.83 (d, J=2.7 Hz, 1H), 4.18 (s, 2H), 4.05 (t, J=6.0 Hz, 2H), 2.83 (t, J=6.1 Hz, 2H), 2.60 (q, J=7.1 Hz, 4H), 2.19 (s, 3H), 0.98 (t, J=7.1 Hz, 6H). MS: 485 $[M+H]^+$.

Example 135

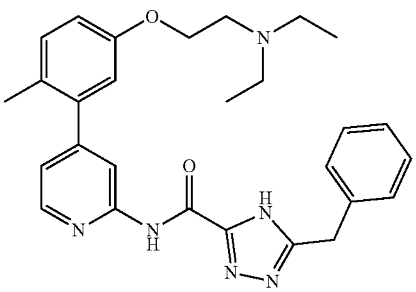

Example 136

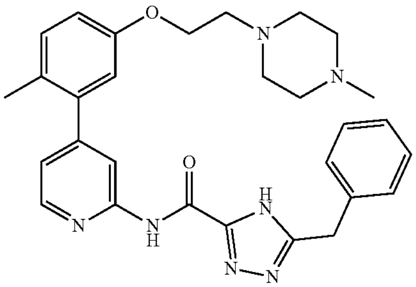

Example 136: 5-benzyl-N-(4-(2-methyl-5-(2-(4-methylpiperazin-1-yl)ethoxy)phenyl)pyridin-2-yl)-4H-1,2,4-triazole-3-carboxamide The preparation was carried out in a similar manner to Example 92, except that in step 1, 1-(2-chloroethyl)-4-methylpiperazine dihydrochloride was used in place of iodomethane, and 3-bromo-4-methylphenol was used in place of 2-bromo-3-methylphenol. $^1$H NMR (400 MHz, DMSO-$d_6$) δ 13.97 (s, 1H), 9.90 (s, 1H), 8.41 (d, J=5.2 Hz, 1H), 8.12 (s, 1H), 7.40-7.15 (m, 7H), 6.94 (dd, J=8.6, 2.8 Hz, 1H), 6.84 (d, J=2.8 Hz, 1H), 4.17 (s, 2H), 4.08 (t, J=5.9 Hz, 2H), 2.67 (t, J=5.8 Hz, 2H), 2.46 (s, 4H), 2.30 (s, 4H), 2.19 (s, 3H), 2.13 (s, 3H). MS: 512 $[M+H]^+$.

Example 137: N-(4-(5-(2-(1,3-dioxolan-2-yl)ethoxy)-2-methylphenyl)pyridin-2-yl)-5-benzyl-4H-1,2,4-triazole-3-carboxamide The preparation was carried out in a similar manner to Example 92, except that in step 1, 2-(2-bromoethyl)-1,3-dioxolane was used in place of iodomethane, and 3-bromo-4-methylphenol was used in place of 2-bromo-3-methylphenol. $^1$H NMR (400 MHz, DMSO-$d_6$) δ 14.60 (s, 1H), 9.91 (s, 1H), 8.42 (d, J=5.1 Hz, 1H), 8.11 (s, 1H), 7.45-7.15 (m, 7H), 6.94 (dd, J=8.4, 2.7 Hz, 1H), 6.82 (d, J=2.7 Hz, 1H), 4.98 (t, J=4.9 Hz, 1H), 4.18 (s, 2H), 4.08 (t, J=6.6 Hz, 2H), 3.96-3.84 (m, 2H), 3.84-3.71 (m, 2H), 2.19 (s, 3H), 2.10-1.95 (m, 2H). MS: 486 $[M+H]^+$.

Example 137

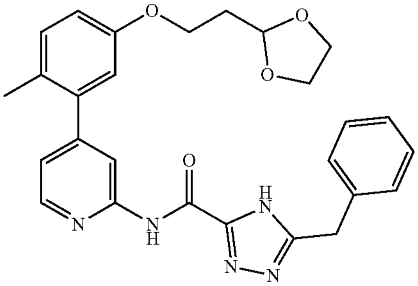

Example 138

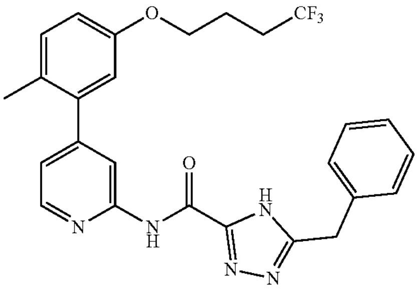

Example 138: 5-benzyl-N-(4-(2-methyl-5-(4,4,4-trifluorobutoxy)phenyl)pyridin-2-yl)-4H-1,2,4-triazole-3-carboxamide The preparation was carried out in a similar manner to Example 92, except that in step 1, 4-bromo-1,1,1-trifluorobutane was used in place of iodomethane, and 3-bromo-4-methylphenol was used in place of 2-bromo-3-methylphenol. $^1$H NMR (400 MHz, DMSO-$d_6$) δ 14.62 (s, 1H), 9.91 (s, 1H), 8.42 (d, J=5.1 Hz, 1H), 8.12 (d, J=1.5 Hz, 1H), 7.41-7.30 (m, 4H), 7.30-7.23 (m, 2H), 7.21 (dd, J=5.1, 1.6 Hz, 1H), 6.95 (dd, J=8.4, 2.7 Hz, 1H), 6.84 (d, J=2.7 Hz, 1H), 4.18 (s, 2H), 4.05 (t, J=6.2 Hz, 2H), 2.47-2.31 (m, 2H), 2.19 (s, 3H), 1.99-1.85 (m, 2H). MS: 496 $[M+H]^+$.

Example 139: 5-benzyl-N-(4-(5-(3-(dimethylamino)propoxy)-2-methylphenyl)pyridin-2-yl)-4H-1,2,4-triazole-3-carboxamide The preparation was carried out in a similar manner to Example 92, except that in step 1, 3-bromo-N,N-dimethyl-1-propylamine hydrochloride was used in place of iodomethane, and 3-bromo-4-methylphenol was used in place of 2-bromo-3-methylphenol. $^1$H NMR (400 MHz, DMSO-$d_6$) δ 13.57 (s, 1H), 9.91 (s, 1H), 8.41 (d, J=5.1 Hz, 1H), 8.13 (s, 1H), 7.39-7.29 (m, 4H), 7.29-7.14 (m, 3H), 6.92 (dd, J=8.4, 2.6 Hz, 1H), 6.80 (d, J=2.7 Hz, 1H), 4.17 (s, 2H), 3.99 (t, J=6.4 Hz, 2H), 2.36 (t, J=7.1 Hz, 2H), 2.18 (s, 3H), 2.14 (s, 6H), 1.89-1.77 (m, 2H). MS: 471 $[M+H]^+$.

Example 139

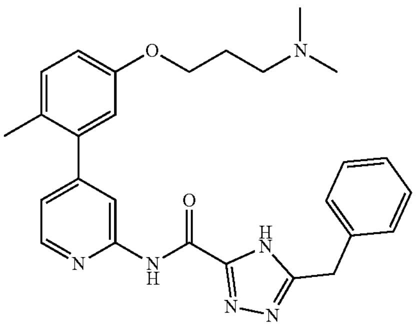

Example 140

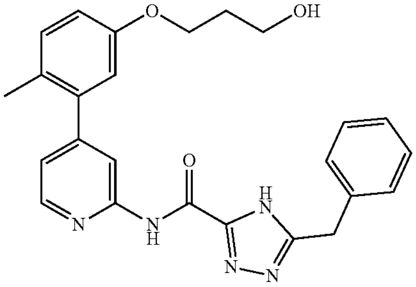

Example 140: 5-benzyl-N-(4-(5-(3-hydroxylpropoxy)-2-methylphenyl)pyridin-2-yl)-4H-1,2,4-triazole-3-carboxamide The preparation was carried out in a similar manner to Example 92, except that in step 1, 3-bromo-1-propanol was used in place of iodomethane, and 3-bromo-4-methylphenol was used in place of 2-bromo-3-methylphenol. $^1H$ NMR (400 MHz, DMSO-$d_6$) δ 14.80 (s, 1H), 9.90 (s, 1H), 8.41 (d, J=5.1 Hz, 1H), 8.11 (s, 1H), 7.38-7.30 (m, 4H), 7.26 (dd, J=7.5, 4.8 Hz, 2H), 7.21 (dd, J=5.1, 1.6 Hz, 1H), 6.93 (dd, J=8.4, 2.7 Hz, 1H), 6.81 (d, J=2.7 Hz, 1H), 4.54 (t, J=5.1 Hz, 1H), 4.17 (s, 2H), 4.04 (t, J=6.4 Hz, 2H), 3.57-3.52 (m, 2H), 2.19 (s, 3H), 1.91-1.79 (m, 2H). MS: 444 $[M+H]^+$.

Example 141: 5-benzyl-N-(4-(5-(3-methoxypropoxy)-2-methylphenyl)pyridin-2-yl)-4H-1,2,4-triazole-3-carboxamide The preparation was carried out in a similar manner to Example 92, except that in step 1, 1-bromo-3-methoxypropane was used in place of iodomethane, and 3-bromo-4-methylphenol was used in place of 2-bromo-3-methylphenol. $^1H$ NMR (400 MHz, DMSO-$d_6$) δ 14.40 (s, 1H), 9.90 (s, 1H), 8.41 (dd, J=5.2, 2.1 Hz, 1H), 8.11 (d, J=1.6 Hz, 1H), 7.45-7.15 (m, 7H), 6.94 (dd, J=8.4, 2.7 Hz, 1H), 6.81 (d, J=2.6 Hz, 1H), 4.17 (s, 2H), 4.03 (t, J=6.3 Hz, 2H), 3.48-3.44 (m, 2H), 3.23 (d, J=2.1 Hz, 3H), 2.19 (d, J=2.1 Hz, 3H), 2.02-1.85 (m, 2H). MS: 458 $[M+H]^+$.

Example 141

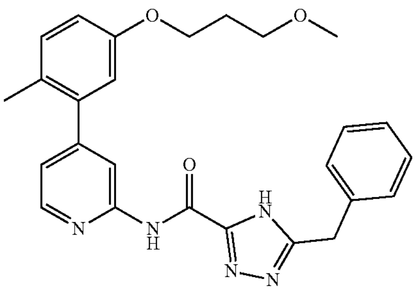

Example 142

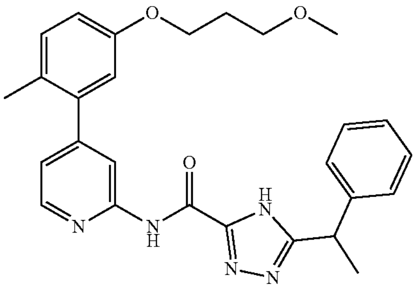

Example 142: N-(4-(5-(3-methoxypropoxy)-2-methylphenyl)pyridin-2-yl)-5-(1-phenylethyl)-4H-1,2,4-triazole-3-carboxamide The preparation was carried out in a similar manner to Example 92, except that in step 1, 1-bromo-3-methoxypropane was used in place of iodomethane, 3-bromo-4-methylphenol was used in place of 2-bromo-3-methylphenol, and in step 3, ethyl 5-(1-phenylethyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.54 (s, 1H), 9.91 (s, 1H), 8.42 (d, J=5.1 Hz, 1H), 8.12 (s, 1H), 7.44-7.28 (m, 4H), 7.29-7.17 (m, 3H), 6.94 (dd, J=8.4, 2.7 Hz, 1H), 6.82 (d, J=2.7 Hz, 1H), 4.41 (q, J=7.2 Hz, 1H), 4.03 (t, J=6.4 Hz, 2H), 3.46 (t, J=6.3 Hz, 2H), 3.24 (s, 3H), 2.19 (s, 3H), 1.98-1.87 (m, 2H), 1.67 (d, J=7.2 Hz, 3H). MS: 472 $[M+H]^+$.

Example 143: N-(4-(5-(3-methoxypropoxy)-2-methylphenyl)pyridin-2-yl)-5-(1-phenylethyl)-1,3,4-oxadiazol-2-carboxamide The preparation was carried out in a similar manner to Example 92, except that in step 1, 1-bromo-3-methoxypropane was used in place of iodomethane, and 3-bromo-4-methylphenol was used in place of 2-bromo-3-methylphenol, in step 3, ethyl 5-(1-phenylethyl)-1,3,4-oxadiazol-2-carboxylate was used in place of ethyl 5-benzyl-4H-1,2,4-triazol-3-carboxylate. $^1H$ NMR (400 MHz, DMSO-$d_6$) δ 11.29 (s, 1H), 8.46 (d, J=5.1 Hz, 1H), 7.96 (s, 1H), 7.43-7.20 (m, 7H), 6.93 (dd, J=8.4, 2.7 Hz, 1H), 6.80 (d, J=2.7 Hz, 1H), 4.63 (q, J=7.2 Hz, 1H), 4.02 (t, J=6.4 Hz, 2H), 3.45 (t, J=6.3 Hz, 2H), 3.34 (s, 3H), 2.18 (s, 3H), 1.98-1.87 (m, 2H), 1.71 (d, J=7.2 Hz, 3H). MS: 473 $[M+H]^+$.

Example 143

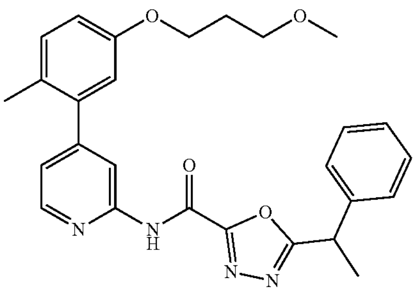

Example 144

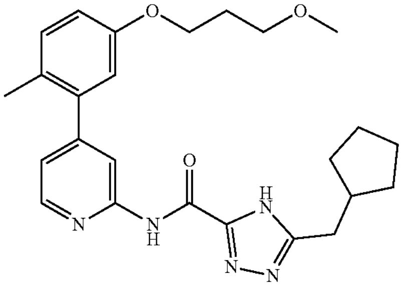

Example 144: 5-(cyclopentylmethyl)-N-(4-(5-(3-methoxypropoxy)-2-methylphenyl)pyridin-2-yl)-4H-1,2,4-triazole-3-carboxamide The preparation was carried out in a similar manner to Example 92, except that in step 1, 1-bromo-3-methoxypropane was used in place of iodomethane, 3-bromo-4-methylphenol was used in place of 2-bromo-3-methylphenol, and in step 3, ethyl 5-(cyclopentylmethyl)-4H-1,2,4-triazole-3-carboxylate was used in place of ethyl 5-benzyl-4H-1,2,4-triazol-3-carboxylate. $^1$H NMR (400 MHz, DMSO-$d_6$) δ 14.38 (s, 1H), 9.84 (s, 1H), 8.42 (d, J=5.1 Hz, 1H), 8.14 (s, 1H), 7.33-7.14 (m, 2H), 6.94 (dd, J=8.4, 2.7 Hz, 1H), 6.82 (d, J=2.7 Hz, 1H), 4.03 (t, J=6.4 Hz, 2H), 3.46 (t, J=6.3 Hz, 2H), 3.24 (s, 3H), 2.84-2.74 (m, 2H), 2.36-2.22 (m, 1H), 2.20 (s, 3H), 2.00-1.88 (m, 2H), 1.79-1.66 (m, 2H), 1.66-1.56 (m, 2H), 1.56-1.45 (m, 2H), 1.27-1.18 (m, 2H). MS: 450 $[M+H]^+$.

Example 145: 5-(cyclohexylmethyl)-N-(4-(5-(3-methoxypropoxy)-2-methylphenyl)pyridin-2-yl)-4H-1,2,4-triazole-3-carboxamide The preparation was carried out in a similar manner to Example 92, except that in step 1, 1-bromo-3-methoxypropane was used in place of iodomethane, 3-bromo-4-methylphenol was used in place of 2-bromo-3-methylphenol, and in step 3, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.37 (s, 1H), 9.97-9.76 (m, 1H), 8.42 (d, J=5.1 Hz, 1H), 8.13 (s, 1H), 7.34-7.12 (m, 2H), 6.94 (dd, J=8.4, 2.7 Hz, 1H), 6.82 (d, J=2.8 Hz, 1H), 4.03 (t, J=6.4 Hz, 2H), 3.46 (t, J=6.3 Hz, 2H), 3.24 (s, 3H), 2.67 (d, J=7.0 Hz, 2H), 2.19 (s, 3H), 2.01-1.86 (m, 2H), 1.84-1.53 (m, 6H), 1.30-1.06 (m, 3H), 1.06-0.87 (m, 2H). MS: 464 $[M+H]^+$.

Example 145

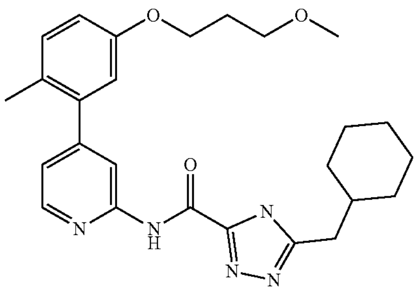

Example 146

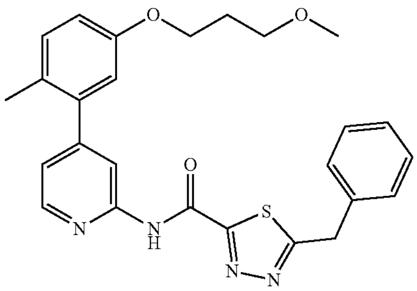

Example 146: 5-benzyl-N-(4-(5-(3-methoxypropoxy)-2-methylphenyl)pyridin-2-yl)-1,3,4-thiodiazol-2-carboxamide The preparation was carried out in a similar manner to Example 92, except that in step 1, 1-bromo-3-methoxypropane was used in place of iodomethane, 3-bromo-4-methylphenol was used in place of 2-bromo-3-methylphenol, and in step 3, methyl 5-benzyl-1,3,4-thiodiazol-2-carboxylate was used in place of ethyl 5-benzyl-4H-1,2,4-triazol-3-carboxylate. $^1$H NMR (400 MHz, DMSO-$d_6$) δ 10.84 (s, 1H), 8.47 (dd, J=5.1, 0.8 Hz, 1H), 7.99 (dd, J=1.6, 0.8 Hz, 1H), 7.46-7.17 (m, 7H), 6.93 (dd, J=8.4, 2.7 Hz, 1H), 6.81 (d, J=2.7 Hz, 1H), 4.58 (s, 2H), 4.02 (t, J=6.4 Hz, 2H), 3.46 (t, J=6.3 Hz, 2H), 3.23 (s, 3H), 2.18 (s, 3H), 2.00-1.87 (m, 2H). MS: 475 $[M+H]^+$.

Example 147: 5-benzyl-N-(4-(5-(3-ethoxypropoxy)-2-methylphenyl)pyridin-2-yl)-4H-1,2,4-triazole-3-carboxamide The preparation was carried out in a similar manner to Example 92, except that in step 1, 1-bromo-3-ethoxypropane was used in place of iodomethane, and 3-bromo-4-methylphenol was used in place of 2-bromo-3-methylphenol. $^1$H NMR (400 MHz, DMSO-$d_6$) δ 14.63 (s, 1H), 9.92 (s, 1H), 8.41 (d, J=5.1 Hz, 1H), 8.11 (s, 1H), 7.46-7.29 (m, 4H), 7.29-7.14 (m, 3H), 6.94 (dd, J=8.4, 2.7 Hz, 1H), 6.82 (d, J=2.7 Hz, 1H), 4.18 (s, 2H), 4.03 (t, J=6.4 Hz, 2H), 3.49 (t, J=6.3 Hz, 2H), 3.41 (q, J=7.0 Hz, 2H), 2.19 (s, 3H), 2.00-1.86 (m, 2H), 1.08 (t, J=7.0 Hz, 3H). MS: 472 $[M+H]^+$.

Example 147

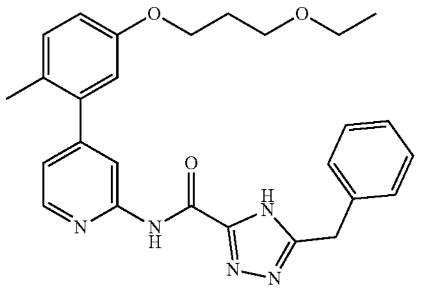

Example 148

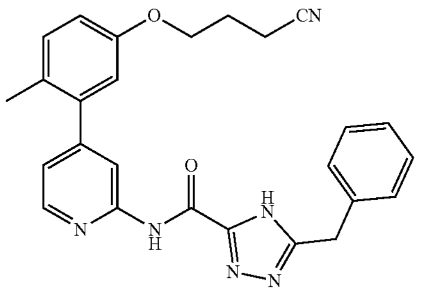

Example 148: 5-benzyl-N-(4-(5-(3-cyanopropoxy)-2-methylphenyl)pyridin-2-yl)-4H-1,2,4-triazole-3-carboxamide The preparation was carried out in a similar manner to Example 92, except that in step 1, 4-bromo-1-butanenitrile was used in place of iodomethane, and 3-bromo-4-methylphenol was used in place of 2-bromo-3-methylphenol. $^{1}$H NMR (400 MHz, DMSO-$d_6$) δ 14.59 (s, 1H), 9.91 (s, 1H), 8.42 (d, J=5.1 Hz, 1H), 8.12 (s, 1H), 7.45-7.14 (m, 7H), 6.96 (dd, J=8.4, 2.7 Hz, 1H), 6.85 (d, J=2.7 Hz, 1H), 4.18 (s, 2H), 4.05 (t, J=6.0 Hz, 2H), 2.65 (t, J=7.1 Hz, 2H), 2.19 (s, 3H), 2.06-1.96 (m, 2H). MS: 453 $[M+H]^+$.

Example 149: 5-benzyl-N-(4-(2-methyl-5-(pent-4-en-1-yloxy)phenyl)pyridin-2-yl)-4H-1,2,4-triazole-3-carboxamide The preparation was carried out in a similar manner to Example 92, except that in step 1, 5-bromo-1-pentene was used in place of iodomethane, and 3-bromo-4-methylphenol was used in place of 2-bromo-3-methylphenol. $^{1}$H NMR (400 MHz, DMSO-$d_6$) δ 14.58 (s, 1H), 9.97 (s, 1H), 8.42 (d, J=5.1 Hz, 1H), 8.11 (s, 1H), 7.44-7.16 (m, 7H), 6.94 (dd, J=8.4, 2.7 Hz, 1H), 6.81 (d, J=2.7 Hz, 1H), 5.94-5.77 (m, 1H), 5.62-5.40 (m, 1H), 5.12-4.91 (m, 1H), 4.18 (s, 2H), 4.06-3.91 (m, 2H), 2.44-2.32 (m, 1H), 2.19 (s, 3H), 1.87-1.72 (m, 1H), 1.69-1.55 (m, 2H). MS: 454 $[M+H]^+$.

Example 149

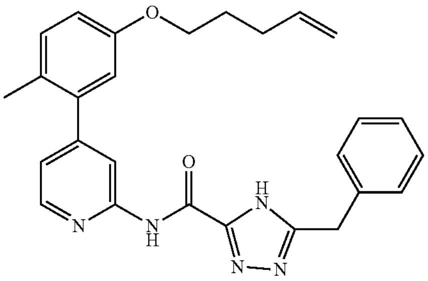

Example 150

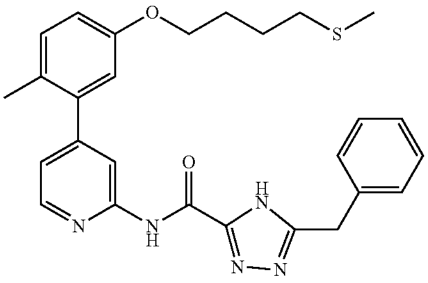

Example 150: 5-benzyl-N-(4-(2-methyl-5-(4-(methylthio)butoxy)phenyl)pyridin-2-yl)-4H-1,2,4-triazole-3-carboxamide The preparation was carried out in a similar manner to Example 92, except that in step 1, (4-bromobutyl)(methyl) sulfane was used in place of iodomethane, and 3-bromo-4-methylphenol was used in place of 2-bromo-3-methylphenol. $^{1}$H NMR (400 MHz, DMSO-$d_6$) δ 14.62 (s, 1H), 9.91 (s, 1H), 8.41 (d, J=5.1 Hz, 1H), 8.11 (s, 1H), 7.41-7.29 (m, 4H), 7.29-7.23 (m, 2H), 7.21 (dd, J=5.1, 1.6 Hz, 1H), 6.94 (dd, J=8.4, 2.7 Hz, 1H), 6.82 (d, J=2.7 Hz, 1H), 4.17 (s, 2H), 4.00 (t, J=6.4 Hz, 2H), 2.58-2.52 (m, 2H), 2.19 (s, 3H), 2.03 (s, 3H), 1.85-1.73 (m, 2H), 1.73-1.61 (m, 2H). MS: 488 $[M+H]^+$.

Example 151: 5-benzyl-N-(4-(5-(4-hydroxybutoxy)-2-methylphenyl)pyridin-2-yl)-4H-1,2,4-triazole-3-carboxamide The preparation was carried out in a similar manner to Example 92, except that in step 1, 4-bromo-1-butanol was used in place of iodomethane, and 3-bromo-4-methylphenol was used in place of 2-bromo-3-methylphenol. $^{1}$H NMR (400 MHz, DMSO-$d_6$) δ 14.60 (s, 1H), 9.90 (s, 1H), 8.41 (d, J=5.1 Hz, 1H), 8.11 (s, 1H), 7.39-7.29 (m, 4H), 7.29-7.22 (m, 2H), 7.21 (dd, J=5.2, 1.6 Hz, 1H), 6.93 (dd, J=8.4, 2.8 Hz, 1H), 6.81 (d, J=2.7 Hz, 1H), 4.51-4.35 (m, 1H), 4.17 (s, 2H), 3.98 (t, J=6.5 Hz, 2H), 3.44 (t, J=6.4 Hz, 2H), 2.19 (s, 3H), 1.80-1.67 (m, 2H), 1.62-1.49 (m, 2H). MS: 458 $[M+H]^+$.

Example 151

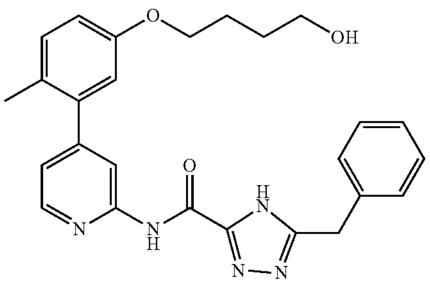

Example 152

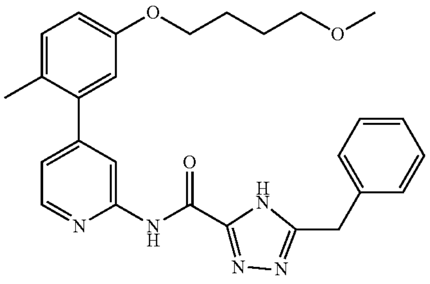

Example 152: 5-benzyl-N-(4-(5-(4-methoxybutoxy)-2-methylphenyl)pyridin-2-yl)-4H-1,2,4-triazole-3-carboxamide The preparation was carried out in a similar manner to Example 92, except that in step 1, 1-bromo-4-methoxybutane was used in place of iodomethane, and 3-bromo-4-methylphenol was used in place of 2-bromo-3-methylphenol. $^1$H NMR (400 MHz, DMSO-$d_6$) δ 14.62 (s, 1H), 9.91 (s, 1H), 8.47-8.34 (m, 1H), 8.18-8.03 (m, 1H), 7.43-7.13 (m, 7H), 6.93 (dd, J=8.4, 2.7 Hz, 1H), 6.81 (d, J=2.7 Hz, 1H), 4.17 (s, 2H), 3.98 (t, J=6.4 Hz, 2H), 3.35 (t, J=6.3 Hz, 2H), 3.22 (s, 3H), 2.19 (s, 3H), 1.81-1.68 (m, 2H), 1.68-1.56 (m, 2H). MS: 472 $[M+H]^+$.

Example 153: 5-benzyl-N-(4-(5-((5-hydroxylpentyl)oxy)-2-methylphenyl)pyridin-2-yl)-4H-1,2,4-triazole-3-carboxamide The preparation was carried out in a similar manner to Example 92, except that in step 1, 5-bromo-1-pentanol was used in place of iodomethane, and 3-bromo-4-methylphenol was used in place of 2-bromo-3-methylphenol. $^1$H NMR (400 MHz, DMSO-$d_6$) δ 14.61 (s, 1H), 9.91 (s, 1H), 8.41 (d, J=5.1 Hz, 1H), 8.11 (s, 1H), 7.42-7.30 (m, 4H), 7.30-7.13 (m, 3H), 6.93 (dd, J=8.4, 2.7 Hz, 1H), 6.81 (d, J=2.7 Hz, 1H), 4.45-4.31 (m, 1H), 4.18 (s, 2H), 3.97 (t, J=6.5 Hz, 2H), 3.46-3.36 (m, 2H), 2.19 (s, 3H), 1.70 (t, J=6.9 Hz, 2H), 1.54-1.36 (m, 4H). MS: 472 $[M+H]^+$.

Example 153

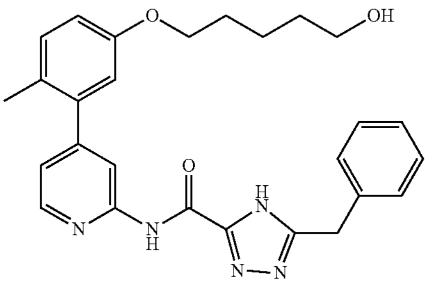

Example 154

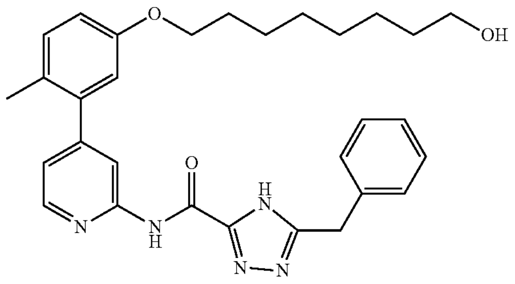

Example 154: 5-benzyl-N-(4-(5-((8-hydroxyoctyl)oxy)-2-methylphenyl)pyridin-2-yl)-4H-1,2,4-triazole-3-carboxamide The preparation was carried out in a similar manner to Example 92, except that in step 1, 8-bromo-1-octanol was used in place of iodomethane, and 3-bromo-4-methylphenol was used in place of 2-bromo-3-methylphenol. $^1$H NMR (400 MHz, DMSO-$d_6$) δ 14.64 (s, 1H), 9.92 (s, 1H), 8.41 (d, J=5.1 Hz, 1H), 8.11 (d, J=1.5 Hz, 1H), 7.42-7.11 (m, 7H), 6.92 (dd, J=8.4, 2.7 Hz, 1H), 6.80 (d, J=2.7 Hz, 1H), 4.46-4.24 (m, 1H), 4.17 (s, 2H), 3.96 (t, J=6.5 Hz, 2H), 3.37-3.34 (m, 2H), 2.18 (s, 3H), 1.78-1.60 (m, 2H), 1.50-1.34 (m, 4H), 1.34-1.13 (m, 6H). MS: 514 $[M+H]^+$.

Example 155: 5-benzyl-N-(4-(5-cyclopropoxy-2-methylphenyl)pyridin-2-yl)-4H-1,2,4-triazole-3-carboxamide The preparation was carried out in a similar manner to Example 92, except that in step 1, bromocyclopropane was used in place of iodomethane, and 3-bromo-4-methylphenol was used in place of 2-bromo-3-methylphenol. $^1$H NMR (400 MHz, DMSO-$d_6$) δ 14.54 (s, 1H), 9.85 (s, 1H), 8.42 (d, J=5.2 Hz, 1H), 8.13 (s, 1H), 7.39-7.30 (m, 4H), 7.30-7.23 (m, 2H), 7.23-7.18 (m, 1H), 7.05 (dd, J=8.4, 2.7 Hz, 1H), 6.93 (d, J=2.7 Hz, 1H), 4.19 (s, 2H), 3.91-3.82 (m, 1H), 2.20 (s, 3H), 0.83-0.71 (m, 2H), 0.71-0.60 (m, 2H). MS: 426 $[M+H]^+$.

Example 155

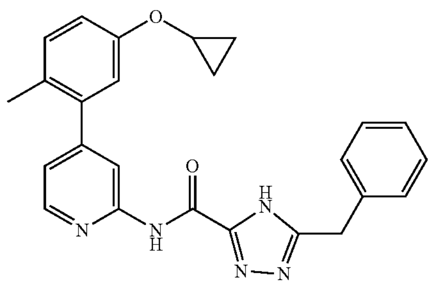

Example 156

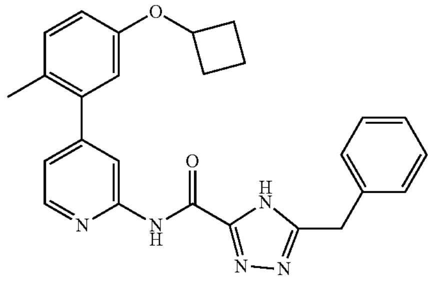

Example 156: 5-benzyl-N-(4-(5-cyclobutoxy-2-methylphenyl)pyridin-2-yl)-4H-1,2,4-triazole-3-carboxamide The preparation was carried out in a similar manner to Example 92, except that in step 1, bromocyclobutane was used in place of iodomethane, and 3-bromo-4-methylphenol was used in place of 2-bromo-3-methylphenol. $^1$H NMR (400 MHz, DMSO-$d_6$) δ 14.58 (s, 1H), 9.89 (s, 1H), 8.41 (d, J=5.1 Hz, 1H), 8.11 (s, 1H), 7.40-7.29 (m, 4H), 7.29-7.15 (m, 3H), 6.84 (dd, J=8.4, 2.7 Hz, 1H), 6.72 (d, J=2.7 Hz, 1H), 4.77-4.64 (m, 1H), 4.18 (s, 2H), 2.46-2.35 (m, 2H), 2.18 (s, 3H), 2.11-1.94 (m, 2H), 1.83-1.70 (m, 1H), 1.70-1.54 (m, 1H). MS: 440 [M+H]$^+$.

Example 157: N-(4-(5-(4-amino-4-oxobutoxy)-2-methylphenyl)pyridin-2-yl)-5-benzyl-4H-1,2,4-triazole-3-carboxamide

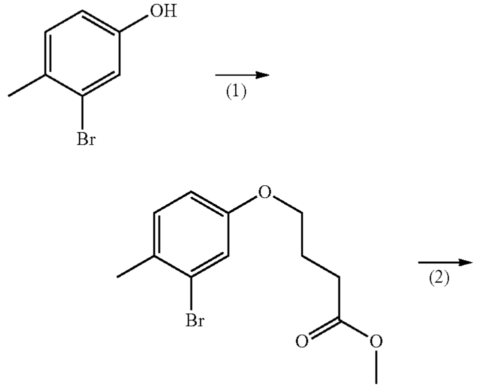

-continued

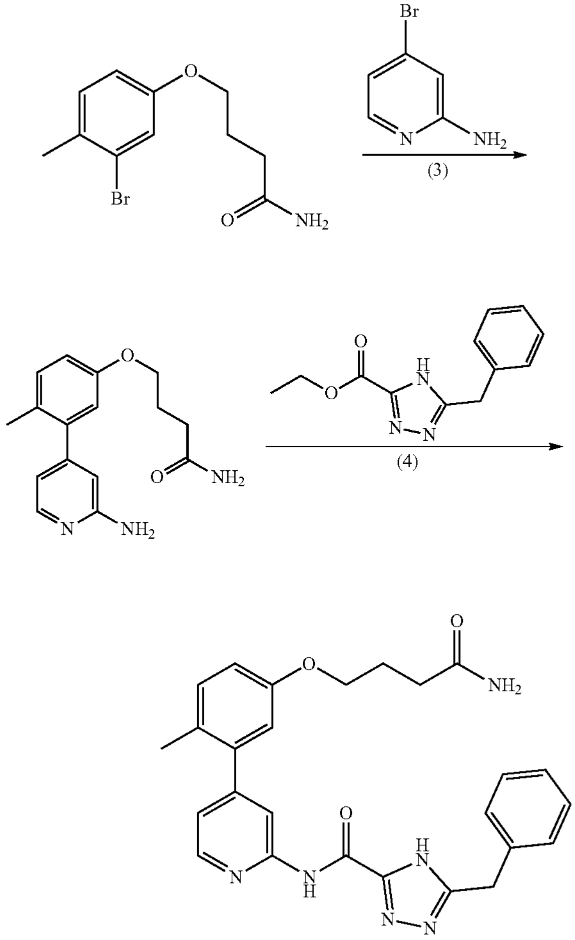

Step 1: Synthesis of methyl 4-(3-bromo-4-methylphenoxy)butanoate

The operation is the same as step 1 of Example 92, but methyl 4-bromobutanoate was used in place of iodomethane in step 1, and 3-bromo-4-methylphenol was used in place of 2-bromo-3-methylphenol in step 1.

Step 2: Synthesis of 4-(3-bromo-4-methylphenoxy)butanamide

Methyl 4-(3-bromo-4-methylphenoxy)butanoate (287 mg, 1 mmol) was dissolved in 7M ammonia in methanol, and reacted at 80° C. for 36 hours in sealed tube. The reaction solution was cooled, evaporated to dryness, and used directly in the next step.

Step 3 to Step 4: The preparation was carried out in a similar manner to Example 33, except that in step 1, 4-(3-bromo-4-methylphenoxy)butanamide was used in place of 2-bromo-4-fluoro-1-methylbenzene. $^1$H NMR (400 MHz, DMSO-$d_6$) δ 14.63 (s, 1H), 9.91 (s, 1H), 8.42 (d, J=5.1 Hz, 1H), 8.11 (s, 1H), 7.41-7.30 (m, 5H), 7.26 (dd, J=7.6, 5.2 Hz, 2H), 7.21 (dd, J=5.1, 1.6 Hz, 1H), 6.93 (dd, J=8.4, 2.7 Hz, 1H), 6.88-6.67 (m, 2H), 4.18 (s, 2H), 3.97 (t, J=6.4 Hz, 2H), 2.28-2.12 (m, 5H), 1.97-1.83 (m, 2H). MS: 471 [M+H]$^+$.

Example 158: 5-benzyl-N-(4-(5-carbamoyl-2-methylphenyl)pyridin-2-yl)-4H-1,2,4-triazole-3-carboxamide

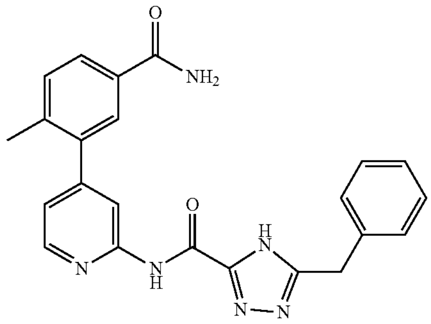 [SMILES: Cc1ccc(C(N)=O)cc1-c1ccnc(NC(=O)c2nnc(Cc3ccccc3)[nH]2)c1]

The operation is the same as steps 2 to 4 of Example 157, but methyl 3-bromo-4-methylbenzoate was used in place of methyl 4-(3-bromo-4-methylphenoxy)butanoate in step 2. $^1$H NMR (400 MHz, DMSO-$d_6$) δ 14.39 (s, 1H), 9.95 (s, 1H), 8.45 (d, J=5.1 Hz, 1H), 8.15 (d, J=5.3 Hz, 1H), 8.04 (d, J=5.5 Hz, 1H), 7.86 (d, J=7.5 Hz, 1H), 7.81 (d, J=5.4 Hz, 1H), 7.51-7.42 (m, 1H), 7.42-7.30 (m, 5H), 7.30-7.18 (m, 2H), 4.18 (s, 2H), 2.33 (s, 3H). MS: 413 $[M+H]^+$.

Example 159: 5-benzyl-N-(4-(5-((1-hydroxycyclopropyl)methoxy)-2-methylphenyl)pyridin-2-yl)-4H-1,2,4-triazole-3-carboxamide

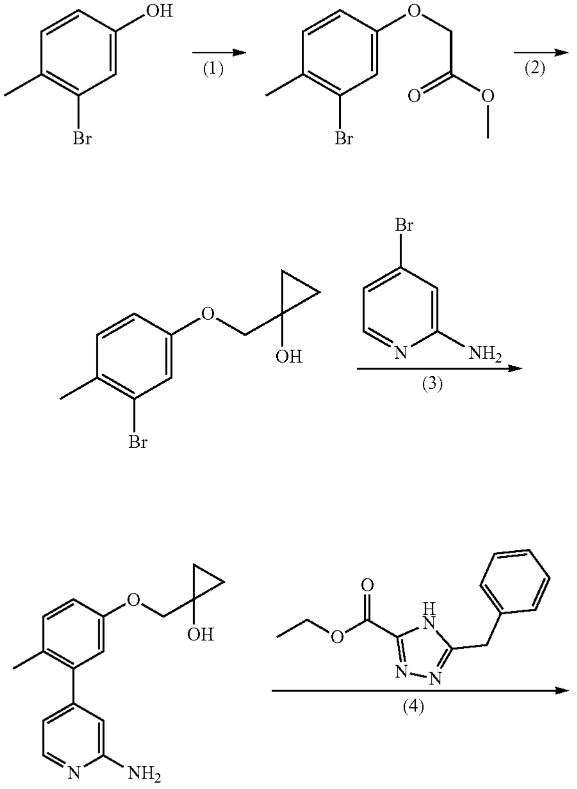

-continued

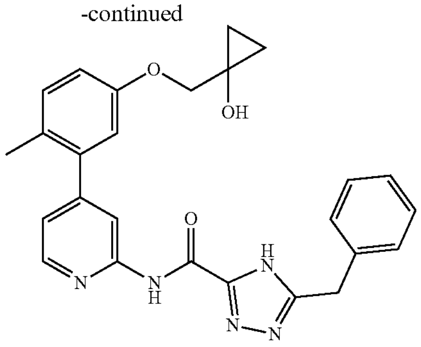

Step 1: Synthesis of methyl 2-(3-bromo-4-methylphenoxy)acetate

The operation is the same as step 1 of Example 92, but methyl bromoacetate was used in place of iodomethane in step 1, and 3-bromo-4-methylphenol was used in place of 2-bromo-3-methylphenol in step 1.

Step 2: Synthesis of 1-((3-bromo-4-methylphenoxy)methyl)cyclopropane-1-ol

Methyl 2-(3-bromo-4-methylphenoxy)acetate (259 mg, 1 mmol) and tetraisopropyl titanate (57 mg, 0.2 mmol) were dissolved in anhydrous tetrahydrofuran, and ethyl Grignard reagent (1M in THF, 2.5 mL, 2.5 mmol) slowly added at 0° C. under argon protection. Then the mixture was slowly warmed to 25° C. after the addition, and reacted for 4 hours. The reaction solution is quenched with saturated solution of ammonium chloride, extracted with ethyl acetate, washed with saturated brine, dried over anhydrous sodium sulfate, filtered and evaporated to dryness, and used directly in the next step.

Step 3 to Step 4: The preparation was carried out in a similar manner to Example 33, except that in step 1, 1-((3-bromo-4-methylphenoxy)methyl)cyclopropan-1-ol was used in place of 2-bromo-4-fluoro-1-methylbenzene. $^1$H NMR (400 MHz, DMSO-$d_6$) δ 14.54 (s, 1H), 9.90 (s, 1H), 8.42 (d, J=5.1 Hz, 1H), 8.12 (s, 1H), 7.41-7.30 (m, 4H), 7.30-7.14 (m, 3H), 6.95 (dd, J=8.4, 2.7 Hz, 1H), 6.84 (d, J=2.8 Hz, 1H), 5.59 (s, 1H), 4.18 (s, 2H), 3.97 (s, 2H), 2.19 (s, 3H), 0.73-0.63 (m, 2H), 0.63-0.53 (m, 2H). MS: 456 $[M+H]^+$.

Example 160: 5-benzyl-N-(4-(5-((4-hydroxy-4-methylpentyl)oxy)-2-methylphenyl)pyridin-2-yl)-4H-1,2,4-triazole-3-carboxamide

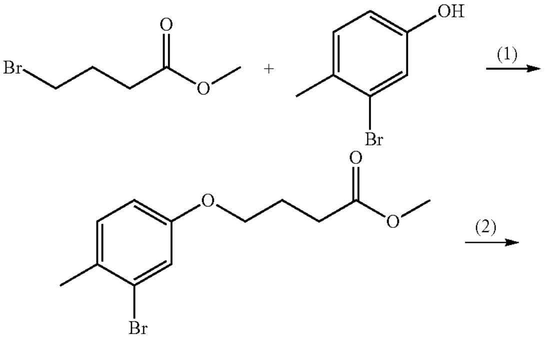

-continued

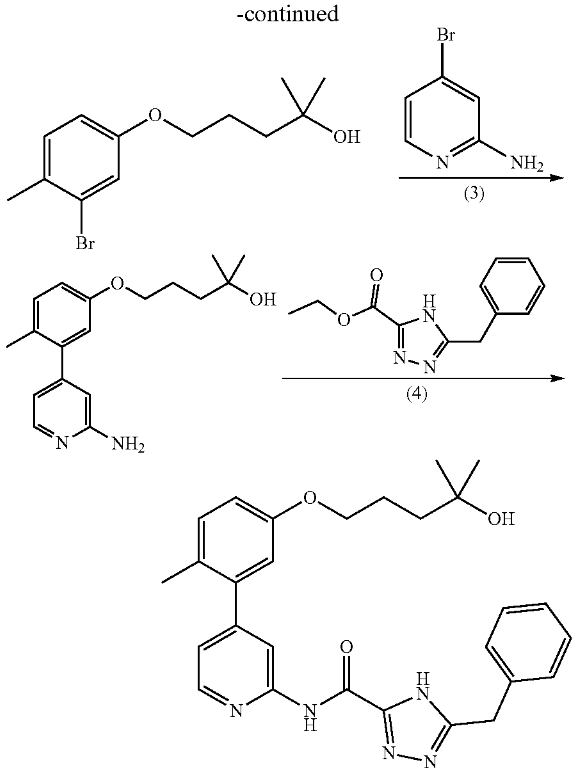

Step 1: Synthesis of methyl 4-(3-bromo-4-methylphenoxy)butanoate

The operation is the same as step 4 of Example 55, but 3-bromo-4-methylphenol was used in place of 3-bromo-N,4-dimethylaniline in the fourth step, and methyl 4-bromobutanoate was used in place of 1-bromo-2-methoxyethane in the fourth step.

Step 2: Synthesis of 5-(3-bromo-4-methylphenoxy)-2-methylpentan-2-ol

Methyl 4-(3-bromo-4-methylphenoxy)butanoate (287 mg, 1 mmol) was dissolved in anhydrous tetrahydrofuran (3 mL), to which methylmagnesium bromide (3M, 1 mL, 3 mmol) was added dropwise under argon protection at 0° C., and reacted at 25° C. for 2 hours. The reaction was quenched with saturated aqueous solution of ammonium chloride, extracted with dichloromethane, dried over anhydrous sodium sulfate, filtered and evaporated to dryness, and subjected to column chromatography to afford 260 mg of product. MS: 287 $[M+H]^+$.

Step 3 to Step 4: The preparation was carried out in a similar manner to Example 33, except that in step 1, 5-(3-bromo-4-methylphenoxy)-2-methylpentan-2-ol was used in place of 2-bromo-4-fluoro-1-methylbenzene. $^1H$ NMR (400 MHz, DMSO-$d_6$) δ 14.57 (s, 1H), 9.88 (s, 1H), 8.42 (d, J=5.1 Hz, 1H), 8.11 (s, 1H), 7.41-7.30 (m, 4H), 7.30-7.16 (m, 3H), 6.93 (dd, J=8.4, 2.7 Hz, 1H), 6.80 (d, J=2.7 Hz, 1H), 4.26-4.10 (m, 3H), 3.96 (t, J=6.6 Hz, 2H), 2.19 (s, 3H), 1.82-1.68 (m, 2H), 1.54-1.40 (m, 2H), 1.09 (s, 6H). MS: 486 $[M+H]^+$.

Example 161: 5-benzyl-N-(4-(4-(2-hydroxypropan-2-yl)-2-methylphenyl)pyridin-2-yl)-4H-1,2,4-triazole-3-carboxamide

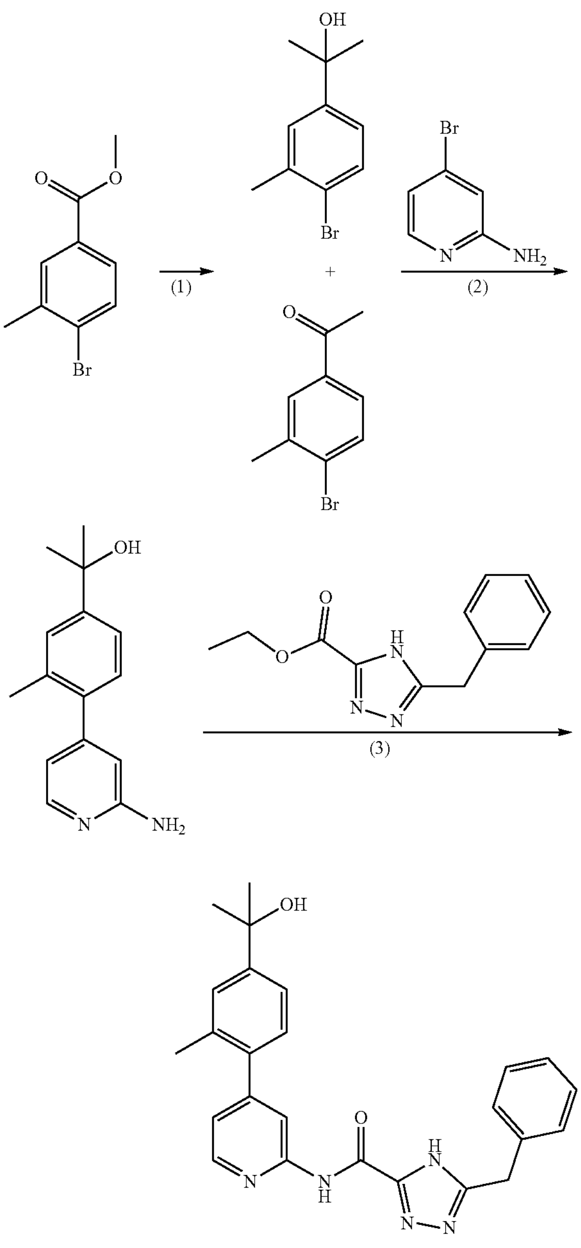

The operation is the same as steps 2 to 4 of Example 160, but methyl 4-bromo-3-methylbenzoate was used in place of methyl 4-(3-bromo-4-methylphenoxy)butanoate in step 2 of Example 160 to carry out the reaction. In this step of reaction, two products of 2-(3-bromo-4-methylphenyl)propan-2-ol and 1-(3-bromo-4-methylphenyl)ethan-1-one were obtained, and 2-(3-bromo-4-methylphenyl)propan-2-ol was used for the subsequent reactions in the present Example. $^1H$ NMR (400 MHz, DMSO-$d_6$) δ 14.58 (s, 1H), 9.87 (s, 1H), 8.41 (d, J=5.1 Hz, 1H), 8.12 (s, 1H), 7.51-7.14 (m, 9H), 5.07 (s, 1H), 4.18 (s, 2H), 2.29 (s, 3H), 1.45 (s, 6H). MS: 428 $[M+H]^+$.

Example 162: N-(4-(4-acetyl-2-methylphenyl)pyridin-2-yl)-5-benzyl-4H-1,2,4-triazole-3-carboxamide The operation is the same as Example 161, but the product 1-(3-bromo-4-methylphenyl)ethan-1-one obtained in the first step was used for the subsequent reactions. $^1$H NMR (400 MHz, DMSO-$d_6$) δ 14.59 (s, 1H), 9.95 (s, 1H), 8.46 (d, J=5.1 Hz, 1H), 8.14 (s, 1H), 7.99-7.93 (m, 1H), 7.93-7.84 (m, 1H), 7.43 (d, J=8.0 Hz, 1H), 7.38-7.29 (m, 4H), 7.29-7.20 (m, 2H), 4.18 (s, 2H), 2.62 (s, 3H), 2.35 (s, 3H). MS: 412 [M+H]$^+$.

Example 162

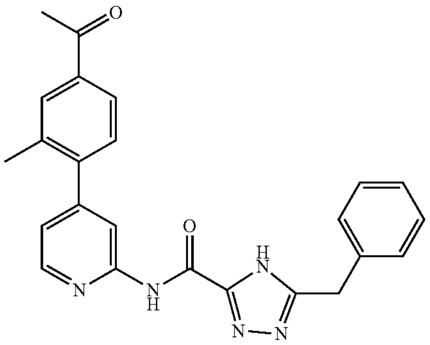

Example 163

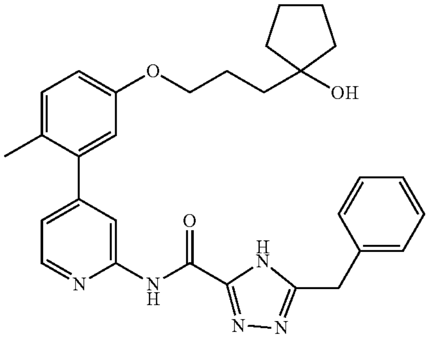

Example 163: 5-benzyl-N-(4-(5-(3-(1-hydroxycyclopentyl)propoxy)-2-methylphenyl)pyridin-2-yl)-4H-1,2,4-triazole-3-carboxamide The preparation was carried out in a similar manner to Example 160, except that in step 2, (butane-1,4-diyl)dimagnesium dibromide was used in place of methylmagnesium bromide. $^1$H NMR (400 MHz, DMSO-$d_6$) δ 14.39 (s, 1H), 9.92 (s, 1H), 8.41 (d, J=5.2 Hz, 1H), 8.11 (s, 1H), 7.47-7.29 (m, 4H), 7.29-7.13 (m, 3H), 6.93 (dd, J=8.4, 2.7 Hz, 1H), 6.80 (d, J=2.7 Hz, 1H), 4.18 (s, 2H), 4.05 (s, 1H), 3.98 (t, J=6.6 Hz, 2H), 2.19 (s, 3H), 1.87-1.33 (m, 12H). MS: 512 [M+H]$^+$.

Example 164: 5-benzyl-N-(4-(5-(3-(1-hydroxycyclohexyl)propoxy)-2-methylphenyl)pyridin-2-yl)-4H-1,2,4-triazole-3-carboxamide The preparation was carried out in a similar manner to Example 160, except that in step 2, (pentane-1,5-diyl)dimagnesium dibromide was used in place of methylmagnesium bromide. $^1$H NMR (400 MHz, DMSO-$d_6$) δ 14.61 (s, 1H), 9.91 (s, 1H), 8.41 (d, J=5.1 Hz, 1H), 8.11 (s, 1H), 7.49-7.29 (m, 4H), 7.29-7.12 (m, 3H), 6.92 (dd, J=8.4, 2.7 Hz, 1H), 6.80 (d, J=2.7 Hz, 1H), 4.17 (s, 2H), 4.01-3.86 (m, 3H), 2.19 (s, 3H), 1.75 (t, J=8.3 Hz, 2H), 1.63-1.49 (m, 2H), 1.49-1.38 (m, 5H), 1.38-1.24 (m, 5H). MS: 526 [M+H]$^+$.

Example 164

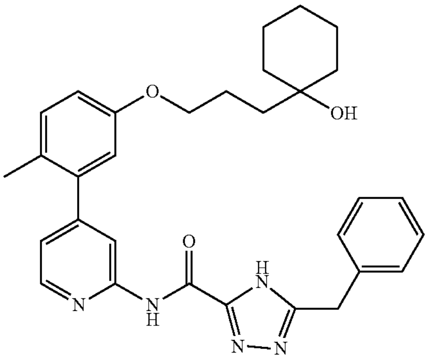

Example 165

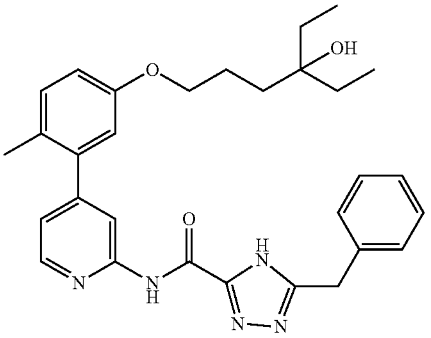

Example 165: 5-benzyl-N-(4-(5-((4-ethyl-4-(hydroxyhexyl)oxy)-2-methylphenyl)pyridin-2-yl)-4H-1,2,4-triazole-3-carboxamide The preparation was carried out in a similar manner to Example 160, except that in step 2, ethylmagnesium bromide was used in place of methylmagnesium bromide. $^1$H NMR (400 MHz, DMSO-$d_6$) δ 14.52 (s, 1H), 9.90 (s, 1H), 8.41 (d, J=5.0 Hz, 1H), 8.11 (s, 1H), 7.40-7.28 (m, 4H), 7.28-7.22 (m, 2H), 7.21 (dd, J=5.1, 1.5 Hz, 1H), 6.92 (dd, J=8.4, 2.7 Hz, 1H), 6.80 (d, J=2.7 Hz, 1H), 4.17 (s, 2H), 3.96 (t, J=6.5 Hz, 2H), 3.88 (s, 1H), 2.19 (s, 3H), 1.74-1.63 (m, 2H), 1.48-1.38 (m, 2H), 1.34 (q, J=7.4 Hz, 4H), 0.77 (t, J=7.4 Hz, 6H). MS: 514 [M+H]$^+$.

Example 166: 5-(cyclopentylmethyl)-N-(4-(5-((4-ethyl-4-hydroxyhexyl)oxy)-2-methylphenyl)pyridin-2-yl)-4H-1,2,4-triazole-3-carboxamide The preparation was carried out in a similar manner to Example 160, except that in step 2, ethylmagnesium bromide was used in place of methylmagnesium bromide, and in step 3, ethyl 5-(cyclopentylmethyl)-4H-1,2,4-triazole-3-carboxylate was used in place of ethyl 5-benzyl-4H-1,2,4-triazol-3-carboxylate. $^1$H NMR (400 MHz, DMSO-$d_6$) δ 14.38 (s, 1H), 9.85 (s, 1H), 8.42 (d, J=5.1 Hz, 1H), 8.13 (s, 1H), 7.32-7.12 (m, 2H), 6.93 (dd, J=8.4, 2.7 Hz, 1H), 6.80 (d, J=2.7 Hz, 1H), 3.96 (t, J=6.5 Hz, 2H), 3.88 (s, 1H), 2.78 (d, J=7.5 Hz, 2H), 2.36-2.21 (m, 1H), 2.19 (s, 3H), 1.79-1.47

(m, 8H), 1.47-1.38 (m, 2H), 1.34 (q, J=7.4 Hz, 4H), 1.28-1.11 (m, 2H), 0.77 (t, J=7.4 Hz, 6H). MS: 506 $[M+H]^+$.

Example 166

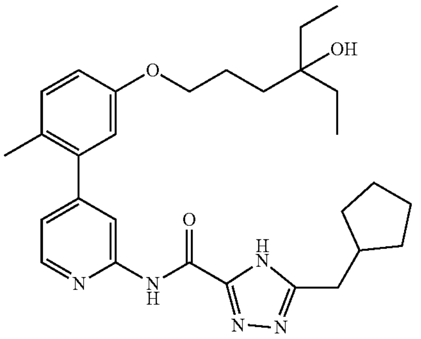

Example 167

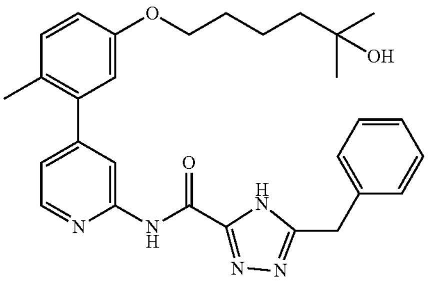

Example 167: 5-benzyl-N-(4-(5-((5-hydroxyl-5-methylhexyl)oxy)-2-methylphenyl)pyridin-2-yl)-4H-1,2,4-triazole-3-carboxamide The preparation was carried out in a similar manner to Example 160, except that in step 1, methyl 5-bromopentanoate was used in place of methyl 4-bromobutanoate. $^1$H NMR (400 MHz, DMSO-$d_6$) δ 14.42 (s, 1H), 9.91 (s, 1H), 8.41 (d, J=5.1 Hz, 1H), 8.11 (s, 1H), 7.41-7.29 (m, 4H), 7.29-7.22 (m, 2H), 7.21 (dd, J=5.1, 1.5 Hz, 1H), 6.93 (dd, J=8.4, 2.7 Hz, 1H), 6.81 (d, J=2.7 Hz, 1H), 4.17 (s, 2H), 4.10 (s, 1H), 3.97 (t, J=6.5 Hz, 2H), 2.19 (s, 3H), 1.68 (t, J=6.9 Hz, 2H), 1.50-1.33 (m, 4H), 1.06 (s, 6H). MS: 500 $[M+H]^+$.

Example 168: 5-benzyl-N-(4-(5-((4-hydroxy-4-(methylpentyl)(methyl)amino)-2-methylphenyl)pyridin-2-yl)-4H-1,2,4-triazole-3-carboxamide The preparation was carried out in a similar manner to Example 160, except that in step 1, tert-butyl (3-bromo-4-methylphenyl)(methyl)carbamate was used in place of 3-bromo-4-methylphenol. $^1$H NMR (400 MHz, DMSO-$d_6$) δ 14.62 (s, 1H), 9.88 (s, 1H), 8.40 (d, J=5.1 Hz, 1H), 8.11 (s, 1H), 7.46-7.29 (m, 4H), 7.29-7.22 (m, 1H), 7.18 (dd, J=5.0, 1.5 Hz, 1H), 7.12 (d, J=8.5 Hz, 1H), 6.70 (dd, J=8.5, 2.8 Hz, 1H), 6.52 (d, J=2.7 Hz, 1H), 4.17 (s, 2H), 4.12 (s, 1H), 3.28 (t, J=7.4 Hz, 2H), 2.86 (s, 3H), 2.13 (s, 3H), 1.63-1.46 (m, 2H), 1.42-1.27 (m, 2H), 1.05 (s, 6H). MS: 499 $[M+H]^+$.

Example 168

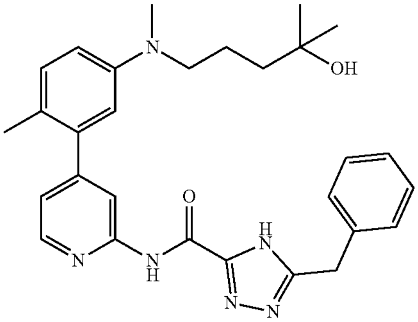

Example 169

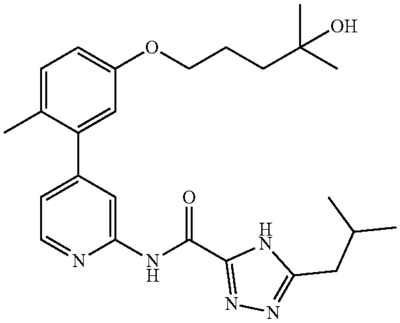

Example 169: N-(4-(5-((4-hydroxy-4-methylpentyl)oxy)-2-methylphenyl)pyridin-2-yl)-5-isobutyl-4H-1,2,4-triazole-3-carboxamide The preparation was carried out in a similar manner to Example 160, except that in step 3, ethyl 5-isobutyl-4H-1,2,4-triazol-5-carboxylate was used in place of ethyl 5-benzyl-4H-1,2,4-triazol-3-carboxylate. $^1$H NMR (400 MHz, DMSO-$d_6$) δ 14.35 (s, 1H), 9.86 (s, 1H), 8.42 (d, J=5.1 Hz, 1H), 8.13 (s, 1H), 7.33-7.16 (m, 2H), 6.93 (dd, J=8.4, 2.7 Hz, 1H), 6.81 (d, J=2.7 Hz, 1H), 4.19 (s, 1H), 3.97 (t, J=6.6 Hz, 2H), 2.72-2.62 (m, 2H), 2.19 (s, 3H), 2.16-2.02 (m, 1H), 1.84-1.68 (m, 2H), 1.56-1.41 (m, 2H), 1.09 (s, 6H), 0.93 (d, J=6.6 Hz, 6H). MS: 452 $[M+H]^+$.

Example 170: N-(4-(5-((4-hydroxy-4-methylpentyl)oxy)-2-methylphenyl)pyridin-2-yl)-5-neopentyl-4H-1,2,4-triazole-3-carboxamide The preparation was carried out in a similar manner to Example 160, except that in step 3, ethyl 5-neopentyl-4H-1,2,4-triazol-5-carboxylate was used in place of ethyl 5-benzyl-4H-1,2,4-triazol-3-carboxylate. $^1$H NMR (400 MHz, DMSO-$d_6$) δ 14.39 (s, 1H), 9.85 (s, 1H), 8.42 (d, J=5.1 Hz, 1H), 8.15 (s, 1H), 7.31-7.16 (m, 2H), 6.93 (dd, J=8.4, 2.7 Hz, 1H), 6.81 (d, J=2.7 Hz, 1H), 4.18 (s, 1H), 3.97 (t, J=6.6 Hz, 2H), 2.67 (s, 2H), 2.20 (s, 3H), 1.83-1.66 (m, 2H), 1.57-1.39 (m, 2H), 1.09 (s, 6H), 0.97 (s, 9H). MS: 466 $[M+H]^+$.

Example 170

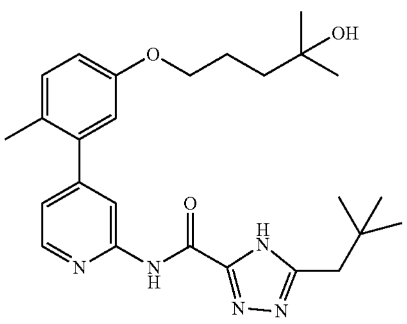

Example 171

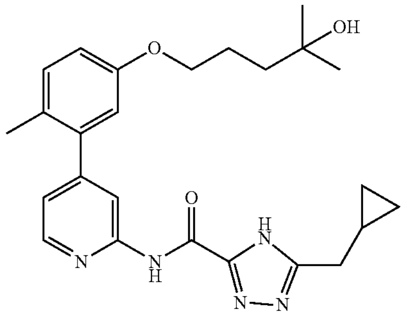

Example 172

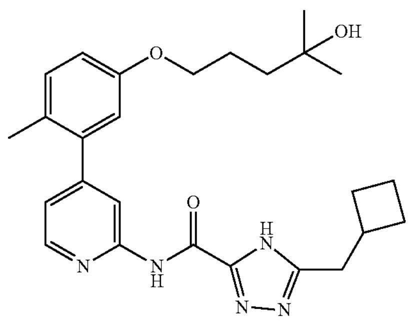

Example 173

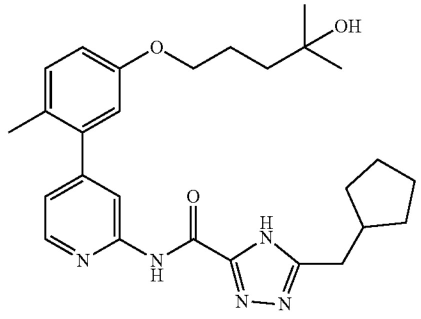

Example 171: 5-(cyclopropylmethyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 3, ethyl 5-(cyclopropylmethyl)-4H-1,2,4-triazol-5-carboxylate was used in place of ethyl 5-benzyl-4H-1,2,4-triazol-3-carboxylate. $^1$H NMR (400 MHz, DMSO-$d_6$) δ 14.47 (s, 1H), 9.88 (s, 1H), 8.42 (d, J=5.1 Hz, 1H), 8.14 (s, 1H), 7.37-7.16 (m, 2H), 6.93 (dd, J=8.4, 2.6 Hz, 1H), 6.81 (d, J=2.7 Hz, 1H), 4.18 (s, 1H), 3.97 (t, J=6.5 Hz, 2H), 2.72 (d, J=7.0 Hz, 2H), 2.19 (s, 3H), 1.83-1.66 (m, 2H), 1.55-1.39 (m, 2H), 1.18-1.03 (m, 7H), 0.59-0.46 (m, 2H), 0.33-0.22 (m, 2H). MS: 450 $[M+H]^+$.

Example 172: 5-(cyclobutylmethyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 3, ethyl 5-(cyclobutylmethyl)-4H-1,2,4-triazol-5-carboxylate was used in place of ethyl 5-benzyl-4H-1,2,4-triazol-3-carboxylate. $^1$H NMR (400 MHz, DMSO-$d_6$) δ 14.36 (s, 1H), 9.85 (s, 1H), 8.42 (d, J=5.1 Hz, 1H), 8.13 (s, 1H), 7.34-7.16 (m, 2H), 6.93 (dd, J=8.4, 2.7 Hz, 1H), 6.81 (d, J=2.7 Hz, 1H), 4.18 (s, 1H), 3.97 (t, J=6.5 Hz, 2H), 2.88 (d, J=7.5 Hz, 2H), 2.79-2.62 (m, 1H), 2.19 (s, 3H), 2.12-1.97 (m, 2H), 1.94-1.79 (m, 2H), 1.79-1.64 (m, 4H), 1.55-1.42 (m, 2H), 1.09 (s, 6H). MS: 464 $[M+H]^+$.

Example 173: 5-(cyclopentylmethyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 3, ethyl 5-(cyclopentylmethyl)-4H-1,2,4-triazole-3-carboxylate was used in place of ethyl 5-benzyl-4H-1,2,4-triazol-3-carboxylate. $^1$H NMR (400 MHz, DMSO-$d_6$) δ 14.38 (s, 1H), 9.85 (s, 1H), 8.42 (d, J=5.1 Hz, 1H), 8.14 (s, 1H), 7.33-7.16 (m, 2H), 6.93 (dd, J=8.4, 2.7 Hz, 1H), 6.81 (d, J=2.7 Hz, 1H), 4.19 (s, 1H), 3.96 (t, J=6.6 Hz, 2H), 2.78 (d, J=7.5 Hz, 2H), 2.34-2.22 (m, 1H), 2.19 (s, 3H), 1.83-1.66 (m, 4H), 1.66-1.55 (m, 2H), 1.55-1.41 (m, 4H), 1.27-1.18 (m, 2H), 1.09 (s, 6H). MS: 478 $[M+H]^+$.

Example 174: 5-(cyclopentylmethyl)-N-(4-(5-((4-hydroxy-4-methylpentyl)oxy)-2-methylphenyl)pyridin-2-yl)-4H-1,3,4-oxadiazole-2-carboxamide The preparation was carried out in a similar manner to Example 160, except that in step 3, ethyl 5-(cyclopentylmethyl)-1,3,4-oxadiazol-2-carboxylate was used in place of ethyl 5-benzyl-4H-1,2,4-triazol-3-carboxylate. $^1$H NMR (400 MHz, DMSO-$d_6$) δ 11.23 (s, 1H), 8.47 (d, J=5.1 Hz, 1H), 7.99 (s, 1H), 7.32-7.20 (m, 2H), 6.93 (dd, J=8.4, 2.7 Hz, 1H), 6.81 (d, J=2.7 Hz, 1H), 4.18 (s, 1H), 3.96 (t, J=6.5 Hz, 2H), 2.97 (d, J=7.4 Hz, 2H), 2.38-2.24 (m, 1H), 2.19 (s, 3H), 1.87-1.69 (m, 4H), 1.69-1.39 (m, 6H), 1.32-1.20 (m, 2H), 1.09 (s, 6H). MS: 479 $[M+H]^+$.

Example 174

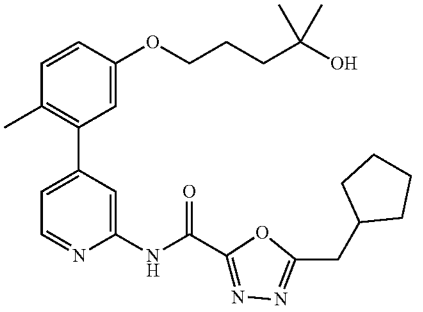

Example 175

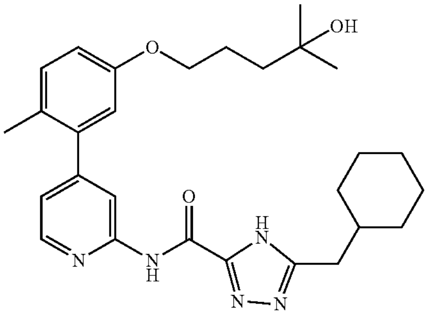

Example 175: 5-(cyclohexylmethyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 3, ethyl 5-(cyclohexylmethyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.37 (s, 1H), 9.85 (s, 1H), 8.42 (d, J=5.1 Hz, 1H), 8.13 (s, 1H), 7.31-7.17 (m, 2H), 6.93 (dd, J=8.4, 2.7 Hz, 1H), 6.81 (d, J=2.7 Hz, 1H), 4.18 (s, 1H), 3.97 (t, J=6.6 Hz, 2H), 2.67 (d, J=7.0 Hz, 2H), 2.19 (s, 3H), 1.84-1.70 (m, 3H), 1.70-1.56 (m, 5H), 1.54-1.41 (m, 2H), 1.29-1.15 (m, 3H), 1.09 (s, 6H), 1.05-0.89 (m, 2H). MS: 492 $[M+H]^+$.

Example 176: 5-(2-cyclopentylethyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 3, ethyl 5-(2-cyclopentylethyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.32 (s, 1H), 9.86 (s, 1H), 8.42 (d, J=5.1 Hz, 1H), 8.13 (s, 1H), 7.33-7.15 (m, 2H), 6.93 (dd, J=8.4, 2.7 Hz, 1H), 6.81 (d, J=2.7 Hz, 1H), 4.18 (s, 1H), 3.97 (t, J=6.5 Hz, 2H), 2.79 (t, J=7.2 Hz, 2H), 2.19 (s, 3H), 1.84-1.66 (m, 7H), 1.66-1.39 (m, 6H), 1.18-0.98 (m, 8H). MS: 492 $[M+H]^+$.

Example 176

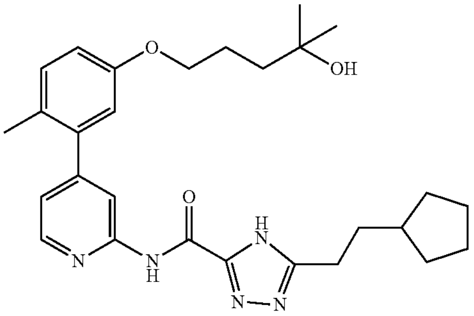

Example 177

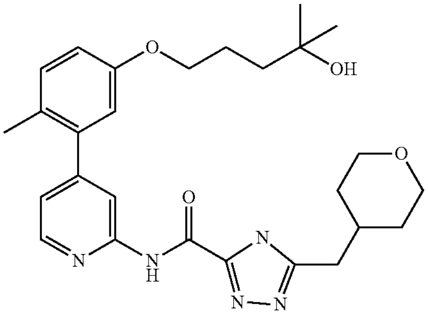

Example 177: N-(4-(5-((4-hydroxy-4-methylpentyl)oxy)-2-methylphenyl)pyridin-2-yl)-5-((tetrahydro-2H-pyran-4-yl)methyl)-4H-1,2,4-triazole-3-carboxamide The preparation was carried out in a similar manner to Example 160, except that in step 3, ethyl 5-((tetrahydro-2H-pyran-4-yl)methyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.41 (s, 1H), 9.87 (s, 1H), 8.42 (d, J=5.1 Hz, 1H), 8.13 (s, 1H), 7.34-7.14 (m, 2H), 6.93 (dd, J=8.4, 2.7 Hz, 1H), 6.81 (d, J=2.7 Hz, 1H), 4.18 (s, 1H), 3.97 (t, J=6.5 Hz, 2H), 3.89-3.78 (m, 2H), 3.31-3.19 (m, 2H), 2.73 (d, J=7.1 Hz, 2H), 2.19 (s, 3H), 2.07-1.92 (m, 1H), 1.81-1.68 (m, 2H), 1.61-1.51 (m, 2H), 1.51-1.42 (m, 2H), 1.30-1.22 (m, 2H), 1.09 (s, 6H). MS: 494 $[M+H]^+$.

Example 178: 5-((4,4-difluorocyclohexyl)methyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 3, ethyl 5-((4,4-difluorocyclohexyl)methyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.41 (s, 1H), 9.87 (s, 1H), 8.42 (d, J=5.1 Hz, 1H), 8.13 (s, 1H), 7.32-7.13 (m, 2H), 6.93 (dd, J=8.5, 2.6 Hz, 1H), 6.81 (d, J=2.7 Hz, 1H), 4.18 (s, 1H), 3.97 (t, J=6.6 Hz, 2H), 2.75 (d, J=7.0 Hz, 2H), 2.19 (s, 3H), 2.09-1.64 (m, 9H), 1.55-1.40 (m, 2H), 1.35-1.23 (m, 2H), 1.09 (s, 6H). MS: 528 $[M+H]^+$.

Example 178

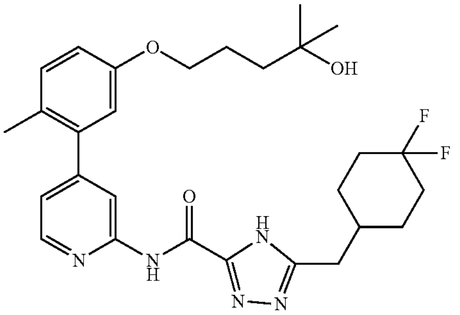

Example 179

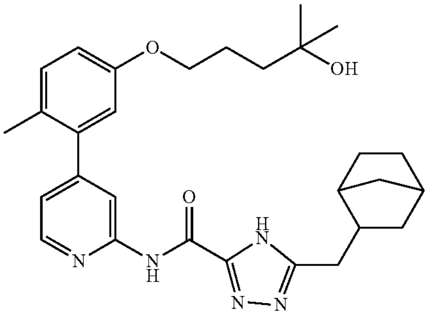

Example 179: 5-(bicyclo[2.2.1]heptan-2-ylmethyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 3, ethyl 5-(bicyclo[2.2.1]heptan-2-ylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.32 (s, 1H), 9.86 (s, 1H), 8.42 (d, J=5.1 Hz, 1H), 8.13 (s, 1H), 7.35-7.12 (m, 2H), 6.93 (dd, J=8.4, 2.7 Hz, 1H), 6.81 (d, J=2.7 Hz, 1H), 4.18 (s, 1H), 3.97 (t, J=6.6 Hz, 2H), 3.17 (d, J=4.1 Hz, 1H), 2.74 (dd, J=14.6, 8.0 Hz, 1H), 2.59 (dd, J=14.6, 7.7 Hz, 1H), 2.28-2.16 (m, 4H), 1.96-1.85 (m, 1H), 1.81-1.68 (m, 2H), 1.54-1.33 (m, 6H), 1.29-1.20 (m, 2H), 1.19-1.12 (m, 2H), 1.09 (s, 6H). MS: 504 $[M+H]^+$.

Example 180: 5-(adamantan-1-ylmethyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 3, ethyl 5-(adamantan-1-ylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.32 (s, 1H), 9.83 (s, 1H), 8.39 (d, J=5.1 Hz, 1H), 8.12 (s, 1H), 7.30-7.13 (m, 2H), 6.90 (dd, J=8.4, 2.7 Hz, 1H), 6.78 (d, J=2.7 Hz, 1H), 4.17 (s, 1H), 3.94 (t, J=6.6 Hz, 2H), 2.51 (s, 2H), 2.17 (s, 3H), 1.95-1.83 (m, 3H), 1.79-1.66 (m, 2H), 1.66-1.57 (m, 3H), 1.57-1.38 (m, 11H), 1.06 (s, 6H). MS: 544 $[M+H]^+$.

Example 180

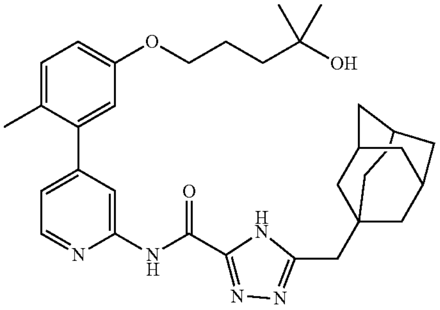

Example 181

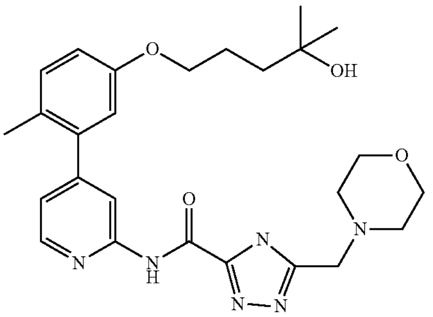

Example 181: N-(4-(5-((4-hydroxy-4-methylpentyl)oxy)-2-methylphenyl)pyridin-2-yl)-5-(morpholinomethyl)-4H-1,2,4-triazole-3-carboxamide The preparation was carried out in a similar manner to Example 160, except that in step 3, ethyl 5-(morpholinomethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.09 (s, 1H), 9.95 (s, 1H), 8.42 (d, J=5.1 Hz, 1H), 8.12 (s, 1H), 7.32-7.16 (m, 2H), 6.93 (dd, J=8.4, 2.7 Hz, 1H), 6.81 (d, J=2.7 Hz, 1H), 4.20 (s, 1H), 3.97 (t, J=6.5 Hz, 2H), 3.71 (s, 2H), 3.59 (t, J=4.6 Hz, 4H), 2.49-2.40 (m, 4H), 2.19 (s, 3H), 1.81-1.67 (m, 2H), 1.52-1.41 (m, 2H), 1.09 (s, 6H). MS: 495 $[M+H]^+$.

Example 182: N-(4-(5-((4-hydroxy-4-methylpentyl)oxy)-2-methylphenyl)pyridin-2-yl)-5-phenethyl-4H-1,2,4-triazole-3-carboxamide The preparation was carried out in a similar manner to Example 160, except that in step 3, ethyl 5-(phenethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.43 (s, 1H), 9.89 (s, 1H), 8.43 (d, J=5.2 Hz, 1H), 8.14 (s, 1H), 7.40-7.10 (m, 7H), 6.93 (dd, J=8.4, 2.7 Hz, 1H), 6.81 (d, J=2.7 Hz, 1H), 4.18 (s, 1H), 3.97 (t, J=6.6 Hz, 2H), 3.22-2.99 (m, 4H), 2.20 (s, 3H), 1.84-1.66 (m, 2H), 1.57-1.37 (m, 2H), 1.09 (s, 6H). MS: 500 $[M+H]^+$.

Example 182

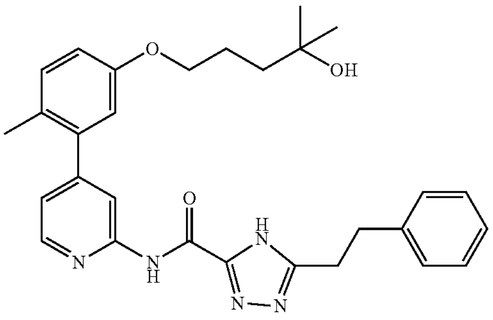

Example 183

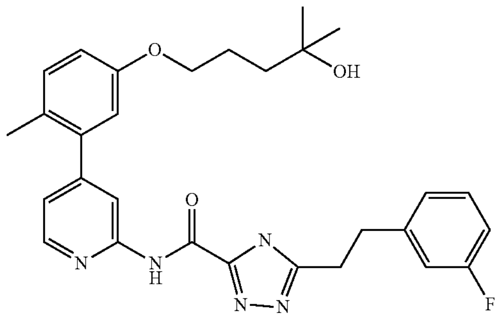

Example 183: 5-(2-fluorobenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 3, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.65 (s, 1H), 9.90 (s, 1H), 8.41 (d, J=5.1 Hz, 1H), 8.10 (s, 1H), 7.44-7.29 (m, 2H), 7.28-7.13 (m, 4H), 6.92 (dd, J=8.4, 2.7 Hz, 1H), 6.80 (d, J=2.7 Hz, 1H), 4.29-4.09 (m, 3H), 3.96 (t, J=6.5 Hz, 2H), 2.18 (s, 3H), 1.83-1.68 (m, 2H), 1.52-1.39 (m, 2H), 1.09 (s, 6H). MS: 504 $[M+H]^+$.

Example 184: 5-(3-fluorobenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 3, ethyl 5-(3-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 13.74 (s, 1H), 9.93 (s, 1H), 8.41 (d, J=5.1 Hz, 1H), 8.11 (s, 1H), 7.50-7.30 (m, 2H), 7.30-7.06 (m, 4H), 6.92 (d, J=8.6 Hz, 1H), 6.80 (s, 1H), 4.34-4.06 (m, 3H), 3.96 (t, J=6.6 Hz, 2H), 2.19 (s, 3H), 1.84-1.66 (m, 2H), 1.47 (t, J=8.1 Hz, 2H), 1.09 (s, 6H). MS: 504 $[M+H]^+$.

Example 184

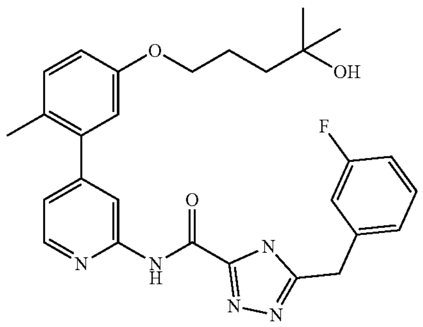

Example 185

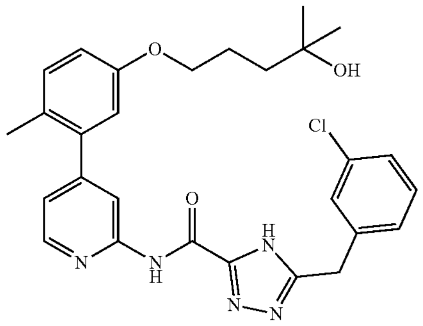

Example 185: 5-(3-chlorobenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 3, ethyl 5-(3-chlorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.54 (s, 1H), 9.95 (s, 1H), 8.42 (d, J=5.1 Hz, 1H), 8.11 (s, 1H), 7.49-7.13 (m, 6H), 6.92 (dd, J=8.4, 2.7 Hz, 1H), 6.80 (d, J=2.7 Hz, 1H), 4.31-4.07 (m, 3H), 3.96 (t, J=6.5 Hz, 2H), 2.19 (s, 3H), 1.83-1.66 (m, 2H), 1.54-1.38 (m, 2H), 1.09 (s, 6H). MS: 520 $[M+H]^+$.

Example 186: 5-(3-methoxybenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 3, ethyl 5-(3-methoxybenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.66 (s, 1H), 9.92 (s, 1H), 8.41 (d, J=5.1 Hz, 1H), 8.12 (s, 1H), 7.41-7.12 (m, 3H), 7.05-6.70 (m, 5H), 4.26-4.05 (m, 3H), 3.96 (t, J=6.5 Hz, 2H), 3.74 (s, 3H), 2.19 (s, 3H), 1.83-1.65 (m, 2H), 1.56-1.37 (m, 2H), 1.09 (s, 6H). MS: 516 $[M+H]^+$.

Example 186

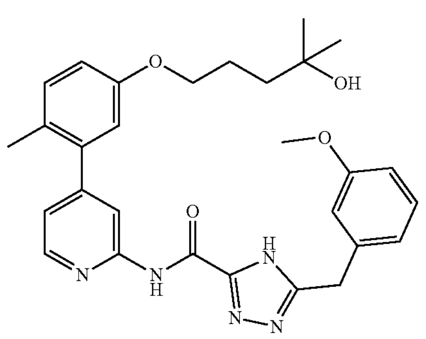

Example 187

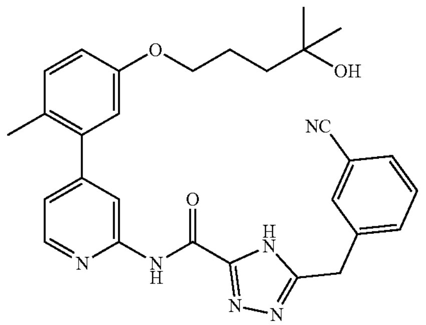

Example 187: 5-(3-cyanobenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 3, ethyl 5-(3-cyanobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.69 (s, 1H), 9.98 (s, 1H), 8.42 (d, J=5.1 Hz, 1H), 8.11 (s, 1H), 7.84 (s, 1H), 7.76 (d, J=7.7 Hz, 1H), 7.69 (d, J=7.8 Hz, 1H), 7.62-7.51 (m, 1H), 7.30-7.17 (m, 2H), 6.93 (dd, J=8.4, 2.7 Hz, 1H), 6.80 (d, J=2.7 Hz, 1H), 4.27 (s, 2H), 4.19 (s, 1H), 3.96 (t, J=6.5 Hz, 2H), 2.19 (s, 3H), 1.81-1.68 (m, 2H), 1.53-1.40 (m, 2H), 1.09 (s, 6H). MS: 511 $[M+H]^+$.

Example 188: 5-(4-fluorobenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 3, ethyl 5-(4-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.54 (s, 1H), 9.93 (s, 1H), 8.42 (d, J=5.1 Hz, 1H), 8.11 (s, 1H), 7.46-7.31 (m, 2H), 7.31-7.10 (m, 4H), 6.93 (dd, J=8.4, 2.7 Hz, 1H), 6.80 (d, J=2.7 Hz, 1H), 4.29-4.08 (m, 3H), 3.96 (t, J=6.5 Hz, 2H), 2.19 (s, 3H), 1.83-1.65 (m, 2H), 1.54-1.40 (m, 2H), 1.09 (s, 6H). MS: 504 $[M+H]^+$.

Example 188

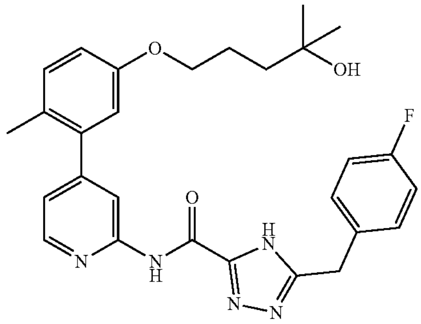

Example 189

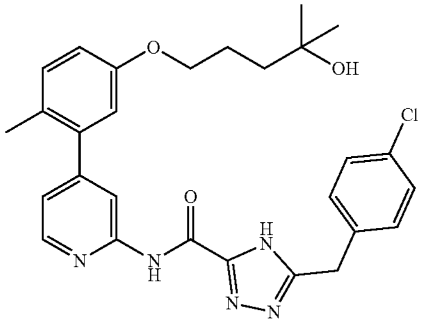

Example 189: 5-(4-chlorobenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 3, ethyl 5-(4-chlorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.65 (s, 1H), 9.93 (s, 1H), 8.42 (d, J=5.2 Hz, 1H), 8.11 (s, 1H), 7.51-7.29 (m, 4H), 7.29-7.13 (m, 2H), 6.93 (dd, J=8.5, 2.8 Hz, 1H), 6.80 (d, J=2.8 Hz, 1H), 4.28-4.07 (m, 3H), 3.96 (t, J=6.6 Hz, 2H), 2.19 (s, 3H), 1.75 (t, J=8.2 Hz, 2H), 1.54-1.39 (m, 2H), 1.09 (s, 6H). MS: 520 $[M+H]^+$.

Example 190: 5-(4-methoxybenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 3, ethyl 5-(4-methoxybenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.59 (s, 1H), 9.89 (s, 1H), 8.41 (d, J=5.1 Hz, 1H), 8.11 (s, 1H), 7.40-7.09 (m, 4H), 7.04-6.70 (m, 4H), 4.18 (s, 1H), 4.10 (s, 2H), 3.96 (t, J=6.8 Hz, 2H), 2.19 (s, 3H), 1.83-1.64 (m, 2H), 1.57-1.35 (m, 2H), 1.09 (s, 6H). MS: 516 $[M+H]^+$.

Example 190

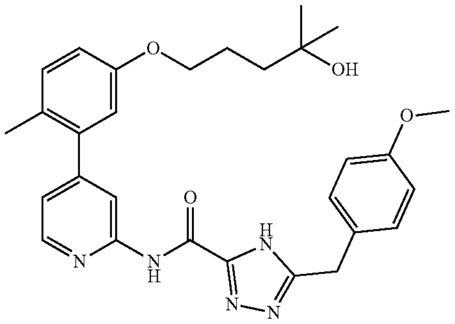

Example 191

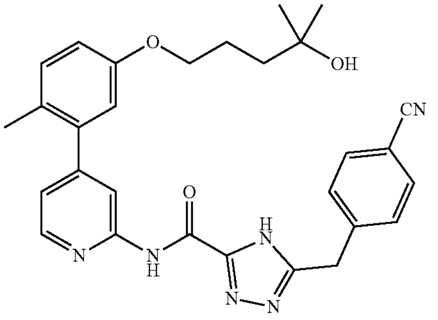

Example 191: 5-(4-cyanobenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 3, ethyl 5-(4-cyanobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.65 (s, 1H), 9.95 (s, 1H), 8.42 (d, J=5.1 Hz, 1H), 8.11 (s, 1H), 7.91-7.76 (m, 2H), 7.62-7.47 (m, 2H), 7.32-7.13 (m, 2H), 6.93 (dd, J=8.4, 2.7 Hz, 1H), 6.80 (d, J=2.7 Hz, 1H), 4.29 (s, 2H), 4.18 (s, 1H), 3.96 (t, J=6.5 Hz, 2H), 2.19 (s, 3H), 1.81-1.67 (m, 2H), 1.53-1.41 (m, 2H), 1.09 (s, 6H). MS: 511 $[M+H]^+$.

Example 192: 5-(3,4-difluorobenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 3, ethyl 5-(3,4-difluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.62 (s, 1H), 9.96 (s, 1H), 8.42 (d, J=5.1 Hz, 1H), 8.11 (d, J=1.4 Hz, 1H), 7.51-7.32 (m, 2H), 7.32-7.13 (m, 3H), 6.93 (dd, J=8.4, 2.7 Hz, 1H), 6.80 (d, J=2.7 Hz, 1H), 4.25-4.12 (m, 3H), 3.96 (t, J=6.5 Hz, 2H), 2.19 (s, 3H), 1.82-1.67 (m, 2H), 1.53-1.41 (m, 2H), 1.09 (s, 6H). MS: 522 $[M+H]^+$.

Example 192

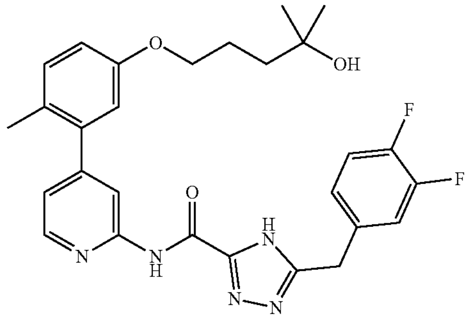

Example 193

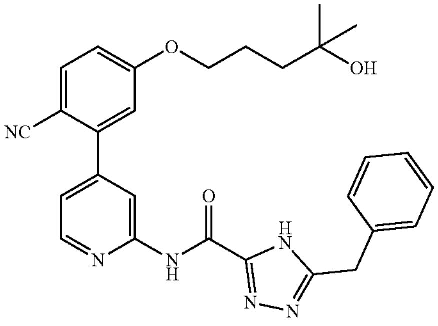

Example 193: 5-benzyl-N-(4-(2-cyano-5-((4-hydroxy-4-methylpentyl)oxy)phenyl)pyridin-2-yl)-4H-1,2,4-triazole-3-carboxamide The preparation was carried out in a similar manner to Example 160, except that in step 1, 2-chloro-4-hydroxybenzonitrile was used in place of 3-bromo-4-methylphenol. $^1$H NMR (400 MHz, DMSO-$d_6$) δ 14.54 (s, 1H), 10.04 (s, 1H), 8.52 (d, J=5.1 Hz, 1H), 8.34 (d, J=1.4 Hz, 1H), 7.94 (d, J=8.5 Hz, 1H), 7.41 (dd, J=5.1, 1.6 Hz, 1H), 7.38-7.29 (m, 4H), 7.29-7.15 (m, 3H), 4.27-4.08 (m, 5H), 1.87-1.72 (m, 2H), 1.56-1.41 (m, 2H), 1.10 (s, 6H). MS: 497 $[M+H]^+$.

Example 194: 5-benzyl-N-(4-(5-((4-hydroxy-4-methylpentyl)oxy)-2-(trifluoromethyl)phenyl)pyridin-2-yl)-4H-1,2,4-triazole-3-carboxamide The preparation was carried out in a similar manner to Example 160, except that in step 1, 3-chloro-4-(trifluoromethyl)phenol was used in place of 3-bromo-4-methylphenol. $^1$H NMR (400 MHz, DMSO-$d_6$) δ 14.61 (s, 1H), 9.96 (s, 1H), 8.43 (d, J=5.1 Hz, 1H), 8.16 (s, 1H), 7.79 (d, J=8.9 Hz, 1H), 7.43-7.29 (m, 4H), 7.29-7.22 (m, 1H), 7.22-7.11 (m, 2H), 6.97 (d, J=2.5 Hz, 1H), 4.26-4.13 (m, 3H), 4.09 (t, J=6.6 Hz, 2H), 1.86-1.69 (m, 2H), 1.54-1.39 (m, 2H), 1.09 (s, 6H). MS: 540 $[M+H]^+$.

Example 194

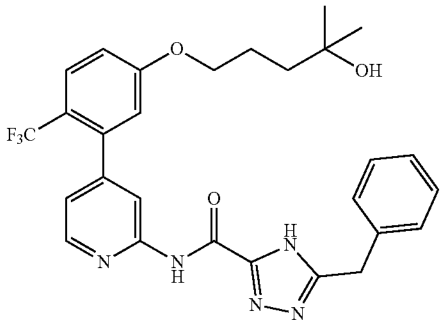

Example 195

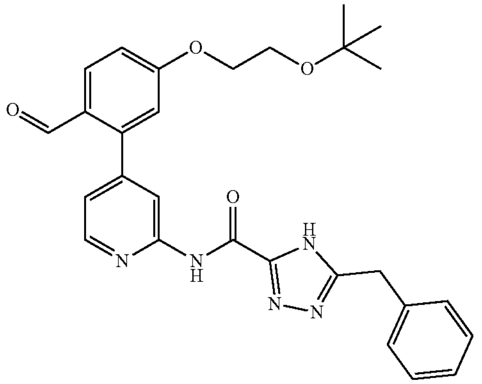

Example 195: 5-benzyl-N-(4-(5-(2-(tert-butoxy) ethoxy)-2-formylphenyl)pyridin-2-yl)-4H-1,2,4-triazole-3-carboxamide The preparation was carried out in a similar manner to Example 64, except that in step 1, 2-bromo-4-hydoxylbenzaldehyde was used in place of 3-bromo-4-methylphenol. $^1$H NMR (400 MHz, DMSO-$d_6$) δ 14.60 (s, 1H), 9.99 (s, 1H), 9.80 (s, 1H), 8.46 (d, J=5.1 Hz, 1H), 8.16 (s, 1H), 7.96 (d, J=8.7 Hz, 1H), 7.43-7.29 (m, 5H), 7.29-7.15 (m, 2H), 7.05 (d, J=2.5 Hz, 1H), 4.28-4.20 (m, 2H), 4.18 (s, 2H), 3.73-3.61 (m, 2H), 1.15 (s, 9H). MS: 500 $[M+H]^+$.

Example 196: 5-benzyl-N-(5-(5-methoxy-2-methylphenyl)pyridin-3-yl)-4H-1,2,4-triazole-3-carboxamide The preparation was carried out in a similar manner to Example 92, except that in step 1, 3-bromo-4-methylphenol was used in place of 2-bromo-3-methylphenol, and in step 2, 5-bromopyridin-3-amine was used in place of 4-bromopyridin-2-amine. $^1$H NMR (600 MHz, DMSO-$d_6$) δ 14.54 (s, 1H), 10.75 (s, 1H), 9.02 (s, 1H), 8.32 (s, 1H), 8.21 (s, 1H), 7.43-7.18 (m, 6H), 6.91 (d, J=8.2 Hz, 1H), 6.83 (s, 1H), 4.18 (s, 2H), 3.76 (s, 3H), 2.18 (s, 3H). MS: 400 $[M+H]^+$.

Example 196

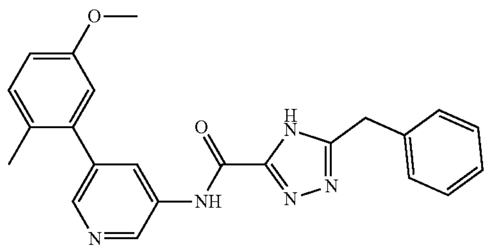

Example 197

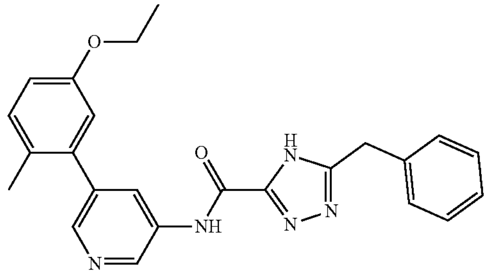

Example 197: 5-benzyl-N-(5-(5-ethoxy-2-methylphenyl)pyridin-3-yl)-4H-1,2,4-triazole-3-carboxamide The preparation was carried out in a similar manner to Example 92, except that in step 1, 3-bromo-4-methylphenol was used in place of 2-bromo-3-methylphenol, bromoethane was used in place of iodomethane, and in step 2, 5-bromopyridin-3-amine was used in place of 4-bromopyridin-2-amine. $^1$H NMR (600 MHz, DMSO-$d_6$) δ 14.49 (s, 1H), 10.70 (s, 1H), 9.02 (d, J=2.4 Hz, 1H), 8.41-8.08 (m, 2H), 7.48-7.12 (m, 6H), 6.90 (dd, J=8.4, 2.7 Hz, 1H), 6.80 (d, J=2.7 Hz, 1H), 4.18 (s, 2H), 4.03 (q, J=7.0 Hz, 2H), 2.18 (s, 3H), 1.32 (t, J=7.0 Hz, 3H). MS: 414 $[M+H]^+$.

Example 198: 5-benzyl-N-(4-(5-butoxy-2-methylphenyl)pyridin-2-yl)-4H-1,2,4-triazole-3-carboxamide The preparation was carried out in a similar manner to Example 92, except that in step 1, 3-bromo-4-methylphenol was used in place of 2-bromo-3-methylphenol, and 1-bromobutane was used in place of iodomethane. $^1$H NMR (400 MHz, DMSO-$d_6$) δ 14.58 (s, 1H), 9.92 (s, 1H), 8.41 (d, J=5.1 Hz, 1H), 8.11 (d, J=1.5 Hz, 1H), 7.48-7.10 (m, 7H), 6.93 (dd, J=8.4, 2.7 Hz, 1H), 6.81 (d, J=2.7 Hz, 1H), 4.17 (s, 2H), 3.97 (t, J=6.5 Hz, 2H), 2.19 (s, 3H), 1.83-1.54 (m, 2H), 1.54-1.27 (m, 2H), 0.92 (t, J=7.4 Hz, 3H). MS: 442 $[M+H]^+$.

Example 198

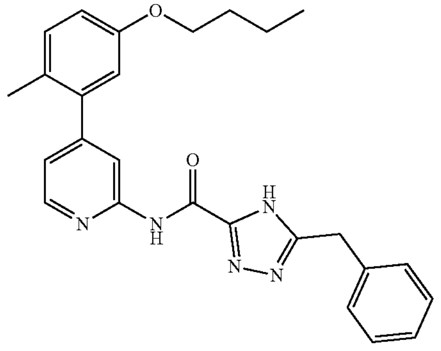

Example 199

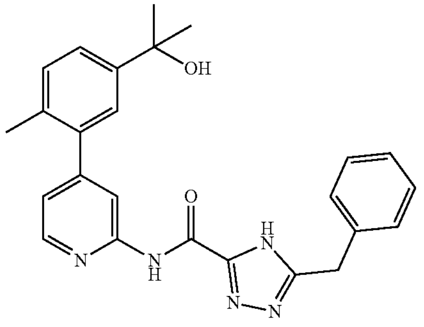

Example 199: 5-benzyl-N-(4-(5-(2-hydroxypropan-2-yl)-2-methylphenyl)pyridin-2-yl)-4H-1,2,4-triazole-3-carboxamide The preparation was carried out in a similar manner to Example 161, except that in step 1, methyl 3-bromo-4-methylbenzoate was used in place of methyl 4-bromo-3-methylbenzoate. $^1$H NMR (400 MHz, DMSO-$d_6$) δ 14.59 (s, 1H), 9.89 (s, 1H), 8.42 (d, J=5.1 Hz, 1H), 8.12 (d, J=1.3 Hz, 1H), 7.42 (dd, J=7.9, 2.0 Hz, 1H), 7.39-7.30 (m, 5H), 7.30-7.23 (m, 2H), 7.21 (dd, J=5.1, 1.6 Hz, 1H), 5.05 (s, 1H), 4.17 (s, 2H), 2.25 (s, 3H), 1.43 (s, 6H). MS: 428 [M+H]$^+$.

Example 200: 5-(3,5-difluorobenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 4, ethyl 5-(3,5-difluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.56 (s, 1H), 9.91 (s, 1H), 8.42 (d, J=5.1 Hz, 1H), 8.12 (s, 1H), 7.29-7.03 (m, 5H), 6.93 (dd, J=8.4, 2.7 Hz, 1H), 6.80 (d, J=2.7 Hz, 1H), 4.26 (s, 2H), 4.18 (s, 1H), 3.96 (t, J=6.6 Hz, 2H), 2.19 (s, 3H), 1.81-1.67 (m, 2H), 1.53-1.40 (m, 2H), 1.09 (s, 6H). MS: 522 [M+H]$^+$.

Example 200

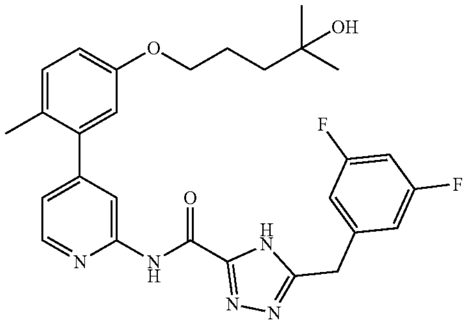

Example 201

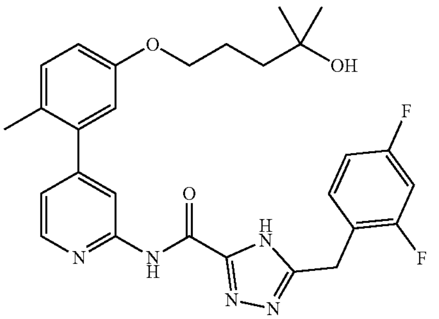

Example 201: 5-(2,4-difluorobenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 4, ethyl 5-(2,4-difluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.63 (s, 1H), 9.89 (s, 1H), 8.42 (d, J=5.1 Hz, 1H), 8.11 (s, 1H), 7.57-7.38 (m, 1H), 7.38-7.17 (m, 3H), 7.17-7.01 (m, 1H), 6.93 (dd, J=8.4, 2.7 Hz, 1H), 6.81 (d, J=2.7 Hz, 1H), 4.28-4.11 (m, 3H), 3.97 (t, J=6.5 Hz, 2H), 2.19 (s, 3H), 1.83-1.66 (m, 2H), 1.56-1.40 (m, 2H), 1.10 (s, 6H). MS: 522 [M+H]$^+$.

Example 202: 5-(2,3-difluorobenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 4, ethyl 5-(2,3-difluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.70 (s, 1H), 9.92 (s, 1H), 8.41 (d, J=5.1 Hz, 1H), 8.10 (s, 1H), 7.47-7.30 (m, 1H), 7.30-7.12 (m, 4H), 6.93 (dd, J=8.4, 2.7 Hz, 1H), 6.80 (d, J=2.7 Hz, 1H), 4.27 (s, 2H), 4.17 (s, 1H), 3.96 (t, J=6.5 Hz, 2H), 2.19 (s, 3H), 1.82-1.66 (m, 2H), 1.55-1.40 (m, 2H), 1.09 (s, 6H). MS: 522 [M+H]$^+$.

Example 202

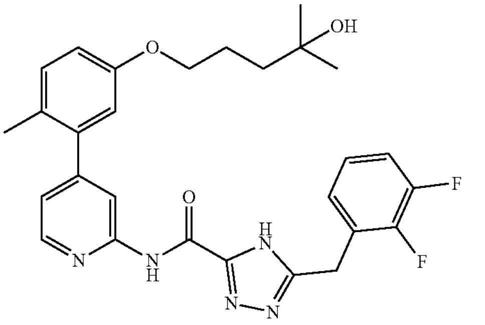

Example 204

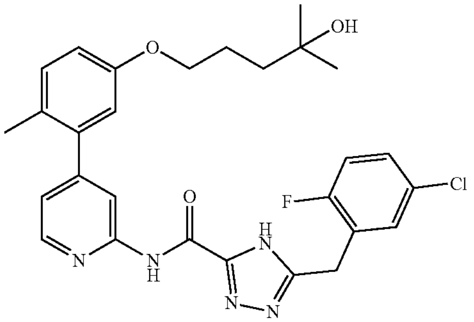

Example 203

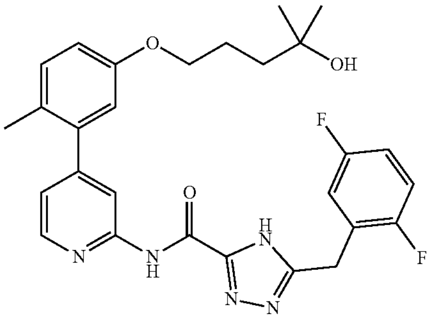

Example 205

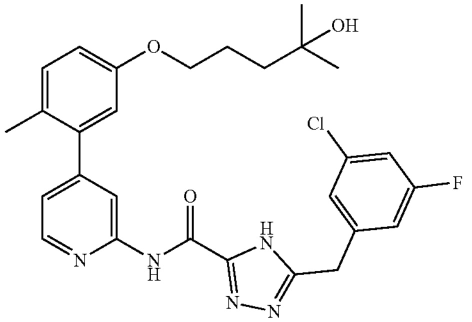

Example 203: 5-(2,5-difluorobenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 4, ethyl 5-(2,5-difluorobenzyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.73 (s, 1H), 9.94 (s, 1H), 8.42 (d, J=5.1 Hz, 1H), 8.11 (s, 1H), 7.42-7.11 (m, 5H), 6.93 (dd, J=8.4, 2.7 Hz, 1H), 6.81 (d, J=2.7 Hz, 1H), 4.22 (s, 2H), 4.17 (s, 1H), 3.97 (t, J=6.5 Hz, 2H), 2.19 (s, 3H), 1.80-1.70 (m, 2H), 1.54-1.42 (m, 2H), 1.10 (s, 6H). MS: 522 $[M+H]^+$.

Example 204: 5-(5-chloro-2-fluorobenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 4, ethyl 5-(5-chloro-2-fluorobenzyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.69 (s, 1H), 9.93 (s, 1H), 8.42 (d, J=5.1 Hz, 1H), 8.10 (s, 1H), 7.53 (dd, J=6.6, 2.7 Hz, 1H), 7.48-7.36 (m, 1H), 7.36-7.14 (m, 3H), 6.93 (dd, J=8.4, 2.7 Hz, 1H), 6.80 (d, J=2.7 Hz, 1H), 4.22 (s, 2H), 4.17 (s, 1H), 3.96 (t, J=6.5 Hz, 2H), 2.19 (s, 3H), 1.83-1.68 (m, 2H), 1.55-1.42 (m, 2H), 1.09 (s, 6H). MS: 538 $[M+H]^+$.

Example 205: 5-(5-chloro-3-fluorobenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 4, ethyl 5-(5-chloro-3-fluorobenzyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.56 (s, 1H), 9.91 (s, 1H), 8.42 (d, J=5.1 Hz, 1H), 8.11 (s, 1H), 7.43-7.14 (m, 5H), 6.93 (dd, J=8.4, 2.7 Hz, 1H), 6.80 (d, J=2.7 Hz, 1H), 4.24 (s, 2H), 4.17 (s, 1H), 3.96 (t, J=6.6 Hz, 2H), 2.19 (s, 3H), 1.82-1.68 (m, 2H), 1.52-1.42 (m, 2H), 1.09 (s, 6H). MS: 538 $[M+H]^+$.

Example 206: 5-(3-chloro-4-fluorobenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 4, ethyl 5-(3-chloro-4-fluorobenzyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.61 (s, 1H), 9.95 (s, 1H), 8.42 (d, J=5.1 Hz, 1H), 8.11 (s, 1H), 7.59 (dd, J=7.2, 2.1 Hz, 1H), 7.47-7.29 (m, 2H), 7.29-7.15 (m, 2H), 6.93 (dd, J=8.4, 2.7 Hz, 1H), 6.80 (d, J=2.7 Hz, 1H), 4.24-4.14 (m, 3H), 3.96 (t, J=6.6 Hz, 2H), 2.19 (s, 3H), 1.83-1.66 (m, 2H), 1.54-1.41 (m, 2H), 1.09 (s, 6H). MS: 538 $[M+H]^+$.

Example 206

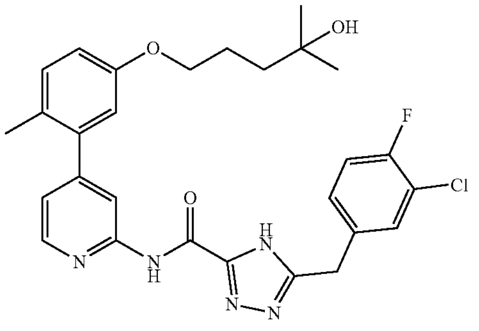

Example 207

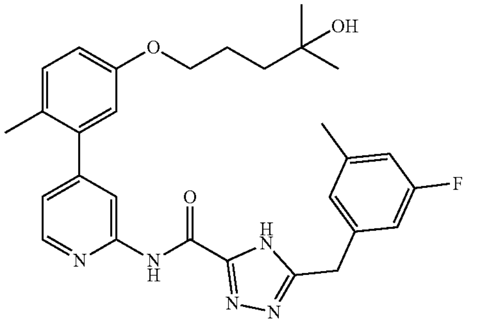

Example 207: 5-(3-fluoro-5-methylbenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 4, ethyl 5-(3-fluoro-5-methylbenzyl)-4H-1,2,4-triazol-3-carboxylate was used in place of ethyl 5-benzyl-4H-1,2,4-triazol-3-carboxylate. $^{1}H$ NMR (400 MHz, DMSO-$d_6$) δ 14.55 (s, 1H), 9.90 (s, 1H), 8.42 (d, J=5.1 Hz, 1H), 8.11 (s, 1H), 7.32-7.14 (m, 2H), 7.03-6.86 (m, 4H), 6.80 (d, J=2.7 Hz, 1H), 4.22-4.10 (m, 3H), 3.96 (t, J=6.6 Hz, 2H), 2.30 (s, 3H), 2.19 (s, 3H), 1.82-1.68 (m, 2H), 1.54-1.42 (m, 2H), 1.09 (s, 6H). MS: 518 $[M+H]^+$.

Example 208: 5-(4-fluoro-3-methylbenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 4, ethyl 5-(4-fluoro-3-methylbenzyl)-4H-1,2,4-triazol-3-carboxylate was used in place of ethyl 5-benzyl-4H-1,2,4-triazol-3-carboxylate. $^{1}H$ NMR (400 MHz, DMSO-$d_6$) δ 14.53 (s, 1H), 9.89 (s, 1H), 8.42 (d, J=5.1 Hz, 1H), 8.11 (s, 1H), 7.34-7.00 (m, 5H), 6.93 (dd, J=8.4, 2.7 Hz, 1H), 6.80 (d, J=2.7 Hz, 1H), 4.24-4.04 (m, 3H), 3.96 (t, J=6.5 Hz, 2H), 2.27-2.12 (m, 6H), 1.83-1.67 (m, 2H), 1.56-1.41 (m, 2H), 1.09 (s, 6H). MS: 518 $[M+H]^+$.

Example 208

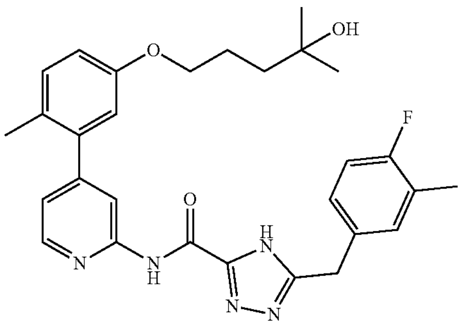

Example 209

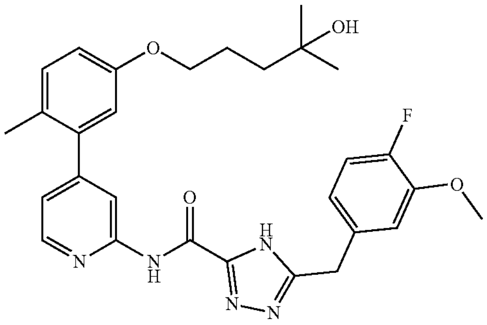

Example 209: 5-(4-fluoro-3-methoxybenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 4, ethyl 5-(4-fluoro-3-methoxybenzyl)-4H-1,2,4-triazol-3-carboxylate was used in place of ethyl 5-benzyl-4H-1,2,4-triazol-3-carboxylate. $^{1}H$ NMR (400 MHz, DMSO-$d_6$) δ 14.52 (s, 1H), 9.89 (s, 1H), 8.42 (d, J=5.1 Hz, 1H), 8.11 (s, 1H), 7.30-7.08 (m, 4H), 6.93 (dd, J=8.4, 2.7 Hz, 1H), 6.90-6.83 (m, 1H), 6.80 (d, J=2.7 Hz, 1H), 4.22-4.09 (m, 3H), 3.96 (t, J=6.5 Hz, 2H), 3.83 (s, 3H), 2.19 (s, 3H), 1.81-1.69 (m, 2H), 1.54-1.41 (m, 2H), 1.09 (s, 6H). MS: 534 $[M+H]^+$.

Example 210: 5-(2-fluoro-3-trifluoromethylbenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 4, ethyl 5-(2-fluoro-3-trifluoromethylbenzyl)-4H-1,2,4-triazol-3-carboxylate was used in place of ethyl 5-benzyl-4H-1,2,4-triazol-3-carboxylate. $^{1}H$ NMR (400 MHz, DMSO-$d_6$) δ 14.69 (s, 1H), 9.91 (s, 1H), 8.41 (d, J=5.1 Hz, 1H), 8.10 (s, 1H), 7.88-7.64 (m, 2H), 7.49-7.34 (m, 1H), 7.30-7.13 (m, 2H), 6.93 (dd, J=8.4, 2.7 Hz, 1H), 6.80 (d, J=2.7 Hz, 1H), 4.32 (s, 2H), 4.16 (s, 1H), 3.96 (t, J=6.5 Hz, 2H), 2.19 (s, 3H), 1.81-1.69 (m, 2H), 1.53-1.41 (m, 2H), 1.09 (s, 6H). MS: 572 $[M+H]^+$.

Example 210

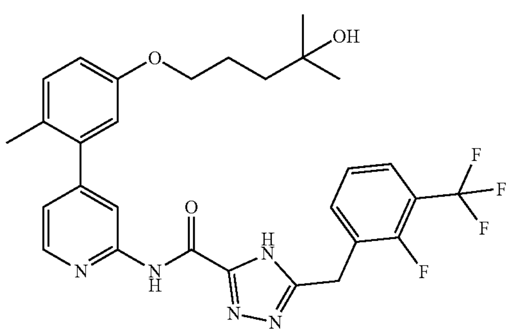

Example 211

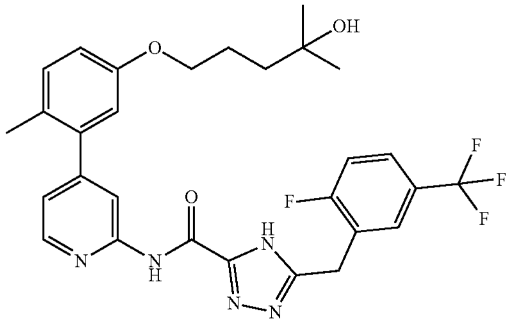

Example 211: 5-(2-fluoro-5-trifluoromethylbenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 4, ethyl 5-(2-fluoro-5-trifluoromethylbenzyl)-4H-1,2,4-triazol-3-carboxylate was used in place of ethyl 5-benzyl-4H-1,2,4-triazol-3-carboxylate. $^{1}$H NMR (400 MHz, DMSO-$d_6$) δ 14.76 (s, 1H), 9.92 (s, 1H), 8.41 (d, J=5.1 Hz, 1H), 8.10 (s, 1H), 7.90 (dd, J=6.7, 2.4 Hz, 1H), 7.83-7.67 (m, 1H), 7.56-7.37 (m, 1H), 7.33-7.12 (m, 2H), 6.92 (dd, J=8.4, 2.7 Hz, 1H), 6.80 (d, J=2.7 Hz, 1H), 4.32 (s, 2H), 4.17 (s, 1H), 3.96 (t, J=6.5 Hz, 2H), 2.18 (s, 3H), 1.80-1.68 (m, 2H), 1.52-1.41 (m, 2H), 1.09 (s, 6H). MS: 572 $[M+H]^+$.

Example 212: 5-(4-fluoro-3-trifluoromethylbenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 4, ethyl 5-(4-fluoro-3-trifluoromethylbenzyl)-4H-1,2,4-triazol-3-carboxylate was used in place of ethyl 5-benzyl-4H-1,2,4-triazol-3-carboxylate. $^{1}$H NMR (400 MHz, DMSO-$d_6$) δ 14.55 (s, 1H), 9.90 (s, 1H), 8.42 (d, J=5.1 Hz, 1H), 8.11 (s, 1H), 7.84-7.76 (m, 1H), 7.76-7.67 (m, 1H), 7.50 (dd, J=10.6, 8.8 Hz, 1H), 7.29-7.16 (m, 2H), 6.93 (dd, J=8.4, 2.7 Hz, 1H), 6.80 (d, J=2.7 Hz, 1H), 4.30 (s, 2H), 4.16 (s, 1H), 3.96 (t, J=6.6 Hz, 2H), 2.19 (s, 3H), 1.82-1.66 (m, 2H), 1.52-1.42 (m, 2H), 1.09 (s, 6H). MS: 572 $[M+H]^+$.

Example 212

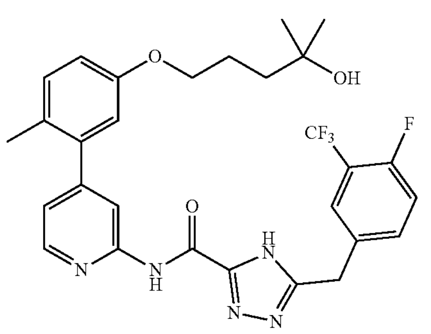

Example 213

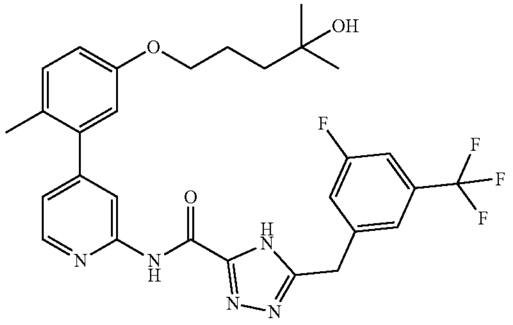

Example 213: 5-(3-fluoro-5-trifluoromethylbenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 4, ethyl 5-(3-fluoro-5-trifluoromethylbenzyl)-4H-1,2,4-triazol-3-carboxylate was used in place of ethyl 5-benzyl-4H-1,2,4-triazol-3-carboxylate. $^{1}$H NMR (400 MHz, DMSO-$d_6$) δ 14.57 (s, 1H), 9.90 (s, 1H), 8.42 (d, J=5.1 Hz, 1H), 8.12 (s, 1H), 7.70-7.50 (m, 3H), 7.30-7.15 (m, 2H), 6.93 (dd, J=8.4, 2.7 Hz, 1H), 6.80 (d, J=2.7 Hz, 1H), 4.36 (s, 2H), 4.17 (s, 1H), 3.96 (t, J=6.5 Hz, 2H), 2.19 (s, 3H), 1.82-1.67 (m, 2H), 1.53-1.42 (m, 2H), 1.09 (s, 6H). MS: 572 $[M+H]^+$.

Example 214: 5-(2,3,4-trifluorobenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 4, ethyl 5-(2,3,4-trifluorobenzyl)-4H-1,2,4-triazol-3-carboxylate was used in place of ethyl 5-benzyl-4H-1,2,4-triazol-3-carboxylate. $^{1}$H NMR (400 MHz, DMSO-$d_6$) δ 14.60 (s, 1H), 9.87 (s, 1H), 8.42 (d, J=5.1 Hz, 1H), 8.10 (s, 1H), 7.40-7.15 (m, 4H), 6.93 (dd, J=8.4, 2.7 Hz, 1H), 6.80 (d, J=2.7 Hz, 1H), 4.26 (s, 2H), 4.16 (s, 1H), 3.96 (t, J=6.5 Hz, 2H), 2.19 (s, 3H), 1.80-1.66 (m, 2H), 1.53-1.41 (m, 2H), 1.09 (s, 6H). MS: 540 $[M+H]^+$.

Example 214

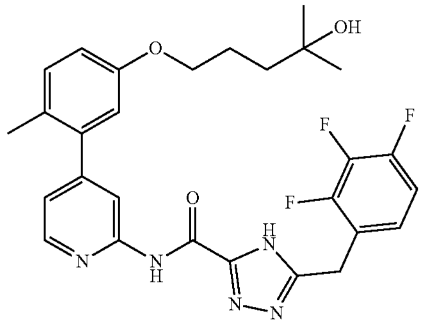

Example 215

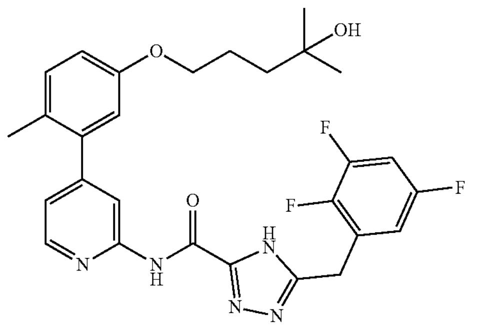

Example 215: 5-(2,3,5-trifluorobenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 4, ethyl 5-(2,3,5-trifluorobenzyl)-4H-1,2,4-triazol-3-carboxylate was used in place of ethyl 5-benzyl-4H-1,2,4-triazol-3-carboxylate. $^{1}H$ NMR (400 MHz, DMSO-$d_6$) δ 14.75 (s, 1H), 9.96 (s, 1H), 8.42 (d, J=5.1 Hz, 1H), 8.10 (s, 1H), 7.58-7.41 (m, 1H), 7.33-7.13 (m, 3H), 7.01-6.87 (m, 1H), 6.80 (d, J=2.7 Hz, 1H), 4.28 (s, 2H), 4.16 (s, 1H), 3.96 (t, J=6.5 Hz, 2H), 2.19 (s, 3H), 1.81-1.67 (m, 2H), 1.52-1.42 (m, 2H), 1.09 (s, 6H). MS: 540 $[M+H]^+$.

Example 216: 5-(2,3,6-trifluorobenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 4, ethyl 5-(2,3,6-trifluorobenzyl)-4H-1,2,4-triazol-3-carboxylate was used in place of ethyl 5-benzyl-4H-1,2,4-triazol-3-carboxylate. $^{1}H$ NMR (400 MHz, DMSO-$d_6$) δ 14.75 (s, 1H), 9.89 (s, 1H), 8.41 (d, J=5.1 Hz, 1H), 8.08 (s, 1H), 7.59-7.42 (m, 1H), 7.31-7.12 (m, 3H), 6.92 (dd, J=8.4, 2.7 Hz, 1H), 6.80 (d, J=2.7 Hz, 1H), 4.25 (s, 2H), 4.17 (s, 1H), 3.96 (t, J=6.5 Hz, 2H), 2.18 (s, 3H), 1.80-1.68 (m, 2H), 1.55-1.41 (m, 2H), 1.09 (s, 6H). MS: 540 $[M+H]^+$ Example 216

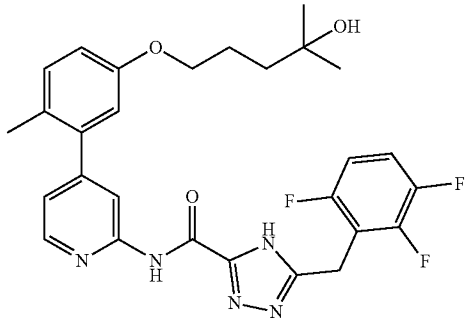

Example 217

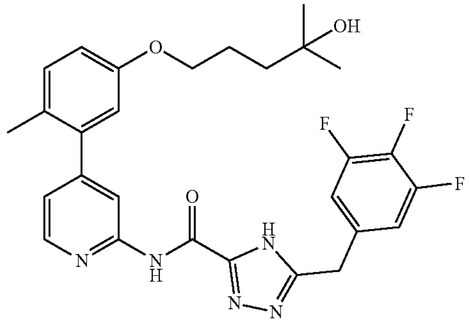

Example 217: 5-(3,4,5-trifluorobenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 4, ethyl 5-(3,4,5-trifluorobenzyl)-4H-1,2,4-triazol-3-carboxylate was used in place of ethyl 5-benzyl-4H-1,2,4-triazol-3-carboxylate. $^{1}H$ NMR (400 MHz, DMSO-$d_6$) δ 14.66 (s, 1H), 10.00 (s, 1H), 8.42 (d, J=5.1 Hz, 1H), 8.11 (s, 1H), 7.45-7.28 (m, 2H), 7.28-7.15 (m, 2H), 6.93 (dd, J=8.4, 2.7 Hz, 1H), 6.81 (d, J=2.7 Hz, 1H), 4.26-4.13 (m, 3H), 3.96 (t, J=6.5 Hz, 2H), 2.19 (s, 3H), 1.81-1.67 (m, 2H), 1.52-1.41 (m, 2H), 1.09 (s, 6H). MS: 540 $[M+H]^+$.

Example 218: 5-(2,4,5-trifluorobenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 4, ethyl 5-(2,4,5-trifluorobenzyl)-4H-1,2,4-triazol-3-carboxylate was used in place of ethyl 5-benzyl-4H-1,2,4-triazol-3-carboxylate. $^{1}H$ NMR (400 MHz, DMSO-$d_6$) δ 14.60 (s, 1H), 9.92 (s, 1H), 8.42 (d, J=5.1 Hz, 1H), 8.10 (s, 1H), 7.73-7.46 (m, 2H), 7.30-7.14 (m, 2H), 6.93 (dd, J=8.4, 2.7 Hz, 1H), 6.80 (d, J=2.7 Hz, 1H), 4.24-4.13 (m, 3H), 3.96 (t, J=6.5 Hz, 2H), 2.19 (s, 3H), 1.81-1.67 (m, 2H), 1.53-1.40 (m, 2H), 1.09 (s, 6H). MS: 540 $[M+H]^+$.

Example 218

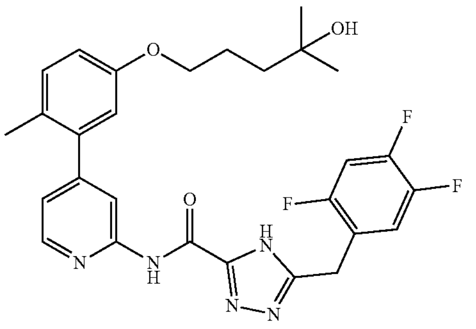

Example 219

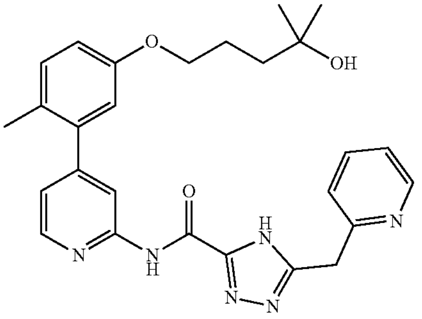

Example 219: N-(4-(5-((4-hydroxy-4-methylpentyl)oxy)-2-methylphenyl)pyridin-2-yl)-5-(pyridin-2-ylmethyl)-4H-1,2,4-triazole-3-carboxamide The preparation was carried out in a similar manner to Example 160, except that in step 4, ethyl 5-(pyridin-2-ylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.65 (s, 1H), 9.89 (s, 1H), 8.54-8.45 (m, 1H), 8.41 (d, J=5.1 Hz, 1H), 8.11 (s, 1H), 7.84-7.75 (m, 1H), 7.43 (d, J=7.8 Hz, 1H), 7.34-7.17 (m, 3H), 6.93 (dd, J=8.4, 2.7 Hz, 1H), 6.80 (d, J=2.7 Hz, 1H), 4.34 (s, 2H), 4.17 (s, 1H), 3.96 (t, J=6.5 Hz, 2H), 2.19 (s, 3H), 1.82-1.68 (m, 2H), 1.54-1.40 (m, 2H), 1.09 (s, 6H). MS: 487 $[M+H]^+$.

Example 220: N-(4-(5-((4-hydroxy-4-methylpentyl)oxy)-2-methylphenyl)pyridin-2-yl)-5-(pyridin-3-ylmethyl)-4H-1,2,4-triazole-3-carboxamide The preparation was carried out in a similar manner to Example 160, except that in step 4, ethyl 5-(pyridin-3-ylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.66 (s, 1H), 9.95 (s, 1H), 8.58 (d, J=2.2 Hz, 1H), 8.48 (dd, J=4.8, 1.7 Hz, 1H), 8.41 (d, J=5.1 Hz, 1H), 8.13-8.09 (m, 1H), 7.82-7.70 (m, 1H), 7.43-7.32 (m, 1H), 7.28-7.17 (m, 2H), 6.93 (dd, J=8.4, 2.7 Hz, 1H), 6.80 (d, J=2.8 Hz, 1H), 4.22 (s, 2H), 4.17 (s, 1H), 3.96 (t, J=6.6 Hz, 2H), 2.19 (s, 3H), 1.81-1.69 (m, 2H), 1.54-1.42 (m, 2H), 1.09 (s, 6H). MS: 487 $[M+H]^+$.

Example 220

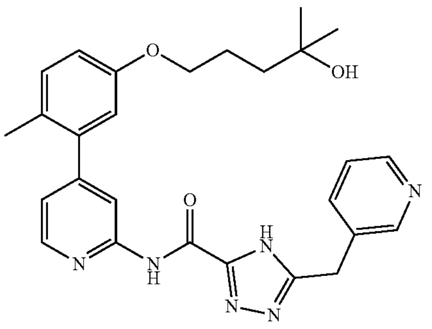

Example 221

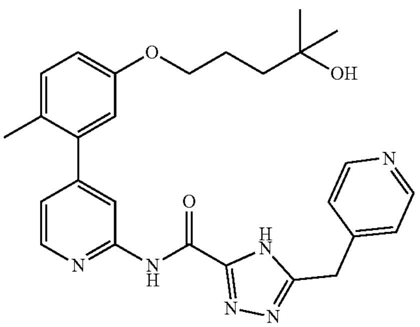

Example 221: N-(4-(5-((4-hydroxy-4-methylpentyl)oxy)-2-methylphenyl)pyridin-2-yl)-5-(pyridin-4-ylmethyl)-4H-1,2,4-triazole-3-carboxamide The preparation was carried out in a similar manner to Example 160, except that in step 4, ethyl 5-(pyridin-4-ylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.63 (s, 1H), 9.90 (s, 1H), 8.53 (d, J=5.0 Hz, 2H), 8.42 (d, J=5.2 Hz, 1H), 8.11 (s, 1H), 7.42-7.29 (m, 2H), 7.29-7.15 (m, 2H), 6.93 (dd, J=8.4, 2.7 Hz, 1H), 6.81 (d, J=2.7 Hz, 1H), 4.29-4.20 (m, 2H), 4.17 (s, 1H), 3.96 (t, J=6.6 Hz, 2H), 2.19 (s, 3H), 1.83-1.68 (m, 2H), 1.55-1.42 (m, 2H), 1.09 (s, 6H). MS: 487 $[M+H]^+$.

Example 222: 5-(cycloheptylmethyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 4, ethyl 5-(cycloheptylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.37 (s, 1H), 9.85 (s, 1H), 8.42 (dd, J=5.0, 0.8 Hz, 1H), 8.13 (s, 1H), 7.33-7.15 (m, 2H), 6.93 (dd, J=8.4, 2.7 Hz, 1H), 6.81 (d, J=2.7 Hz, 1H), 4.17 (s, 1H), 3.97 (t, J=6.6 Hz, 2H), 2.69 (d, J=7.3 Hz, 2H), 2.19 (s, 3H), 2.07-1.91 (m, 1H), 1.82-1.70 (m, 2H), 1.70-1.30 (m, 12H), 1.30-1.15 (m, 2H), 1.09 (s, 6H). MS: 506 $[M+H]^+$.

Example 222

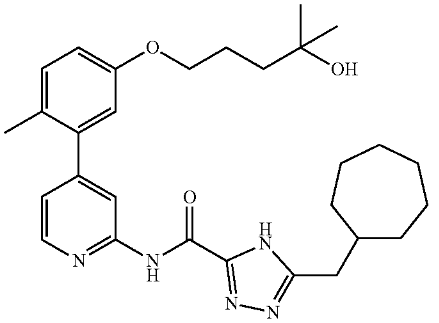

Example 223

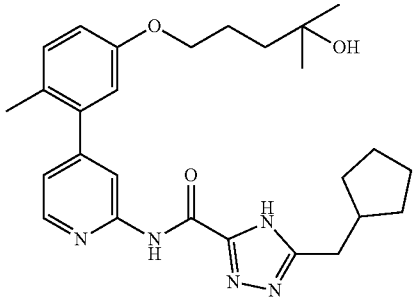

Example 223: 5-(cyclopentylmethyl)-N-(4-(5-((5-hydroxyl-5-methylhexyl)oxy)-2-methylphenyl)pyridin-2-yl)-4H-1,2,4-triazole-3-carboxamide The preparation was carried out in a similar manner to Example 160, except that in step 1, methyl 5-bromopentanoate was used in place of methyl 4-bromobutanoate, and in step 4, ethyl 5-(cyclopentylmethyl)-4H-1,2,4-triazole-3-carboxylate was used in place of ethyl 5-benzyl-4H-1,2,4-triazol-3-carboxylate. $^1$H NMR (400 MHz, DMSO-$d_6$) δ 14.37 (s, 1H), 9.83 (s, 1H), 8.42 (d, J=5.2 Hz, 1H), 8.14 (s, 1H), 7.29-7.16 (m, 2H), 6.94 (dd, J=8.4, 2.7 Hz, 1H), 6.82 (d, J=2.7 Hz, 1H), 4.09 (s, 1H), 3.98 (t, J=6.5 Hz, 2H), 2.79 (d, J=7.5 Hz, 2H), 2.37-2.22 (m, 1H), 2.19 (s, 3H), 1.82-1.65 (m, 4H), 1.65-1.57 (m, 2H), 1.57-1.47 (m, 2H), 1.47-1.32 (m, 4H), 1.30-1.17 (m, 2H), 1.06 (s, 6H). MS: 492 $[M+H]^+$.

Example 224: 5-(cyclopentylmethyl)-N-(4-(5-((5-hydroxypentyl)oxy)-2-methylphenyl)pyridin-2-yl)-4H-1,2,4-triazole-3-carboxamide The preparation was carried out in a similar manner to Example 92, except that in step 1, 5-bromo-1-pentanol was used in place of iodomethane, 3-bromo-4-methylphenol was used in place of 2-bromo-3-methylphenol, and in step 3, ethyl 5-(cyclopentylmethyl)-4H-1,2,4-triazole-3-carboxylate was used in place of ethyl 5-benzyl-4H-1,2,4-triazol-3-carboxylate. $^1$H NMR (400 MHz, DMSO-$d_6$) δ 14.36 (s, 1H), 9.83 (s, 1H), 8.42 (d, J=5.1 Hz, 1H), 8.14 (s, 1H), 7.29-7.16 (m, 2H), 6.93 (dd, J=8.4, 2.7 Hz, 1H), 6.81 (d, J=2.7 Hz, 1H), 4.37 (t, J=5.1 Hz, 1H), 3.97 (t, J=6.5 Hz, 2H), 3.51-3.36 (m, 2H), 2.79 (d, J=7.5 Hz, 2H), 2.37-2.22 (m, 1H), 2.19 (s, 3H), 1.79-1.66 (m, 4H), 1.66-1.56 (m, 2H), 1.56-1.36 (m, 6H), 1.30-1.15 (m, 2H). MS: 464 $[M+H]^+$.

Example 224

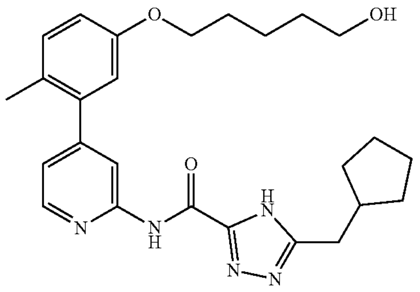

Example 225

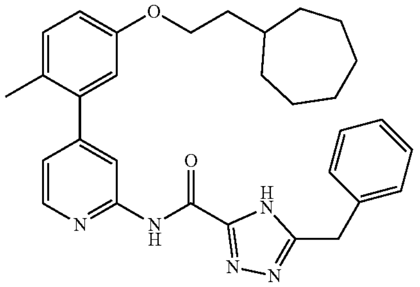

Example 225: 5-benzyl-N-(4-(5-(2-cycloheptylethoxy)-2-methylphenyl)pyridin-2-yl)-4H-1,2,4-triazole-3-carboxamide The preparation was carried out in a similar manner to Example 64, except that in step 1, 2-cycloheptyl-1-ethanol was used in place of 2-(tert-butoxy)ethan-1-ol. $^1$H NMR (400 MHz, DMSO-$d_6$) δ 14.56 (s, 1H), 9.88 (s, 1H), 8.41 (d, J=5.1 Hz, 1H), 8.11 (s, 1H), 7.44-7.30 (m, 4H), 7.30-7.14 (m, 3H), 6.93 (dd, J=8.4, 2.7 Hz, 1H), 6.81 (d, J=2.7 Hz, 1H), 4.18 (s, 2H), 3.99 (t, J=6.3 Hz, 2H), 2.18 (s, 3H), 1.77-1.50 (m, 9H), 1.50-1.31 (m, 4H), 1.23-1.13 (m, 2H). MS: 510 $[M+H]^+$.

Example 226: 5-(2-fluorobenzyl)-N-(4-(2-methyl-5-(2-(tetrahydro-2H-pyran-4-yl)ethoxy)phenyl)pyridin-2-yl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 15.08-14.30 (m, 1H), 9.88 (s, 1H), 8.48-8.32 (m, 1H), 8.11 (s, 1H), 7.48-7.29 (m, 2H), 7.29-7.09 (m, 4H), 6.93 (d, J=8.5 Hz, 1H), 6.82 (s, 1H), 4.21 (s, 2H), 4.01 (t, J=6.4 Hz, 2H), 3.92-3.67 (m, 2H), 3.30-3.14 (m, 2H), 2.18 (s, 3H), 1.80-1.48 (m, 5H), 1.33-1.08 (m, 2H). MS: 516 $[M+H]^+$.

Example 226

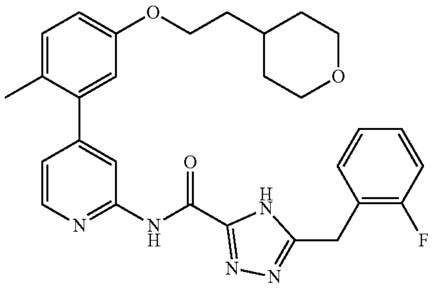

Example 227

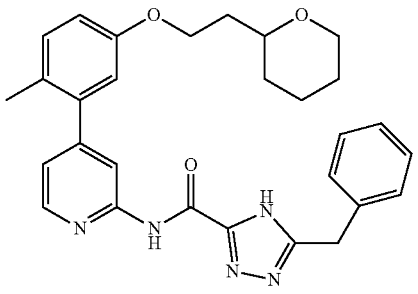

Example 227: 5-benzyl-N-(4-(2-methyl-5-(2-(tetrahydro-2H-pyran-2-yl)ethoxy)phenyl)pyridin-2-yl)-4H-1,2,4-triazole-3-carboxamide The preparation was carried out in a similar manner to Example 92, except that in step 1, 2-(2-bromoethyl)tetrahydro-2H-pyran was used in place of iodomethane, and 3-bromo-4-methylphenol was used in place of 2-bromo-3-methylphenol. $^1$H NMR (400 MHz, DMSO-$d_6$) δ 14.59 (s, 1H), 9.91 (s, 1H), 8.41 (d, J=5.1 Hz, 1H), 8.11 (s, 1H), 7.46-7.29 (m, 4H), 7.29-7.15 (m, 3H), 6.93 (dd, J=8.4, 2.8 Hz, 1H), 6.81 (d, J=2.8 Hz, 1H), 4.17 (s, 2H), 4.11-3.95 (m, 2H), 3.90-3.78 (m, 1H), 3.46-3.19 (m, 4H), 2.19 (s, 3H), 1.87-1.76 (m, 2H), 1.76-1.68 (m, 1H), 1.65-1.55 (m, 1H), 1.47-1.39 (m, 2H). MS: 498 $[M+H]^+$.

Example 228: 5-benzyl-N-(4-(2-methyl-5-(2-(piperidin-1-yl)ethoxy)phenyl)pyridin-2-yl)-4H-1,2,4-triazole-3-carboxamide The preparation was carried out in a similar manner to Example 92, except that in step 1, 1-(2-chloroethyl)piperidine hydrochloride was used in place of iodomethane, and 3-bromo-4-methylphenol was used in place of 2-bromo-3-methylphenol. $^1$H NMR (400 MHz, DMSO-$d_6$) δ 14.59 (s, 1H), 9.91 (s, 1H), 8.41 (d, J=5.2 Hz, 1H), 8.12 (s, 1H), 7.39-7.29 (m, 4H), 7.29-7.15 (m, 3H), 6.93 (dd, J=8.4, 2.7 Hz, 1H), 6.83 (d, J=2.8 Hz, 1H), 4.17 (s, 2H), 4.07 (t, J=5.9 Hz, 2H), 2.64 (t, J=5.9 Hz, 2H), 2.42 (t, J=5.3 Hz, 4H), 2.19 (s, 3H), 1.55-1.41 (m, 4H), 1.41-1.27 (m, 2H). MS: 497 $[M+H]^+$.

Example 228

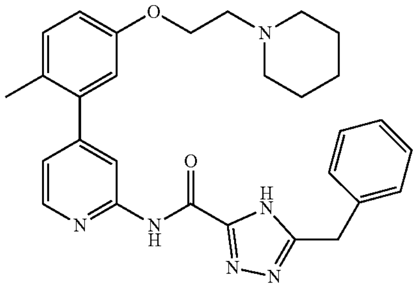

Example 229

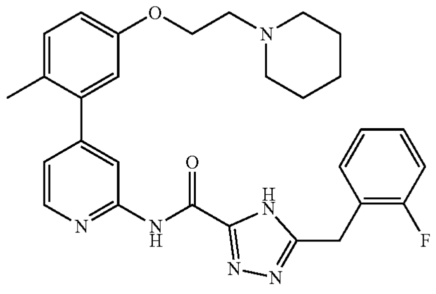

Example 229: 5-(2-fluorobenzyl)-N-(4-(2-methyl-5-(2-(piperidin-1-yl)ethoxy)phenyl)pyridin-2-yl)-4H-1,2,4-triazole-3-carboxamide The preparation was carried out in a similar manner to Example 92, except that in step 1, 1-(2-chloroethyl)piperidine hydrochloride was used in place of iodomethane, 3-bromo-4-methylphenol was used in place of 2-bromo-3-methylphenol, and in step 3, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.59 (s, 1H), 9.89 (s, 1H), 8.41 (d, J=5.1 Hz, 1H), 8.11 (d, J=1.4 Hz, 1H), 7.36-7.11 (m, 6H), 6.95 (dd, J=8.4, 2.7 Hz, 1H), 6.84 (d, J=2.7 Hz, 1H), 4.33-4.24 (m, 2H), 4.21 (s, 2H), 4.11 (t, J=5.8 Hz, 2H), 2.75 (t, J=5.8 Hz, 2H), 2.19 (s, 3H), 1.56-1.43 (m, 4H), 1.43-1.32 (m, 2H), 1.31-1.23 (m, 2H). MS: 515 $[M+H]^+$.

Example 230: 5-(2,4-difluorobenzyl)-N-(4-(2-methyl-5-(2-(piperidin-1-yl)ethoxy)phenyl)pyridin-2-yl)-4H-1,2,4-triazole-3-carboxamide The preparation was carried out in a similar manner to Example 92, except that in step 1, 1-(2-chloroethyl)piperidine hydrochloride was used in place of iodomethane, 3-bromo-4-methylphenol was used in place of 2-bromo-3-methylphenol, and in step 3, ethyl 5-(2,4-difluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.59 (s, 1H), 9.90 (s, 1H), 8.41 (d, J=5.1 Hz, 1H), 8.11 (s, 1H), 7.52-7.40 (m, 1H), 7.31-7.16 (m, 3H), 7.13-7.04 (m, 1H), 6.94 (dd, J=8.4, 2.8 Hz, 1H), 6.83 (d, J=2.8 Hz, 1H), 4.18 (s, 2H), 4.07 (t, J=5.9 Hz, 2H), 2.65 (t, J=5.9 Hz, 2H), 2.47-2.35 (m, 4H), 2.19 (s, 3H), 1.55-1.41 (m, 4H), 1.41-1.28 (m, 2H). MS: 533 $[M+H]^+$.

Example 230

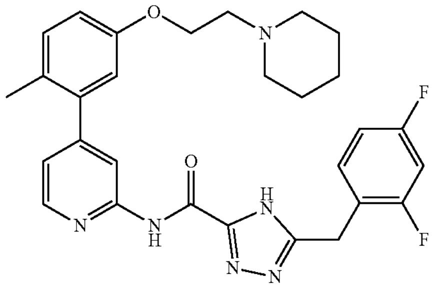

Example 231

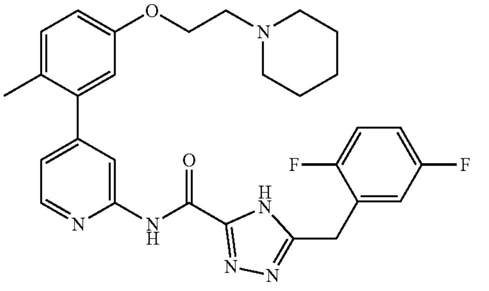

Example 231: 5-(2,5-difluorobenzyl)-N-(4-(2-methyl-5-(2-(piperidin-1-yl)ethoxy)phenyl)pyridin-2-yl)-4H-1,2,4-triazole-3-carboxamide The preparation was carried out in a similar manner to Example 92, except that in step 1, 1-(2-chloroethyl)piperidine hydrochloride was used in place of iodomethane, 3-bromo-4-methylphenol was used in place of 2-bromo-3-methylphenol, and in step 3, ethyl 5-(2,5-difluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.59 (s, 1H), 9.93 (s, 1H), 8.40 (d, J=5.1 Hz, 1H), 8.12 (s, 1H), 7.45-7.03 (m, 5H), 7.03-6.67 (m, 2H), 4.20 (s, 2H), 4.07 (t, J=5.9 Hz, 2H), 2.65 (t, J=5.9 Hz, 2H), 2.50-2.33 (m, 4H), 2.18 (s, 3H), 1.62-1.41 (m, 4H), 1.41-1.21 (m, 2H). MS: 533 $[M+H]^+$.

Example 232: 5-(3,5-difluorobenzyl)-N-(4-(2-methyl-5-(2-(piperidin-1-yl)ethoxy)phenyl)pyridin-2-yl)-4H-1,2,4-triazole-3-carboxamide The preparation was carried out in a similar manner to Example 92, except that in step 1, 1-(2-chloroethyl)piperidine hydrochloride was used in place of iodomethane, 3-bromo-4-methylphenol was used in place of 2-bromo-3-methylphenol, and in step 3, ethyl 5-(3,5-difluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.54 (s, 1H), 9.99 (s, 1H), 8.42 (d, J=5.1 Hz, 1H), 8.14-8.06 (m, 1H), 7.28-7.05 (m, 5H), 6.94 (dd, J=8.4, 2.7 Hz, 1H), 6.84 (d, J=2.7 Hz, 1H), 4.22 (s, 2H), 4.08 (t, J=5.9 Hz, 2H), 2.66 (t, J=5.9 Hz, 2H), 2.47-2.36 (m, 4H), 2.19 (s, 3H), 1.53-1.42 (m, 4H), 1.42-1.30 (m, 2H). MS: 533 $[M+H]^+$.

Example 232

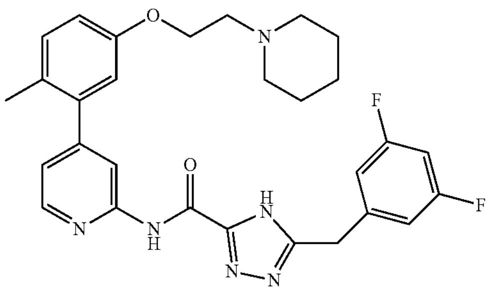

Example 233

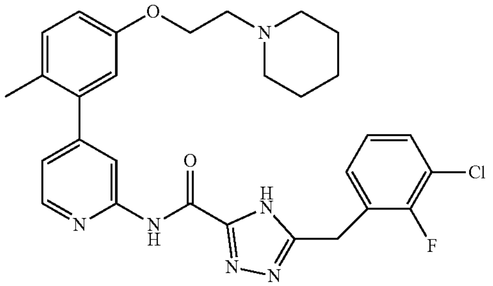

Example 233: 5-(2-fluoro-3-chlorobenzyl)-N-(4-(2-methyl-5-(2-(piperidin-1-yl)ethoxy)phenyl)pyridin-2-yl)-4H-1,2,4-triazole-3-carboxamide The preparation was carried out in a similar manner to Example 92, except that in step 1, 1-(2-chloroethyl)piperidine hydrochloride was used in place of iodomethane, 3-bromo-4-methylphenol was used in place of 2-bromo-3-methylphenol, and in step 3, ethyl 5-(2-fluoro-3-chlorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.61 (s, 1H), 9.93 (s, 1H), 8.41 (d, J=5.1 Hz, 1H), 8.10 (s, 1H), 7.57-7.48 (m, 1H), 7.43-7.36 (m, 1H), 7.28-7.17 (m, 3H), 6.94 (dd, J=8.4, 2.7 Hz, 1H), 6.83 (d, J=2.7 Hz, 1H), 4.26 (s, 2H), 4.08 (t, J=5.9 Hz, 2H), 2.66 (t, J=5.8 Hz, 2H), 2.46-2.38 (m, 4H), 2.19 (s, 3H), 1.53-1.43 (m, 4H), 1.37 (t, J=6.2 Hz, 2H). MS: 549 $[M+H]^+$.

Example 234: 5-(2-fluorobenzyl)-N-(4-(2-methyl-5-((1-methylpiperidin-4-yl)methoxy)phenyl)pyridin-2-yl)-4H-1,2,4-triazole-3-carboxamide The preparation was carried out in a similar manner to Example 92, except that in step 1, 4-(chloromethyl)-1-methylpiperidine hydrochloride was used in place of iodomethane, 3-bromo-4-methylphenol was used in place of 2-bromo-3-methylphenol, and in step 3, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.11 (s, 1H), 9.90 (s, 1H), 8.41 (d, J=5.1 Hz, 1H), 8.10 (s, 1H), 7.44-7.30 (m, 2H), 7.28-7.14 (m, 4H), 6.93 (dd, J=8.4, 2.7 Hz, 1H), 6.81 (d, J=2.7 Hz, 1H), 4.19 (s, 2H), 3.97 (t, J=6.6 Hz, 1H), 3.86-3.79 (m, 1H), 2.82-2.66 (m, 2H), 2.27 (s, 1H), 2.18 (s, 3H), 2.16 (s, 3H), 2.01-1.83 (m, 2H), 1.79-1.67 (m, 2H), 1.47-1.26 (m, 2H). MS: 515 $[M+H]^+$.

Example 234

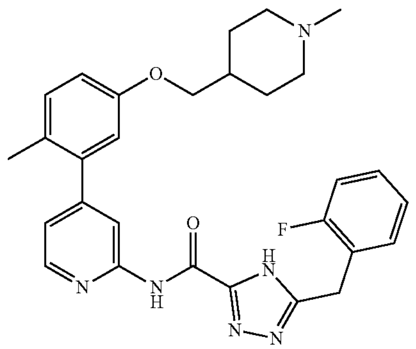

Example 235

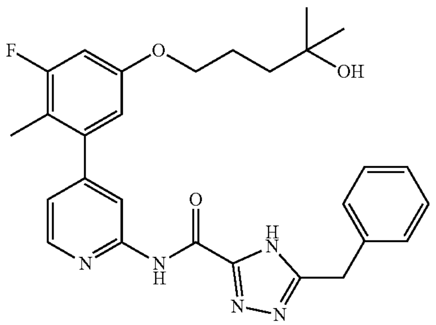

Example 235: 5-benzyl-N-(4-(3-fluoro-5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 1, 3-bromo-5-fluoro-4-methylphenol was used in place of 3-bromo-4-methylphenol. $^1$H NMR (400 MHz, DMSO-$d_6$) δ 14.56 (s, 1H), 9.90 (s, 1H), 8.44 (d, J=5.1 Hz, 1H), 8.11 (s, 1H), 7.39-7.30 (m, 4H), 7.24 (dd, J=20.1, 5.8 Hz, 2H), 6.91 (dd, J=11.7, 2.5 Hz, 1H), 6.70 (d, J=2.1 Hz, 1H), 4.18 (d, J=5.4 Hz, 3H), 3.99 (t, J=6.6 Hz, 2H), 2.12-2.04 (m, 3H), 1.79-1.68 (m, 2H), 1.53-1.39 (m, 2H), 1.09 (s, 6H). MS: 504 $[M+H]^+$.

Example 236: 5-(2-fluorobenzyl)-N-(4-(3-fluoro-5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 1, 3-bromo-5-fluoro-4-methylphenol was used in place of 3-bromo-4-methylphenol, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.67 (s, 1H), 9.92 (s, 1H), 8.43 (d, J=5.1 Hz, 1H), 8.09 (s, 1H), 7.52-7.29 (m, 2H), 7.29-7.14 (m, 3H), 6.90 (dd, J=11.7, 2.5 Hz, 1H), 6.70 (d, J=2.5 Hz, 1H), 4.21 (s, 2H), 4.17 (s, 1H), 3.99 (t, J=6.5 Hz, 2H), 2.07 (d, J=2.2 Hz, 3H), 1.81-1.70 (m, 2H), 1.51-1.37 (m, 2H), 1.09 (s, 6H). MS: 522 $[M+H]^+$.

Example 236

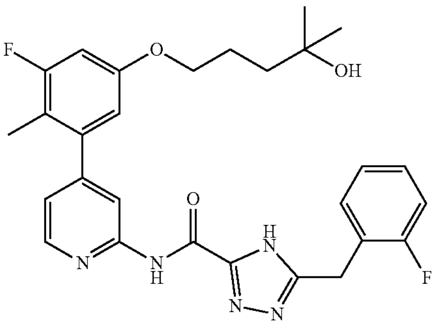

Example 237

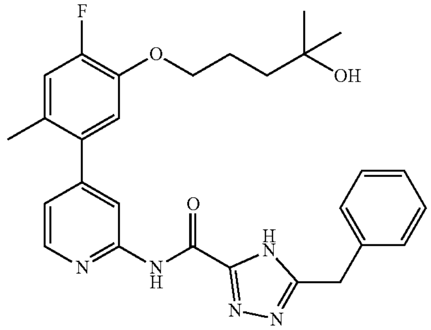

Example 237: 5-benzyl-N-(4-(4-fluoro-5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 1, 5-bromo-2-fluoro-4-methylphenol was used in place of 3-bromo-4-methylphenol. $^1$H NMR (400 MHz, DMSO-$d_6$) δ 14.57 (s, 1H), 9.89 (s, 1H), 8.42 (d, J=5.1 Hz, 1H), 8.10 (s, 1H), 7.40-7.29 (m, 4H), 7.29-7.15 (m, 3H), 7.03 (d, J=8.7 Hz, 1H), 4.23-4.11 (m, 3H), 4.04 (t, J=6.6 Hz, 2H), 2.19 (s, 3H), 1.76 (dd, J=10.3, 6.0 Hz, 2H), 1.53-1.41 (m, 2H), 1.09 (s, 6H). MS: 504 $[M+H]^+$.

Example 238: N-(5-chloro-4-(5-((4-hydroxy-4-methylpentyl)oxy)-2-methylphenyl)pyridin-2-yl)-5-(2-fluorobenzyl)-4H-1,2,4-triazole-3-carboxamide The preparation was carried out in a similar manner to Example 160, except that in step 3, 5-chloro-4-bromopyridin-2-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.60 (s, 1H), 10.06 (s, 1H), 8.54 (s, 1H), 8.05 (s, 1H), 7.44-7.30 (m, 2H), 7.28-7.16 (m, 3H), 6.95 (dd, J=8.4, 2.7 Hz, 1H), 6.74 (d, J=2.7 Hz, 1H), 4.21 (s, 2H), 4.16 (s, 1H), 3.95 (t, J=6.6 Hz, 2H), 2.01 (s, 3H), 1.80-1.67 (m, 2H), 1.51-1.41 (m, 2H), 1.09 (s, 6H). MS: 538 $[M+H]^+$.

Example 238

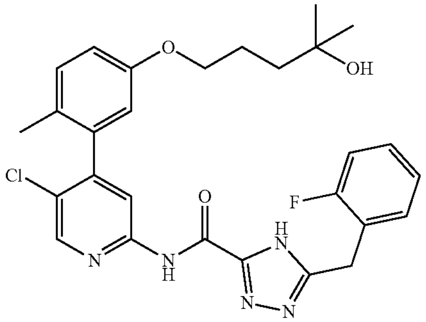

Example 239

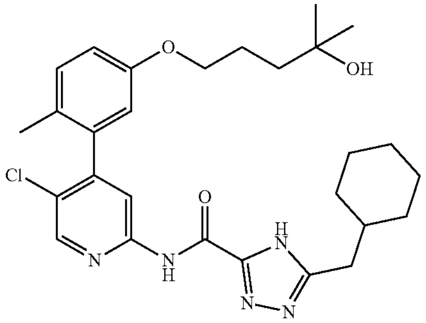

Example 239: N-(5-chloro-4-(5-((4-hydroxy-4-methylpentyl)oxy)-2-methylphenyl)pyridin-2-yl)-5-(cyclohexylmethyl)-4H-1,2,4-triazole-3-carboxamide The preparation was carried out in a similar manner to Example 160, except that in step 3, 5-chloro-4-bromopyridin-2-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.41 (s, 1H), 10.06 (s, 1H), 8.55 (s, 1H), 8.08 (s, 1H), 7.26 (d, J=8.5 Hz, 1H), 6.95 (dd, J=8.4, 2.7 Hz, 1H), 6.75 (d, J=2.7 Hz, 1H), 4.17 (s, 1H), 3.95 (t, J=6.6 Hz, 2H), 2.66 (d, J=7.1 Hz, 2H), 2.01 (s, 3H), 1.84-1.56 (m, 9H), 1.52-1.41 (m, 2H), 1.20-1.12 (m, 2H), 1.09 (s, 6H), 1.05-0.90 (m, 2H). MS: 526 $[M+H]^+$.

Example 240: 5-(2-fluorobenzyl)-N-(4-(5-((4-hydroxy-4-methylpentyl)oxy)-2-methylphenyl)-5-methylpyridin-2-yl)-4H-1,2,4-triazole-3-carboxamide The preparation was carried out in a similar manner to Example 160, except that in step 3, 4-bromo-5-methylpyridin-2-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.58 (s, 1H), 9.75 (s, 1H), 8.30 (s, 1H), 7.87 (s, 1H), 7.44-7.29 (m, 2H), 7.29-7.14 (m, 3H), 6.90 (dd, J=8.4, 2.7 Hz, 1H), 6.66 (d, J=2.7 Hz, 1H), 4.20 (s, 2H), 4.17 (s, 1H), 3.94 (t, J=6.6 Hz, 2H), 1.99 (s, 3H), 1.94 (s, 3H), 1.79-1.68 (m, 2H), 1.52-1.39 (m, 2H), 1.08 (s, 6H). MS: 518 $[M+H]^+$.

Example 240

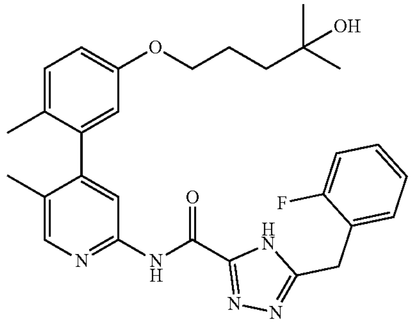

Example 241

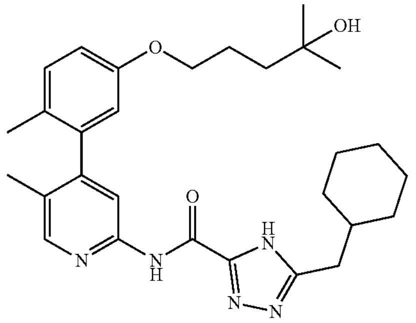

Example 241: 5-(cyclohexylmethyl)-N-(4-(5-((4-hydroxy-4-methylpentyl)oxy)-2-methylphenyl)-5-methylpyridin-2-yl)-4H-1,2,4-triazole-3-carboxamide The preparation was carried out in a similar manner to Example 160, except that in step 3, 4-bromo-5-methylpyridin-2-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.34 (s, 1H), 9.74 (s, 1H), 8.31 (s, 1H), 7.90 (s, 1H), 7.24 (d, J=8.4 Hz, 1H), 6.91 (dd, J=8.4, 2.7 Hz, 1H), 6.66 (d, J=2.7 Hz, 1H), 4.18 (s, 1H), 3.94 (t, J=6.6 Hz, 2H), 2.66 (d, J=7.2 Hz, 2H), 2.00 (s, 3H), 1.95 (s, 3H), 1.82-1.57 (m, 8H), 1.52-1.40 (m, 2H), 1.24-1.13 (m, 3H), 1.08 (s, 6H), 1.05-0.90 (m, 2H). MS: 506 $[M+H]^+$.

Example 242: N-(4-(5-((4-ethyl-4-hydroxyhexyl)oxy)-2-methylphenyl)-5-fluoropyridin-2-yl)-5-(2-fluorobenzyl)-4H-1,2,4-triazole-3-carboxamide The preparation was carried out in a similar manner to Example 160, except that in step 2, ethylmagnesium bromide was used in place of methylmagnesium bromide, in step 3, 5-fluoro-4-bromopyridin-2-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.64 (s, 1H), 10.08 (s, 1H), 8.47 (s, 1H), 8.06 (d, J=5.6 Hz, 1H), 7.45-7.30 (m, 2H), 7.30-7.14 (m, 3H), 6.97 (dd, J=8.5, 2.7 Hz, 1H), 6.83 (d, J=2.7 Hz, 1H), 4.20 (s, 2H), 3.95 (t, J=6.5 Hz, 2H), 3.87 (s, 1H), 2.09 (s, 3H), 1.73-1.59 (m, 2H), 1.46-1.38 (m, 2H), 1.34 (q, J=7.4 Hz, 4H), 0.77 (t, J=7.4 Hz, 6H). MS: 550 $[M+H]^+$.

Example 242

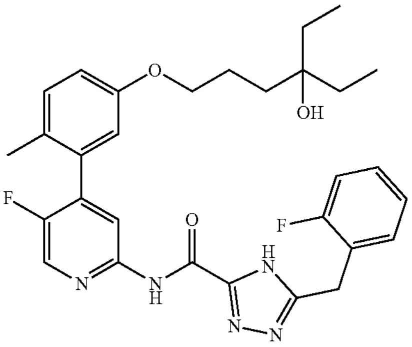

Example 243

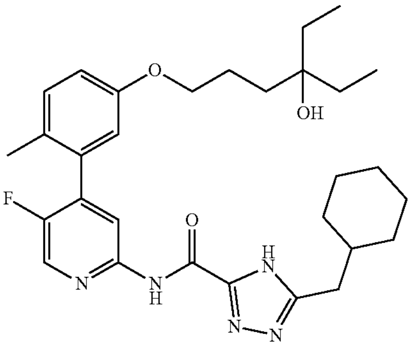

Example 244

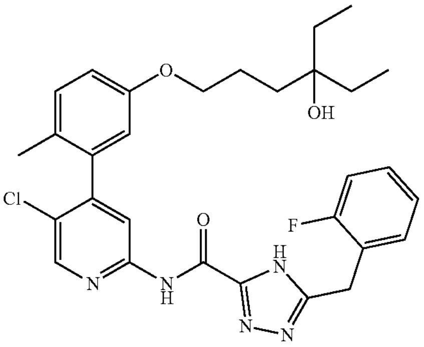

Example 245

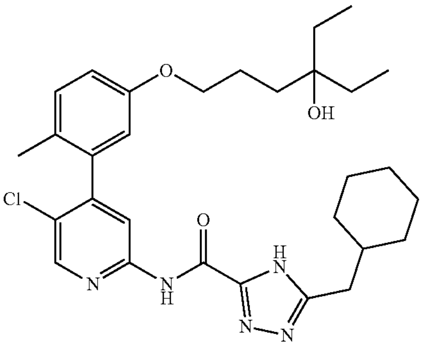

Example 243: 5-(cyclohexylmethyl)-N-(4-(5-((4-ethyl-4-hydroxyhexyl)oxy)-2-methylphenyl)-5-fluoropyridin-2-yl)-4H-1,2,4-triazole-3-carboxamide The preparation was carried out in a similar manner to Example 160, except that in step 2, ethylmagnesium bromide was used in place of methylmagnesium bromide, in step 3, 5-fluoro-4-bromopyridin-2-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-d$_6$) δ 14.38 (s, 1H), 10.02 (s, 1H), 8.48 (d, J=1.2 Hz, 1H), 8.09 (d, J=5.6 Hz, 1H), 7.27 (d, J=8.5 Hz, 1H), 6.97 (dd, J=8.4, 2.7 Hz, 1H), 6.84 (d, J=2.7 Hz, 1H), 3.96 (t, J=6.5 Hz, 2H), 3.87 (s, 1H), 2.66 (d, J=7.0 Hz, 2H), 2.10 (s, 3H), 1.81-1.55 (m, 8H), 1.46-1.38 (m, 2H), 1.34 (q, J=7.4 Hz, 4H), 1.26-1.06 (m, 3H), 1.03-0.90 (m, 2H), 0.77 (t, J=7.4 Hz, 6H). MS: 538 [M+H]$^+$.

Example 244: N-(5-chloro-4-(5-((4-ethyl-4-hydroxyhexyl)oxy)-2-methylphenyl)pyridin-2-yl)-5-(2-fluorobenzyl)-4H-1,2,4-triazole-3-carboxamide The preparation was carried out in a similar manner to Example 160, except that in step 2, ethylmagnesium bromide was used in place of methylmagnesium bromide, in step 3, 5-chloro-4-bromopyridin-2-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-d$_6$) δ 14.57 (s, 1H), 10.10 (s, 1H), 8.54 (s, 1H), 8.05 (s, 1H), 7.45-7.30 (m, 2H), 7.30-7.14 (m, 3H), 6.94 (dd, J=8.4, 2.7 Hz, 1H), 6.74 (d, J=2.7 Hz, 1H), 4.20 (s, 2H), 3.95 (t, J=6.5 Hz, 2H), 3.86 (s, 1H), 2.00 (s, 3H), 1.73-1.60 (m, 2H), 1.46-1.38 (m, 2H), 1.34 (q, J=7.4 Hz, 4H), 0.77 (t, J=7.4 Hz, 6H). MS: 566 [M+H]$^+$.

Example 245: N-(5-chloro-4-(5-((4-ethyl-4-hydroxyhexyl)oxy)-2-methylphenyl)pyridin-2-yl)-5-(cyclohexylmethyl)-4H-1,2,4-triazole-3-carboxamide The preparation was carried out in a similar manner to Example 160, except that in step 2, ethylmagnesium bromide was used in place of methylmagnesium bromide, in step 3, 5-chloro-4-bromopyridin-2-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-d$_6$) δ 14.37 (s, 1H), 10.03 (s, 1H), 8.55 (s, 1H), 8.08 (s, 1H), 7.26 (d, J=8.5 Hz, 1H), 6.95 (dd, J=8.5, 2.7 Hz, 1H), 6.74 (d, J=2.7 Hz, 1H), 3.95 (t, J=6.6 Hz, 2H), 3.87 (s, 1H), 2.71-2.62 (m, 2H), 2.01 (s, 3H), 1.81-1.71 (m, 1H), 1.71-1.56 (m, 7H), 1.46-1.38 (m, 2H), 1.34 (q, J=7.4 Hz, 4H), 1.29-1.14 (m, 3H), 1.03-0.90 (m, 2H), 0.77 (t, J=7.5 Hz, 6H). MS: 554 [M+H]$^+$.

Example 246: 5-(cyclohexylmethyl)-N-(4-(5-((4-ethyl-4-hydroxyhexyl)oxy)-2-methylphenyl)-5-methylpyridin-2-yl)-4H-1,2,4-triazole-3-carboxamide The preparation was carried out in a similar manner to Example 160, except that in step 2, ethylmagnesium bromide was used in place of methylmagnesium bromide, in step 3, 5-methyl-4-bromopyridin-2-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-d$_6$) δ 14.33 (s, 1H), 9.74 (s, 1H), 8.31 (s, 1H), 7.90 (s, 1H), 7.25 (d, J=8.5 Hz, 1H), 6.91 (dd, J=8.4, 2.7 Hz, 1H), 6.66 (d, J=2.7 Hz, 1H), 3.94 (t, J=6.5 Hz, 2H), 3.87 (s, 1H), 2.71-2.61 (m, 2H), 2.00 (s, 3H), 1.95 (s, 3H), 1.83-1.55 (m, 8H), 1.44-1.37 (m, 2H), 1.34 (q, J=7.4 Hz, 4H), 1.23-1.09 (m, 3H), 1.04-0.91 (m, 2H), 0.77 (t, J=7.4 Hz, 6H). MS: 534 [M+H]+.

Example 246

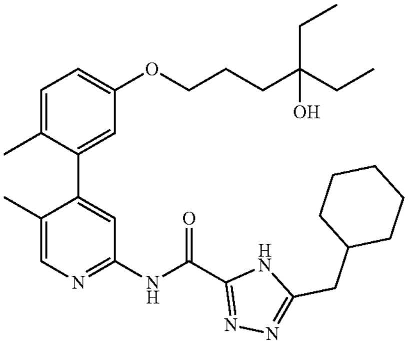

Example 247

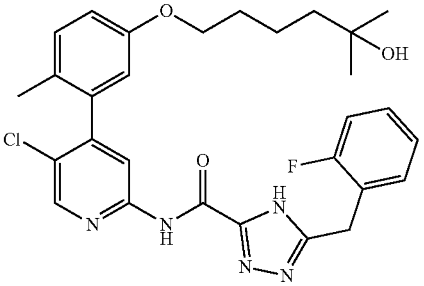

Example 247: N-(5-chloro-4-(5-((5-hydroxyl-5-methylhexyl)oxy)-2-methylphenyl)pyridin-2-yl)-5-(2-fluorobenzyl)-4H-1,2,4-triazole-3-carboxamide The preparation was carried out in a similar manner to Example 160, except that in step 1, methyl 5-bromopentanoate was used in place of methyl 4-bromobutanoate, in step 3, 5-chloro-4-bromopyridin-2-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.59 (s, 1H), 10.11 (s, 1H), 8.53 (s, 1H), 8.05 (s, 1H), 7.45-7.29 (m, 2H), 7.29-7.12 (m, 3H), 6.95 (d, J=9.0 Hz, 1H), 6.75 (d, J=2.7 Hz, 1H), 4.19 (s, 2H), 4.09 (s, 1H), 3.95 (t, J=6.5 Hz, 2H), 2.00 (s, 3H), 1.74-1.59 (m, 2H), 1.51-1.37 (m, 4H), 1.06 (s, 6H). MS: 552 [M+H]+.

Example 248: 5-(cyclohexylmethyl)-N-(5-chloro-4-(5-((5-hydroxyl-5-methylhexyl)oxy)-2-methylphenyl)pyridin-2-yl)-4H-1,2,4-triazole-3-carboxamide The preparation was carried out in a similar manner to Example 160, except that in step 1, methyl 5-bromopentanoate was used in place of methyl 4-bromobutanoate, in step 3, 5-chloro-4-bromopyridin-2-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.37 (s, 1H), 10.04 (s, 1H), 8.55 (s, 1H), 8.08 (s, 1H), 7.26 (d, J=8.5 Hz, 1H), 6.96 (dd, J=8.4, 2.7 Hz, 1H), 6.76 (d, J=2.7 Hz, 1H), 4.09 (s, 1H), 3.96 (t, J=6.5 Hz, 2H), 2.66 (d, J=6.9 Hz, 2H), 2.01 (s, 3H), 1.65 (dd, J=13.9, 9.1 Hz, 8H), 1.49-1.35 (m, 4H), 1.22-1.10 (m, 3H), 1.06 (s, 6H), 1.04-0.94 (m, 2H). MS: 540 [M+H]+.

Example 248

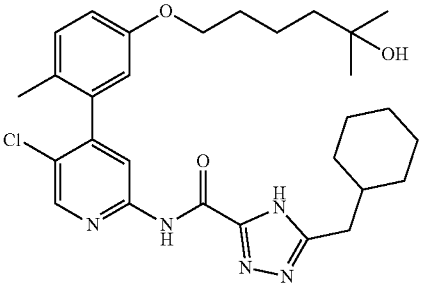

Example 249

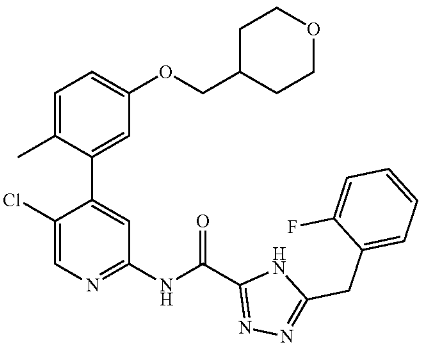

Example 249: N-(5-chloro-4-(2-methyl-5-((tetrahydro-2H-pyran-4-yl)methoxy)phenyl)pyridin-2-yl)-5-(2-fluorobenzyl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, in step 2, 5-chloro-4-bromopyridin-2-amine was used in place of 4-bromopyridin-2-amine, and in step 3, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.60 (s, 1H), 10.05 (s, 1H), 8.53 (s, 1H), 8.06 (s, 1H), 7.47-7.29 (m, 2H), 7.29-7.11 (m, 3H), 6.96 (dd, J=8.5, 2.8 Hz, 1H), 6.76 (d, J=2.7 Hz, 1H), 4.23 (s, 2H), 3.92-3.78 (m, 4H), 3.32-3.26 (m, 2H), 2.01 (s, 3H), 1.99-1.92 (m, 1H), 1.73-1.59 (m, 2H), 1.37-1.26 (m, 2H). MS: 536 [M+H]+.

Example 250: N-(5-chloro-4-(2-methyl-5-((tetrahydro-2H-pyran-4-yl)methoxy)phenyl)pyridin-2-yl)-5-(cyclohexylmethyl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, in step 2, 5-chloro-4-bromopyridin-2-amine was used in place of 4-bromopyridin-2-amine, and in step 3, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.41 (s, 1H), 10.07 (s, 1H), 8.55 (s, 1H), 8.08 (s, 1H), 7.26 (d, J=8.5 Hz, 1H), 6.97 (dd, J=8.5, 2.7 Hz, 1H), 6.77 (d, J=2.7 Hz, 1H), 3.92-3.77 (m, 4H), 2.66 (d, J=7.1 Hz, 2H), 2.02 (s, 3H), 1.97 (dd, J=9.5, 5.2 Hz, 1H), 1.82-1.56 (m, 8H), 1.39-1.13 (m, 7H), 1.04-0.91 (m, 2H). MS: 524 [M+H]+.

Example 250

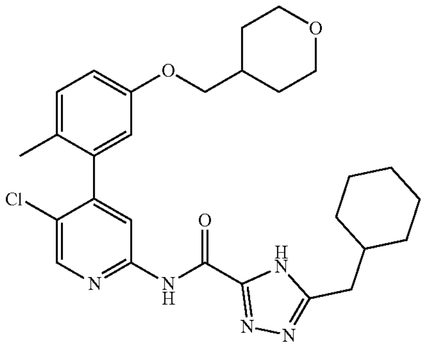

Example 251

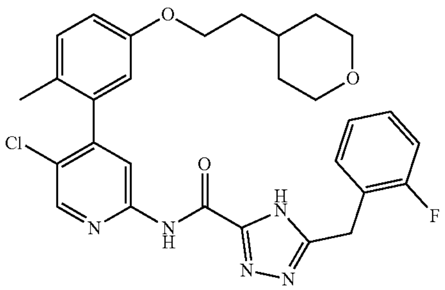

Example 251: N-(5-chloro-4-(2-methyl-5-(2-(tetrahydro-2H-pyran-4-yl)ethoxy)phenyl)pyridin-2-yl)-5-(2-fluorobenzyl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, in step 3, 5-chloro-4-bromopyridin-2-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.66 (s, 1H), 10.12 (s, 1H), 8.54 (s, 1H), 8.05 (s, 1H), 7.44-7.29 (m, 2H), 7.28-7.15 (m, 3H), 6.96 (dd, J=8.4, 2.7 Hz, 1H), 6.77 (d, J=2.7 Hz, 1H), 4.20 (s, 2H), 4.00 (t, J=6.3 Hz, 2H), 3.87-3.75 (m, 2H), 3.31-3.21 (m, 2H), 2.00 (s, 3H), 1.76-1.55 (m, 5H), 1.27-1.11 (m, 2H). MS: 550 $[M+H]^+$.

Example 252: N-(5-chloro-4-(2-methyl-5-(2-(tetrahydro-2H-pyran-4-yl)ethoxy)phenyl)pyridin-2-yl)-5-(cyclohexylmethyl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, in step 3, 5-chloro-4-bromopyridin-2-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.39 (s, 1H), 10.06 (s, 1H), 8.55 (s, 1H), 8.08 (s, 1H), 7.26 (d, J=8.5 Hz, 1H), 6.96 (dd, J=8.4, 2.7 Hz, 1H), 6.77 (d, J=2.7 Hz, 1H), 4.01 (t, J=6.3 Hz, 2H), 3.86-3.76 (m, 2H), 3.30-3.20 (m, 2H), 2.71-2.61 (m, 2H), 2.01 (s, 3H), 1.82-1.55 (m, 11H), 1.29-1.08 (m, 5H), 1.05-0.89 (m, 2H). MS: 538 $[M+H]^+$.

Example 252

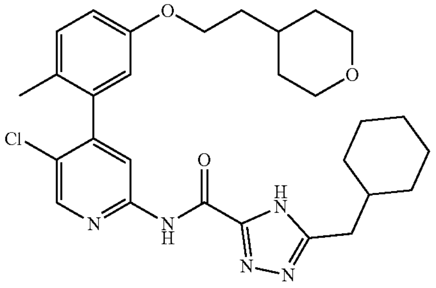

Example 253

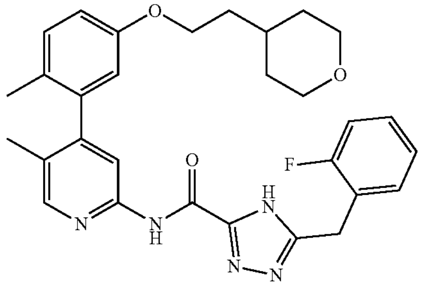

Example 253: 5-(2-fluorobenzyl)-N-(5-methyl-4-(2-methyl-5-(2-(tetrahydro-2H-pyran-4-yl)ethoxy)phenyl)pyridin-2-yl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, in step 3, 5-methyl-4-bromopyridin-2-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.59 (s, 1H), 9.76 (s, 1H), 8.30 (s, 1H), 7.87 (s, 1H), 7.46-7.28 (m, 2H), 7.28-7.12 (m, 3H), 6.91 (dd, J=8.4, 2.7 Hz, 1H), 6.68 (d, J=2.7 Hz, 1H), 4.20 (s, 2H), 3.99 (t, J=6.3 Hz, 2H), 3.86-3.75 (m, 2H), 3.30-3.19 (m, 2H), 1.99 (s, 3H), 1.94 (s, 3H), 1.72-1.54 (m, 5H), 1.25-1.17 (m, 2H). MS: 530 $[M+H]^+$.

Example 254: 5-(cyclohexylmethyl)-N-(5-methyl-4-(2-methyl-5-(2-(tetrahydro-2H-pyran-4-yl)ethoxy)phenyl)pyridin-2-yl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, in step 3, 5-methyl-4-bromopyridin-2-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.34 (s, 1H), 9.74 (s, 1H), 8.31 (s, 1H), 7.91 (s, 1H), 7.24 (d, J=8.5 Hz, 1H), 6.92 (dd, J=8.5, 2.7 Hz, 1H), 6.69 (d, J=2.7 Hz, 1H), 4.00 (t, J=6.3 Hz, 2H), 3.81 (dd, J=11.8, 4.3 Hz, 2H), 3.26 (t, J=11.6 Hz, 2H), 2.66 (d, J=7.1 Hz, 2H), 2.00 (s, 3H), 1.95 (s, 3H), 1.81-1.52 (m, 11H), 1.25-1.10 (m, 5H), 1.05-0.87 (m, 2H). MS: 518 $[M+H]^+$.

Example 254

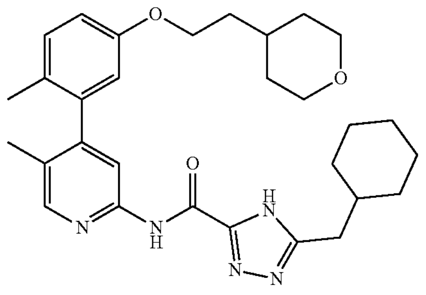

Example 255

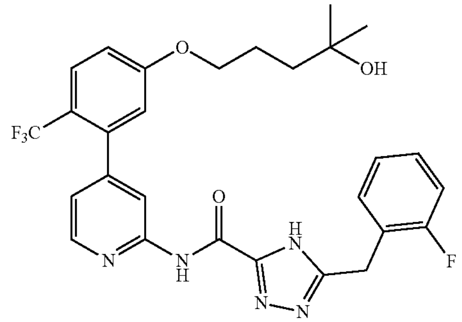

Example 255: 5-(2-fluorobenzyl)-N-(4-(5-((4-hydroxy-4-methylpentyl)oxy)-2-(trifluoromethyl)phenyl)pyridin-2-yl)-4H-1,2,4-triazole-3-carboxamide The preparation was carried out in a similar manner to Example 160, except that in step 1, 3-chloro-4-(trifluoromethyl)phenol was used in place of 3-bromo-4-methylphenol, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.66 (s, 1H), 9.94 (s, 1H), 8.43 (d, J=5.1 Hz, 1H), 8.15 (s, 1H), 7.79 (d, J=8.9 Hz, 1H), 7.45-7.29 (m, 2H), 7.26-7.12 (m, 4H), 6.96 (d, J=2.6 Hz, 1H), 4.31-4.14 (m, 3H), 4.09 (t, J=6.6 Hz, 2H), 1.86-1.67 (m, 2H), 1.53-1.39 (m, 2H), 1.09 (s, 6H). MS: 558 $[M+H]^+$.

Example 256: 5-(3-fluorobenzyl)-N-(4-(5-((4-hydroxy-4-methylpentyl)oxy)-2-(trifluoromethyl)phenyl)pyridin-2-yl)-4H-1,2,4-triazole-3-carboxamide The preparation was carried out in a similar manner to Example 160, except that in step 1, 3-chloro-4-(trifluoromethyl)phenol was used in place of 3-bromo-4-methylphenol, and in step 4, ethyl 5-(3-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.62 (s, 1H), 10.00 (s, 1H), 8.44 (d, J=5.1 Hz, 1H), 8.16 (s, 1H), 7.79 (d, J=8.8 Hz, 1H), 7.44-7.33 (m, 1H), 7.24-7.05 (m, 5H), 6.97 (d, J=2.5 Hz, 1H), 4.20 (d, J=6.3 Hz, 3H), 4.09 (t, J=6.6 Hz, 2H), 1.84-1.69 (m, 2H), 1.55-1.42 (m, 2H), 1.09 (s, 6H). MS: 558 $[M+H]^+$.

Example 256

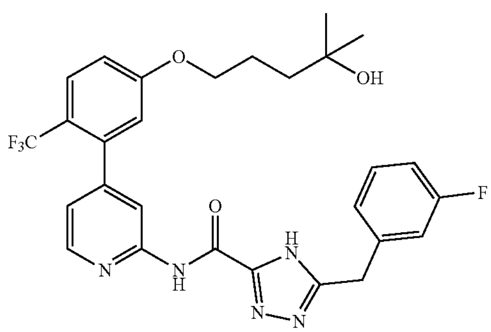

Example 257

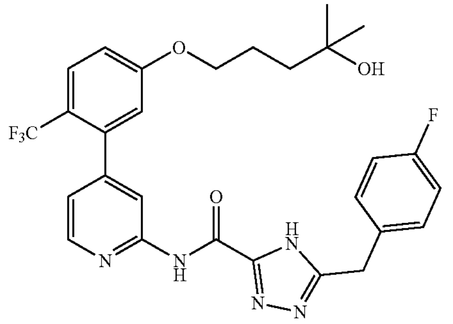

Example 257: 5-(4-fluorobenzyl)-N-(4-(5-((4-hydroxy-4-methylpentyl)oxy)-2-(trifluoromethyl)phenyl)pyridin-2-yl)-4H-1,2,4-triazole-3-carboxamide The preparation was carried out in a similar manner to Example 160, except that in step 1, 3-chloro-4-(trifluoromethyl)phenol was used in place of 3-bromo-4-methylphenol, and in step 4, ethyl 5-(4-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.61 (s, 1H), 9.97 (s, 1H), 8.43 (dd, J=5.1, 0.8 Hz, 1H), 8.16 (s, 1H), 7.79 (d, J=8.9 Hz, 1H), 7.43-7.32 (m, 2H), 7.23-7.11 (m, 4H), 6.97 (d, J=2.5 Hz, 1H), 4.31-4.13 (m, 3H), 4.09 (t, J=6.5 Hz, 2H), 1.86-1.69 (m, 2H), 1.54-1.41 (m, 2H), 1.09 (s, 6H). MS: 558 $[M+H]^+$.

Example 258: 5-(cyclopentylmethyl)-N-(4-(5-((4-hydroxy-4-methylpentyl)oxy)-2-(trifluoromethyl)phenyl)pyridin-2-yl)-4H-1,2,4-triazole-3-carboxamide The preparation was carried out in a similar manner to Example 160, except that in step 1, 3-chloro-4-(trifluoromethyl)phenol was used in place of 3-bromo-4-methylphenol, and in step 4, ethyl 5-(cyclopentylmethyl)-4H-1,2,4-triazole-3-carboxylate was used in place of ethyl 5-benzyl-4H-1,2,4-triazol-3-carboxylate. $^1$H NMR (400 MHz, DMSO-$d_6$) δ 14.39 (s, 1H), 9.90 (s, 1H), 8.44 (d, J=5.1 Hz, 1H), 8.17 (s, 1H), 7.79 (d, J=8.9 Hz, 1H), 7.26-7.13 (m, 2H), 6.97 (d, J=2.6 Hz, 1H), 4.20 (s, 1H), 4.09 (t, J=6.5 Hz, 2H), 2.78 (d, J=7.4 Hz, 2H), 2.37-2.19 (m, 1H), 1.85-1.66 (m, 4H), 1.66-1.56 (m, 2H), 1.56-1.41 (m, 4H), 1.26-1.20 (m, 2H), 1.09 (s, 6H). MS: 532 $[M+H]^+$.

Example 258

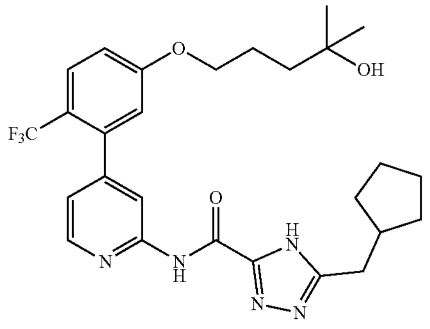

Example 259

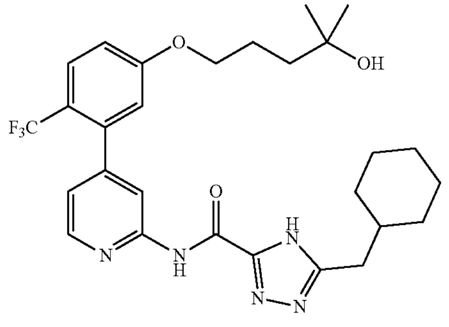

Example 259: 5-(cyclohexylmethyl)-N-(4-(5-((4-hydroxy-4-methylpentyl)oxy)-2-(trifluoromethyl)phenyl)pyridin-2-yl)-4H-1,2,4-triazole-3-carboxamide The preparation was carried out in a similar manner to Example 160, except that in step 1, 3-chloro-4-(trifluoromethyl)phenol was used in place of 3-bromo-4-methylphenol, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.37 (s, 1H), 9.89 (s, 1H), 8.44 (d, J=5.1 Hz, 1H), 8.17 (s, 1H), 7.79 (d, J=8.9 Hz, 1H), 7.28-7.12 (m, 2H), 6.97 (d, J=2.6 Hz, 1H), 4.19 (s, 1H), 4.09 (t, J=6.6 Hz, 2H), 2.67 (d, J=7.0 Hz, 2H), 1.82-1.55 (m, 8H), 1.52-1.43 (m, 2H), 1.27-1.13 (m, 3H), 1.10 (s, 6H), 1.05-0.88 (m, 2H). MS: 546 $[M+H]^+$.

Example 260: 5-benzyl-N-(4-(5-((4-ethyl-4-hydroxyhexyl)oxy)-2-(trifluoromethyl)phenyl)pyridin-2-yl)-4H-1,2,4-triazole-3-carboxamide The preparation was carried out in a similar manner to Example 160, except that in step 1, 3-chloro-4-(trifluoromethyl)phenol was used in place of 3-bromo-4-methylphenol, and in step 2, ethylmagnesium bromide was used in place of methylmagnesium bromide. $^1$H NMR (400 MHz, DMSO-$d_6$) δ 14.61 (s, 1H), 9.95 (s, 1H), 8.51-8.36 (m, 1H), 8.15 (s, 1H), 7.79 (d, J=8.9 Hz, 1H), 7.43-7.29 (m, 4H), 7.29-7.22 (m, 1H), 7.22-7.11 (m, 2H), 6.96 (d, J=2.5 Hz, 1H), 4.17 (s, 2H), 4.08 (t, J=6.5 Hz, 2H), 3.89 (s, 1H), 1.78-1.63 (m, 2H), 1.49-1.38 (m, 2H), 1.34 (q, J=7.5 Hz, 4H), 0.77 (t, J=7.5 Hz, 6H). MS: 568 $[M+H]^+$.

Example 260

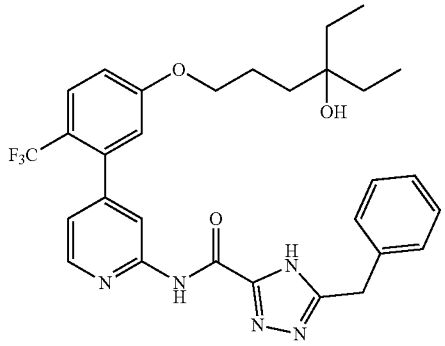

Example 261

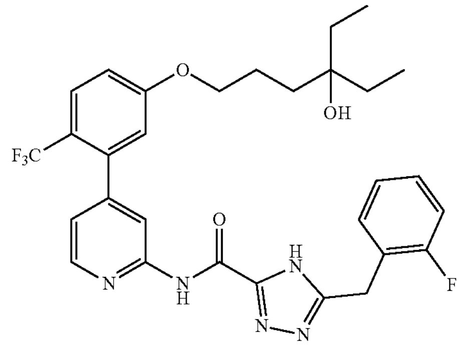

Example 261: 5-(2-fluorobenzyl)-N-(4-(5-((4-ethyl-4-hydroxyhexyl)oxy)-2-(trifluoromethyl)phenyl)pyridin-2-yl)-4H-1,2,4-triazole-3-carboxamide The preparation was carried out in a similar manner to Example 160, except that in step 1, 3-chloro-4-(trifluoromethyl)phenol was used in place of 3-bromo-4-methylphenol, in step 2, ethylmagnesium bromide was used in place of methylmagnesium bromide, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.64 (s, 1H), 9.88 (d, J=46.2 Hz, 1H), 8.42 (dd, J=12.1, 5.2 Hz, 1H), 8.15 (s, 1H), 7.80 (dd, J=8.7, 4.7 Hz, 1H), 7.48-7.32 (m, 3H), 7.22-7.15 (m, 3H), 6.96 (d, J=2.6 Hz, 1H), 4.21 (s, 2H), 4.16-4.04 (m, 2H), 3.89 (s, 1H), 1.77-1.60 (m, 2H), 1.48-1.39 (m, 2H), 1.35 (q, J=7.5 Hz, 4H), 0.78 (t, J=7.4 Hz, 6H). MS: 586 $[M+H]^+$.

Example 262: 5-(cyclopentylmethyl)-N-(4-(5-((4-ethyl-4-hydroxyhexyl)oxy)-2-(trifluoromethyl)phenyl)pyridin-2-yl)-4H-1,2,4-triazole-3-carboxamide The preparation was carried out in a similar manner to Example 160, except that in step 1, 3-chloro-4-(trifluoromethyl)phenol was used in place of 3-bromo-4-methylphenol, in step 2, ethylmagnesium bromide was used in place of methylmagnesium bromide, and in step 4, ethyl 5-(cyclopentylmethyl)-4H-1,2,4-triazole-3-carboxylate was used in place of ethyl 5-benzyl-4H-1,2,4-triazol-3-carboxylate. $^1$H NMR (400 MHz, DMSO-$d_6$) δ 14.38 (s, 1H), 9.89 (s, 1H), 8.44 (d, J=5.1 Hz, 1H), 8.17 (s, 1H), 7.79 (d, J=8.9 Hz, 1H), 7.26-7.11 (m, 2H), 6.97 (d, J=2.5 Hz, 1H), 4.09 (t, J=6.5 Hz, 2H), 3.89 (s, 1H), 2.78 (d, J=7.5 Hz, 2H), 2.36-2.18 (m, 1H), 1.79-1.66 (m, 4H), 1.66-1.47 (m, 4H), 1.47-1.39 (m, 2H), 1.35 (q, J=7.5 Hz, 4H), 1.29-1.21 (m, 2H), 0.77 (t, J=7.4 Hz, 6H). MS: 560 $[M+H]^+$.

Example 262

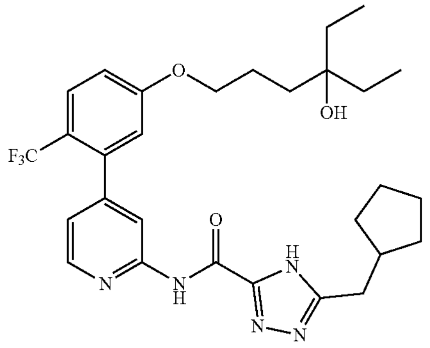

Example 263

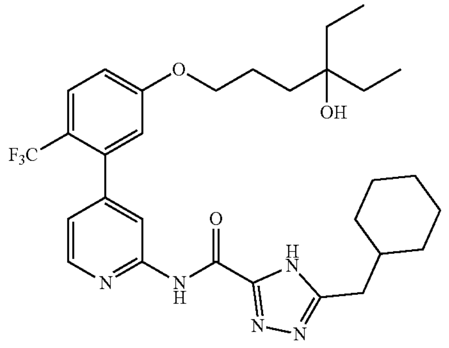

Example 263: 5-(cyclohexylmethyl)-N-(4-(5-((4-ethyl-4-hydroxyhexyl)oxy)-2-(trifluoromethyl)phenyl)pyridin-2-yl)-4H-1,2,4-triazole-3-carboxamide The preparation was carried out in a similar manner to Example 160, except that in step 1, 3-chloro-4-(trifluoromethyl)phenol was used in place of 3-bromo-4-methylphenol, in step 2, ethylmagnesium bromide was used in place of methylmagnesium bromide, and in step 4, ethyl 5-(cyclohexylmethyl)-4H-1,2,4-triazol-3-carboxylate was used in place of ethyl 5-benzyl-4H-1,2,4-triazol-3-carboxylate. $^{1}$H NMR (400 MHz, DMSO-$d_6$) δ 14.37 (s, 1H), 9.89 (s, 1H), 8.44 (d, J=5.1 Hz, 1H), 8.17 (s, 1H), 7.79 (d, J=8.9 Hz, 1H), 7.28-7.13 (m, 2H), 6.97 (d, J=2.6 Hz, 1H), 4.09 (t, J=6.5 Hz, 2H), 3.89 (s, 1H), 2.67 (d, J=7.0 Hz, 2H), 1.83-1.56 (m, 8H), 1.51-1.39 (m, 2H), 1.35 (q, J=7.5 Hz, 4H), 1.27-1.09 (m, 3H), 1.06-0.89 (m, 2H), 0.77 (t, J=7.5 Hz, 6H). MS: 574 $[M+H]^+$.

Example 264: 5-benzyl-N-(4-(5-(2-hydroxyl-2-methylpropoxy)-2-(trifluoromethyl)phenyl)pyridin-2-yl)-4H-1,2,4-triazole-3-carboxamide The preparation was carried out in a similar manner to Example 160, except that in step 1, 3-chloro-4-(trifluoromethyl)phenol was used in place of 3-bromo-4-methylphenol, and methyl bromoacetate was used in place of methyl 4-bromobutanoate. $^{1}$H NMR (400 MHz, DMSO-$d_6$) δ 14.66 (s, 1H), 9.96 (s, 1H), 8.43 (d, J=5.1 Hz, 1H), 8.16 (s, 1H), 7.79 (d, J=8.8 Hz, 1H), 7.41-7.29 (m, 4H), 7.29-7.13 (m, 3H), 6.99 (d, J=2.6 Hz, 1H), 4.69 (s, 1H), 4.17 (s, 2H), 3.85 (s, 2H), 1.20 (s, 6H). MS: 512 $[M+H]^+$.

Example 264

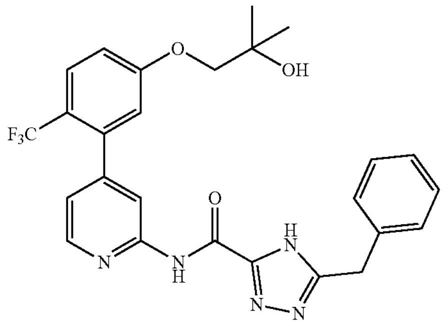

Example 265

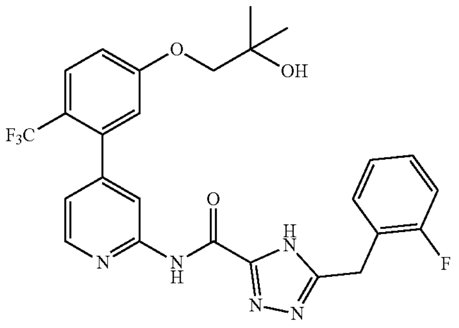

Example 265: 5-(2-fluorobenzyl)-N-(4-(5-(2-hydroxyl-2-methylpropoxy)-2-(trifluoromethyl)phenyl)pyridin-2-yl)-4H-1,2,4-triazole-3-carboxamide The preparation was carried out in a similar manner to Example 160, except that in step 1, 3-chloro-4-(trifluoromethyl)phenol was used in place of 3-bromo-4-methylphenol, methyl bromoacetate was used in place of methyl 4-bromobutanoate, and in step 4, ethyl 5-(2-fluorobenzyl)-4H-1,2,4-triazol-3-carboxylate was used in place of ethyl 5-benzyl-4H-1,2,4-triazol-3-carboxylate. $^{1}$H NMR (400 MHz, DMSO-$d_6$) δ 14.69 (s, 1H), 9.95 (s, 1H), 8.43 (d, J=5.1 Hz, 1H), 8.15 (s, 1H), 7.79 (d, J=8.9 Hz, 1H), 7.48-7.29 (m, 2H), 7.29-7.13 (m, 4H), 6.99 (d, J=2.6 Hz, 1H), 4.68 (s, 1H), 4.20 (s, 2H), 3.85 (s, 2H), 1.20 (s, 6H). MS: 530 $[M+H]^+$.

Example 266: 5-(cyclopentylmethyl)-N-(4-(5-(2-hydroxyl-2-methylpropoxy)-2-(trifluoromethyl)phenyl)pyridin-2-yl)-4H-1,2,4-triazole-3-carboxamide The preparation was carried out in a similar manner to Example 160, except that in step 1, 3-chloro-4-(trifluoromethyl)phenol was used in place of 3-bromo-4-methylphenol, methyl bromoacetate was used in place of methyl 4-bromobutanoate, and in step 4, ethyl 5-(cyclopentylmethyl)-4H-1,2,4-triazole-3-carboxylate was used in place of ethyl 5-benzyl-4H-1,2,4-triazol-3-carboxylate. $^{1}$H NMR (400 MHz, DMSO-$d_6$) δ 14.40 (s, 1H), 9.91 (s, 1H), 8.44 (d, J=5.1 Hz, 1H), 8.18 (s, 1H), 7.79 (d, J=8.9 Hz, 1H), 7.27-7.14 (m, 2H), 7.00 (d, J=2.6 Hz, 1H), 4.69 (s, 1H), 3.85 (s, 2H), 2.77 (d, J=7.5 Hz, 2H), 2.34-2.20 (m, 1H), 1.79-1.66 (m, 2H), 1.66-1.56 (m, 2H), 1.56-1.43 (m, 2H), 1.23-1.14 (m, 8H). MS: 504 $[M+H]^+$.

Example 266

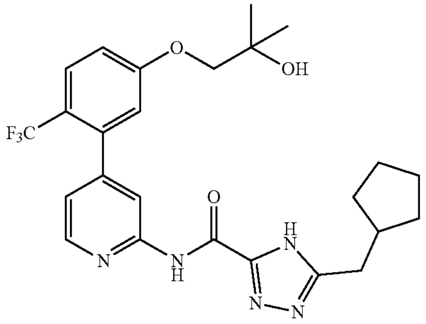

Example 267

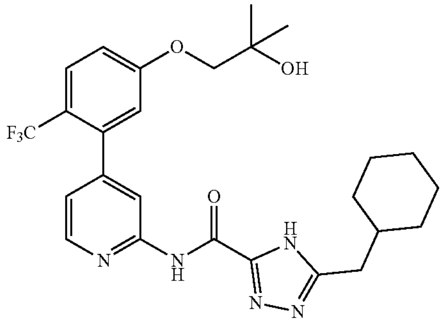

Example 267: 5-(cyclohexylmethyl)-N-(4-(5-(2-hydroxyl-2-methylpropoxy)-2-(trifluoromethyl)phenyl)pyridin-2-yl)-4H-1,2,4-triazole-3-carboxamide The preparation was carried out in a similar manner to Example 160, except that in step 1, 3-chloro-4-(trifluoromethyl)phenol was used in place of 3-bromo-4-methylphenol, methyl bromoacetate was used in place of methyl 4-bromobutanoate, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.41 (s, 1H), 9.91 (s, 1H), 8.49-8.38 (m, 1H), 8.17 (d, J=1.4 Hz, 1H), 7.79 (d, J=8.9 Hz, 1H), 7.29-7.11 (m, 2H), 7.00 (d, J=2.6 Hz, 1H), 4.69 (s, 1H), 3.85 (s, 2H), 2.66 (d, J=7.1 Hz, 2H), 1.85-1.52 (m, 6H), 1.30-1.07 (m, 9H), 1.07-0.90 (m, 2H). MS: 518 [M+H]$^+$.

Example 268: 5-benzyl-N-(4-(5-((5-hydroxyl-5-methylhexyl)oxy)-2-(trifluoromethyl)phenyl)pyridin-2-yl)-4H-1,2,4-triazole-3-carboxamide The preparation was carried out in a similar manner to Example 160, except that in step 1, 3-chloro-4-(trifluoromethyl)phenol was used in place of 3-bromo-4-methylphenol, and methyl 5-bromopentanoate was used in place of methyl 4-bromobutanoate. $^1$H NMR (400 MHz, DMSO-$d_6$) δ 14.62 (s, 1H), 9.95 (s, 1H), 8.43 (dd, J=5.1, 0.8 Hz, 1H), 8.16 (s, 1H), 7.78 (d, J=8.9 Hz, 1H), 7.44-7.29 (m, 4H), 7.29-7.22 (m, 1H), 7.22-7.10 (m, 2H), 6.98 (d, J=2.6 Hz, 1H), 4.17 (s, 2H), 4.14-4.00 (m, 3H), 1.71 (t, J=6.9 Hz, 2H), 1.51-1.32 (m, 4H), 1.06 (s, 6H). MS: 554 [M+H]$^+$.

Example 268

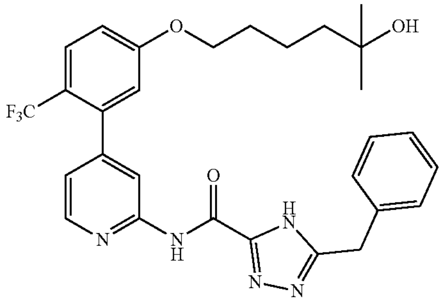

Example 269

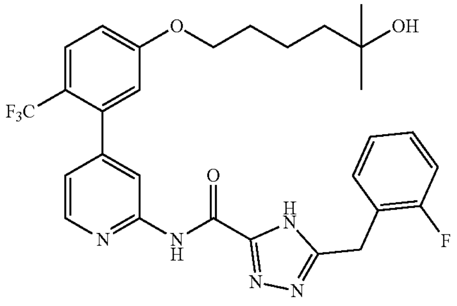

Example 269: 5-(2-fluorobenzyl)-N-(4-(5-((5-hydroxyl-5-methylhexyl)oxy)-2-(trifluoromethyl)phenyl)pyridin-2-yl)-4H-1,2,4-triazole-3-carboxamide The preparation was carried out in a similar manner to Example 160, except that in step 1, 3-chloro-4-(trifluoromethyl)phenol was used in place of 3-bromo-4-methylphenol, methyl 5-bromopentanoate was used in place of methyl 4-bromobutanoate, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.65 (s, 1H), 9.93 (s, 1H), 8.43 (d, J=5.1 Hz, 1H), 8.15 (s, 1H), 7.78 (d, J=8.9 Hz, 1H), 7.46-7.28 (m, 2H), 7.28-7.12 (m, 4H), 6.97 (d, J=2.5 Hz, 1H), 4.21 (s, 2H), 4.15-4.02 (m, 3H), 1.71 (t, J=7.0 Hz, 2H), 1.52-1.34 (m, 4H), 1.06 (s, 6H). MS: 572 [M+H]$^+$.

Example 270: 5-(cyclopentylmethyl)-N-(4-(5-((5-hydroxyl-5-methylhexyl)oxy)-2-(trifluoromethyl)phenyl)pyridin-2-yl)-4H-1,2,4-triazole-3-carboxamide The preparation was carried out in a similar manner to Example 160, except that in step 1, 3-chloro-4-(trifluoromethyl)phenol was used in place of 3-bromo-4-methylphenol, methyl 5-bromopentanoate was used in place of methyl 4-bromobutanoate, and in step 4, ethyl 5-(cyclopentylmethyl)-4H-1,2,4-triazole-3-carboxylate was used in place of ethyl 5-benzyl-4H-1,2,4-triazol-3-carboxylate. $^1$H NMR (400 MHz, DMSO-$d_6$) δ 14.41 (s, 1H), 9.90 (s, 1H), 8.44 (dd, J=5.1, 0.8 Hz, 1H), 8.17 (s, 1H), 7.79 (d, J=8.9 Hz, 1H), 7.27-7.13 (m, 2H), 6.98 (d, J=2.5 Hz, 1H), 4.17-4.01 (m, 3H), 2.78 (d, J=7.4 Hz, 2H), 2.35-2.19 (m, 1H), 1.81-1.66 (m, 4H), 1.66-1.33 (m, 8H), 1.29-1.15 (m, 2H), 1.06 (s, 6H). MS: 546 [M+H]$^+$.

Example 270

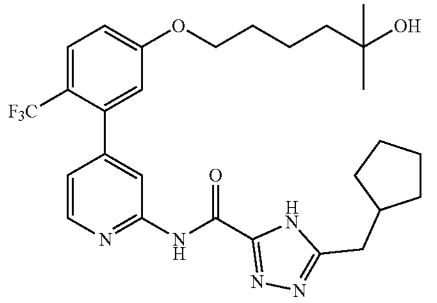

Example 271

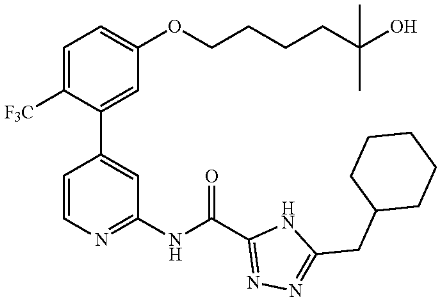

Example 271: 5-(cyclohexylmethyl)-N-(4-(5-((5-hydroxyl-5-methylhexyl)oxy)-2-(trifluoromethyl) phenyl)pyridin-2-yl)-4H-1,2,4-triazole-3-carboxamide The preparation was carried out in a similar manner to Example 160, except that in step 1, 3-chloro-4-(trifluoromethyl)phenol was used in place of 3-bromo-4-methylphenol, methyl 5-bromopentanoate was used in place of methyl 4-bromobutanoate, and in step 4, ethyl 5-(cyclohexylmethyl)-4H-1,2,4-triazol-3-carboxylate was used in place of ethyl 5-benzyl-4H-1,2,4-triazol-3-carboxylate. $^{1}$H NMR (400 MHz, DMSO-$d_6$) δ 14.38 (s, 1H), 9.90 (s, 1H), 8.43 (dd, J=5.1, 0.8 Hz, 1H), 8.17 (s, 1H), 7.79 (d, J=8.9 Hz, 1H), 7.27-7.12 (m, 2H), 6.98 (d, J=2.5 Hz, 1H), 4.17-4.01 (m, 3H), 2.66 (d, J=7.1 Hz, 2H), 1.86-1.55 (m, 8H), 1.51-1.33 (m, 4H), 1.28-1.09 (m, 3H), 1.06 (s, 6H), 1.04-0.89 (m, 2H). MS: 560 $[M+H]^+$.

Example 272: 5-benzyl-N-(4-(5-(4-hydroxybutoxy)-2-(trifluoromethyl)phenyl)pyridin-2-yl)-4H-1,2,4-triazole-3-carboxamide The preparation was carried out in a similar manner to Example 92, except that in step 1, 4-bromo-1-butanol was used in place of iodomethane, and 3-chloro-4-(trifluoromethyl)phenol was used in place of 2-bromo-3-methylphenol. $^{1}$H NMR (400 MHz, DMSO-$d_6$) δ 14.59 (s, 1H), 9.95 (s, 1H), 8.43 (d, J=5.1 Hz, 1H), 8.15 (s, 1H), 7.79 (d, J=8.9 Hz, 1H), 7.39-7.29 (m, 4H), 7.29-7.22 (m, 1H), 7.22-7.14 (m, 2H), 6.98 (d, J=2.6 Hz, 1H), 4.45 (t, J=5.1 Hz, 1H), 4.17 (s, 2H), 4.11 (t, J=6.5 Hz, 2H), 3.48-3.41 (m, 2H), 1.82-1.69 (m, 2H), 1.61-1.49 (m, 2H). MS: 512 $[M+H]^+$.

Example 272

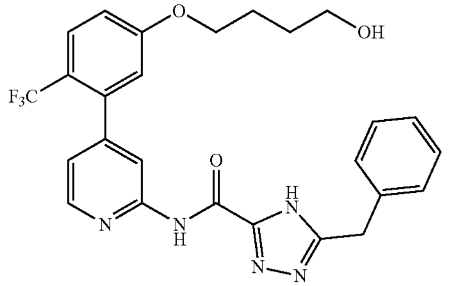

Example 273

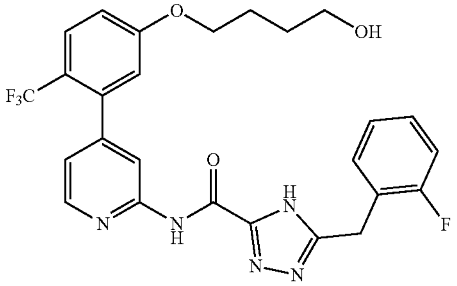

Example 273: 5-(2-fluorobenzyl)-N-(4-(5-(4-hydroxybutoxy)-2-(trifluoromethyl)phenyl)pyridin-2-yl)-4H-1,2,4-triazole-3-carboxamide The preparation was carried out in a similar manner to Example 92, except that in step 1, 4-bromo-1-butanol was used in place of iodomethane, 3-chloro-4-(trifluoromethyl) phenol was used in place of 2-bromo-3-methylphenol, and in step 3, ethyl 5-(2-fluorobenzyl)-4H-1,2,4-triazol-3-carboxylate was used in place of ethyl 5-benzyl-4H-1,2,4-triazol-3-carboxylate. $^{1}$H NMR (400 MHz, DMSO-$d_6$) δ 14.63 (s, 1H), 9.93 (s, 1H), 8.43 (d, J=5.1 Hz, 1H), 8.15 (s, 1H), 7.79 (d, J=8.9 Hz, 1H), 7.44-7.29 (m, 2H), 7.26-7.14 (m, 4H), 6.97 (d, J=2.5 Hz, 1H), 4.45 (t, J=5.1 Hz, 1H), 4.21 (s, 2H), 4.10 (t, J=6.5 Hz, 2H), 3.48-3.40 (m, 2H), 1.81-1.70 (m, 2H), 1.61-1.50 (m, 2H). MS: 530 $[M+H]^+$.

Example 274: 5-(cyclopentylmethyl)-N-(4-(5-(4-hydroxybutoxy)-2-(trifluoromethyl)phenyl)pyridin-2-yl)-4H-1,2,4-triazole-3-carboxamide The preparation was carried out in a similar manner to Example 92, except that in step 1, 4-bromo-1-butanol was used in place of iodomethane, 3-chloro-4-(trifluoromethyl) phenol was used in place of 2-bromo-3-methylphenol, and in step 3, ethyl 5-(cyclopentylmethyl)-4H-1,2,4-triazol-3-carboxylate was used in place of ethyl 5-benzyl-4H-1,2,4-triazol-3-carboxylate. $^{1}$H NMR (400 MHz, DMSO-$d_6$) δ 14.39 (s, 1H), 9.90 (s, 1H), 8.44 (d, J=5.1 Hz, 1H), 8.17 (s, 1H), 7.79 (d, J=8.9 Hz, 1H), 7.23-7.15 (m, 2H), 6.98 (d, J=2.6 Hz, 1H), 4.45 (t, J=5.2 Hz, 1H), 4.11 (t, J=6.6 Hz, 2H), 3.49-3.39 (m, 2H), 2.77 (d, J=7.5 Hz, 2H), 2.37-2.19 (m, 1H), 1.83-1.67 (m, 4H), 1.67-1.45 (m, 6H), 1.30-1.14 (m, 2H). MS: 504 $[M+H]^+$.

Example 274

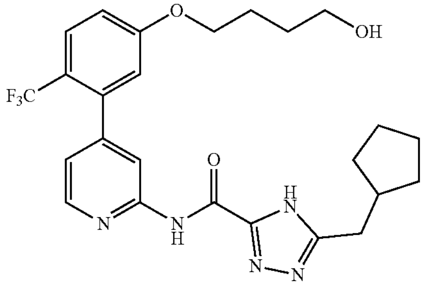

Example 275

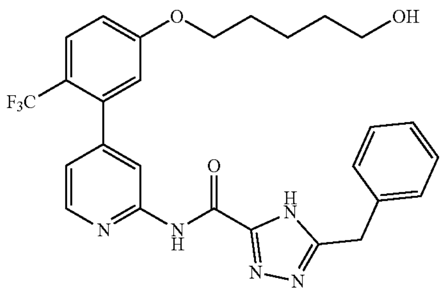

Example 275: 5-benzyl-N-(4-(5-((5-hydroxypentyl) oxy)-2-(trifluoromethyl)phenyl)pyridin-2-yl)-4H-1, 2,4-triazole-3-carboxamide The preparation was carried out in a similar manner to Example 92, except that in step 1, 5-bromo-1-pentanol was used in place of iodomethane, and 3-chloro-4-(trifluoromethyl)phenol was used in place of 2-bromo-3-methylphenol. $^{1}$H NMR (400 MHz, DMSO-$d_6$) δ 14.61 (s, 1H), 9.95 (s, 1H), 8.43 (d, J=5.1 Hz, 1H), 8.15 (s, 1H), 7.79 (d, J=8.9 Hz, 1H), 7.44-7.30 (m, 4H), 7.30-7.22 (m, 1H), 7.22-7.10 (m, 2H), 6.98 (d, J=2.6 Hz, 1H), 4.37 (t, J=5.1 Hz, 1H), 4.17 (s, 2H), 4.09 (t, J=6.5 Hz, 2H), 3.42-3.38 (m, 2H), 1.80-1.68 (m, 2H), 1.54-1.36 (m, 4H). MS: 526 [M+H]$^+$.

Example 276: 5-(2-fluorobenzyl)-N-(4-(5-((5-hydroxypentyl)oxy)-2-(trifluoromethyl)phenyl)pyridin-2-yl)-4H-1,2,4-triazole-3-carboxamide The preparation was carried out in a similar manner to Example 92, except that in step 1, 5-bromo-1-pentanol was used in place of iodomethane, 3-chloro-4-(trifluoromethyl) phenol was used in place of 2-bromo-3-methylphenol, and in step 3, ethyl 5-(2-fluorobenzyl)-4H-1,2,4-triazol-3-carboxylate was used in place of ethyl 5-benzyl-4H-1,2,4-triazol-3-carboxylate. $^{1}$H NMR (400 MHz, DMSO-$d_6$) δ 14.67 (s, 1H), 9.94 (s, 1H), 8.43 (d, J=5.0 Hz, 1H), 8.15 (s, 1H), 7.78 (d, J=8.8 Hz, 1H), 7.47-7.29 (m, 2H), 7.29-7.12 (m, 4H), 6.97 (d, J=2.6 Hz, 1H), 4.38 (d, J=5.5 Hz, 1H), 4.20 (s, 2H), 4.09 (t, J=6.5 Hz, 2H), 3.42-3.38 (m, 2H), 1.81-1.65 (m, 2H), 1.55-1.34 (m, 4H). MS: 544 [M+H]$^+$.

Example 276

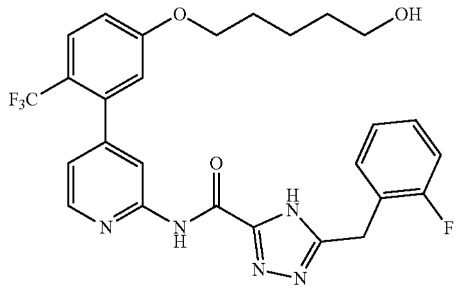

Example 277

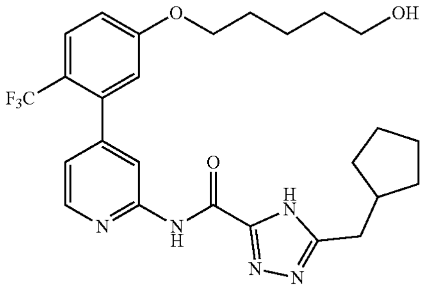

Example 277: 5-(cyclopentylmethyl)-N-(4-(5-((5-hydroxypentyl)oxy)-2-(trifluoromethyl)phenyl)pyridin-2-yl)-4H-1,2,4-triazole-3-carboxamide The preparation was carried out in a similar manner to Example 92, except that in step 1, 5-bromo-1-pentanol was used in place of iodomethane, 3-chloro-4-(trifluoromethyl) phenol was used in place of 2-bromo-3-methylphenol, and in step 3, ethyl 5-(cyclopentylmethyl)-4H-1,2,4-triazol-3-carboxylate was used in place of ethyl 5-benzyl-4H-1,2,4-triazol-3-carboxylate. $^{1}$H NMR (400 MHz, DMSO-$d_6$) δ 14.39 (s, 1H), 9.90 (s, 1H), 8.44 (d, J=5.1 Hz, 1H), 8.17 (s, 1H), 7.79 (d, J=8.9 Hz, 1H), 7.28-7.12 (m, 2H), 6.98 (d, J=2.6 Hz, 1H), 4.37 (t, J=5.1 Hz, 1H), 4.09 (t, J=6.5 Hz, 2H), 3.45-3.36 (m, 2H), 2.78 (d, J=7.5 Hz, 2H), 2.36-2.21 (m, 1H), 1.81-1.66 (m, 4H), 1.66-1.38 (m, 8H), 1.28-1.15 (m, 2H). MS: 518 [M+H]$^+$.

Example 278: 5-(cyclohexylmethyl)-N-(4-(5-((5-hydroxypentyl)oxy)-2-(trifluoromethyl)phenyl)pyridin-2-yl)-4H-1,2,4-triazole-3-carboxamide The preparation was carried out in a similar manner to Example 92, except that in step 1, 5-bromo-1-pentanol was used in place of iodomethane, 3-chloro-4-(trifluoromethyl) phenol was used in place of 2-bromo-3-methylphenol, and in step 3, ethyl 5-(cyclohexylmethyl)-4H-1,2,4-triazol-3-carboxylate was used in place of ethyl 5-benzyl-4H-1,2,4-triazol-3-carboxylate. $^{1}$H NMR (400 MHz, DMSO-$d_6$) δ 14.36 (s, 1H), 9.89 (s, 1H), 8.44 (dd, J=5.1, 0.8 Hz, 1H), 8.17 (s, 1H), 7.79 (d, J=8.9 Hz, 1H), 7.28-7.12 (m, 2H), 6.98 (d, J=2.6 Hz, 1H), 4.37 (t, J=5.1 Hz, 1H), 4.09 (t, J=6.5 Hz, 2H), 3.45-3.36 (m, 2H), 2.67 (d, J=7.0 Hz, 2H), 1.83-1.53 (m, 8H), 1.53-1.36 (m, 4H), 1.26-1.15 (m, 3H), 1.03-0.90 (m, 2H). MS: 532 [M+H]$^+$.

Example 278

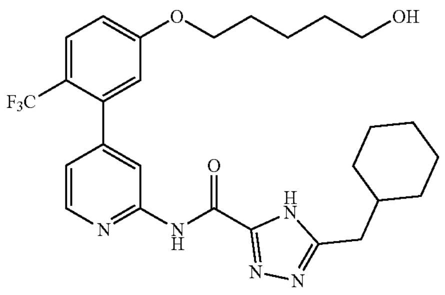

Example 279

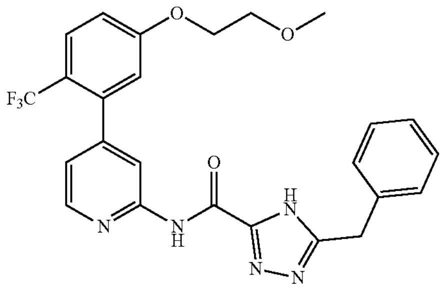

Example 279: 5-benzyl-N-(4-(5-(2-methoxyethoxy)-2-(trifluoromethyl)phenyl)pyridin-2-yl)-4H-1,2,4-triazole-3-carboxamide The preparation was carried out in a similar manner to Example 92, except that in step 1, 1-bromo-2-methoxyethane was used in place of iodomethane, and 3-chloro-4-(trifluoromethyl)phenol was used in place of 2-bromo-3-methylphenol. $^1$H NMR (400 MHz, DMSO-$d_6$) δ 14.62 (s, 1H), 9.96 (s, 1H), 8.44 (dd, J=5.1, 0.8 Hz, 1H), 8.16 (d, J=1.4 Hz, 1H), 7.79 (d, J=8.9 Hz, 1H), 7.48-7.29 (m, 4H), 7.29-7.13 (m, 3H), 7.01 (d, J=2.6 Hz, 1H), 4.28-4.20 (m, 2H), 4.17 (s, 2H), 3.73-3.62 (m, 2H), 3.30 (s, 3H). MS: 498 $[M+H]^+$.

Example 280: 5-(2-fluorobenzyl)-N-(4-(5-(2-methoxyethoxy)-2-(trifluoromethyl)phenyl)pyridin-2-yl)-4H-1,2,4-triazole-3-carboxamide The preparation was carried out in a similar manner to Example 92, except that in step 1, 1-bromo-2-methoxyethane was used in place of iodomethane, 3-chloro-4-(trifluoromethyl)phenol was used in place of 2-bromo-3-methylphenol, and in step 3, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.68 (s, 1H), 9.95 (s, 1H), 8.43 (dd, J=5.1, 0.8 Hz, 1H), 8.15 (s, 1H), 7.79 (d, J=8.9 Hz, 1H), 7.46-7.28 (m, 2H), 7.28-7.07 (m, 4H), 7.00 (d, J=2.5 Hz, 1H), 4.29-4.15 (m, 4H), 3.70-3.62 (m, 2H), 3.30 (s, 3H). MS: 516 $[M+H]^+$.

Example 280

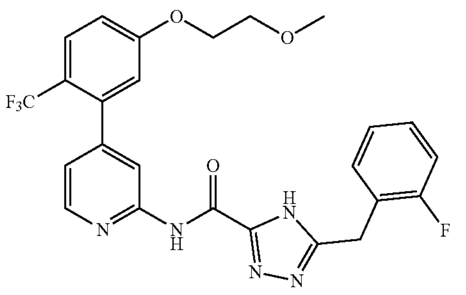

Example 281

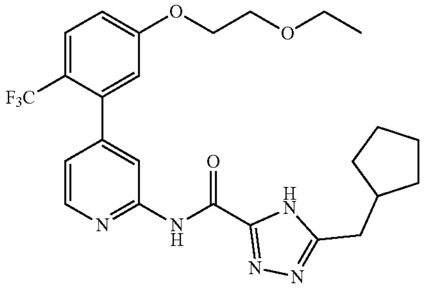

Example 281: 5-(cyclopentylmethyl)-N-(4-(5-(2-methoxyethoxy)-2-(trifluoromethyl)phenyl)pyridin-2-yl)-4H-1,2,4-triazole-3-carboxamide The preparation was carried out in a similar manner to Example 92, except that in step 1, 1-bromo-2-methoxyethane was used in place of iodomethane, 3-chloro-4-(trifluoromethyl)phenol was used in place of 2-bromo-3-methylphenol, and in step 3, ethyl 5-(cyclopentylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.42 (s, 1H), 9.91 (s, 1H), 8.44 (d, J=5.1 Hz, 1H), 8.18 (s, 1H), 7.80 (d, J=8.9 Hz, 1H), 7.32-7.12 (m, 2H), 7.01 (d, J=2.6 Hz, 1H), 4.31-4.17 (m, 2H), 3.72-3.62 (m, 2H), 3.30 (s, 3H), 2.77 (d, J=7.4 Hz, 2H), 2.37-2.18 (m, 1H), 1.79-1.66 (m, 2H), 1.66-1.44 (m, 4H), 1.29-1.12 (m, 2H). MS: 490 $[M+H]^+$.

Example 282: 5-(cyclohexylmethyl)-N-(4-(5-(2-methoxyethoxy)-2-(trifluoromethyl)phenyl)pyridin-2-yl)-4H-1,2,4-triazole-3-carboxamide The preparation was carried out in a similar manner to Example 92, except that in step 1, 1-bromo-2-methoxyethane was used in place of iodomethane, 3-chloro-4-(trifluoromethyl)phenol was used in place of 2-bromo-3-methylphenol, and in step 3, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.38 (s, 1H), 9.90 (s, 1H), 8.52-8.39 (m, 1H), 8.18 (s, 1H), 7.80 (d, J=8.9 Hz, 1H), 7.30-7.14 (m, 2H), 7.01 (d, J=2.6 Hz, 1H), 4.31-4.17 (m, 2H), 3.73-3.60 (m, 2H), 3.30 (s, 3H), 2.67 (d, J=7.0 Hz, 2H), 1.83-1.54 (m, 6H), 1.27-1.12 (m, 3H), 1.04-0.91 (m, 2H). MS: 504 $[M+H]^+$.

Example 282

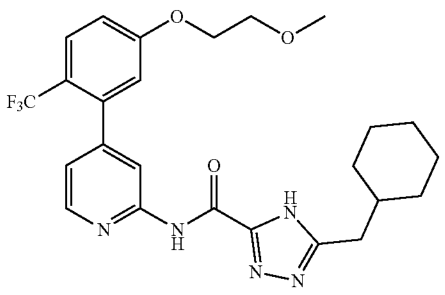

Example 283

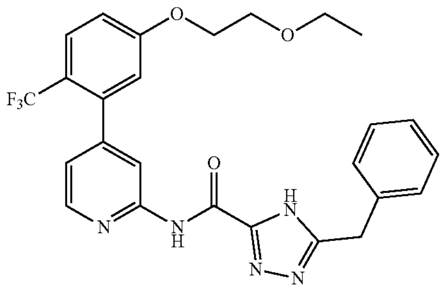

Example 283: 5-benzyl-N-(4-(5-(2-ethoxyethoxy)-2-(trifluoromethyl)phenyl)pyridin-2-yl)-4H-1,2,4-triazole-3-carboxamide The preparation was carried out in a similar manner to Example 92, except that in step 1, 1-bromo-2-ethoxyethane was used in place of iodomethane, and 3-chloro-4-(trifluoromethyl)phenol was used in place of 2-bromo-3-methylphenol. $^1$H NMR (400 MHz, DMSO-$d_6$) δ 14.61 (s, 1H), 9.96 (s, 1H), 8.43 (d, J=5.1 Hz, 1H), 8.16 (s, 1H), 7.79 (d, J=8.9 Hz, 1H), 7.43-7.09 (m, 7H), 7.01 (d, J=2.6 Hz, 1H), 4.28-4.20 (m, 2H), 4.17 (s, 2H), 3.75-3.66 (m, 2H), 3.49 (q, J=7.0 Hz, 2H), 1.11 (t, J=7.0 Hz, 3H). MS: 512 $[M+H]^+$.

Example 284: 5-(2-fluorobenzyl)-N-(4-(5-(2-ethoxyethoxy)-2-(trifluoromethyl)phenyl)pyridin-2-yl)-4H-1,2,4-triazole-3-carboxamide The preparation was carried out in a similar manner to Example 92, except that in step 1, 1-bromo-2-ethoxyethane was used in place of iodomethane, 3-chloro-4-(trifluoromethyl)phenol was used in place of 2-bromo-3-methylphenol, and in step 3, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.67 (s, 1H), 9.94 (s, 1H), 8.48-8.37 (m, 1H), 8.15 (s, 1H), 7.79 (d, J=8.8 Hz, 1H), 7.45-7.29 (m, 2H), 7.26-7.14 (m, 4H), 7.01 (d, J=2.6 Hz, 1H), 4.30-4.14 (m, 4H), 3.74-3.64 (m, 2H), 3.49 (q, J=7.0 Hz, 2H), 1.11 (t, J=7.0 Hz, 3H). MS: 530 $[M+H]^+$.

Example 284

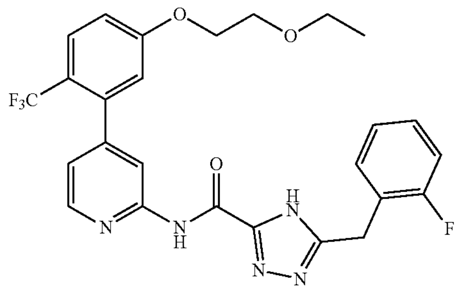

Example 285

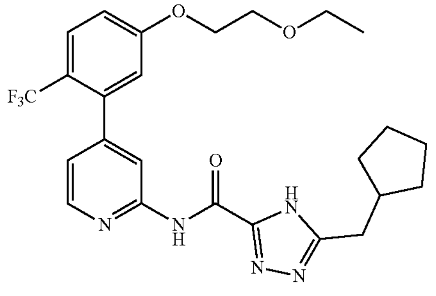

Example 285: 5-(cyclopentylmethyl)-N-(4-(5-(2-ethoxyethoxy)-2-(trifluoromethyl)phenyl)pyridin-2-yl)-4H-1,2,4-triazole-3-carboxamide The preparation was carried out in a similar manner to Example 92, except that in step 1, 1-bromo-2-ethoxyethane was used in place of iodomethane, 3-chloro-4-(trifluoromethyl)phenol was used in place of 2-bromo-3-methylphenol, and in step 3, ethyl 5-(cyclopentylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.39 (s, 1H), 9.90 (s, 1H), 8.44 (d, J=5.1 Hz, 1H), 8.18 (s, 1H), 7.80 (d, J=8.9 Hz, 1H), 7.29-7.13 (m, 2H), 7.02 (d, J=2.6 Hz, 1H), 4.29-4.17 (m, 2H), 3.76-3.65 (m, 2H), 3.49 (q, J=7.0 Hz, 2H), 2.78 (d, J=7.5 Hz, 2H), 2.35-2.18 (m, 1H), 1.79-1.67 (m, 2H), 1.67-1.44 (m, 4H), 1.30-1.16 (m, 2H), 1.11 (t, J=7.0 Hz, 3H). MS: 504 $[M+H]^+$.

Example 286: 5-(cyclohexylmethyl)-N-(4-(5-(2-ethoxyethoxy)-2-(trifluoromethyl)phenyl)pyridin-2-yl)-4H-1,2,4-triazole-3-carboxamide The preparation was carried out in a similar manner to Example 92, except that in step 1, 1-bromo-2-ethoxyethane was used in place of iodomethane, 3-chloro-4-(trifluoromethyl)phenol was used in place of 2-bromo-3-methylphenol, and in step 3, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.40 (s, 1H), 9.90 (s, 1H), 8.44 (d, J=5.1 Hz, 1H), 8.18 (s, 1H), 7.80 (d, J=8.9 Hz, 1H), 7.28-7.13 (m, 2H), 7.02 (d, J=2.6 Hz, 1H), 4.28-4.19 (m, 2H), 3.76-3.66 (m, 2H), 3.49 (q, J=7.0 Hz, 2H), 2.66 (d, J=7.0 Hz, 2H), 1.80-1.57 (m, 6H), 1.25-1.14 (m, 3H), 1.11 (t, J=7.0 Hz, 3H), 1.06-0.91 (m, 2H). MS: 518 $[M+H]^+$.

Example 286

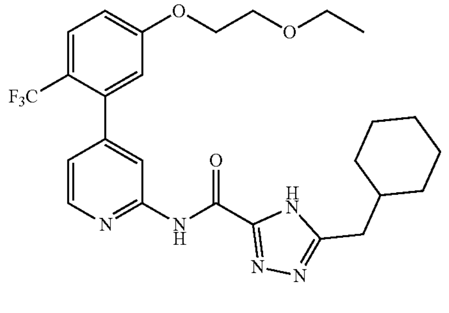

Example 287

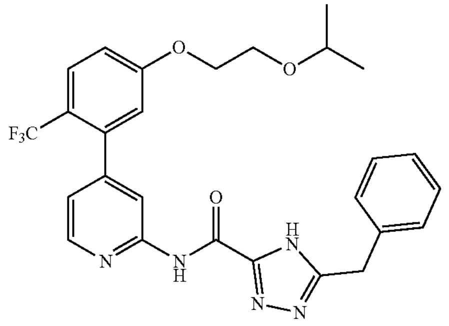

Example 287: 5-benzyl-N-(4-(5-(2-isopropoxyethoxy)-2-(trifluoromethyl)phenyl)pyridin-2-yl)-4H-1,2,4-triazole-3-carboxamide The preparation was carried out in a similar manner to Example 92, except that in step 1, 1-bromo-2-isopropoxyethane was used in place of iodomethane, and 3-chloro-4-(trifluoromethyl)phenol was used in place of 2-bromo-3-methylphenol. $^1$H NMR (400 MHz, DMSO-$d_6$) δ 14.58 (s, 1H), 9.94 (s, 1H), 8.43 (dd, J=5.0, 0.8 Hz, 1H), 8.16 (s, 1H), 7.79 (d, J=8.9 Hz, 1H), 7.41-7.11 (m, 7H), 7.01 (d, J=2.6 Hz, 1H), 4.25-4.12 (m, 4H), 3.74-3.67 (m, 2H), 3.62 (p, J=6.1 Hz, 1H), 1.09 (d, J=6.1 Hz, 6H). MS: 526 $[M+H]^+$.

Example 288: 5-(2-fluorobenzyl)-N-(4-(5-(2-isopropoxyethoxy)-2-(trifluoromethyl)phenyl)pyridin-2-yl)-4H-1,2,4-triazole-3-carboxamide The preparation was carried out in a similar manner to Example 92, except that in step 1, 1-bromo-2-isopropoxyethane was used in place of iodomethane, 3-chloro-4-(trifluoromethyl)phenol was used in place of 2-bromo-3-methylphenol, and in step 3, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.68 (s, 1H), 9.94 (s, 1H), 8.43 (d, J=5.1 Hz, 1H), 8.15 (s, 1H), 7.79 (d, J=8.9 Hz, 1H), 7.48-7.28 (m, 2H), 7.28-7.11 (m, 4H), 7.01 (d, J=2.6 Hz, 1H), 4.29-4.13 (m, 4H), 3.76-3.66 (m, 2H), 3.61 (p, J=6.1 Hz, 1H), 1.09 (d, J=6.1 Hz, 6H). MS: 544 $[M+H]^+$.

Example 288

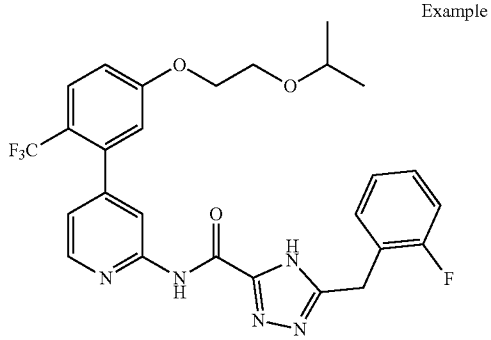

Example 289

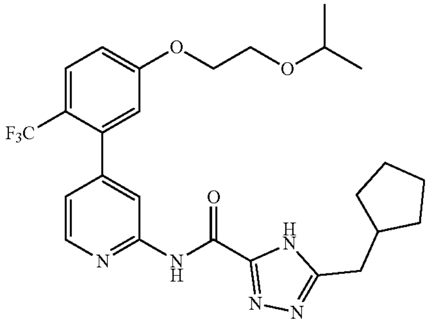

Example 289: 5-(cyclopentylmethyl)-N-(4-(5-(2-isopropoxyethoxy)-2-(trifluoromethyl)phenyl)pyridin-2-yl)-4H-1,2,4-triazole-3-carboxamide The preparation was carried out in a similar manner to Example 92, except that in step 1, 1-bromo-2-isopropoxyethane was used in place of iodomethane, 3-chloro-4-(trifluoromethyl)phenol was used in place of 2-bromo-3-methylphenol, and in step 3, ethyl 5-(cyclopentylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.33 (s, 1H), 9.90 (s, 1H), 8.44 (d, J=5.1 Hz, 1H), 8.18 (s, 1H), 7.79 (d, J=8.9 Hz, 1H), 7.28-7.11 (m, 2H), 7.01 (d, J=2.5 Hz, 1H), 4.26-4.15 (m, 2H), 3.75-3.67 (m, 2H), 3.62 (p, J=6.1 Hz, 1H), 2.78 (d, J=7.5 Hz, 2H), 2.36-2.21 (m, 1H), 1.78-1.66 (m, 2H), 1.66-1.44 (m, 4H), 1.24-1.16 (m, 2H), 1.09 (d, J=6.1 Hz, 6H). MS: 518 $[M+H]^+$.

Example 290: 5-(cyclohexylmethyl)-N-(4-(5-(2-isopropoxyethoxy)-2-(trifluoromethyl)phenyl)pyridin-2-yl)-4H-1,2,4-triazole-3-carboxamide The preparation was carried out in a similar manner to Example 92, except that in step 1, 1-bromo-2-isopropoxyethane was used in place of iodomethane, 3-chloro-4-(trifluoromethyl)phenol was used in place of 2-bromo-3-methylphenol, and in step 3, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.36 (s, 1H), 9.88 (s, 1H), 8.44 (d, J=5.1 Hz, 1H), 8.17 (s, 1H), 7.79 (d, J=8.9 Hz, 1H), 7.28-7.14 (m, 2H), 7.01 (d, J=2.6 Hz, 1H), 4.25-4.16 (m, 2H), 3.75-3.67 (m, 2H), 3.62 (p, J=6.1 Hz, 1H), 2.67 (d, J=6.9 Hz, 2H), 1.84-1.54 (m, 6H), 1.24-1.13 (m, 3H), 1.09 (d, J=6.1 Hz, 6H), 1.05-0.91 (m, 2H). MS: 532 $[M+H]^+$.

Example 290

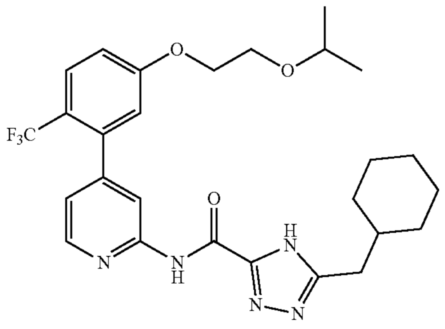

Example 291

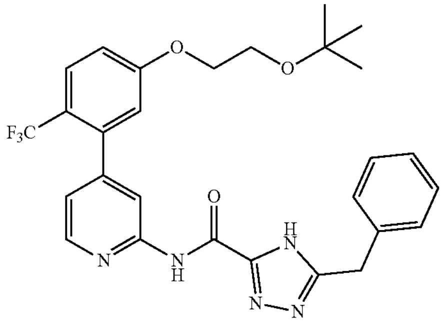

Example 291: 5-benzyl-N-(4-(5-(2-(tert-butoxy)ethoxy)-2-(trifluoromethyl)phenyl)pyridin-2-yl)-4H-1,2,4-triazole-3-carboxamide The preparation was carried out in a similar manner to Example 64, except that in step 1, 3-chloro-4-(trifluoromethyl)phenol was used in place of 2-bromo-3-methylphenol. $^1$H NMR (400 MHz, DMSO-$d_6$) δ 14.53 (s, 1H), 9.95 (s, 1H), 8.43 (d, J=5.0 Hz, 1H), 8.16 (s, 1H), 7.79 (d, J=8.9 Hz, 1H), 7.40-7.11 (m, 7H), 7.00 (d, J=2.5 Hz, 1H), 4.22-4.10 (m, 4H), 3.69-3.59 (m, 2H), 1.14 (s, 9H). MS: 540 $[M+H]^+$.

Example 292: 5-(2-fluorobenzyl)-N-(4-(5-(2-(tert-butoxy)ethoxy)-2-(trifluoromethyl)phenyl)pyridin-2-yl)-4H-1,2,4-triazole-3-carboxamide The preparation was carried out in a similar manner to Example 64, except that in step 1, 3-chloro-4-(trifluoromethyl)phenol was used in place of 2-bromo-3-methylphenol, and in step 3, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.67 (s, 1H), 9.94 (s, 1H), 8.43 (d, J=5.2 Hz, 1H), 8.15 (s, 1H), 7.78 (d, J=8.8 Hz, 1H), 7.51-7.27 (m, 2H), 7.27-7.10 (m, 4H), 7.00 (d, J=2.6 Hz, 1H), 4.28-4.09 (m, 4H), 3.65 (t, J=4.8 Hz, 2H), 1.14 (s, 9H). MS: 558 $[M+H]^+$.

Example 292

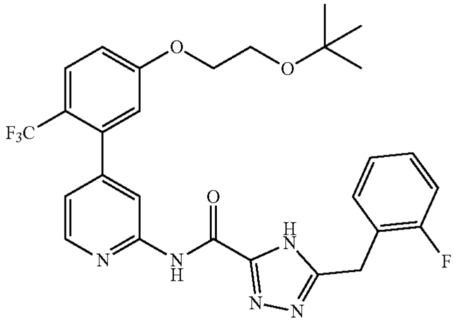

Example 293

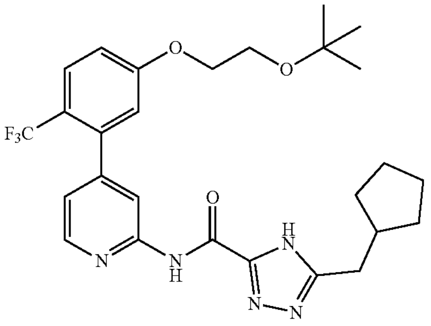

Example 293: 5-(cyclopentylmethyl)-N-(4-(5-(2-(tert-butoxy)ethoxy)-2-(trifluoromethyl)phenyl)pyridin-2-yl)-4H-1,2,4-triazole-3-carboxamide The preparation was carried out in a similar manner to Example 64, except that in step 1, 3-chloro-4-(trifluoromethyl)phenol was used in place of 2-bromo-3-methylphenol, and in step 3, ethyl 5-(cyclopentylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.37 (s, 1H), 9.88 (s, 1H), 8.44 (d, J=5.1 Hz, 1H), 8.18 (s, 1H), 7.79 (d, J=8.9 Hz, 1H), 7.28-7.11 (m, 2H), 7.01 (d, J=2.6 Hz, 1H), 4.24-4.11 (m, 2H), 3.71-3.60 (m, 2H), 2.78 (d, J=7.5 Hz, 2H), 2.28 (p, J=7.6 Hz, 1H), 1.79-1.66 (m, 2H), 1.66-1.43 (m, 4H), 1.25-1.20 (m, 2H), 1.15 (s, 9H). MS: 532 $[M+H]^+$.

Example 294: 5-(cyclohexylmethyl)-N-(4-(5-(2-(tert-butoxy)ethoxy)-2-(trifluoromethyl)phenyl)pyridin-2-yl)-4H-1,2,4-triazole-3-carboxamide The preparation was carried out in a similar manner to Example 64, except that in step 1, 3-chloro-4-(trifluoromethyl)phenol was used in place of 2-bromo-3-methylphenol, and in step 3, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.32 (s, 1H), 9.89 (s, 1H), 8.44 (d, J=5.1 Hz, 1H), 8.17 (s, 1H), 7.79 (d, J=8.9 Hz, 1H), 7.29-7.12 (m, 2H), 7.01 (d, J=2.6 Hz, 1H), 4.24-4.13 (m, 2H), 3.66 (dd, J=5.5, 4.0 Hz, 2H), 2.67 (d, J=7.0 Hz, 2H), 1.83-1.56 (m, 6H), 1.23-1.16 (m, 3H), 1.15 (s, 9H), 1.05-0.93 (m, 2H). MS: 546 $[M+H]^+$ Example 294

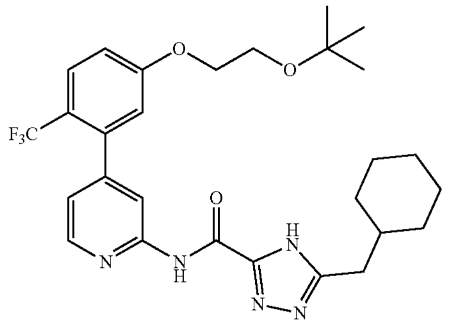

Example 295

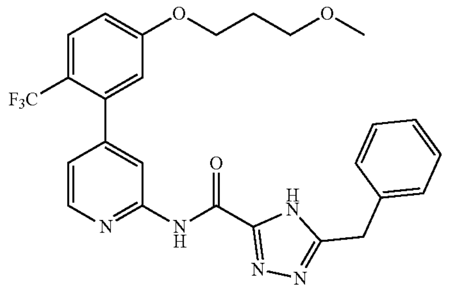

Example 295: 5-benzyl-N-(4-(5-(3-methoxy-propoxy)-2-(trifluoromethyl)phenyl)pyridin-2-yl)-4H-1,2,4-triazole-3-carboxamide The preparation was carried out in a similar manner to Example 92, except that in step 1, 1-bromo-3-methoxypropane was used in place of iodomethane, and 3-chloro-4-(trifluoromethyl)phenol was used in place of 2-bromo-3-methylphenol. $^1$H NMR (400 MHz, DMSO-$d_6$) δ 14.61 (s, 1H), 9.96 (s, 1H), 8.43 (d, J=5.1 Hz, 1H), 8.16 (s, 1H), 7.79 (d, J=8.9 Hz, 1H), 7.42-7.29 (m, 4H), 7.29-7.23 (m, 1H), 7.23-7.12 (m, 2H), 6.98 (d, J=2.6 Hz, 1H), 4.22-4.08 (m, 4H), 3.46 (t, J=6.2 Hz, 2H), 3.23 (s, 3H), 2.02-1.90 (m, 2H). MS: 512 $[M+H]^+$.

Example 296: 5-(2-fluorobenzyl)-N-(4-(5-(3-methoxypropoxy)-2-(trifluoromethyl)phenyl)pyridin-2-yl)-4H-1,2,4-triazole-3-carboxamide The preparation was carried out in a similar manner to Example 92, except that in step 1, 1-bromo-3-methoxypropane was used in place of iodomethane, 3-chloro-4-(trifluoromethyl)phenol was used in place of 2-bromo-3-methylphenol, and in step 3, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.67 (s, 1H), 9.94 (s, 1H), 8.43 (dd, J=5.1, 0.8 Hz, 1H), 8.15 (s, 1H), 7.79 (d, J=8.9 Hz, 1H), 7.46-7.28 (m, 2H), 7.28-7.12 (m, 4H), 6.98 (d, J=2.6 Hz, 1H), 4.21 (s, 2H), 4.14 (t, J=6.4 Hz, 2H), 3.46 (t, J=6.2 Hz, 2H), 3.23 (s, 3H), 2.01-1.91 (m, 2H). MS: 530 $[M+H]^+$.

Example 296

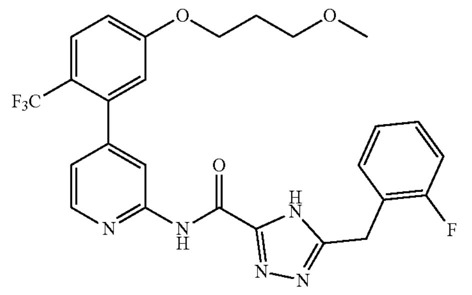

Example 297

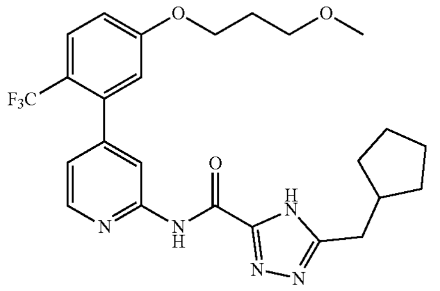

Example 297: 5-(cyclopentylmethyl)-N-(4-(5-(3-methoxypropoxy)-2-(trifluoromethyl)phenyl)pyridin-2-yl)-4H-1,2,4-triazole-3-carboxamide The preparation was carried out in a similar manner to Example 92, except that in step 1, 1-bromo-3-methoxypropane was used in place of iodomethane, 3-chloro-4-(trifluoromethyl)phenol was used in place of 2-bromo-3-methylphenol, and in step 3, ethyl 5-(cyclopentylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.40 (s, 1H), 9.91 (s, 1H), 8.44 (dd, J=5.1, 0.8 Hz, 1H), 8.23-8.13 (m, 1H), 7.79 (d, J=8.9 Hz, 1H), 7.28-7.12 (m, 2H), 6.99 (d, J=2.5 Hz, 1H), 4.15 (t, J=6.4 Hz, 2H), 3.46 (t, J=6.2 Hz, 2H), 3.24 (s, 3H), 2.77 (d, J=7.5 Hz, 2H), 2.36-2.19 (m, 1H), 2.04-1.91 (m, 2H), 1.78-1.66 (m, 2H), 1.66-1.44 (m, 4H), 1.29-1.14 (m, 2H). MS: 504 $[M+H]^+$.

Example 298: 5-(cyclohexylmethyl)-N-(4-(5-(3-methoxypropoxy)-2-(trifluoromethyl)phenyl)pyridin-2-yl)-4H-1,2,4-triazole-3-carboxamide The preparation was carried out in a similar manner to Example 92, except that in step 1, 1-bromo-3-methoxypropane was used in place of iodomethane, 3-chloro-4-(trifluoromethyl)phenol was used in place of 2-bromo-3-methylphenol, and in step 3, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.38 (s, 1H), 9.90 (s, 1H), 8.49-8.39 (m, 1H), 8.17 (s, 1H), 7.79 (d, J=8.8 Hz, 1H), 7.29-7.13 (m, 2H), 6.99 (d, J=2.6 Hz, 1H), 4.15 (t, J=6.4 Hz, 2H), 3.47 (t, J=6.2 Hz, 2H), 3.24 (s, 3H), 2.67 (d, J=7.0 Hz, 2H), 2.03-1.90 (m, 2H), 1.81-1.57 (m, 6H), 1.24-1.10 (m, 3H), 1.03-0.89 (m, 2H). MS: 518 $[M+H]^+$.

Example 298

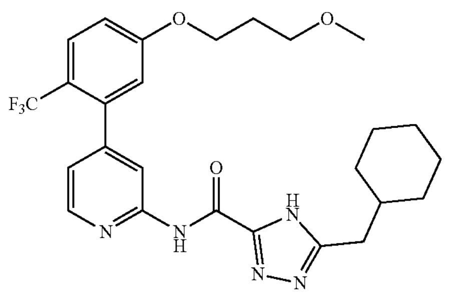

Example 299

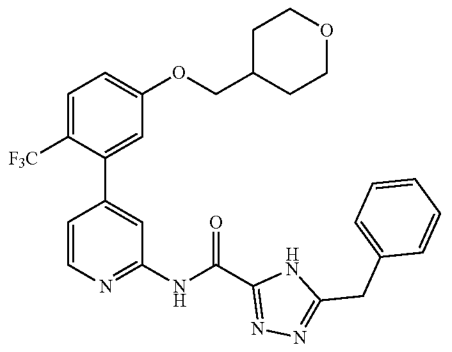

Example 299: 5-benzyl-N-(4-(5-((tetrahydro-2H-pyran-4-yl)methoxy)-2-(trifluoromethyl)phenyl)pyridin-2-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, and 3-chloro-4-(trifluoromethyl)phenol was used in place of 2-bromo-3-methylphenol. $^1H$ NMR (400 MHz, DMSO-$d_6$) δ 14.56 (s, 1H), 9.95 (s, 1H), 8.43 (d, J=5.1 Hz, 1H), 8.16 (s, 1H), 7.79 (d, J=8.9 Hz, 1H), 7.41-7.29 (m, 4H), 7.29-7.13 (m, 3H), 6.99 (d, J=2.6 Hz, 1H), 4.17 (s, 2H), 3.97 (d, J=6.5 Hz, 2H), 3.92-3.79 (m, 2H), 2.10-1.93 (m, 1H), 1.72-1.60 (m, 2H), 1.42-1.18 (m, 4H). MS: 538 $[M+H]^+$.

Example 300: 5-(2-fluorobenzyl)-N-(4-(5-((tetrahydro-2H-pyran-4-yl)methoxy)-2-(trifluoromethyl)phenyl)pyridin-2-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-chloro-4-(trifluoromethyl)phenol was used in place of 2-bromo-3-methylphenol, and in step 3, ethyl 5-(2-fluorobenzyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.66 (s, 1H), 9.94 (s, 1H), 8.43 (d, J=5.1 Hz, 1H), 8.15 (s, 1H), 7.79 (d, J=8.9 Hz, 1H), 7.45-7.29 (m, 2H), 7.26-7.13 (m, 4H), 6.99 (d, J=2.6 Hz, 1H), 4.21 (s, 2H), 3.96 (d, J=6.5 Hz, 2H), 3.92-3.80 (m, 2H), 2.09-1.91 (m, 1H), 1.72-1.62 (m, 2H), 1.41-1.16 (m, 4H). MS: 556 $[M+H]^+$.

Example 300

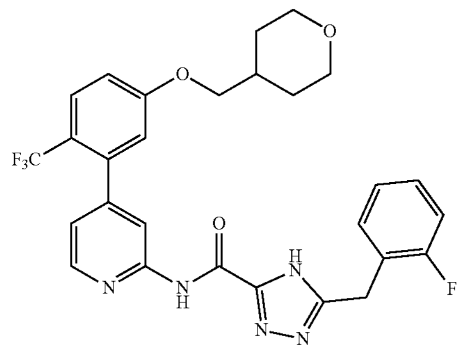

Example 301

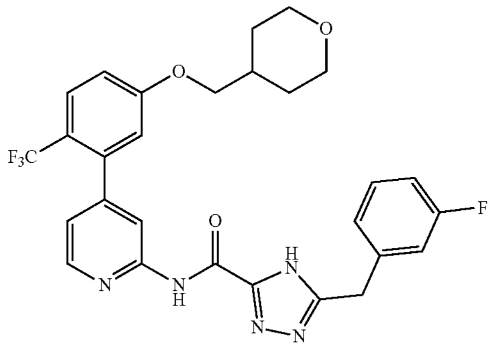

Example 301: 5-(3-fluorobenzyl)-N-(4-(5-((tetrahydro-2H-pyran-4-yl)methoxy)-2-(trifluoromethyl)phenyl)pyridin-2-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-chloro-4-(trifluoromethyl)phenol was used in place of 2-bromo-3-methylphenol, and in step 3, ethyl 5-(3-fluorobenzyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.64 (s, 1H), 9.99 (s, 1H), 8.43 (d, J=5.1 Hz, 1H), 8.16 (s, 1H), 7.79 (d, J=8.9 Hz, 1H), 7.44-7.32 (m, 1H), 7.26-7.13 (m, 4H), 7.13-7.04 (m, 1H), 6.99 (d, J=2.5 Hz, 1H), 4.21 (s, 2H), 3.96 (d, J=6.5 Hz, 2H), 3.91-3.80 (m, 2H), 3.35-3.29 (m, 2H), 2.07-1.95 (m, 1H), 1.73-1.60 (m, 2H), 1.41-1.25 (m, 2H). MS: 556 $[M+H]^+$.

Example 302: 5-(4-fluorobenzyl)-N-(4-(5-((tetrahydro-2H-pyran-4-yl)methoxy)-2-(trifluoromethyl)phenyl)pyridin-2-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-chloro-4-(trifluoromethyl)phenol was used in place of 2-bromo-3-methylphenol, and in step 3, ethyl 5-(4-fluorobenzyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.53 (s, 1H), 9.91 (s, 1H), 8.43 (d, J=5.1 Hz, 1H), 8.15 (s, 1H), 7.79 (d, J=8.9 Hz, 1H), 7.42-7.31 (m, 2H), 7.26-7.09 (m, 4H), 6.99 (d, J=2.5 Hz, 1H), 4.18 (s, 2H), 3.97 (d, J=6.5 Hz, 2H), 3.92-3.79 (m, 2H), 3.33-3.31 (m, 2H), 2.13-1.92 (m, 1H), 1.74-1.60 (m, 2H), 1.42-1.23 (m, 2H). MS: 556 $[M+H]^+$.

Example 302

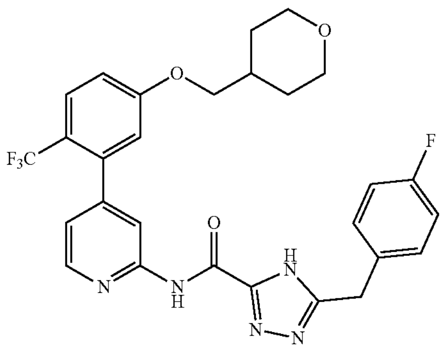

Example 303

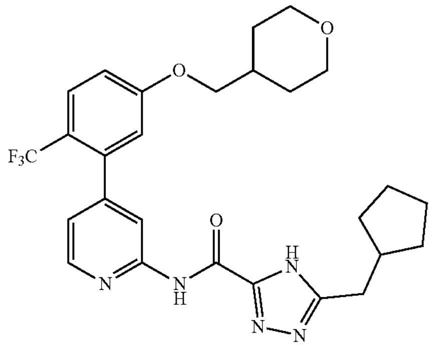

Example 303: 5-(cyclopentylmethyl)-N-(4-(5-((tetrahydro-2H-pyran-4-yl)methoxy)-2-(trifluoromethyl)phenyl)pyridin-2-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-chloro-4-(trifluoromethyl)phenol was used in place of 2-bromo-3-methylphenol, and in step 3, ethyl 5-(cyclopentylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.37 (s, 1H), 9.89 (s, 1H), 8.44 (d, J=5.0 Hz, 1H), 8.17 (s, 1H), 7.79 (d, J=8.9 Hz, 1H), 7.25-7.14 (m, 2H), 6.99 (d, J=2.5 Hz, 1H), 3.97 (d, J=6.5 Hz, 2H), 3.91-3.81 (m, 2H), 3.33-3.26 (m, 2H), 2.78 (d, J=7.5 Hz, 2H), 2.35-2.18 (m, 1H), 2.11-1.93 (m, 1H), 1.79-1.42 (m, 8H), 1.41-1.27 (m, 2H), 1.27-1.18 (m, 2H). MS: 530 $[M+H]^+$.

Example 304: 5-(cyclohexylmethyl)-N-(4-(5-((tetrahydro-2H-pyran-4-yl)methoxy)-2-(trifluoromethyl)phenyl)pyridin-2-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-chloro-4-(trifluoromethyl)phenol was used in place of 2-bromo-3-methylphenol, and in step 3, ethyl 5-(cyclohexylmethyl)-4H-1,2,4-triazol-3-carboxylate was used in place of ethyl 5-benzyl-4H-1,2,4-triazol-3-carboxylate.

$^1$H NMR (400 MHz, DMSO-$d_6$) δ 14.38 (s, 1H), 9.90 (s, 1H), 8.44 (d, J=5.1 Hz, 1H), 8.17 (s, 1H), 7.79 (d, J=8.9 Hz,

1H), 7.29-7.13 (m, 2H), 7.00 (d, J=2.6 Hz, 1H), 3.97 (d, J=6.4 Hz, 2H), 3.92-3.79 (m, 2H), 3.37-3.33 (m, 2H), 2.67 (d, J=7.0 Hz, 2H), 2.10-1.92 (m, 1H), 1.81-1.72 (m, 1H), 1.70-1.62 (m, 6H), 1.40-1.11 (m, 6H), 1.05-0.89 (m, 2H). MS: 544 $[M+H]^+$.

Example 304

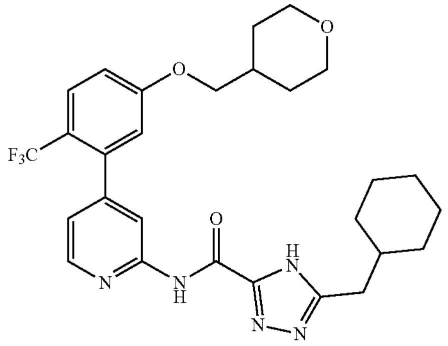

Example 305

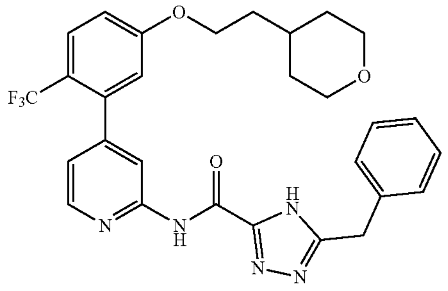

Example 305: 5-benzyl-N-(4-(5-(2-(tetrahydro-2H-pyran-4-yl)ethoxy)-2-(trifluoromethyl)phenyl)pyridin-2-yl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, and in step 2, 3-chloro-4-(trifluoromethyl)phenol was used in place of 2-bromo-3-methylphenol. $^1$H NMR (400 MHz, DMSO-$d_6$) δ 14.59 (s, 1H), 9.95 (s, 1H), 8.43 (d, J=5.1 Hz, 1H), 8.16 (s, 1H), 7.78 (d, J=8.9 Hz, 1H), 7.42-7.29 (m, 4H), 7.29-7.23 (m, 1H), 7.23-7.13 (m, 2H), 6.99 (d, J=2.6 Hz, 1H), 4.25-4.06 (m, 4H), 3.89-3.71 (m, 2H), 3.29-3.16 (m, 2H), 1.77-1.65 (m, 3H), 1.65-1.53 (m, 2H), 1.29-1.18 (m, 2H). MS: 552 $[M+H]^+$.

Example 306: 5-(2-fluorobenzyl)-N-(4-(5-(2-(tetrahydro-2H-pyran-4-yl)ethoxy)-2-(trifluoromethyl)phenyl)pyridin-2-yl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, in step 2, 3-chloro-4-(trifluoromethyl)phenol was used in place of 2-bromo-3-methylphenol, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.66 (s, 1H), 9.94 (s, 1H), 8.43 (d, J=5.1 Hz, 1H), 8.15 (s, 1H), 7.78 (d, J=8.9 Hz, 1H), 7.48-7.28 (m, 2H), 7.28-7.12 (m, 4H), 6.99 (d, J=2.6 Hz, 1H), 4.21 (s, 2H), 4.14 (t, J=6.1 Hz, 2H), 3.89-3.76 (m, 2H), 3.31-3.20 (m, 2H), 1.77-1.55 (m, 5H), 1.31-1.12 (m, 2H). MS: 570 $[M+H]^+$.

Example 306

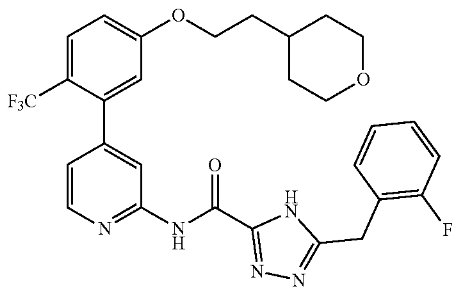

Example 307

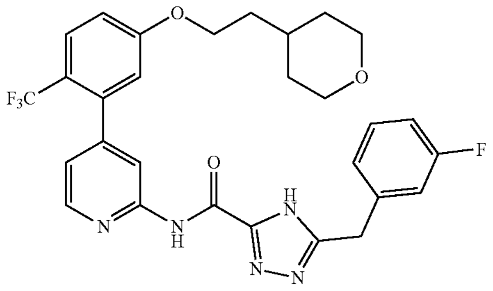

Example 307: 5-(3-fluorobenzyl)-N-(4-(5-(2-(tetrahydro-2H-pyran-4-yl)ethoxy)-2-(trifluoromethyl)phenyl)pyridin-2-yl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, in step 2, 3-chloro-4-(trifluoromethyl)phenol was used in place of 2-bromo-3-methylphenol, and in step 4, ethyl 5-(3-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.57 (s, 1H), 9.97 (s, 1H), 8.44 (d, J=5.1 Hz, 1H), 8.15 (s, 1H), 7.79 (d, J=8.9 Hz, 1H), 7.45-7.32 (m, 1H), 7.23-7.13 (m, 4H), 7.13-7.05 (m, 1H), 7.00 (d, J=2.6 Hz, 1H), 4.21 (s, 2H), 4.14 (t, J=6.1 Hz, 2H), 3.93-3.72 (m, 2H), 3.32-3.21 (m, 2H), 1.75-1.57 (m, 5H), 1.29-1.13 (m, 2H). MS: 570 $[M+H]^+$.

Example 308: 5-(4-fluorobenzyl)-N-(4-(5-(2-(tetrahydro-2H-pyran-4-yl)ethoxy)-2-(trifluoromethyl)phenyl)pyridin-2-yl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, in step 2, 3-chloro-4-(trifluoromethyl)phenol was used in place of 2-bromo-3-methylphenol, and in step 4, ethyl 5-(4-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.58 (s, 1H), 9.96 (s, 1H), 8.44 (d, J=5.1 Hz, 1H), 8.16 (s, 1H), 7.79 (d, J=8.9 Hz, 1H), 7.44-7.31 (m, 2H), 7.27-7.10 (m, 4H), 7.00 (d, J=2.6 Hz, 1H), 4.23-4.10 (m, 4H), 3.87-3.77 (m, 2H), 3.31-3.20 (m, 2H), 1.79-1.57 (m, 5H), 1.30-1.14 (m, 2H). MS: 570 $[M+H]^+$.

Example 308

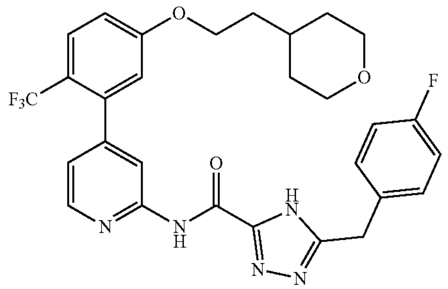

Example 309

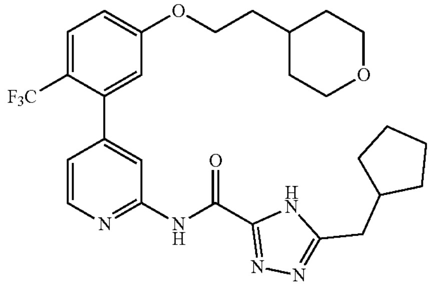

Example 309: 5-(cyclopentylmethyl)-N-(4-(5-(2-(tetrahydro-2H-pyran-4-yl)ethoxy)-2-(trifluoromethyl)phenyl)pyridin-2-yl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, in step 2, 3-chloro-4-(trifluoromethyl)phenol was used in place of 2-bromo-3-methylphenol, and in step 4, ethyl 5-(cyclopentylmethyl)-4H-1,2,4-triazole-3-carboxylate was used in place of ethyl 5-benzyl-4H-1,2,4-triazol-3-carboxylate. $^1$H NMR (400 MHz, DMSO-$d_6$) δ 14.41 (s, 1H), 9.90 (s, 1H), 8.44 (d, J=5.1 Hz, 1H), 8.17 (d, J=1.4 Hz, 1H), 7.79 (d, J=8.9 Hz, 1H), 7.25-7.14 (m, 2H), 7.00 (d, J=2.5 Hz, 1H), 4.14 (t, J=6.1 Hz, 2H), 3.93-3.69 (m, 2H), 3.30-3.23 (m, 2H), 2.77 (d, J=7.5 Hz, 2H), 2.36-2.19 (m, 1H), 1.78-1.42 (m, 11H), 1.31-1.13 (m, 4H). MS: 544 $[M+H]^+$.

Example 310: 5-(cyclohexylmethyl)-N-(4-(5-(2-(tetrahydro-2H-pyran-4-yl)ethoxy)-2-(trifluoromethyl)phenyl)pyridin-2-yl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, in step 2, 3-chloro-4-(trifluoromethyl)phenol was used in place of 2-bromo-3-methylphenol, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.38 (s, 1H), 9.90 (s, 1H), 8.44 (d, J=5.0 Hz, 1H), 8.17 (s, 1H), 7.79 (d, J=8.9 Hz, 1H), 7.25-7.14 (m, 2H), 7.00 (d, J=2.5 Hz, 1H), 4.15 (t, J=6.1 Hz, 2H), 3.88-3.76 (m, 2H), 3.30-3.21 (m, 2H), 2.67 (d, J=7.0 Hz, 2H), 1.82-1.52 (m, 10H), 1.31-1.07 (m, 6H), 1.07-0.91 (m, 2H). MS: 558 [M+H]$^+$.

Example 310

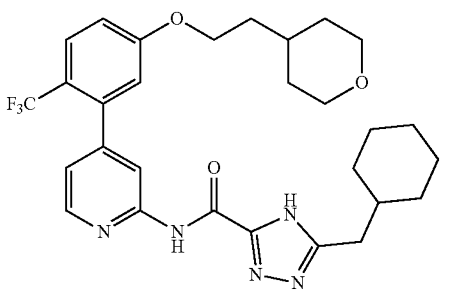

Example 311

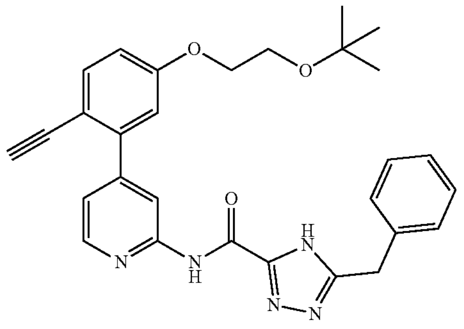

Example 311: 5-benzyl-N-(4-(5-(2-(tert-butoxy)ethoxy)-2-ethynylphenyl)pyridin-2-yl)-4H-1,2,4-triazole-3-carboxamide The preparation was carried out in a similar manner to Example 64, except that in step 1, 3-bromo-4-ethynylphenol was used in place of 3-bromo-4-methylphenol. $^1$H NMR (400 MHz, DMSO-$d_6$) δ 14.56 (s, 1H), 9.87 (s, 1H), 8.43 (d, J=5.3 Hz, 1H), 8.37 (s, 1H), 7.57 (d, J=8.5 Hz, 1H), 7.42-7.29 (m, 5H), 7.26 (s, 1H), 7.10-6.97 (m, 2H), 4.18 (s, 2H), 4.16-4.09 (m, 2H), 4.05 (s, 1H), 3.65 (t, J=4.8 Hz, 2H), 1.15 (s, 9H). MS: 496 [M+H]$^+$.

Example 312: 5-benzyl-N-(4-(2-fluoro-5-((4-hydroxy-4-methylpentyl)oxy)phenyl)pyridin-2-yl)-4H-1,2,4-triazole-3-carboxamide The preparation was carried out in a similar manner to Example 160, except that in step 1, 3-bromo-4-fluorophenol was used in place of 3-bromo-4-methylphenol. $^1$H NMR (400 MHz, DMSO-$d_6$) δ 14.57 (s, 1H), 9.90 (s, 1H), 8.46 (d, J=5.2 Hz, 1H), 8.35 (s, 1H), 7.40 (d, J=5.2 Hz, 1H), 7.38-7.29 (m, 5H), 7.29-7.19 (m, 1H), 7.16-6.99 (m, 2H), 4.24-4.11 (m, 3H), 4.01 (t, J=6.5 Hz, 2H), 1.84-1.69 (m, 2H), 1.55-1.43 (m, 2H), 1.10 (s, 6H). MS: 490 [M+H]$^+$.

Example 312

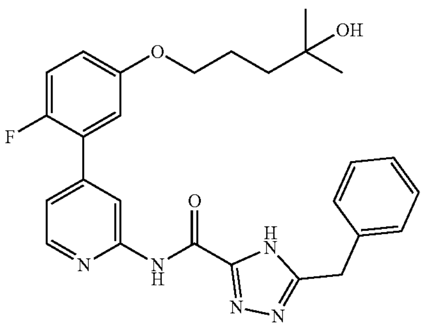

Example 313

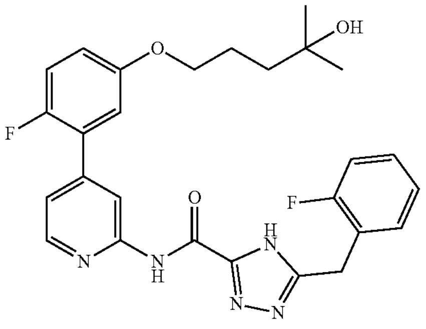

Example 313: 5-(2-fluorobenzyl)-N-(4-(2-fluoro-5-((4-hydroxy-4-methylpentyl)oxy)phenyl)pyridin-2-yl)-4H-1,2,4-triazole-3-carboxamide The preparation was carried out in a similar manner to Example 160, except that in step 1, 3-bromo-4-fluorophenol was used in place of 3-bromo-4-methylphenol, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.70 (s, 1H), 9.92 (s, 1H), 8.45 (d, J=5.2 Hz, 1H), 8.34 (s, 1H), 7.48-7.26 (m, 4H), 7.26-7.15 (m, 2H), 7.15-6.99 (m, 2H), 4.26-4.14 (m, 3H), 4.01 (t, J=6.5 Hz, 2H), 1.84-1.68 (m, 2H), 1.56-1.41 (m, 2H), 1.10 (s, 6H). MS: 508 [M+H]$^+$.

Example 314: N-(4-(5-((4-ethyl-4-hydroxyhexyl)oxy)-2-fluorophenyl)pyridin-2-yl)-5-(2-fluorobenzyl)-4H-1,2,4-triazole-3-carboxamide The preparation was carried out in a similar manner to Example 160, except that in step 1, 3-bromo-4-fluorophenol was used in place of 3-bromo-4-methylphenol, in step 2, ethylmagnesium bromide was used in place of methylmagnesium bromide, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.21 (s, 1H), 9.91 (s, 1H), 8.45 (d, J=5.2 Hz, 1H), 8.34 (s, 1H), 7.48-7.26 (m, 4H), 7.26-7.14 (m, 2H), 7.14-6.97 (m, 2H), 4.21 (s, 2H), 4.01 (t, J=6.5 Hz, 2H), 3.91-3.88 (m, 1H), 1.77-1.57 (m, 2H), 1.48-1.39 (m, 2H), 1.35 (q, J=7.5 Hz, 4H), 0.78 (t, J=7.6 Hz, 6H). MS: 536 [M+H]$^+$.

Example 314

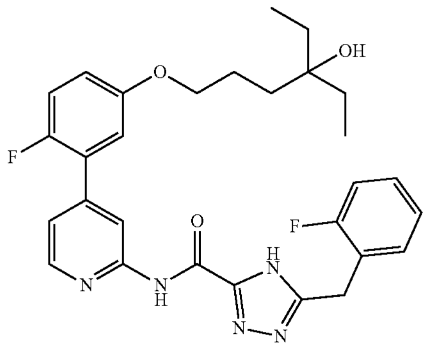

Example 315

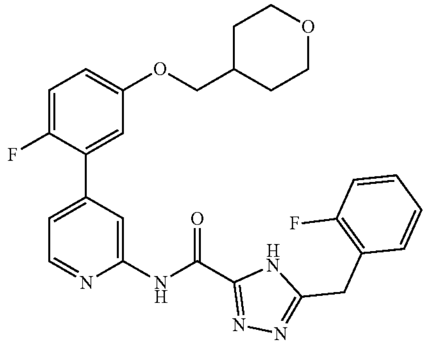

Example 315: 5-(2-fluorobenzyl)-N-(4-(2-fluoro-5-((tetrahydro-2H-pyran-4-yl)methoxy)phenyl)pyridin-2-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-bromo-4-fluorophenol was used in place of 2-bromo-3-methylphenol, and in step 3, ethyl 5-(2-fluorobenzyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.63 (s, 1H), 9.89 (s, 1H), 8.45 (d, J=5.2 Hz, 1H), 8.33 (s, 1H), 7.48-7.26 (m, 4H), 7.26-7.15 (m, 2H), 7.15-7.02 (m, 2H), 4.21 (s, 2H), 3.95-3.81 (m, 4H), 3.40-3.33 (m, 2H), 2.07-1.93 (m, 1H), 1.75-1.60 (m, 2H), 1.41-1.25 (m, 2H). MS: 506 $[M+H]^+$.

Example 316: N-(4-(2-fluoro-5-(2-(tetrahydro-2H-pyran-4-yl)ethoxy)phenyl)pyridin-2-yl)-5-(2-fluorobenzyl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, in step 2, 3-bromo-4-fluorophenol was used in place of 3-bromo-4-methylphenol, and in step 4, ethyl 5-(2-fluorobenzyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.66 (s, OH), 9.89 (s, 1H), 8.45 (d, J=5.2 Hz, 1H), 8.33 (s, 1H), 7.46-7.26 (m, 4H), 7.26-7.16 (m, 2H), 7.13 (dd, J=6.3, 3.1 Hz, 1H), 7.11-7.04 (m, 1H), 4.21 (s, 2H), 4.07 (t, J=6.2 Hz, 2H), 3.87-3.77 (m, 2H), 3.27 (dd, J=11.6, 2.1 Hz, 2H), 2.09-1.90 (m, 1H), 1.70-1.59 (m, 4H), 1.23-1.12 (m, 2H). MS: 520 $[M+H]^+$.

Example 316

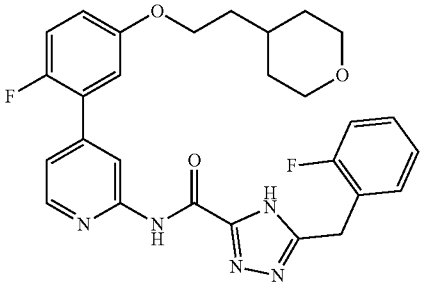

Example 317

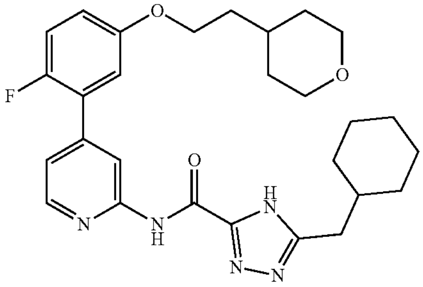

Example 317: 5-(cyclohexylmethyl)-N-(4-(2-fluoro-5-(2-(tetrahydro-2H-pyran-4-yl)ethoxy)phenyl)pyridin-2-yl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, in step 2, 3-bromo-4-fluorophenol was used in place of 3-bromo-4-methylphenol, and in step 4, ethyl 5-(cyclohexylmethyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.36 (s, 1H), 9.85 (s, 1H), 8.46 (d, J=5.2 Hz, 1H), 8.37 (s, 1H), 7.41 (d, J=5.2 Hz, 1H), 7.32 (dd, J=10.4, 9.0 Hz, 1H), 7.13 (dd, J=6.3, 3.1 Hz, 1H), 7.11-7.04 (m, 1H), 4.08 (t, J=6.3 Hz, 2H), 3.88-3.76 (m, 2H), 3.30-3.20 (m, 2H), 2.68 (d, J=7.1 Hz, 2H), 1.77-1.60 (m, 10H), 1.29-1.14 (m, 6H), 1.06-0.90 (m, 2H). MS: 508 $[M+H]^+$.

Example 318: N-(5-fluoro-4-(2-fluoro-5-((4-hydroxy-4-methylpentyl)oxy)phenyl)pyridin-2-yl)-5-(2-fluorobenzyl)-4H-1,2,4-triazole-3-carboxamide The preparation was carried out in a similar manner to Example 160, except that in step 1, 3-bromo-4-fluorophenol was used in place of 3-bromo-4-methylphenol, in step 3, 4-bromo-5-fluoropyridin-2-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.59 (s, 1H), 10.07 (s, 1H), 8.51 (d, J=1.4 Hz, 1H), 8.20 (d, J=5.4 Hz, 1H), 7.44-7.29 (m, 3H), 7.26-7.16 (m, 2H), 7.15-7.04 (m, 2H), 4.21 (s, 2H), 4.17 (s, 1H), 4.00 (t, J=6.5 Hz, 2H), 1.82-1.68 (m, 2H), 1.54-1.42 (m, 2H), 1.10 (s, 6H). MS: 526 $[M+H]^+$.

Example 318

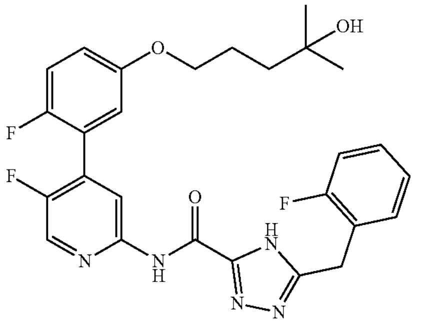

Example 319

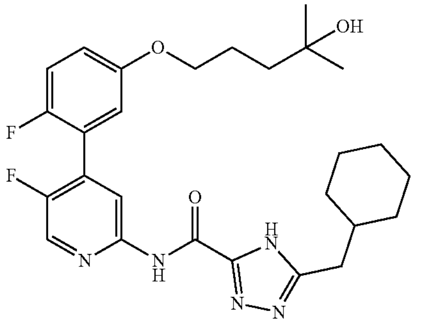

Example 319: 5-(cyclohexylmethyl)-N-(5-fluoro-4-(2-fluoro-5-((4-hydroxy-4-methylpentyl)oxy)phenyl)pyridin-2-yl)-4H-1,2,4-triazole-3-carboxamide The preparation was carried out in a similar manner to Example 160, except that in step 1, 3-bromo-4-fluorophenol was used in place of 3-bromo-4-methylphenol, in step 3, 4-bromo-5-fluoropyridin-2-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.35 (s, 1H), 10.04 (s, 1H), 8.52 (d, J=1.4 Hz, 1H), 8.23 (d, J=5.5 Hz, 1H), 7.40-7.26 (m, 1H), 7.17-7.03 (m, 2H), 4.18 (s, 1H), 4.00 (t, J=6.5 Hz, 2H), 2.67 (d, J=7.0 Hz, 2H), 1.84-1.71 (m, 3H), 1.71-1.61 (m, 4H), 1.55-1.44 (m, 2H), 1.29-1.12 (m, 4H), 1.10 (s, 6H), 1.05-0.92 (m, 2H). MS: 514 $[M+H]^+$.

Example 320: N-(5-chloro-4-(2-fluoro-5-((4-hydroxy-4-methylpentyl)oxy)phenyl)pyridin-2-yl)-5-(2-fluorobenzyl)-4H-1,2,4-triazole-3-carboxamide The preparation was carried out in a similar manner to Example 160, except that in step 1, 3-bromo-4-fluorophenol was used in place of 3-bromo-4-methylphenol, in step 3, 4-bromo-5-chloropyridin-2-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.61 (s, 1H), 10.10 (s, 1H), 8.56 (s, 1H), 8.18 (s, 1H), 7.51-7.14 (m, 5H), 7.14-7.04 (m, 1H), 6.99 (dd, J=5.9, 3.1 Hz, 1H), 4.26-4.14 (m, 3H), 3.98 (t, J=6.6 Hz, 2H), 1.83-1.67 (m, 2H), 1.54-1.39 (m, 2H), 1.09 (s, 6H). MS: 542 $[M+H]^+$.

Example 320

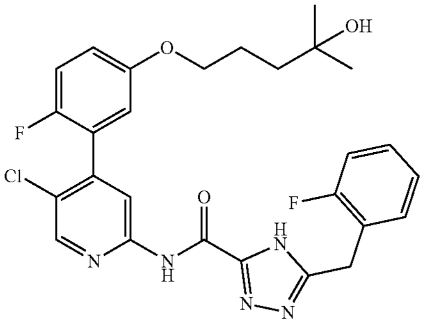

Example 321

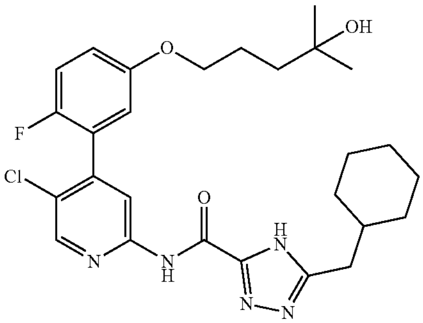

Example 321: N-(5-chloro-4-(2-fluoro-5-((4-hydroxy-4-methylpentyl)oxy)phenyl)pyridin-2-yl)-5-(cyclohexylmethyl)-4H-1,2,4-triazole-3-carboxamide The preparation was carried out in a similar manner to Example 160, except that in step 1, 3-bromo-4-fluorophenol was used in place of 3-bromo-4-methylphenol, in step 3, 4-bromo-5-chloropyridin-2-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.38 (s, 1H), 10.08 (s, 1H), 8.58 (s, 1H), 8.20 (s, 1H), 7.37-7.26 (m, 1H), 7.14-7.06 (m, 1H), 7.00 (dd, J=5.9, 3.1 Hz, 1H), 4.18 (s, 1H), 3.99 (t, J=6.5 Hz, 2H), 2.72-2.61 (m, 2H), 1.83-1.71 (m, 3H), 1.71-1.62 (m, 4H), 1.51-1.43 (m, 2H), 1.28-1.11 (m, 4H), 1.10 (s, 6H), 1.06-0.90 (m, 2H). MS: 530 $[M+H]^+$.

Example 322: N-(4-(2-fluoro-5-((4-hydroxy-4-methylpentyl)oxy)phenyl)-5-methylpyridin-2-yl)-5-(2-fluorobenzyl)-4H-1,2,4-triazole-3-carboxamide The preparation was carried out in a similar manner to Example 160, except that in step 1, 3-bromo-4-fluorophenol was used in place of 3-bromo-4-methylphenol, in step 3, 5-methyl-4-bromopyridin-2-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.64 (s, 1H), 9.83 (s, 1H), 8.33 (s, 1H), 8.00 (s, 1H), 7.49-7.12 (m, 5H), 7.12-6.97 (m, 1H), 6.90 (dd, J=6.0, 3.1 Hz, 1H), 4.27-4.13 (m, 3H), 3.98 (t, J=6.6 Hz, 2H), 2.12 (s, 3H), 1.83-1.67 (m, 2H), 1.53-1.42 (m, 2H), 1.09 (s, 6H). MS: 522 $[M+H]^+$.

Example 322

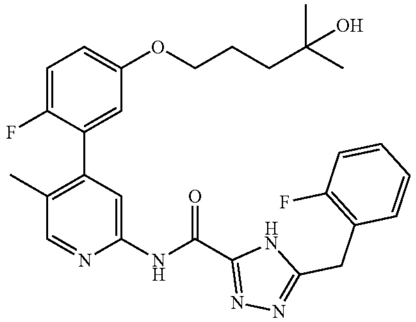

Example 323

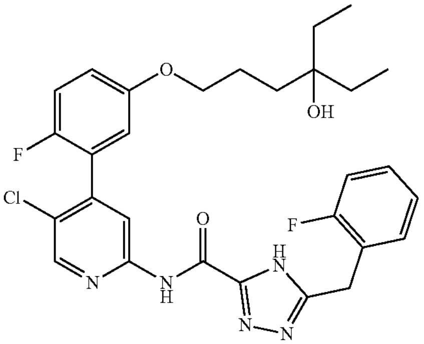

Example 323: N-(5-chloro-4-(5-((4-ethyl-4-hydroxyhexyl)oxy)-2-fluorophenyl)pyridin-2-yl)-5-(2-fluorobenzyl)-4H-1,2,4-triazole-3-carboxamide The preparation was carried out in a similar manner to Example 160, except that in step 1, 3-bromo-4-fluorophenol was used in place of 3-bromo-4-methylphenol, in step 2, ethylmagnesium bromide was used in place of methylmagnesium bromide, in step 3, 5-chloro-4-bromopyridin-2-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.65 (s, 1H), 10.14 (s, 1H), 8.57 (s, 1H), 8.17 (s, 1H), 7.46-7.25 (m, 3H), 7.25-7.15 (m, 2H), 7.14-7.05 (m, 1H), 6.99 (dd, J=5.9, 3.1 Hz, 1H), 4.21 (s, 2H), 3.98 (t, J=6.5 Hz, 2H), 3.88 (s, 1H), 1.75-1.61 (m, 2H), 1.48-1.38 (m, 2H), 1.34 (q, J=7.4 Hz, 4H), 0.77 (t, J=7.4 Hz, 6H). MS: 570 $[M+H]^+$.

Example 324: 5-(cyclohexylmethyl)-N-(5-chloro-4-(5-((4-ethyl-4-hydroxyhexyl)oxy)-2-fluorophenyl)pyridin-2-yl)-4H-1,2,4-triazole-3-carboxamide The preparation was carried out in a similar manner to Example 160, except that in step 1, 3-bromo-4-fluorophenol was used in place of 3-bromo-4-methylphenol, in step 2, ethylmagnesium bromide was used in place of methylmagnesium bromide, in step 3, 5-chloro-4-bromopyridin-2-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.38 (s, 1H), 10.08 (s, 1H), 8.58 (s, 1H), 8.20 (s, 1H), 7.39-7.23 (m, 1H), 7.15-7.04 (m, 1H), 6.99 (dd, J=5.8, 3.1 Hz, 1H), 3.99 (t, J=6.5 Hz, 2H), 3.88 (s, 1H), 2.67 (d, J=6.9 Hz, 2H), 1.82-1.57 (m, 8H), 1.49-1.38 (m, 2H), 1.34 (q, J=7.4 Hz, 4H), 1.28-1.09 (m, 3H), 1.06-0.91 (m, 2H), 0.77 (t, J=7.5 Hz, 6H). MS: 558 $[M+H]^+$.

Example 324

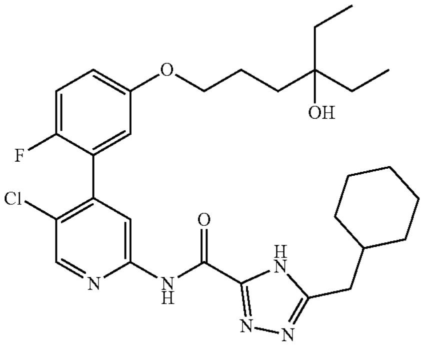

Example 325

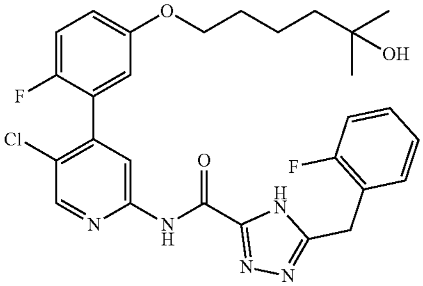

Example 325: N-(5-chloro-4-(2-fluoro-5-((5-hydroxyl-5-methylhexyl)oxy)phenyl)pyridin-2-yl)-5-(2-fluorobenzyl)-4H-1,2,4-triazole-3-carboxamide The preparation was carried out in a similar manner to Example 160, except that in step 1, methyl 5-bromopentanoate was used in place of methyl 4-bromobutanoate, 3-bromo-4-fluorophenol was used in place of 3-bromo-4-methylphenol, in step 3, 5-chloro-4-bromopyridin-2-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.66 (s, 1H), 10.16 (s, 1H), 8.57 (s, 1H), 8.17 (s, 1H), 7.45-7.26 (m, 3H), 7.26-7.15 (m, 2H), 7.15-7.04 (m, 1H), 7.00 (dd, J=5.8, 3.1 Hz, 1H), 4.21 (s, 2H), 4.10 (s, 1H), 3.99 (t, J=6.4 Hz, 2H), 1.74-1.63 (m, 2H), 1.51-1.34 (m, 4H), 1.06 (s, 6H). MS: 556 $[M+H]^+$.

Example 326: 5-(cyclohexylmethyl)-N-(5-chloro-4-(2-fluoro-5-((5-hydroxyl-5-methylhexyl)oxy)phenyl)pyridin-2-yl)-4H-1,2,4-triazole-3-carboxamide The preparation was carried out in a similar manner to Example 160, except that in step 1, methyl 5-bromopentanoate was used in place of methyl 4-bromobutanoate, 3-bromo-4-fluorophenol was used in place of 3-bromo-4-methylphenol, in step 3, 5-chloro-4-bromopyridin-2-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.39 (s, 1H), 10.10 (s, 1H), 8.58 (s, 1H), 8.20 (s, 1H), 7.37-7.26 (m, 1H), 7.16-7.06 (m, 1H), 7.01 (dd, J=5.8, 3.1 Hz, 1H), 4.10 (s, 1H), 4.00 (t, J=6.5 Hz, 2H), 2.70-2.61 (m, 2H), 1.81-1.56

(m, 8H), 1.51-1.34 (m, 4H), 1.28-1.14 (m, 3H), 1.07 (s, 6H), 1.04-0.89 (m, 2H). MS: 544 [M+H]+.

Example 326

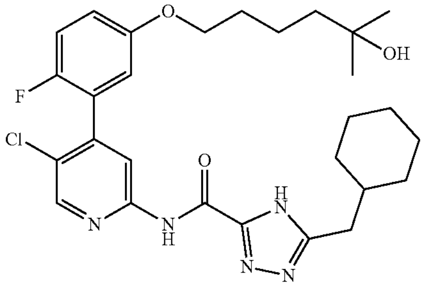

Example 327

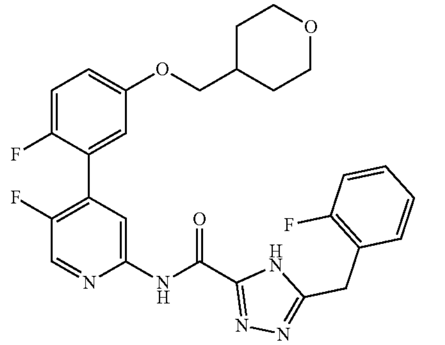

Example 327: N-(5-fluoro-4-(2-fluoro-5-((tetrahydro-2H-pyran-4-yl)methoxy)phenyl)pyridin-2-yl)-5-(2-fluorobenzyl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-bromo-4-fluorophenol was used in place of 3-bromo-4-methylphenol, in step 2, 5-fluoro-4-bromopyridin-2-amine was used in place of 4-bromopyridin-2-amine, and in step 3, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.58 (s, 1H), 10.05 (s, 1H), 8.51 (s, 1H), 8.25-8.09 (m, 1H), 7.45-7.07 (m, 6H), 6.53 (s, 1H), 4.23 (s, 2H), 3.93-3.82 (m, 4H), 3.35 (d, J=2.1 Hz, 2H), 2.05-1.92 (m, 1H), 1.72-1.61 (m, 2H), 1.39-1.24 (m, 2H). MS: 524 [M+H]+.

Example 328: 5-(cyclohexylmethyl)-N-(5-fluoro-4-(2-fluoro-5-((tetrahydro-2H-pyran-4-yl)methoxy)phenyl)pyridin-2-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-bromo-4-fluorophenol was used in place of 3-bromo-4-methylphenol, in step 2, 5-fluoro-4-bromopyridin-2-amine was used in place of 4-bromopyridin-2-amine, and in step 3, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.35 (s, 1H), 10.03 (s, 1H), 8.55-8.49 (m, 1H), 8.24 (d, J=5.4 Hz, 1H), 7.37-7.30 (m, 1H), 7.18-7.06 (m, 2H), 3.93-3.82 (m, 4H), 3.41-3.33 (m, 2H), 2.67 (d, J=7.0 Hz, 2H), 2.05-1.90 (m, 1H), 1.83-1.55 (m, 8H), 1.40-1.26 (m, 2H), 1.26-1.06 (m, 3H), 1.06-0.91 (m, 2H). MS: 512 [M+H]+.

Example 328

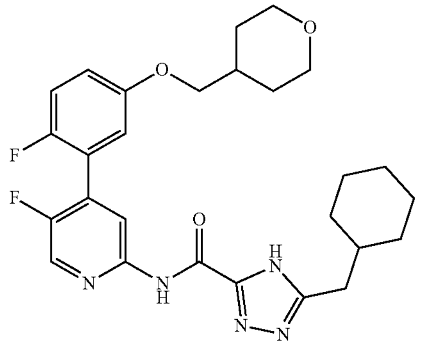

Example 329

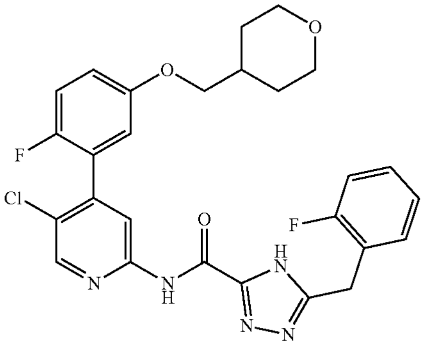

Example 329: N-(5-chloro-4-(2-fluoro-5-((tetrahydro-2H-pyran-4-yl)methoxy)phenyl)pyridin-2-yl)-5-(2-fluorobenzyl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-bromo-4-fluorophenol was used in place of 3-bromo-4-methylphenol, in step 2, 5-chloro-4-bromopyridin-2-amine was used in place of 4-bromopyridin-2-amine, and in step 3, ethyl 5-(2-fluorobenzyl)-4H-1,2,4-triazol-3-carboxylate was used in place of ethyl 5-benzyl-4H-1,2,4-triazol-3-carboxylate. $^1$HNMR (400 MHz, DMSO-$d_6$) δ 14.62 (s, 1H), 10.12 (s, 1H), 8.57 (s, 1H), 8.17 (s, 1H), 7.46-7.26 (m, 3H), 7.26-7.15 (m, 2H), 7.15-7.06 (m, 1H), 7.01 (dd, J=5.9, 3.1 Hz, 1H), 4.21 (s, 2H), 3.92-3.76 (m, 4H), 3.33-3.25 (m, 2H), 2.04-1.91 (m, 1H), 1.72-1.59 (m, 2H), 1.41-1.25 (m, 2H). MS: 540 [M+H]+.

Example 330: 5-(cyclohexylmethyl)-N-(5-chloro-4-(2-fluoro-5-((tetrahydro-2H-pyran-4-yl)methoxy)phenyl)pyridin-2-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-bromo-4-fluorophenol was used in place of 3-bromo-4-methylphenol, in step 2, 5-chloro-4-bromopyridin-2-amine was used in place of 4-bromopyridin-2-amine, and in step 3, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.38 (s, 1H), 10.09 (s, 1H), 8.58 (s, 1H), 8.20 (s, 1H), 7.37-7.26 (m, 1H), 7.16-7.07 (m, 1H), 7.02 (dd, J=5.9, 3.1 Hz, 1H), 3.93-3.82 (m, 4H), 3.34-3.27 (m, 2H), 2.71-2.63 (m, 2H), 2.06-1.92 (m, 1H), 1.85-1.52 (m, 8H), 1.39-1.14 (m, 5H), 1.06-0.90 (m, 2H). MS: 528 [M+H]$^+$.

Example 330

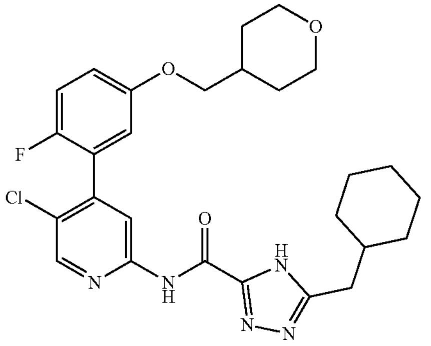

Example 331

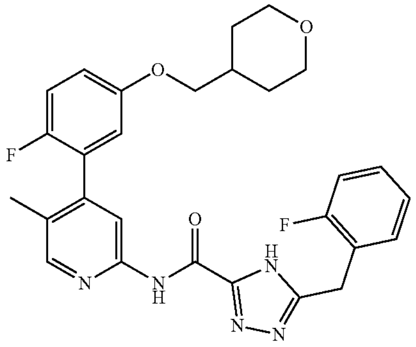

Example 331: N-(4-(2-fluoro-5-((tetrahydro-2H-pyran-4-yl)methoxy)phenyl)-5-methylpyridin-2-yl)-5-(2-fluorobenzyl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-bromo-4-fluorophenol was used in place of 3-bromo-4-methylphenol, in step 2, 5-methyl-4-bromopyridin-2-amine was used in place of 4-bromopyridin-2-amine, and in step 3, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.62 (s, 1H), 9.83 (s, 1H), 8.33 (s, 1H), 8.00 (s, 1H), 7.46-7.14 (m, 5H), 7.10-7.01 (m, 1H), 6.92 (dd, J=5.9, 3.1 Hz, 1H), 4.20 (s, 2H), 3.95-3.76 (m, 4H), 3.32-3.24 (m, 2H), 2.12 (s, 3H), 2.05-1.92 (m, 1H), 1.74-1.61 (m, 2H), 1.39-1.24 (m, 2H). MS: 520 [M+H]$^+$.

Example 332: 5-(cyclohexylmethyl)-N-(4-(2-fluoro-5-((tetrahydro-2H-pyran-4-yl)methoxy)phenyl)-5-methylpyridin-2-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-bromo-4-fluorophenol was used in place of 3-bromo-4-methylphenol, in step 2, 5-methyl-4-bromopyridin-2-amine was used in place of 4-bromopyridin-2-amine, and in step 3, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.35 (s, 1H), 9.80 (s, 1H), 8.34 (s, 1H), 8.03 (s, 1H), 7.34-7.24 (m, 1H), 7.11-7.02 (m, 1H), 6.92 (dd, J=6.0, 3.1 Hz, 1H), 3.93-3.79 (m, 4H), 3.33-3.27 (m, 2H), 2.70-2.62 (m, 2H), 2.13 (s, 3H), 2.05-1.93 (m, 1H), 1.82-1.55 (m, 8H), 1.40-1.14 (m, 5H), 1.05-0.90 (m, 2H). MS: 508 [M+H]$^+$.

Example 332

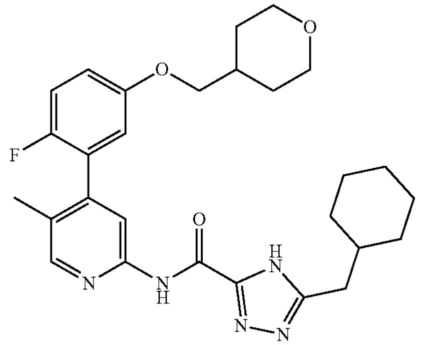

Example 333

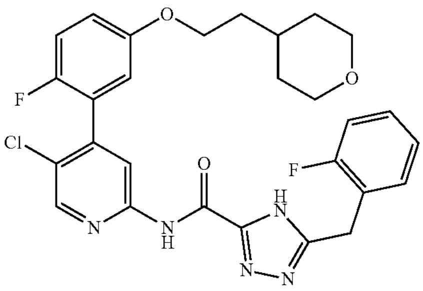

Example 333: N-(5-chloro-4-(2-fluoro-5-(2-(tetrahydro-2H-pyran-4-yl)ethoxy)phenyl)pyridin-2-yl)-5-(2-fluorobenzyl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, in step 2, 3-bromo-4-fluorophenol was used in place of 3-bromo-4-methylphenol, in step 3, 5-chloro-4-bromopyridin-2-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.61 (s, 1H), 10.11 (s, 1H), 8.57 (s, 1H), 8.18 (s, 1H), 7.50-7.27 (m, 3H), 7.27-7.15 (m, 2H), 7.15-7.06 (m, 1H), 7.02 (dd, J=5.9, 3.1 Hz, 1H), 4.22 (s, 2H), 4.04 (t, J=6.3 Hz, 2H), 3.86-3.78 (m, 2H), 3.32-3.23 (m, 2H), 1.78-1.56 (m, 5H), 1.29-1.12 (m, 2H). MS: 554 [M+H]$^+$.

Example 334: N-(5-chloro-4-(2-fluoro-5-(2-(tetrahydro-2H-pyran-4-yl)ethoxy)phenyl)pyridin-2-yl)-5-(cyclohexylmethyl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, in step 2, 3-bromo-4-fluorophenol was used in place of 3-bromo-4-methylphenol, in step 3, 5-chloro-4-bromopyridin-2-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.38 (s, 1H), 10.08 (s, 1H), 8.58 (s, 1H), 8.20 (s, 1H), 7.36-7.25 (m, 1H), 7.16-7.06 (m, 1H), 7.02 (dd, J=5.9, 3.1 Hz, 1H), 4.05 (t, J=6.2 Hz, 2H), 3.87-3.78 (m, 2H), 3.31-3.24 (m, 2H), 2.67 (d, J=7.0 Hz, 2H), 1.81-1.56 (m, 11H), 1.28-1.13 (m, 5H), 1.04-0.90 (m, 2H). MS: 542 [M+H]$^+$.

Example 334

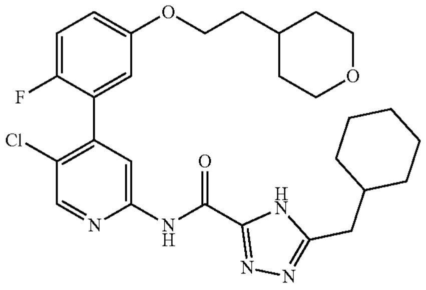

Example 335

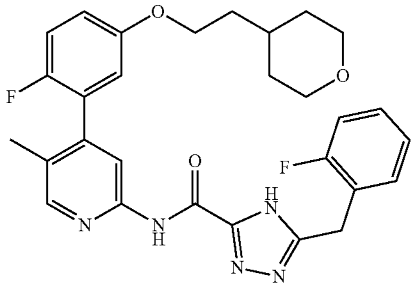

Example 335: N-(4-(2-fluoro-5-(2-(tetrahydro-2H-pyran-4-yl)ethoxy)phenyl)-5-methylpyridin-2-yl)-5-(2-fluorobenzyl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy) ethan-1-ol, in step 2, 3-bromo-4-fluorophenol was used in place of 3-bromo-4-methylphenol, in step 3, 5-methyl-4-bromopyridin-2-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.69 (s, 1H), 9.86 (s, 1H), 8.33 (s, 1H), 8.00 (s, 1H), 7.45-7.14 (m, 5H), 7.11-7.01 (m, 1H), 6.92 (dd, J=6.0, 3.1 Hz, 1H), 4.20 (s, 2H), 4.03 (t, J=6.3 Hz, 2H), 3.86-3.78 (m, 2H), 3.30-3.24 (m, 2H), 2.12 (s, 3H), 1.77-1.54 (m, 5H), 1.30-1.08 (m, 2H). MS: 534 [M+H]$^+$.

Example 336: 5-(cyclohexylmethyl)-N-(4-(2-fluoro-5-(2-(tetrahydro-2H-pyran-4-yl)ethoxy)phenyl)-5-methylpyridin-2-yl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy) ethan-1-ol, in step 2, 3-bromo-4-fluorophenol was used in place of 3-bromo-4-methylphenol, in step 3, 5-methyl-4-bromopyridin-2-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.35 (s, 1H), 9.79 (s, 1H), 8.34 (s, 1H), 8.03 (s, 1H), 7.35-7.22 (m, 1H), 7.11-7.02 (m, 1H), 6.93 (dd, J=6.0, 3.1 Hz, 1H), 4.04 (t, J=6.3 Hz, 2H), 3.87-3.77 (m, 2H), 3.32-3.22 (m, 2H), 2.66 (d, J=7.1 Hz, 2H), 2.13 (s, 3H), 1.81-1.55 (m, 11H), 1.30-1.11 (m, 5H), 1.05-0.89 (m, 2H). MS: 522 [M+H]$^+$.

Example 336

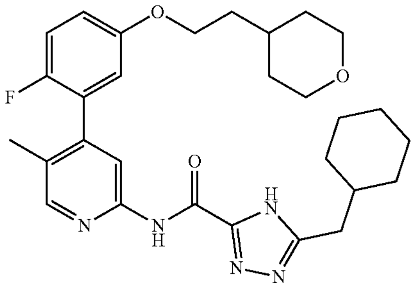

Example 337

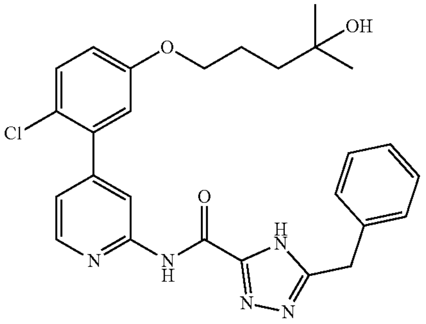

Example 337: 5-benzyl-N-(4-(5-((4-hydroxy-4-methylpentyl)oxy)-2-chlorophenyl)pyridin-2-yl)-4H-1,2,4-triazole-3-carboxamide The preparation was carried out in a similar manner to Example 160, except that in step 1, 3-bromo-4-chlorophenol was used in place of 3-bromo-4-methylphenol. $^1$H NMR (400 MHz, DMSO-$d_6$) δ 14.58 (s, 1H), 9.93 (s, 1H), 8.45 (d, J=5.1 Hz, 1H), 8.23 (s, 1H), 7.51 (d, J=8.8 Hz, 1H), 7.43-7.18 (m, 6H), 7.13-6.93 (m, 2H), 4.26-4.09 (m, 3H), 4.01 (t, J=6.6 Hz, 2H), 1.83-1.69 (m, 2H), 1.53-1.41 (m, 2H), 1.09 (s, 6H). MS: 506 [M+H]$^+$.

Example 338: N-(4-(2-chloro-5-((4-hydroxy-4-methylpentyl)oxy)phenyl)pyridin-2-yl)-5-(2-fluorobenzyl)-4H-1,2,4-triazole-3-carboxamide The preparation was carried out in a similar manner to Example 160, except that in step 1, 3-bromo-4-chlorophenol was used in place of 3-bromo-4-methylphenol, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.66 (s, 1H), 9.95 (s, 1H), 8.45 (d, J=5.2 Hz, 1H), 8.21 (s, 1H), 7.51 (d, J=8.8 Hz, 1H), 7.45-7.14 (m, 5H), 7.06 (dd, J=8.7, 3.0 Hz, 1H), 7.01 (d, J=3.0 Hz, 1H), 4.27-4.16 (m, 3H), 4.01 (t, J=6.6 Hz, 2H), 1.83-1.69 (m, 2H), 1.53-1.39 (m, 2H), 1.09 (s, 6H). MS: 524 [M+H]$^+$.

Example 338

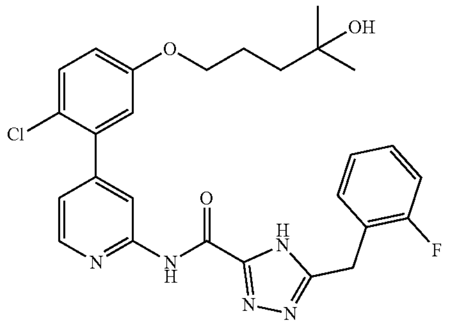

Example 339

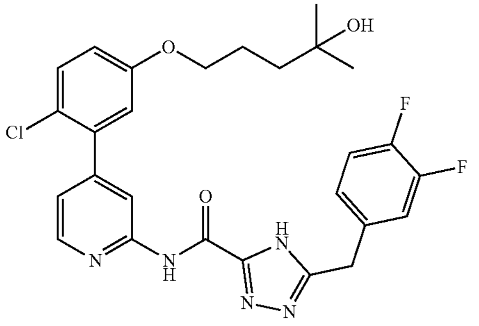

Example 339: N-(4-(2-chloro-5-((4-hydroxy-4-methylpentyl)oxy)phenyl)pyridin-2-yl)-5-(3,4-difluorobenzyl)-4H-1,2,4-triazole-3-carboxamide The preparation was carried out in a similar manner to Example 160, except that in step 1, 3-bromo-4-chlorophenol was used in place of 3-bromo-4-methylphenol, and in step 4, ethyl 5-(3,4-difluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.57 (s, 1H), 9.99 (s, 1H), 8.46 (d, J=5.1 Hz, 1H), 8.22 (s, 1H), 7.51 (d, J=8.8 Hz, 1H), 7.48-7.36 (m, 2H), 7.29 (dd, J=5.1, 1.6 Hz, 1H), 7.22-7.14 (m, 1H), 7.06 (dd, J=8.8, 3.0 Hz, 1H), 7.01 (d, J=3.0 Hz, 1H), 4.26-4.13 (m, 3H), 4.01 (t, J=6.6 Hz, 2H), 1.83-1.69 (m, 2H), 1.52-1.41 (m, 2H), 1.09 (s, 6H). MS: 542 $[M+H]^+$.

Example 340: 5-(5-chloro-2-fluorobenzyl)-N-(4-(2-chloro-5-((4-hydroxy-4-methylpentyl)oxy)phenyl)pyridin-2-yl)-4H-1,2,4-triazole-3-carboxamide The preparation was carried out in a similar manner to Example 160, except that in step 1, 3-bromo-4-chlorophenol was used in place of 3-bromo-4-methylphenol, and in step 4, ethyl 5-(5-chloro-2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.62 (s, 1H), 9.94 (s, 1H), 8.46 (d, J=5.1 Hz, 1H), 8.21 (s, 1H), 7.60-7.46 (m, 2H), 7.46-7.36 (m, 1H), 7.36-7.22 (m, 2H), 7.13-6.95 (m, 2H), 4.27-4.15 (m, 3H), 4.01 (t, J=6.6 Hz, 2H), 1.82-1.69 (m, 2H), 1.52-1.41 (m, 2H), 1.09 (s, 6H). MS: 558 $[M+H]^+$.

Example 340

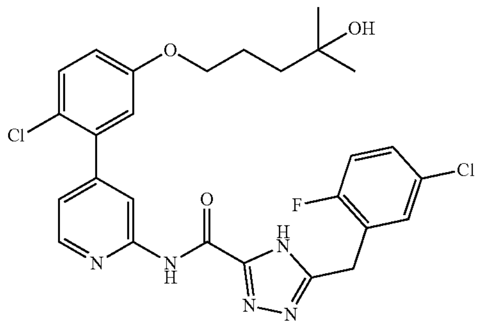

Example 341

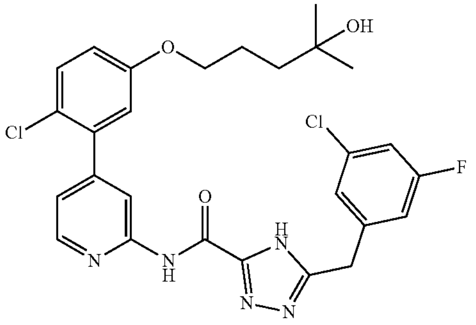

Example 341: N-(4-(2-chloro-5-((4-hydroxy-4-methylpentyl)oxy)phenyl)pyridin-2-yl)-5-(3-chloro-5-fluorobenzyl)-4H-1,2,4-triazole-3-carboxamide The preparation was carried out in a similar manner to Example 160, except that in step 1, 3-bromo-4-chlorophenol was used in place of 3-bromo-4-methylphenol, and in step 4, ethyl 5-(3-chloro-5-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.66 (s, 1H), 10.02 (s, 1H), 8.46 (d, J=5.1 Hz, 1H), 8.22 (s, 1H), 7.51 (d, J=8.8 Hz, 1H), 7.43-7.33 (m, 1H), 7.33-7.26 (m, 2H), 7.26-7.16 (m, 1H), 7.06 (dd, J=8.8, 3.0 Hz, 1H), 7.01 (d, J=3.0 Hz, 1H), 4.23 (s, 2H), 4.19 (s, 1H), 4.01 (t, J=6.6 Hz, 2H), 1.82-1.69 (m, 2H), 1.53-1.42 (m, 2H), 1.09 (s, 6H). MS: 558 $[M+H]^+$.

Example 342: 5-(3-chloro-4-fluorobenzyl)-N-(4-(2-chloro-5-((4-hydroxy-4-methylpentyl)oxy)phenyl)pyridin-2-yl)-4H-1,2,4-triazole-3-carboxamide The preparation was carried out in a similar manner to Example 160, except that in step 1, 3-bromo-4-chlorophenol was used in place of 3-bromo-4-methylphenol, and in step 4, ethyl 5-(3-chloro-4-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.58 (s, 1H), 9.98 (s, 1H), 8.46 (d, J=5.1 Hz, 1H), 8.22 (s, 1H), 7.59 (dd, J=7.2, 2.0 Hz, 1H), 7.51 (d, J=8.8 Hz, 1H), 7.43-7.32 (m, 2H), 7.29 (dd, J=5.1, 1.6 Hz, 1H), 7.06 (dd, J=8.8, 3.0 Hz, 1H), 7.01 (d, J=3.0 Hz, 1H), 4.28-4.14 (m, 3H), 4.01 (t, J=6.5 Hz, 2H), 1.82-1.70 (m, 2H), 1.52-1.42 (m, 2H), 1.09 (s, 6H). MS: 558 $[M+H]^+$.

Example 342

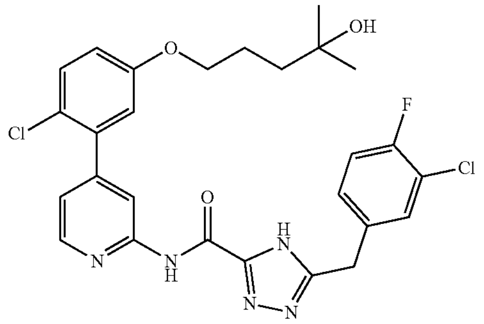

Example 343

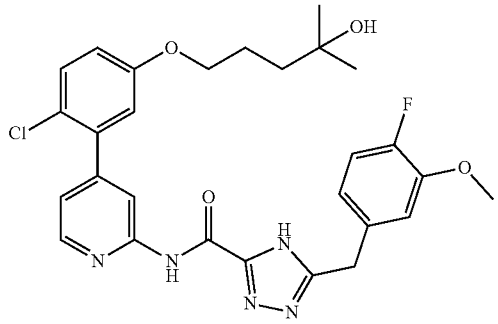

Example 343: N-(4-(2-chloro-5-((4-hydroxy-4-methylpentyl)oxy)phenyl)pyridin-2-yl)-5-(4-fluoro-3-methoxybenzyl)-4H-1,2,4-triazole-3-carboxamide The preparation was carried out in a similar manner to Example 160, except that in step 1, 3-bromo-4-chlorophenol was used in place of 3-bromo-4-methylphenol, and in step 4, ethyl 5-(4-fluoro-3-methoxybenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.52 (s, 1H), 9.92 (s, 1H), 8.46 (d, J=5.1 Hz, 1H), 8.23 (s, 1H), 7.51 (d, J=8.8 Hz, 1H), 7.31-7.25 (m, 1H), 7.20-7.12 (m, 2H), 7.06 (dd, J=8.8, 3.0 Hz, 1H), 7.01 (d, J=3.0 Hz, 1H), 6.89-6.83 (m, 1H), 4.24-4.11 (m, 3H), 4.01 (t, J=6.5 Hz, 2H), 3.83 (s, 3H), 1.83-1.69 (m, 2H), 1.53-1.41 (m, 2H), 1.09 (s, 6H). MS: 554 $[M+H]^+$.

Example 344: N-(4-(2-chloro-5-((4-hydroxy-4-methylpentyl)oxy)phenyl)pyridin-2-yl)-5-(3-fluoro-5-methylbenzyl)-4H-1,2,4-triazole-3-carboxamide The preparation was carried out in a similar manner to Example 160, except that in step 1, 3-bromo-4-chlorophenol was used in place of 3-bromo-4-methylphenol, and in step 4, ethyl 5-(3-fluoro-5-methylbenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.58 (s, 1H), 9.96 (s, 1H), 8.46 (d, J=5.1 Hz, 1H), 8.22 (s, 1H), 7.51 (d, J=8.8 Hz, 1H), 7.28 (dd, J=5.1, 1.6 Hz, 1H), 7.11-6.85 (m, 5H), 4.23-4.09 (m, 3H), 4.01 (t, J=6.6 Hz, 2H), 2.30 (s, 3H), 1.82-1.70 (m, 2H), 1.55-1.39 (m, 2H), 1.09 (s, 6H). MS: 538 $[M+H]^+$.

Example 344

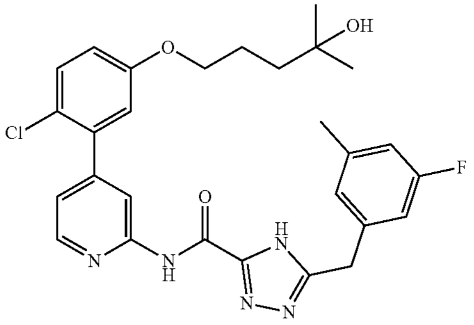

Example 345

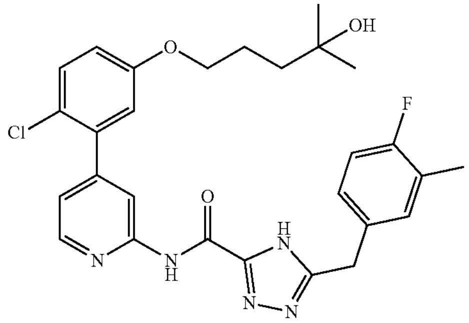

Example 345: N-(4-(2-chloro-5-((4-hydroxy-4-methylpentyl)oxy)phenyl)pyridin-2-yl)-5-(4-fluoro-3-methylbenzyl)-4H-1,2,4-triazole-3-carboxamide The preparation was carried out in a similar manner to Example 160, except that in step 1, 3-bromo-4-chlorophenol was used in place of 3-bromo-4-methylphenol, and in step 4, ethyl 5-(4-fluoro-3-methylbenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.52 (s, 1H), 9.91 (s, 1H), 8.46 (d, J=5.1 Hz, 1H), 8.22 (s, 1H), 7.51 (d, J=8.8 Hz, 1H), 7.36-6.94 (m, 6H), 4.18 (s, 1H), 4.13 (s, 2H), 4.01 (t, J=6.6 Hz, 2H), 2.21 (d, J=2.0 Hz, 3H), 1.83-1.69 (m, 2H), 1.54-1.41 (m, 2H), 1.09 (s, 6H). MS: 538 $[M+H]^+$.

Example 346: N-(4-(2-chloro-5-((4-hydroxy-4-methylpentyl)oxy)phenyl)pyridin-2-yl)-5-(2-fluoro-3-(trifluoromethyl)benzyl)-4H-1,2,4-triazole-3-carboxamide The preparation was carried out in a similar manner to Example 160, except that in step 1, 3-bromo-4-chlorophenol was used in place of 3-bromo-4-methylphenol, and in step 4, ethyl 5-(2-fluoro-3-(trifluoromethyl)benzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.76 (s, 1H), 9.98 (s, 1H), 8.45 (d, J=5.2 Hz, 1H), 8.21 (s, 1H), 7.86-7.65 (m, 2H), 7.57-7.34 (m, 2H), 7.28 (d, J=5.1 Hz, 1H), 7.11-6.91 (m, 2H), 4.32 (s, 2H), 4.18 (s, 1H), 4.01 (t, J=6.5 Hz, 2H), 1.83-1.66 (m, 2H), 1.55-1.39 (m, 2H), 1.09 (s, 6H). MS: 592 $[M+H]^+$.

Example 346

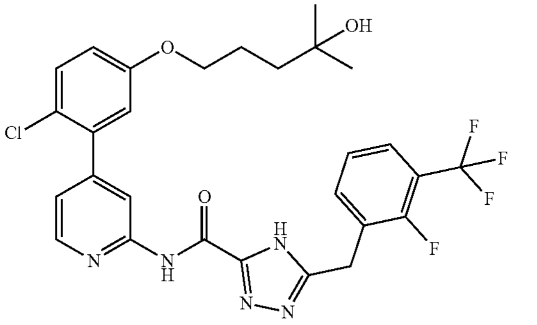

Example 347

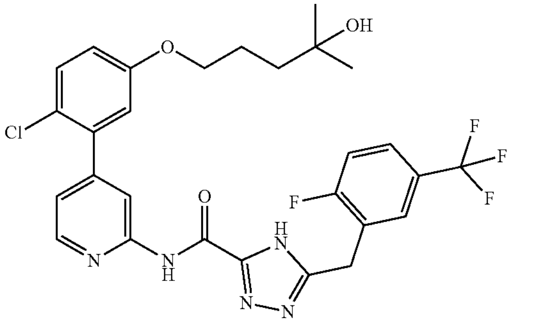

Example 347: N-(4-(2-chloro-5-((4-hydroxy-4-methylpentyl)oxy)phenyl)pyridin-2-yl)-5-(2-fluoro-5-(trifluoromethyl)benzyl)-4H-1,2,4-triazole-3-carboxamide The preparation was carried out in a similar manner to Example 160, except that in step 1, 3-bromo-4-chlorophenol was used in place of 3-bromo-4-methylphenol, and in step 4, ethyl 5-(2-fluoro-5-(trifluoromethyl)benzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.65 (s, 1H), 9.92 (s, 1H), 8.45 (d, J=5.1 Hz, 1H), 8.21 (s, 1H), 7.90 (d, J=6.4 Hz, 1H), 7.78 (d, J=8.8 Hz, 1H), 7.56-7.41 (m, 2H), 7.28 (dd, J=5.2, 1.6 Hz, 1H), 7.11-6.93 (m, 2H), 4.32 (s, 2H), 4.18 (s, 1H), 4.01 (t, J=6.6 Hz, 2H), 1.83-1.68 (m, 2H), 1.54-1.40 (m, 2H), 1.09 (s, 6H). MS: 592 $[M+H]^+$.

Example 348: N-(4-(2-chloro-5-((4-hydroxy-4-methylpentyl)oxy)phenyl)pyridin-2-yl)-5-(3-fluoro-5-(trifluoromethyl)benzyl)-4H-1,2,4-triazole-3-carboxamide The preparation was carried out in a similar manner to Example 160, except that in step 1, 3-bromo-4-chlorophenol was used in place of 3-bromo-4-methylphenol, in step 4, ethyl 5-(3-fluoro-5-(trifluoromethyl)benzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.66 (s, 1H), 10.02 (s, 1H), 8.46 (d, J=5.1 Hz, 1H), 8.22 (s, 1H), 7.68-7.45 (m, 4H), 7.29 (dd, J=5.1, 1.6 Hz, 1H), 7.12-6.94 (m, 2H), 4.34 (s, 2H), 4.19 (s, 1H), 4.01 (t, J=6.6 Hz, 2H), 1.84-1.69 (m, 2H), 1.53-1.41 (m, 2H), 1.09 (s, 6H). MS: 592 $[M+H]^+$.

Example 348

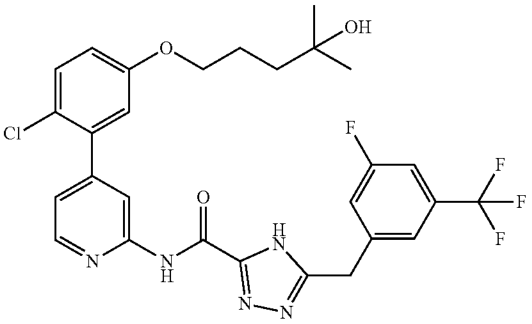

Example 349

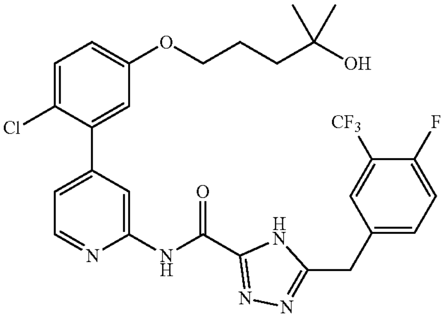

Example 349: N-(4-(2-chloro-5-((4-hydroxy-4-methylpentyl)oxy)phenyl)pyridin-2-yl)-5-(4-fluoro-3-(trifluoromethyl)benzyl)-4H-1,2,4-triazole-3-carboxamide The preparation was carried out in a similar manner to Example 160, except that in step 1, 3-bromo-4-chlorophenol was used in place of 3-bromo-4-methylphenol, and in step 4, ethyl 5-(4-fluoro-3-(trifluoromethyl)benzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.53 (s, 1H), 9.91 (s, 1H), 8.45 (d, J=5.2 Hz, 1H), 8.20 (d, J=20.8 Hz, 1H), 7.88-7.64 (m, 2H), 7.57-7.44 (m, 2H), 7.33-7.21 (m, 1H), 7.06 (dd, J=8.9, 3.0 Hz, 1H), 7.01 (d, J=3.0 Hz, 1H), 4.32 (s, 2H), 4.17 (s, 1H), 4.01 (t, J=6.6 Hz, 2H), 1.82-1.70 (m, 2H), 1.52-1.41 (m, 2H), 1.09 (s, 6H). MS: 592 $[M+H]^+$.

Example 350: N-(4-(2-chloro-5-((4-hydroxy-4-methylpentyl)oxy)phenyl)pyridin-2-yl)-5-(5-ethyl-2-fluorobenzyl)-4H-1,2,4-triazole-3-carboxamide The preparation was carried out in a similar manner to Example 160, except that in step 1, 3-bromo-4-chlorophenol was used in place of 3-bromo-4-methylphenol, and in step 4, ethyl 5-(5-ethyl-2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.58 (s, 1H), 9.88 (s, 1H), 8.45 (d, J=5.2 Hz, 1H), 8.22 (s, 1H), 7.50 (d, J=8.8 Hz, 1H), 7.35-6.93 (m, 6H), 4.25-4.09 (m, 3H), 4.09-3.93 (m, 2H), 2.58 (q, J=7.6 Hz, 2H), 1.82-1.68 (m, 2H), 1.55-1.38 (m, 2H), 1.16 (t, J=7.6 Hz, 3H), 1.09 (s, 6H). MS: 552 $[M+H]^+$.

Example 350

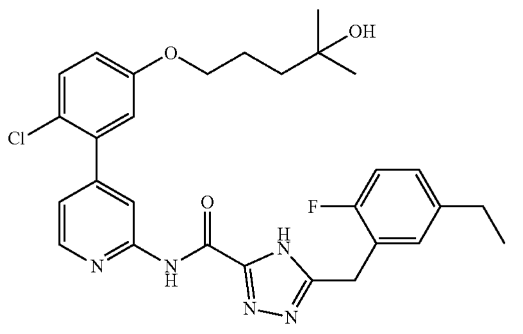

Example 351

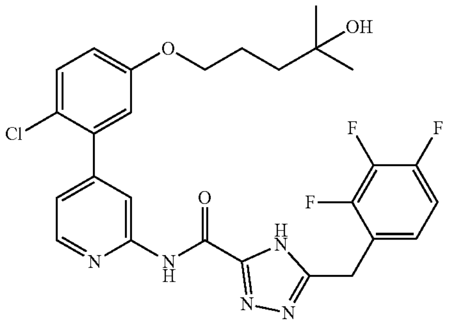

Example 351: N-(4-(2-chloro-5-((4-hydroxy-4-methylpentyl)oxy)phenyl)pyridin-2-yl)-5-(2,3,4-trifluorobenzyl)-4H-1,2,4-triazole-3-carboxamide The preparation was carried out in a similar manner to Example 160, except that in step 1, 3-bromo-4-chlorophenol was used in place of 3-bromo-4-methylphenol, and in step 4, ethyl 5-(2,3,4-trifluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.59 (s, 1H), 9.89 (s, 1H), 8.46 (d, J=5.2 Hz, 1H), 8.22 (s, 1H), 7.51 (d, J=8.8 Hz, 1H), 7.41-7.21 (m, 3H), 7.12-6.95 (m, 2H), 4.28 (s, 2H), 4.17 (s, 1H), 4.01 (t, J=6.5 Hz, 2H), 1.84-1.69 (m, 2H), 1.53-1.39 (m, 2H), 1.09 (s, 6H). MS: 560 $[M+H]^+$.

Example 352: N-(4-(2-chloro-5-((4-hydroxy-4-methylpentyl)oxy)phenyl)pyridin-2-yl)-5-(2,3,5-trifluorobenzyl)-4H-1,2,4-triazole-3-carboxamide The preparation was carried out in a similar manner to Example 160, except that in step 1, 3-bromo-4-chlorophenol was used in place of 3-bromo-4-methylphenol, and in step 4, ethyl 5-(2,3,5-trifluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.75 (s, 1H), 10.01 (s, 1H), 8.46 (d, J=5.1 Hz, 1H), 8.28-8.13 (m, 1H), 7.56-7.41 (m, 2H), 7.29 (dd, J=5.1, 1.6 Hz, 1H), 7.25-7.14 (m, 1H), 7.10-6.95 (m, 2H), 4.28 (s, 2H), 4.17 (s, 1H), 4.01 (t, J=6.6 Hz, 2H), 1.82-1.69 (m, 2H), 1.54-1.39 (m, 2H), 1.09 (s, 6H). MS: 560 $[M+H]^+$.

Example 352

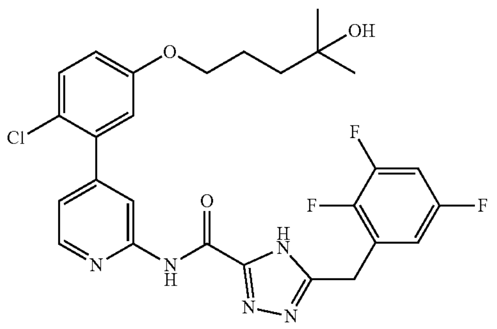

Example 353

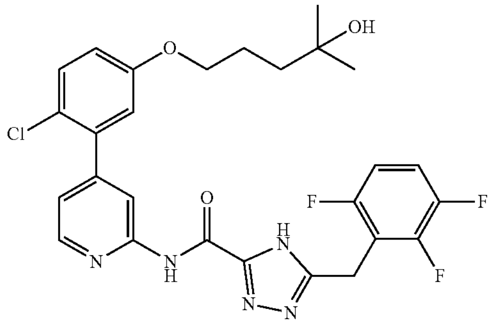

Example 353: N-(4-(2-chloro-5-((4-hydroxy-4-methylpentyl)oxy)phenyl)pyridin-2-yl)-5-(2,3,6-trifluorobenzyl)-4H-1,2,4-triazole-3-carboxamide The preparation was carried out in a similar manner to Example 160, except that in step 1, 3-bromo-4-chlorophenol was used in place of 3-bromo-4-methylphenol, and in step 4, ethyl 5-(2,3,6-trifluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.78 (s, 1H), 9.95 (s, 1H), 8.46 (d, J=5.1 Hz, 1H), 8.20 (s, 1H), 7.58-7.42 (m, 2H), 7.29 (dd, J=5.1, 1.6 Hz, 1H), 7.25-7.14 (m, 1H), 7.10-6.93 (m, 2H), 4.26 (s, 2H), 4.19 (s, 1H), 4.01 (t, J=6.6 Hz, 2H), 1.84-1.69 (m, 2H), 1.53-1.39 (m, 2H), 1.10 (s, 6H). MS: 560 $[M+H]^+$.

Example 354: N-(4-(2-chloro-5-((4-hydroxy-4-methylpentyl)oxy)phenyl)pyridin-2-yl)-5-(3,4,5-trifluorobenzyl)-4H-1,2,4-triazole-3-carboxamide The preparation was carried out in a similar manner to Example 160, except that in step 1, 3-bromo-4-chlorophenol was used in place of 3-bromo-4-methylphenol, and in step 4, ethyl 5-(3,4,5-trifluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.61 (s, 1H), 10.04 (s, 1H), 8.47 (d, J=5.1 Hz, 1H), 8.23 (s, 1H), 7.51 (d, J=8.8 Hz, 1H), 7.41-7.23 (m, 3H), 7.08-6.97 (m, 2H), 4.26-4.15 (m, 3H), 4.01 (t, J=6.6 Hz, 2H), 1.82-1.70 (m, 2H), 1.53-1.42 (m, 2H), 1.09 (s, 6H). MS: 560 $[M+H]^+$.

Example 354

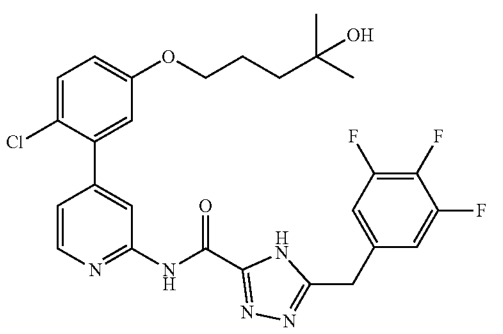

Example 355

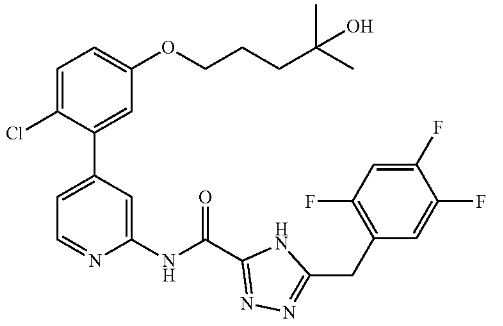

Example 355: N-(4-(2-chloro-5-((4-hydroxy-4-methylpentyl)oxy)phenyl)pyridin-2-yl)-5-(2,4,5-trifluorobenzyl)-4H-1,2,4-triazole-3-carboxamide The preparation was carried out in a similar manner to Example 160, except that in step 1, 3-bromo-4-chlorophenol was used in place of 3-bromo-4-methylphenol, and in step 4, ethyl 5-(2,4,5-trifluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.57 (s, 1H), 9.92 (s, 1H), 8.46 (d, J=5.1 Hz, 1H), 8.22 (s, 1H), 7.72-7.44 (m, 3H), 7.29 (d, J=4.8 Hz, 1H), 7.12-6.94 (m, 2H), 4.28-4.07 (m, 3H), 4.01 (t, J=6.5 Hz, 2H), 1.83-1.66 (m, 2H), 1.55-1.39 (m, 2H), 1.09 (s, 6H). MS: 560 $[M+H]^+$.

Example 356: N-(4-(2-chloro-5-((4-hydroxy-4-methylpentyl)oxy)phenyl)pyridin-2-yl)-5-(cyclopentylmethyl)-4H-1,2,4-triazole-3-carboxamide The preparation was carried out in a similar manner to Example 160, except that in step 1, 3-bromo-4-chlorophenol was used in place of 3-bromo-4-methylphenol, and in step 4, ethyl 5-(cyclopentylmethyl)-4H-1,2,4-triazole-3-carboxylate was used in place of ethyl 5-benzyl-4H-1,2,4-triazol-3-carboxylate. $^1$H NMR (400 MHz, DMSO-$d_6$) δ 14.39 (s, 1H), 9.90 (s, 1H), 8.46 (d, J=5.2 Hz, 1H), 8.24 (s, 1H), 7.51 (d, J=8.8 Hz, 1H), 7.28 (dd, J=5.1, 1.6 Hz, 1H), 7.12-6.96 (m, 2H), 4.19 (s, 1H), 4.02 (t, J=6.5 Hz, 2H), 2.78 (d, J=7.5 Hz, 2H), 2.36-2.20 (m, 1H), 1.82-1.66 (m, 4H), 1.66-1.57 (m, 2H), 1.57-1.43 (m, 4H), 1.24-1.20 (m, 2H), 1.09 (s, 6H). MS: 498 $[M+H]^+$.

Example 356

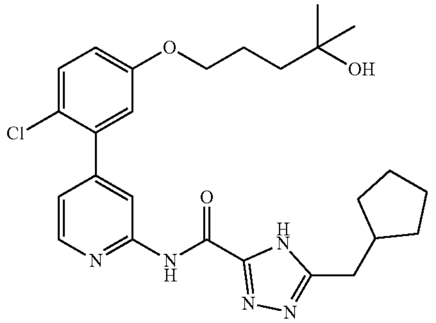

Example 357

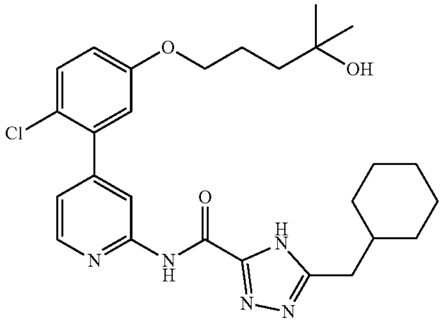

Example 357: N-(4-(2-chloro-5-((4-hydroxy-4-methylpentyl)oxy)phenyl)pyridin-2-yl)-5-(cyclohexylmethyl)-4H-1,2,4-triazole-3-carboxamide The preparation was carried out in a similar manner to Example 160, except that in step 1, 3-bromo-4-chlorophenol was used in place of 3-bromo-4-methylphenol, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.41 (s, 1H), 9.92 (s, 1H), 8.46 (d, J=5.1 Hz, 1H), 8.30-8.18 (m, 1H), 7.51 (d, J=8.8 Hz, 1H), 7.28 (dd, J=5.1, 1.6 Hz, 1H), 7.13-6.94 (m, 2H), 4.21 (s, 1H), 4.01 (t, J=6.5 Hz, 2H), 2.67 (d, J=7.0 Hz, 2H), 1.87-1.55 (m, 8H), 1.51-1.41 (m, 2H), 1.21-1.12 (m, 3H), 1.09 (s, 6H), 1.05-0.89 (m, 2H). MS: 512 $[M+H]^+$.

Example 358: N-(4-(2-chloro-5-((4-hydroxy-4-methylpentyl)oxy)phenyl)pyridin-2-yl)-5-(pyrrolidin-1-ylmethyl)-4H-1,2,4-triazole-3-carboxamide The preparation was carried out in a similar manner to Example 160, except that in step 1, 3-bromo-4-chlorophenol was used in place of 3-bromo-4-methylphenol, and in step 4, ethyl 5-(pyrrolidin-1-ylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 13.83 (s, 1H), 9.95 (s, 1H), 8.52-8.40 (m, 1H), 8.29-8.19 (m, 1H), 7.51 (d, J=8.8 Hz, 1H), 7.27 (dd, J=5.1, 1.6 Hz, 1H), 7.13-6.94 (m, 2H), 4.18 (s, 1H), 4.01 (t, J=6.6 Hz, 2H), 3.82 (s, 2H), 2.60-2.53 (m, 4H), 1.85-1.63 (m, 6H), 1.55-1.42 (m, 2H), 1.09 (s, 6H). MS: 499 $[M+H]^+$.

Example 358

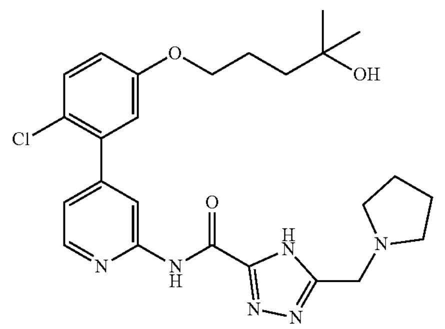

Example 359

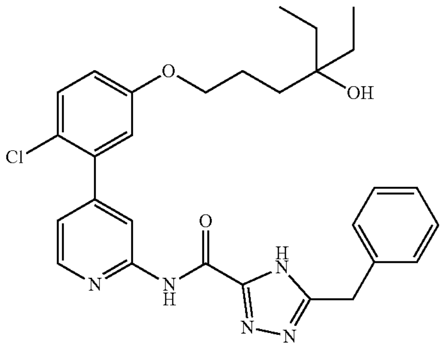

Example 359: 5-benzyl-N-(4-(2-chloro-5-((4-ethyl-4-hydroxyhexyl)oxy)phenyl)pyridin-2-yl)-4H-1,2,4-triazole-3-carboxamide The preparation was carried out in a similar manner to Example 160, except that in step 1, 3-bromo-4-chlorophenol was used in place of 3-bromo-4-methylphenol, and in step 2, ethylmagnesium bromide was used in place of methylmagnesium bromide. $^1H$ NMR (400 MHz, DMSO-$d_6$) δ 14.64 (s, 1H), 9.96 (s, 1H), 8.45 (d, J=5.1 Hz, 1H), 8.30-8.17 (m, 1H), 7.50 (d, J=8.8 Hz, 1H), 7.44-7.18 (m, 6H), 7.13-6.92 (m, 2H), 4.18 (s, 2H), 4.00 (t, J=6.5 Hz, 2H), 3.89 (s, 1H), 1.78-1.59 (m, 2H), 1.51-1.38 (m, 2H), 1.34 (q, J=7.4 Hz, 4H), 0.77 (t, J=7.4 Hz, 6H). MS: 534 $[M+H]^+$.

Example 360: N-(4-(2-chloro-5-((4-ethyl-4-hydroxyhexyl)oxy)phenyl)pyridin-2-yl)-5-(2-fluorobenzyl)-4H-1,2,4-triazole-3-carboxamide The preparation was carried out in a similar manner to Example 160, except that in step 1, 3-bromo-4-chlorophenol was used in place of 3-bromo-4-methylphenol, in step 2, ethylmagnesium bromide was used in place of methylmagnesium bromide, and in step 4, ethyl 5-(2-fluorobenzyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.68 (s, 1H), 9.94 (s, 1H), 8.45 (d, J=5.1 Hz, 1H), 8.21 (d, J=1.6 Hz, 1H), 7.50 (d, J=8.8 Hz, 1H), 7.47-7.30 (m, 2H), 7.28 (dd, J=5.1, 1.6 Hz, 1H), 7.25-7.16 (m, 2H), 7.05 (dd, J=8.8, 3.0 Hz, 1H), 7.00 (d, J=3.0 Hz, 1H), 4.21 (s, 2H), 4.01 (t, J=6.5 Hz, 2H), 3.89 (s, 1H), 1.76-1.62 (m, 2H), 1.47-1.38 (m, 2H), 1.34 (q, J=7.4 Hz, 4H), 0.77 (t, J=7.5 Hz, 6H). MS: 552 $[M+H]^+$.

Example 360

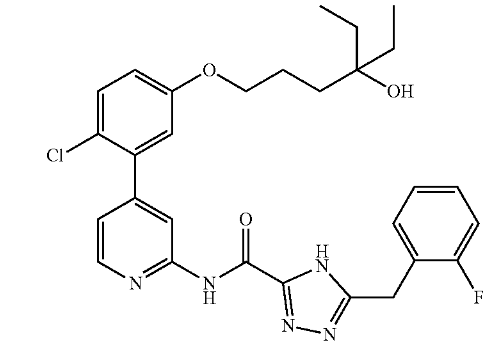

Example 361

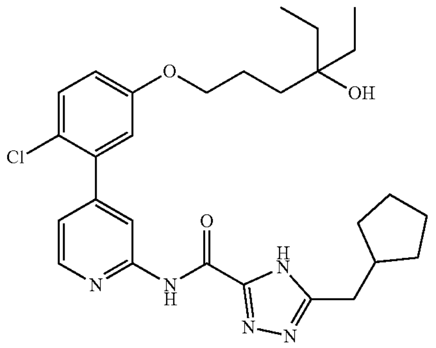

Example 361: N-(4-(2-chloro-5-((4-ethyl-4-hydroxyhexyl)oxy)phenyl)pyridin-2-yl)-5-(cyclopentylmethyl)-4H-1,2,4-triazole-3-carboxamide The preparation was carried out in a similar manner to Example 160, except that in step 1, 3-bromo-4-chlorophenol was used in place of 3-bromo-4-methylphenol, in step 2, ethylmagnesium bromide was used in place of methylmagnesium bromide, and in step 4, ethyl 5-(cyclopentylmethyl)-4H-1,2,4-triazole-3-carboxylate was used in place of ethyl 5-benzyl-4H-1,2,4-triazol-3-carboxylate. $^1H$ NMR (400 MHz, DMSO-$d_6$) δ 14.42 (s, 1H), 9.90 (s, 1H), 8.46 (dd, J=5.1, 0.8 Hz, 1H), 8.32-8.18 (m, 1H), 7.51 (d, J=8.8 Hz, 1H), 7.28 (dd, J=5.1, 1.6 Hz, 1H), 7.12-6.94 (m, 2H), 4.01 (t, J=6.5 Hz, 2H), 3.89 (s, 1H), 2.78 (d, J=7.5 Hz, 2H), 2.36-2.19 (m, 1H), 1.80-1.64 (m, 4H), 1.64-1.47 (m, 4H), 1.47-1.29 (m, 6H), 1.29-1.14 (m, 2H), 0.77 (t, J=7.4 Hz, 6H). MS: 526 $[M+H]^+$.

Example 362: N-(4-(2-chloro-5-((4-ethyl-4-hydroxyhexyl)oxy)phenyl)pyridin-2-yl)-5-(cyclohexylmethyl)-4H-1,2,4-triazole-3-carboxamide The preparation was carried out in a similar manner to Example 160, except that in step 1, 3-bromo-4-chlorophenol was used in place of 3-bromo-4-methylphenol, in step 2, ethylmagnesium bromide was used in place of methylmagnesium bromide, and in step 4, ethyl 5-(cyclohexylmethyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.40 (s, 1H), 9.90 (s, 1H), 8.46 (d, J=5.1 Hz, 1H), 8.24 (d, J=1.4 Hz, 1H), 7.51 (d, J=8.8 Hz, 1H), 7.28 (dd, J=5.1, 1.6 Hz, 1H), 7.16-6.95 (m, 2H), 4.01 (t, J=6.5 Hz, 2H), 3.89 (s, 1H), 2.67 (d, J=7.1 Hz, 2H), 1.86-1.56 (m, 8H), 1.48-1.39 (m, 2H), 1.35 (q, J=7.5 Hz, 4H), 1.25-1.12 (m, 3H), 1.05-0.92 (m, 2H), 0.78 (t, J=7.5 Hz, 6H). MS: 540 $[M+H]^+$.

Example 362

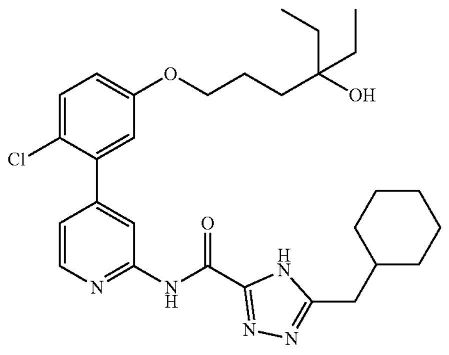

Example 363

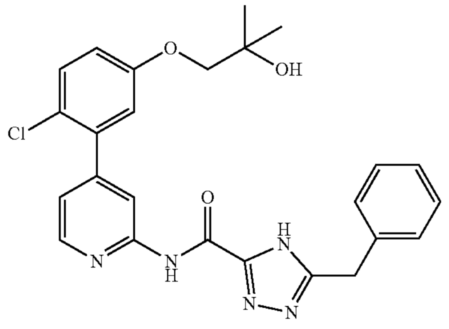

Example 363: 5-benzyl-N-(4-(2-chloro-5-(2-hydroxyl-2-methylpropoxy)phenyl)pyridin-2-yl)-4H-1,2,4-triazole-3-carboxamide The preparation was carried out in a similar manner to Example 160, except that in step 1, 3-bromo-4-chlorophenol was used in place of 3-bromo-4-methylphenol, and methyl bromoacetate was used in place of methyl 4-bromobutanoate. $^1$H NMR (400 MHz, DMSO-$d_6$) δ 14.63 (s, 1H), 9.96 (s, 1H), 8.55-8.39 (m, 1H), 8.29-8.16 (m, 1H), 7.51 (d, J=8.8 Hz, 1H), 7.41-7.19 (m, 6H), 7.13-6.99 (m, 2H), 4.66 (s, 1H), 4.18 (s, 2H), 3.77 (s, 2H), 1.19 (s, 6H). MS: 478 $[M+H]^+$.

Example 364: 5-(2-fluorobenzyl)-N-(4-(2-chloro-5-(2-hydroxyl-2-methylpropoxy)phenyl)pyridin-2-yl)-4H-1,2,4-triazole-3-carboxamide The preparation was carried out in a similar manner to Example 160, except that in step 1, 3-bromo-4-chlorophenol was used in place of 3-bromo-4-methylphenol, methyl bromoacetate was used in place of methyl 4-bromobutanoate, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.70 (s, 1H), 9.94 (s, 1H), 8.45 (d, J=5.1 Hz, 1H), 8.31-8.12 (m, 1H), 7.51 (d, J=8.8 Hz, 1H), 7.47-7.26 (m, 3H), 7.26-7.13 (m, 2H), 7.13-6.96 (m, 2H), 4.66 (s, 1H), 4.21 (s, 2H), 3.77 (s, 2H), 1.19 (s, 6H). MS: 496 $[M+H]^+$.

Example 364

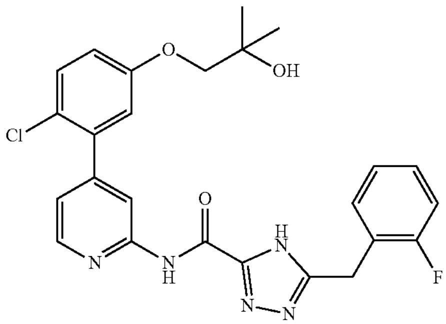

Example 365

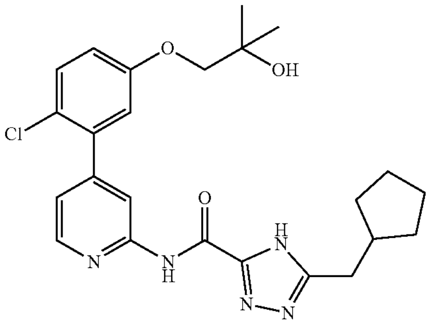

Example 365: N-(4-(2-chloro-5-(2-hydroxyl-2-methylpropoxy)phenyl)pyridin-2-yl)-5-(cyclopentylmethyl)-4H-1,2,4-triazole-3-carboxamide The preparation was carried out in a similar manner to Example 160, except that in step 1, 3-bromo-4-chlorophenol was used in place of 3-bromo-4-methylphenol, methyl bromoacetate was used in place of methyl 4-bromobutanoate, and in step 4, ethyl 5-(cyclopentylmethyl)-4H-1,2,4-triazole-3-carboxylate was used in place of ethyl 5-benzyl-4H-1,2,4-triazol-3-carboxylate. $^1$H NMR (400 MHz, DMSO-$d_6$) δ 14.40 (s, 1H), 9.91 (s, 1H), 8.46 (dd, J=5.1, 0.8 Hz, 1H), 8.34-8.19 (m, 1H), 7.52 (d, J=8.8 Hz, 1H), 7.29 (dd, J=5.1, 1.6 Hz, 1H), 7.15-6.93 (m, 2H), 4.66 (s, 1H), 3.78 (s, 2H), 2.78 (d, J=7.5 Hz, 2H), 2.37-2.19 (m, 1H), 1.82-1.66 (m, 2H), 1.66-1.44 (m, 4H), 1.30-1.12 (m, 8H). MS: 470 $[M+H]^+$.

Example 366: N-(4-(2-chloro-5-(2-hydroxyl-2-methylpropoxy)phenyl)pyridin-2-yl)-5-(cyclohexylmethyl)-4H-1,2,4-triazole-3-carboxamide The preparation was carried out in a similar manner to Example 160, except that in step 1, 3-bromo-4-chlorophenol was used in place of 3-bromo-4-methylphenol, methyl bromoacetate was used in place of methyl 4-bromobutanoate, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.39 (s, 1H), 9.90 (s, 1H), 8.46 (d, J=5.1 Hz, 1H), 8.24 (d, J=1.4 Hz, 1H), 7.52 (d, J=8.8 Hz, 1H), 7.29 (dd, J=5.1, 1.6 Hz, 1H), 7.16-6.95 (m, 2H), 4.66 (s, 1H), 3.78 (s, 2H), 2.67 (d, J=7.0 Hz, 2H), 1.83-1.71 (m, 1H), 1.71-1.53 (m, 5H), 1.29-1.06 (m, 9H), 1.06-0.89 (m, 2H). MS: 484 $[M+H]^+$.

Example 366

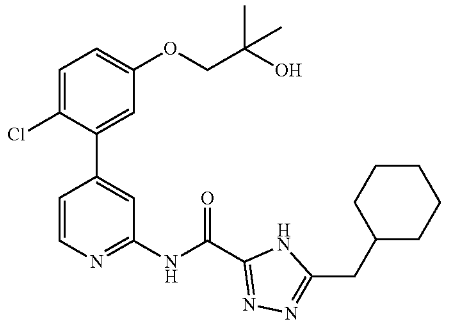

Example 367

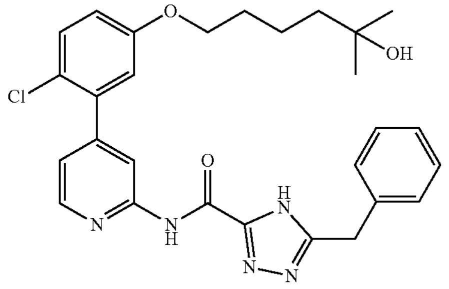

Example 367: 5-benzyl-N-(4-(2-chloro-5-((5-hydroxyl-5-methylhexyl)oxy)phenyl)pyridin-2-yl)-4H-1,2,4-triazole-3-carboxamide The preparation was carried out in a similar manner to Example 160, except that in step 1, 3-bromo-4-chlorophenol was used in place of 3-bromo-4-methylphenol, and methyl 5-bromopentanoate was used in place of methyl 4-bromobutanoate. $^{1}$H NMR (400 MHz, DMSO-$d_6$) δ 14.65 (s, 1H), 9.96 (s, 1H), 8.45 (dd, J=5.1, 0.8 Hz, 1H), 8.23 (dd, J=1.5, 0.8 Hz, 1H), 7.50 (d, J=8.8 Hz, 1H), 7.45-7.20 (m, 6H), 7.13-6.97 (m, 2H), 4.18 (s, 2H), 4.10 (s, 1H), 4.02 (t, J=6.5 Hz, 2H), 1.75-1.62 (m, 2H), 1.51-1.32 (m, 4H), 1.06 (s, 6H). MS: 520 $[M+H]^+$.

Example 368: 5-(2-fluorobenzyl)-N-(4-(2-chloro-5-((5-hydroxyl-5-methylhexyl)oxy)phenyl)pyridin-2-yl)-4H-1,2,4-triazole-3-carboxamide The preparation was carried out in a similar manner to Example 160, except that in step 1, 3-bromo-4-chlorophenol was used in place of 3-bromo-4-methylphenol, methyl 5-bromopentanoate was used in place of methyl 4-bromobutanoate, and in step 4, ethyl 5-(2-fluorobenzyl)-4H-1,2,4-triazol-3-carboxylate was used in place of ethyl 5-benzyl-4H-1,2,4-triazol-3-carboxylate. $^{1}$H NMR (400 MHz, DMSO-$d_6$) δ 14.71 (s, 1H), 9.94 (s, 1H), 8.44 (d, J=5.1 Hz, 1H), 8.31-8.13 (m, 1H), 7.49 (d, J=8.8 Hz, 1H), 7.45-7.30 (m, 2H), 7.27 (dd, J=5.1, 1.6 Hz, 1H), 7.25-7.15 (m, 2H), 7.09-6.98 (m, 2H), 4.21 (s, 2H), 4.11 (s, 1H), 4.01 (t, J=6.4 Hz, 2H), 1.69 (t, J=7.0 Hz, 2H), 1.49-1.33 (m, 4H), 1.06 (s, 6H). MS: 538 $[M+H]^+$.

Example 368

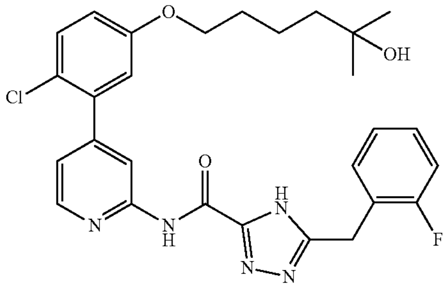

Example 369

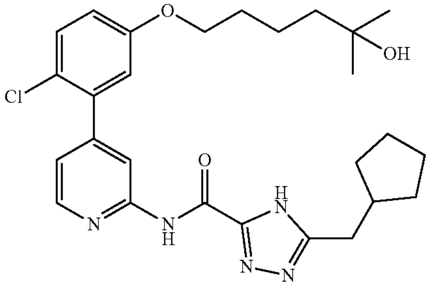

Example 369: N-(4-(2-chloro-5-((5-hydroxyl-5-methylhexyl)oxy)phenyl)pyridin-2-yl)-5-(cyclopentylmethyl)-4H-1,2,4-triazole-3-carboxamide The preparation was carried out in a similar manner to Example 160, except that in step 1, 3-bromo-4-chlorophenol was used in place of 3-bromo-4-methylphenol, methyl 5-bromopentanoate was used in place of methyl 4-bromobutanoate, and in step 4, ethyl 5-(cyclopentylmethyl)-4H-1,2,4-triazole-3-carboxylate was used in place of ethyl 5-benzyl-4H-1,2,4-triazol-3-carboxylate. $^{1}$H NMR (400 MHz, DMSO-$d_6$) δ 14.42 (s, 1H), 9.90 (s, 1H), 8.46 (dd, J=5.1, 0.8 Hz, 1H), 8.25 (dd, J=1.6, 0.8 Hz, 1H), 7.51 (d, J=8.8 Hz, 1H), 7.28 (dd, J=5.1, 1.6 Hz, 1H), 7.11-6.96 (m, 2H), 4.10 (s, 1H), 4.02 (t, J=6.5 Hz, 2H), 2.78 (d, J=7.5 Hz, 2H), 2.36-2.19 (m, 1H), 1.79-1.65 (m, 4H), 1.65-1.33 (m, 8H), 1.30-1.15 (m, 2H), 1.06 (s, 6H). MS: 512 $[M+H]^+$.

Example 370: N-(4-(2-chloro-5-((5-hydroxyl-5-methylhexyl)oxy)phenyl)pyridin-2-yl)-5-(cyclohexylmethyl)-4H-1,2,4-triazole-3-carboxamide The preparation was carried out in a similar manner to Example 160, except that in step 1, 3-bromo-4-chlorophenol was used in place of 3-bromo-4-methylphenol, methyl 5-bromopentanoate was used in place of methyl 4-bromobutanoate, and in step 4, ethyl 5-(cyclohexylmethyl)-4H-1,2,4-triazol-3-carboxylate was used in place of ethyl 5-benzyl-4H-1,2,4-triazol-3-carboxylate. $^{1}$H NMR (400 MHz, DMSO-$d_6$) δ 14.38 (s, 1H), 9.90 (s, 1H), 8.46 (d, J=5.1 Hz, 1H), 8.24 (s, 1H), 7.51 (d, J=8.8 Hz, 1H), 7.28 (dd, J=5.1, 1.6 Hz, 1H), 7.13-6.97 (m, 2H), 4.10 (s, 1H), 4.03 (t, J=6.4 Hz, 2H), 2.67 (d, J=7.0 Hz, 2H), 1.84-1.58 (m, 7H), 1.52-1.35 (m, 4H), 1.31-1.10 (m, 4H), 1.06 (s, 6H), 1.02-0.92 (m, 2H). MS: 526 $[M+H]^+$.

Example 370

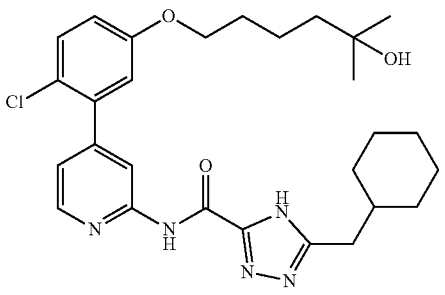

Example 371

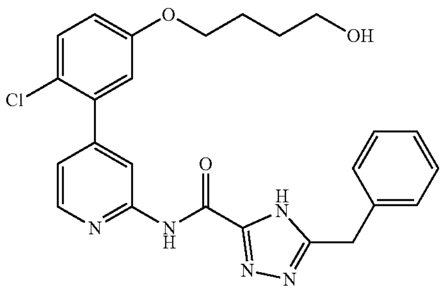

Example 371: 5-benzyl-N-(4-(2-chloro-5-(4-hydroxybutoxy)phenyl)pyridin-2-yl)-4H-1,2,4-triazole-3-carboxamide The preparation was carried out in a similar manner to Example 92, except that in step 1, 4-bromo-1-butanol was used in place of iodomethane, and 3-bromo-4-chlorophenol was used in place of 2-bromo-3-methylphenol. $^1$H NMR (400 MHz, DMSO-$d_6$) δ 14.56 (s, 1H), 9.92 (s, 1H), 8.45 (d, J=5.1 Hz, 1H), 8.22 (s, 1H), 7.51 (d, J=8.8 Hz, 1H), 7.40-7.30 (m, 4H), 7.30-7.21 (m, 2H), 7.06 (dd, J=8.8, 3.0 Hz, 1H), 7.02 (d, J=3.0 Hz, 1H), 4.45 (t, J=5.1 Hz, 1H), 4.18 (s, 2H), 4.03 (t, J=6.5 Hz, 2H), 3.47-3.41 (m, 2H), 1.81-1.69 (m, 2H), 1.61-1.50 (m, 2H). MS: 478 $[M+H]^+$.

Example 372: 5-(2-fluorobenzyl)-N-(4-(2-chloro-5-(4-hydroxybutoxy)phenyl)pyridin-2-yl)-4H-1,2,4-triazole-3-carboxamide The preparation was carried out in a similar manner to Example 92, except that in step 1, 4-bromo-1-butanol was used in place of iodomethane, 3-bromo-4-chlorophenol was used in place of 2-bromo-3-methylphenol, and in step 3, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.54 (s, 1H), 9.91 (s, 1H), 8.45 (d, J=5.1 Hz, 1H), 8.21 (s, 1H), 7.51 (d, J=8.8 Hz, 1H), 7.46-7.31 (m, 2H), 7.28 (d, J=5.2 Hz, 1H), 7.26-7.15 (m, 2H), 7.11-6.98 (m, 2H), 4.45 (t, J=5.2 Hz, 1H), 4.21 (s, 2H), 4.03 (t, J=6.5 Hz, 2H), 3.46-3.42 (m, 2H), 1.80-1.67 (m, 2H), 1.62-1.49 (m, 2H). MS: 496 $[M+H]^+$.

Example 372

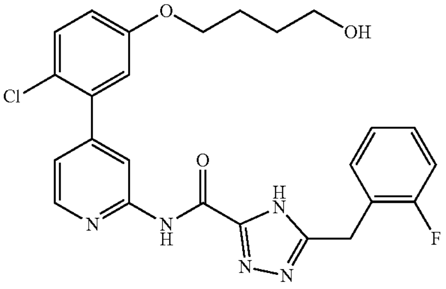

Example 373

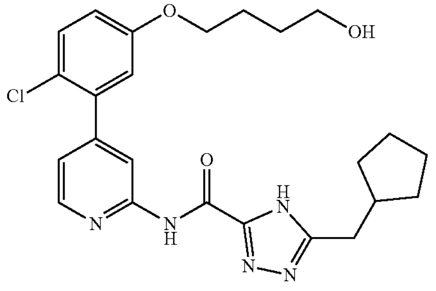

Example 373: N-(4-(2-chloro-5-(4-hydroxybutoxy)phenyl)pyridin-2-yl)-5-(cyclopentylmethyl)-4H-1,2,4-triazole-3-carboxamide The preparation was carried out in a similar manner to Example 92, except that in step 1, 4-bromo-1-butanol was used in place of iodomethane, 3-bromo-4-chlorophenol was used in place of 2-bromo-3-methylphenol, and in step 3, ethyl 5-(cyclopentylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.38 (s, 1H), 9.88 (s, 1H), 8.46 (d, J=5.2 Hz, 1H), 8.24 (s, 1H), 7.51 (d, J=8.8 Hz, 1H), 7.29 (d, J=5.0 Hz, 1H), 7.12-6.99 (m, 2H), 4.45 (t, J=5.2 Hz, 1H), 4.04 (t, J=6.5 Hz, 2H), 3.46-3.43 (m, 2H), 2.78 (d, J=7.5 Hz, 2H), 2.31-2.23 (m, 1H), 1.78-1.68 (m, 4H), 1.65-1.48 (m, 6H), 1.25-1.22 (m, 2H). MS: 470 $[M+H]^+$.

Example 374: N-(4-(2-chloro-5-(4-hydroxybutoxy)phenyl)pyridin-2-yl)-5-(cyclohexylmethyl)-4H-1,2,4-triazole-3-carboxamide The preparation was carried out in a similar manner to Example 92, except that in step 1, 4-bromo-1-butanol was used in place of iodomethane, 3-bromo-4-chlorophenol was used in place of 2-bromo-3-methylphenol, and in step 3, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.39 (s, 1H), 9.89 (s, 1H), 8.46 (dd, J=5.1, 0.8 Hz, 1H), 8.24 (d, J=1.1 Hz, 1H), 7.51 (d, J=8.8 Hz, 1H), 7.28 (dd, J=5.1, 1.6 Hz, 1H), 7.13-6.98 (m, 2H), 4.45 (t, J=5.2 Hz, 1H), 4.04 (t, J=6.5 Hz, 2H), 3.47-3.41 (m, 2H), 2.67 (d, J=7.0 Hz, 2H), 1.81-1.52 (m, 10H), 1.22-0.90 (m, 5H). MS: 484 $[M+H]^+$.

Example 374

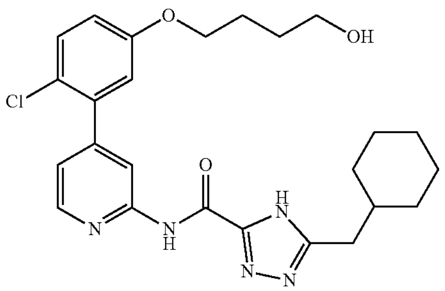

Example 375

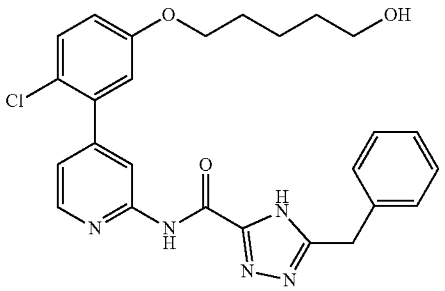

Example 375: 5-benzyl-N-(4-(2-chloro-5-((5-hydroxypentyl)oxy)phenyl)pyridin-2-yl)-4H-1,2,4-triazole-3-carboxamide The preparation was carried out in a similar manner to Example 92, except that in step 1, 5-bromo-1-pentanol was used in place of iodomethane, and 3-bromo-4-chlorophenol was used in place of 2-bromo-3-methylphenol. $^{1}H$ NMR (400 MHz, DMSO-$d_6$) δ 14.61 (s, 1H), 9.95 (s, 1H), 8.45 (d, J=5.0 Hz, 1H), 8.22 (d, J=1.6 Hz, 1H), 7.51 (d, J=8.8 Hz, 1H), 7.39-7.30 (m, 4H), 7.30-7.19 (m, 2H), 7.06 (dd, J=8.8, 3.0 Hz, 1H), 7.02 (d, J=3.0 Hz, 1H), 4.44-4.30 (m, 1H), 4.18 (s, 2H), 4.02 (t, J=6.5 Hz, 2H), 3.44-3.37 (m, 2H), 1.78-1.64 (m, 2H), 1.53-1.35 (m, 4H). MS: 492 $[M+H]^+$.

Example 376: 5-(2-fluorobenzyl)-N-(4-(2-chloro-5-((5-hydroxypentyl)oxy)phenyl)pyridin-2-yl)-4H-1,2,4-triazole-3-carboxamide The preparation was carried out in a similar manner to Example 92, except that in step 1, 5-bromo-1-pentanol was used in place of iodomethane, 3-bromo-4-chlorophenol was used in place of 2-bromo-3-methylphenol, and in step 3, ethyl 5-(2-fluorobenzyl)-4H-1,2,4-triazol-3-carboxylate was used in place of ethyl 5-benzyl-4H-1,2,4-triazol-3-carboxylate. $^{1}H$ NMR (400 MHz, DMSO-$d_6$) δ 14.68 (s, 1H), 9.94 (s, 1H), 8.45 (d, J=5.2 Hz, 1H), 8.21 (d, J=1.6 Hz, 1H), 7.50 (d, J=8.8 Hz, 1H), 7.45-7.31 (m, 2H), 7.28 (dd, J=5.1, 1.6 Hz, 1H), 7.26-7.13 (m, 2H), 7.11-6.99 (m, 2H), 4.38 (s, 1H), 4.21 (s, 2H), 4.01 (t, J=6.5 Hz, 2H), 3.45-3.37 (m, 2H), 1.79-1.66 (m, 2H), 1.52-1.37 (m, 4H). MS: 510 $[M+H]^+$.

Example 376

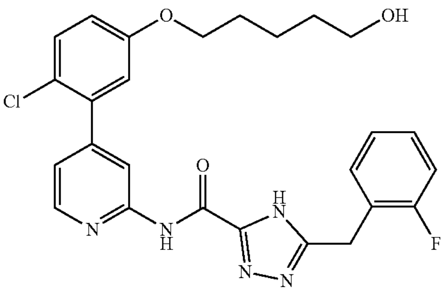

Example 377

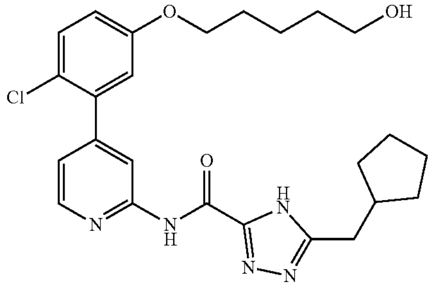

Example 377: N-(4-(2-chloro-5-((5-hydroxypentyl)oxy)phenyl)pyridin-2-yl)-5-(cyclopentylmethyl)-4H-1,2,4-triazole-3-carboxamide The preparation was carried out in a similar manner to Example 92, except that in step 1, 5-bromo-1-pentanol was used in place of iodomethane, 3-bromo-4-chlorophenol was used in place of 2-bromo-3-methylphenol, and in step 3, ethyl 5-(cyclopentylmethyl)-4H-1,2,4-triazol-3-carboxylate was used in place of ethyl 5-benzyl-4H-1,2,4-triazol-3-carboxylate. $^{1}H$ NMR (400 MHz, DMSO-$d_6$) δ 14.38 (s, 1H), 9.89 (s, 1H), 8.46 (d, J=5.1 Hz, 1H), 8.24 (s, 1H), 7.51 (d, J=8.8 Hz, 1H), 7.28 (dd, J=5.1, 1.6 Hz, 1H), 7.14-6.96 (m, 2H), 4.38 (t, J=5.2 Hz, 1H), 4.02 (t, J=6.5 Hz, 2H), 3.46-3.35 (m, 2H), 2.78 (d, J=7.5 Hz, 2H), 2.36-2.20 (m, 1H), 1.80-1.67 (m, 4H), 1.67-1.38 (m, 8H), 1.30-1.15 (m, 2H). MS: 484 $[M+H]^+$.

Example 378: N-(4-(2-chloro-5-((5-hydroxypentyl)oxy)phenyl)pyridin-2-yl)-5-(cyclohexylmethyl)-4H-1,2,4-triazole-3-carboxamide The preparation was carried out in a similar manner to Example 92, except that in step 1, 5-bromo-1-pentanol was used in place of iodomethane, 3-bromo-4-chlorophenol was used in place of 2-bromo-3-methylphenol, and in step 3, ethyl 5-(cyclohexylmethyl)-4H-1,2,4-triazol-3-carboxylate was used in place of ethyl 5-benzyl-4H-1,2,4-triazol-3-carboxylate. $^{1}H$ NMR (400 MHz, DMSO-$d_6$) δ 14.38 (s, 1H), 9.89 (s, 1H), 8.46 (d, J=5.1 Hz, 1H), 8.24 (d, J=1.5 Hz, 1H), 7.51 (d, J=8.8 Hz, 1H), 7.28 (dd, J=5.1, 1.6 Hz, 1H), 7.07 (dd, J=8.8, 3.1 Hz, 1H), 7.02 (d, J=3.0 Hz, 1H), 4.38 (t, J=5.2 Hz, 1H), 4.02 (t, J=6.5 Hz, 2H), 3.45-3.37 (m, 2H), 2.67 (d, J=7.0 Hz, 2H), 1.84-1.54 (m, 8H), 1.52-1.36 (m, 4H), 1.27-1.11 (m, 3H), 1.04-0.91 (m, 2H). MS: 498 $[M+H]^+$.

Example 378

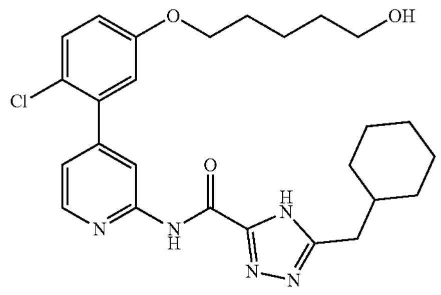

Example 379

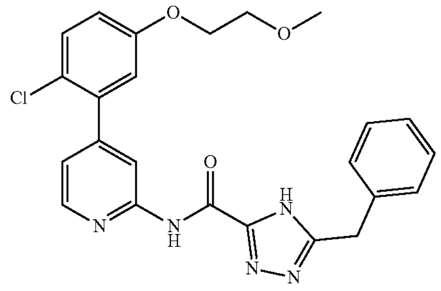

Example 379: 5-benzyl-N-(4-(2-chloro-5-(2-methoxyethoxy)phenyl)pyridin-2-yl)-4H-1,2,4-triazole-3-carboxamide The preparation was carried out in a similar manner to Example 92, except that in step 1, 1-bromo-2-methoxyethane was used in place of iodomethane, and 3-bromo-4-chlorophenol was used in place of 2-bromo-3-methylphenol. $^1$H NMR (400 MHz, DMSO-$d_6$) δ 14.63 (s, 1H), 9.96 (s, 1H), 8.45 (dd, J=5.1, 0.8 Hz, 1H), 8.24 (dd, J=1.6, 0.8 Hz, 1H), 7.51 (d, J=8.7 Hz, 1H), 7.43-7.30 (m, 4H), 7.30-7.20 (m, 2H), 7.15-6.98 (m, 2H), 4.25-4.10 (m, 4H), 3.71-3.59 (m, 2H), 3.30 (s, 3H). MS: 464 $[M+H]^+$.

Example 380: 5-(2-fluorobenzyl)-N-(4-(2-chloro-5-(2-methoxyethoxy)phenyl)pyridin-2-yl)-4H-1,2,4-triazole-3-carboxamide The preparation was carried out in a similar manner to Example 92, except that in step 1, 1-bromo-2-methoxyethane was used in place of iodomethane, 3-bromo-4-chlorophenol was used in place of 2-bromo-3-methylphenol, and in step 3, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.69 (s, 1H), 9.94 (s, 1H), 8.56-8.38 (m, 1H), 8.31-8.14 (m, 1H), 7.51 (d, J=8.8 Hz, 1H), 7.46-7.14 (m, 5H), 7.14-6.94 (m, 2H), 4.21 (s, 2H), 4.18-4.11 (m, 2H), 3.73-3.60 (m, 2H), 3.30 (s, 3H). MS: 482 $[M+H]^+$.

Example 380

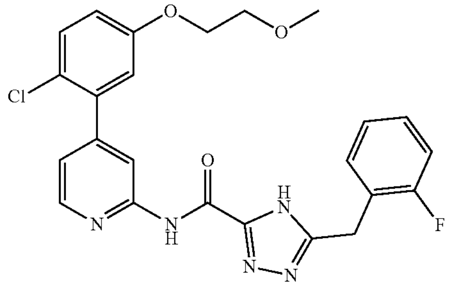

Example 381

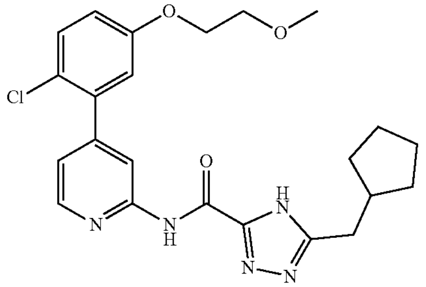

Example 381: N-(4-(2-chloro-5-(2-methoxyethoxy)phenyl)pyridin-2-yl)-5-(cyclopentylmethyl)-4H-1,2,4-triazole-3-carboxamide The preparation was carried out in a similar manner to Example 92, except that in step 1, 1-bromo-2-methoxyethane was used in place of iodomethane, 3-bromo-4-chlorophenol was used in place of 2-bromo-3-methylphenol, and in step 3, ethyl 5-(cyclopentylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.40 (s, 1H), 9.90 (s, 1H), 8.46 (d, J=5.1 Hz, 1H), 8.25 (t, J=1.1 Hz, 1H), 7.52 (d, J=8.8 Hz, 1H), 7.29 (dd, J=5.1, 1.6 Hz, 1H), 7.16-6.98 (m, 2H), 4.25-4.09 (m, 2H), 3.75-3.61 (m, 2H), 3.30 (s, 3H), 2.78 (d, J=7.5 Hz, 2H), 2.37-2.18 (m, 1H), 1.81-1.67 (m, 2H), 1.67-1.44 (m, 4H), 1.32-1.13 (m, 2H). MS: 456 $[M+H]^+$.

Example 382: N-(4-(2-chloro-5-(2-methoxyethoxy)phenyl)pyridin-2-yl)-5-(cyclohexylmethyl)-4H-1,2,4-triazole-3-carboxamide The preparation was carried out in a similar manner to Example 92, except that in step 1, 1-bromo-2-methoxyethane was used in place of iodomethane, 3-bromo-4-chlorophenol was used in place of 2-bromo-3-methylphenol, and in step 3, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.40 (s, 1H), 9.90 (s, 1H), 8.46 (d, J=5.1 Hz, 1H), 8.25 (d, J=1.5 Hz, 1H), 7.52 (d, J=8.8 Hz, 1H), 7.29 (dd, J=5.1, 1.6 Hz, 1H), 7.16-7.00 (m, 2H), 4.23-4.10 (m, 2H), 3.72-3.61 (m, 2H), 3.30 (s, 3H), 2.67 (d, J=7.1 Hz, 2H), 1.85-1.53 (m, 6H), 1.28-1.11 (m, 3H), 1.03-0.90 (m, 2H). MS: 470 $[M+H]^+$.

Example 382

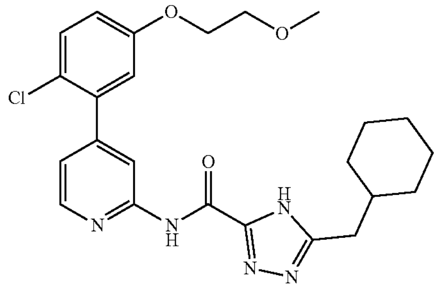

Example 383

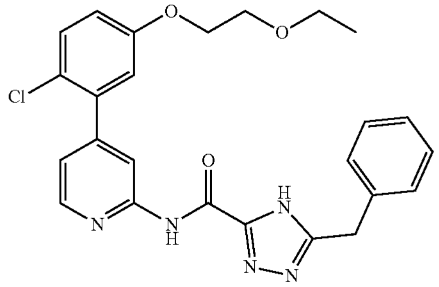

Example 383: 5-benzyl-N-(4-(2-chloro-5-(2-ethoxy-ethoxy)phenyl)pyridin-2-yl)-4H-1,2,4-triazole-3-carboxamide The preparation was carried out in a similar manner to Example 92, except that in step 1, 1-bromo-2-ethoxyethane was used in place of iodomethane, and 3-bromo-4-chlorophenol was used in place of 2-bromo-3-methylphenol. $^1$H NMR (400 MHz, DMSO-$d_6$) δ 14.60 (s, 1H), 9.94 (s, 1H), 8.46 (d, J=5.2 Hz, 1H), 8.23 (s, 1H), 7.52 (d, J=8.8 Hz, 1H), 7.43-7.30 (m, 4H), 7.30-7.22 (m, 2H), 7.18-6.97 (m, 2H), 4.22-4.11 (m, 4H), 3.73-3.66 (m, 2H), 3.49 (q, J=7.0 Hz, 2H), 1.12 (t, J=7.0 Hz, 3H). MS: 478 $[M+H]^+$.

Example 384: 5-(2-fluorobenzyl)-N-(4-(2-chloro-5-(2-ethoxyethoxy)phenyl)pyridin-2-yl)-4H-1,2,4-triazole-3-carboxamide The preparation was carried out in a similar manner to Example 92, except that in step 1, 1-bromo-2-ethoxyethane was used in place of iodomethane, 3-bromo-4-chlorophenol was used in place of 2-bromo-3-methylphenol, and in step 3, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.68 (s, 1H), 9.94 (s, 1H), 8.45 (d, J=5.2 Hz, 1H), 8.28-8.16 (m, 1H), 7.51 (d, J=8.8 Hz, 1H), 7.46-7.13 (m, 5H), 7.13-6.97 (m, 2H), 4.21 (s, 2H), 4.18-4.09 (m, 2H), 3.75-3.63 (m, 2H), 3.49 (q, J=7.0 Hz, 2H), 1.11 (t, J=7.0 Hz, 3H). MS: 496 $[M+H]^+$.

Example 384

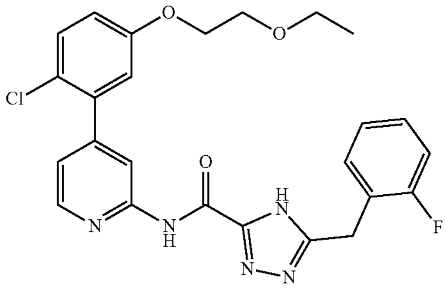

Example 385

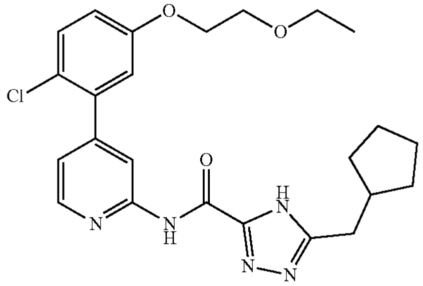

Example 385: N-(4-(2-chloro-5-(2-ethoxyethoxy)phenyl)pyridin-2-yl)-5-(cyclopentylmethyl)-4H-1,2,4-triazole-3-carboxamide The preparation was carried out in a similar manner to Example 92, except that in step 1, 1-bromo-2-ethoxyethane was used in place of iodomethane, 3-bromo-4-chlorophenol was used in place of 2-bromo-3-methylphenol, and in step 3, ethyl 5-(cyclopentylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.42 (s, 1H), 9.90 (s, 1H), 8.46 (dd, J=5.1, 0.8 Hz, 1H), 8.25 (t, J=1.1 Hz, 1H), 7.52 (d, J=8.8 Hz, 1H), 7.29 (dd, J=5.1, 1.6 Hz, 1H), 7.17-6.96 (m, 2H), 4.23-4.09 (m, 2H), 3.75-3.65 (m, 2H), 3.49 (q, J=7.0 Hz, 2H), 2.78 (d, J=7.5 Hz, 2H), 2.36-2.18 (m, 1H), 1.80-1.67 (m, 2H), 1.67-1.57 (m, 2H), 1.57-1.44 (m, 2H), 1.25-1.16 (m, 2H), 1.12 (t, J=7.0 Hz, 3H). MS: 470 $[M+H]^+$.

Example 386: N-(4-(2-chloro-5-(2-ethoxyethoxy)phenyl)pyridin-2-yl)-5-(cyclohexylmethyl)-4H-1,2,4-triazole-3-carboxamide The preparation was carried out in a similar manner to Example 92, except that in step 1, 1-bromo-2-ethoxyethane was used in place of iodomethane, 3-bromo-4-chlorophenol was used in place of 2-bromo-3-methylphenol, and in step 3, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.41 (s, 1H), 9.90 (s, 1H), 8.46 (d, J=5.1 Hz, 1H), 8.25 (s, 1H), 7.52 (d, J=8.8 Hz, 1H), 7.29 (dd, J=5.1, 1.7 Hz, 1H), 7.20-7.00 (m, 2H), 4.16 (dd, J=5.6, 3.5 Hz, 2H), 3.70 (dd, J=5.6, 3.4 Hz, 2H), 3.50 (q, J=7.0 Hz, 2H), 2.67 (d, J=7.0 Hz, 2H), 1.83-1.53 (m, 6H), 1.25-1.14 (m, 3H), 1.12 (t, J=7.0 Hz, 3H), 1.06-0.88 (m, 2H). MS: 484 $[M+H]^+$.

Example 386

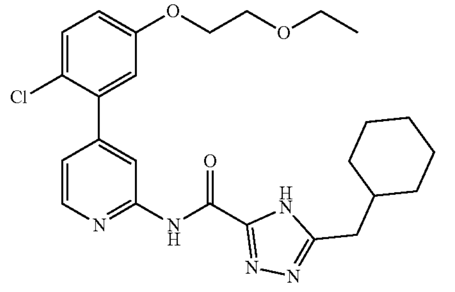

Example 387

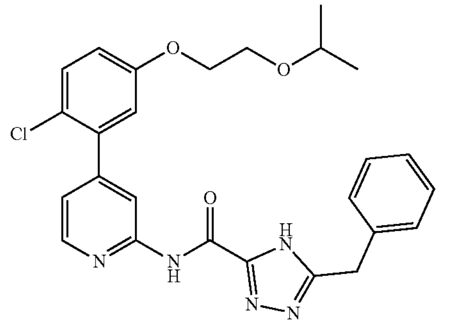

Example 387: 5-benzyl-N-(4-(2-chloro-5-(2-isopropoxyethoxy)phenyl)pyridin-2-yl)-4H-1,2,4-triazole-3-carboxamide The preparation was carried out in a similar manner to Example 92, except that in step 1, 1-bromo-2-isopropoxyethane was used in place of iodomethane, and 3-bromo-4-chlorophenol was used in place of 2-bromo-3-methylphenol. $^{1}$H NMR (400 MHz, DMSO-$d_6$) δ 14.63 (s, 1H), 9.96 (s, 1H), 8.46 (dd, J=5.1, 0.8 Hz, 1H), 8.29-8.16 (m, 1H), 7.51 (d, J=8.7 Hz, 1H), 7.44-7.18 (m, 6H), 7.18-6.96 (m, 2H), 4.18 (s, 2H), 4.15-4.05 (m, 2H), 3.75-3.66 (m, 2H), 3.61 (p, J=6.1 Hz, 1H), 1.09 (d, J=6.0 Hz, 6H). MS: 492 $[M+H]^+$.

Example 388: 5-(2-fluorobenzyl)-N-(4-(2-chloro-5-(2-isopropoxyethoxy)phenyl)pyridin-2-yl)-4H-1,2,4-triazole-3-carboxamide The preparation was carried out in a similar manner to Example 92, except that in step 1, 1-bromo-2-isopropoxyethane was used in place of iodomethane, 3-bromo-4-chlorophenol was used in place of 2-bromo-3-methylphenol, and in step 3, ethyl 5-(2-fluorobenzyl)-4H-1,2,4-triazol-3-carboxylate was used in place of ethyl 5-benzyl-4H-1,2,4-triazol-3-carboxylate. $^{1}$H NMR (400 MHz, DMSO-$d_6$) δ 14.68 (s, 1H), 9.94 (s, 1H), 8.45 (dd, J=5.1, 0.8 Hz, 1H), 8.30-8.14 (m, 1H), 7.51 (d, J=8.8 Hz, 1H), 7.46-7.25 (m, 3H), 7.25-7.13 (m, 2H), 7.13-6.97 (m, 2H), 4.21 (s, 2H), 4.17-4.06 (m, 2H), 3.74-3.65 (m, 2H), 3.61 (p, J=6.1 Hz, 1H), 1.09 (d, J=6.1 Hz, 6H). MS: 510 $[M+H]^+$.

Example 388

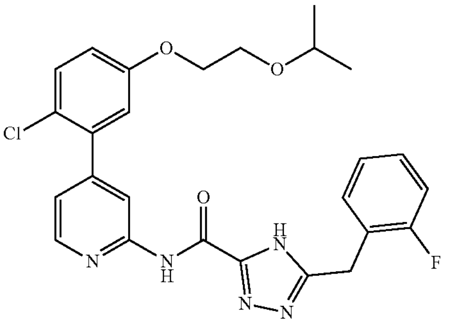

Example 389

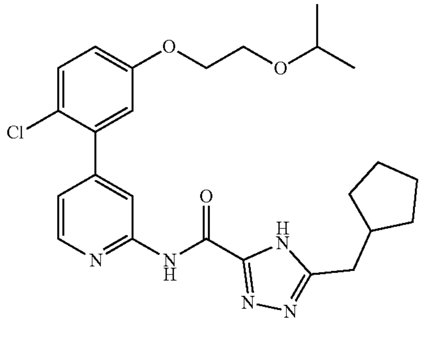

Example 389: N-(4-(2-chloro-5-(2-isopropoxyethoxy)phenyl)pyridin-2-yl)-5-(cyclopentylmethyl)-4H-1,2,4-triazole-3-carboxamide The preparation was carried out in a similar manner to Example 92, except that in step 1, 1-bromo-2-isopropoxyethane was used in place of iodomethane, 3-bromo-4-chlorophenol was used in place of 2-bromo-3-methylphenol, and in step 3, ethyl 5-(cyclopentylmethyl)-4H-1,2,4-triazol-3-carboxylate was used in place of ethyl 5-benzyl-4H-1,2,4-triazol-3-carboxylate. $^{1}$H NMR (400 MHz, DMSO-$d_6$) δ 14.42 (s, 1H), 9.90 (s, 1H), 8.46 (d, J=5.1 Hz, 1H), 8.25 (d, J=1.4 Hz, 1H), 7.52 (d, J=8.7 Hz, 1H), 7.29 (dd, J=5.1, 1.6 Hz, 1H), 7.19-6.99 (m, 2H), 4.22-4.05 (m, 2H), 3.75-3.66 (m, 2H), 3.62 (p, J=6.1 Hz, 1H), 2.78 (d, J=7.5 Hz, 2H), 2.36-2.20 (m, 1H), 1.84-1.66 (m, 2H), 1.66-1.46 (m, 4H), 1.26-1.18 (m, 2H), 1.10 (d, J=6.1 Hz, 6H). MS: 484 $[M+H]^+$.

Example 390: N-(4-(2-chloro-5-(2-isopropoxyethoxy)phenyl)pyridin-2-yl)-5-(cyclohexylmethyl)-4H-1,2,4-triazole-3-carboxamide The preparation was carried out in a similar manner to Example 92, except that in step 1, 1-bromo-2-isopropoxyethane was used in place of iodomethane, 3-bromo-4-chlorophenol was used in place of 2-bromo-3-methylphenol, and in step 3, ethyl 5-(cyclohexylmethyl)-4H-1,2,4-triazol-3-carboxylate was used in place of ethyl 5-benzyl-4H-1,2,4-triazol-3-carboxylate. $^{1}$H NMR (400 MHz, DMSO-$d_6$) δ 14.40 (s, 1H), 9.90 (s, 1H), 8.47 (d, J=5.2 Hz, 1H), 8.25 (s, 1H), 7.52 (d, J=8.8 Hz, 1H), 7.29 (dd, J=5.1, 1.6 Hz, 1H), 7.15-6.96 (m, 2H), 4.18-4.09 (m, 2H), 3.74-3.65 (m, 2H), 3.62 (p, J’$^{2}$ 6.1 Hz, 1H), 2.67 (d, J=7.1 Hz, 2H), 1.85-1.56 (m, 6H), 1.26-1.17 (m, 3H), 1.10 (d, J=6.1 Hz, 6H), 1.05-0.91 (m, 2H). MS: 498 $[M+H]^+$.

Example 390

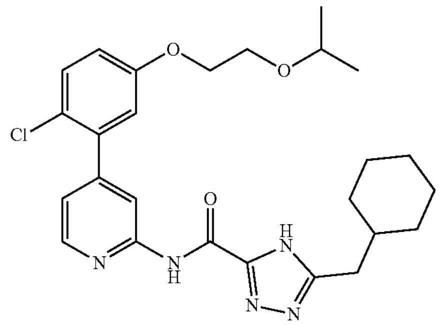

Example 391

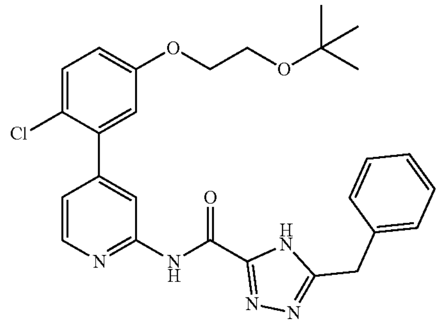

Example 391: 5-benzyl-N-(4-(5-(2-(tert-butoxy)ethoxy)-2-chlorophenyl)pyridin-2-yl)-4H-1,2,4-triazole-3-carboxamide The preparation was carried out in a similar manner to Example 64, except that in step 1, 3-bromo-4-chlorophenol was used in place of 3-bromo-4-methylphenol. $^1$H NMR (400 MHz, DMSO-$d_6$) δ 14.58 (s, 1H), 9.93 (s, 1H), 8.45 (d, J=5.2 Hz, 1H), 8.23 (s, 1H), 7.51 (d, J=8.7 Hz, 1H), 7.43-7.18 (m, 6H), 7.14-6.97 (m, 2H), 4.18 (s, 2H), 4.13-4.00 (m, 2H), 3.64 (t, J=4.8 Hz, 2H), 1.15 (s, 9H). MS: 506 $[M+H]^+$.

Example 392: 5-(2-fluorobenzyl)-N-(4-(5-(2-(tert-butoxy)ethoxy)-2-chlorophenyl)pyridin-2-yl)-4H-1,2,4-triazole-3-carboxamide The preparation was carried out in a similar manner to Example 64, except that in step 1, 3-bromo-4-chlorophenol was used in place of 3-bromo-4-methylphenol, and in step 3, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.61 (s, 1H), 9.90 (s, 1H), 8.45 (d, J=5.1 Hz, 1H), 8.22 (s, 1H), 7.51 (d, J=8.8 Hz, 1H), 7.45-7.31 (m, 2H), 7.28 (dd, J=5.2, 1.6 Hz, 1H), 7.26-7.15 (m, 2H), 7.12-7.01 (m, 2H), 4.21 (s, 2H), 4.14-4.03 (m, 2H), 3.69-3.58 (m, 2H), 1.15 (s, 9H). MS: 524 $[M+H]^+$.

Example 392

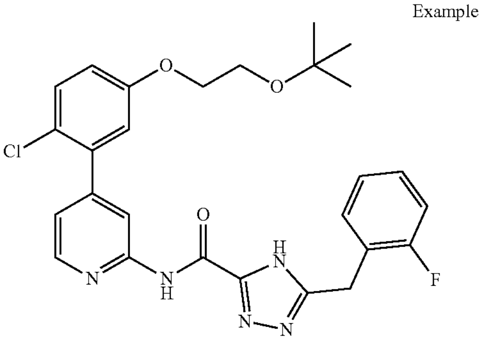

Example 393

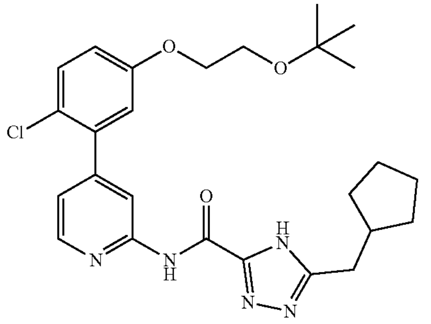

Example 393: N-(4-(5-(2-(tert-butoxy)ethoxy)-2-chlorophenyl)pyridin-2-yl)-5-(cyclopentylmethyl)-4H-1,2,4-triazole-3-carboxamide The preparation was carried out in a similar manner to Example 64, except that in step 1, 3-bromo-4-chlorophenol was used in place of 3-bromo-4-methylphenol, and in step 3, ethyl 5-(cyclopentylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.37 (s, 1H), 9.87 (s, 1H), 8.46 (d, J=5.2 Hz, 1H), 8.25 (s, 1H), 7.51 (d, J=8.7 Hz, 1H), 7.34-7.24 (m, 1H), 7.16-6.96 (m, 2H), 4.16-4.03 (m, 2H), 3.70-3.56 (m, 2H), 2.79 (d, J=7.5 Hz, 2H), 2.37-2.22 (m, 1H), 1.80-1.66 (m, 2H), 1.66-1.57 (m, 2H), 1.57-1.41 (m, 2H), 1.29-1.18 (m, 2H), 1.15 (s, 9H). MS: 498 $[M+H]^+$.

Example 394: N-(4-(5-(2-(tert-butoxy)ethoxy)-2-chlorophenyl)pyridin-2-yl)-5-(cyclohexylmethyl)-4H-1,2,4-triazole-3-carboxamide The preparation was carried out in a similar manner to Example 64, except that in step 1, 3-bromo-4-chlorophenol was used in place of 3-bromo-4-methylphenol, and in step 3, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.37 (s, 1H), 9.88 (s, 1H), 8.46 (d, J=5.1 Hz, 1H), 8.25 (s, 1H), 7.52 (d, J=8.7 Hz, 1H), 7.29 (dd, J=5.1, 1.6 Hz, 1H), 7.13-7.00 (m, 2H), 4.17-4.03 (m, 2H), 3.70-3.60 (m, 2H), 2.67 (d, J=7.0 Hz, 2H), 1.84-1.57 (m, 6H), 1.28-1.13 (m, 12H), 1.03-0.91 (m, 2H). MS: 512 $[M+H]^+$.

Example 394

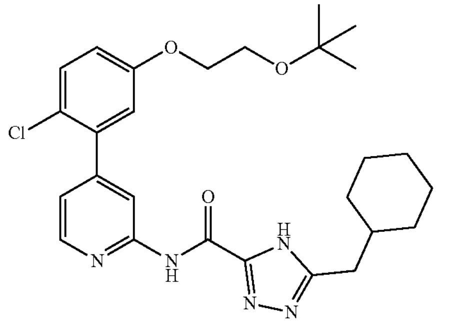

Example 395

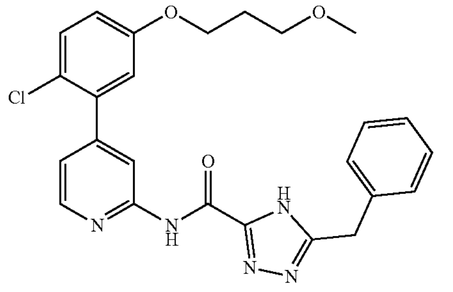

Example 395: 5-benzyl-N-(4-(2-chloro-5-(3-methoxypropoxy)phenyl)pyridin-2-yl)-4H-1,2,4-triazole-3-carboxamide The preparation was carried out in a similar manner to Example 92, except that in step 1, 1-bromo-3-methoxypropane was used in place of iodomethane, and 3-bromo-4-chlorophenol was used in place of 2-bromo-3-methylphenol. $^1H$ NMR (400 MHz, DMSO-$d_6$) δ 14.63 (s, 1H), 9.96 (s, 1H), 8.45 (dd, J=5.1, 0.8 Hz, 1H), 8.22 (d, J=1.2 Hz, 1H), 7.51 (d, J=8.8 Hz, 1H), 7.40-7.23 (m, 6H), 7.13-6.95 (m, 2H), 4.18 (s, 2H), 4.07 (t, J=6.4 Hz, 2H), 3.46 (t, J=6.2 Hz, 2H), 3.24 (s, 3H), 2.00-1.89 (m, 2H). MS: 478 $[M+H]^+$.

Example 396: 5-(2-fluorobenzyl)-N-(4-(2-chloro-5-(3-methoxypropoxy)phenyl)pyridin-2-yl)-4H-1,2,4-triazole-3-carboxamide The preparation was carried out in a similar manner to Example 92, except that in step 1, 1-bromo-3-methoxypropane was used in place of iodomethane, 3-bromo-4-chlorophenol was used in place of 2-bromo-3-methylphenol, and in step 3, ethyl 5-(2-fluorobenzyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.69 (s, 1H), 9.94 (s, 1H), 8.45 (dd, J=5.1, 0.8 Hz, 1H), 8.28-8.13 (m, 1H), 7.51 (d, J=8.8 Hz, 1H), 7.44-7.31 (m, 2H), 7.28 (dd, J=5.1, 1.6 Hz, 1H), 7.26-7.16 (m, 2H), 7.10-6.95 (m, 2H), 4.21 (s, 2H), 4.07 (t, J=6.4 Hz, 2H), 3.46 (t, J=6.2 Hz, 2H), 3.23 (s, 3H), 2.03-1.89 (m, 2H). MS: 496 $[M+H]^+$.

Example 396

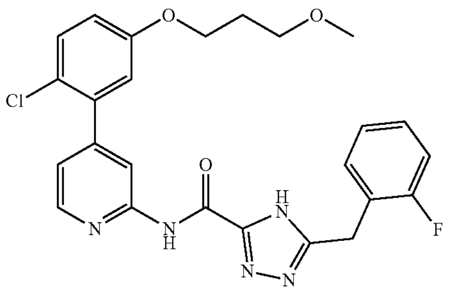

Example 397

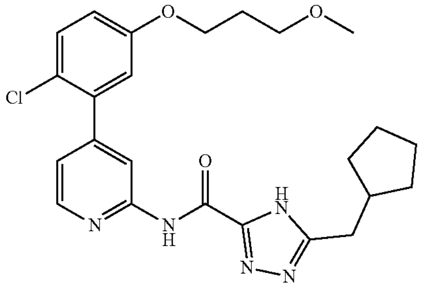

Example 397: N-(4-(2-chloro-5-(3-methoxypropoxy)phenyl)pyridin-2-yl)-5-(cyclopentylmethyl)-4H-1,2,4-triazole-3-carboxamide The preparation was carried out in a similar manner to Example 92, except that in step 1, 1-bromo-3-methoxypropane was used in place of iodomethane, 3-bromo-4-chlorophenol was used in place of 2-bromo-3-methylphenol, and in step 3, ethyl 5-(cyclopentylmethyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.42 (s, 1H), 9.91 (s, 1H), 8.46 (dd, J=5.1, 0.8 Hz, 1H), 8.24 (dd, J=1.5, 0.8 Hz, 1H), 7.51 (d, J=8.8 Hz, 1H), 7.28 (dd, J=5.1, 1.6 Hz, 1H), 7.13-6.99 (m, 2H), 4.08 (t, J=6.4 Hz, 2H), 3.46 (t, J=6.3 Hz, 2H), 3.24 (s, 3H), 2.78 (d, J=7.5 Hz, 2H), 2.36-2.18 (m, 1H), 2.00-1.89 (m, 2H), 1.79-1.67 (m, 2H), 1.67-1.44 (m, 4H), 1.30-1.15 (m, 2H). MS: 470 $[M+H]^+$.

Example 398: N-(4-(2-chloro-5-(3-methoxypropoxy)phenyl)pyridin-2-yl)-5-(cyclohexylmethyl)-4H-1,2,4-triazole-3-carboxamide The preparation was carried out in a similar manner to Example 92, except that in step 1, 1-bromo-3-methoxypropane was used in place of iodomethane, 3-bromo-4-chlorophenol was used in place of 2-bromo-3-methylphenol, and in step 3, ethyl 5-(cyclohexylmethyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.40 (s, 1H), 9.90 (s, 1H), 8.52-8.40 (m, 1H), 8.24 (d, J=1.2 Hz, 1H), 7.51 (d, J=8.8 Hz, 1H), 7.28 (dd, J=5.1, 1.6 Hz, 1H), 7.14-6.96 (m, 2H), 4.07 (t, J=6.4 Hz, 2H), 3.46 (t, J=6.3 Hz, 2H), 3.24 (s, 3H), 2.67 (d, J=7.1 Hz, 2H), 2.02-1.87 (m, 2H), 1.82-1.58 (m, 6H), 1.28-1.11 (m, 3H), 1.05-0.89 (m, 2H). MS: 484 $[M+H]^+$.

Example 398

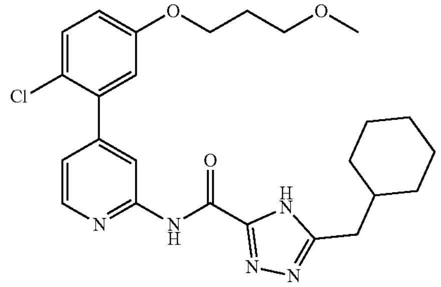

Example 399

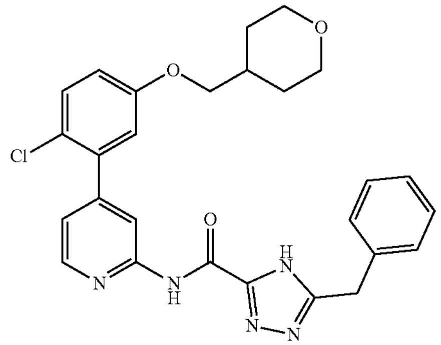

Example 399: 5-benzyl-N-(4-(2-chloro-5-((tetrahydro-2H-pyran-4-yl)methoxy)phenyl)pyridin-2-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, and 3-bromo-4-chlorophenol was used in place of 3-bromo-4-methylphenol. $^1$H NMR (400 MHz, DMSO-$d_6$) δ 14.57 (s, 1H), 9.95 (s, 1H), 8.45 (d, J=5.1 Hz, 1H), 8.22 (d, J=1.5 Hz, 1H), 7.51 (d, J=8.8 Hz, 1H), 7.42-7.30 (m, 4H), 7.30-7.19 (m, 2H), 7.14-6.97 (m, 2H), 4.18 (s, 2H), 3.96-3.80 (m, 4H), 3.35-3.26 (m, 2H), 2.05-1.94 (m, 1H), 1.73-1.61 (m, 2H), 1.40-1.24 (m, 2H). MS: 504 [M+H]$^+$.

Example 400: 5-(2-fluorobenzyl)-N-(4-(2-chloro-5-((tetrahydro-2H-pyran-4-yl)methoxy)phenyl)pyridin-2-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-bromo-4-chlorophenol was used in place of 3-bromo-4-methylphenol, and in step 3, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.66 (s, 1H), 9.94 (s, 1H), 8.45 (d, J=5.1 Hz, 1H), 8.21 (d, J=1.5 Hz, 1H), 7.51 (d, J=8.8 Hz, 1H), 7.47-7.12 (m, 5H), 7.12-6.95 (m, 2H), 4.21 (s, 2H), 3.95-3.79 (m, 4H), 3.33-3.26 (m, 2H), 2.06-1.92 (m, 1H), 1.75-1.62 (m, 2H), 1.41-1.19 (m, 2H). MS: 522 [M+H]$^+$.

Example 400

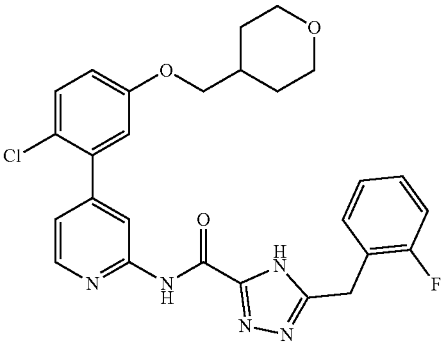

Example 401

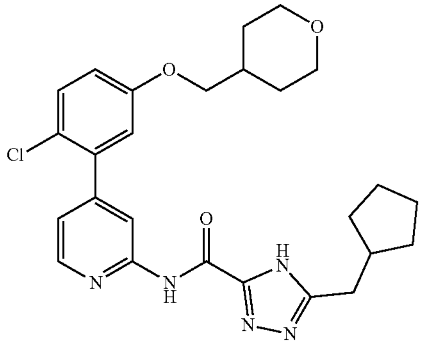

Example 401: N-(4-(2-chloro-5-((tetrahydro-2H-pyran-4-yl)methoxy)phenyl)pyridin-2-yl)-5-(cyclopentylmethyl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-bromo-4-chlorophenol was used in place of 3-bromo-4-methylphenol, and in step 3, ethyl 5-(cyclopentylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.41 (s, 1H), 9.91 (s, 1H), 8.46 (d, J=5.1 Hz, 1H), 8.30-8.19 (m, 1H), 7.51 (d, J=8.8 Hz, 1H), 7.28 (dd, J=5.1, 1.6 Hz, 1H), 7.15-6.97 (m, 2H), 3.94-3.81 (m, 4H), 3.32-3.22 (m, 2H), 2.78 (d, J=7.5 Hz, 2H), 2.36-2.17 (m, 1H), 2.06-1.93 (m, 1H), 1.79-1.46 (m, 8H), 1.39-1.14 (m, 4H). MS: 496 [M+H]$^+$.

Example 402: N-(4-(2-chloro-5-((tetrahydro-2H-pyran-4-yl)methoxy)phenyl)pyridin-2-yl)-5-(cyclohexylmethyl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-bromo-4-chlorophenol was used in place of 3-bromo-4-methylphenol, and in step 3, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.41 (s, 1H), 9.91 (s, 1H), 8.46 (d, J=5.1 Hz, 1H), 8.24 (d, J=1.6 Hz, 1H), 7.61-7.44 (m, 1H), 7.28 (dd, J=5.1, 1.6 Hz, 1H), 7.18-6.96 (m, 2H), 4.00-3.80 (m, 4H), 3.33-3.23 (m, 2H), 2.67 (d, J=7.0 Hz, 2H), 2.10-1.91 (m, 1H), 1.83-1.54 (m, 8H), 1.38-1.09 (m, 5H), 1.04-0.90 (m, 2H). MS: 510 [M+H]$^+$.

Example 402

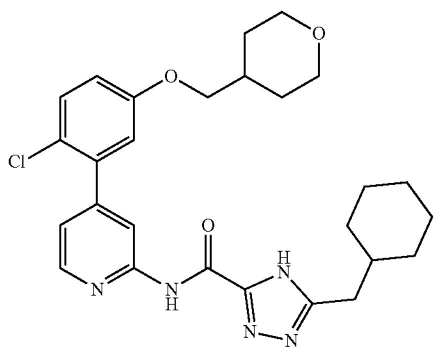

Example 403

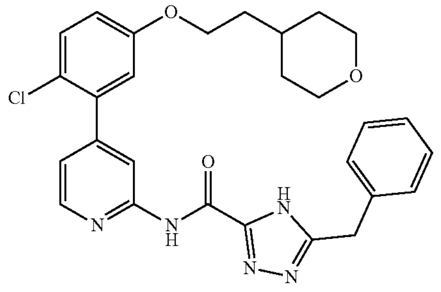

Example 403: 5-benzyl-N-(4-(2-chloro-5-(2-(tetrahydro-2H-pyran-4-yl)ethoxy)phenyl)pyridin-2-yl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy) ethan-1-ol, and in step 2, 3-bromo-4-chlorophenol was used in place of 3-bromo-4-methylphenol. $^1$H NMR (400 MHz, DMSO-$d_6$) δ 14.63 (s, 1H), 9.96 (s, 1H), 8.46 (d, J=5.1 Hz, 1H), 8.23 (d, J=1.5 Hz, 1H), 7.51 (d, J=8.8 Hz, 1H), 7.41-7.21 (m, 6H), 7.12-7.00 (m, 2H), 4.18 (s, 2H), 4.07 (t, J=6.2 Hz, 2H), 3.88-3.76 (m, 2H), 3.31-3.22 (m, 2H), 1.76-1.55 (m, 5H), 1.23-1.14 (m, 2H). MS: 518 $[M+H]^+$.

Example 404: N-(4-(2-chloro-5-(2-(tetrahydro-2H-pyran-4-yl)ethoxy)phenyl)pyridin-2-yl)-5-(2-fluorobenzyl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy) ethan-1-ol, in step 2, 3-bromo-4-chlorophenol was used in place of 3-bromo-4-methylphenol, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.60 (s, 1H), 9.95 (s, 1H), 8.45 (d, J=5.1 Hz, 1H), 8.28-8.14 (m, 1H), 7.51 (d, J=8.7 Hz, 1H), 7.46-7.30 (m, 2H), 7.28 (dd, J=5.1, 1.6 Hz, 1H), 7.26-7.12 (m, 2H), 7.12-7.00 (m, 2H), 4.20 (s, 2H), 4.07 (t, J=6.2 Hz, 2H), 3.88-3.76 (m, 2H), 3.30-3.24 (m, 2H), 1.79-1.56 (m, 5H), 1.22-1.13 (m, 2H). MS: 536 $[M+H]^+$.

Example 404

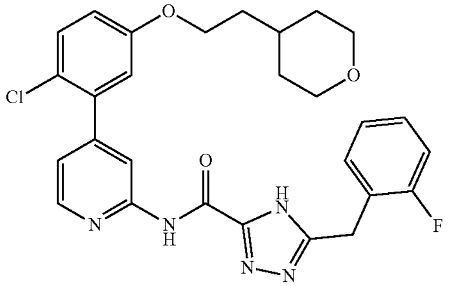

Example 405

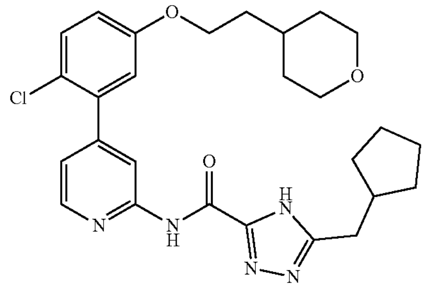

Example 405: N-(4-(2-chloro-5-(2-(tetrahydro-2H-pyran-4-yl)ethoxy)phenyl)pyridin-2-yl)-5-(cyclopentylmethyl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy) ethan-1-ol, in step 2, 3-bromo-4-chlorophenol was used in place of 3-bromo-4-methylphenol, and in step 4, ethyl 5-(cyclopentylmethyl)-4H-1,2,4-triazole-3-carboxylate was used in place of ethyl 5-benzyl-4H-1,2,4-triazol-3-carboxylate. $^1$H NMR (400 MHz, DMSO-$d_6$) δ 14.42 (s, 1H), 9.91 (s, 1H), 8.46 (d, J=5.1 Hz, 1H), 8.24 (d, J=1.5 Hz, 1H), 7.51 (d, J=8.7 Hz, 1H), 7.28 (dd, J=5.1, 1.6 Hz, 1H), 7.14-6.99 (m, 2H), 4.07 (t, J=6.2 Hz, 2H), 3.88-3.75 (m, 2H), 3.31-3.21 (m, 2H), 2.78 (d, J=7.5 Hz, 2H), 2.36-2.19 (m, 1H), 1.78-1.55 (m, 9H), 1.55-1.46 (m, 2H), 1.26-1.19 (m, 4H). MS: 510 $[M+H]^+$.

Example 406: N-(4-(2-chloro-5-(2-(tetrahydro-2H-pyran-4-yl)ethoxy)phenyl)pyridin-2-yl)-5-(cyclohexylmethyl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy) ethan-1-ol, in step 2, 3-bromo-4-chlorophenol was used in place of 3-bromo-4-methylphenol, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.42 (s, 1H), 9.91 (s, 1H), 8.46 (d, J=5.1 Hz, 1H), 8.33-8.17 (m, 1H), 7.51 (d, J=8.7 Hz, 1H), 7.28 (dd, J=5.1, 1.6 Hz, 1H), 7.14-6.98 (m, 2H), 4.07 (t, J=6.2 Hz, 2H), 3.87-3.76 (m, 2H), 3.30-3.21 (m, 2H), 2.67 (d, J=7.1 Hz, 2H), 1.83-1.51 (m, 11H), 1.27-1.12 (m, 5H), 1.05-0.89 (m, 2H). MS: 524 $[M+H]^+$.

Example 406

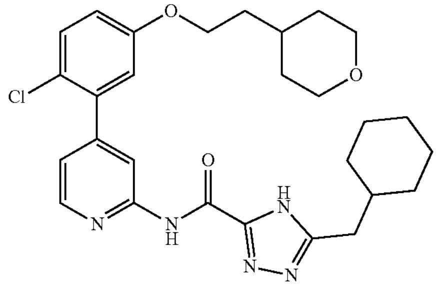

Example 407

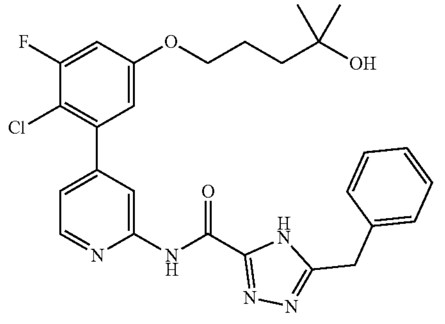

Example 407: 5-benzyl-N-(4-(2-chloro-3-fluoro-5-((4-hydroxy-4-methylpentyl)oxy)phenyl)pyridin-2-yl)-4H-1,2,4-triazole-3-carboxamide The preparation was carried out in a similar manner to Example 160, except that in step 1, 3-bromo-4-chloro-5-fluorophenol was used in place of 3-bromo-4-methylphenol. $^1$H NMR (400 MHz, DMSO-$d_6$) δ 14.65 (s, 1H), 9.91 (s, 1H), 8.45 (d, J=5.2 Hz, 1H), 8.34 (s, 1H), 7.46-7.26 (m, 4H), 7.26-7.15 (m, 2H), 7.15-7.02 (m, 2H), 4.21 (s, 2H), 4.10 (s, 1H), 4.02 (t, J=6.4 Hz, 2H), 1.77-1.64 (m, 2H), 1.52-1.42 (m, 2H), 1.07 (s, 6H). MS: 524 $[M+H]^+$.

Example 408: N-(4-(2-chloro-3-fluoro-5-((4-hydroxy-4-methylpentyl)oxy)phenyl)pyridin-2-yl)-5-(2-fluorobenzyl)-4H-1,2,4-triazole-3-carboxamide The preparation was carried out in a similar manner to Example 160, except that in step 1, 3-bromo-4-chloro-5-fluorophenol was used in place of 3-bromo-4-methylphenol, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.62 (s, 1H), 9.98 (s, 1H), 8.47 (d, J=5.2 Hz, 1H), 8.40 (d, J=1.7 Hz, 1H), 7.58 (dd, J=5.2, 1.7 Hz, 1H), 7.41 (dd, J=9.8, 1.8 Hz, 1H), 7.35-7.31 (m, 4H), 7.29-7.23 (m, 1H), 4.29-4.20 (m, 3H), 4.18 (s, 2H), 1.89-1.77 (m, 2H), 1.58-1.47 (m, 2H), 1.12 (s, 6H). MS: 542 $[M+H]^+$.

Example 408

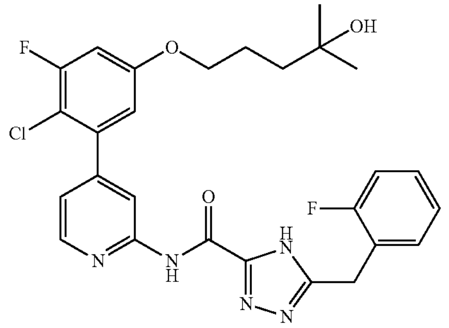

Example 409

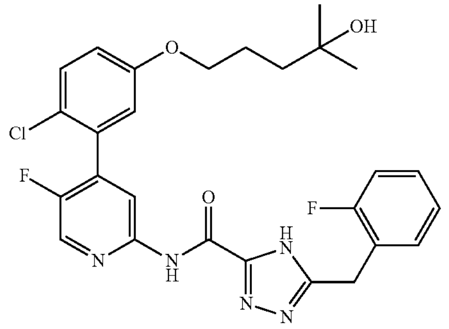

Example 409: N-(4-(2-chloro-5-((4-hydroxy-4-methylpentyl)oxy)phenyl)-5-fluoropyridin-2-yl)-5-(2-fluorophenyl)-4H-1,2,4-triazole-3-carboxamide The preparation was carried out in a similar manner to Example 160, except that in step 1, 3-bromo-4-chlorophenol was used in place of 3-bromo-4-methylphenol, in step 3, 4-bromo-5-fluoropyridin-2-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.68 (s, 1H), 10.13 (s, 1H), 8.51 (d, J=1.1 Hz, 1H), 8.12 (d, J=5.5 Hz, 1H), 7.53 (d, J=8.7 Hz, 1H), 7.43-7.29 (m, 2H), 7.26-7.14 (m, 2H), 7.14-7.03 (m, 2H), 4.20 (s, 2H), 4.17 (s, 1H), 4.01 (t, J=6.5 Hz, 2H), 1.83-1.69 (m, 2H), 1.52-1.42 (m, 2H), 1.09 (s, 6H). MS: 542 $[M+H]^+$.

Example 410: N-(4-(2-chloro-5-((4-hydroxy-4-methylpentyl)oxy)phenyl)-5-fluoropyridin-2-yl)-5-(cyclohexylmethyl)-4H-1,2,4-triazole-3-carboxamide The preparation was carried out in a similar manner to Example 160, except that in step 1, 3-bromo-4-chlorophenol was used in place of 3-bromo-4-methylphenol, in step 3, 4-bromo-5-fluoropyridin-2-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.37 (s, 1H), 10.06 (s, 1H), 8.52 (d, J=1.2 Hz, 1H), 8.15 (d, J=5.5 Hz, 1H), 7.54 (d, J=8.7 Hz, 1H), 7.15-7.04 (m, 2H), 4.17 (s, 1H), 4.01 (t, J=6.6 Hz, 2H), 2.67 (d, J=7.0 Hz, 2H), 1.82-1.56 (m, 8H), 1.52-1.41 (m, 2H), 1.28-1.12 (m, 3H), 1.09 (s, 6H), 1.05-0.90 (m, 2H). MS: 530 $[M+H]^+$.

Example 410

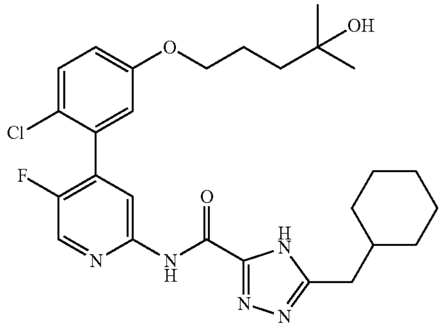

Example 411

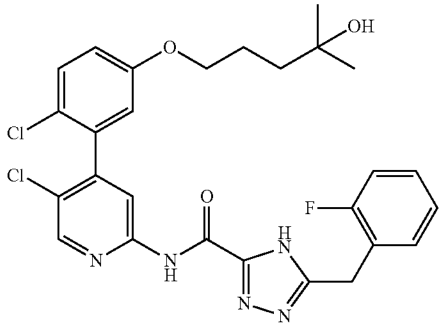

Example 411: N-(5-chloro-4-(2-chloro-5-((4-hydroxy-4-methylpentyl)oxy)phenyl)pyridin-2-yl)-5-(2-fluorobenzyl)-4H-1,2,4-triazole-3-carboxamide The preparation was carried out in a similar manner to Example 160, except that in step 1, 3-bromo-4-chlorophenol was used in place of 3-bromo-4-methylphenol, in step 3, 4-bromo-5-chloropyridin-2-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.63 (s, 1H), 10.14 (s, 1H), 8.57 (s, 1H), 8.11 (s, 1H), 7.51 (d, J=8.9 Hz, 1H), 7.44-7.29 (m, 2H), 7.26-7.15 (m, 2H), 7.08 (dd, J=8.9, 3.0 Hz, 1H), 7.00 (d, J=3.0 Hz, 1H), 4.25-4.14 (m, 3H), 3.99 (t, J=6.6 Hz, 2H), 1.81-1.69 (m, 2H), 1.52-1.40 (m, 2H), 1.09 (s, 6H). MS: 558 $[M+H]^+$.

Example 412: N-(5-chloro-4-(2-chloro-5-((4-hydroxy-4-methylpentyl)oxy)phenyl)pyridin-2-yl)-5-(cyclohexylmethyl)-4H-1,2,4-triazole-3-carboxamide The preparation was carried out in a similar manner to Example 160, except that in step 1, 3-bromo-4-chlorophenol was used in place of 3-bromo-4-methylphenol, in step 3, 4-bromo-5-chloropyridin-2-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.38 (s, 1H), 10.09 (s, 1H), 8.58 (s, 1H), 8.13 (s, 1H), 7.52 (d, J=8.9 Hz, 1H), 7.09 (dd, J=8.9, 3.0 Hz, 1H), 7.00 (d, J=3.0 Hz, 1H), 4.18 (s, 1H), 4.00 (t, J=6.6 Hz, 2H), 2.67 (d, J=6.9 Hz, 2H), 1.82-1.55 (m, 8H), 1.52-1.42 (m, 2H), 1.28-1.12 (m, 3H), 1.09 (s, 6H), 1.05-0.87 (m, 2H). MS: 546 $[M+H]^+$.

Example 412

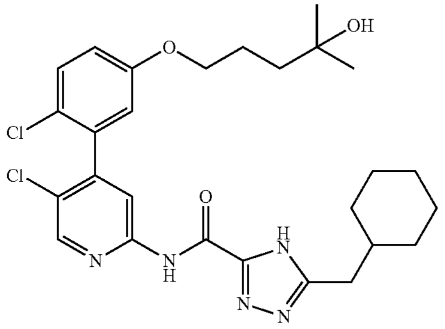

Example 413

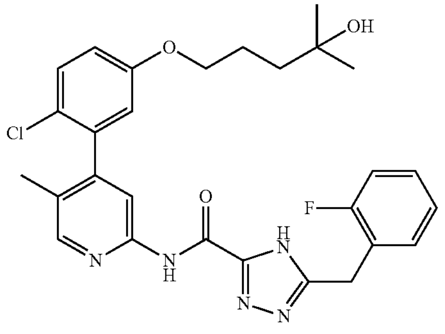

Example 413: N-(4-(2-chloro-5-((4-hydroxy-4-methylpentyl)oxy)phenyl)-5-methylpyridin-2-yl)-5-(2-fluorobenzyl)-4H-1,2,4-triazole-3-carboxamide The preparation was carried out in a similar manner to Example 160, except that in step 1, 3-bromo-4-chlorophenol was used in place of 3-bromo-4-methylphenol, in step 3, 4-bromo-5-methylpyridin-2-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.58 (s, 1H), 9.80 (s, 1H), 8.32 (s, 1H), 7.93 (s, 1H), 7.50 (d, J=8.9 Hz, 1H), 7.45-7.28 (m, 2H), 7.28-7.14 (m, 2H), 7.05 (dd, J=8.9, 3.0 Hz, 1H), 6.90 (d, J=3.0 Hz, 1H), 4.26-4.12 (m, 3H), 3.99 (t, J=6.6 Hz, 2H), 2.05 (s, 3H), 1.82-1.66 (m, 2H), 1.51-1.41 (m, 2H), 1.08 (s, 6H). MS: 538 $[M+H]^+$.

Example 414: N-(4-(2-chloro-5-((4-hydroxy-4-methylpentyl)oxy)phenyl)-5-methylpyridin-2-yl)-5-(cyclohexylmethyl)-4H-1,2,4-triazole-3-carboxamide The preparation was carried out in a similar manner to Example 160, except that in step 1, 3-bromo-4-chlorophenol was used in place of 3-bromo-4-methylphenol, in step 3, 4-bromo-5-methylpyridin-2-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.34 (s, 1H), 9.79 (s, 1H), 8.33 (s, 1H), 7.96 (s, 1H), 7.50 (d, J=8.9 Hz, 1H), 7.05 (dd, J=8.9, 3.0 Hz, 1H), 6.91 (d, J=3.0 Hz, 1H), 4.18 (s, 1H), 3.99 (t, J=6.6 Hz, 2H), 2.66 (d, J=7.1 Hz, 2H), 2.05 (s, 3H), 1.82-1.56 (m, 8H), 1.52-1.41 (m, 2H), 1.30-1.12 (m, 3H), 1.09 (s, 6H), 1.04-0.90 (m, 2H). MS: 526 $[M+H]^+$.

Example 414

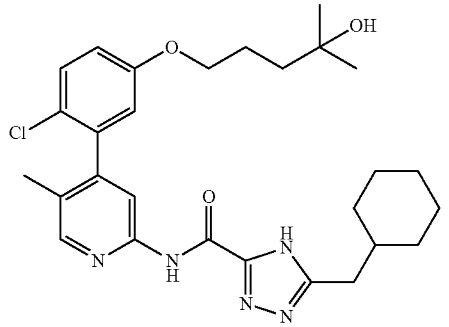

Example 415

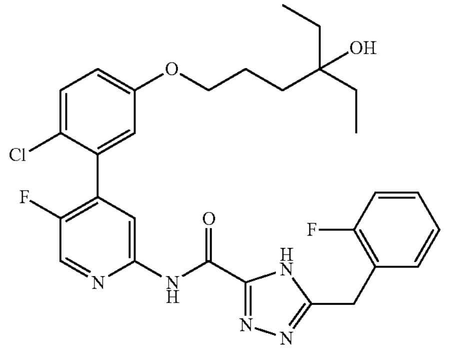

Example 415: N-(4-(2-chloro-5-((4-ethyl-4-hydroxyhexyl)oxy)phenyl)-5-fluoropyridin-2-yl)-5-(2-fluorobenzyl)-4H-1,2,4-triazole-3-carboxamide The preparation was carried out in a similar manner to Example 160, except that in step 1, 3-bromo-4-chlorophenol was used in place of 3-bromo-4-methylphenol, in step 2, ethylmagnesium bromide was used in place of methylmagnesium bromide, in step 3, 4-bromo-5-fluoropyridin-2-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^{1}H$ NMR (400 MHz, DMSO-$d_6$) δ 14.65 (s, 1H), 10.13 (s, 1H), 8.51 (d, J=1.1 Hz, 1H), 8.12 (d, J=5.5 Hz, 1H), 7.53 (d, J=8.7 Hz, 1H), 7.45-7.29 (m, 2H), 7.26-7.15 (m, 2H), 7.14-7.04 (m, 2H), 4.20 (s, 2H), 4.00 (t, J=6.5 Hz, 2H), 3.87 (s, 1H), 1.76-1.61 (m, 2H), 1.47-1.38 (m, 2H), 1.34 (q, J=7.5 Hz, 4H), 0.77 (t, J=7.4 Hz, 6H). MS: 570 $[M+H]^+$.

Example 416: N-(4-(2-chloro-5-((4-ethyl-4-hydroxyhexyl)oxy)phenyl)-5-fluoropyridin-2-yl)-5-(cyclohexylmethyl)-4H-1,2,4-triazole-3-carboxamide The preparation was carried out in a similar manner to Example 160, except that in step 1, 3-bromo-4-chlorophenol was used in place of 3-bromo-4-methylphenol, in step 2, ethylmagnesium bromide was used in place of methylmagnesium bromide, in step 3, 4-bromo-5-fluoropyridin-2-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^{1}H$ NMR (400 MHz, DMSO-$d_6$) δ 14.39 (s, 1H), 10.07 (s, 1H), 8.52 (d, J=1.1 Hz, 1H), 8.15 (d, J=5.5 Hz, 1H), 7.53 (d, J=8.7 Hz, 1H), 7.13-7.04 (m, 2H), 4.01 (t, J=6.5 Hz, 2H), 3.88 (s, 1H), 2.66 (d, J=7.1 Hz, 2H), 1.82-1.55 (m, 8H), 1.46-1.39 (m, 2H), 1.34 (q, J=7.5 Hz, 4H), 1.28-1.09 (m, 3H), 1.05-0.91 (m, 2H), 0.77 (t, J=7.5 Hz, 6H). MS: 558 $[M+H]^+$.

Example 416

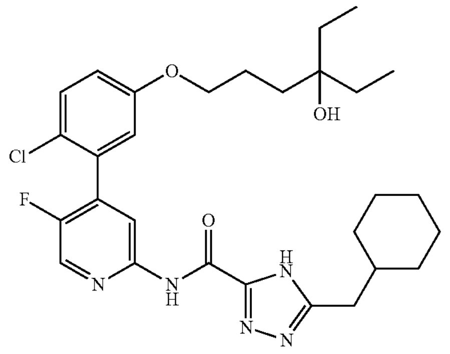

Example 417

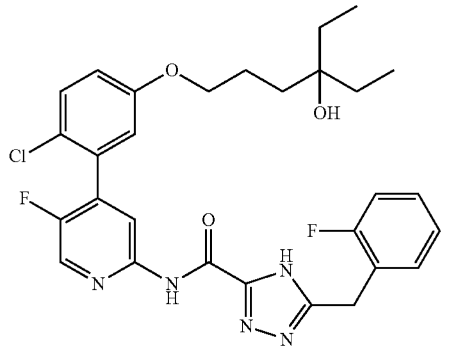

Example 417: N-(5-chloro-4-(2-chloro-5-((4-ethyl-4-hydroxyhexyl)oxy)phenyl)pyridin-2-yl)-5-(2-fluorobenzyl)-4H-1,2,4-triazole-3-carboxamide The preparation was carried out in a similar manner to Example 160, except that in step 1, 3-bromo-4-chlorophenol was used in place of 3-bromo-4-methylphenol, in step 2, ethylmagnesium bromide was used in place of methylmagnesium bromide, in step 3, 4-bromo-5-chloropyridin-2-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^{1}H$ NMR (400 MHz, DMSO-$d_6$) δ 14.62 (s, 1H), 10.13 (s, 1H), 8.57 (s, 1H), 8.11 (s, 1H), 7.51 (d, J=8.8 Hz, 1H), 7.46-7.29 (m, 2H), 7.26-7.15 (m, 2H), 7.08 (dd, J=8.9, 3.0 Hz, 1H), 6.99 (d, J=3.0 Hz, 1H), 4.21 (s, 2H), 3.99 (t, J=6.5 Hz, 2H), 3.88 (s, 1H), 1.74-1.61 (m, 2H), 1.45-1.37 (m, 2H), 1.34 (q, J=7.5 Hz, 4H), 0.77 (t, J=7.5 Hz, 6H). MS: 586 $[M+H]^+$.

Example 418: N-(5-chloro-4-(2-chloro-5-((4-ethyl-4-hydroxyhexyl)oxy)phenyl)pyridin-2-yl)-5-(cyclohexylmethyl)-4H-1,2,4-triazole-3-carboxamide The preparation was carried out in a similar manner to Example 160, except that in step 1, 3-bromo-4-chlorophenol was used in place of 3-bromo-4-methylphenol, in step 2, ethylmagnesium bromide was used in place of methylmagnesium bromide, in step 3, 4-bromo-5-chloropyridin-2-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.38 (s, 1H), 10.09 (s, 1H), 8.58 (s, 1H), 8.13 (s, 1H), 7.52 (d, J=8.9 Hz, 1H), 7.09 (dd, J=8.9, 3.0 Hz, 1H), 7.00 (d, J=3.0 Hz, 1H), 4.00 (t, J=6.5 Hz, 2H), 3.88 (s, 1H), 2.67 (d, J=6.8 Hz, 2H), 1.82-1.56 (m, 8H), 1.48-1.38 (m, 2H), 1.34 (q, J=7.4 Hz, 4H), 1.27-1.09 (m, 3H), 1.05-0.89 (m, 2H), 0.77 (t, J=7.4 Hz, 6H). MS: 574 [M+H]$^+$.

Example 418

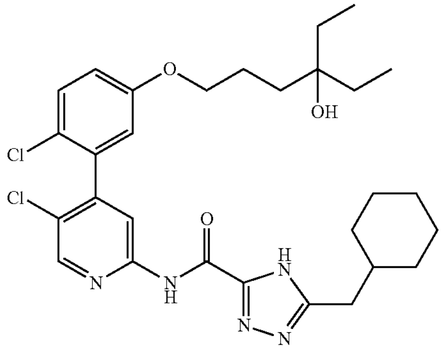

Example 419

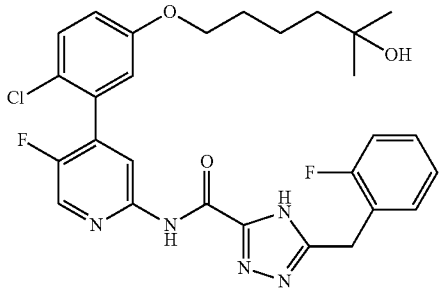

Example 419: N-(4-(2-chloro-5-((5-hydroxyl-5-methylhexyl)oxy)phenyl)-5-fluoropyridin-2-yl)-5-(2-fluorobenzyl)-4H-1,2,4-triazole-3-carboxamide The preparation was carried out in a similar manner to Example 160, except that in step 1, methyl 5-bromopentanoate was used in place of methyl 4-bromobutanoate, 3-bromo-4-chlorophenol was used in place of 3-bromo-4-methylphenol, in step 3, 5-fluoro-4-bromopyridin-2-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.58 (s, 1H), 10.05 (s, 1H), 8.52 (d, J=15.7 Hz, 1H), 8.14 (d, J=5.5 Hz, 1H), 7.53 (d, J=8.6 Hz, 1H), 7.44-7.07 (m, 6H), 4.23 (s, 2H), 4.08 (s, 1H), 4.01 (t, J=6.4 Hz, 2H), 1.76-1.63 (m, 2H), 1.50-1.33 (m, 4H), 1.06 (s, 6H). MS: 556 [M+H]$^+$.

Example 420: N-(5-chloro-4-(2-chloro-5-((5-hydroxyl-5-methylhexyl)oxy)phenyl)pyridin-2-yl)-5-(2-fluorobenzyl)-4H-1,2,4-triazole-3-carboxamide The preparation was carried out in a similar manner to Example 160, except that in step 1, methyl 5-bromopentanoate was used in place of methyl 4-bromobutanoate, 3-bromo-4-chlorophenol was used in place of 3-bromo-4-methylphenol, in step 3, 5-chloro-4-bromopyridin-2-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.60 (s, 1H), 10.11 (s, 1H), 8.56 (s, 1H), 8.12 (s, 1H), 7.51 (d, J=8.9 Hz, 1H), 7.46-7.27 (m, 2H), 7.27-7.13 (m, 2H), 7.09 (dd, J=8.9, 3.0 Hz, 1H), 7.01 (d, J=3.0 Hz, 1H), 4.23 (s, 2H), 4.11 (s, 1H), 4.00 (t, J=6.7 Hz, 2H), 1.74-1.62 (m, 2H), 1.48-1.29 (m, 4H), 1.06 (s, 6H). MS: 572 [M+H]$^+$.

Example 420

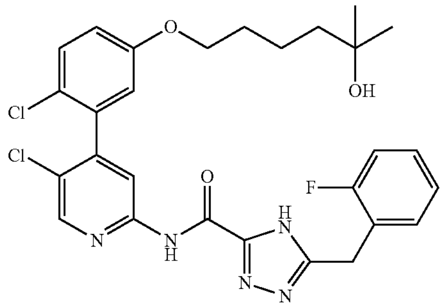

Example 421

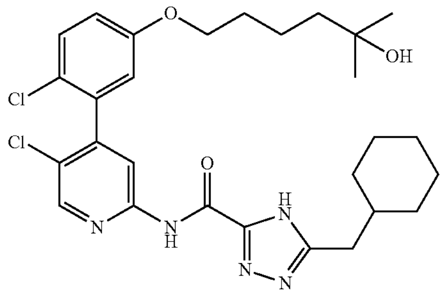

Example 421: N-(5-chloro-4-(2-chloro-5-((5-hydroxyl-5-methylhexyl)oxy)phenyl)pyridin-2-yl)-5-(cyclohexylmethyl)-4H-1,2,4-triazole-3-carboxamide The preparation was carried out in a similar manner to Example 160, except that in step 1, methyl 5-bromopentanoate was used in place of methyl 4-bromobutanoate, 3-bromo-4-chlorophenol was used in place of 3-bromo-4-methylphenol, in step 3, 5-chloro-4-bromopyridin-2-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.41 (s, 1H), 10.12 (s, 1H), 8.58 (s, 1H), 8.13 (s, 1H), 7.52 (d, J=8.9 Hz, 1H), 7.10 (dd, J=8.9, 3.0 Hz, 1H), 7.02 (d, J=3.0 Hz, 1H), 4.10 (s, 1H), 4.01 (t, J=6.7 Hz, 2H), 2.66 (d, J=7.0 Hz, 2H), 1.83-1.40 (m, 11H), 1.30-1.08 (m, 4H), 1.06 (s, 6H), 1.03-0.88 (m, 2H). MS: 560 [M+H]$^+$.

Example 422: N-(4-(2-chloro-5-((tetrahydro-2H-pyran-4-yl)methoxy)phenyl)-5-fluoropyridin-2-yl)-5-(2-fluorobenzyl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-bromo-4-chlorophenol was used in place of 3-bromo-4-methylphenol, in step 2, 5-fluoro-4-bromopyridin-2-amine was used in place of 4-bromopyridin-2-amine, and in step 3, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.64 (s, 1H), 10.13 (s, 1H), 8.51 (d, J=1.2 Hz, 1H), 8.12 (d, J=5.5 Hz, 1H), 7.53 (d, J=8.5 Hz, 1H), 7.43-7.29 (m, 2H), 7.25-7.16 (m, 2H), 7.14-7.09 (m, 2H), 4.21 (s, 2H), 3.92-3.80 (m, 4H), 3.38-3.32 (m, 2H), 2.05-1.92 (m, 1H), 1.72-1.58 (m, 2H), 1.41-1.23 (m, 2H). MS: 540 [M+H]+.

Example 422

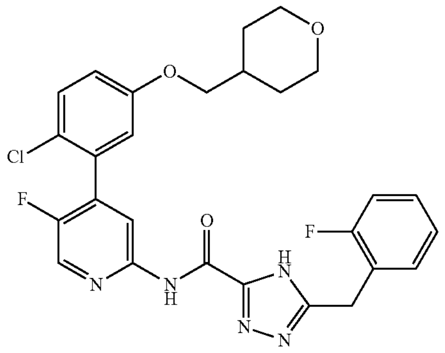

Example 423

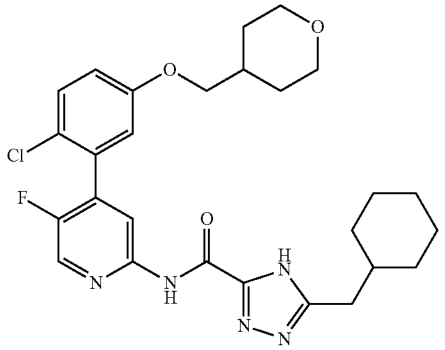

Example 423: N-(4-(2-chloro-5-((tetrahydro-2H-pyran-4-yl)methoxy)phenyl)-5-fluoropyridin-2-yl)-5-(cyclohexylmethyl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-bromo-4-chlorophenol was used in place of 3-bromo-4-methylphenol, in step 2, 5-fluoro-4-bromopyridin-2-amine was used in place of 4-bromopyridin-2-amine, and in step 3, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.39 (s, 1H), 10.07 (s, 1H), 8.52 (s, 1H), 8.15 (d, J=5.5 Hz, 1H), 7.54 (d, J=8.5 Hz, 1H), 7.17-7.07 (m, 2H), 3.94-3.82 (m, 4H), 3.37-3.30 (m, 2H), 2.66 (d, J=7.1 Hz, 2H), 2.06-1.92 (m, 1H), 1.82-1.56 (m, 8H), 1.39-1.25 (m, 2H), 1.25-1.10 (m, 3H), 1.05-0.90 (m, 2H). MS: 528 [M+H]+.

Example 424: N-(5-chloro-4-(2-chloro-5-((tetrahydro-2H-pyran-4-yl)methoxy)phenyl)pyridin-2-yl)-5-(2-fluorobenzyl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-bromo-4-chlorophenol was used in place of 3-bromo-4-methylphenol, in step 2, 5-chloro-4-bromopyridin-2-amine was used in place of 4-bromopyridin-2-amine, and in step 3, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.63 (s, 1H), 10.14 (s, 1H), 8.57 (s, 1H), 8.11 (s, 1H), 7.52 (d, J=8.9 Hz, 1H), 7.45-7.29 (m, 2H), 7.26-7.14 (m, 2H), 7.10 (dd, J=8.9, 3.0 Hz, 1H), 7.02 (d, J=3.0 Hz, 1H), 4.21 (s, 2H), 3.96-3.75 (m, 4H), 3.34-3.23 (m, 2H), 2.06-1.90 (m, 1H), 1.73-1.60 (m, 2H), 1.40-1.24 (m, 2H). MS: 556 [M+H]+.

Example 424

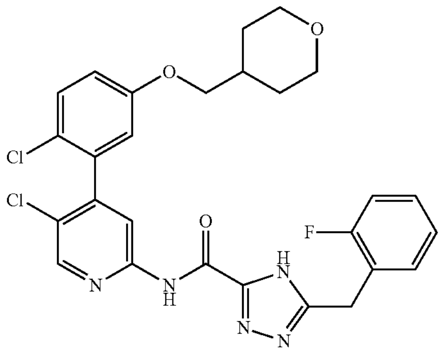

Example 425

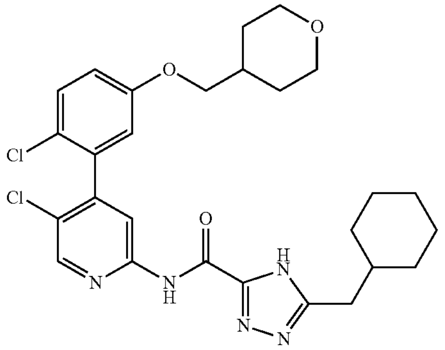

Example 425: N-(5-chloro-4-(2-chloro-5-((tetrahydro-2H-pyran-4-yl)methoxy)phenyl)pyridin-2-yl)-5-(cyclohexylmethyl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-bromo-4-chlorophenol was used in place of 3-bromo-4-methylphenol, in step 2, 5-chloro-4-bromopyridin-2-amine was used in place of 4-bromopyridin-2-amine, and in step 3, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.38 (s, 1H), 10.10 (s, 1H), 8.58 (s, 1H), 8.13 (s, 1H), 7.52 (d, J=8.8 Hz, 1H), 7.11 (dd, J=8.9, 3.0 Hz, 1H), 7.03 (d, J=3.0 Hz, 1H), 3.95-3.81 (m, 4H), 3.34-3.26 (m, 2H), 2.66 (d, J=7.0 Hz, 2H), 2.07-1.92 (m, 1H), 1.83-1.55 (m, 8H), 1.39-1.07 (m, 5H), 1.07-0.89 (m, 2H). MS: 544 [M+H]+.

Example 426: N-(4-(2-chloro-5-((tetrahydro-2H-pyran-4-yl)methoxy)phenyl)-5-methylpyridin-2-yl)-5-(2-fluorobenzyl)-4H-1,2,4-triazole-3-carboxamide The preparation was carried out in a similar manner to Example 64, except that in step 1, (tetrahy dro-2H-pyran- 4-yl)methanol was used in place of 2-(tert-butoxy)ethan-1-ol, 3-bromo-4-chlorophenol was used in place of 3-bromo-4-methylphenol, in step 2, 4-bromo-5-methylpyridin-2-amine was used in place of 4-bromopyridin-2-amine, and in step 3, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.59 (s, 1H), 9.81 (s, 1H), 8.32 (s, 1H), 7.93 (s, 1H), 7.50 (d, J=8.8 Hz, 1H), 7.46-7.29 (m, 2H), 7.26-7.15 (m, 2H), 7.06 (dd, J=8.9, 3.0 Hz, 1H), 6.92 (d, J=3.0 Hz, 1H), 4.20 (s, 2H), 3.95-3.78 (m, 4H), 3.38-3.30 (m, 2H), 2.05 (s, 3H), 2.02-1.92 (m, 1H), 1.66 (dd, J=12.8, 3.1 Hz, 2H), 1.39-1.24 (m, 2H). MS: 536 [M+H]$^+$.

Example 426

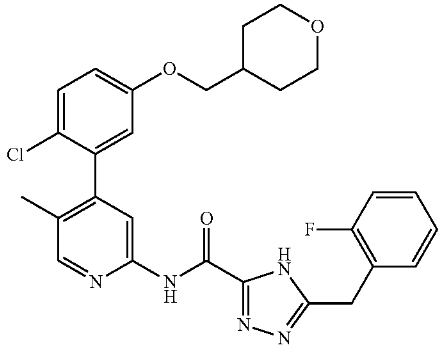

Example 427

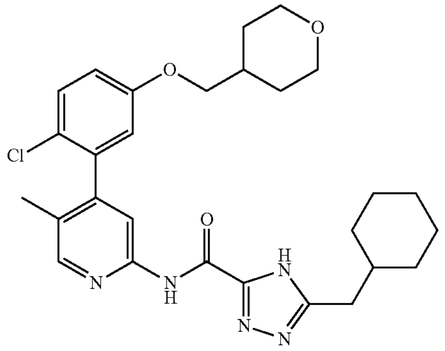

Example 427: N-(4-(2-chloro-5-((tetrahydro-2H-pyran-4-yl)methoxy)phenyl)-5-methylpyridin-2-yl)-5-(cyclohexylmethyl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-bromo-4-chlorophenol was used in place of 3-bromo-4-methylphenol, in step 2, 4-bromo-5-methylpyridin-2-amine was used in place of 4-bromopyridin-2-amine, and in step 3, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.35 (s, 1H), 9.79 (s, 1H), 8.33 (s, 1H), 7.96 (s, 1H), 7.51 (d, J=8.9 Hz, 1H), 7.07 (dd, J=8.9, 3.0 Hz, 1H), 6.93 (d, J=3.0 Hz, 1H), 3.92-3.81 (m, 4H), 3.38-3.33 (m, 2H), 2.70-2.62 (m, 2H), 2.05 (s, 3H), 2.04-1.92 (m, 1H), 1.82-1.58 (m, 8H), 1.38-1.12 (m, 5H), 1.05-0.89 (m, 2H). MS: 524 [M+H]$^+$.

Example 428: N-(4-(2-chloro-5-(2-(tetrahydro-2H-pyran-4-yl)ethoxy)phenyl)-5-fluoropyridin-2-yl)-5-(2-fluorobenzyl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, in step 2, 3-bromo-4-chlorophenol was used in place of 3-bromo-4-methylphenol, in step 3, 4-bromo-5-fluoropyridin-2-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.65 (s, 1H), 10.14 (s, 1H), 8.51 (d, J=1.1 Hz, 1H), 8.12 (d, J=5.5 Hz, 1H), 7.56-7.49 (m, 1H), 7.45-7.29 (m, 2H), 7.25-7.15 (m, 2H), 7.15-7.06 (m, 2H), 4.20 (s, 2H), 4.06 (t, J=6.2 Hz, 2H), 3.87-3.76 (m, 2H), 3.35-3.28 (m, 2H), 1.77-1.55 (m, 5H), 1.29-1.12 (m, 2H). MS: 554 [M+H]$^+$.

Example 428

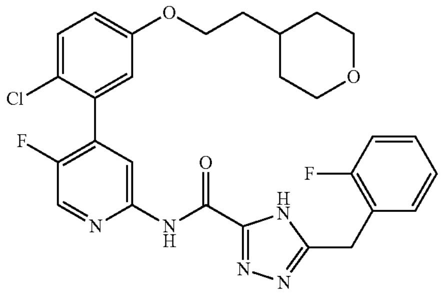

Example 429

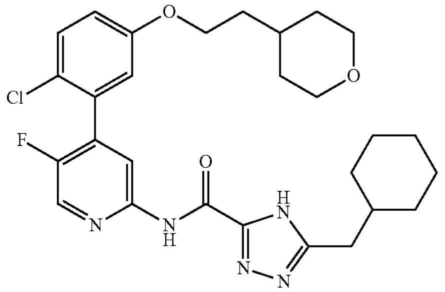

Example 429: N-(4-(2-chloro-5-(2-(tetrahydro-2H-pyran-4-yl)ethoxy)phenyl)-5-fluoropyridin-2-yl)-5-(cyclohexylmethyl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, 3-bromo-4-chlorophenol was used in place of 3-bromo-4-methylphenol, in step 3, 4-bromo-5-fluoropyridin-2-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.38 (s, 1H), 10.07 (s, 1H), 8.52 (d, J=1.2 Hz, 1H), 8.15 (d, J=5.5 Hz, 1H), 7.57-7.48 (m, 1H), 7.17-7.08 (m, 2H), 4.07 (t, J=6.2 Hz, 2H), 3.88-3.75 (m, 2H), 3.31-3.21 (m, 2H), 2.66 (d, J=7.0 Hz, 2H), 1.83-1.55 (m, 12H), 1.30-1.12 (m, 4H), 1.05-0.90 (m, 2H). MS: 542 [M+H]$^+$.

Example 430: N-(5-chloro-4-(2-chloro-5-(2-(tetrahydro-2H-pyran-4-yl)ethoxy)phenyl)pyridin-2-yl)-5-(2-fluorobenzyl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy) ethan-1-ol, 3-bromo-4-chlorophenol was used in place of 3-bromo-4-methylphenol, in step 3, 4-bromo-5-chloropyridin-2-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1$HNMR (400 MHz, DMSO-$d_6$) δ 14.64 (s, 1H), 10.15 (s, 1H), 8.57 (s, 1H), 8.10 (s, 1H), 7.51 (d, J=8.9 Hz, 1H), 7.45-7.29 (m, 2H), 7.26-7.14 (m, 2H), 7.10 (dd, J=8.9, 3.0 Hz, 1H), 7.03 (d, J=3.0 Hz, 1H), 4.21 (s, 2H), 4.05 (t, J=6.3 Hz, 2H), 3.86-3.74 (m, 2H), 3.31-3.19 (m, 2H), 1.76-1.54 (m, 5H), 1.27-1.13 (m, 2H). MS: 570 $[M+H]^+$.

Example 430

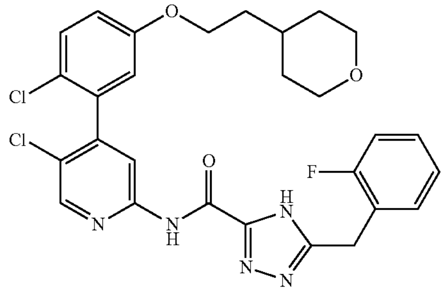

Example 431

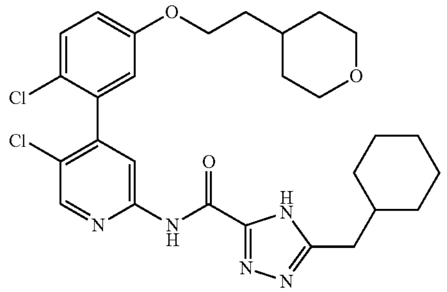

Example 431: N-(5-chloro-4-(2-chloro-5-(2-(tetrahydro-2H-pyran-4-yl)ethoxy)phenyl)pyridin-2-yl)-5-(cyclohexylmethyl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy) ethan-1-ol, 3-bromo-4-chlorophenol was used in place of 3-bromo-4-methylphenol, in step 3, 4-bromo-5-chloropyridin-2-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.38 (s, 1H), 10.09 (s, 1H), 8.58 (s, 1H), 8.13 (s, 1H), 7.52 (d, J=8.9 Hz, 1H), 7.10 (dd, J=8.9, 3.0 Hz, 1H), 7.03 (d, J=3.0 Hz, 1H), 4.05 (t, J=6.4 Hz, 2H), 3.86-3.75 (m, 2H), 3.31-3.20 (m, 2H), 2.67 (d, J=6.8 Hz, 2H), 1.82-1.54 (m, 11H), 1.28-1.13 (m, 5H), 1.05-0.89 (m, 2H). MS: 558 $[M+H]^+$.

Example 432: 5-benzyl-N-(6-(5-((4-hydroxy-4-methylpentyl)oxy)-2-methylphenyl)pyrimidin-4-yl)-4H-1,2,4-triazole-3-carboxamide The preparation was carried out in a similar manner to Example 160, except that in step 3, 6-chloropyrimidin-4-amine was used in place of 4-bromopyridin-2-amine. $^1$H NMR (400 MHz, DMSO-$d_6$) δ 14.68 (s, 1H), 10.35 (s, 1H), 9.01 (d, J=1.3 Hz, 1H), 8.24 (d, J=1.3 Hz, 1H), 7.48-7.16 (m, 6H), 7.09-6.90 (m, 2H), 4.26-4.12 (m, 3H), 3.98 (t, J=6.6 Hz, 2H), 2.31 (s, 3H), 1.86-1.66 (m, 2H), 1.56-1.40 (m, 2H), 1.09 (s, 6H). MS: 487 $[M+H]^+$.

Example 432

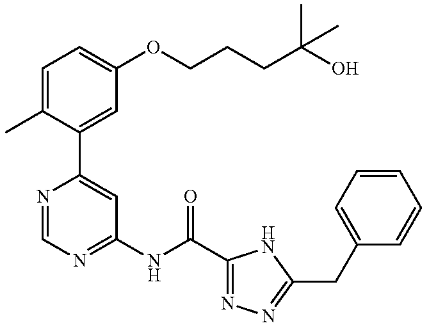

Example 433

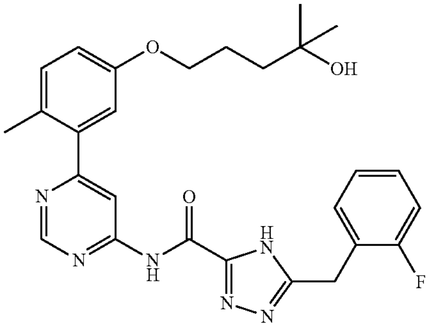

Example 433: 5-(2-fluorobenzyl)-N-(6-(5-((4-hydroxy-4-methylpentyl)oxy)-2-methylphenyl)pyrimidin-4-yl)-4H-1,2,4-triazole-3-carboxamide The preparation was carried out in a similar manner to Example 160, except that in step 3, 6-chloropyrimidin-4-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.73 (s, 1H), 10.33 (s, 1H), 9.01 (d, J=1.2 Hz, 1H), 8.23 (d, J=1.3 Hz, 1H), 7.51-7.29 (m, 2H), 7.29-7.13 (m, 3H), 7.08-6.91 (m, 2H), 4.22 (s, 2H), 4.18 (s, 1H), 3.97 (t, J=6.6 Hz, 2H), 2.31 (s, 3H), 1.83-1.68 (m, 2H), 1.54-1.42 (m, 2H), 1.09 (s, 6H). MS: 505 $[M+H]^+$.

Example 434: 5-(3-fluorobenzyl)-N-(6-(5-((4-hydroxy-4-methylpentyl)oxy)-2-methylphenyl)pyrimidin-4-yl)-4H-1,2,4-triazole-3-carboxamide The preparation was carried out in a similar manner to Example 160, except that in step 3, 6-chloropyrimidin-4-amine was used in place of 4-bromopyridin-2-amine, and in step 4, ethyl 5-(3-fluorobenzyl)-4H-1,2,4-triazol-3-carboxylate was used in place of ethyl 5-benzyl-4H-1,2,4-triazol-3-carboxylate. $^{1}$H NMR (400 MHz, DMSO-$d_6$) δ 14.70 (s, 1H), 10.39 (s, 1H), 9.02 (d, J=1.2 Hz, 1H), 8.24 (d, J=1.2 Hz, 1H), 7.46-7.31 (m, 1H), 7.26 (d, J=8.4 Hz, 1H), 7.23-7.14 (m, 2H), 7.14-7.06 (m, 1H), 7.03 (d, J=2.7 Hz, 1H), 6.98 (dd, J=8.3, 2.8 Hz, 1H), 4.22 (s, 2H), 4.18 (s, 1H), 3.98 (t, J=6.6 Hz, 2H), 2.31 (s, 3H), 1.83-1.69 (m, 2H), 1.54-1.43 (m, 2H), 1.09 (s, 6H). MS: 505 [M+H]$^+$.

Example 434

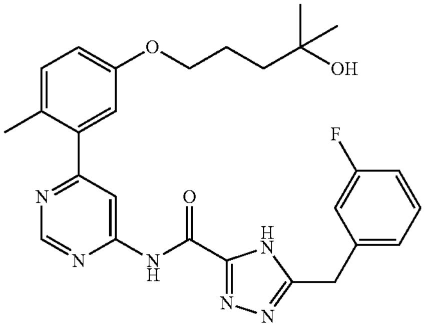

Example 435

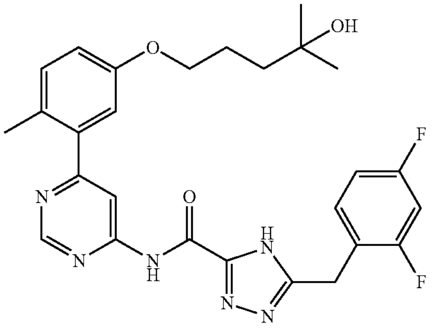

Example 435: 5-(2,4-difluorobenzyl)-N-(6-(5-((4-hydroxy-4-methylpentyl)oxy)-2-methylphenyl)pyrimidin-4-yl)-4H-1,2,4-triazole-3-carboxamide The preparation was carried out in a similar manner to Example 160, except that in step 3, 6-chloropyrimidin-4-amine was used in place of 4-bromopyridin-2-amine, and in step 4, ethyl 5-(2,4-difluorobenzyl)-4H-1,2,4-triazol-3-carboxylate was used in place of ethyl 5-benzyl-4H-1,2,4-triazol-3-carboxylate. $^{1}$H NMR (400 MHz, DMSO-$d_6$) δ 14.72 (s, 1H), 10.35 (s, 1H), 9.01 (d, J=1.2 Hz, 1H), 8.23 (d, J=1.2 Hz, 1H), 7.56-7.40 (m, 1H), 7.27 (dd, J=10.8, 7.8 Hz, 2H), 7.16-7.06 (m, 1H), 7.06-6.91 (m, 2H), 4.25-4.13 (m, 3H), 3.97 (t, J=6.5 Hz, 2H), 2.31 (s, 3H), 1.82-1.67 (m, 2H), 1.53-1.42 (m, 2H), 1.09 (s, 6H). MS: 523 [M+H]$^+$.

Example 436: 5-(2,5-difluorobenzyl)-N-(6-(5-((4-hydroxy-4-methylpentyl)oxy)-2-methylphenyl)pyrimidin-4-yl)-4H-1,2,4-triazole-3-carboxamide The preparation was carried out in a similar manner to Example 160, except that in step 3, 6-chloropyrimidin-4-amine was used in place of 4-bromopyridin-2-amine, and in step 4, ethyl 5-(2,5-difluorobenzyl)-4H-1,2,4-triazol-3-carboxylate was used in place of ethyl 5-benzyl-4H-1,2,4-triazol-3-carboxylate. $^{1}$H NMR (400 MHz, DMSO-$d_6$) δ 14.51 (s, 1H), 10.33 (s, 1H), 9.00 (d, J=1.2 Hz, 1H), 8.24 (d, J=1.3 Hz, 1H), 7.39-7.11 (m, 4H), 7.08-6.90 (m, 2H), 4.24-4.12 (m, 3H), 3.98 (t, J=6.5 Hz, 2H), 2.31 (s, 3H), 1.82-1.69 (m, 2H), 1.53-1.42 (m, 2H), 1.10 (s, 6H). MS: 523 [M+H]$^+$.

Example 436

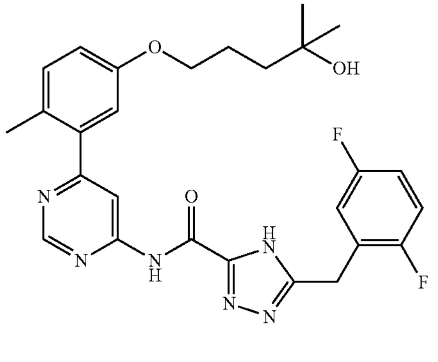

Example 437

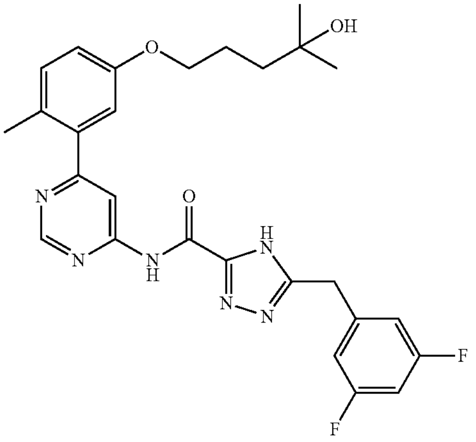

Example 437: 5-(3,5-difluorobenzyl)-N-(6-(5-((4-hydroxy-4-methylpentyl)oxy)-2-methylphenyl)pyrimidin-4-yl)-4H-1,2,4-triazole-3-carboxamide The preparation was carried out in a similar manner to Example 160, except that in step 3, 6-chloropyrimidin-4-amine was used in place of 4-bromopyridin-2-amine, and in step 4, ethyl 5-(3,5-difluorobenzyl)-4H-1,2,4-triazol-3-carboxylate was used in place of ethyl 5-benzyl-4H-1,2,4-triazol-3-carboxylate. $^{1}$H NMR (400 MHz, DMSO-$d_6$) δ 14.73 (s, 1H), 10.44 (s, 1H), 9.02 (d, J=1.2 Hz, 1H), 8.24 (d, J=1.2 Hz, 1H), 7.26 (d, J=8.4 Hz, 1H), 7.22-7.06 (m, 3H), 7.03 (d, J=2.7 Hz, 1H), 6.98 (dd, J=8.4, 2.8 Hz, 1H), 4.24 (s, 2H), 4.18 (s, 1H), 3.98 (t, J=6.5 Hz, 2H), 2.31 (s, 3H), 1.82-1.68 (m, 2H), 1.53-1.43 (m, 2H), 1.09 (s, 6H). MS: 523 [M+H]$^+$.

Example 438: 5-(3-chloro-2-fluorobenzyl)-N-(6-(5-((4-hydroxy-4-methylpentyl)oxy)-2-methylphenyl)pyrimidin-4-yl)-4H-1,2,4-triazole-3-carboxamide The preparation was carried out in a similar manner to Example 160, except that in step 3, 6-chloropyrimidin-4-amine was used in place of 4-bromopyridin-2-amine, and in step 4, ethyl 5-(3-chloro-2-fluorobenzyl)-4H-1,2,4-triazol-3-carboxylate was used in place of ethyl 5-benzyl-4H-1,2,4-triazol-3-carboxylate. $^{1}$H NMR (400 MHz, DMSO-$d_6$) δ 14.71 (s, 1H), 10.31 (s, 1H), 9.01 (d, J=1.2 Hz, 1H), 8.23 (d, J=1.3 Hz, 1H), 7.60-7.45 (m, 1H), 7.45-7.33 (m, 1H), 7.33-7.15 (m, 2H), 7.08-6.91 (m, 2H), 4.27 (s, 2H), 4.18 (s, 1H), 3.97 (t, J=6.5 Hz, 2H), 2.31 (s, 3H), 1.83-1.69 (m, 2H), 1.54-1.40 (m, 2H), 1.09 (s, 6H). MS: 539 $[M+H]^+$.

Example 438

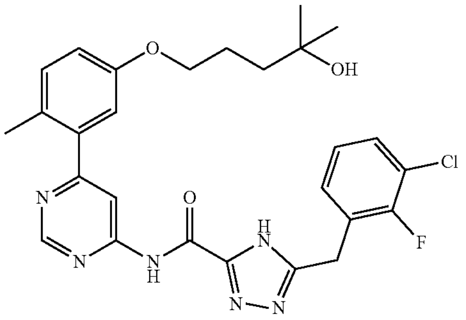

Example 439

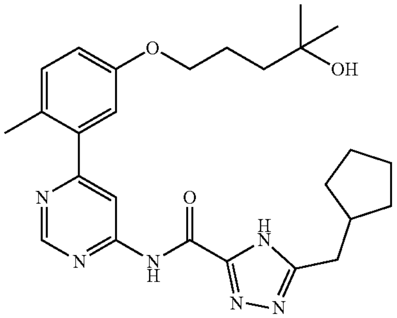

Example 439: 5-(cyclopentylmethyl)-N-(6-(5-((4-hydroxy-4-methylpentyl)oxy)-2-methylphenyl)pyrimidin-4-yl)-4H-1,2,4-triazole-3-carboxamide The preparation was carried out in a similar manner to Example 160, except that in step 3, 6-chloropyrimidin-4-amine was used in place of 4-bromopyridin-2-amine, and in step 4, ethyl 5-(cyclopentylmethyl)-4H-1,2,4-triazole-3-carboxylate was used in place of ethyl 5-benzyl-4H-1,2,4-triazol-3-carboxylate. $^1$H NMR (400 MHz, DMSO-$d_6$) δ 14.47 (s, 1H), 10.27 (s, 1H), 9.02 (d, J=1.2 Hz, 1H), 8.26 (d, J=1.3 Hz, 1H), 7.26 (d, J=8.4 Hz, 1H), 7.09-6.90 (m, 2H), 4.18 (s, 1H), 3.98 (t, J=6.5 Hz, 2H), 2.79 (d, J=7.5 Hz, 2H), 2.32 (s, 3H), 2.30-2.18 (m, 1H), 1.82-1.67 (m, 4H), 1.67-1.56 (m, 2H), 1.56-1.43 (m, 4H), 1.25-1.21 (m, 2H), 1.10 (s, 6H). MS: 479 $[M+H]^+$.

Example 440: 5-(cyclohexylmethyl)-N-(6-(5-((4-hydroxy-4-methylpentyl)oxy)-2-methylphenyl)pyrimidin-4-yl)-4H-1,2,4-triazole-3-carboxamide The preparation was carried out in a similar manner to Example 160, except that in step 3, 6-chloropyrimidin-4-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.42 (s, 1H), 10.28 (s, 1H), 9.02 (s, 1H), 8.26 (s, 1H), 7.26 (d, J=8.4 Hz, 1H), 7.03 (d, J=2.7 Hz, 1H), 6.99 (dd, J=8.3, 2.8 Hz, 1H), 4.18 (s, 1H), 3.98 (t, J=6.6 Hz, 2H), 2.67 (d, J=7.0 Hz, 2H), 2.32 (s, 3H), 1.83-1.55 (m, 8H), 1.52-1.42 (m, 2H), 1.25-1.14 (m, 3H), 1.10 (s, 6H), 1.04-0.89 (m, 2H). MS: 493 $[M+H]^+$.

Example 440

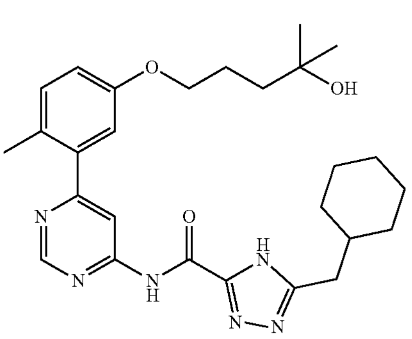

Example 441

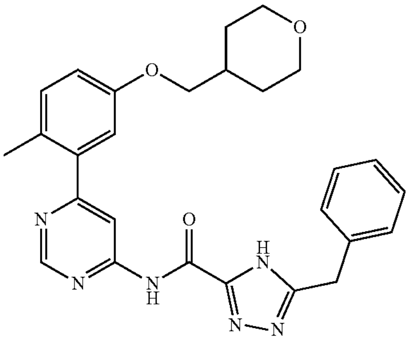

Example 441: 5-benzyl-N-(6-(2-methyl-5-((tetrahydro-2H-pyran-4-yl)methoxy)phenyl)pyrimidin-4-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, and in step 2, 6-chloropyrimidin-4-amine was used in place of 4-bromopyridin-2-amine. $^1$H NMR (400 MHz, DMSO-$d_6$) δ 14.68 (s, 1H), 10.34 (s, 1H), 9.02 (d, J=1.2 Hz, 1H), 8.24 (d, J=1.3 Hz, 1H), 7.39-7.29 (m, 4H), 7.29-7.22 (m, 2H), 7.04 (d, J=2.7 Hz, 1H), 7.00 (dd, J=8.3, 2.8 Hz, 1H), 4.19 (s, 2H), 3.92-3.80 (m, 4H), 3.33-3.28 (m, 2H), 2.31 (s, 3H), 2.05-1.93 (m, 1H), 1.76-1.62 (m, 2H), 1.39-1.26 (m, 2H). MS: 485 $[M+H]^+$.

Example 442: 5-(2-fluorobenzyl)-N-(6-(2-methyl-5-((tetrahydro-2H-pyran-4-yl)methoxy)phenyl)pyrimidin-4-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, in step 2, 6-chloropyrimidin-4-amine was used in place of 4-bromopyridin-2-amine, and in step 3, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.75 (s, 1H), 10.34 (s, 1H), 9.01 (d, J=1.3 Hz, 1H), 8.23 (d, J=1.3 Hz, 1H), 7.46-7.30 (m, 2H), 7.30-7.16 (m, 3H), 7.04 (d, J=2.8 Hz, 1H), 6.99 (dd, J=8.4, 2.8 Hz, 1H), 4.22 (s, 2H), 3.92-3.79 (m, 4H), 3.32-3.25 (m, 2H), 2.31 (s, 3H), 2.05-1.92 (m, 1H), 1.73-1.62 (m, 2H), 1.40-1.26 (m, 2H). MS: 503 $[M+H]^+$.

Example 442

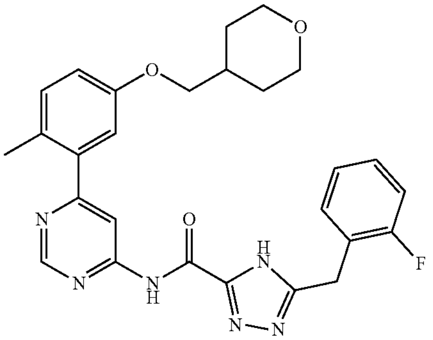

Example 443

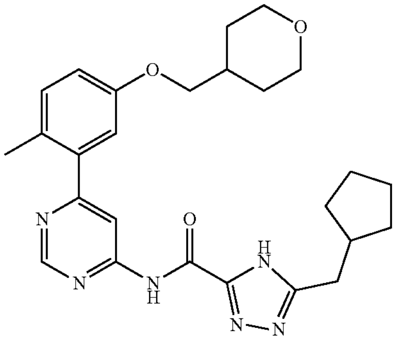

Example 443: 5-(cyclopentylmethyl)-N-(6-(2-methyl-5-((tetrahydro-2H-pyran-4-yl)methoxy)phenyl)pyrimidin-4-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, in step 2, 6-chloropyrimidin-4-amine was used in place of 4-bromopyridin-2-amine, and in step 3, ethyl 5-(cyclopentylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.48 (s, 1H), 10.27 (s, 1H), 9.03 (d, J=1.3 Hz, 1H), 8.26 (d, J=1.3 Hz, 1H), 7.27 (d, J=8.4 Hz, 1H), 7.05 (d, J=2.8 Hz, 1H), 7.00 (dd, J=8.3, 2.8 Hz, 1H), 3.93-3.81 (m, 4H), 3.33-3.29 (m, 2H), 2.79 (d, J=7.5 Hz, 2H), 2.32 (s, 3H), 2.31-2.21 (m, 1H), 2.08-1.93 (m, 1H), 1.79-1.45 (m, 8H), 1.38-1.27 (m, 2H), 1.27-1.17 (m, 2H). MS: 477 $[M+H]^+$.

Example 444: 5-(cyclohexylmethyl)-N-(6-(2-methyl-5-((tetrahydro-2H-pyran-4-yl)methoxy)phenyl)pyrimidin-4-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, in step 2, 6-chloropyrimidin-4-amine was used in place of 4-bromopyridin-2-amine, and in step 3, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.47 (s, 1H), 10.26 (s, 1H), 9.02 (d, J=1.3 Hz, 1H), 8.25 (d, J=1.3 Hz, 1H), 7.26 (d, J=8.4 Hz, 1H), 7.05 (d, J=2.7 Hz, 1H), 7.00 (dd, J=8.4, 2.8 Hz, 1H), 3.92-3.81 (m, 4H), 3.37-3.32 (m, 2H), 2.67 (d, J=7.1 Hz, 2H), 2.31 (s, 3H), 2.06-1.93 (m, 1H), 1.82-1.53 (m, 8H), 1.42-1.25 (m, 2H), 1.25-1.06 (m, 3H), 1.06-0.91 (m, 2H). MS: 491 $[M+H]^+$.

Example 444

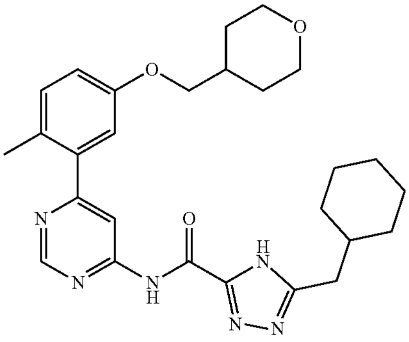

Example 445

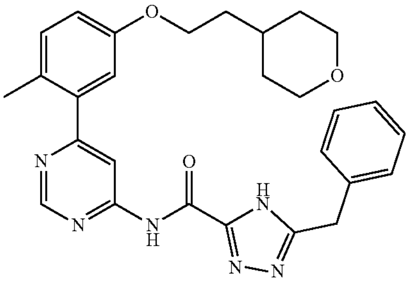

Example 445: 5-benzyl-N-(6-(2-methyl-5-(2-(tetrahydro-2H-pyran-4-yl)ethoxy)phenyl)pyrimidin-4-yl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, and in step 2, 6-chloropyrimidin-4-amine was used in place of 4-bromopyridin-2-amine. $^1$H NMR (400 MHz, DMSO-$d_6$) δ 14.68 (s, 1H), 10.35 (s, 1H), 9.02 (d, J=1.2 Hz, 1H), 8.24 (d, J=1.3 Hz, 1H), 7.45-7.17 (m, 6H), 7.17-6.86 (m, 2H), 4.19 (s, 2H), 4.04 (t, J=6.3 Hz, 2H), 3.93-3.66 (m, 2H), 3.30-3.20 (m, 2H), 2.31 (s, 3H), 1.82-1.56 (m, 5H), 1.28-1.17 (m, 2H). MS: 499 $[M+H]^+$.

Example 446: 5-(2-fluorobenzyl)-N-(6-(2-methyl-5-(2-(tetrahydro-2H-pyran-4-yl)ethoxy)phenyl)pyrimidin-4-yl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, in step 3, 6-chloropyrimidin-4-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.71 (s, 1H), 10.34 (s, 1H), 9.01 (d, J=1.2 Hz, 1H), 8.23 (d, J=1.3 Hz, 1H), 7.47-7.29 (m, 2H), 7.29-7.15 (m, 3H), 7.08-6.93 (m, 2H), 4.22 (s, 2H), 4.03 (t, J=6.3 Hz, 2H), 3.91-3.74 (m, 2H), 3.30-3.18 (m, 2H), 2.30 (s, 3H), 1.83-1.53 (m, 5H), 1.24-1.13 (m, 2H). MS: 517 $[M+H]^+$.

Example 446

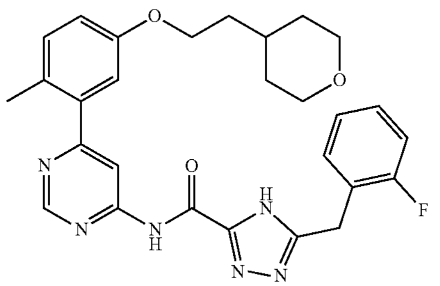

Example 447

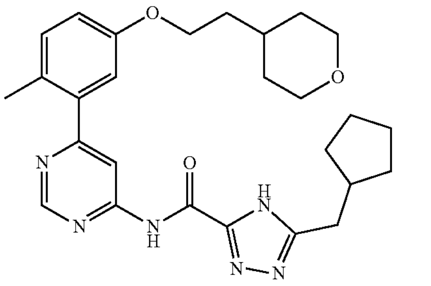

Example 447: 5-(cyclopentylmethyl)-N-(6-(2-methyl-5-(2-(tetrahydro-2H-pyran-4-yl)ethoxy)phenyl)pyrimidin-4-yl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, in step 3, 6-chloropyrimidin-4-amine was used in place of 4-bromopyridin-2-amine, and in step 4, ethyl 5-(cyclopentylmethyl)-4H-1,2,4-triazole-3-carboxylate was used in place of ethyl 5-benzyl-4H-1,2,4-triazol-3-carboxylate. $^1H$ NMR (400 MHz, DMSO-$d_6$) δ 14.49 (s, 1H), 10.27 (s, 1H), 9.02 (d, J=1.3 Hz, 1H), 8.25 (d, J=1.3 Hz, 1H), 7.26 (d, J=8.4 Hz, 1H), 7.12-6.83 (m, 2H), 4.04 (t, J=6.3 Hz, 2H), 3.93-3.66 (m, 2H), 3.30-3.17 (m, 2H), 2.78 (d, J=7.5 Hz, 2H), 2.31 (s, 3H), 2.29-2.14 (m, 1H), 1.80-1.43 (m, 11H), 1.26-1.14 (m, 4H). MS: 491 $[M+H]^+$.

Example 448: 5-(cyclohexylmethyl)-N-(6-(2-methyl-5-(2-(tetrahydro-2H-pyran-4-yl)ethoxy)phenyl)pyrimidin-4-yl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, in step 3, 6-chloropyrimidin-4-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.39 (s, 1H), 10.26 (s, 1H), 9.01 (s, 1H), 8.25 (s, 1H), 7.26 (d, J=8.4 Hz, 1H), 7.05 (d, J=2.8 Hz, 1H), 7.00 (dd, J=8.4, 2.8 Hz, 1H), 4.04 (t, J=6.3 Hz, 2H), 3.82 (dd, J=11.2, 4.3 Hz, 2H), 3.28-3.22 (m, 2H), 2.67 (d, J=7.0 Hz, 2H), 2.31 (s, 3H), 1.83-1.55 (m, 12H), 1.25-1.17 (m, 4H), 1.04-0.89 (m, 2H). MS: 505 $[M+H]^+$.

Example 448

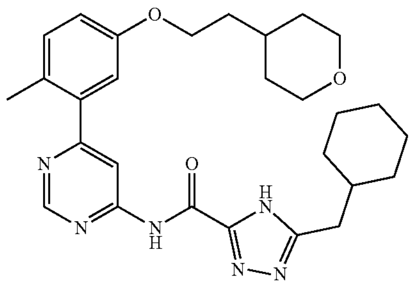

Example 449

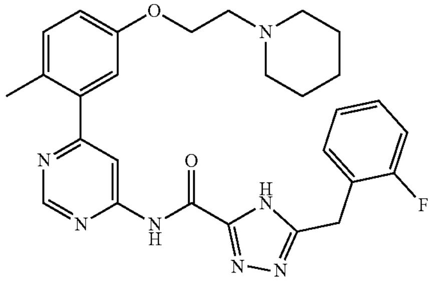

Example 449: 5-(2-fluorobenzyl)-N-(6-(2-methyl-5-(2-(piperidin-1-yl)ethoxy)phenyl)pyrimidin-4-yl)-4H-1,2,4-triazole-3-carboxamide The preparation was carried out in a similar manner to Example 92, except that in step 1, 1-(2-chloroethyl)piperidine hydrochloride was used in place of iodomethane, 3-bromo-4-methylphenol was used in place of 2-bromo-3-methylphenol, in step 2, 6-chloropyrimidin-4-amine was used in place of 4-bromopyridin-2-amine, and in step 3, ethyl 5-(2-fluorobenzyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.57 (s, 1H), 10.33 (s, 1H), 9.01 (d, J=1.2 Hz, 1H), 8.23 (d, J=1.3 Hz, 1H), 7.46-7.29 (m, 2H), 7.29-7.16 (m, 3H), 7.05 (d, J=2.7 Hz, 1H), 7.00 (dd, J=8.4, 2.8 Hz, 1H), 4.21 (s, 2H), 4.09 (t, J=5.9 Hz, 2H), 2.67 (t, J=5.9 Hz, 2H), 2.47-2.39 (m, 4H), 2.31 (s, 3H), 1.54-1.44 (m, 4H), 1.41-1.31 (m, 2H). MS: 516 $[M+H]^+$.

Example 450: 5-benzyl-N-(6-(5-((4-hydroxy-4-methylpentyl)oxy)-2-(trifluoromethyl)phenyl)pyrimidin-4-yl)-4H-1,2,4-triazole-3-carboxamide The preparation was carried out in a similar manner to Example 160, except that in step 1, 3-chloro-4-(trifluoromethyl)phenol was used in place of 3-bromo-4-methylphenol, and in step 3, 6-chloropyrimidin-4-amine was used in place of 4-bromopyridin-2-amine. $^1H$ NMR (400 MHz, DMSO-$d_6$) δ 14.68 (s, 1H), 10.45 (s, 1H), 9.02 (d, J=1.2 Hz, 1H), 8.25 (d, J=1.2 Hz, 1H), 7.81 (d, J=8.9 Hz, 1H), 7.38-7.29 (m, 4H), 7.29-7.20 (m, 2H), 7.11 (d, J=2.6 Hz, 1H), 4.24-4.15 (m, 3H), 4.10 (t, J=6.6 Hz, 2H), 1.84-1.69 (m, 2H), 1.54-1.41 (m, 2H), 1.10 (s, 6H). MS: 541 $[M+H]^+$.

Example 450

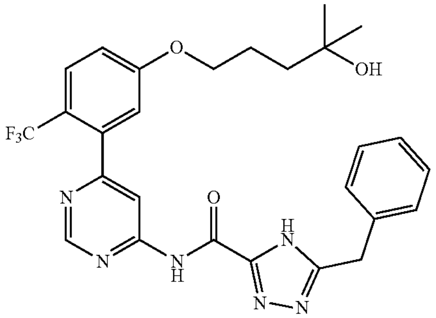

Example 451

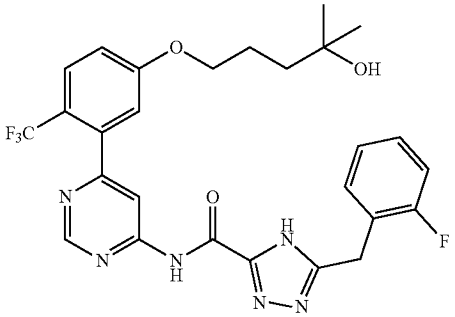

Example 451: 5-(2-fluorobenzyl)-N-(6-(5-((4-hydroxy-4-methylpentyl)oxy)-2-(trifluoromethyl)phenyl)pyrimidin-4-yl)-4H-1,2,4-triazole-3-carboxamide The preparation was carried out in a similar manner to Example 160, except that in step 1, 3-chloro-4-(trifluoromethyl)phenol was used in place of 3-bromo-4-methylphenol, in step 3, 6-chloropyrimidin-4-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.75 (s, 1H), 10.46 (s, 1H), 9.02 (d, J=1.3 Hz, 1H), 8.24 (d, J=1.3 Hz, 1H), 7.81 (d, J=8.9 Hz, 1H), 7.45-7.30 (m, 2H), 7.27-7.16 (m, 3H), 7.11 (d, J=2.6 Hz, 1H), 4.27-4.16 (m, 3H), 4.10 (t, J=6.6 Hz, 2H), 1.86-1.71 (m, 2H), 1.55-1.42 (m, 2H), 1.10 (s, 6H). MS: 559 $[M+H]^+$.

Example 452: 5-(cyclopentylmethyl)-N-(6-(5-((4-hydroxy-4-methylpentyl)oxy)-2-(trifluoromethyl)phenyl)pyrimidin-4-yl)-4H-1,2,4-triazole-3-carboxamide The preparation was carried out in a similar manner to Example 160, except that in step 1, 3-chloro-4-(trifluoromethyl)phenol was used in place of 3-bromo-4-methylphenol, in step 3, 6-chloropyrimidin-4-amine was used in place of 4-bromopyridin-2-amine, and in step 4, ethyl 5-(cyclopentylmethyl)-4H-1,2,4-triazole-3-carboxylate was used in place of ethyl 5-benzyl-4H-1,2,4-triazol-3-carboxylate. $^1$H NMR (400 MHz, DMSO-$d_6$) δ 14.54 (s, 1H), 10.39 (s, 1H), 9.03 (d, J=1.3 Hz, 1H), 8.26 (d, J=1.3 Hz, 1H), 7.81 (d, J=8.9 Hz, 1H), 7.24 (dd, J=8.7, 2.6 Hz, 1H), 7.12 (d, J=2.6 Hz, 1H), 4.20 (s, 1H), 4.10 (t, J=6.5 Hz, 2H), 2.78 (d, J=7.5 Hz, 2H), 2.36-2.17 (m, 1H), 1.86-1.66 (m, 4H), 1.66-1.43 (m, 6H), 1.25-1.18 (m, 2H), 1.10 (s, 6H). MS: 533 $[M+H]^+$.

Example 452

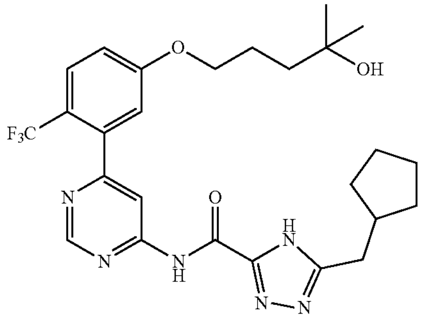

Example 453

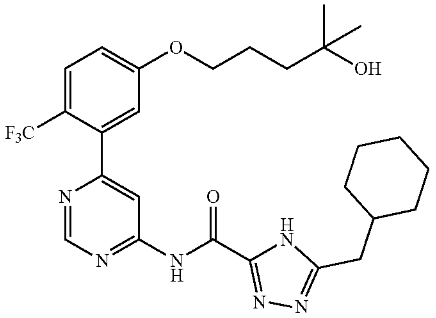

Example 453: 5-(cyclohexylmethyl)-N-(6-(5-((4-hydroxy-4-methylpentyl)oxy)-2-(trifluoromethyl)phenyl)pyrimidin-4-yl)-4H-1,2,4-triazole-3-carboxamide The preparation was carried out in a similar manner to Example 160, except that in step 1, 3-chloro-4-(trifluoromethyl)phenol was used in place of 3-bromo-4-methylphenol, in step 3, 6-chloropyrimidin-4-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.47 (s, 1H), 10.37 (s, 1H), 9.03 (d, J=1.2 Hz, 1H), 8.26 (d, J=1.3 Hz, 1H), 7.81 (d, J=8.9 Hz, 1H), 7.24 (dd, J=8.9, 2.6 Hz, 1H), 7.12 (d, J=2.6 Hz, 1H), 4.20 (s, 1H), 4.10 (t, J=6.6 Hz, 2H), 2.67 (d, J=7.1 Hz, 2H), 1.85-1.54 (m, 8H), 1.54-1.41 (m, 2H), 1.23-1.16 (m, 3H), 1.10 (s, 6H), 1.05-0.89 (m, 2H). MS: 547 $[M+H]^+$.

Example 454: 5-benzyl-N-(6-(5-((tetrahydro-2H-pyran-4-yl)methoxy)-2-(trifluoromethyl)phenyl)pyrimidin-4-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-chloro-4-(trifluoromethyl)phenol was used in place of 3-bromo-4-methylphenol, and in step 2, 6-chloropyrimidin-4-amine was used in place of 4-bromopyridin-2-amine. $^1$H NMR (400 MHz, DMSO-$d_6$) δ 14.65 (s, 1H), 10.45 (s, 1H), 9.02 (d, J=1.2 Hz, 1H), 8.25 (d, J=1.2 Hz, 1H), 7.81 (d, J=8.9 Hz, 1H), 7.39-7.29 (m, 4H), 7.29-7.19 (m, 2H), 7.13 (d, J=2.6 Hz, 1H), 4.19 (s, 2H), 3.98 (d, J=6.5 Hz, 2H), 3.92-3.81 (m, 2H), 3.37-3.32 (m, 2H), 2.07-1.94 (m, 1H), 1.74-1.60 (m, 2H), 1.40-1.26 (m, 2H). MS: 539 $[M+H]^+$.

Example 454

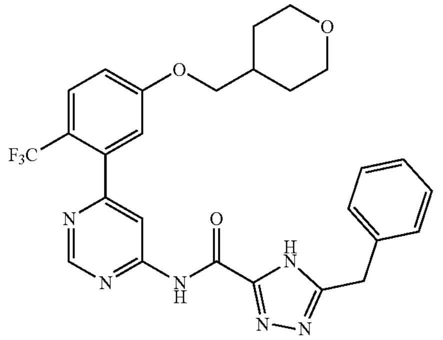

Example 455

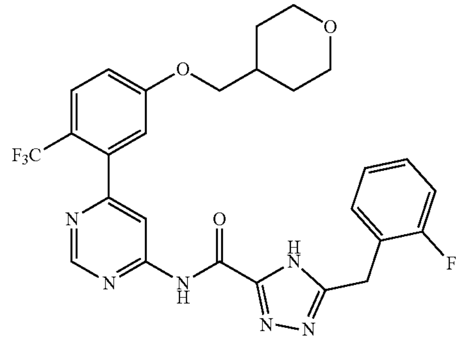

Example 455: 5-(2-fluorobenzyl)-N-(6-(5-((tetrahydro-2H-pyran-4-yl)methoxy)-2-(trifluoromethyl) phenyl)pyrimidin-4-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-chloro-4-(trifluoromethyl)phenol was used in place of 3-bromo-4-methylphenol, in step 2, 6-chloropyrimidin-4-amine was used in place of 4-bromopyridin-2-amine, and in step 3, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.73 (s, 1H), 10.46 (s, 1H), 9.02 (d, J=1.3 Hz, 1H), 8.24 (d, J=1.3 Hz, 1H), 7.81 (d, J=8.9 Hz, 1H), 7.49-7.28 (m, 2H), 7.28-7.07 (m, 4H), 4.22 (s, 2H), 3.97 (d, J=6.5 Hz, 2H), 3.93-3.82 (m, 2H), 3.36-3.30 (m, 2H), 2.09-1.95 (m, 1H), 1.74-1.62 (m, 2H), 1.42-1.24 (m, 2H). MS: 557 [M+H]$^+$.

Example 456: 5-(cyclopentylmethyl)-N-(6-(5-((tetrahydro-2H-pyran-4-yl)methoxy)-2-(trifluoromethyl) phenyl)pyrimidin-4-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-chloro-4-(trifluoromethyl)phenol was used in place of 3-bromo-4-methylphenol, in step 2, 6-chloropyrimidin-4-amine was used in place of 4-bromopyridin-2-amine, and in step 3, ethyl 5-(cyclopentylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.47 (s, 1H), 10.38 (s, 1H), 9.03 (d, J=1.2 Hz, 1H), 8.26 (d, J=1.2 Hz, 1H), 7.81 (d, J=8.9 Hz, 1H), 7.26 (dd, J=8.8, 2.6 Hz, 1H), 7.14 (d, J=2.6 Hz, 1H), 3.98 (d, J=6.4 Hz, 2H), 3.93-3.83 (m, 2H), 3.43-3.36 (m, 2H), 2.78 (d, J=7.5 Hz, 2H), 2.36-2.21 (m, 1H), 2.08-1.95 (m, 1H), 1.75-1.64 (m, 4H), 1.64-1.56 (m, 2H), 1.56-1.46 (m, 2H), 1.39-1.28 (m, 2H), 1.23-1.14 (m, 2H). MS: 531 [M+H]$^+$.

Example 456

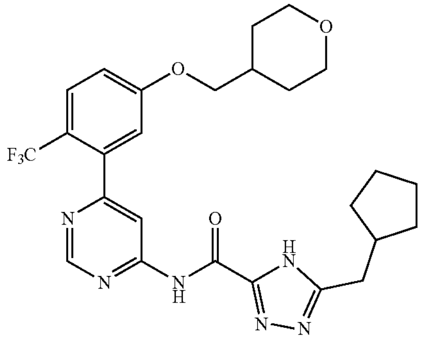

Example 457

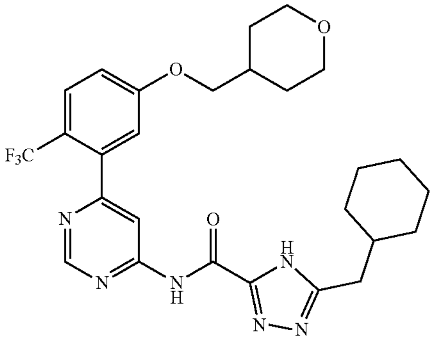

Example 457: 5-(cyclohexylmethyl)-N-(6-(5-((tetrahydro-2H-pyran-4-yl)methoxy)-2-(trifluoromethyl) phenyl)pyrimidin-4-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-chloro-4-(trifluoromethyl)phenol was used in place of 3-bromo-4-methylphenol, in step 2, 6-chloropyrimidin-4-amine was used in place of 4-bromopyridin-2-amine, and in step 3, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.47 (s, 1H), 10.38 (s, 1H), 9.03 (d, J=1.3 Hz, 1H), 8.26 (d, J=1.3 Hz, 1H), 7.81 (d, J=8.9 Hz, 1H), 7.26 (dd, J=8.7, 2.6 Hz, 1H), 7.14 (d, J=2.6 Hz, 1H), 3.98 (d, J=6.5 Hz, 2H), 3.93-3.81 (m, 2H), 3.35-3.30 (m, 2H), 2.67 (d, J=7.1 Hz, 2H), 2.11-1.96 (m, 1H), 1.83-1.57 (m, 8H), 1.42-1.26 (m, 2H), 1.26-1.07 (m, 3H), 1.07-0.91 (m, 2H). MS: 545 [M+H]$^+$.

Example 458: 5-benzyl-N-(6-(5-(2-(tetrahydro-2H-pyran-4-yl)ethoxy)-2-(trifluoromethyl)phenyl)pyrimidin-4-yl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)

ethan-1-ol, in step 2, 3-chloro-4-(trifluoromethyl)phenol was used in place of 3-bromo-4-methylphenol, and in step 3, 6-chloropyrimidin-4-amine was used in place of 4-bromopyridin-2-amine. $^1$H NMR (400 MHz, DMSO-$d_6$) δ 14.59 (s, 1H), 10.47 (s, 1H), 9.02 (d, J=1.2 Hz, 1H), 8.25 (d, J=1.2 Hz, 1H), 7.80 (d, J=8.9 Hz, 1H), 7.39-7.29 (m, 4H), 7.29-7.18 (m, 2H), 7.13 (d, J=2.6 Hz, 1H), 4.25-4.10 (m, 4H), 3.88-3.76 (m, 2H), 3.27-3.23 (m, 2H), 1.77-1.65 (m, 3H), 1.65-1.56 (m, 2H), 1.26-1.19 (m, 2H). MS: 553 $[M+H]^+$.

Example 458

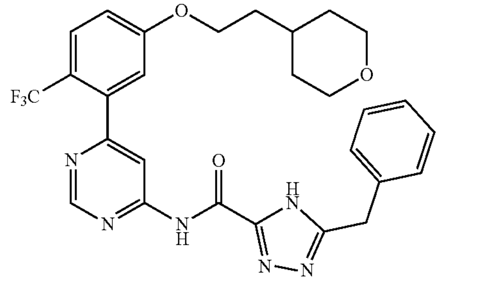

Example 459

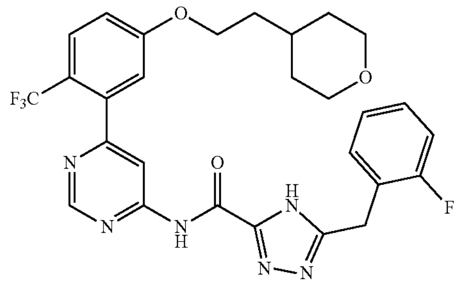

Example 459: 5-(2-fluorobenzyl)-N-(6-(5-(2-(tetrahydro-2H-pyran-4-yl)ethoxy)-2-(trifluoromethyl)phenyl)pyrimidin-4-yl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, in step 2, 3-chloro-4-(trifluoromethyl)phenol was used in place of 3-bromo-4-methylphenol, in step 3, 6-chloropyrimidin-4-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.70 (s, 1H), 10.47 (s, 1H), 9.02 (d, J=1.2 Hz, 1H), 8.24 (d, J=1.2 Hz, 1H), 7.80 (d, J=8.9 Hz, 1H), 7.50-7.30 (m, 2H), 7.30-7.06 (m, 4H), 4.21 (s, 2H), 4.15 (t, J=6.1 Hz, 2H), 3.88-3.76 (m, 2H), 3.29-3.18 (m, 2H), 1.71-1.56 (m, 4H), 1.30-1.13 (m, 3H). MS: 571 $[M+H]^+$.

Example 460: 5-(cyclopentylmethyl)-N-(6-(5-(2-(tetrahydro-2H-pyran-4-yl)ethoxy)-2-(trifluoromethyl)phenyl)pyrimidin-4-yl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, in step 2, 3-chloro-4-(trifluoromethyl)phenol was used in place of 3-bromo-4-methylphenol, in step 3, 6-chloropyrimidin-4-amine was used in place of 4-bromopyridin-2-amine, and in step 4, ethyl 5-(cyclopentylmethyl)-4H-1,2,4-triazole-3-carboxylate was used in place of ethyl 5-benzyl-4H-1,2,4-triazol-3-carboxylate. $^1$H NMR (400 MHz, DMSO-$d_6$) δ 14.47 (s, 1H), 10.40 (s, 1H), 9.03 (s, 1H), 8.26 (s, 1H), 7.81 (d, J=8.9 Hz, 1H), 7.26 (dd, J=8.8, 2.6 Hz, 1H), 7.14 (d, J=2.6 Hz, 1H), 4.16 (t, J=6.0 Hz, 2H), 3.82 (dd, J=10.8, 4.3 Hz, 2H), 3.29-3.21 (m, 2H), 2.78 (d, J=7.5 Hz, 2H), 2.37-2.18 (m, 1H), 1.82-1.66 (m, 5H), 1.66-1.57 (m, 4H), 1.57-1.46 (m, 2H), 1.25-1.14 (m, 4H). MS: 545 $[M+H]^+$.

Example 460

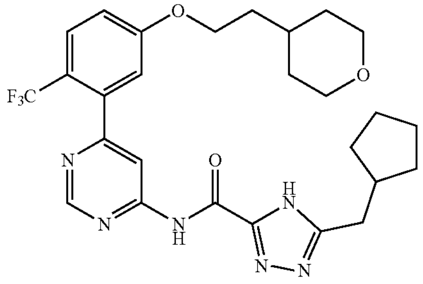

Example 461

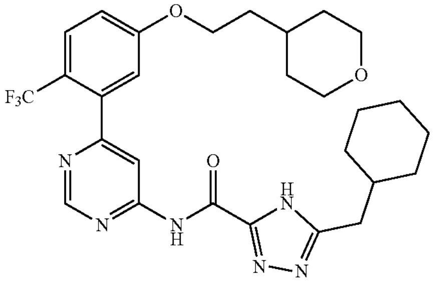

Example 461: 5-(cyclohexylmethyl)-N-(6-(5-(2-(tetrahydro-2H-pyran-4-yl)ethoxy)-2-(trifluoromethyl)phenyl)pyrimidin-4-yl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, in step 2, 3-chloro-4-(trifluoromethyl)phenol was used in place of 3-bromo-4-methylphenol, in step 3, 6-chloropyrimidin-4-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.47 (s, 1H), 10.40 (s, 1H), 9.03 (d, J=1.2 Hz, 1H), 8.26 (d, J=1.2 Hz, 1H), 7.81 (d, J=8.9 Hz, 1H), 7.26 (dd, J=8.7, 2.6 Hz, 1H), 7.14 (d, J=2.6 Hz, 1H), 4.16 (t, J=6.1 Hz, 2H), 3.90-3.73 (m, 2H), 3.31-3.20 (m, 2H), 2.67 (d, J=7.1 Hz, 2H), 1.83-1.54 (m, 11H), 1.24-1.06 (m, 5H), 1.06-0.89 (m, 2H). MS: 559 $[M+H]^+$.

Example 462: 5-benzyl-N-(6-(2-chloro-5-((4-hydroxy-4-methylpentyl)oxy)phenyl)pyrimidin-4-yl)-4H-1,2,4-triazole-3-carboxamide The preparation was carried out in a similar manner to Example 160, except that in step 1, 3-bromo-4-chlorophenol was used in place of 3-bromo-4-methylphenol, and in step 3, 6-chloropyrimidin-4-amine was used in place of 4-bromopyridin-2-amine. $^1$H NMR (400 MHz, DMSO-$d_6$) δ 14.61 (s, 1H), 10.42 (s, 1H), 9.06 (d, J=1.3 Hz, 1H), 8.45 (d, J=1.3 Hz, 1H), 7.52 (d, J=8.8 Hz, 1H), 7.38-7.30 (m, 4H), 7.30-7.22 (m, 1H), 7.20 (d, J=3.0 Hz, 1H), 7.11 (dd, J=8.8, 3.1 Hz, 1H), 4.27-4.13 (m, 3H), 4.01 (t, J=6.5 Hz, 2H), 1.84-1.70 (m, 2H), 1.53-1.43 (m, 2H), 1.09 (s, 6H). MS: 507 $[M+H]^+$.

Example 462

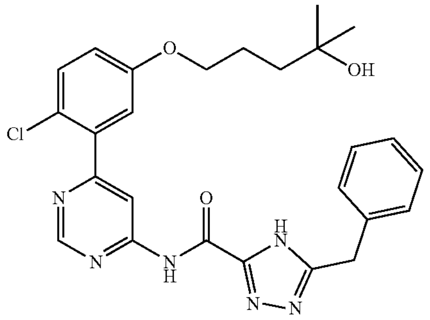

Example 463

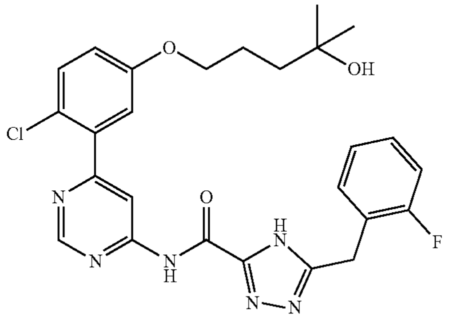

Example 463: 5-(2-fluorobenzyl)-N-(6-(2-chloro-5-((4-hydroxy-4-methylpentyl)oxy)phenyl)pyrimidin-4-yl)-4H-1,2,4-triazole-3-carboxamide The preparation was carried out in a similar manner to Example 160, except that in step 1, 3-bromo-4-chlorophenol was used in place of 3-bromo-4-methylphenol, in step 3, 6-chloropyrimidin-4-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.71 (s, 1H), 10.42 (s, 1H), 9.05 (d, J=1.2 Hz, 1H), 8.44 (d, J=1.2 Hz, 1H), 7.52 (d, J=8.8 Hz, 1H), 7.46-7.30 (m, 2H), 7.27-7.15 (m, 3H), 7.11 (dd, J=8.8, 3.1 Hz, 1H), 4.31-4.14 (m, 3H), 4.01 (t, J=6.6 Hz, 2H), 1.84-1.68 (m, 2H), 1.55-1.41 (m, 2H), 1.09 (s, 6H). MS: 525 $[M+H]^+$.

Example 464: 5-(cyclopentylmethyl)-N-(6-(2-chloro-5-((4-hydroxy-4-methylpentyl)oxy)phenyl) pyrimidin-4-yl)-4H-1,2,4-triazole-3-carboxamide The preparation was carried out in a similar manner to Example 160, except that in step 1, 3-bromo-4-chlorophenol was used in place of 3-bromo-4-methylphenol, in step 3, 6-chloropyrimidin-4-amine was used in place of 4-bromopyridin-2-amine, and in step 4, ethyl 5-(cyclopentylmethyl)-4H-1,2,4-triazole-3-carboxylate was used in place of ethyl 5-benzyl-4H-1,2,4-triazol-3-carboxylate. $^1$H NMR (400 MHz, DMSO-$d_6$) δ 14.32 (s, 1H), 10.34 (s, 1H), 9.06 (d, J=1.3 Hz, 1H), 8.46 (d, J=1.2 Hz, 1H), 7.52 (d, J=8.8 Hz, 1H), 7.21 (d, J=3.1 Hz, 1H), 7.11 (dd, J=8.8, 3.1 Hz, 1H), 4.19 (s, 1H), 4.02 (t, J=6.5 Hz, 2H), 2.78 (d, J=7.5 Hz, 2H), 2.37-2.20 (m, 1H), 1.85-1.66 (m, 4H), 1.66-1.42 (m, 6H), 1.25-1.16 (m, 2H), 1.10 (s, 6H). MS: 499 $[M+H]^+$.

Example 464

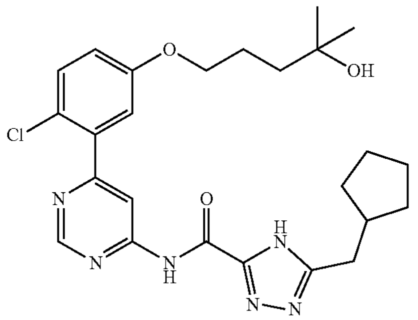

Example 465

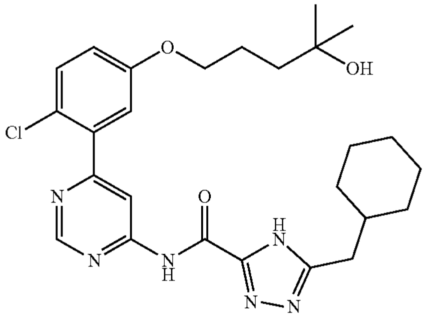

Example 465: 5-(cyclohexylmethyl)-N-(6-(2-chloro-5-((4-hydroxy-4-methylpentyl)oxy)phenyl)pyrimidin-4-yl)-4H-1,2,4-triazole-3-carboxamide The preparation was carried out in a similar manner to Example 160, except that in step 1, 3-bromo-4-chlorophenol was used in place of 3-bromo-4-methylphenol, in step 3, 6-chloropyrimidin-4-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.42 (s, 1H), 10.35 (s, 1H), 9.06 (s, 1H), 8.46 (s, 1H), 7.52 (d, J=8.8 Hz, 1H), 7.21 (d, J=3.0 Hz, 1H), 7.11 (dd, J=8.9, 3.1 Hz, 1H), 4.19 (s, 1H), 4.02 (t, J=6.5 Hz, 2H), 2.67 (d, J=7.0 Hz, 2H), 1.84-1.55 (m, 8H), 1.55-1.41 (m, 2H), 1.26-1.14 (m, 3H), 1.10 (s, 6H), 1.05-0.91 (m, 2H). MS: 513 $[M+H]^+$.

Example 466: 5-benzyl-N-(6-(2-chloro-5-((tetrahydro-2H-pyran-4-yl)methoxy)phenyl)pyrimidin-4-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-bromo-4-chlorophenol was used in place of 3-bromo-4-methylphenol, and in step 2, 6-chloropyrimidin-4-amine was used in place of 4-bromopyridin-2-amine. $^1$H NMR (400 MHz, DMSO-$d_6$) δ 14.59 (s, 1H), 10.42 (s, 1H), 9.06

(d, J=1.3 Hz, 1H), 8.45 (d, J=1.3 Hz, 1H), 7.52 (d, J=8.9 Hz, 1H), 7.41-7.29 (m, 4H), 7.29-7.19 (m, 2H), 7.12 (dd, J=8.9, 3.1 Hz, 1H), 4.18 (s, 2H), 3.97-3.82 (m, 4H), 3.30-3.28 (m, 2H), 2.05-1.93 (m, 1H), 1.75-1.60 (m, 2H), 1.40-1.25 (m, 2H). MS: 505 $[M+H]^+$.

Example 466

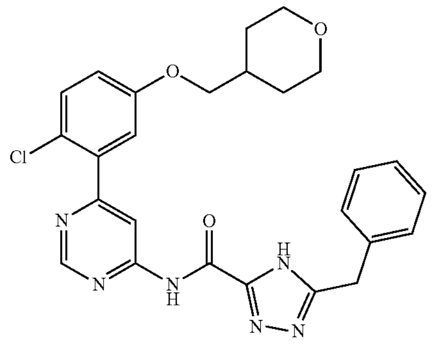

Example 467

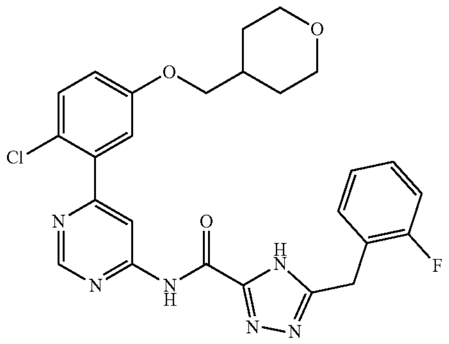

Example 467: 5-(2-fluorobenzyl)-N-(6-(2-chloro-5-((tetrahydro-2H-pyran-4-yl)methoxy)phenyl)pyrimidin-4-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-bromo-4-chlorophenol was used in place of 3-bromo-4-methylphenol, in step 2, 6-chloropyrimidin-4-amine was used in place of 4-bromopyridin-2-amine, and in step 3, ethyl 5-(2-fluorobenzyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.66 (s, 1H), 10.41 (s, 1H), 9.05 (d, J=1.2 Hz, 1H), 8.44 (d, J=1.3 Hz, 1H), 7.52 (d, J=8.8 Hz, 1H), 7.46-7.30 (m, 2H), 7.28-7.16 (m, 3H), 7.12 (dd, J=8.9, 3.1 Hz, 1H), 4.21 (s, 2H), 3.94-3.81 (m, 4H), 3.31-3.29 (m, 2H), 2.09-1.92 (m, 1H), 1.73-1.60 (m, 2H), 1.40-1.25 (m, 2H). MS: 523 $[M+H]^+$.

Example 468: 5-(cyclopentylmethyl)-N-(6-(2-chloro-5-((tetrahydro-2H-pyran-4-yl)methoxy)phenyl)pyrimidin-4-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-bromo-4-chlorophenol was used in place of 3-bromo-4-methylphenol, in step 2, 6-chloropyrimidin-4-amine was used in place of 4-bromopyridin-2-amine, and in step 3, ethyl 5-(cyclopentylmethyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.50 (s, 1H), 10.35 (s, 1H), 9.06 (d, J=1.3 Hz, 1H), 8.46 (d, J=1.3 Hz, 1H), 7.53 (d, J=8.9 Hz, 1H), 7.23 (d, J=3.1 Hz, 1H), 7.13 (dd, J=8.8, 3.1 Hz, 1H), 3.95-3.81 (m, 4H), 3.31-3.28 (m, 2H), 2.78 (d, J=7.5 Hz, 2H), 2.37-2.19 (m, 1H), 2.09-1.94 (m, 1H), 1.80-1.44 (m, 8H), 1.39-1.27 (m, 2H), 1.27-1.22 (m, 2H). MS: 497 $[M+H]^+$.

Example 468

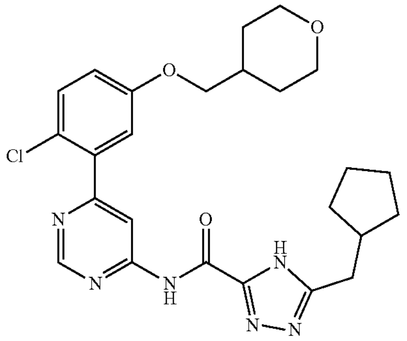

Example 469

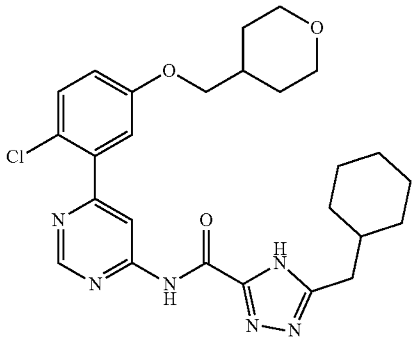

Example 469: 5-(cyclohexylmethyl)-N-(6-(2-chloro-5-((tetrahydro-2H-pyran-4-yl)methoxy)phenyl)pyrimidin-4-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, 3-bromo-4-chlorophenol was used in place of 3-bromo-4-methylphenol, in step 2, 6-chloropyrimidin-4-amine was used in place of 4-bromopyridin-2-amine, and in step 3, ethyl 5-(cyclohexylmethyl)-4H-1,2,4-triazol-3-carboxylate was used in place of ethyl 5-benzyl-4H-1,2,4-triazol-3-carboxylate. $^1H$ NMR (400 MHz, DMSO-$d_6$) δ 14.54 (s, 1H), 10.35 (s, 1H), 9.06 (d, J=1.3 Hz, 1H), 8.46 (d, J=1.2 Hz, 1H), 7.53 (d, J=8.8 Hz, 1H), 7.23 (d, J=3.1 Hz, 1H), 7.13 (dd, J=8.9, 3.1 Hz, 1H), 3.98-3.82 (m, 4H), 3.31-3.28 (m, 2H), 2.67 (d, J=7.0 Hz, 2H), 2.11-1.92 (m, 1H), 1.83-1.56 (m, 8H), 1.41-1.26 (m, 2H), 1.26-1.10 (m, 3H), 1.07-0.92 (m, 2H). MS: 511 $[M+H]^+$.

Example 470: 5-benzyl-N-(6-(2-chloro-5-(2-(tetrahydro-2H-pyran-4-yl)ethoxy)phenyl)pyrimidin-4-yl)-4H-1,2,4-triazole-3-carboxamide The preparation was carried out in a similar manner to Example 85, except that in step 1, 2-(tetrahydro-2H-pyran- 4-yl)ethan-1-ol was used in place of 2-(2-methoxyethoxy) ethan-1-ol, in step 2, 3-bromo-4-chlorophenol was used in place of 3-bromo-4-methylphenol, and in step 3, 6-chloropyrimidin-4-amine was used in place of 4-bromopyridin-2-amine. $^1$H NMR (400 MHz, DMSO-$d_6$) δ 14.71 (s, 1H), 10.43 (s, 1H), 9.06 (d, J=1.3 Hz, 1H), 8.44 (d, J=1.3 Hz, 1H), 7.52 (d, J=8.9 Hz, 1H), 7.37-7.30 (m, 4H), 7.29-7.21 (m, 2H), 7.12 (dd, J=8.9, 3.1 Hz, 1H), 4.18 (s, 2H), 4.07 (t, J=6.2 Hz, 2H), 3.90-3.73 (m, 2H), 3.28-3.20 (m, 2H), 1.77-1.56 (m, 5H), 1.30-1.15 (m, 2H). MS: 519 $[M+H]^+$.

Example 470

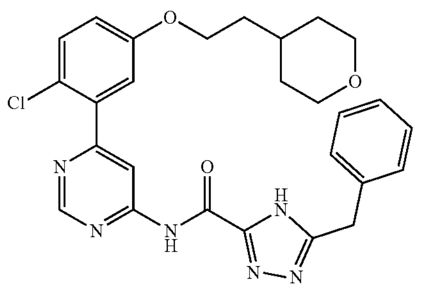

Example 471

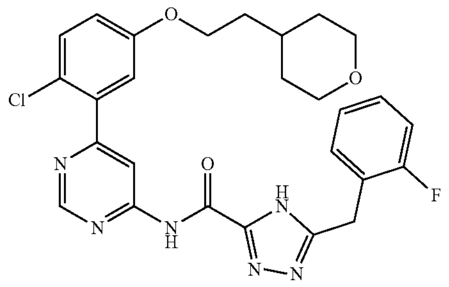

Example 471: N-(6-(2-chloro-5-(2-(tetrahydro-2H-pyran-4-yl)ethoxy)phenyl)pyrimidin-4-yl)-5-(2-fluorobenzyl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy) ethan-1-ol, in step 2, 3-bromo-4-chlorophenol was used in place of 3-bromo-4-methylphenol, in step 3, 6-chloropyrimidin-4-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.34 (s, 1H), 10.58 (s, 1H), 9.04 (d, J=1.3 Hz, 1H), 8.44 (d, J=1.3 Hz, 1H), 7.51 (d, J=8.9 Hz, 1H), 7.43-7.28 (m, 2H), 7.25-7.15 (m, 3H), 7.12 (dd, J=8.8, 3.1 Hz, 1H), 4.19 (s, 2H), 4.07 (t, J=6.2 Hz, 2H), 3.86-3.78 (m, 2H), 3.29-3.27 (m, 2H), 1.74-1.57 (m, 5H), 1.28-1.19 (m, 2H). MS: 537 $[M+H]^+$.

Example 472: N-(6-(2-chloro-5-(2-(tetrahydro-2H-pyran-4-yl)ethoxy)phenyl)pyrimidin-4-yl)-5-(cyclopentylmethyl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy) ethan-1-ol, in step 2, 3-bromo-4-chlorophenol was used in place of 3-bromo-4-methylphenol, in step 3, 6-chloropyrimidin-4-amine was used in place of 4-bromopyridin-2-amine, and in step 4, ethyl 5-(cyclopentylmethyl)-4H-1,2,4-triazole-3-carboxylate was used in place of ethyl 5-benzyl-4H-1,2,4-triazol-3-carboxylate. $^1$H NMR (400 MHz, DMSO-$d_6$) δ 14.39 (s, 1H), 10.33 (s, 1H), 9.06 (d, J=1.3 Hz, 1H), 8.46 (d, J=1.3 Hz, 1H), 7.52 (d, J=8.8 Hz, 1H), 7.23 (d, J=3.1 Hz, 1H), 7.13 (dd, J=8.9, 3.1 Hz, 1H), 4.08 (t, J=6.2 Hz, 2H), 3.89-3.77 (m, 2H), 3.28-3.23 (m, 2H), 2.82-2.75 (m, 2H), 2.36-2.21 (m, 1H), 1.77-1.56 (m, 10H), 1.56-1.46 (m, 2H), 1.24-1.16 (m, 3H). MS: 511 $[M+H]^+$.

Example 472

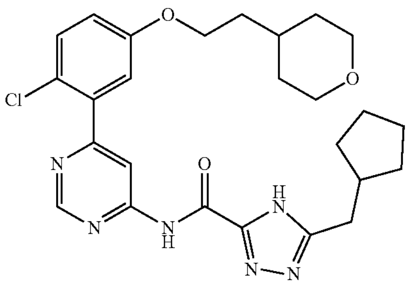

Example 473

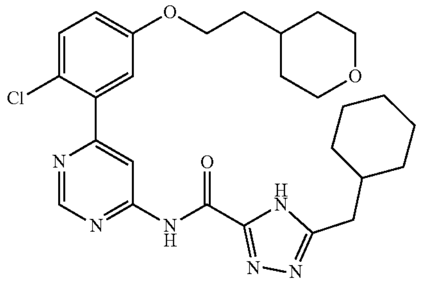

Example 473: N-(6-(2-chloro-5-(2-(tetrahydro-2H-pyran-4-yl)ethoxy)phenyl)pyrimidin-4-yl)-5-(cyclohexylmethyl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy) ethan-1-ol, in step 2, 3-bromo-4-chlorophenol was used in place of 3-bromo-4-methylphenol, in step 3, 6-chloropyrimidin-4-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.42 (s, 1H), 10.36 (s, 1H), 9.06 (s, 1H), 8.46 (s, 1H), 7.52 (d, J=8.8 Hz, 1H), 7.23 (d, J=3.1 Hz, 1H), 7.12 (dd, J=8.8, 3.1 Hz, 1H), 4.08 (t, J=6.2 Hz, 2H), 3.86-3.78 (m, 2H), 3.28-3.23 (m, 2H), 2.67 (d, J=7.1 Hz, 2H), 1.79-1.72 (m, 1H), 1.72-1.55 (m, 10H), 1.24-1.08 (m, 5H), 1.05-0.92 (m, 2H). MS: 525 $[M+H]^+$.

Example 474: 5-benzyl-N-(4-(5-((4-hydroxy-4-methylpentyl)sulfonyl)-2-methylphenyl)pyridin-2-yl)-4H-1,2,4-triazole-3-carboxamide

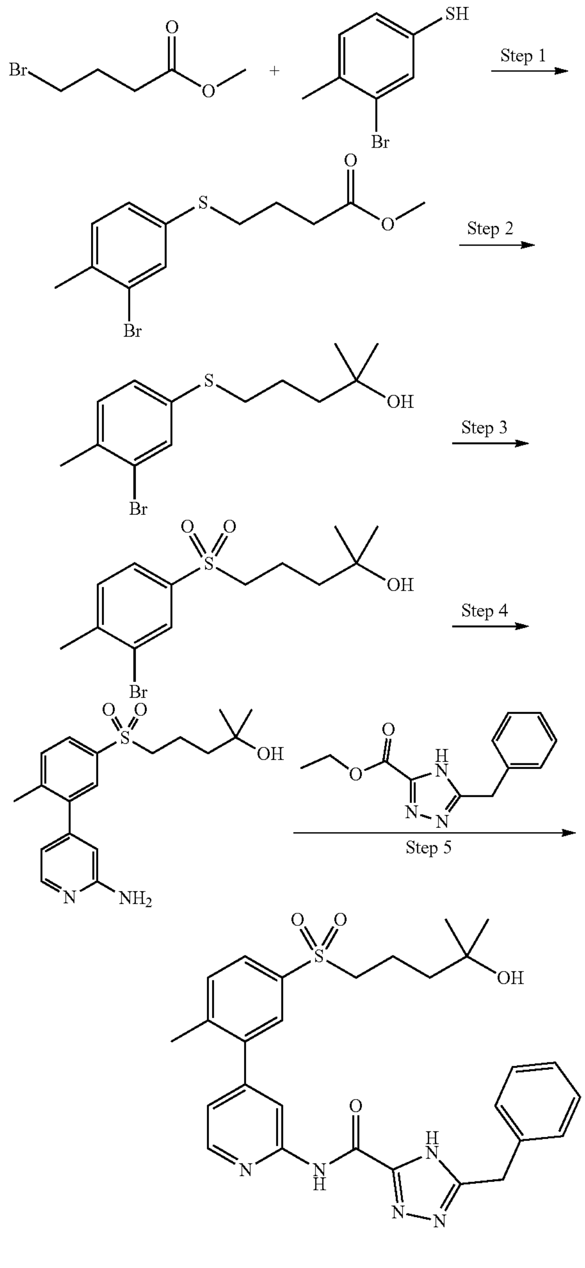

Steps 1 to 2 were carried out in a similar manner to Steps 1 to 2 of Example 160, except that 3-bromo-4-methylbenzenethio was used in place of 3-bromo-4-methylphenol.

Step 3: 5-((3-bromo-4-methylphenyl)thio)-2-methylpentan-2-ol (606 mg, 2 mmol) was dissolved in dichloromethane (6 mL), m-chloroperoxybenzoic acid (520 mg, 3 mmol) was added in batches at 0° C., and reacted at 25° C. for 1.5 hours. The reaction solution was diluted with dichloromethane, washed with saturated aqueous solution of sodium carbonate and saturated brine, dried over anhydrous sodium sulfate, filtered and evaporated to dryness, purified by column chromatography to afford 600 mg of 5-((3-bromo-4-methylphenyl)sulfonyl)-2-methylpentan-2-ol.

Steps 4 to 5 were carried out in a similar manner to Steps 3 to 4 of Example 160, except that 5-((3-bromo-4-methylphenyl)sulfonyl)-2-methylpentan-2-ol was used in place of 5-(3-bromo-4-methylphenoxy)-2-methylpentan-2-ol.

$^1$H NMR (400 MHz, DMSO-$d_6$) δ 14.59 (s, 1H), 10.00 (s, 1H), 8.48 (d, J=5.1 Hz, 1H), 8.15 (d, J=1.5 Hz, 1H), 7.88 (dd, J=8.1, 2.0 Hz, 1H), 7.74 (d, J=2.0 Hz, 1H), 7.67 (d, J=8.1 Hz, 1H), 7.40-7.20 (m, 6H), 4.20 (s, 1H), 4.18 (s, 2H), 3.32-3.23 (m, 2H), 2.38 (s, 3H), 1.71-1.55 (m, 2H), 1.44-1.32 (m, 2H), 1.02 (s, 6H). MS: 534 [M+H]$^+$.

Example 475: 5-(cyclopentylmethyl)-N-(4-(5-((4-hydroxy-4-methylpentyl)sulfonyl)-2-methylphenyl)pyridin-2-yl)-4H-1,2,4-triazole-3-carboxamide The preparation was carried out in a similar manner to Example 474, except that in step 5, ethyl 5-(cyclopentylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.41 (s, 1H), 9.94 (s, 1H), 8.49 (d, J=5.1 Hz, 1H), 8.25-8.10 (m, 1H), 7.88 (dd, J=8.0, 2.0 Hz, 1H), 7.75 (d, J=2.0 Hz, 1H), 7.67 (d, J=8.1 Hz, 1H), 7.29 (dd, J=5.1, 1.6 Hz, 1H), 4.20 (s, 1H), 3.39-3.34 (m, 2H), 2.78 (d, J=7.5 Hz, 2H), 2.39 (s, 3H), 2.35-2.18 (m, 1H), 1.81-1.67 (m, 2H), 1.67-1.56 (m, 4H), 1.56-1.45 (m, 2H), 1.44-1.33 (m, 2H), 1.26-1.18 (m, 2H), 1.03 (s, 6H). MS: 526 [M+H]$^+$.

Example 475

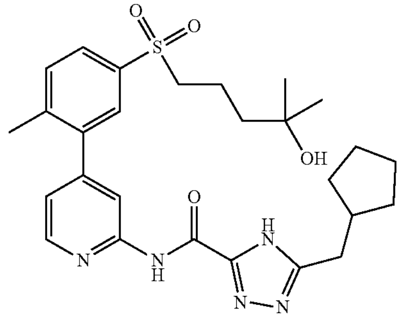

Example 476

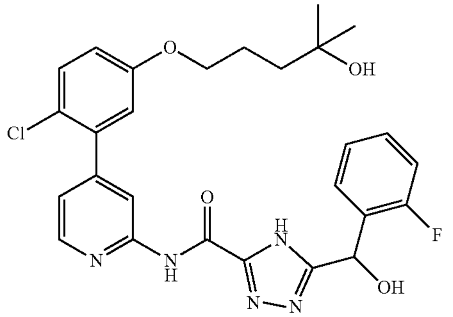

Example 476: N-(4-(2-chloro-5-((4-hydroxy-4-methylpentyl)oxy)phenyl)pyridin-2-yl)-5-((2-fluorophenyl)(hydroxyl)methyl)-4H-1,2,4-triazole-3-carboxamide The preparation was carried out in a similar manner to Example 160, except that in step 1, 3-bromo-4-chlorophenol was used in place of 3-bromo-4-methylphenol, and in step 4, ethyl 5-((2-fluorophenyl)(hydroxyl)methyl)-4H-1,2,4-triazol-3-carboxylate was used in place of ethyl 5-benzyl-4H-1,2,4-triazol-3-carboxylate. $^1$H NMR (400 MHz, DMSO-$d_6$)

δ 14.89 (s, 1H), 9.87 (s, 1H), 8.44 (d, J=5.1 Hz, 1H), 8.20 (d, J=1.5 Hz, 1H), 7.58 (s, 1H), 7.50 (d, J=8.8 Hz, 1H), 7.43-7.34 (m, 1H), 7.32-7.16 (m, 3H), 7.05 (dd, J=8.8, 3.0 Hz, 1H), 7.00 (d, J=3.0 Hz, 1H), 6.77 (s, 1H), 6.15 (d, J=4.9 Hz, 1H), 4.19 (s, 1H), 4.00 (t, J=6.6 Hz, 2H), 1.82-1.70 (m, 2H), 1.52-1.41 (m, 2H), 1.09 (s, 6H). MS: 540 $[M+H]^+$.

Example 477: (R)-N-(4-(2-chloro-5-((4-hydroxy-4-methylpentyl)oxy)phenyl)pyridin-2-yl)-5-(hydroxyl(phenyl)methyl)-4H-1,2,4-triazole-3-carboxamide The preparation was carried out in a similar manner to Example 160, except that in step 1, 3-bromo-4-chlorophenol was used in place of 3-bromo-4-methylphenol, and in step 4, ethyl (R)-5-(hydroxyl(phenyl)methyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.78 (s, 1H), 9.86 (s, 1H), 8.44 (d, J=5.2 Hz, 1H), 8.22 (s, 1H), 7.54-7.44 (m, 3H), 7.44-7.34 (m, 2H), 7.34-7.23 (m, 2H), 7.06 (dd, J=8.8, 3.0 Hz, 1H), 7.00 (d, J=3.0 Hz, 1H), 6.71 (d, J=4.3 Hz, 1H), 5.96 (d, J=4.3 Hz, 1H), 4.18 (s, 1H), 4.01 (t, J=6.5 Hz, 2H), 1.82-1.68 (m, 2H), 1.53-1.41 (m, 2H), 1.09 (s, 6H). MS: 522 $[M+H]^+$.

Example 477

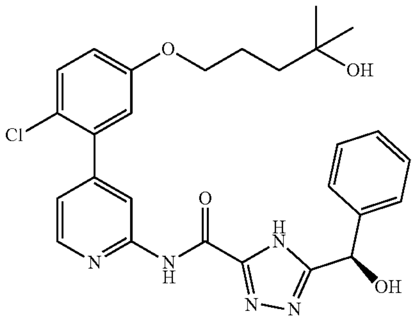

Example 478

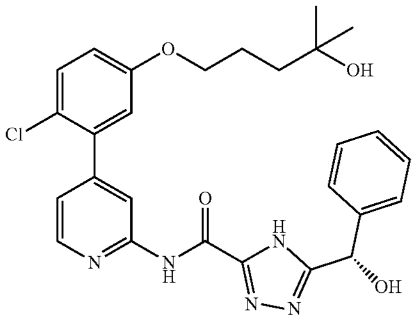

Example 478: (S)-N-(4-(2-chloro-5-((4-hydroxy-4-methylpentyl)oxy)phenyl)pyridin-2-yl)-5-(hydroxyl(phenyl)methyl)-4H-1,2,4-triazole-3-carboxamide The preparation was carried out in a similar manner to Example 160, except that in step 1, 3-bromo-4-chlorophenol was used in place of 3-bromo-4-methylphenol, and in step 4, ethyl (S)-5-(hydroxyl(phenyl)methyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.78 (s, 1H), 9.88 (s, 1H), 8.45 (d, J=5.1 Hz, 1H), 8.21 (s, 1H), 7.54-7.44 (m, 3H), 7.38 (t, J=7.5 Hz, 2H), 7.34-7.24 (m, 2H), 7.06 (dd, J=8.8, 3.0 Hz, 1H), 7.00 (d, J=3.1 Hz, 1H), 6.71 (s, 1H), 5.95 (s, 1H), 4.19 (s, 1H), 4.01 (t, J=6.6 Hz, 2H), 1.82-1.69 (m, 2H), 1.51-1.40 (m, 2H), 1.09 (s, 6H). MS: 522 $[M+H]^+$.

Example 479: 5-benzyl-N-(4-(2-methyl-5-(tetrahydro-2H-pyran-4-yl)phenyl)pyridin-2-yl)-4H-1,2,4-triazole-3-carboxamide

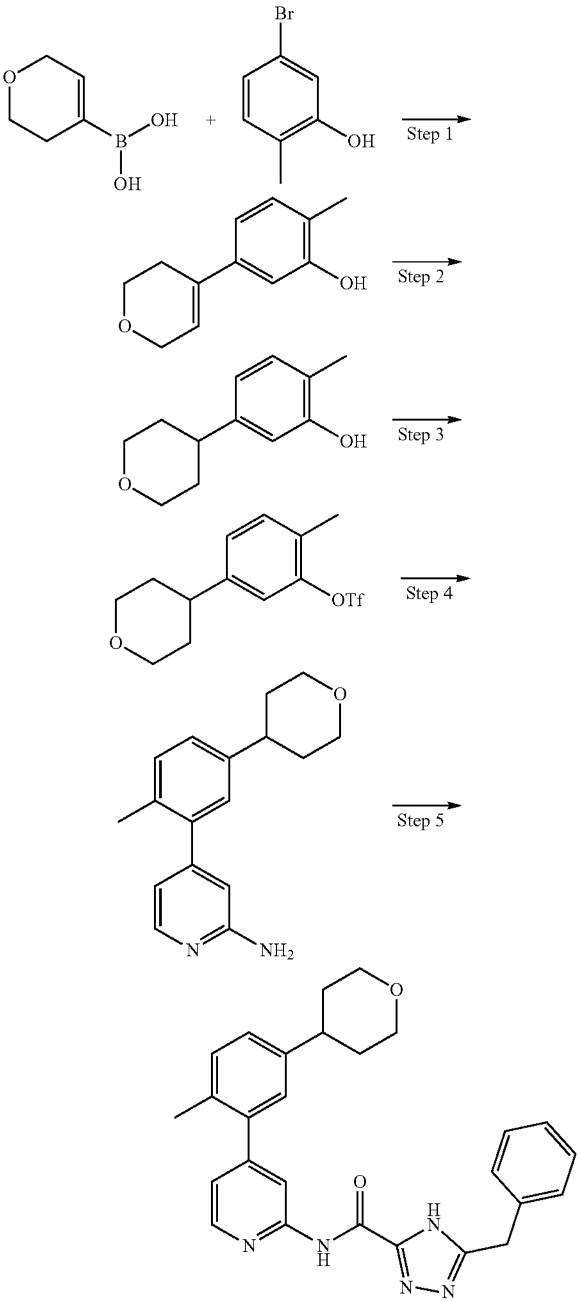

Steps 1 to 2 were carried out in a similar manner to Steps 1 to 2 of Example 47, except that (3,6-dihydro-2H-pyran-4-yl)boronic acid was used in place of cyclopent-1-en-1-ylboronic acid, and 5-bromo-2-methylphenol was used in place of 4-bromopyridin-2-amine.

Steps 3 to 5 were carried out in a similar manner to Example 43, except that 2-methyl-5-(tetrahydro-2H-pyran)-

4-yl)phenol was used in place of 5,6,7,8-tetrahydronaphthalen-1-ol. $^1H$ NMR (400 MHz, DMSO-$d_6$) δ 14.59 (s, 1H), 9.90 (s, 1H), 8.41 (d, J=5.1 Hz, 1H), 8.11 (d, J=1.5 Hz, 1H), 7.45-7.29 (m, 4H), 7.29-7.13 (m, 5H), 4.18 (s, 2H), 4.01-3.91 (m, 2H), 3.50-3.41 (m, 2H), 2.85-2.71 (m, 1H), 2.28 (s, 3H), 1.81-1.64 (m, 4H). MS: 454 $[M+H]^+$.

Example 480: Methyl 3-(3-(2-(5-benzyl-4H-1,2,4-triazol-3-carboxamido)pyridin-4-yl)-4-methylphenyl)acrylate

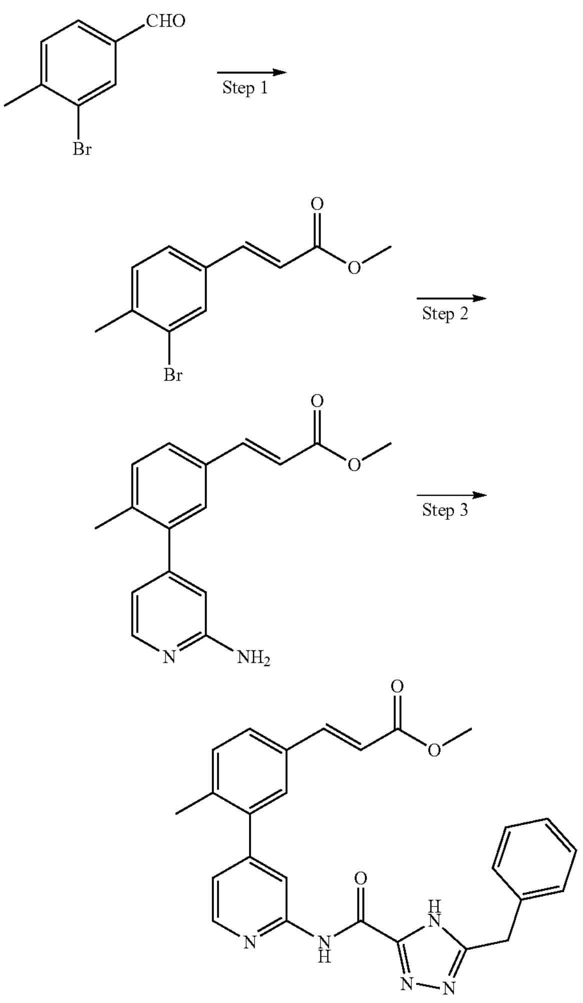

Step 1 was carried out in a similar manner to Step 2 of Example 78, except that 3-bromo-4-methylbenzaldehyde was used in place of 2-bromo-4-(2-(tert-butoxy)ethoxy) benzaldehyde, and trimethyl phosphonoacetate was used in place of methyltriphenylphosphonium bromide.

Steps 2 to 3 were carried out in a similar manner to Example 33, except that methyl 3-(3-bromo-4-methylphenyl)acrylate was used in place of 2-bromo-4-fluoro-1-methylbenzene. $^1H$ NMR (400 MHz, DMSO-$d_6$) δ 14.59 (s, 1H), 9.93 (s, 1H), 8.44 (d, J=5.1 Hz, 1H), 8.13 (s, 1H), 7.77-7.62 (m, 3H), 7.42 (d, J=8.0 Hz, 1H), 7.38-7.30 (m, 4H), 7.30-7.18 (m, 2H), 6.69 (d, J=16.0 Hz, 1H), 4.18 (s, 2H), 3.72 (s, 3H), 2.29 (s, 3H). MS: 454 $[M+H]^+$.

Example 481: Methyl 3-(3-(2-(5-(cyclopentylmethyl)-4H-1,2,4-triazol-3-carboxamido)pyridin-4-yl)-4-methylphenyl)propionate

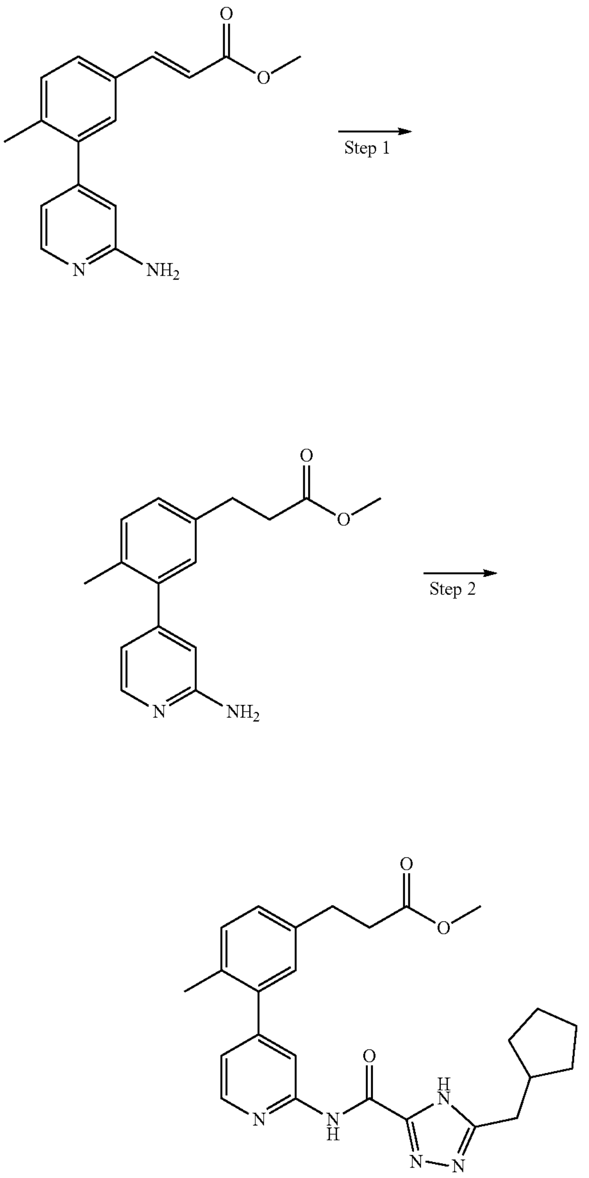

It was carried out in a similar manner to steps 2 to 3 of Example 47, except that methyl (E)-3-(3-(2-aminopyridin-4-yl)-4-methylphenyl)acrylate (see Example 480 for the synthetic method) was used in place of 4-(cyclopent-1-en-1-yl)pyridin-2-amine, and ethyl 5-(cyclopentylmethyl)-4H-1,2,4-triazol-3-carboxylate was used in place of ethyl 5-benzyl-4H-1,2,4-triazol-3-carboxylate.

$^1H$ NMR (400 MHz, DMSO-$d_6$) δ 14.43 (s, 1H), 9.86 (s, 1H), 8.42 (d, J=5.1 Hz, 1H), 8.13 (d, J=1.4 Hz, 1H), 7.35-7.17 (m, 3H), 7.14 (d, J=1.8 Hz, 1H), 3.58 (s, 3H), 2.87 (t, J=7.6 Hz, 2H), 2.82-2.72 (m, 2H), 2.66 (t, J=7.6 Hz, 2H), 2.35-2.25 (m, 1H), 2.24 (s, 3H), 1.79-1.67 (m, 2H), 1.67-1.56 (m, 2H), 1.56-1.48 (m, 2H), 1.26-1.21 (m, 2H). MS: 448 $[M+H]^+$.

Example 482: 5-benzyl-N-(4-(5-(3-hydroxyl-3-methylbutyl)-2-methylphenyl)pyridin-2-yl)-4H-1,2,4-triazole-3-carboxamide

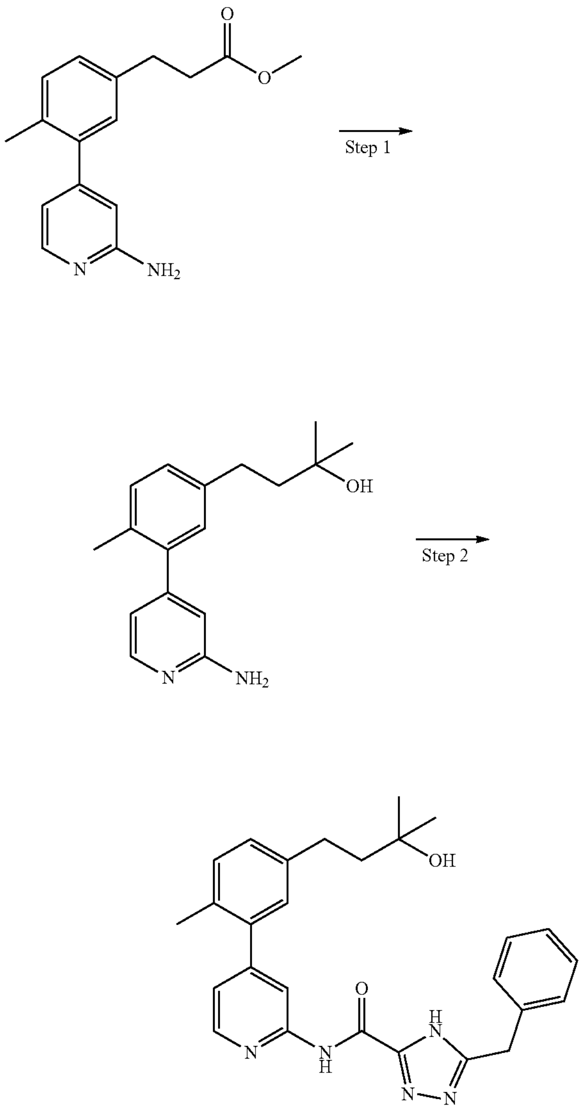

Step 1: The preparation was carried out in a similar manner to step 2 of Example 160, except that methyl 3-(3-(2-aminopyridin-4-yl)-4-methylphenyl)propionate was used in place of methyl 4-(3-bromo-4-methylphenoxy)butanoate.

Step 2: The preparation was carried out in a similar manner to step 3 of Example 100, except that 4-(3-(2-aminopyridin-4-yl)-4-methylphenyl)-2-methylbutan-2-ol was used in place of 4-(2-methyl-5-(octyloxy)phenyl)pyridin-2-amine.

$^1$H NMR (400 MHz, DMSO-$d_6$) δ 14.58 (s, 1H), 9.90 (s, 1H), 8.41 (d, J=5.1 Hz, 1H), 8.11 (d, J=1.4 Hz, 1H), 7.39-7.30 (m, 4H), 7.29-7.23 (m, 2H), 7.23-7.16 (m, 2H), 7.09 (d, J=1.8 Hz, 1H), 4.24 (s, 1H), 4.18 (s, 2H), 2.70-2.59 (m, 2H), 2.24 (s, 3H), 1.71-1.60 (m, 2H), 1.13 (s, 6H). MS: 456 $[M+H]^+$.

Example 483: 5-benzyl-N-(4-(5-(3-hydroxylpropyl)-2-methylphenyl)pyridin-2-yl)-4H-1,2,4-triazole-3-carboxamide

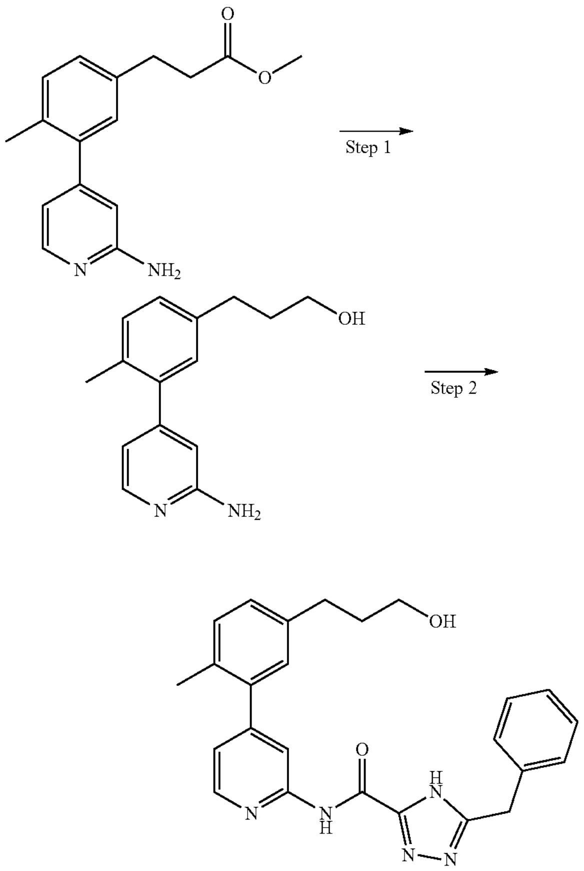

Step 1: Synthesis of 3-(3-(2-aminopyridin-4-yl)-4-methylphenyl)propanol

Methyl 3-(3-(2-aminopyridin-4-yl)-4-methylphenyl)propionate (270 mg, 1 mmol) was placed in anhydrous tetrahydrofuran (3 mL), and lithium aluminum hydride (115 mg, 3 mmol) was added in batches under argon protection at 0° C. After reacting at 50° C. for 2 hours, the reaction solution was quenched with saturated ammonium chloride, diluted with dichloromethane, washed with saturated brine, dried over anhydrous sodium sulfate, filtered and evaporated to dryness, and purified by column chromatography to afford 150 mg of product.

Step 2: It was carried out in a similar manner to step 2 of Example 1, except that 3-(3-(2-aminopyridin-4-yl)-4-methylphenyl)propanol was used in place of 4-phenylpyridin-2-amine.

$^1$H NMR (400 MHz, DMSO-$d_6$) δ 14.47 (s, 1H), 9.90 (s, 1H), 8.41 (d, J=5.1 Hz, 1H), 8.15-8.08 (m, 1H), 7.40-7.30 (m, 4H), 7.30-7.23 (m, 2H), 7.23-7.13 (m, 2H), 7.09 (d, J=1.8 Hz, 1H), 4.67-4.34 (m, 1H), 4.17 (s, 2H), 3.41 (t, J=6.4 Hz, 2H), 2.63 (t, J=7.7 Hz, 2H), 2.24 (s, 3H), 1.80-1.66 (m, 2H). MS: 428 $[M+H]^+$.

Example 484: 5-benzyl-N-(4-(5-(1-hydroxyl-4-methoxybutyl)-2-methylphenyl)pyridin-2-yl)-4H-1,2,4-triazole-3-carboxamide

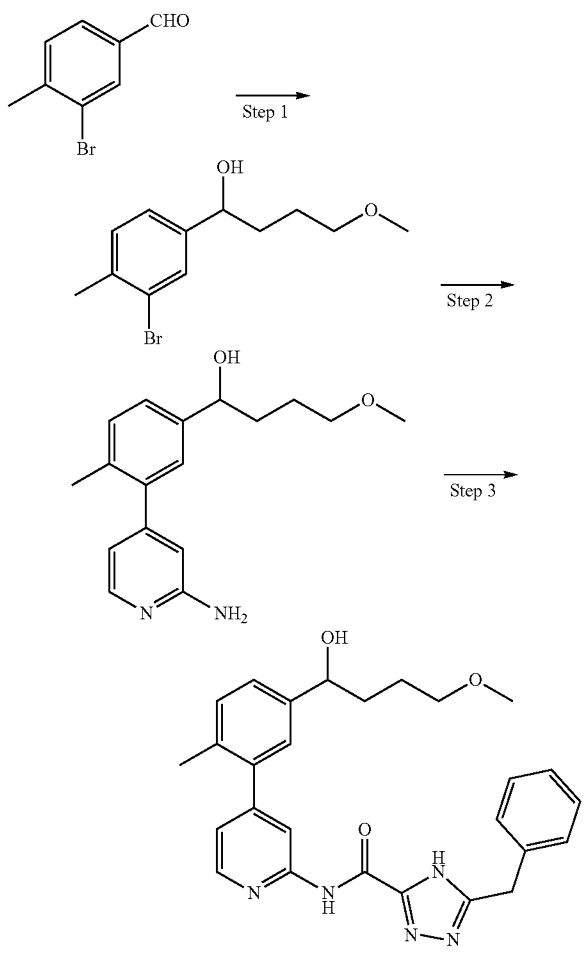

It was carried out in a similar manner to steps 2 to 4 of Example 160, except that 3-bromo-4-methylbenzaldehyde was used in place of methyl 4-(3-bromo-4-methylphenoxy) butanoate, and (3-methoxypropyl)magnesium bromide was used in place of methylmagnesium bromide. $^{1}$H NMR (400 MHz, DMSO-$d_6$) δ 14.48 (s, 1H), 9.90 (s, 1H), 8.42 (d, J=5.1 Hz, 1H), 8.12 (s, 1H), 7.38-7.22 (m, 7H), 7.22-7.17 (m, 2H), 5.19 (d, J=4.5 Hz, 1H), 4.67-4.43 (m, 1H), 4.18 (s, 2H), 3.29 (t, J=6.3 Hz, 2H), 3.18 (s, 3H), 2.26 (s, 3H), 1.69-1.52 (m, 3H), 1.52-1.39 (m, 1H). MS: 472 $[M+H]^+$.

Example 485: 5-benzyl-N-(4-(2-methyl-5-(2-(tetrahydro-2H-pyran-4-yl)acetyl)phenyl)pyridin-2-yl)-4H-1,2,4-triazole-3-carboxamide

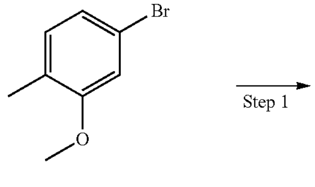

-continued

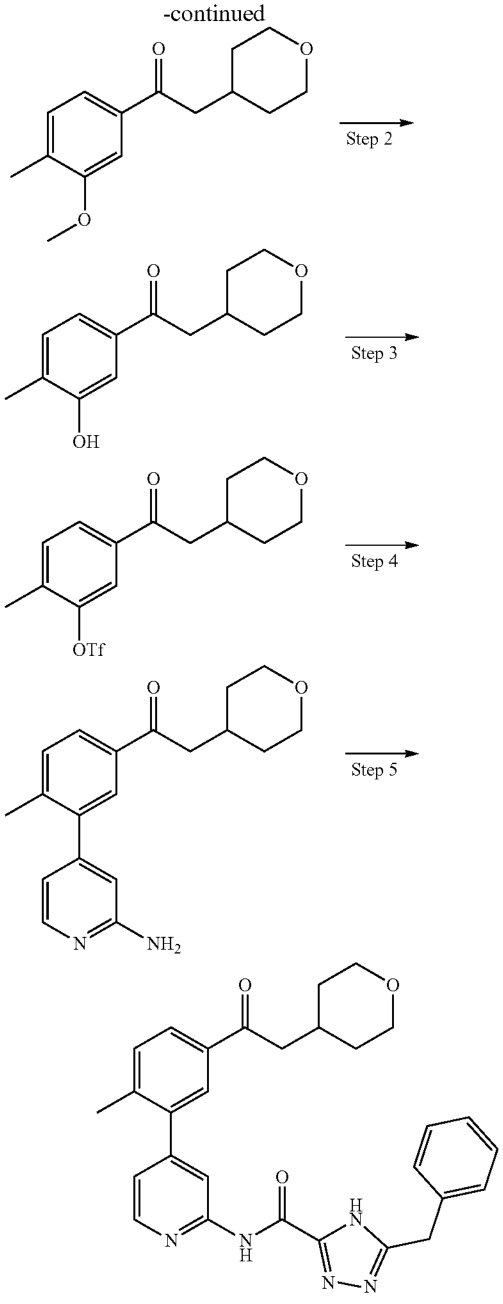

Step 1: Synthesis of 1-(3-methoxy-4-methylphenyl)-2-(tetrahydro-2H-pyran-4-yl)ethan-1-one 4-Bromo-2-methoxy-1-methylbenzene (500 mg, 2.5 mmol) was dissolved in anhydrous tetrahydrofuran (5 mL), and n-butyl lithium (2.5M, 1 mL, 2.5 mmol) was added dropwise at −78° C. under argon protection. After reacting at this temperature for 30 minutes, N-methoxy-N-methyl-2-(tetrahydro-2H-pyran-4-yl)acetamide (505 mg, 2.7 mmol) in anhydrous tetrahydrofuran (1 mL) was added, warmed slowly, and reacted at room temperature for 2 hours. The reaction solution was quenched with saturated aqueous solution of ammonium chloride, extracted with ethyl acetate, the organic phase was washed with saturated brine, dried over anhydrous sodium sulfate, filtered and evaporated to dryness, and purified by column chromatography to afford 500 mg of product.

Step 2: Synthesis of 1-(3-hydroxyl-4-methylphenyl)-2-(tetrahydro-2H-pyran-4-yl)ethan-1-one 1-(3-Methoxy-4-methylphenyl)-2-(tetrahydro-2H-pyran-4-yl)ethan-1-one (500 mg, 2.0 mmol) was dissolved in anhydrous dichloromethane (5 mL), a solution of boron tribromide in dichloromethane (1M, 3 mL, 3 mmol) was added dropwise at 0° C. under argon protection, and the reaction was slowly warmed to room temperature and reacted for 2 hours. The reaction solution was quenched with saturated aqueous solution of ammonium chloride, extracted with dichloromethane, and the organic phase was washed with saturated brine, dried over anhydrous sodium sulfate, filtered and evaporated to dryness, and purified by column chromatography to afford 350 mg of product.

Steps 3 to 5 were carried out in a similar manner to Example 43, except that 1-(3-hydroxyl-4-methylphenyl)-2-(tetrahydro-2H-pyran-4-yl)ethan-1-one was used in place of 5,6,7,8-tetrahydronaphthalen-1-ol.

$^1$H NMR (400 MHz, DMSO-$d_6$) δ 14.60 (s, 1H), 9.96 (s, 1H), 8.46 (d, J=5.1 Hz, 1H), 8.14 (s, 1H), 7.96 (d, J=1.7 Hz, 1H), 7.91 (dd, J=7.9, 1.8 Hz, 1H), 7.43 (d, J=7.9 Hz, 1H), 7.39-7.29 (m, 4H), 7.29-7.21 (m, 2H), 4.18 (s, 2H), 3.88-3.75 (m, 2H), 3.32-3.25 (m, 2H), 3.00 (d, J=6.7 Hz, 2H), 2.35 (s, 3H), 2.20-2.05 (m, 1H), 1.66-1.54 (m, 2H), 1.34-1.22 (m, 2H). MS: 496 $[M+H]^+$.

Example 486: 5-(cyclopentylmethyl)-N-(4-(2-methyl-5-(2-(tetrahydro-2H-pyran-4-yl)acetyl)phenyl)pyridin-2-yl)-4H-1,2,4-triazole-3-carboxamide

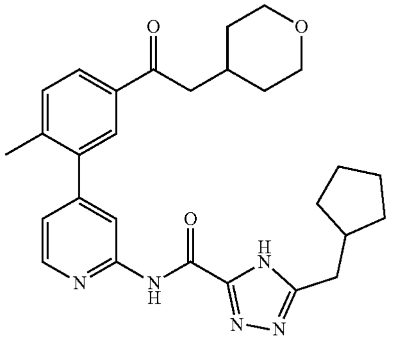 [SMILES: Cc1ccc(C(=O)CC2CCOCC2)cc1-c1ccnc(NC(=O)c2nnc(CC3CCCC3)[nH]2)c1]

It was carried out in a similar manner to Example 485, except that in step 5, ethyl 5-(cyclopentylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.42 (s, 1H), 9.91 (s, 1H), 8.47 (d, J=5.1 Hz, 1H), 8.16 (d, J=1.4 Hz, 1H), 7.97 (d, J=1.7 Hz, 1H), 7.92 (dd, J=8.0, 1.8 Hz, 1H), 7.43 (d, J=7.9 Hz, 1H), 7.25 (dd, J=5.1, 1.6 Hz, 1H), 3.89-3.76 (m, 2H), 3.32-3.24 (m, 2H), 3.00 (d, J=6.7 Hz, 2H), 2.78 (d, J=7.5 Hz, 2H), 2.35 (s, 3H), 2.31-2.22 (m, 1H), 2.18-2.05 (m, 1H), 1.80-1.67 (m, 2H), 1.67-1.56 (m, 4H), 1.56-1.44 (m, 2H), 1.32-1.21 (m, 4H). MS: 488 $[M+H]^+$.

Example 487: 5-benzyl-N-(4-(5-((3-hydroxyl-3-methylbutyl)carbamoyl)-2-methylphenyl)pyridin-2-yl)-4H-1,2,4-triazole-3-carboxamide

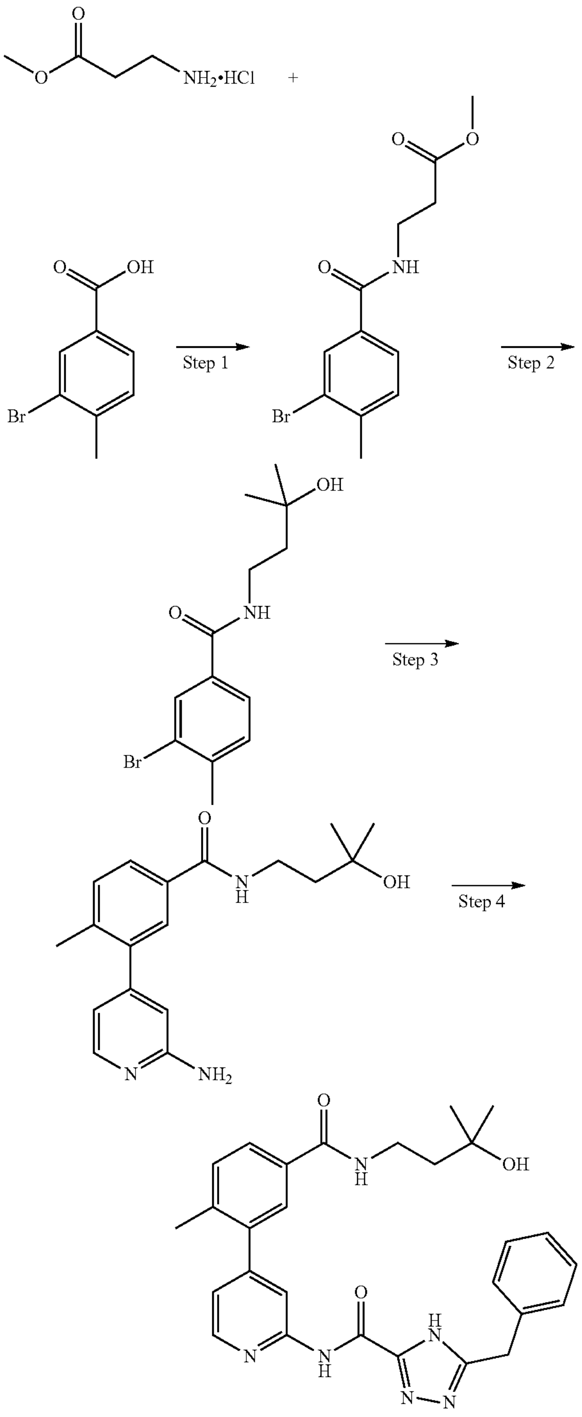

Step 1: Synthesis of methyl 3-(3-bromo-4-methylbenzamido)propionate

3-Bromo-4-methylbenzoic acid (430 mg, 2 mmol), methyl 3-aminopropionate hydrochloride (280 mg, 2 mmol), T3P (2,4,6-tripropyl-1,3,5,2,4,6-trioxatriphosphorinane-2,4, 6-trioxide) (950 mg, 50%, 3 mmol) and DIEA (780 mg, 6 mmol) were dissolved in dichloromethane (6 mL), and reacted at 25° C. for 2 hours. The reaction solution was diluted with dichloromethane, washed with saturated brine, dried over anhydrous sodium sulfate, filtered and evaporated to dryness, purified by column chromatography to afford 540 mg of product.

Steps 2 to 4 were carried out in a similar manner to steps 2 to 4 of Example 160, except that methyl 3-(3-bromo-4-methylbenzamido)propionate was used in place of methyl 4-(3-bromo-4-methylphenoxy)butanoate.

$^1$H NMR (400 MHz, DMSO-$d_6$) δ 14.54 (s, 1H), 9.94 (s, 1H), 8.50-8.38 (m, 2H), 8.14 (s, 1H), 7.82 (dd, J=8.0, 1.9 Hz, 1H), 7.75 (d, J=2.0 Hz, 1H), 7.45 (d, J=8.0 Hz, 1H), 7.39-7.29 (m, 4H), 7.29-7.17 (m, 2H), 4.33 (s, 1H), 4.18 (s, 2H), 3.38-3.34 (m, 2H), 2.32 (s, 3H), 1.71-1.58 (m, 2H), 1.12 (s, 6H). MS: 499 [M+H]$^+$.

Example 488: 5-(cyclopentylmethyl)-N-(4-(5-((3-hydroxyl-3-methylbutyl)carbamoyl)-2-methylphenyl)pyridin-2-yl)-4H-1,2,4-triazole-3-carboxamide The preparation was carried out in a similar manner to Example 487, except that in step 4, ethyl 5-(cyclopentylmethyl)-4H-1,2,4-triazole-3-carboxylate was used in place of ethyl 5-benzyl-4H-1,2,4-triazol-3-carboxylate. $^1$H NMR (400 MHz, DMSO-$d_6$) δ 14.34 (s, 1H), 9.89 (s, 1H), 8.55-8.34 (m, 2H), 8.16 (s, 1H), 7.82 (dd, J=8.0, 1.9 Hz, 1H), 7.75 (d, J=1.9 Hz, 1H), 7.45 (d, J=8.0 Hz, 1H), 7.26 (dd, J=5.1, 1.6 Hz, 1H), 4.33 (s, 1H), 3.38-3.35 (m, 2H), 2.78 (d, J=7.5 Hz, 2H), 2.32 (s, 3H), 2.30-2.19 (m, 1H), 1.83-1.68 (m, 2H), 1.68-1.56 (m, 4H), 1.56-1.41 (m, 2H), 1.26-1.20 (m, 2H), 1.13 (s, 6H). MS: 491 [M+H]$^+$.

Example 488

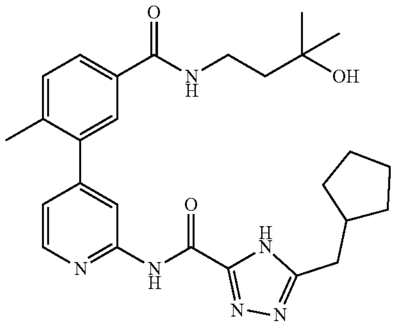

Example 489

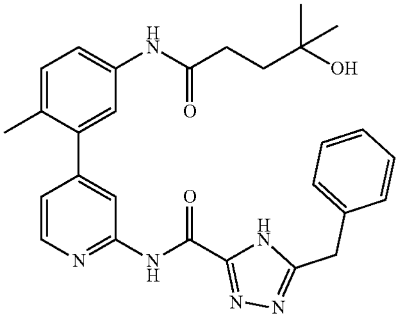

Example 489: 5-benzyl-N-(4-(5-(4-hydroxy-4-methylvaleramido)-2-methylphenyl)pyridin-2-yl)-4H-1,2,4-triazole-3-carboxamide The preparation was carried out in a similar manner to Example 487, except that in step 1, monomethyl succinate was used in place of 3-bromo-4-methylbenzoic acid, and 3-bromo-4-methylaniline was used in place of methyl 3-aminopropionate hydrochloride. $^1$H NMR (400 MHz, DMSO-$d_6$) δ 14.56 (s, 1H), 9.97 (s, 1H), 9.86 (s, 1H), 8.42 (d, J=5.3 Hz, 1H), 8.12 (s, 1H), 7.56 (d, J=8.1 Hz, 2H), 7.40-7.30 (m, 4H), 7.30-7.22 (m, 2H), 7.22-7.15 (m, 1H), 4.25 (s, 1H), 4.19 (s, 2H), 2.41-2.30 (m, 2H), 2.21 (s, 3H), 1.73-1.61 (m, 2H), 1.10 (s, 6H). MS: 499 [M+H]$^+$.

Example 490: 5-(cyclopentylmethyl)-N-(4-(5-(4-hydroxy-4-methylvaleramido)-2-methylphenyl)pyridin-2-yl)-4H-1,2,4-triazole-3-carboxamide The preparation was carried out in a similar manner to Example 487, except that in step 1, monomethyl succinate was used in place of 3-bromo-4-methyl benzoic acid, 3-bromo-4-methylaniline was used in place of methyl 3-aminopropionate hydrochloride, and in step 4, ethyl 5-(cyclopentylmethyl)-4H-1,2,4-triazole-3-carboxylate was used in place of ethyl 5-benzyl-4H-1,2,4-triazol-3-carboxylate. $^1$H NMR (400 MHz, DMSO-$d_6$) δ 14.37 (s, 1H), 9.98 (s, 1H), 9.83 (s, 1H), 8.42 (d, J=5.2 Hz, 1H), 8.14 (s, 1H), 7.63-7.51 (m, 2H), 7.26 (d, J=8.2 Hz, 1H), 7.19 (d, J=5.2 Hz, 1H), 4.25 (s, 1H), 2.79 (d, J=7.5 Hz, 2H), 2.41-2.32 (m, 2H), 2.32-2.24 (m, 1H), 2.22 (s, 3H), 1.79-1.44 (m, 8H), 1.25-1.19 (m, 2H), 1.10 (s, 6H). MS: 491 [M+H]$^+$.

Example 490

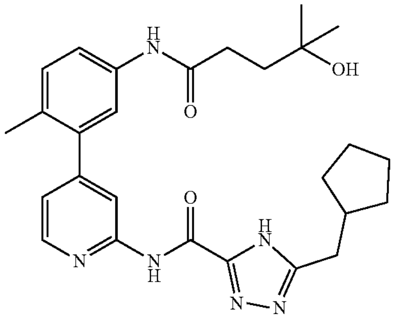

Example 491

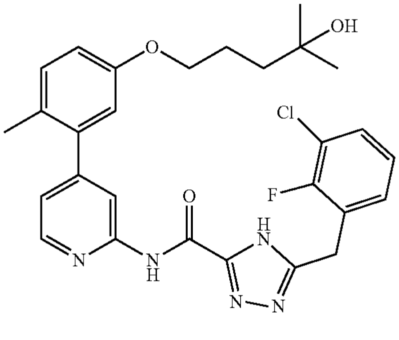

Example 491: 5-(3-chloro-2-fluorobenzyl)-N-(4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 4, ethyl 5-(3-chloro-2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.73 (s, 1H), 9.92 (s, 1H), 8.41 (d, J=5.0 Hz, 1H), 8.10 (s, 1H), 7.57-7.48 (m, 1H), 7.43-7.35 (m, 1H), 7.28-7.18 (m, 3H), 6.93 (dd, J=8.4, 2.7

Hz, 1H), 6.80 (d, J=2.7 Hz, 1H), 4.26 (s, 2H), 4.17 (s, 1H), 3.96 (t, J=6.6 Hz, 2H), 2.19 (s, 3H), 1.82-1.65 (m, 2H), 1.54-1.42 (m, 2H), 1.09 (s, 6H). MS: 538 [M+H]+.

Example 492: N-(5-fluoro-4-(5-((4-hydroxy-4-methylpentyl)oxy)-2-methylphenyl)pyridin-2-yl)-5-(2-fluorobenzyl)-4H-1,2,4-triazole-3-carboxamide The preparation was carried out in a similar manner to Example 160, except that in step 3, 5-fluoro-4-bromopyridin-2-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.70 (s, 1H), 10.09 (s, 1H), 8.47 (s, 1H), 8.06 (d, J=5.6 Hz, 1H), 7.46-7.30 (m, 2H), 7.30-7.14 (m, 3H), 6.97 (dd, J=8.4, 2.7 Hz, 1H), 6.84 (d, J=2.7 Hz, 1H), 4.20 (s, 2H), 4.17 (s, 1H), 3.95 (t, J=6.6 Hz, 2H), 2.09 (s, 3H), 1.81-1.67 (m, 2H), 1.52-1.41 (m, 2H), 1.09 (s, 6H). MS: 522 [M+H]+.

Example 492

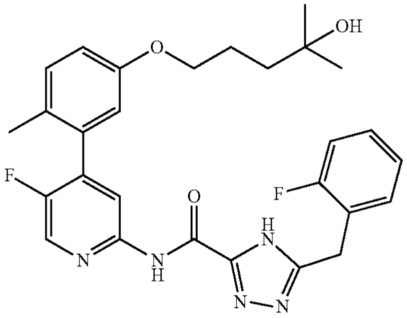

Example 493

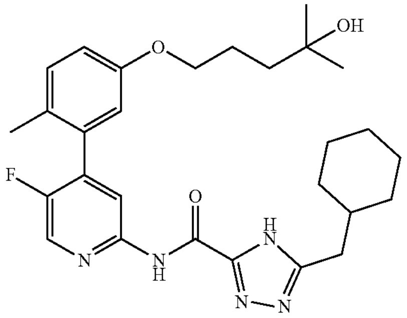

Example 493: 5-(cyclohexylmethyl)-N-(5-fluoro-4-(5-((4-hydroxy-4-methylpentyl)oxy)-2-methylphenyl)pyridin-2-yl)-4H-1,2,4-triazole-3-carboxamide The preparation was carried out in a similar manner to Example 160, except that in step 3, 5-fluoro-4-bromopyridin-2-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.36 (s, 1H), 10.00 (s, 1H), 8.48 (s, 1H), 8.09 (d, J=5.5 Hz, 1H), 7.27 (d, J=8.4 Hz, 1H), 6.97 (dd, J=8.4, 2.7 Hz, 1H), 6.84 (d, J=2.7 Hz, 1H), 4.17 (s, 1H), 3.96 (t, J=6.6 Hz, 2H), 2.66 (d, J=7.0 Hz, 2H), 2.10 (s, 3H), 1.82-1.57 (m, 8H), 1.52-1.41 (m, 2H), 1.24-1.13 (m, 3H), 1.09 (s, 6H), 1.04-0.91 (m, 2H). MS: 510 [M+H]+.

Example 494: N-(5-fluoro-4-(5-((5-hydroxyl-5-methylhexyl)oxy)-2-methylphenyl)pyridin-2-yl)-5-(2-fluorobenzyl)-4H-1,2,4-triazole-3-carboxamide The preparation was carried out in a similar manner to Example 160, except that in step 1, methyl 5-bromopentanoate was used in place of methyl 4-bromobutanoate, in step 3, 5-fluoro-4-bromopyridin-2-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.58 (s, 1H), 10.02 (s, 1H), 8.47 (s, 1H), 8.06 (d, J=5.5 Hz, 1H), 7.46-7.30 (m, 2H), 7.30-7.15 (m, 3H), 6.97 (dd, J=8.5, 2.7 Hz, 1H), 6.85 (d, J=2.7 Hz, 1H), 4.21 (s, 2H), 4.09 (s, 1H), 3.96 (t, J=6.5 Hz, 2H), 2.09 (s, 3H), 1.68 (t, J=6.8 Hz, 2H), 1.52-1.30 (m, 4H), 1.06 (s, 6H). MS: 536 [M+H]+.

Example 494

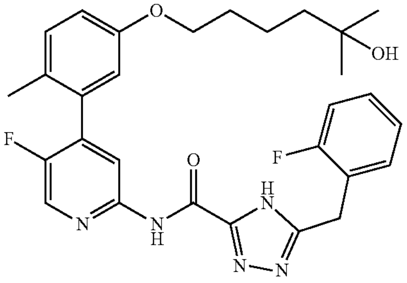

Example 495

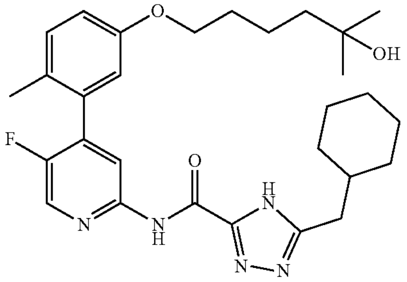

Example 495: 5-(cyclohexylmethyl)-N-(5-fluoro-4-(5-((5-hydroxyl-5-methylhexyl)oxy)-2-methylphenyl)pyridin-2-yl)-4H-1,2,4-triazole-3-carboxamide The preparation was carried out in a similar manner to Example 160, except that in step 1, methyl 5-bromopentanoate was used in place of methyl 4-bromobutanoate, in step 3, 5-fluoro-4-bromopyridin-2-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.34 (s, 1H), 9.99 (s, 1H), 8.48 (s, 1H), 8.09 (d, J=5.5 Hz, 1H), 7.27 (d, J=8.5 Hz, 1H), 6.98 (dd, J=8.4, 2.7 Hz, 1H), 6.85 (d, J=2.7 Hz, 1H), 4.09 (s, 1H), 3.97 (t, J=6.5 Hz, 2H), 2.67 (d, J=6.9 Hz, 2H), 2.10 (s, 3H), 1.79-1.57 (m, 8H), 1.47-1.39 (m, 3H), 1.24-1.10 (m, 4H), 1.06 (s, 6H), 1.02-0.90 (m, 2H). MS: 524 [M+H]+.

Example 496: N-(5-fluoro-4-(2-methyl-5-((tetrahydro-2H-pyran-4-yl)methoxy)phenyl)pyridin-2-yl)-5-(2-fluorobenzyl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, in step 2, 5-fluoro-4-bromopyridin-2-amine was used in place of 4-bromopyridin-2-amine, and in step 3, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.59 (s, 1H), 10.02 (s, 1H), 8.47 (s, 1H), 8.06 (d, J=5.4 Hz, 1H), 7.44-7.29 (m, 2H), 7.29-7.14 (m, 3H), 6.98 (dd, J=8.4, 2.7 Hz, 1H), 6.86 (d, J=2.7 Hz, 1H), 4.21 (s, 2H), 3.91-3.79 (m, 4H), 3.33-3.23 (m, 2H), 2.09 (s, 3H), 2.04-1.90 (m, 1H), 1.72-1.61 (m, 2H), 1.39-1.24 (m, 2H). MS: 520 [M+H]$^+$.

Example 496

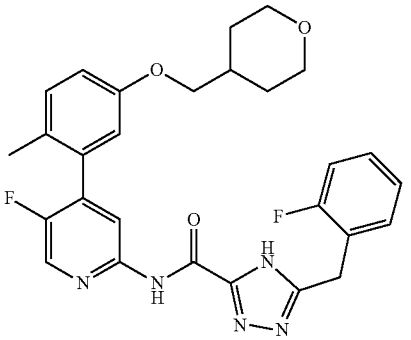

Example 497

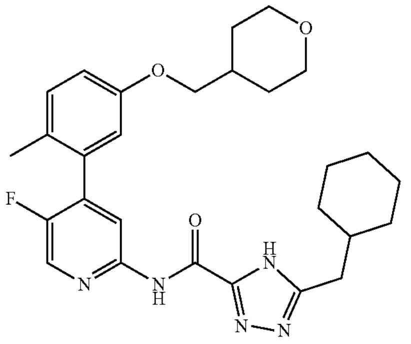

Example 497: 5-(cyclohexylmethyl)-N-(5-fluoro-4-(2-methyl-5-((tetrahydro-2H-pyran-4-yl)methoxy)phenyl)pyridin-2-yl)-4H-1,2,4-triazole-3-carboxamide The preparation was carried out in a similar manner to Example 64, except that in step 1, (tetrahydro-2H-pyran-4-yl)methanol was used in place of 2-(tert-butoxy)ethan-1-ol, in step 2, 5-fluoro-4-bromopyridin-2-amine was used in place of 4-bromopyridin-2-amine, and in step 3, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.35 (s, 1H), 10.00 (s, 1H), 8.48 (s, 1H), 8.09 (d, J=5.5 Hz, 1H), 7.28 (d, J=8.5 Hz, 1H), 6.99 (dd, J=8.4, 2.7 Hz, 1H), 6.86 (d, J=2.7 Hz, 1H), 3.92-3.78 (m, 4H), 3.32-3.24 (m, 2H), 2.66 (d, J=7.1 Hz, 2H), 2.10 (s, 3H), 2.04-1.91 (m, 1H), 1.81-1.55 (m, 8H), 1.36-1.15 (m, 5H), 1.04-0.93 (m, 2H). MS: 508 [M+H]$^+$.

Example 498: N-(5-fluoro-4-(2-methyl-5-(2-(tetrahydro-2H-pyran-4-yl)ethoxy)phenyl)pyridin-2-yl)-5-(2-fluorobenzyl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, in step 3, 5-fluoro-4-bromopyridin-2-amine was used in place of 4-bromopyridin-2-amine, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.66 (s, 1H), 10.09 (s, 1H), 8.47 (s, 1H), 8.06 (d, J=5.6 Hz, 1H), 7.46-7.30 (m, 2H), 7.30-7.14 (m, 3H), 6.98 (dd, J=8.5, 2.7 Hz, 1H), 6.86 (d, J=2.7 Hz, 1H), 4.20 (s, 2H), 4.01 (t, J=6.3 Hz, 2H), 3.81 (dd, J=11.6, 4.2 Hz, 2H), 3.29-3.21 (m, 2H), 2.09 (s, 3H), 1.76-1.52 (m, 5H), 1.25-1.12 (m, 2H). MS: 534 [M+H]$^+$.

Example 498

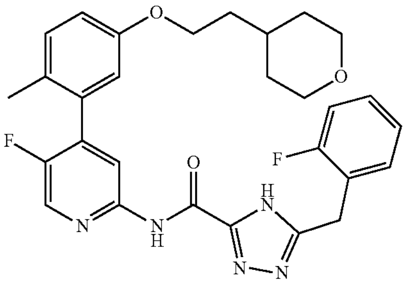

Example 499

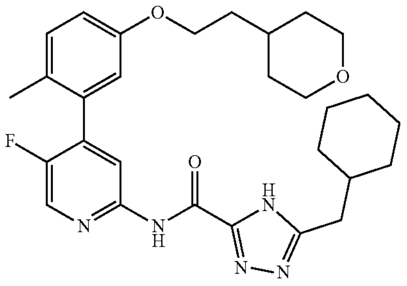

Example 499: N-(5-fluoro-4-(2-methyl-5-(2-(tetrahydro-2H-pyran-4-yl)ethoxy)phenyl)pyridin-2-yl)-5-(cyclohexylmethyl)-4H-1,2,4-triazole-3-carboxamide The preparation was carried out in a similar manner to Example 85, except that in step 1, 2-(tetrahydro-2H-pyran-4-yl)ethan-1-ol was used in place of 2-(2-methoxyethoxy)ethan-1-ol, in step 3, 5-fluoro-4-bromopyridin-2-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.35 (s, 1H), 9.99 (s, 1H), 8.47 (s, 1H), 8.09 (d, J=5.6 Hz, 1H), 7.27 (d, J=8.5 Hz, 1H), 6.98 (dd, J=8.4, 2.7 Hz, 1H), 6.87 (d, J=2.7 Hz, 1H), 4.02 (t, J=6.3 Hz, 2H), 3.89-3.76 (m, 2H), 3.30-3.20 (m, 2H), 2.66 (d, J=7.1 Hz, 2H), 2.10 (s, 3H), 1.80-1.55 (m, 11H), 1.30-1.13 (m, 5H), 1.04-0.92 (m, 2H). MS: 522 [M+H]$^+$.

Example 500: N-(4-(2-fluoro-5-((5-hydroxyl-5-methylhexyl)oxy)phenyl)pyridin-2-yl)-5-(2-fluorobenzyl)-4H-1,2,4-triazole-3-carboxamide The preparation was carried out in a similar manner to Example 160, except that in step 1, 3-bromo-4-fluorophenol was used in place of 3-bromo-4-methylphenol, methyl 5-bromopentanoate was used in place of methyl 4-bromobutanoate, and in step 4, ethyl 5-(2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.60 (s, 1H), 9.85 (s, 1H), 8.45 (d, J=5.2 Hz, 1H), 8.35 (s, 1H), 7.51-7.15 (m, 6H), 7.15-7.00 (m, 2H), 4.23 (s, 2H), 4.11 (s, 1H), 4.02 (t, J=6.4 Hz, 2H), 1.75-1.64 (m, 2H), 1.52-1.37 (m, 4H), 1.07 (s, 6H). MS: 522 [M+H]$^+$.

Example 500

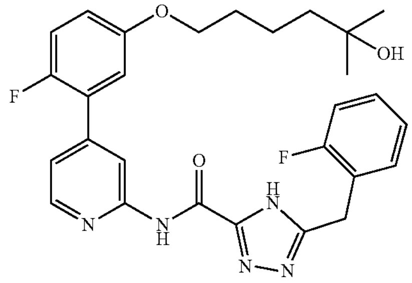

Example 501

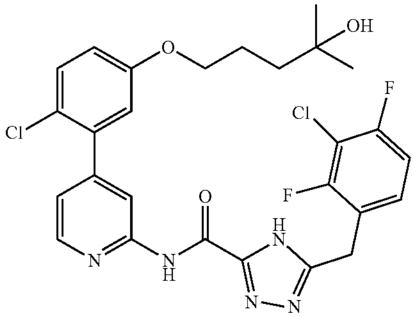

Example 501: 5-(3-chloro-2,4-difluorobenzyl)-N-(4-(2-chloro-5-((4-hydroxy-4-methylpentyl)oxy)phenyl)pyridin-2-yl)-4H-1,2,4-triazole-3-carboxamide The preparation was carried out in a similar manner to Example 160, except that in step 1, 3-bromo-4-chlorophenol was used in place of 3-bromo-4-methylphenol, and in step 4, ethyl 5-(3-chloro-2,4-difluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.72 (s, 1H), 9.98 (s, 1H), 8.45 (d, J=5.1 Hz, 1H), 8.21 (s, 1H), 7.57-7.44 (m, 2H), 7.38-7.25 (m, 2H), 7.06 (dd, J=8.9, 3.0 Hz, 1H), 7.01 (d, J=3.0 Hz, 1H), 4.26 (s, 2H), 4.18 (s, 1H), 4.01 (t, J=6.5 Hz, 2H), 1.82-1.69 (m, 2H), 1.53-1.40 (m, 2H), 1.09 (s, 6H). MS: 576 [M+H]$^+$.

Example 502: N-(4-(2-chloro-5-((5-hydroxyl-5-methylhexyl)oxy)phenyl)-5-fluoropyridin-2-yl)-5-(cyclohexylmethyl)-4H-1,2,4-triazole-3-carboxamide The preparation was carried out in a similar manner to Example 160, except that in step 1, 3-bromo-4-chlorophenol was used in place of 3-bromo-4-methylphenol, methyl 5-bromopentanoate was used in place of methyl 4-bromobutanoate, in step 3, 4-bromo-5-fluoropyridin-2-amine was used in place of 4-bromopyridin-2-amine, and in step 4, ethyl 5-(cyclohexylmethyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.35 (s, 1H), 10.04 (s, 1H), 8.52 (d, J=1.2 Hz, 1H), 8.16 (d, J=5.5 Hz, 1H), 7.53 (d, J=8.6 Hz, 1H), 7.17-7.05 (m, 2H), 4.09 (s, 1H), 4.02 (t, J=6.5 Hz, 2H), 2.67 (d, J=7.1 Hz, 2H), 1.82-1.57 (m, 8H), 1.51-1.33 (m, 4H), 1.28-1.10 (m, 3H), 1.06 (s, 6H), 1.04-0.88 (m, 2H). Ms: 544 [M+H]$^+$.

Example 502

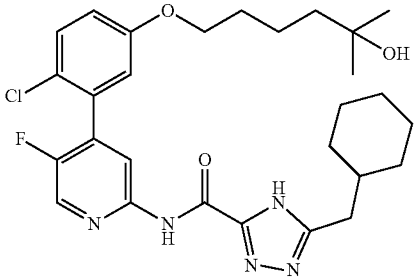

Example 503

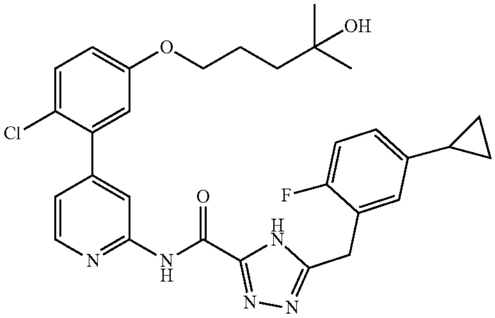

Example 503: N-(4-(2-chloro-5-((4-hydroxy-4-methylpentyl)oxy)phenyl)pyridin-2-yl)-5-(5-cyclopropyl-2-fluorobenzyl)-4H-1,2,4-triazole-3-carboxamide The preparation was carried out in a similar manner to Example 160, except that in step 1, 3-bromo-4-chlorophenol was used in place of 3-bromo-4-methylphenol, and in step 4, ethyl 5-(5-cyclopropyl-2-fluorobenzyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.56 (s, 1H), 9.89 (s, 1H), 8.45 (d, J=5.2 Hz, 1H), 8.22 (s, 1H), 7.51 (d, J=8.8 Hz, 1H), 7.28 (d, J=5.2 Hz, 1H), 7.17-6.95 (m, 5H), 4.22-4.11 (m, 3H), 4.01 (t, J=6.6 Hz, 2H), 1.95-1.85 (m, 1H), 1.82-1.69 (m, 2H), 1.53-1.41 (m, 2H), 1.09 (s, 6H), 0.97-0.88 (m, 2H), 0.68-0.57 (m, 2H). MS: 564 [M+H]$^+$.

Example 504: N-(4-(2-chloro-5-((4-hydroxy-4-methylpentyl)oxy)phenyl)pyridin-2-yl)-5-((4-fluoro-[1,1'-biphenyl]-3-yl)methyl)-4H-1,2,4-triazole-3-carboxamide

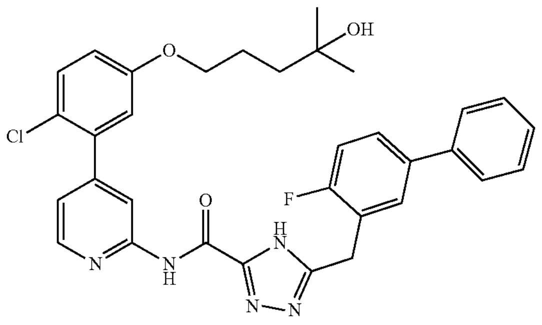 [SMILES: CC(C)(O)CCCOc1ccc(Cl)c(-c2ccnc(NC(=O)c3nnc(Cc4cc(-c5ccccc5)ccc4F)[nH]3)c2)c1]

The preparation was carried out in a similar manner to Example 160, except that in step 1, 3-bromo-4-chlorophenol was used in place of 3-bromo-4-methylphenol, and in step 4, ethyl 5-((4-fluoro-[1,1'-biphenyl]-3-yl)methyl)-4H-1,2,4-triazol-3-carboxylate was used in place of ethyl 5-benzyl-4H-1,2,4-triazol-3-carboxylate. $^1$H NMR (400 MHz, DMSO-$d_6$) δ 14.70 (s, 1H), 9.94 (s, 1H), 8.44 (d, J=5.2 Hz, 1H), 8.21 (s, 1H), 7.82-7.68 (m, 1H), 7.68-7.56 (m, 3H), 7.56-7.41 (m, 3H), 7.41-7.22 (m, 3H), 7.14-6.89 (m, 2H), 4.29 (s, 2H), 4.17 (s, 1H), 4.00 (t, J=6.6 Hz, 2H), 1.82-1.68 (m, 2H), 1.54-1.39 (m, 2H), 1.09 (s, 6H). MS: 600 $[M+H]^+$.

Assay Example 1. Western Blot Determination of Inhibition of Compounds on RIPK1 Phosphorylation in HT29 Cells Western blot was used to determine the effect of the test compounds on the phosphorylation of intracellular RIPK1 during the induction of programmed necrosis of HT29 cells, verifying the effect of compounds on RIPK1 phosphorylation, and initially estimating the $IC_{50}$ range of compounds for RIPK1 phosphorylation.

I. Main Assay Reagents/Instruments

TABLE 2

Main reagents and instruments used in assay example 1

| Name | Item No. | Brand |
|---|---|---|
| McCoy's 5A | SH30200.01 | Hyclone |
| BCA Protein concentration determination kit | P0012 | Beyotime |
| HT29 cells | HTB-38 | ATCC |
| Phospho-RIP (Ser166) (D1L3S) Rabbit mAb | 65746s | CST |
| RIP ($D94C_{12}$) XP Rabbit mAb | 3493s | CST |
| Anti-rabbit IgG (H + L) (DyLight 680 Conjugate) | 5366s | CST |
| Anti-rabbit IgG (H + L) (DyLight 800 4× PEG Conjugate) | 5151s | CST |
| β-Actin(8H10D10)Mouse mAb | 3700s | CST |
| Precision Plus ProteinTM Dual Color Standards | 1610374 | Bio-Rad |
| 10% Mini-PROTEAN ® TGX Stain-Free ™ Protein Gels | 4568034 | Bio-Rad |
| AT-406 (SM-406) | S2754 | Selleck chem |
| Z-VAD-FMK | S7023 | Selleck chem |
| Human TNF-α | 300-01A-10 | Peprotech |
| Electrophoresis power supply PowerPacTM basic electrophoresis power supply | 1645050 | Bio-Rad |

TABLE 2-continued

Main reagents and instruments used in assay example 1

| Name | Item No. | Brand |
|---|---|---|
| Mini-PROTEAN ® Tetra electrophoresis tank | 1658004 | Bio-Rad |
| Trans-Blot ® TurboTM Trans-Blot Turbo Transfer System | 1704155 | Bio-Rad |
| Odyssey CLXInfrared fluorescence scanning imaging system | CLX-1688 | LI-COR |

II. Experiment Procedure

1. Cell collection and protein sample extraction
   a) HT29 cells in good condition were collected, resuspended in McCoy's 5A complete medium and counted, the cells were planted in a 12-well plate at a cell density of 2×10⁶/1 mL/well, and placed in a 37° C. cell culture incubator overnight.
   b) Z-VAD-FMK (at final concentration of 20 μM) was added to the above 12-well plate, after 30 minutes, the inducer (where the final concentration of TNF-α is 20 ng/mL, and the final concentration of AT-406 is 100 nM), and test compounds of different concentrations were then added, and incubated in a cell incubator at 37° C. for 7 hours.
   c) Preparation of complete lysate: A tube of aliquoted RIPA Lysis Buffer was taken, PMSF, Phosphatase Inhibitor, and Roche Protease Inhibitor were added after thawing (volume ratio: PMSF:RIPA=1:100; phosphatase inhibitor:RIPA=1:100; Roche protease inhibitor:RIPA=4:100), and placed on ice for later use.
   d) The cell culture medium supernatant was discarded, washed twice with PBS, 100 μL of the prepared complete cell lysate was added to each well, the cells were lysed on ice for 15 minutes, and shaked intermittently during the lysis;
   e) After the lysis is complete, the lysate was transferred to a 1.5 mL centrifuge tube labeled in advance and centrifuged at 4° C. and 14000 rpm for 20 minutes;
   f) The supernatant was taken, transferred to a labeled 600 μL centrifuge tube, and placed on ice.
   g) The BCA kit was used to detect and the protein concentration was calculated;
2. The protein sample was mixed well with 4× loading buffer and heated in a metal bath at 100° C. for 5 min to fully denature the protein and placed on ice to cool down.
3. 40-50 ug of protein sample to be determined or pre-stained two-color protein molecular weight standard were added to each well.
4. Electrophoresis was carried out at a voltage of 100 V under constant voltage conditions. After 30 minutes of electrophoresis, the voltage was increased to 120V, and the electrophoresis time was set to 120 minutes or appropriately extended. The electrophoresis could be stopped when the pre-stained two-color protein molecular weight standard band on the gel run out of the lower edge of the lane.
5. After the electrophoresis was over, the gel holder was removed, the short glass plate was gently pried up with the peeling spatula, the upper layer of concentrated gel was dicarded, the separation gel was gently peeled off and placed in the transfer buffer;

6. A moderately sized NC membrane was cut according to the size of the gel, soaked with pure water, and then immersed in the pre-cooled transfer buffer; at the same time the filter paper was soaked in the transfer buffer solution.
7. The transfer cartridge was assembled in the order of filter paper, NC membrane, gel, and filter paper, then the transfer cartridge was put into the Trans-Blot® Turbo, and the "Standard SD" program that comes with the instrument was called to complete the transfer.
8. The protein-loaden NC membrane was rinsed with deionized water, blocking solution was added to immerse the membrane, and blocked with slow shaking on a shaker at room temperature for 1 hour.
9. After the blocking was completed, the NC membrane was put into the antibody incubation box, the primary antibody was diluted at a ratio of 1:1000, after adding to the antibody incubation box, the box was incubated on a shaker at room temperature for 1 hour.
10. After the incubation was completed, the membrane was washed with TBST for 3 times, 10 minutes each time.
11. The secondary antibody was selected according to the source of the primary antibody, the secondary antibody was diluted with the diluent of the secondary antibody at a ratio of 1:10000~1:15000, and added into the antibody incubation box and the membrane was immersed therein, and incubated on a shaker at room temperature for 1 hour.
12. After the incubation was completed, the membrane was washed with TBST for 3 times, with 10 minutes each time.
13. The membrane was rinsed once with pure water, Odyssey CLX infrared fluorescence scanning imaging system was used to scan the membrane to afford an image, and the fluorescence intensity value was read at the same time.

III. Typical Assay Results and Analysis

The inhibition rate of compounds on protein phosphorylation was calculated according to the fluorescence intensity value, and the calculation method is as follows:

$$\text{Inhibition rate (\%)}=(1-A/B)\times 100\%$$

A: Fluorescence intensity value after treatment with IL-2 and compound

B: Fluorescence intensity value after treatment with IL-2

The compound of Example 2 was tested by the above method, and the results were shown in FIG. 1 and FIG. 2. FIG. 1 is a Western Blot picture of the inhibition of RIPK1 phosphorylation by the compound of different concentrations. FIG. 2 is a quantitative calculation of the inhibition rate of RIPK1 phosphorylation based on the gray value of the band in the above picture. Therefore, it can be shown that the compound of Example 2 directly inhibit the phosphorylation activation of RIPK1.

Assay Example 2. Assay Method for Compounds Inhibiting Cell Necrosis (CCK8 Method)

In this assay example 2, under the condition of inducing programmed cell necrosis, different concentrations of the test compounds were added to test the IC50 of the rescue effect of the test compounds on the programmed necrosis.

I. Main Assay Reagents, Instruments and Materials

TABLE 3

Main reagents and instruments used in Assay Example 2

| Name | Brand | Item No./Name |
|---|---|---|
| DMSO | Sigma | D2650 (100 mL) |
| Trypan blue | GENIA Stock | G8003 |
| McCOY's 5A | Hylcone | SH30200.01 |
| CCK-8 | Tongren Chemistry | CK04 |
| GSK2982772 | Selleckchem | S8484 |
| AT-406 | Selleckchem | S2754 |
| Z-VAD-FMK | Selleckchem | S7023 |
| TNF-a | PeproTech | 300-01A |
| HT29 | ATCC | HTB-38 |
| Multi-function plate reader | PerkinElmer | Envision |

Compounds: Dissolved in DMSO to make a 10 mM solution;

TNF-α: The initial concentration was 100 μg/mL;

Z-VAD-FMK: Dissolved in DMSO to make a 10 mM solution;

AT-406: Dissolved in DMSO to make a 10 mM solution.

I. Experimental Steps

1) Compound dilution: All test compounds were dissolved in DMSO to prepare a 10 mM stock solution, and the first concentration gradient dilution of the test compounds was completed in DMSO. The gradient dilution factor was 4 times and 9 concentration gradients were made; A 40-fold overall dilution of all compounds was completed in the cell culture medium, and the resulting compound was 10× compound, which will be added to the wells of the 96-well plate containing cells, so that the final cell culture medium was 1× the designed final concentration. The general drug design is 9 concentration gradients, of which the highest final concentration is 25000 nM, the lowest concentration after 4-fold dilution of 9 concentrations is 0.38 nM, and the final concentration of DMSO in all wells is 0.25%. The compound dilution process is shown in FIG. 3.
2) HT 29 cells in good growth condition were selected, trypsinized, the cells was collected by centrifugation, resuspended in McCOY's 5A complete medium (containing 10% FBS) and counted, and the number of cells and survival rate were recorded.
3) Cells were inoculated to the 60 wells in the middle of the 96-well culture plate at a density of 12000 cells/80 μL/well, surrounding wells were filled with sterile water, and incubated overnight.
4) 10 μL of the 10× compound diluted with the medium was added to the assay wells, 10 μL of McCOY's 5A complete medium containing 2.5% DMSO was added to the inducer-free wells and the control wells, mixed and shaked, and incubated for 30 minutes.
5) Then 10 μL of inducer mixture (TNF-α, AT-406, Z-VAD-FMK with the final concentration of 20 ng/mL, 1 μM, 20 μM) was added into the assay wells and control wells. 10 μL McCOY's 5A complete medium was added to wells without inducer. Cells were cultured in an incubator with 5% $CO_2$, at 37° C.
6) After culturing for 16-20 hours, 10 μL of CCK-8 reagent was added to each well, and incubated for about 2 hours;
7) The OD value was read at 450 nm on the multi-function plate reader.
8) Data processing: Inhibition rate of necrosis (%)=100*(X−B)/(A−B)

A: The OD values of the wells without inducer (containing cells, CCK-8, without compound and inducer);

λ: OD values of assay wells (containing cells, CCK-8, compound, inducer);

B: OD values of control wells (containing cells, CCK-8, inducer, without compound). Then the value were imported into Graphpad Prism5 software for curve fitting and the IC50 values were calculated.

Table 4 lists the determination results of some compounds of the present disclosure in inhibiting HT29 cell necrosis, wherein A represents $IC_{50}$ is less than or equal to 100 nM, B represents $IC_{50}$ is greater than 100 nM but less than or equal to 1000 nM, C represents $IC_{50}$ is greater than 1000 nM but less than or equal to 10000 nM, D represents $IC_{50}$ is greater than 10000 nM.

TABLE 4 the determination results of some compounds of the present disclosure in inhibiting necrosis of HT29 cells

| Example No. | HT29 $IC_{50}$ (nM) | Example No. | HT29 $IC_{50}$ (nM) |
|---|---|---|---|
| 1 | C | 101 | B |
| 2 | B | 102 | B |
| 3 | C | 103 | B |
| 4 | C | 104 | C |
| 5 | D | 105 | D |
| 6 | C | 106 | C |
| 7 | B | 107 | C |
| 8 | C | 108 | C |
| 9 | D | 109 | C |
| 10 | C | 110 | D |
| 11 | C | 111 | A |
| 12 | B | 112 | C |
| 13 | C | 113 | D |
| 14 | C | 114 | B |
| 15 | C | 115 | B |
| 16 | C | 116 | B |
| 17 | D | 117 | A |
| 18 | C | 118 | A |
| 19 | C | 119 | A |
| 20 | B | 120 | B |
| 21 | C | 121 | A |
| 22 | C | 122 | A |
| 23 | D | 123 | A |
| 24 | B | 124 | C |
| 25 | C | 125 | B |
| 26 | B | 126 | C |
| 27 | C | 127 | NT |
| 28 | C | 128 | A |
| 29 | D | 129 | B |
| 30 | D | 130 | D |
| 31 | D | 131 | A |
| 32 | D | 132 | B |
| 33 | B | 133 | A |
| 34 | B | 134 | B |
| 35 | A | 135 | A |
| 36 | B | 136 | A |
| 37 | B | 137 | A |
| 38 | C | 138 | A |
| 39 | C | 139 | D |
| 40 | C | 140 | A |
| 41 | D | 141 | A |
| 42 | C | 142 | B |
| 43 | C | 143 | B |
| 44 | NT | 144 | A |
| 45 | B | 145 | A |
| 46 | C | 146 | C |
| 47 | D | 147 | A |
| 48 | D | 148 | A |
| 49 | C | 149 | A |
| 50 | C | 150 | A |
| 51 | C | 151 | A |
| 52 | D | 152 | A |
| 53 | D | 153 | A |

TABLE 4-continued the determination results of some compounds of the present disclosure in inhibiting necrosis of HT29 cells

| Example No. | HT29 $IC_{50}$ (nM) | Example No. | HT29 $IC_{50}$ (nM) |
|---|---|---|---|
| 54 | D | 154 | A |
| 55 | B | 155 | B |
| 56 | B | 156 | B |
| 57 | B | 157 | B |
| 58 | B | 158 | C |
| 59 | A | 159 | A |
| 60 | D | 160 | A |
| 61 | C | 161 | B |
| 62 | D | 162 | B |
| 63 | C | 163 | A |
| 64 | A | 164 | A |
| 65 | A | 165 | A |
| 66 | A | 166 | A |
| 67 | A | 167 | A |
| 68 | B | 168 | B |
| 69 | A | 169 | A |
| 70 | A | 170 | B |
| 71 | A | 171 | B |
| 72 | A | 172 | A |
| 73 | A | 173 | A |
| 74 | B | 174 | B |
| 75 | A | 175 | A |
| 76 | D | 176 | A |
| 77 | A | 177 | A |
| 78 | A | 178 | A |
| 79 | A | 179 | A |
| 80 | A | 180 | A |
| 81 | A | 181 | C |
| 82 | B | 182 | B |
| 83 | A | 183 | A |
| 84 | A | 184 | A |
| 85 | A | 185 | A |
| 86 | A | 186 | B |
| 87 | A | 187 | A |
| 88 | A | 188 | A |
| 89 | A | 189 | A |
| 90 | A | 190 | B |
| 91 | A | 191 | B |
| 92 | B | 192 | A |
| 93 | C | 193 | A |
| 94 | C | 194 | A |
| 95 | B | 195 | A |
| 96 | B | 196 | D |
| 97 | B | 197 | D |
| 98 | B | 198 | B |
| 99 | B | 199 | C |
| 100 | B | 200 | A |
| 201 | A | 353 | A |
| 202 | A | 354 | B |
| 203 | A | 355 | B |
| 204 | A | 356 | A |
| 205 | B | 357 | A |
| 206 | B | 358 | D |
| 207 | B | 359 | A |
| 208 | B | 360 | A |
| 209 | B | 361 | A |
| 210 | B | 362 | A |
| 211 | B | 363 | A |
| 212 | B | 364 | A |
| 213 | C | 365 | A |
| 214 | A | 366 | A |
| 215 | A | 367 | A |
| 216 | A | 368 | A |
| 217 | B | 369 | A |
| 218 | A | 370 | A |
| 219 | A | 371 | A |
| 220 | A | 372 | A |
| 221 | B | 373 | A |
| 222 | A | 374 | A |
| 223 | A | 375 | A |
| 224 | A | 376 | A |
| 225 | A | 377 | A |
| 226 | A | 378 | A |
| 227 | A | 379 | B |

TABLE 4-continued the determination results of some compounds of the present disclosure in inhibiting necrosis of HT29 cells

| Example No. | HT29 $IC_{50}$ (nM) | Example No. | HT29 $IC_{50}$ (nM) |
|---|---|---|---|
| 228 | B | 380 | A |
| 229 | B | 381 | A |
| 230 | B | 382 | A |
| 231 | B | 383 | A |
| 232 | B | 384 | A |
| 233 | C | 385 | A |
| 234 | A | 386 | A |
| 235 | A | 387 | A |
| 236 | A | 388 | A |
| 237 | A | 389 | A |
| 238 | A | 390 | A |
| 239 | A | 391 | A |
| 240 | B | 392 | A |
| 241 | B | 393 | A |
| 242 | A | 394 | A |
| 243 | A | 395 | A |
| 244 | A | 396 | A |
| 245 | A | 397 | A |
| 246 | B | 398 | A |
| 247 | B | 399 | A |
| 248 | B | 400 | A |
| 249 | B | 401 | A |
| 250 | A | 402 | A |
| 251 | A | 403 | A |
| 252 | A | 404 | A |
| 253 | B | 405 | A |
| 254 | B | 406 | A |
| 255 | A | 407 | D |
| 256 | A | 408 | D |
| 257 | A | 409 | A |
| 258 | A | 410 | A |
| 259 | A | 411 | B |
| 260 | A | 412 | B |
| 261 | A | 413 | B |
| 262 | A | 414 | B |
| 263 | A | 415 | A |
| 264 | A | 416 | A |
| 265 | B | 417 | B |
| 266 | A | 418 | B |
| 267 | A | 419 | A |
| 268 | A | 420 | B |
| 269 | A | 421 | B |
| 270 | A | 422 | A |
| 271 | A | 423 | A |
| 272 | A | 424 | B |
| 273 | A | 425 | B |
| 274 | A | 426 | B |
| 275 | A | 427 | B |
| 276 | A | 428 | A |
| 277 | A | 429 | A |
| 278 | A | 430 | B |
| 279 | A | 431 | B |
| 280 | A | 432 | A |
| 281 | A | 433 | A |
| 282 | A | 434 | A |
| 283 | A | 435 | A |
| 284 | A | 436 | A |
| 285 | A | 437 | B |
| 286 | A | 438 | B |
| 287 | A | 439 | A |
| 288 | A | 440 | A |
| 289 | A | 441 | A |
| 290 | A | 442 | A |
| 291 | A | 443 | A |
| 292 | A | 444 | A |
| 293 | A | 445 | A |
| 294 | A | 446 | A |
| 295 | A | 447 | A |
| 296 | A | 448 | A |
| 297 | A | 449 | B |
| 298 | A | 450 | A |
| 299 | A | 451 | A |
| 300 | A | 452 | A |
| 301 | A | 453 | A |

TABLE 4-continued the determination results of some compounds of the present disclosure in inhibiting necrosis of HT29 cells

| Example No. | HT29 $IC_{50}$ (nM) | Example No. | HT29 $IC_{50}$ (nM) |
|---|---|---|---|
| 302 | A | 454 | A |
| 303 | A | 455 | A |
| 304 | A | 456 | A |
| 305 | A | 457 | A |
| 306 | A | 458 | A |
| 307 | A | 459 | A |
| 308 | A | 460 | A |
| 309 | A | 461 | A |
| 310 | A | 462 | A |
| 311 | B | 463 | A |
| 312 | B | 464 | A |
| 313 | B | 465 | A |
| 314 | B | 466 | A |
| 315 | B | 467 | A |
| 316 | B | 468 | A |
| 317 | A | 469 | A |
| 318 | A | 470 | A |
| 319 | A | 471 | A |
| 320 | B | 472 | A |
| 321 | B | 473 | A |
| 322 | B | 474 | B |
| 323 | B | 475 | A |
| 324 | B | 476 | B |
| 325 | B | 477 | C |
| 326 | B | 478 | B |
| 327 | A | 479 | B |
| 328 | A | 480 | A |
| 329 | B | 481 | B |
| 330 | B | 482 | A |
| 331 | C | 483 | B |
| 332 | C | 484 | A |
| 333 | B | 485 | B |
| 334 | B | 486 | A |
| 335 | C | 487 | B |
| 336 | C | 488 | A |
| 337 | A | 489 | B |
| 338 | A | 490 | A |
| 339 | B | 491 | B |
| 340 | B | 492 | A |
| 341 | B | 493 | A |
| 342 | B | 494 | A |
| 343 | C | 495 | A |
| 344 | B | 496 | A |
| 345 | B | 497 | A |
| 346 | B | 498 | A |
| 347 | B | 499 | A |
| 348 | C | 500 | B |
| 349 | D | 501 | B |
| 350 | B | 502 | A |
| 351 | B | 503 | C |
| 352 | B | 504 | B |

The biological data provided by the present disclosure shows that the compounds of the present disclosure are beneficial for the treatment or prevention of diseases caused by abnormal RIP1 kinase. Therefore, the compounds of the present disclosure are beneficial to the treatment of diseases related to RIP1 including ocular fundus disease, xerophthalmia, psoriasis, leucoderma, dermatitis, alopecia areata, rheumatoid arthritis, colitis, multiple sclerosis, systemic lupus erythematosus, Crohn's disease, atherosclerosis, pulmonary fibrosis, liver fibrosis, myelofibrosis, non-small cell lung cancer, small cell lung cancer, breast cancer, pancreatic cancer, glioma, glioblastoma, ovarian cancer, cervical cancer, colorectal cancer, melanoma, endometrial cancer, prostate cancer, bladder cancer, leukemia, gastric cancer, liver cancer, gastrointestinal stromal tumor, thyroid cancer, chronic myeloid leukemia, acute myeloid leukemia, non-Hodgkin's lymphoma, nasopharyngeal cancer, esophageal cancer, brain tumor, B-cell and T-cell lymphoma, lymphoma, multiple myeloma, biliary cancer and sarcoma, cholangiocarcinoma, inflammatory bowel disease, ulcerative colitis, retinal detachment, retinitis pigmentosa, macular degeneration, pancreatitis, atopic dermatitis, spondyloarthritis, gout, SoJIA, Sjogren's syndrome, systemic scleroderma, antiphospholipid syndrome, vasculitis, osteoarthritis, non-alcoholic steatohepatitis, alcoholic steatohepatitis, autoimmune hepatitis, autoimmune hepatobiliary disease, primary sclerosing cholangitis, nephritis, celiac disease, autoimmune ITP, transplant rejection, ischemia-reperfusion injury of solid organs, sepsis, systemic inflammatory response syndrome, cerebrovascular accident, myocardial infarction, Huntington's disease, Alzheimer's disease, Parkinson's disease, allergic diseases, asthma, atopic dermatitis, multiple sclerosis, type I diabetes, Wegener's granulomatosis, pulmonary sarcoidosis, Behcet's disease, interleukin-1 converzyme-related fever syndrome, chronic obstructive pulmonary disease, tumor necrosis factor receptor related periodic syndrome and periodontitis. The compounds of the present disclosure can be used as monotherapy or combination therapy, and can be used in combination with multiple compounds of the present disclosure or in combination with other drugs that are not included in the present disclosure.

The above descriptions are only the preferred embodiments of the present disclosure and are not intended to limit the present disclosure. Any modification, equivalent replacement and improvement made within the spirit and principle of the present disclosure shall be included in the protection scope of the present disclosure.

What is claimed is:

1. A compound of formula (I), or pharmaceutically acceptable salts, diastereomers, enantiomers, solvates or prodrugs thereof, formula (I)

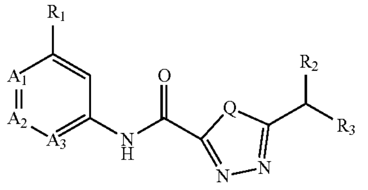

wherein, in formula (I),

Q is NH, O or S;

$A_1$, $A_2$, and $A_3$ are each independently selected from N or $CR_4$ and at least one of $A_1$, $A_2$, and $A_3$ is N, $R_4$ is H, F, Cl or methyl;

$R_1$ is $C_3$-$C_8$ cycloalkyl, which is unsubstituted or substituted with 1 to 3 substituents selected from the group consisting of $C_1$-$C_6$ alkyl, $C_1$-$C_6$ alkoxy, $C_1$-$C_6$ alkylthio, $C_1$-$C_3$ acyl, hydroxyl, halogen, trifluoromethyl, cyano, —$CONH_2$, oxo (═O) and —$NR^aR^b$, or 4- to 8-membered heteroalicyclic group, which is unsubstituted or substituted with 1 to 3 substituents selected from the group consisting of $C_1$-$C_6$ alkyl, $C_1$-$C_6$ alkoxy, $C_1$-$C_6$ alkylthio, $C_1$-$C_3$ acyl, hydroxyl, halogen, trifluoromethyl, cyano, —$CONH_2$, oxo (═O) and —$NR^aR^b$, or aryl or heteroaryl, which is unsubstituted or substituted with 1 to 3 substituents selected from the group consisting of $C_1$-$C_{10}$ alkyl, halogen, $C_3$-$C_8$ cycloalkyl, halogenated $C_1$-$C_{10}$ alkyl, cyano, hydroxyl, $C_1$-$C_6$ alkylthio, —$SO_2$—$R_5$, —SO—$R_5$, —CO—$R_5$, —CONH—$R_5$, —NHCO—$R_5$, —R'—COO—R", —$NR^aR^b$, 4- to 8-membered heteroalicyclic group, $C_2$-$C_6$ alkynyl, $C_2$-$C_6$ alkenyl, $C_1$-$C_3$ alkoxy $C_1$-$C_6$ alkylthio, $C_1$-$C_{10}$ alkyl substituted with hydroxyl and/or $C_1$-$C_6$ alkoxy, $C_3$-$C_8$ cycloalkyl $C_1$-$C_6$ alkyl, ($C_3$-$C_8$ cycloalkyl)-O—($C_1$-$C_6$ alkyl), $C_1$-$C_6$ alkyl substituted with 4- to 8-membered heteroalicyclic group, and —O—$R_6$, the aryl group is a monocyclic or bicyclic group containing 6 to 12 carbon ring atoms and having at least one aromatic ring, the heteroaryl is a monocyclic or bicyclic group having 5 to 10 ring atoms and containing 1 to 3 heteroatoms selected from N, O, or S as ring atoms, the 4- to 8-membered heteroalicyclic group is a 4- to 8-membered heteroalicyclic group containing 1 to 2 atoms selected from N, O, or S as ring atoms, $R_5$ is hydrogen, hydroxyl, $C_1$-$C_6$ alkyl, $C_1$-$C_6$ alkoxy $C_1$-$C_6$ alkyl, $C_1$-$C_6$ alkyl substituted with hydroxyl, $C_3$-$C_8$ cycloalkyl, or $C_1$-$C_6$ alkyl substituted with 4- to 8-membered heteroalicyclic group, $R_6$ is $C_1$-$C_{10}$ alkyl, $C_3$-$C_8$ cycloalkyl, 4- to 8-membered heteroalicyclic group, or $C_1$-$C_{10}$ alkyl which is substituted with 1 to 3 substituents selected from the group consisting of hydroxyl, $C_1$-$C_6$ alkoxy, cyano, —$NR^aR^b$, $C_3$-$C_8$ cycloalkyloxy, —CONH—$R_5$, $C_3$-$C_8$ cycloalkyl, $C_3$-$C_8$ cycloalkyl substituted with hydroxyl and/or $C_1$-$C_4$ alkyl, carboxylic, halogen, halogenated $C_1$-$C_6$ alkoxy, —$SO_2$—$R_5$, —SO—$R_5$, —CO—$R_5$, $C_2$-$C_6$ alkynyl, $C_2$-$C_6$ alkenyl, $C_1$-$C_4$ alkoxy $C_1$-$C_6$ alkoxy, 4- to 8-membered heteroalicyclic group, 4- to 8-membered heteroalicyclic group substituted with oxo, 4- to 8-membered heteroalicyclic group substituted with hydroxyl and/or $C_1$-$C_4$ alkyl, and $C_1$-$C_6$ alkylthio, R' is $C_2$-$C_6$ alkenylene, or $C_1$-$C_6$ alkylene, R" is hydrogen, $C_1$-$C_6$ alkyl, $C_1$-$C_6$ alkoxy $C_1$-$C_6$ alkyl, $C_1$-$C_6$ alkyl substituted with hydroxyl, $C_3$-$C_8$ cycloalkyl, or $C_1$-$C_6$ alkyl substituted with 4- to 8-membered heteroalicyclic group, $R^a$ and $R^b$ are each independently selected from hydrogen, $C_1$-$C_6$ alkyl, $C_3$-$C_8$ cycloalkyl, $C_1$-$C_6$ alkyl substituted with $C_1$-$C_6$ alkoxy, $C_1$-$C_6$ alkyl substituted with hydroxyl, $C_3$-$C_8$ cycloalkyl $C_1$-$C_6$ alkyl, $C_1$-$C_6$ alkyl substituted with 4- to 8-membered heteroalicyclic group, $C_1$-$C_6$ alkyl substituted with $C_1$-$C_3$ alkylthio, or $C_1$-$C_6$ alkyl substituted with substituted amino or unsubstituted amino, wherein the substituted amino is substituted with mono- or di-$C_1$-$C_3$ alkyl;

$R_2$ is $C_3$-$C_8$ cycloalkyl, which is unsubstituted or substituted with 1 to 3 substituents selected from the group consisting of $C_1$-$C_6$ alkyl, $C_1$-$C_6$ alkoxy, $C_1$-$C_6$ alkylthio, $C_1$-$C_3$ acyl, hydroxyl, halogen, trifluoromethyl, cyano, —$CONH_2$, oxo (═O) and —$NR^cR^d$, or $C_7$-$C_{12}$ bridged cyclyl, which is unsubstituted or substituted with 1 to 3 substituents selected from the group consisting of $C_1$-$C_6$ alkyl, $C_1$-$C_6$ alkoxy, $C_1$-$C_6$ alkylthio, $C_1$-$C_3$ acyl, hydroxyl, halogen, trifluoromethyl, cyano, —$CONH_2$, oxo (═O) and —$NR^cR^d$, or $C_1$-$C_{10}$ alkyl, which is unsubstituted or substituted with 1 to 3 substituents selected from the group consisting of $C_1$-$C_6$ alkoxy, $C_1$-$C_6$ alkylthio, $C_1$-$C_3$ acyl, hydroxyl, halogen, cyano, —$CONH_2$, $C_3$-$C_8$ cycloalkyl, and —$NR^cR^d$, or —$(CH_2)$n-$R^e$, wherein $R^e$ is aryl or heteroaryl, which is unsubstituted or substituted with 1 to 3 substituents selected from the group consisting of $C_1$-$C_6$ alkyl, $C_1$-$C_6$ alkoxy, $C_1$-$C_6$ alkylthio, $C_1$-$C_3$ acyl, hydroxyl, halogen, trifluoromethyl, cyano, —$CONH_2$, $C_3$-$C_6$ cycloalkyl, phenyl, naphthyl, $C_2$-$C_6$ alkynyl, $C_2$-$C_6$ alkenyl, and —$NR^cR^d$, wherein n is an integer from 0 to 3, or —$(CH_2)$m-$R^f$, wherein $R^f$ is 4- to 8-membered heteroalicyclic group, which is unsubstituted or substituted with 1 to 3 substituents selected from the group consisting of $C_1$-$C_6$ alkyl, $C_1$-$C_6$ alkoxy, $C_1$-$C_6$ alkylthio, $C_1$-$C_3$ acyl, hydroxyl, halogen, trifluoromethyl, cyano, —$CONH_2$, oxo (=O) and —$NR^cR^d$, m is an integer from 0 to 3, the 4- to 8-membered heteroalicyclic group is a 4- to 8-membered heteroalicyclic group containing 1 to 2 atoms selected from N, O, or S as ring atoms, the aryl group is a monocyclic or bicyclic group containing 6 to 12 carbon ring atoms and having at least one aromatic ring, the heteroaryl is a monocyclic or bicyclic group having 5 to 10 ring atoms and containing 1 to 3 heteroatoms selected from N, O, or S as ring atoms, $R^c$ and $R^d$ are each independently selected from hydrogen, $C_1$-$C_6$ alkyl, $C_3$-$C_8$ cycloalkyl, $C_1$-$C_6$ alkyl substituted with $C_1$-$C_6$ alkoxy, $C_1$-$C_6$ alkyl substituted with hydroxyl, $C_3$-$C_8$ cycloalkyl $C_1$-$C_6$ alkyl, $C_1$-$C_6$ alkyl substituted with 4- to 8-membered heteroalicyclic group, $C_1$-$C_6$ alkyl substituted with $C_1$-$C_3$ alkylthio, or $C_1$-$C_6$ alkyl substituted with substituted amino or unsubstituted amino, wherein the substituted amino is substituted with mono- or di-$C_1$-$C_3$ alkyl;

$R_3$ is hydrogen, $C_1$-$C_3$ alkyl, hydroxyl, halogen, trifluoromethyl, or cyano.

2. The compound, or the pharmaceutically acceptable salts, diastereomers, enantiomers, solvates or prodrugs thereof according to claim 1, wherein, Q is NH, O or S;

$A_1$, $A_2$, and $A_3$ are each independently selected from N or $CR_4$ and at least one of $A_1$, $A_2$, and $A_3$ is N, $R_4$ is H, F, Cl or methyl;

$R_1$ is $C_3$-$C_8$ cycloalkyl, which is unsubstituted or substituted with 1 to 3 substituents selected from the group consisting of $C_1$-$C_6$ alkyl, $C_1$-$C_6$ alkoxy, $C_1$-$C_6$ alkylthio, $C_1$-$C_3$ acyl, hydroxyl, halogen, trifluoromethyl, cyano, —$CONH_2$, oxo (=O) and —$NR^aR^b$, or 4- to 8-membered heteroalicyclic group, which is unsubstituted or substituted with 1 to 3 substituents selected from the group consisting of $C_1$-$C_6$ alkyl, $C_1$-$C_6$ alkoxy, $C_1$-$C_6$ alkylthio, $C_1$-$C_3$ acyl, hydroxyl, halogen, trifluoromethyl, cyano, —$CONH_2$, oxo (=O) and —$NR^aR^b$, or aryl or heteroaryl, which is unsubstituted or substituted with 1 to 3 substituents selected from the group consisting of $C_1$-$C_{10}$ alkyl, halogen, $C_3$-$C_8$ cycloalkyl, halogenated $C_1$-$C_{10}$ alkyl, cyano, hydroxyl, $C_1$-$C_6$ alkylthio, —$SO_2$—$R_5$, —SO—$R_5$, —CO—$R_5$, —CONH—$R_5$, —$NR^aR^b$, 4- to 8-membered heteroalicyclic group, $C_2$-$C_6$ alkynyl, $C_2$-$C_6$ alkenyl, $C_1$-$C_3$ alkoxy $C_1$-$C_6$ alkylthio, $C_1$-$C_{10}$ alkyl substituted with hydroxyl, $C_1$-$C_6$ alkoxy $C_1$-$C_{10}$ alkyl, $C_3$-$C_8$ cycloalkyl $C_1$-$C_6$ alkyl, ($C_3$-$C_8$ cycloalkyl)-O—($C_1$-$C_6$ alkyl), $C_1$-$C_6$ alkyl substituted with 4- to 8-membered heteroalicyclic group, and —O—$R_6$, the aryl group is a monocyclic or bicyclic group containing 6 to 12 carbon ring atoms and having at least one aromatic ring, the heteroaryl is a monocyclic or bicyclic group having 5 to 10 ring atoms and containing 1 to 3 heteroatoms selected from N, O, or S as ring atoms, the 4- to 8-membered heteroalicyclic group is a 4- to 8-membered heteroalicyclic group containing 1 to 2 atoms selected from N, O, or S as ring atoms, $R_5$ is hydrogen, hydroxyl, $C_1$-$C_6$ alkyl, $C_1$-$C_6$ alkoxy $C_1$-$C_6$ alkyl, $C_1$-$C_6$ alkyl substituted with hydroxyl, $C_3$-$C_8$ cycloalkyl, or $C_1$-$C_6$ alkyl substituted with 4- to 8-membered heteroalicyclic group, $R_6$ is $C_1$-$C_{10}$ alkyl, $C_3$-$C_8$ cycloalkyl, 4- to 8-membered heteroalicyclic group, or $C_1$-$C_{10}$ alkyl which is substituted with 1 to 3 substituents selected from the group consisting of hydroxyl, $C_1$-$C_6$ alkoxy, cyano, —$NR^aR^b$, $C_3$-$C_8$ cycloalkyloxy, —CONH—$R_5$, $C_3$-$C_8$ cycloalkyl, $C_3$-$C_8$ cycloalkyl substituted with hydroxyl and/or $C_1$-$C_4$ alkyl, carboxylic, halogen, halogenated $C_1$-$C_6$ alkoxy, —$SO_2$—$R_5$, —SO—$R_5$, —CO—$R_5$, $C_2$-$C_6$ alkynyl, $C_2$-$C_6$ alkenyl, $C_1$-$C_4$ alkoxy $C_1$-$C_6$ alkoxy, 4- to 8-membered heteroalicyclic group, 4- to 8-membered heteroalicyclic group substituted with oxo, 4- to 8-membered heteroalicyclic group substituted with hydroxyl and/or $C_1$-$C_4$ alkyl, and $C_1$-$C_6$ alkylthio, $R^a$ and $R^b$ are each independently selected from hydrogen, $C_1$-$C_6$ alkyl, $C_3$-$C_8$ cycloalkyl, $C_1$-$C_6$ alkyl substituted with $C_1$-$C_6$ alkoxy, $C_1$-$C_6$ alkyl substituted with hydroxyl, $C_3$-$C_8$ cycloalkyl $C_1$-$C_6$ alkyl, $C_1$-$C_6$ alkyl substituted with 4- to 8-membered heteroalicyclic group, $C_1$-$C_6$ alkyl substituted with $C_1$-$C_3$ alkylthio, or $C_1$-$C_6$ alkyl substituted with substituted amino or unsubstituted amino, wherein the substituted amino is substituted with mono- or di-$C_1$-$C_3$ alkyl;

$R_2$ is $C_3$-$C_8$ cycloalkyl, which is unsubstituted or substituted with 1 to 3 substituents selected from the group consisting of $C_1$-$C_6$ alkyl, $C_1$-$C_6$ alkoxy, $C_1$-$C_6$ alkylthio, $C_1$-$C_3$ acyl, hydroxyl, halogen, trifluoromethyl, cyano, —$CONH_2$, oxo (=O) and —$NR^cR^d$, or $C_7$-$C_{12}$ bridged cyclyl, which is unsubstituted or substituted with 1 to 3 substituents selected from the group consisting of $C_1$-$C_6$ alkyl, $C_1$-$C_6$ alkoxy, $C_1$-$C_6$ alkylthio, $C_1$-$C_3$ acyl, hydroxyl, halogen, trifluoromethyl, cyano, —$CONH_2$, oxo (=O) and —$NR^cR^d$, or $C_1$-$C_{10}$ alkyl, which is unsubstituted or substituted with 1 to 3 substituents selected from the group consisting of $C_1$-$C_6$ alkoxy, $C_1$-$C_6$ alkylthio, $C_1$-$C_3$ acyl, hydroxyl, halogen, cyano, —$CONH_2$, $C_3$-$C_8$ cycloalkyl, and —$NR^cR^d$, or —$(CH_2)$n-$R^e$, wherein $R^e$ is aryl or heteroaryl, which is unsubstituted or substituted with 1 to 3 substituents selected from the group consisting of $C_1$-$C_6$ alkyl, $C_1$-$C_6$ alkoxy, $C_1$-$C_6$ alkylthio, $C_1$-$C_3$ acyl, hydroxyl, halogen, trifluoromethyl, cyano, —$CONH_2$, $C_2$-$C_6$ alkynyl, $C_2$-$C_6$ alkenyl, and —$NR^cR_d$, wherein n is an integer from 0 to 3, or —$(CH_2)$m-$R^f$, wherein $R^f$ is 4- to 8-membered heteroalicyclic group, which is unsubstituted or substituted with 1 to 3 substituents selected from the group consisting of $C_1$-$C_6$ alkyl, $C_1$-$C_6$ alkoxy, $C_1$-$C_6$ alkylthio, $C_1$-$C_3$ acyl, hydroxyl, halogen, trifluoromethyl, cyano, —$CONH_2$, oxo (=O) and —$NR^cR^d$, m is an integer from 0 to 3, the 4- to 8-membered heteroalicyclic group is a 4- to 8-membered heteroalicyclic group containing 1 to 2 atoms selected from N, O, or S as ring atoms, the aryl group is a monocyclic or bicyclic group containing 6 to 12 carbon ring atoms and having at least one aromatic ring, the heteroaryl is a monocyclic or bicyclic group having 5 to 10 ring atoms and containing 1 to 3 heteroatoms selected from N, O, or S as ring atoms, $R^c$ and $R^d$ are each independently selected from hydrogen, $C_1$-$C_6$ alkyl, $C_3$-$C_8$ cycloalkyl, $C_1$-$C_6$ alkyl substituted with $C_1$-$C_6$ alkoxy, $C_1$-$C_6$ alkyl substituted with hydroxyl, $C_3$-$C_8$ cycloalkyl $C_1$-$C_6$ alkyl, $C_1$-$C_6$ alkyl substituted with 4- to 8-membered heteroalicyclic group, $C_1$-$C_6$ alkyl substituted with $C_1$-$C_3$ alkylthio, or $C_1$-$C_6$ alkyl substituted with substituted amino or unsubstituted amino, wherein the substituted amino is substituted with mono- or di-$C_1$-$C_3$ alkyl;

$R_3$ is hydrogen, $C_1$-$C_3$ alkyl, hydroxyl, halogen, trifluoromethyl, or cyano.

3. The compound, or the pharmaceutically acceptable salts, diastereomers, enantiomers, solvates or prodrugs thereof according to claim 1, wherein, $A_3$ is N, $A_1$, and $A_2$ are each independently selected from N or $CR_4$, $R_4$ is H, F, Cl or methyl.

4. The compound, or the pharmaceutically acceptable salts, diastereomers, enantiomers, solvates or prodrugs thereof according to claim 1, wherein, Q is NH.

5. The compound, or the pharmaceutically acceptable salts, diastereomers, enantiomers, solvates or prodrugs thereof according to claim 1, wherein, $R_1$ is $C_3$-$C_8$ cycloalkyl, 4- to 8-membered heteroalicyclic group, or aryl or heteroaryl which is unsubstituted or substituted with 1 to 3 substituents selected from the group consisting of $C_1$-$C_{10}$ alkyl, halogen, $C_3$-$C_8$ cycloalkyl, halogenated $C_1$-$C_{10}$ alkyl, cyano, hydroxyl, $C_1$-$C_6$ alkylthio, —CO—$R_5$, —$SO_2$—$R_5$, —SO—$R_5$, —CONH—$R_5$, —$NR^aR^b$, 4- to 8-membered heteroalicyclic group, $C_2$-$C_6$ alkynyl, $C_2$-$C_6$ alkenyl, $C_1$-$C_3$ alkoxy $C_1$-$C_6$ alkylthio, $C_1$-$C_{10}$ alkyl substituted with hydroxyl, $C_1$-$C_6$ alkoxy $C_1$-$C_{10}$ alkyl, $C_3$-$C_8$ cycloalkyl $C_1$-$C_6$ alkyl, ($C_3$-$C_8$ cycloalkyl)-O—($C_1$-$C_6$ alkyl), $C_1$-$C_6$ alkyl substituted with 4- to 8-membered heteroalicyclic group, and —O—$R_6$, the aryl group is phenyl, naphthyl,

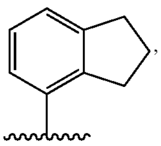, 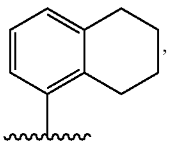, the heteroaryl group is pyrrolyl, furyl, pyridyl, thienyl, imidazolyl, thiazolyl, isothiazolyl, indazolyl, indolyl, isoindolyl, indolinyl, isoindolinyl, isoquinolinyl, indolizinyl, isoxazolyl, 1,5-naphthyridinyl, 1,6-naphthyridinonyl, oxadiazolyl, oxazolyl, 1-phenyl-1H-pyrrolyl, phenazinyl, phenothiazinyl, phenoxazinyl, phthalazinyl, pteridinyl, purinyl, pyranyl, pyrazolyl, pyrazolo[3,4-d]pyrimidinyl, pyrido[3,2-d]pyrimidinyl, pyrido[3,4-d]pyrimidinyl, pyrazinyl, pyrimidinyl, pyridazinyl, quinazolinyl, quinoxalinyl, quinolinyl,

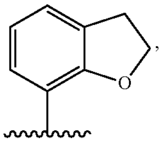, 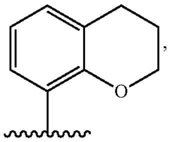, 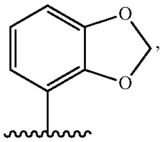,

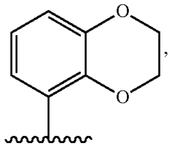, 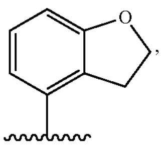, 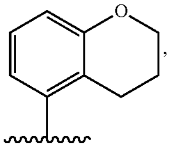, the 4- to 8-membered heteroalicyclic group is a 4- to 8-membered heteroalicyclic group containing 1 to 2 atoms selected from N, O, or S as ring atoms, $R_5$ is hydrogen, hydroxyl, $C_1$-$C_6$ alkyl, $C_1$-$C_6$ alkoxy $C_1$-$C_6$ alkyl, $C_1$-$C_6$ alkyl substituted with hydroxyl, $C_3$-$C_8$ cycloalkyl, or $C_1$-$C_6$ alkyl substituted with 4- to 8-membered heteroalicyclic group, $R_6$ is $C_1$-$C_{10}$ alkyl, $C_3$-$C_8$ cycloalkyl, 4- to 8-membered heteroalicyclic group, or $C_1$-$C_{10}$ alkyl which is unsubstituted or substituted with 1 to 3 substituents selected from the group consisting of hydroxyl, $C_1$-$C_6$ alkoxy, cyano, —$NR^aR^b$, $C_3$-$C_8$ cycloalkyloxy, —CONH—$R_5$, $C_3$-$C_8$ cycloalkyl, $C_3$-$C_8$ cycloalkyl substituted with hydroxyl and/or $C_1$-$C_4$ alkyl, carboxylic, halogen, halogenated $C_1$-$C_6$ alkoxy, —CO—$R_5$, —$SO_2$—$R_5$, —SO—$R_5$, $C_2$-$C_6$ alkynyl, $C_2$-$C_6$ alkenyl, $C_1$-$C_4$ alkoxy $C_1$-$C_6$ alkoxy, 4- to 8-membered heteroalicyclic group, 4- to 8-membered heteroalicyclic group substituted with oxo, 4- to 8-membered heteroalicyclic group substituted with hydroxyl and/or $C_1$-$C_4$ alkyl, or $C_1$-$C_6$ alkylthio, $R^a$ and $R^b$ are each independently selected from hydrogen, $C_1$-$C_6$ alkyl, $C_3$-$C_8$ cycloalkyl, $C_1$-$C_6$ alkyl substituted with $C_1$-$C_6$ alkoxy, $C_1$-$C_6$ alkyl substituted with hydroxyl, $C_3$-$C_8$ cycloalkyl $C_1$-$C_6$ alkyl, $C_1$-$C_6$ alkyl substituted with 4- to 8-membered heteroalicyclic group, $C_1$-$C_6$ alkyl substituted with $C_1$-$C_3$ alkylthio, or $C_1$-$C_6$ alkyl substituted with substituted amino or unsubstituted amino, wherein the substituted amino is substituted with mono- or di-$C_1$-$C_3$ alkyl.

6. The compound, or the pharmaceutically acceptable salts, diastereomers, enantiomers, solvates or prodrugs thereof according to claim 5, wherein, $R_1$ is cyclopropyl, cyclobutyl, cyclopentyl, cyclohexyl, oxetan-3-yl, tetrahydrofuran-3-yl, tetrahydropyran-4-yl, tetrahydropyran-3-yl, pyrrolidinyl, piperidinyl, piperazinyl, morpholinyl, thiomorpholinyl, or aryl or heteroaryl which is unsubstituted or substituted with 1 to 3 substituents selected from the group consisting of $C_1$-$C_{10}$ alkyl, halogen, $C_3$-$C_8$ cycloalkyl, halogenated $C_1$-$C_{10}$ alkyl, cyano, hydroxyl, $C_1$-$C_6$alkylthio, —$SO_2$—$R_5$, —SO—$R_5$, —CO—$R_5$, —CONH—$R_5$, —$NR^aR^b$, 4- to 8-membered heteroalicyclic group, $C_2$-$C_6$ alkynyl, $C_2$-$C_6$ alkenyl, $C_1$-$C_3$ alkoxy $C_1$-$C_6$ alkylthio, $C_1$-$C_{10}$ alkyl substituted with hydroxyl, $C_1$-$C_6$ alkoxy $C_1$-$C_{10}$ alkyl, $C_3$-$C_8$ cycloalkyl $C_1$-$C_6$ alkyl, ($C_3$-$C_8$ cycloalkyl)-O—($C_1$-$C_6$ alkyl), $C_1$-$C_6$ alkyl substituted with 4- to 8-membered heteroalicyclic group, and —O—$R_6$, the aryl group is phenyl,

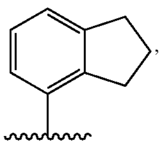, 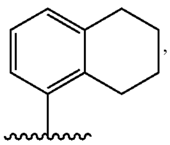, the heteroaryl group is pyrazolyl, pyridyl, pyrimidinyl, thiazolyl, oxazolyl,

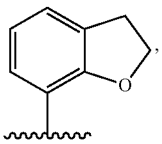, 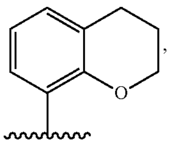, 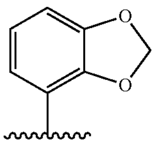,

-continued

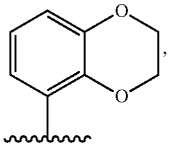, 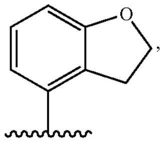, 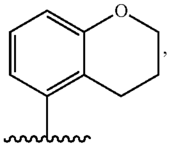, the 4- to 8-membered heteroalicyclic group is a 4- to 8-membered heteroalicyclic group containing 1 to 2 atoms selected from N, O, or S as ring atoms, $R_5$ is hydrogen, $C_1$-$C_6$ alkyl, $C_1$-$C_6$ alkoxy $C_1$-$C_6$ alkyl, $C_1$-$C_6$ alkyl substituted with hydroxyl, $C_3$-$C_8$ cycloalkyl, or $C_1$-$C_6$ alkyl substituted with 4- to 8-membered heteroalicyclic group, $R_6$ is $C_1$-$C_{10}$ alkyl, $C_3$-$C_8$ cycloalkyl, 4- to 8-membered heteroalicyclic group, or $C_1$-$C_{10}$ alkyl which is unsubstituted or substituted with 1 to 3 substituents selected from the group consisting of hydroxyl, $C_1$-$C_6$ alkoxy, cyano, —$NR^aR^b$, $C_3$-$C_8$ cycloalkyloxy, —CONH—$R_5$, $C_3$-$C_8$ cycloalkyl, $C_3$-$C_8$ cycloalkyl substituted with hydroxyl and/or $C_1$-$C_4$ alkyl, carboxylic, halogen, halogenated $C_1$-$C_6$ alkoxy, —$SO_2$—$R_5$, —SO—$R_5$, —CO—$R_5$, $C_2$-$C_6$ alkynyl, $C_2$-$C_6$ alkenyl, $C_1$-$C_4$ alkoxy $C_1$-$C_6$ alkoxy, 4- to 8-membered heteroalicyclic group, 4- to 8-membered heteroalicyclic group substituted with oxo, 4- to 8-membered heteroalicyclic group substituted with hydroxyl and/or $C_1$-$C_4$ alkyl, and $C_1$-$C_6$ alkylthio, $R^a$ and $R^b$ are each independently selected from hydrogen, $C_1$-$C_6$ alkyl, $C_3$-$C_8$ cycloalkyl, $C_1$-$C_6$ alkyl substituted with $C_1$-$C_6$ alkoxy, $C_1$-$C_6$ alkyl substituted with hydroxyl, $C_3$-$C_8$ cycloalkyl $C_1$-$C_6$ alkyl, $C_1$-$C_6$ alkyl substituted with 4- to 8-membered heteroalicyclic group, $C_1$-$C_6$ alkyl substituted with $C_1$-$C_3$ alkylthio, or $C_1$-$C_6$ alkyl substituted with substituted amino or unsubstituted amino, wherein the substituted amino is substituted with mono- or di-$C_1$-$C_3$ alkyl.

7. The compound, or the pharmaceutically acceptable salts, diastereomers, enantiomers, solvates or prodrugs thereof according to claim 5, wherein, $R_1$ is

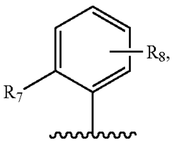 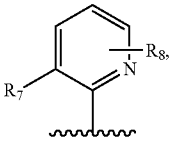 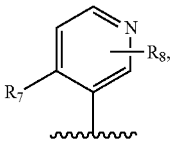

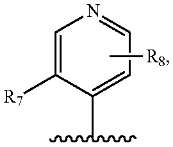 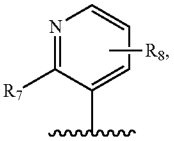 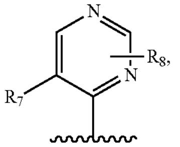

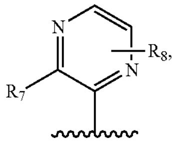 or 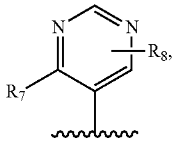

$R_7$ is hydrogen, $C_1$-$C_4$ alkyl, $C_1$-$C_3$ alkoxy, halogen, hydroxyl, trifluoromethyl, trifluoromethoxy, cyano, $C_2$-$C_4$ alkynyl, $C_2$-$C_4$ alkenyl, $C_3$-$C_4$ cycloalkyl, or $C_1$-$C_3$ acyl;

$R_8$ is hydrogen, $C_1$-$C_{10}$ alkyl, halogen, $C_3$-$C_8$ cycloalkyl, halogenated $C_1$-$C_{10}$ alkyl, cyano, hydroxyl, $C_1$-$C_6$ alkylthio, —CO—$R_5$, —$SO_2$—$R_5$, —SO—$R_5$, —CONH—$R_5$, —$NR^aR^b$, 4- to 8-membered heteroalicyclic group, $C_2$-$C_6$ alkynyl, $C_2$-$C_6$ alkenyl, $C_1$-$C_3$ alkoxy $C_1$-$C_6$ alkylthio, $C_1$-$C_{10}$ alkyl substituted with hydroxyl, $C_1$-$C_6$ alkoxy $C_1$-$C_{10}$ alkyl, $C_3$-$C_8$ cycloalkyl $C_1$-$C_6$ alkyl, ($C_3$-$C_8$ cycloalkyl)-O—($C_1$-$C_6$ alkyl), $C_1$-$C_6$ alkyl substituted with 4- to 8-membered heteroalicyclic group, or —O—$R_6$, the 4- to 8-membered heteroalicyclic group is a 4- to 8-membered heteroalicyclic group containing 1 to 2 atoms selected from N, O, or S as ring atoms, $R_5$ is hydrogen, hydroxyl, $C_1$-$C_6$ alkyl, $C_1$-$C_6$ alkoxy $C_1$-$C_6$ alkyl, $C_1$-$C_6$ alkyl substituted with hydroxyl, $C_3$-$C_8$ cycloalkyl, or $C_1$-$C_6$ alkyl substituted with 4- to 8-membered heteroalicyclic group, $R_6$ is $C_1$-$C_{10}$ alkyl, $C_3$-$C_8$ cycloalkyl, 4- to 8-membered heteroalicyclic group, or $C_1$-$C_{10}$ alkyl which is unsubstituted or substituted with 1 to 3 substituents selected from the group consisting of hydroxyl, $C_1$-$C_6$ alkoxy, cyano, —$NR^aR^b$, $C_3$-$C_8$ cycloalkyloxy, —CONH—$R_5$, $C_3$-$C_8$ cycloalkyl, $C_3$-$C_8$ cycloalkyl substituted with hydroxyl and/or $C_1$-$C_4$ alkyl, carboxylic, halogen, halogenated $C_1$-$C_6$ alkoxy, —$SO_2$—$R_5$, —SO—$R_5$, —CO—$R_5$, $C_2$-$C_6$ alkynyl, $C_2$-$C_6$ alkenyl, $C_1$-$C_4$ alkoxy $C_1$-$C_6$ alkoxy, 4- to 8-membered heteroalicyclic group, 4- to 8-membered heteroalicyclic group substituted with oxo, 4- to 8-membered heteroalicyclic group substituted with hydroxyl and/or $C_1$-$C_4$ alkyl, $C_1$-$C_6$ alkylthio, $R^a$ and $R^b$ are each independently selected from hydrogen, $C_1$-$C_6$ alkyl, $C_3$-$C_8$ cycloalkyl, $C_1$-$C_6$ alkyl substituted with $C_1$-$C_6$ alkoxy, $C_1$-$C_6$ alkyl substituted with hydroxyl, $C_3$-$C_8$ cycloalkyl $C_1$-$C_6$ alkyl, $C_1$-$C_6$ alkyl substituted with 4- to 8-membered heteroalicyclic group, $C_1$-$C_6$ alkyl substituted with $C_1$-$C_3$ alkylthio, or $C_1$-$C_6$ alkyl substituted with substituted amino or unsubstituted amino, wherein the substituted amino is substituted with mono- or di-$C_1$-$C_3$ alkyl.

8. The compound, or the pharmaceutically acceptable salts, diastereomers, enantiomers, solvates or prodrugs thereof according to claim 5, wherein, $R_1$ is

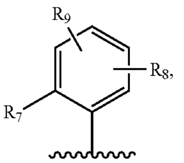 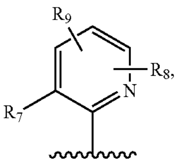

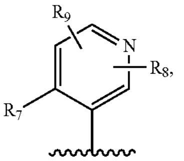 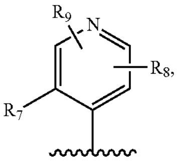

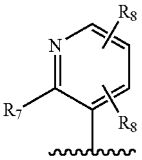, 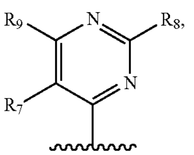

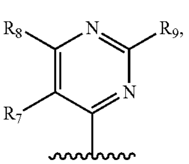 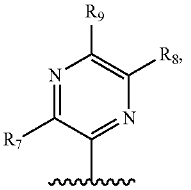

-continued

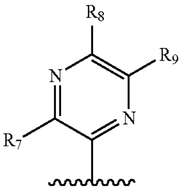 , 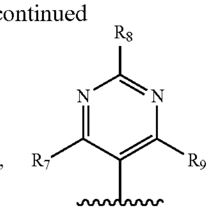 or

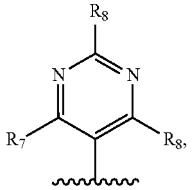

$R_7$ is hydrogen, $C_1$-$C_4$ alkyl, $C_1$-$C_3$ alkoxy, halogen, hydroxyl, trifluoromethyl, trifluoromethoxy, cyano, $C_2$-$C_4$ alkynyl, $C_2$-$C_4$ alkenyl, $C_3$-$C_4$ cycloalkyl, or $C_1$-$C_3$ acyl;

$R_8$ is hydrogen, $C_1$-$C_{10}$ alkyl, halogen, $C_3$-$C_8$ cycloalkyl, halogenated $C_1$-$C_{10}$ alkyl, cyano, hydroxyl, $C_1$-$C_6$ alkylthio, —CO—$R_5$, —$SO_2$—$R_5$, —SO—$R_5$, —CONH—$R_5$, —$NR^aR^b$, 4- to 8-membered heteroalicyclic group, $C_2$-$C_6$ alkynyl, $C_2$-$C_6$ alkenyl, $C_1$-$C_3$ alkoxy $C_1$-$C_6$ alkylthio, $C_1$-$C_{10}$ alkyl substituted with hydroxyl, $C_1$-$C_6$ alkoxy $C_1$-$C_{10}$ alkyl, $C_3$-$C_8$ cycloalkyl $C_1$-$C_6$ alkyl, ($C_3$-$C_8$ cycloalkyl)-O—($C_1$-$C_6$ alkyl), $C_1$-$C_6$ alkyl substituted with 4- to 8-membered heteroalicyclic group, or —O—$R_6$, the 4- to 8-membered heteroalicyclic group is a 4- to 8-membered heteroalicyclic group containing 1 to 2 atoms selected from N, O, or S as ring atoms, $R_5$ is hydrogen, hydroxyl, $C_1$-$C_6$ alkyl, $C_1$-$C_6$ alkoxy $C_1$-$C_6$ alkyl, $C_1$-$C_6$ alkyl substituted with hydroxyl, $C_3$-$C_8$ cycloalkyl, or $C_1$-$C_6$ alkyl substituted with 4- to 8-membered heteroalicyclic group, $R_6$ is $C_1$-$C_{10}$ alkyl, $C_3$-$C_8$ cycloalkyl, 4- to 8-membered heteroalicyclic group, or $C_1$-$C_{10}$ alkyl which is unsubstituted or substituted with 1 to 3 substituents selected from the group consisting of hydroxyl, $C_1$-$C_6$ alkoxy, cyano, —$NR^aR^b$, $C_3$-$C_8$ cycloalkyloxy, —CONH—$R_5$, $C_3$-$C_8$ cycloalkyl, $C_3$-$C_8$ cycloalkyl substituted with hydroxyl and/or $C_1$-$C_4$ alkyl, carboxylic, halogen, halogenated $C_1$-$C_6$ alkoxy, —$SO_2$—$R_5$, —SO—$R_5$, —CO—$R_5$, $C_2$-$C_6$ alkynyl, $C_2$-$C_6$ alkenyl, $C_1$-$C_4$ alkoxy $C_1$-$C_6$ alkoxy, 4- to 8-membered heteroalicyclic group, 4- to 8-membered heteroalicyclic group substituted with oxo, 4- to 8-membered heteroalicyclic group substituted with hydroxyl and/or $C_1$-$C_4$ alkyl, and $C_1$-$C_6$ alkylthio, $R^a$ and $R^b$ are each independently selected from hydrogen, $C_1$-$C_6$ alkyl, $C_3$-$C_8$ cycloalkyl, $C_1$-$C_6$ alkyl substituted with $C_1$-$C_6$ alkoxy, $C_1$-$C_6$ alkyl substituted with hydroxyl, $C_3$-$C_8$ cycloalkyl $C_1$-$C_6$ alkyl, $C_1$-$C_6$ alkyl substituted with 4- to 8-membered heteroalicyclic group, $C_1$-$C_6$ alkyl substituted with $C_1$-$C_3$ alkylthio, or $C_1$-$C_6$ alkyl substituted with substituted amino or unsubstituted amino, wherein the substituted amino is substituted with mono- or di-$C_1$-$C_3$ alkyl;

$R_9$ is hydrogen, $C_1$-$C_4$ alkyl, $C_1$-$C_3$ alkoxy, halogen, hydroxy, trifluoromethyl, trifluoromethoxy, cyano, $C_2$-$C_4$ alkynyl, $C_2$-$C_4$ alkenyl, $C_3$-$C_4$ Cycloalkyl, or $C_1$-$C_3$ acyl.

9. The compound, or the pharmaceutically acceptable salts, diastereomers, enantiomers, solvates or prodrugs thereof according to claim 7, wherein, $R_1$ is:

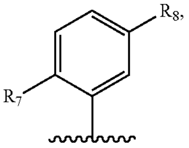 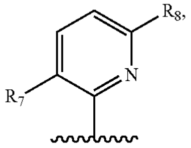 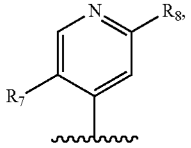

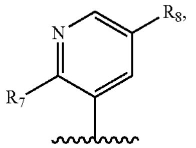 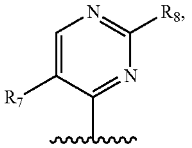 or

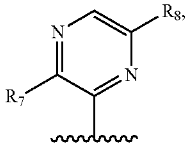

$R_7$ is hydrogen, methyl, ethyl, propyl, isopropyl, methoxy, ethoxy, propoxy, isopropoxy, fluorine, chlorine, hydroxyl, trifluoromethyl, trifluoromethoxy, cyano, ethynyl, propynyl, vinyl, propenyl, cyclopropyl, cyclobutyl, formyl, or acetyl;

$R_8$ is hydrogen, $C_1$-$C_{10}$ alkyl, halogen, $C_3$-$C_8$ cycloalkyl, halogenated $C_1$-$C_{10}$ alkyl, cyano, hydroxyl, $C_1$-$C_6$ alkylthio, —CO—$R_5$, —$SO_2$—$R_5$, —SO—$R_5$, —CONH—$R_5$, —$NR^aR^b$, 4- to 8-membered heteroalicyclic group, $C_2$-$C_6$ alkynyl, $C_2$-$C_6$ alkenyl, $C_1$-$C_3$ alkoxy $C_1$-$C_6$ alkylthio, $C_1$-$C_{10}$ alkyl substituted with hydroxyl, $C_1$-$C_6$ alkoxy $C_1$-$C_{10}$ alkyl, $C_3$-$C_8$ cycloalkyl $C_1$-$C_6$ alkyl, ($C_3$-$C_8$ cycloalkyl)-O—($C_1$-$C_6$ alkyl), $C_1$-$C_6$ alkyl substituted with 4- to 8-membered heteroalicyclic group, or —O—$R_6$, the 4- to 8-membered heteroalicyclic group is a 4- to 8-membered heteroalicyclic group containing 1 to 2 atoms selected from N, O, or S as ring atoms, $R_5$ is hydrogen, hydroxyl, $C_1$-$C_6$ alkyl, $C_1$-$C_6$ alkoxy $C_1$-$C_6$ alkyl, $C_1$-$C_6$ alkyl substituted with hydroxyl, $C_3$-$C_8$ cycloalkyl, $C_1$-$C_6$ alkyl substituted with 4- to 8-membered heteroalicyclic group, $R_6$ is $C_1$-$C_{10}$ alkyl, $C_3$-$C_8$ cycloalkyl, 4- to 8-membered heteroalicyclic group, or $C_1$-$C_{10}$ alkyl substituted with 1 to 3 substituents selected from hydroxyl, $C_1$-$C_6$ alkoxy, cyano, —$NR^aR^b$, $C_3$-$C_8$ cycloalkyloxy, —CONH—$R_5$, $C_3$-$C_8$ cycloalkyl, $C_3$-$C_8$ cycloalkyl substituted with hydroxyl and/or $C_1$-$C_4$ alkyl, carboxylic, halogen, halogenated $C_1$-$C_6$ alkoxy, —$SO_2$—$R_5$, —SO—$R_5$, —CO—$R_5$, $C_2$-$C_6$ alkynyl, $C_2$-$C_6$ alkenyl, $C_1$-$C_4$ alkoxy $C_1$-$C_6$ alkoxy, 4- to 8-membered heteroalicyclic group, 4- to 8-membered heteroalicyclic group substituted with oxo, 4- to 8-membered heteroalicyclic group substituted with hydroxyl and/or $C_1$-$C_4$ alkyl, and $C_1$-$C_6$ alkylthio, $R^a$ and $R^b$ are each independently selected from hydrogen, $C_1$-$C_6$ alkyl, $C_3$-$C_8$ cycloalkyl, $C_1$-$C_6$ alkyl substituted with $C_1$-$C_6$ alkoxy, $C_1$-$C_6$ alkyl substituted with hydroxyl, $C_3$-$C_8$ cycloalkyl $C_1$-$C_6$ alkyl, $C_1$-$C_6$ alkyl substituted with 4- to 8-membered heteroalicyclic group, $C_1$-$C_6$ alkyl substituted with $C_1$-$C_3$ alkylthio, or $C_1$-$C_6$ alkyl substituted with substituted amino or unsubstituted amino, wherein the substituted amino is substituted with mono- or di-$C_1$-$C_3$ alkyl.

10. The compound, or the pharmaceutically acceptable salts, diastereomers, enantiomers, solvates or prodrugs thereof according to claim 1, wherein, $R_2$ is $C_3$-$C_8$ cycloalkyl, which is unsubstituted or substituted with 1 to 3 substituents selected from the group consisting of methyl, ethyl, propyl, isopropyl, methoxy, ethoxy, propoxy, isopropoxy, methylthio, ethylthio, propylthio, formyl, acetyl, hydroxyl, fluorine, chlorine, trifluoromethyl, cyano, —$CONH_2$, oxo (═O), amino, dimethylamino, and diethylamino, or $C_7$-$C_{10}$ bridged cyclyl, which is unsubstituted or substituted with 1 to 3 substituents selected from the group consisting of methyl, ethyl, propyl, isopropyl, methoxy, ethoxy, propoxy, isopropoxy, methylthio, ethylthio, propylthio, formyl, acetyl, hydroxyl, fluorine, chlorine, trifluoromethyl, cyano, —$CONH_2$, oxo (═O), amino, dimethylamino, and diethylamino, or $C_1$-$C_{10}$ alkyl, which is unsubstituted or substituted with 1 to 3 substituents selected from the group consisting of methoxy, ethoxy, propoxy, isopropoxy, methylthio, ethylthio, propylthio, formyl, acetyl, hydroxyl, fluorine, chlorine, cyano, —$CONH_2$, cyclopropyl, cyclobutyl, cyclopentyl, cyclohexyl, amino, dimethylamino, and diethylamino, or —$(CH_2)n$-$R^e$, wherein $R^e$ is aryl or heteroaryl, which is unsubstituted or substituted with 1 to 3 substituents selected from the group consisting of methyl, ethyl, propyl, isopropyl, methoxy, ethoxy, propoxy, isopropoxy, methylthio, ethylthio, propylthio, formyl, acetyl, hydroxyl, fluorine, chlorine, trifluoromethyl, cyano, —$CONH_2$, ethynyl, vinyl, amino, dimethylamino, and diethylamino, n is an integer from 0 to 3, or —$(CH_2)m$-$R^f$, wherein $R^f$ is 4- to 8-membered heteroalicyclic group, which is unsubstituted or substituted with 1 to 3 substituents selected from the group consisting of methyl, ethyl, propyl, isopropyl, methoxy, ethoxy, propoxy, isopropoxy, methylthio, ethylthio, propylthio, formyl, acetyl, hydroxyl, fluorine, chlorine, trifluoromethyl, cyano, —$CONH_2$, oxo (═O), amino, dimethylamino, and diethylamino, m is an integer from 0 to 3, the 4- to 8-membered heteroalicyclic group contains 1 to 2 atoms selected from N, O, or S as ring atoms, the aryl group is phenyl, and the heteroaryl group is pyridyl, pyrimidinyl, pyrazolyl, oxazolyl, isoxazolyl, thiazolyl.

11. The compound, or the pharmaceutically acceptable salts, diastereomers, enantiomers, solvates or prodrugs thereof according to claim 10, wherein, $R_2$ is cyclopropyl, cyclobutyl, cyclopentyl, cyclohexyl, cycloheptyl, cyclooctyl, 4,4-difluorocyclohexyl, bicyclo[2.2.1]heptyl, adamantyl, methyl, ethyl, propyl, isopropyl, butyl, isobutyl, sec-butyl, tert-butyl, pentyl, neopentyl, hexyl, 2-hydroxy-2-methylpropyl, 3,3-dimethylbutyl, 3-hydroxy-3-methylbutyl, cyclopropylmethyl, cyclopropylethyl, cyclopropylpropyl, cyclobutylmethyl, cyclobutylethyl, cyclobutylpropyl, cyclopentylmethyl, cyclopentylethyl, cyclopentylpropyl, cyclohexylmethyl, cyclohexylethyl, cyclohexylpropyl, benzyl, phenethyl, phenyl, 2-fluorophenyl, 2-chlorophenyl, 2-methoxyphenyl, 2-cyanophenyl, 2-ethynylphenyl, 3-fluorophenyl, 3-chlorophenyl, 3-methoxyphenyl, 3-cyanophenyl, 3-ethynylphenyl, 4-fluorophenyl, 4-chlorophenyl, 4-methoxyphenyl, 4-cyanophenyl, 4-ethynylphenyl, 3,4-difluorophenyl, 3-cyano-4-methylphenyl, pyridin-2-yl, pyridin-3-yl, pyridine-4-yl, pyrimidin-2-yl, pyrimidin-4-yl, pyrimidin-5-yl, pyrazinyl, pyrazolyl, oxazolyl, isoxazolyl, thiazolyl, oxetan-3-yl, tetrahydrofuran-3-yl, tetrahydro-2H-pyran-4-yl, tetrahydropyrrolyl, piperidin-1-yl, piperazin-1-yl, morpholin-4-yl, methylpiperazin-4-yl, 1-methylpiperidin-4-yl, 1-acetylpiperidin-4-yl, 4-hydroxypiperidin-1-yl, 4-methyl-4-hydroxypiperidin-1-yl,

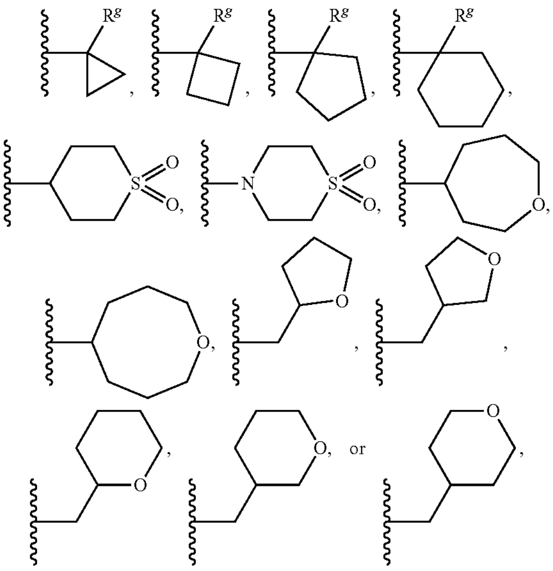

$R^g$ is —$CH_3$ or —OH.

12. The compound, or the pharmaceutically acceptable salts, diastereomers, enantiomers, solvates or prodrugs thereof according to claim 1, wherein, $R_2$ is 2,3-difluorophenyl, 3,5-difluorophenyl, 2,5-difluorophenyl, 2,4-difluorophenyl, 2,3,4-trifluorophenyl, 2,3,5-trifluorophenyl, 2,3,6-trifluorophenyl, 3,4,5-trifluorophenyl, 2,4,5-trifluorophenyl, 3-chloro-2-fluorophenyl, 2-chloro-3-fluorophenyl, 5-chloro-2-fluorophenyl, 2-chloro-5-fluorophenyl, 5-chloro-3-fluorophenyl, 3-chloro-5-fluorophenyl, 3-chloro-4-fluorophenyl, 4-chloro-3-fluorophenyl, 2-chloro-4-fluorophenyl, 4-chloro-2-fluorophenyl, 3-chloro-2,4-difluorophenyl, 5-chloro-2,4-difluorophenyl, 3-chloro-2,5-difluorophenyl, 3-chloro-2,6-difluorophenyl, 3-chloro-4,5-difluorophenyl, 2-chloro-4,5-difluorophenyl, 2-chloro-3,4-difluorophenyl, 2-chloro-3,5-difluorophenyl, 2-chloro-3,6-difluorophenyl, 4-chloro-2,3-difluorophenyl, 4-chloro-3,5-difluorophenyl, 4-chloro-2,5-difluorophenyl, 5-chloro-2,3-difluorophenyl, 5-chloro-3,4-difluorophenyl, 6-chloro-2,3-difluorophenyl, 3-fluoro-5-methylphenyl, 4-fluoro-3-methylphenyl, 2-fluoro-3-methylphenyl, 2-fluoro-4-methylphenyl, 2-fluoro-5-methylphenyl, 3-fluoro-4-methylphenyl, 3-fluoro-2-methylphenyl, 3-fluoro-5-methoxyphenyl, 4-fluoro-3-methoxyphenyl, 2-fluoro-3-methoxyphenyl, 2-fluoro-4-methoxyphenyl, 2-fluoro-5-methoxyphenyl, 3-fluoro-4-methoxyphenyl, 3-fluoro-2-methoxyphenyl, 2-fluoro-3-trifluoromethylphenyl, 2-fluoro-4-trifluoromethylphenyl, 2-fluoro-5-trifluoromethylphenyl, 3-fluoro-2-trifluoromethylphenyl, 4-fluoro-2-trifluoromethylphenyl, 5-fluoro-2-trifluoromethylphenyl, 4-fluoro-3-trifluoromethylphenyl, 3-fluoro-4-trifluoromethylphenyl, 3-fluoro-5-trifluoromethylphenyl, 2-fluoro-5-ethylphenyl, 2-fluoro-5-cyclopropylphenyl, or 2-fluoro-5-phenylphenyl.

13. The compound, or the pharmaceutically acceptable salts, diastereomers, enantiomers, solvates or prodrugs thereof according to claim 1, wherein, $R_3$ is hydrogen, methyl, ethyl, hydroxyl, cyano, trifluoromethyl, fluorine, or chlorine.

14. The compound, or the pharmaceutically acceptable salts, diastereomers, enantiomers, solvates or prodrugs thereof according to claim 1, wherein, the compound is selected from the following structures:
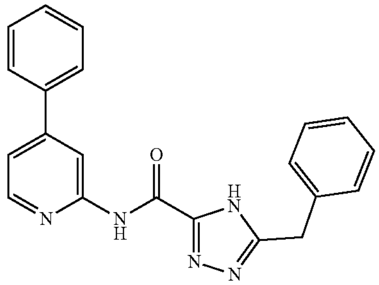
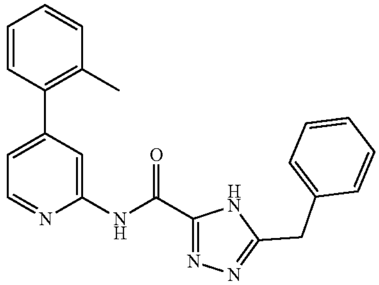
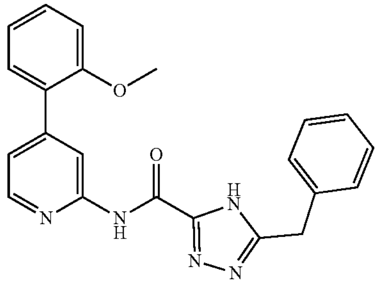
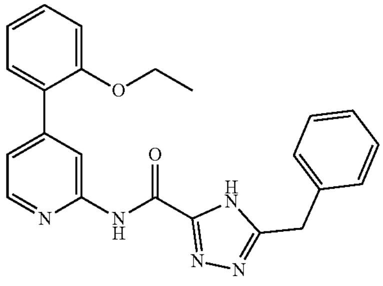
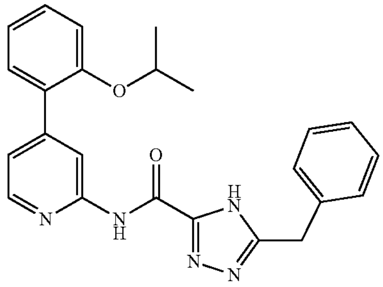
-continued
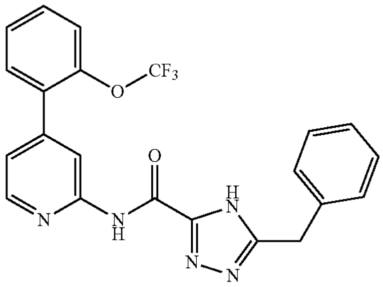
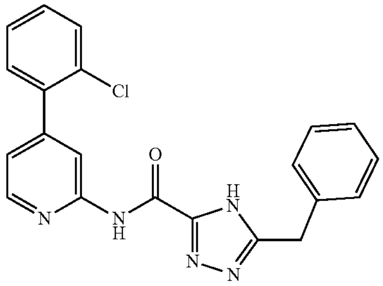
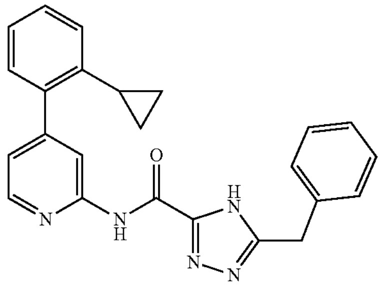
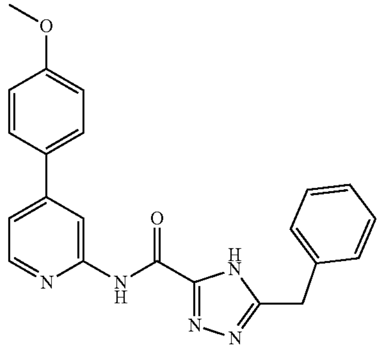
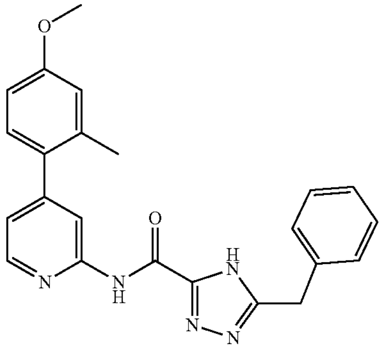

-continued
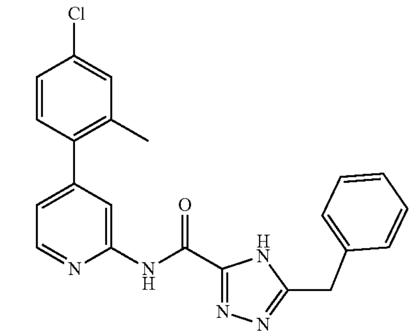
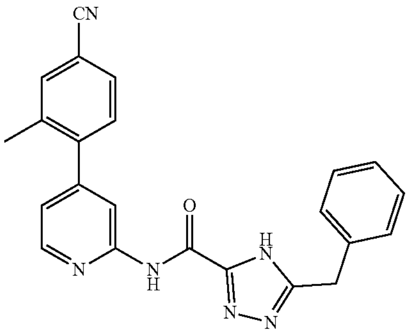
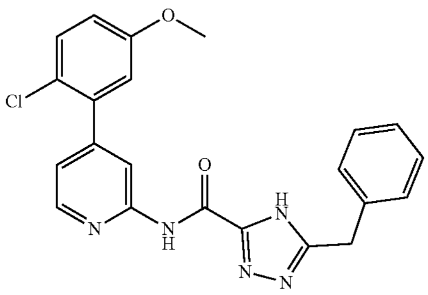
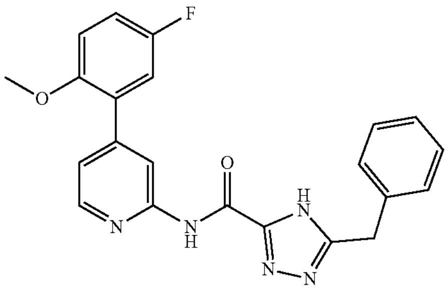
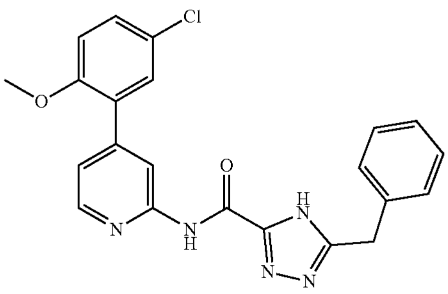
-continued
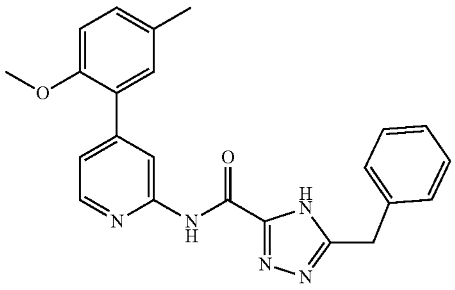
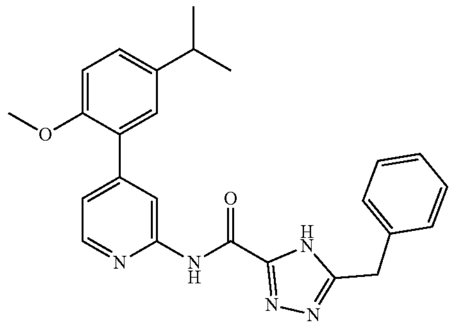
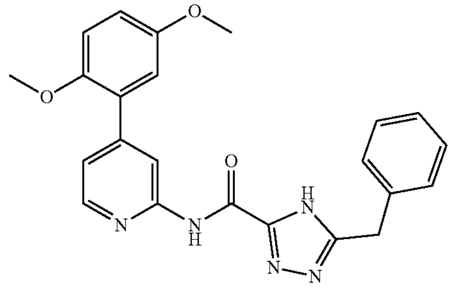
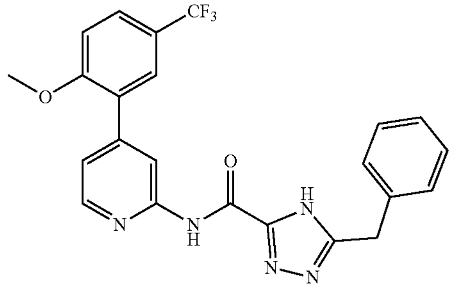
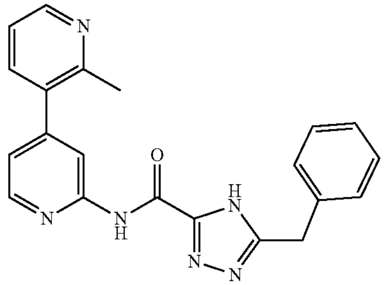

-continued
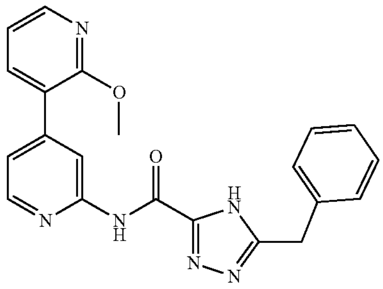
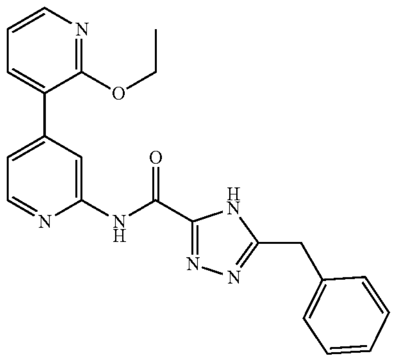
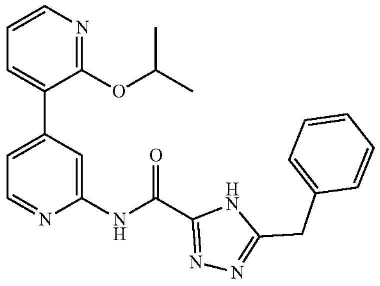
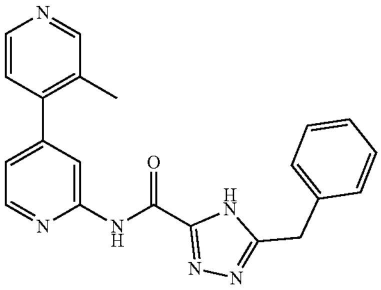
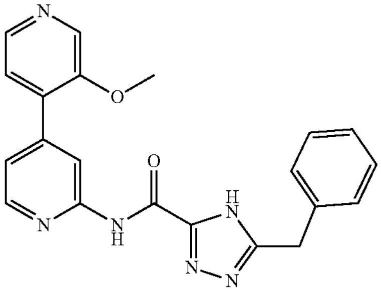
-continued
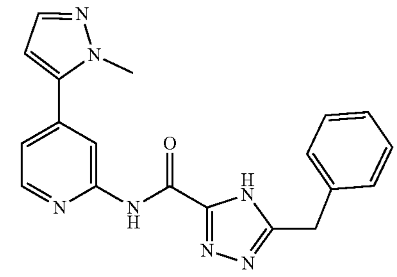
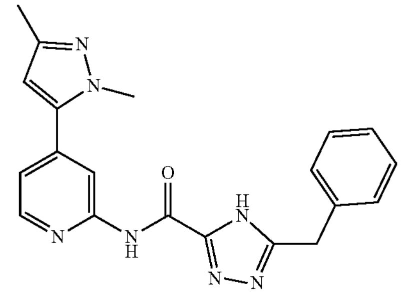
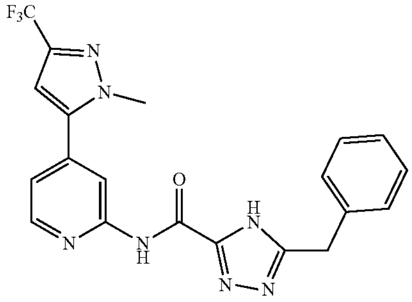
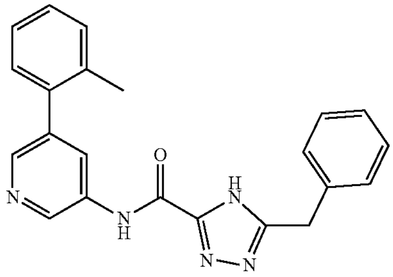
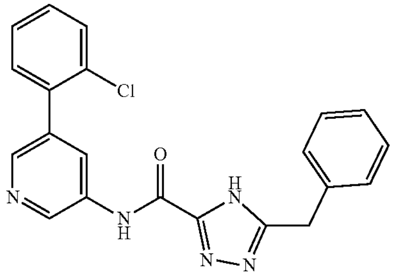
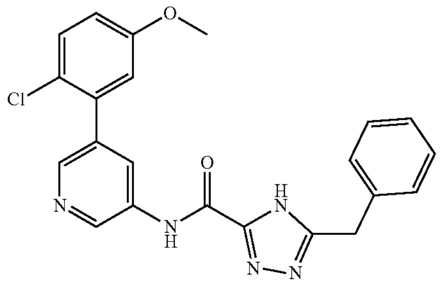

-continued
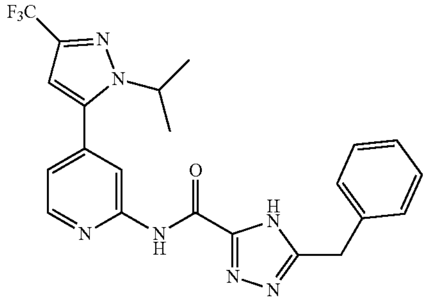
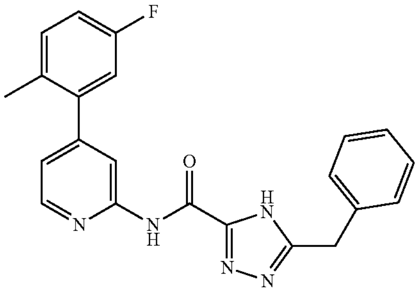
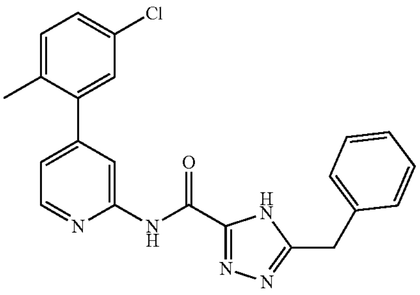
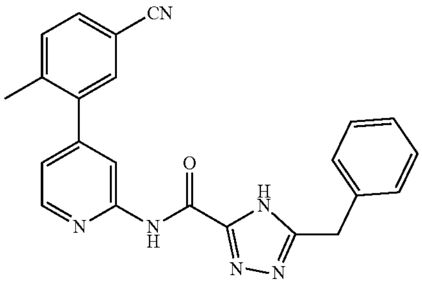
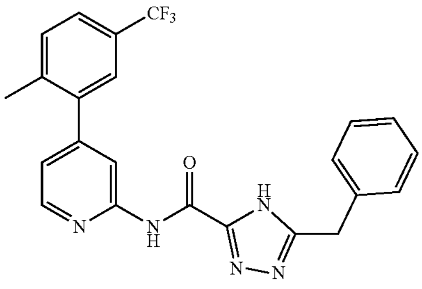
-continued
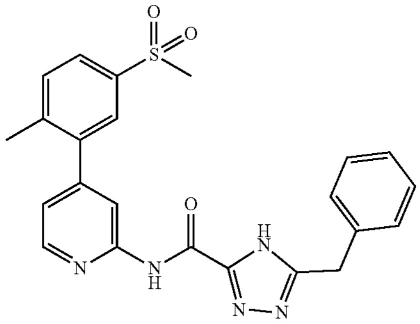
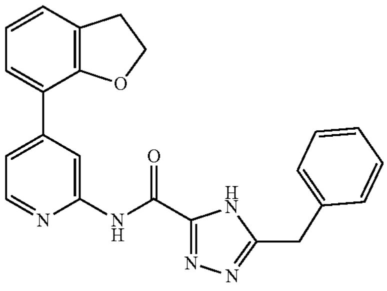
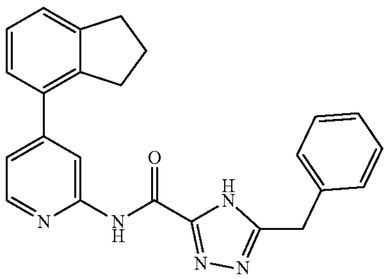
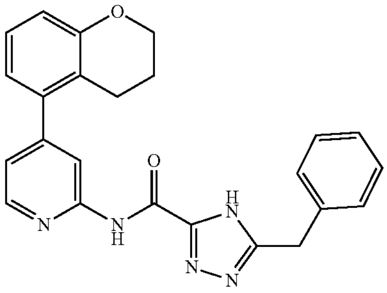
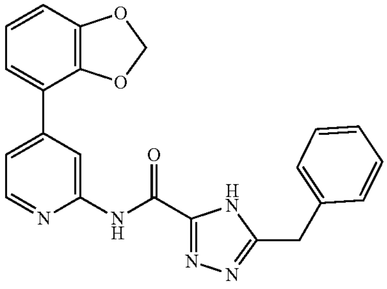

-continued
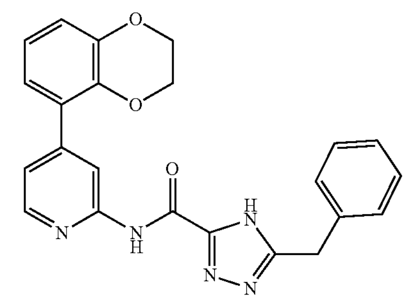
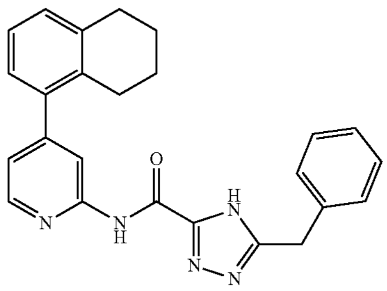
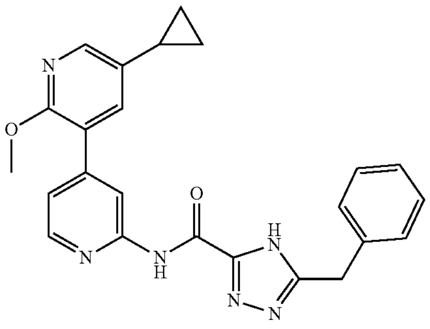
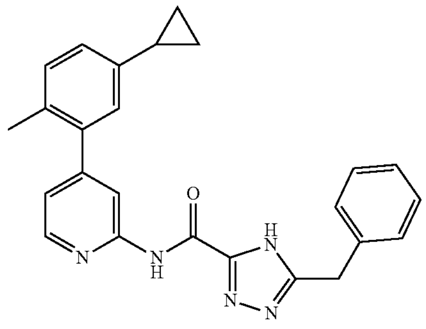
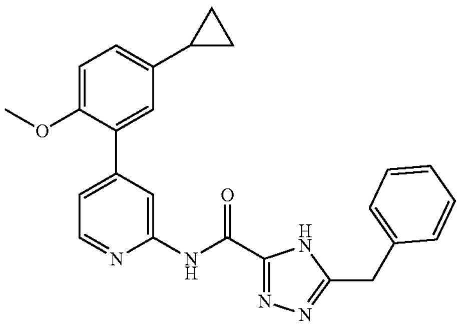
-continued
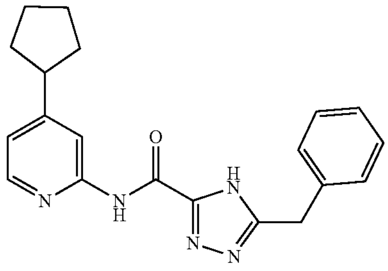
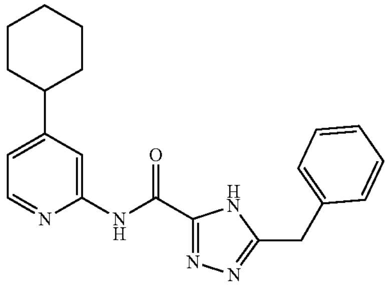
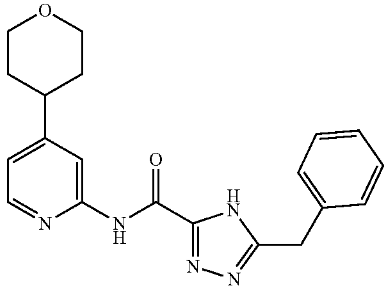
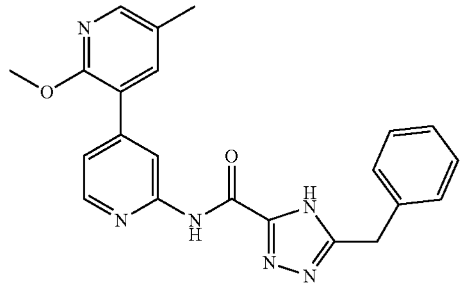
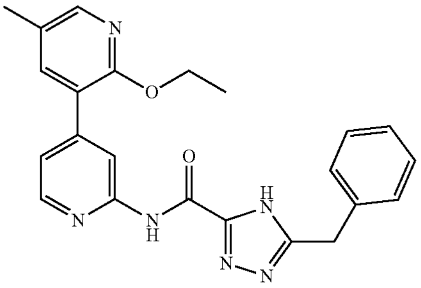
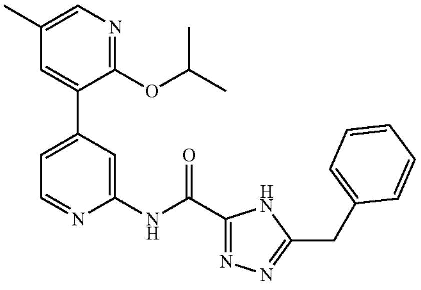

-continued
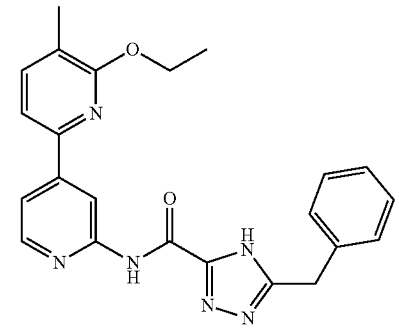
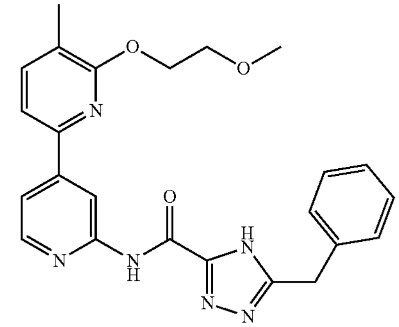
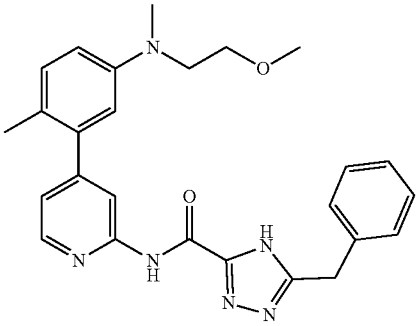
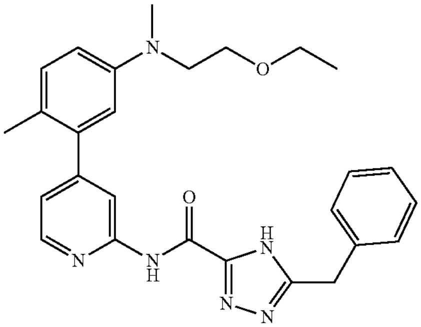
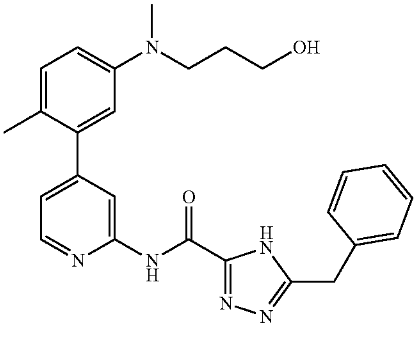
-continued
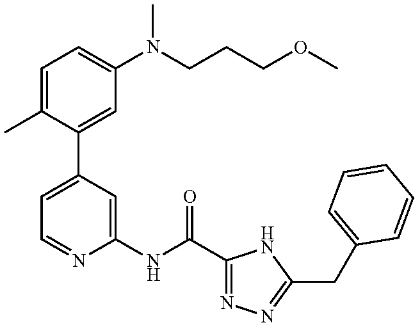
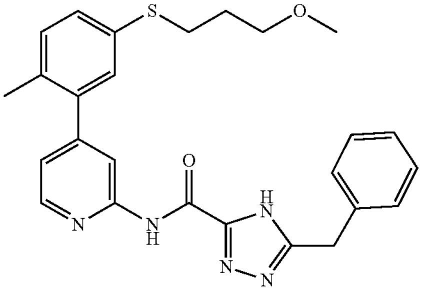
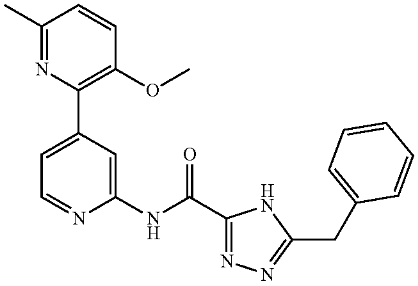
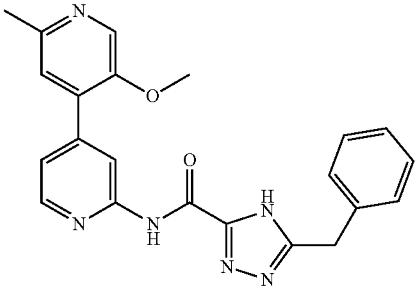
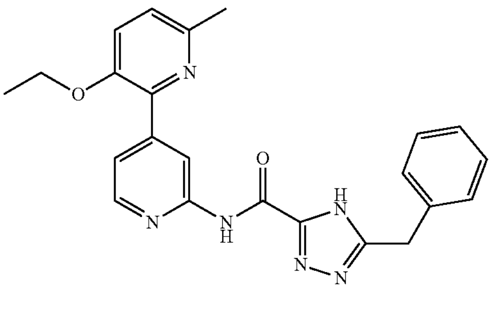

-continued
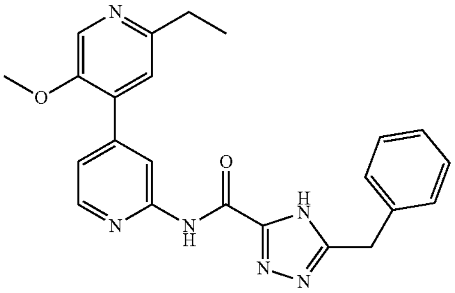
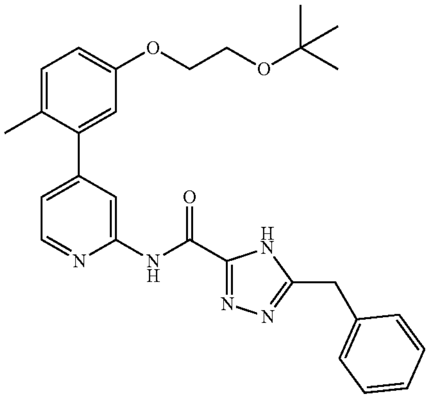
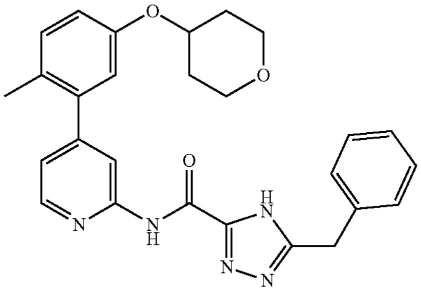
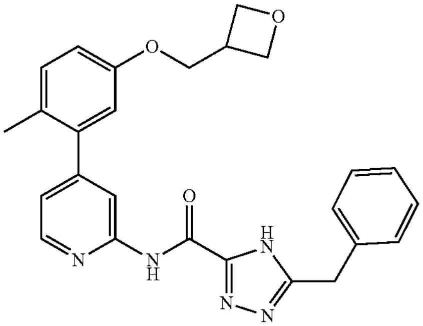
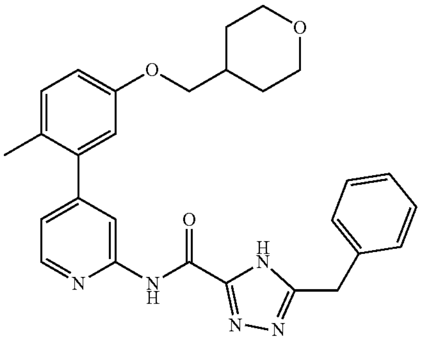
-continued
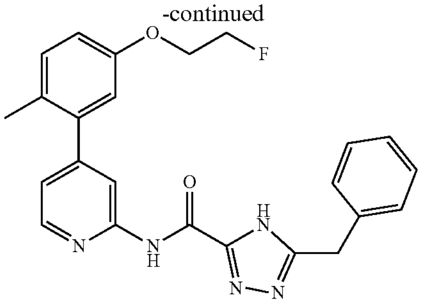
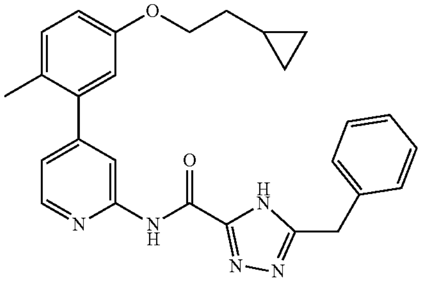
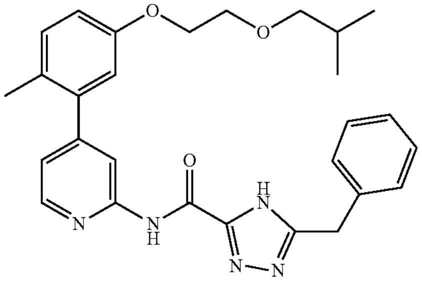
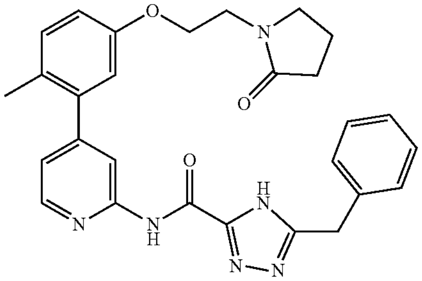
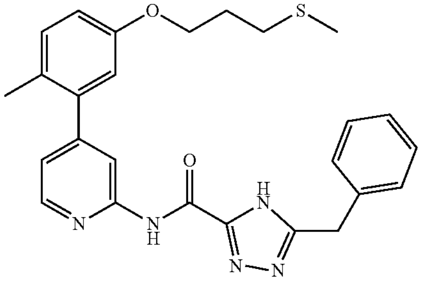
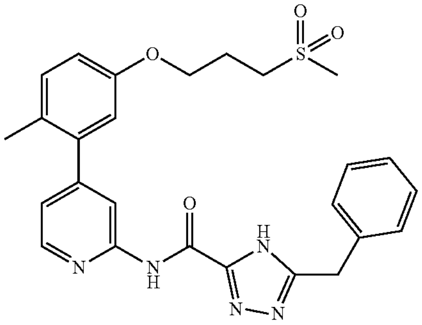

-continued
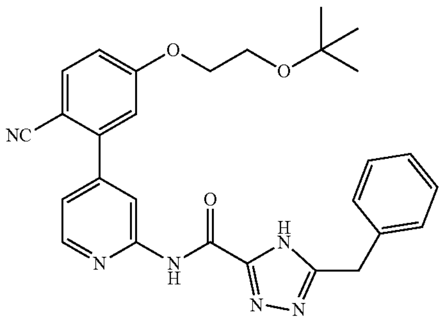
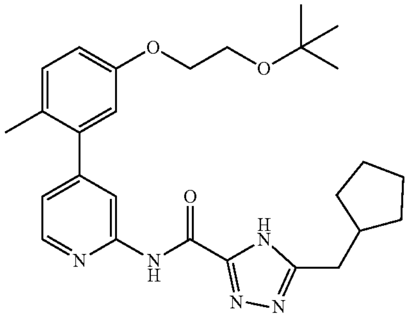
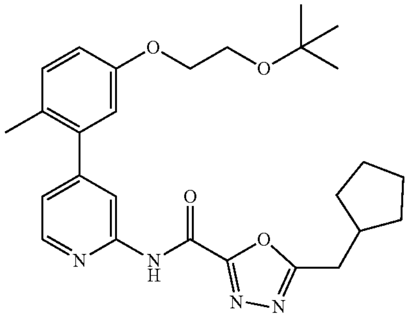
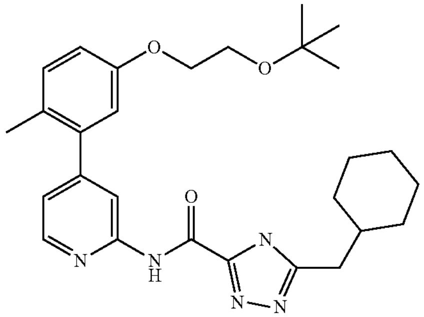
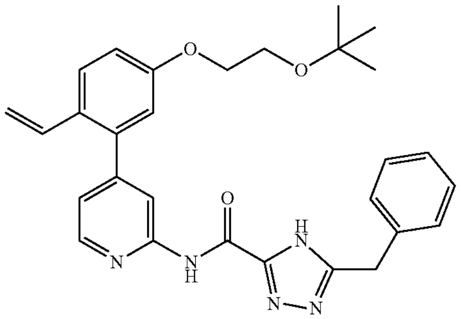
-continued
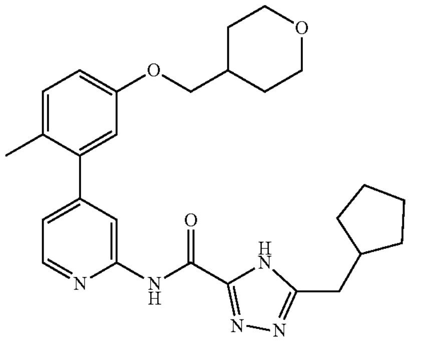
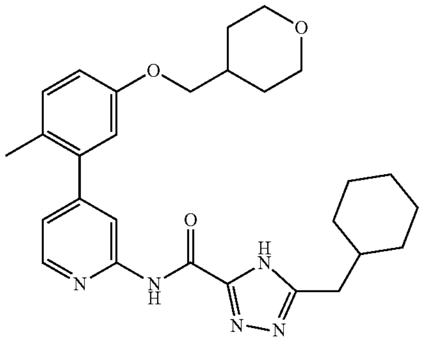
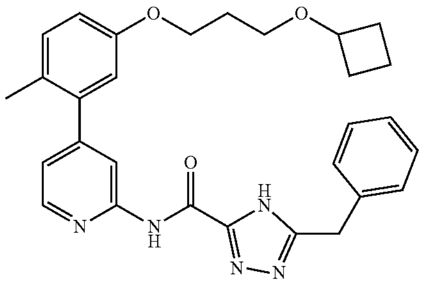
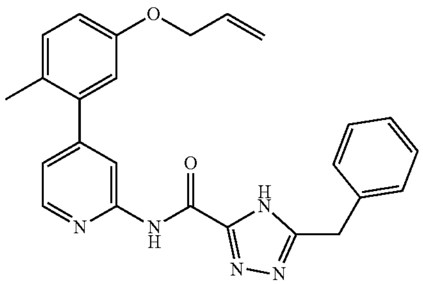
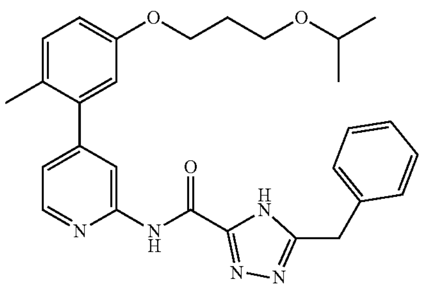

-continued
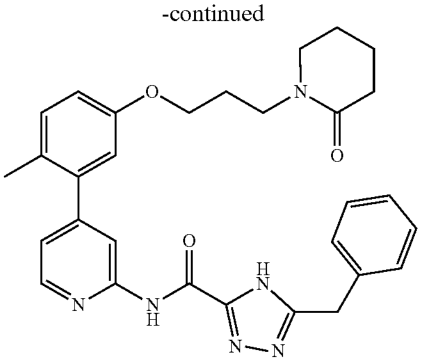
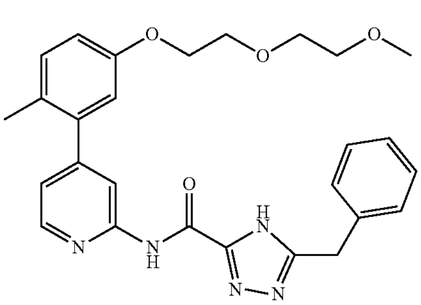
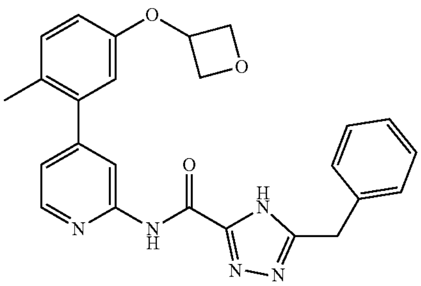
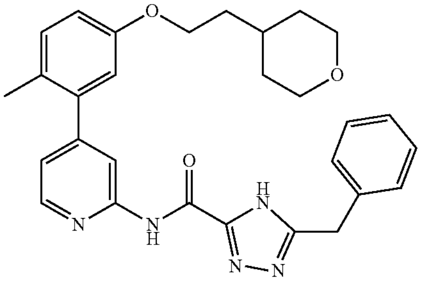
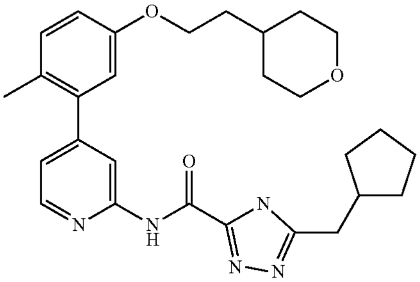
-continued
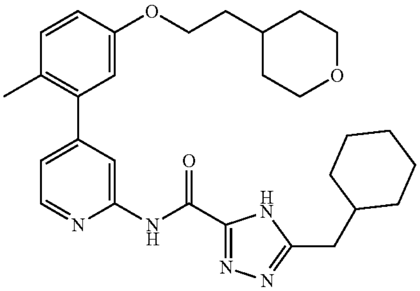
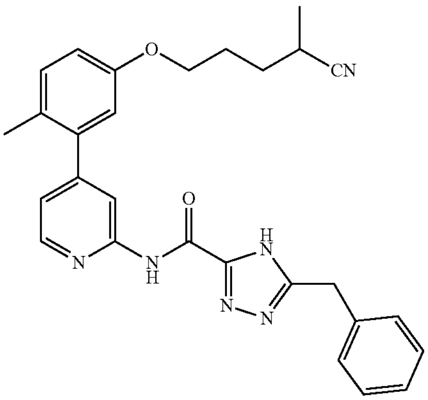
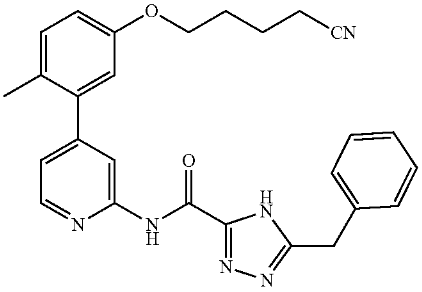
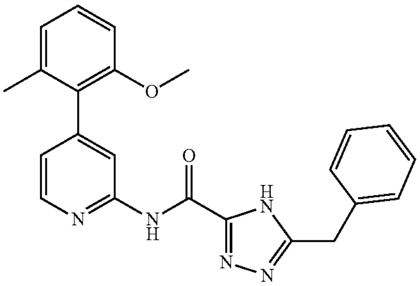
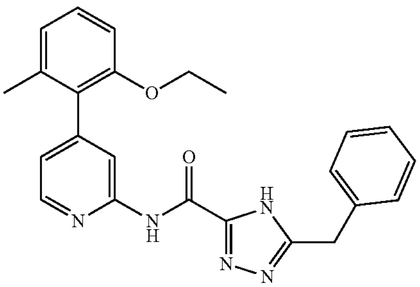

-continued
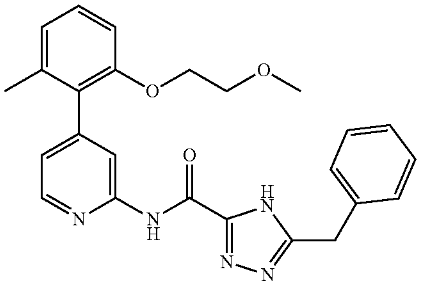
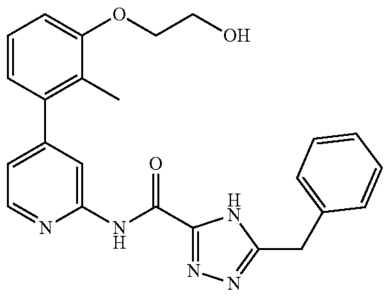
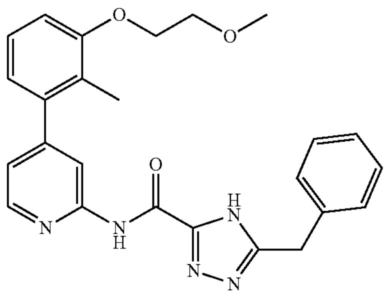
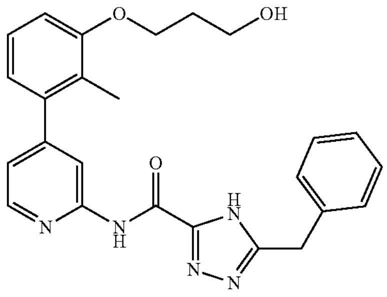
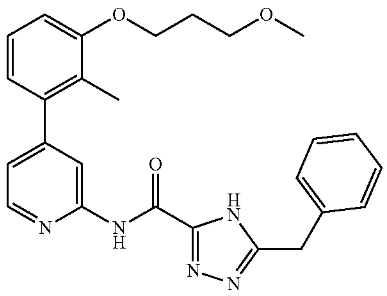
-continued
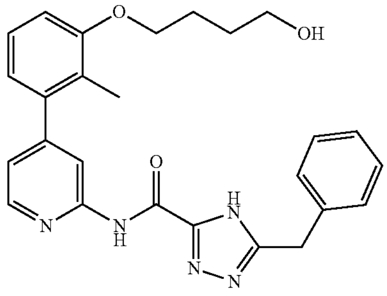
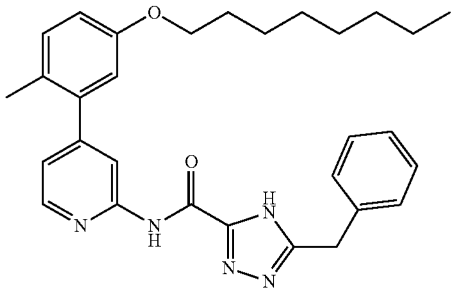
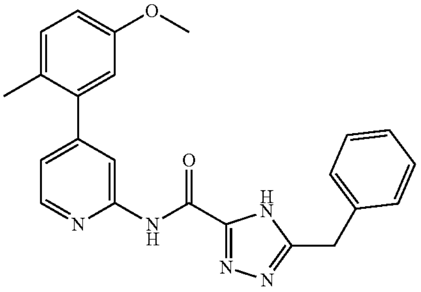
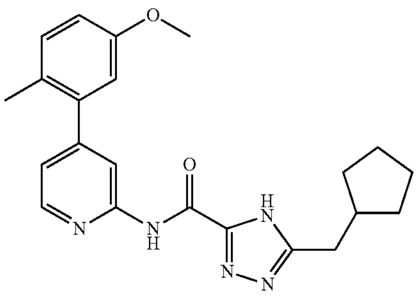
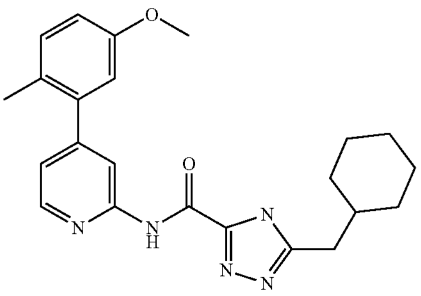

-continued
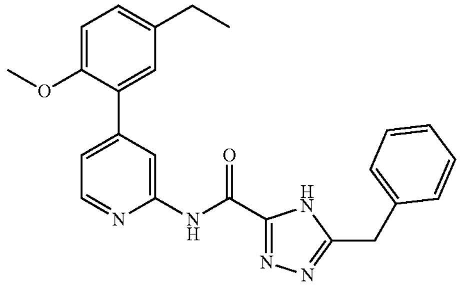
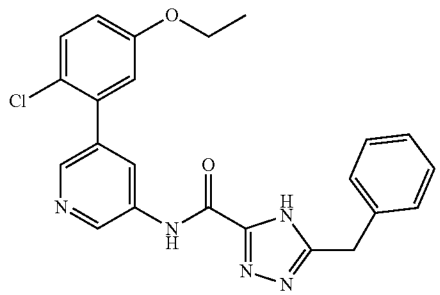
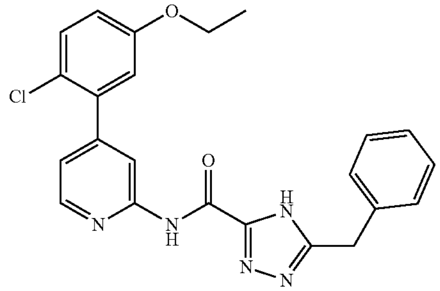
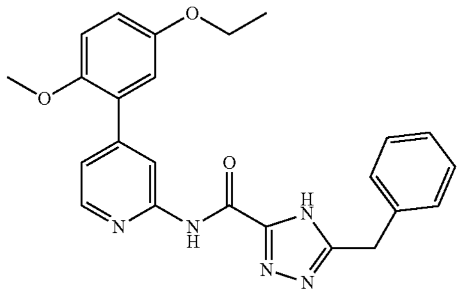
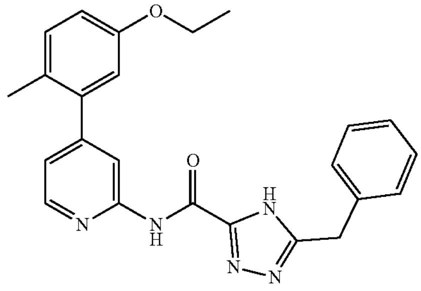
-continued
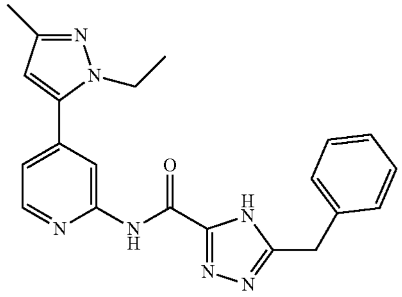
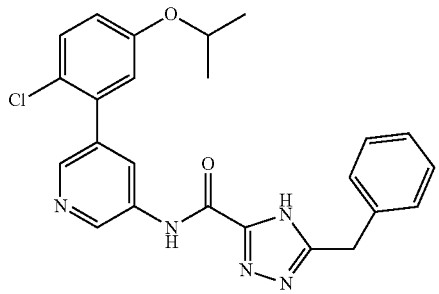
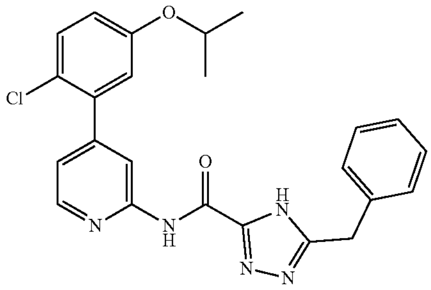
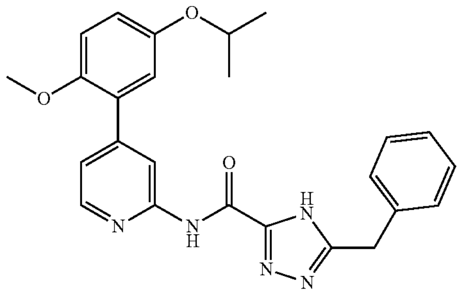
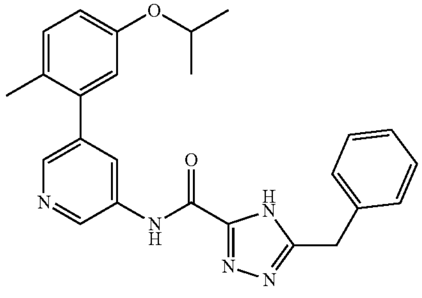

-continued
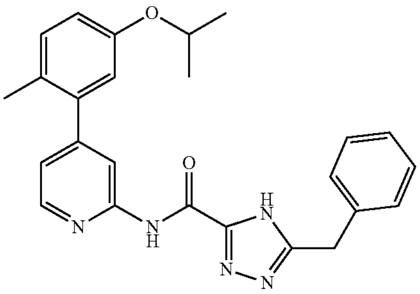
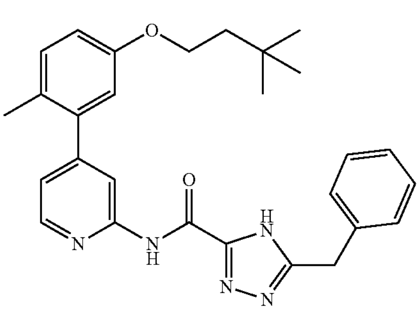
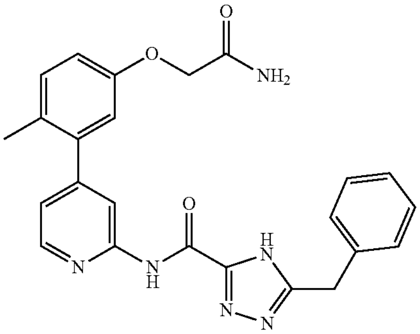
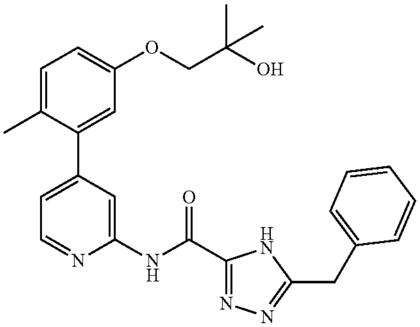
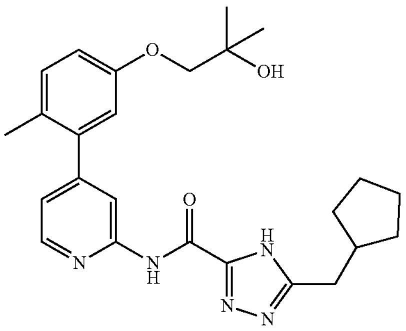
-continued
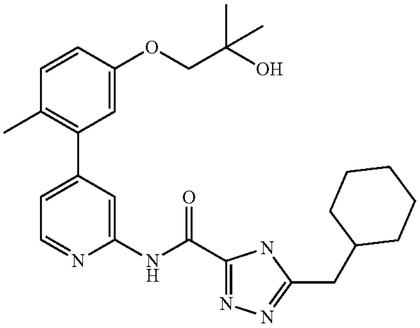
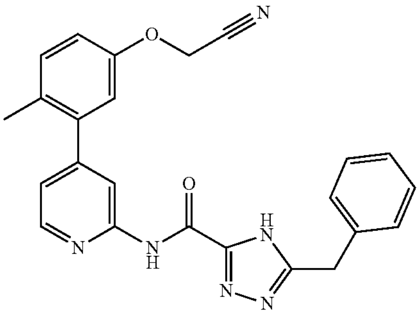
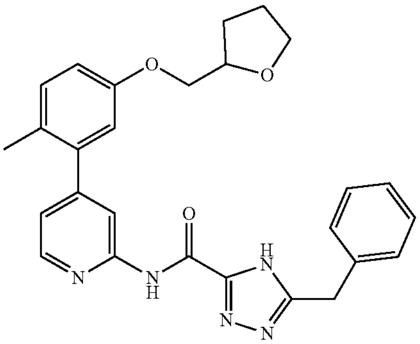
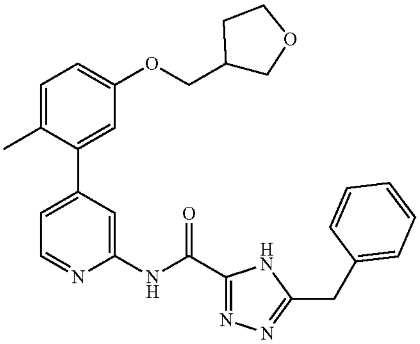
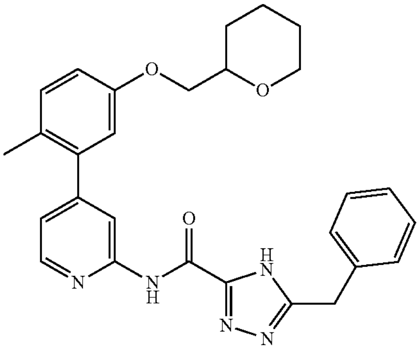

-continued
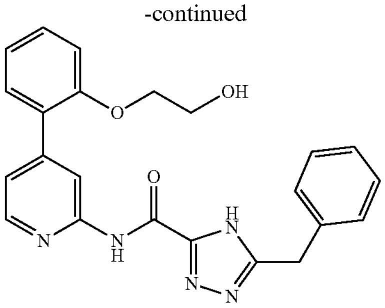
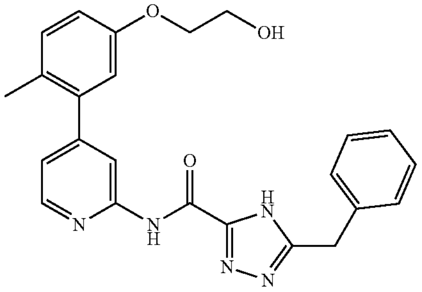
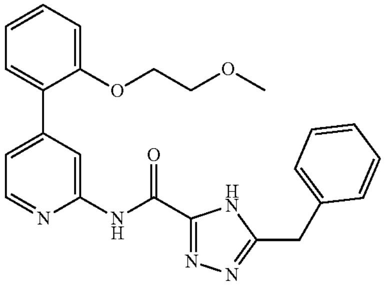
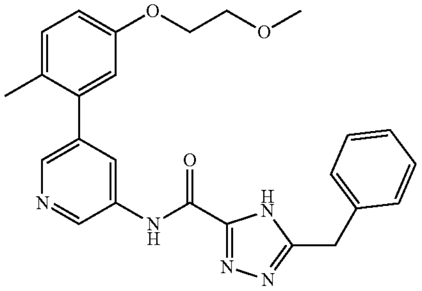
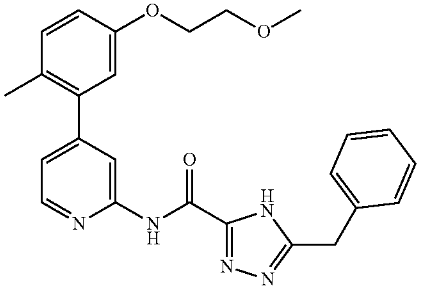
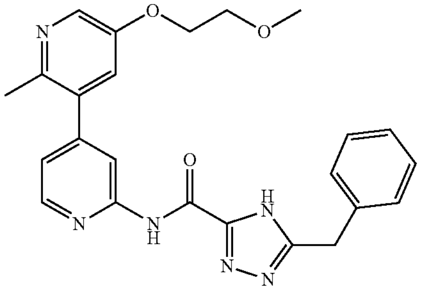
-continued
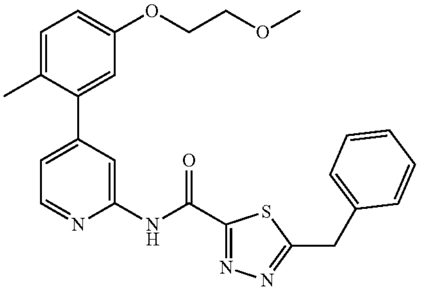
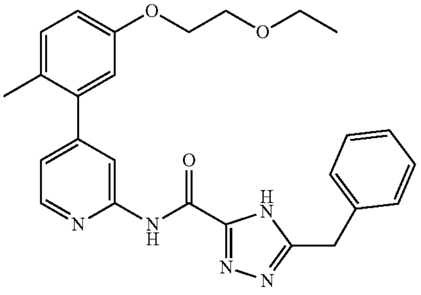
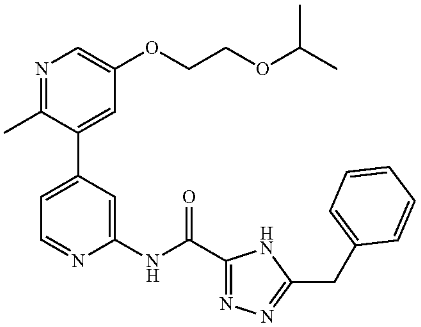
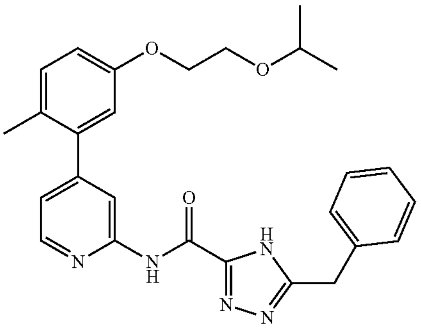
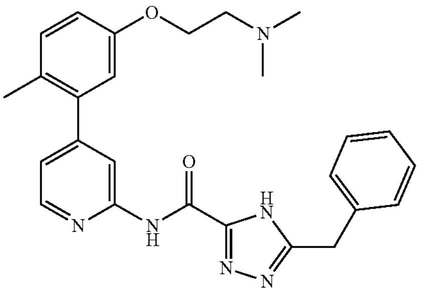

-continued
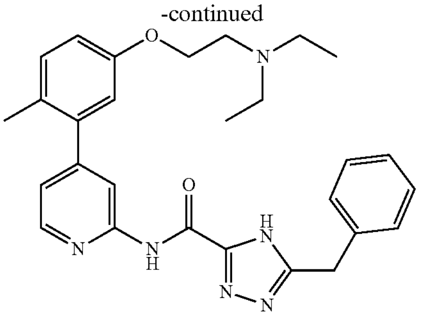
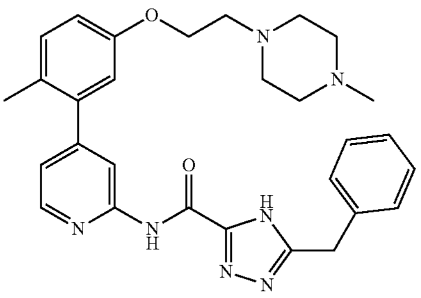
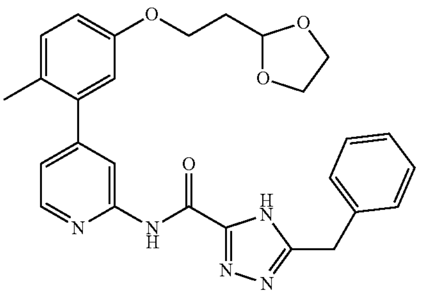
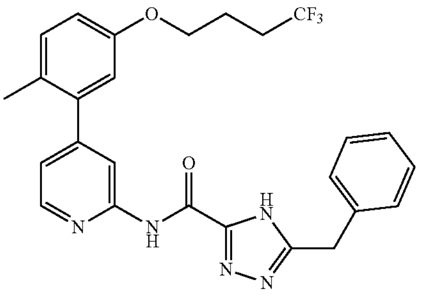
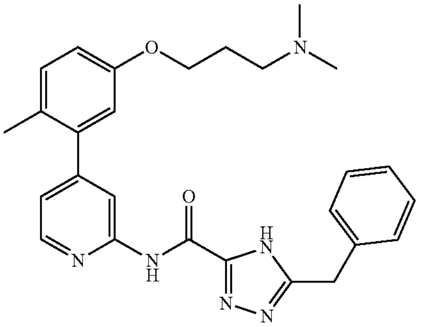
-continued
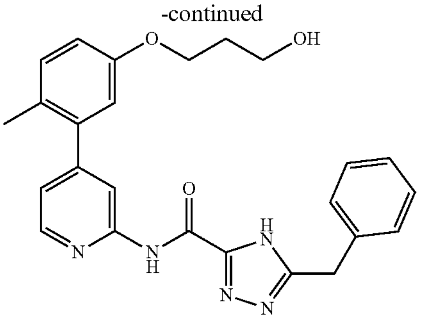
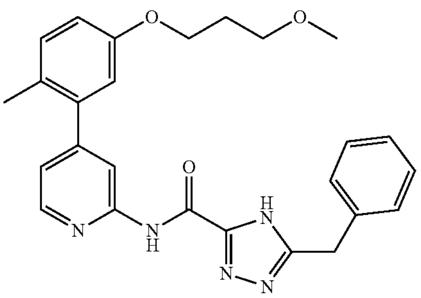
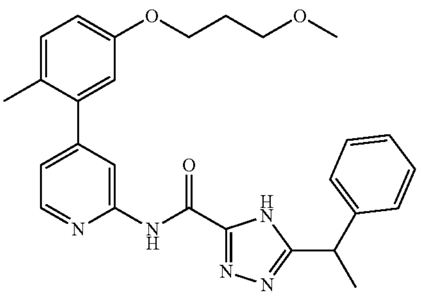
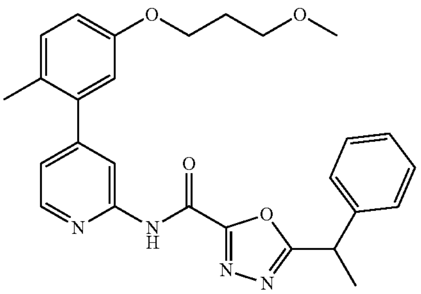
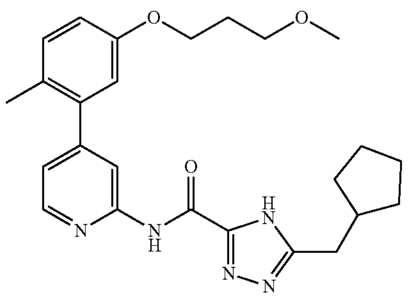

-continued
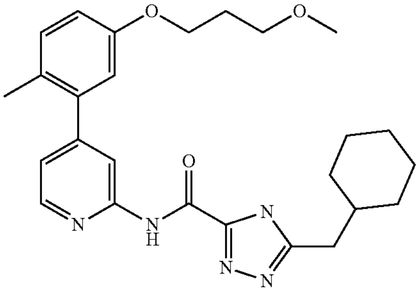
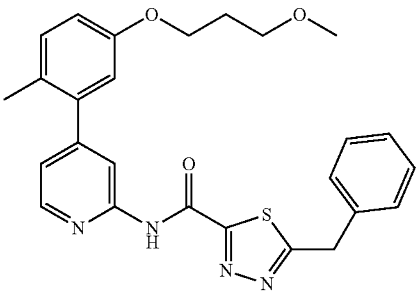
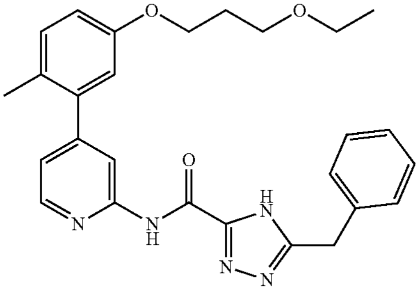
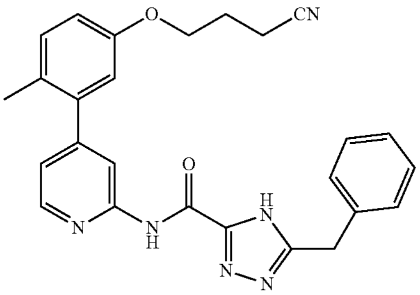
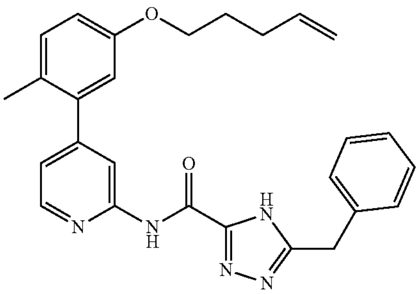
-continued
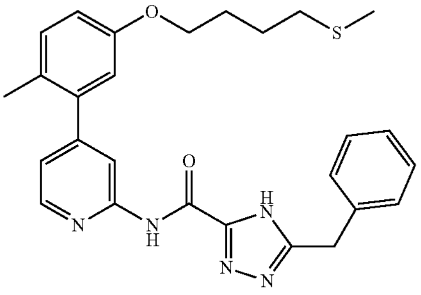
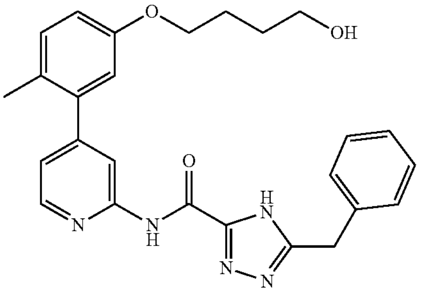
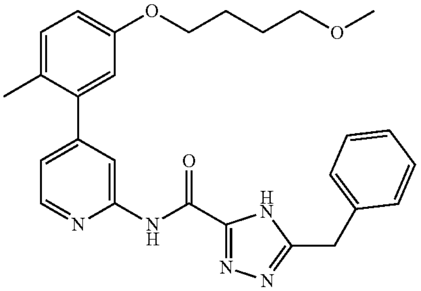
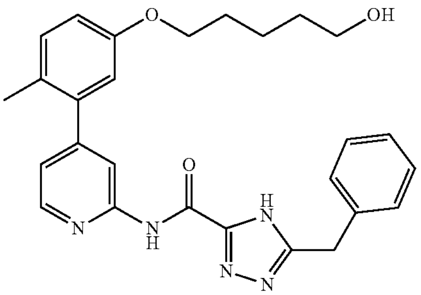
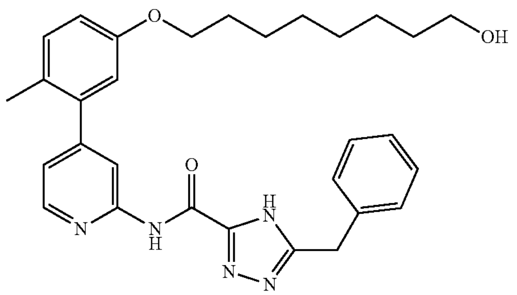

-continued
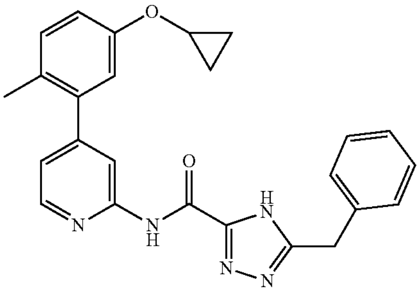
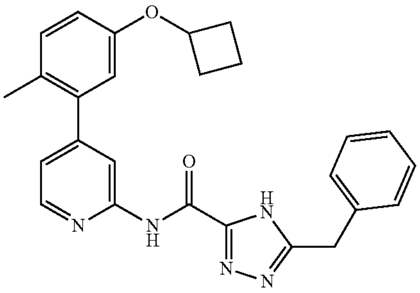
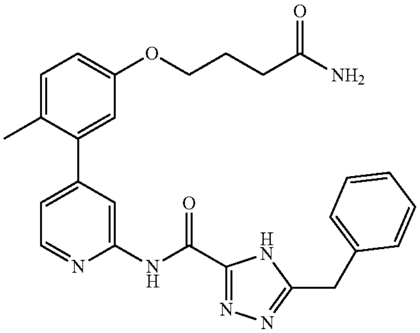
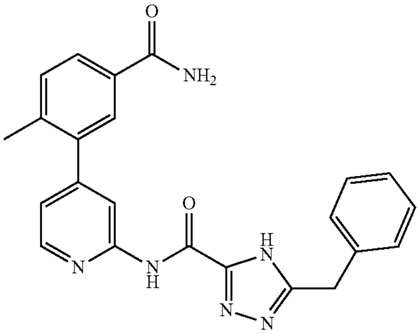
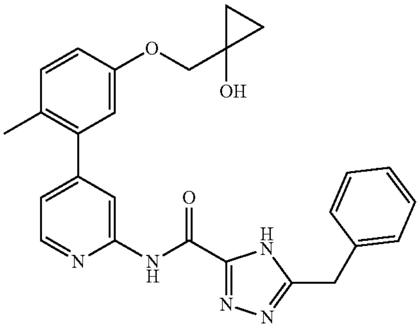
-continued
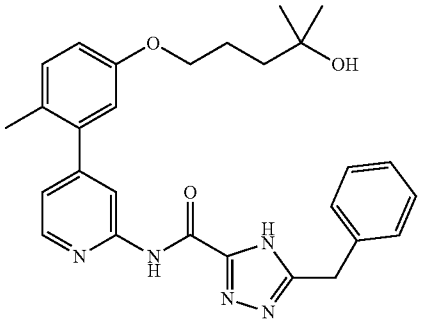
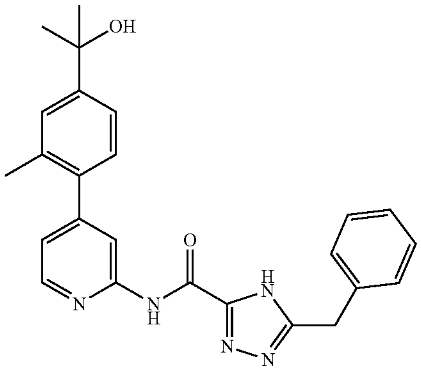
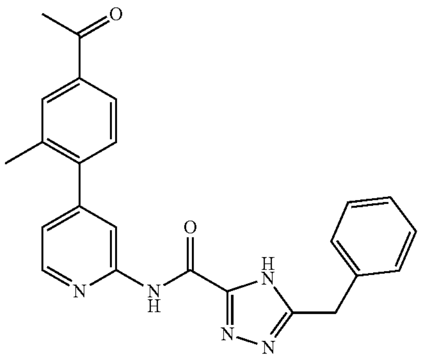
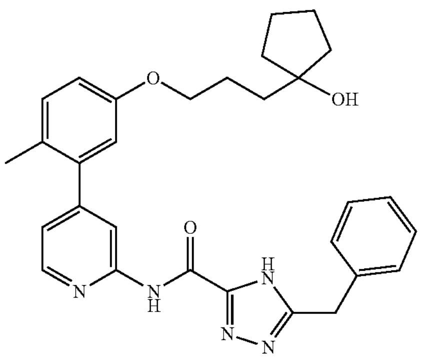

-continued
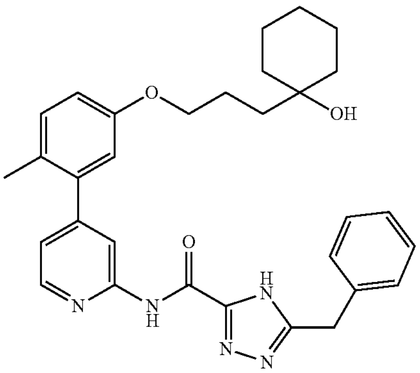
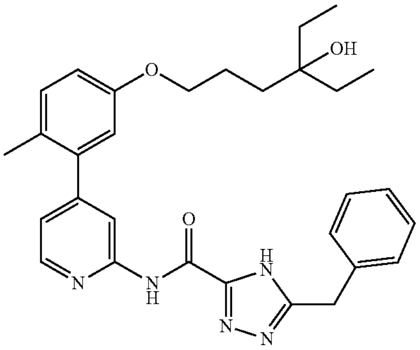
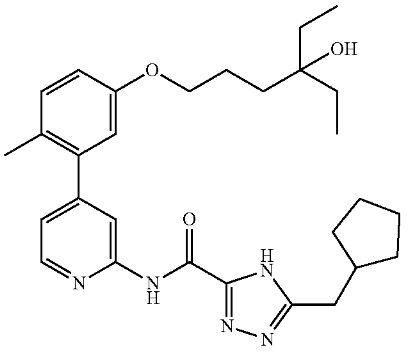
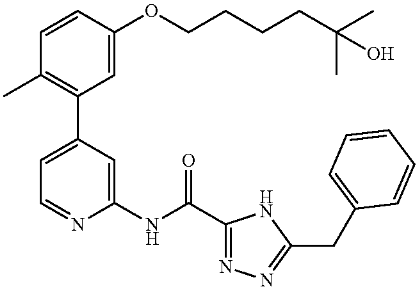
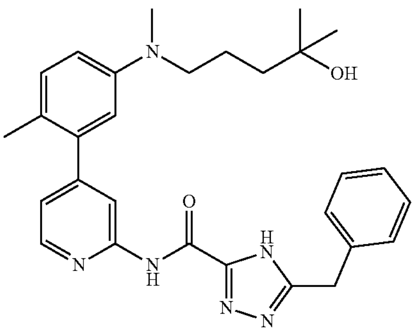
-continued
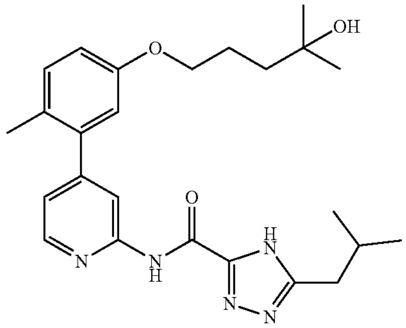
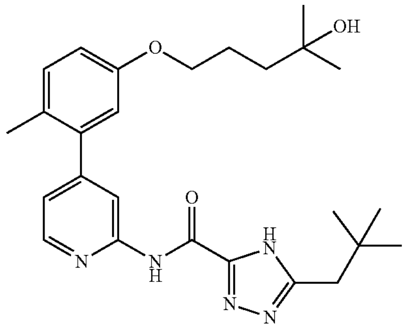
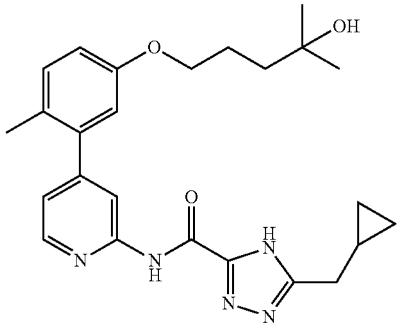
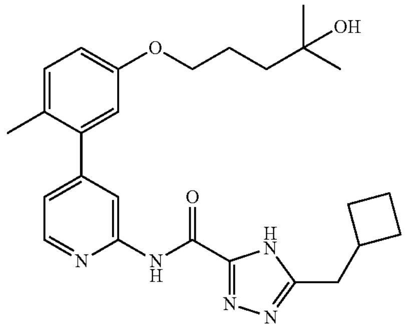
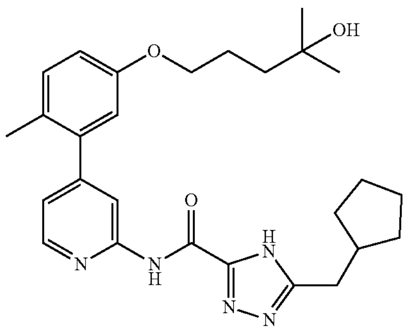

-continued
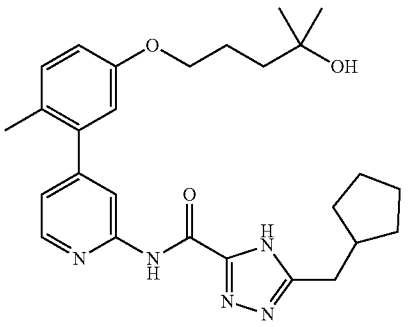
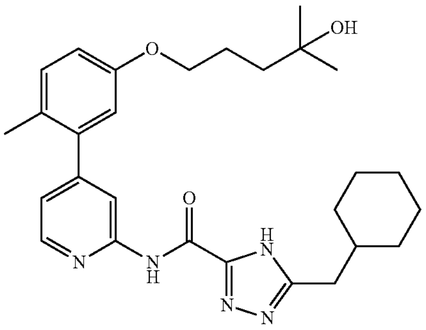
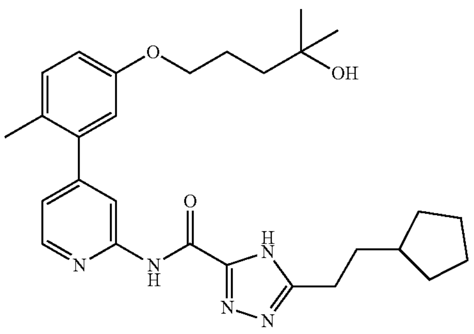
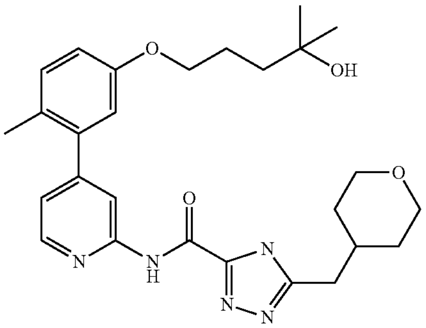
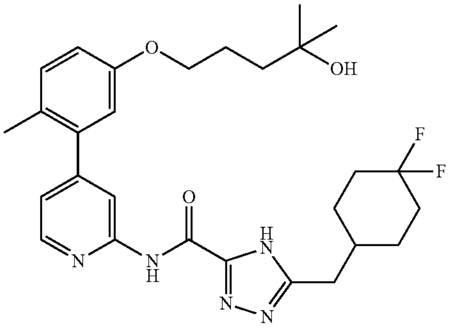
-continued
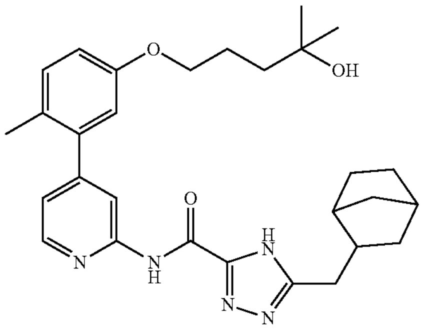
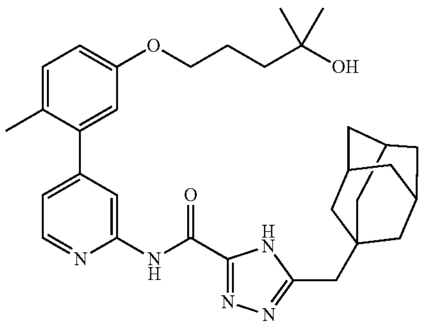
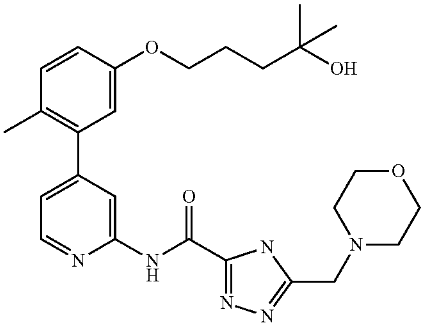
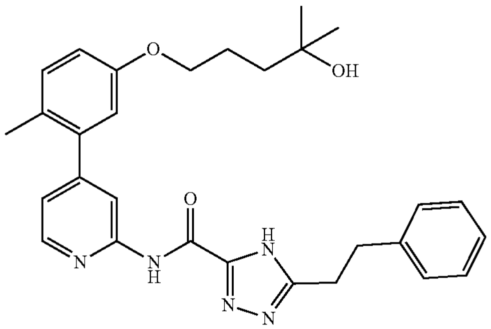
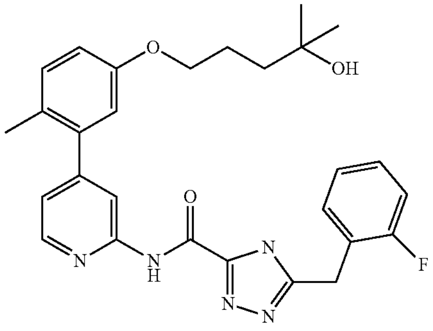

-continued
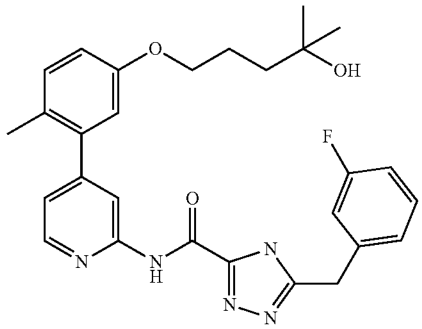
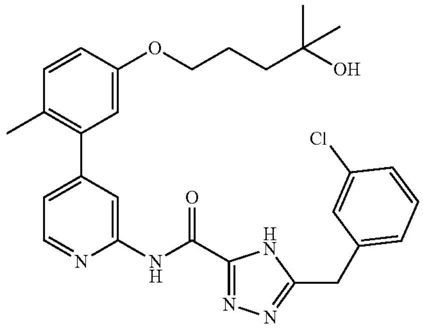
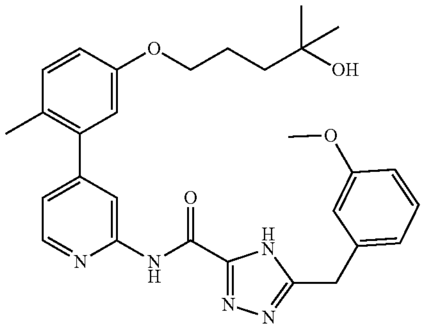
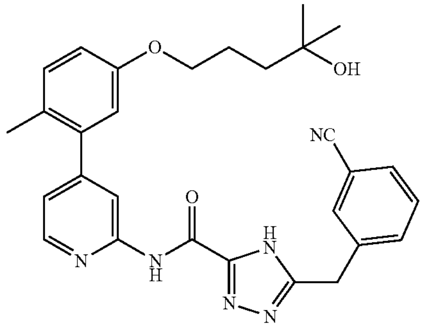
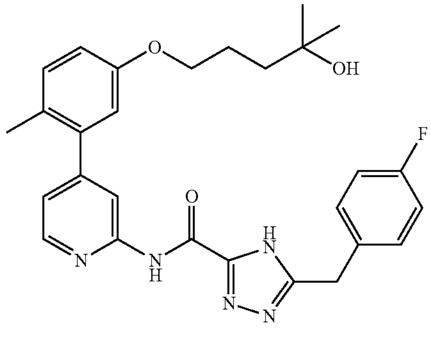
-continued
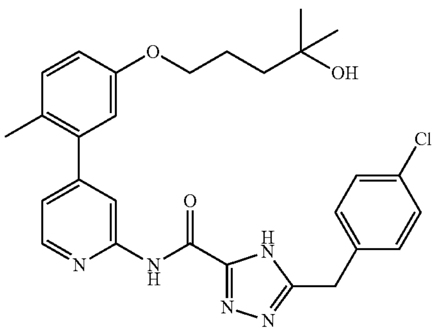
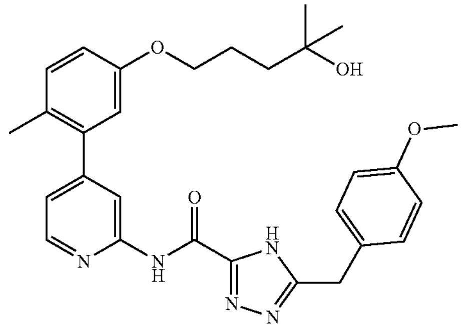
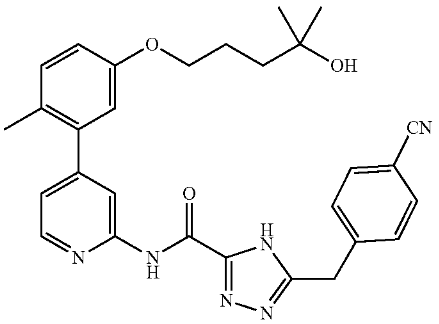
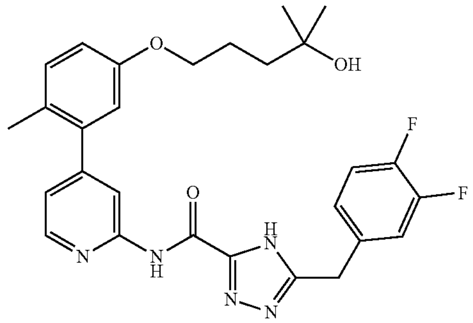
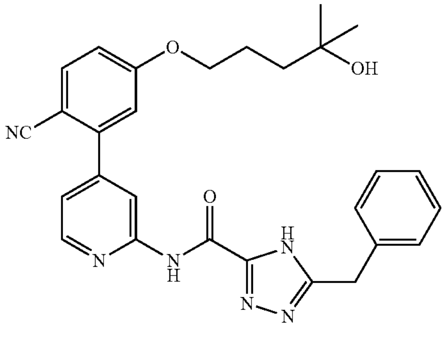

-continued
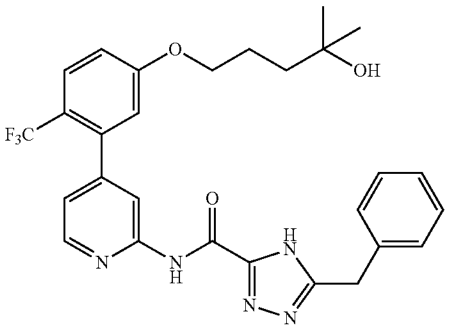
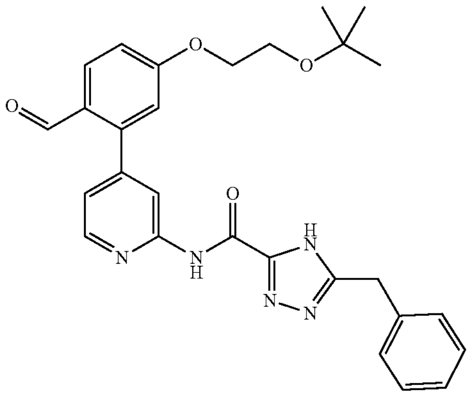
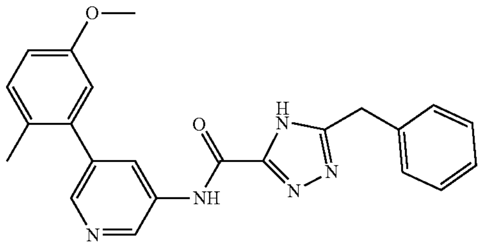
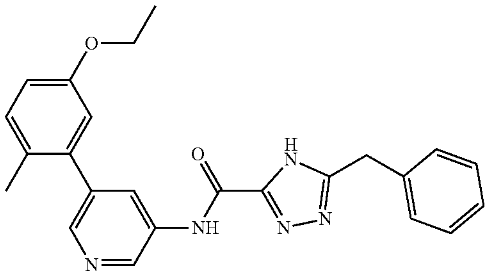
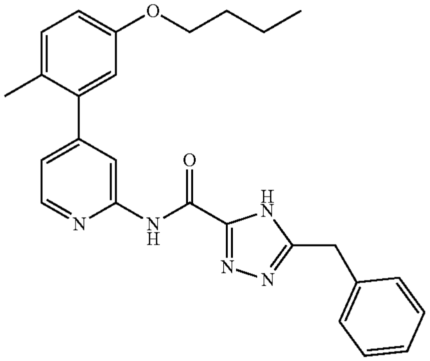
-continued
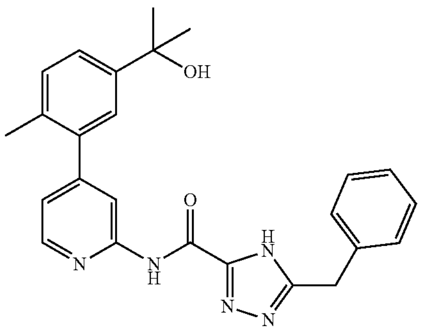
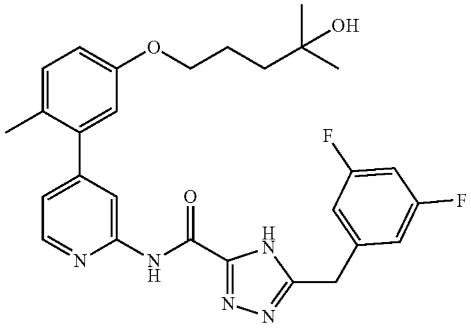
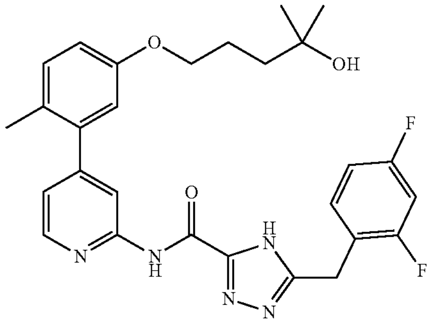
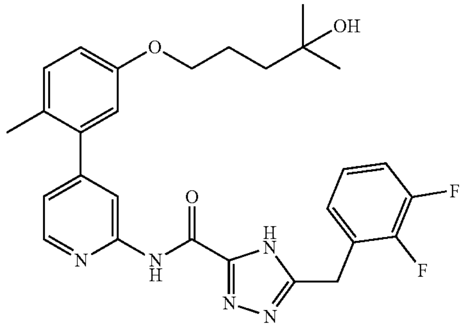
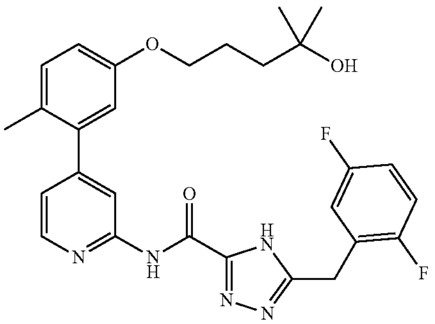

-continued
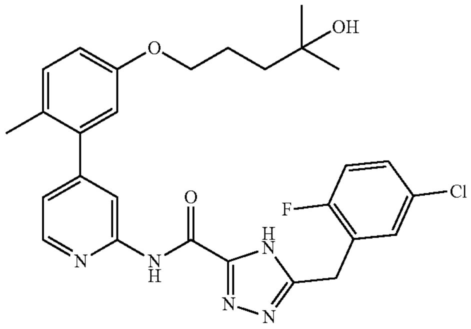
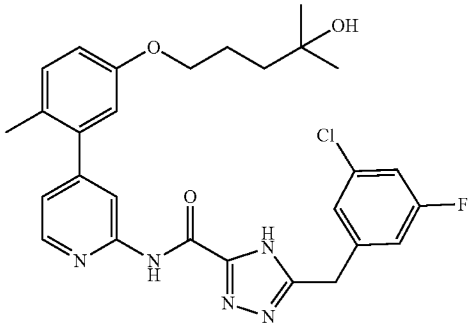
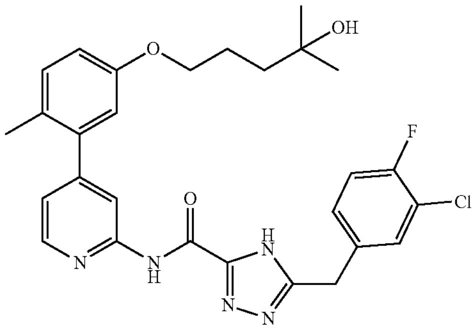
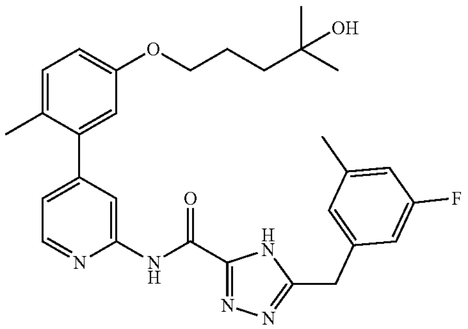
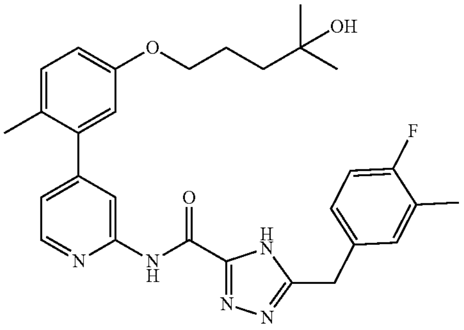
-continued
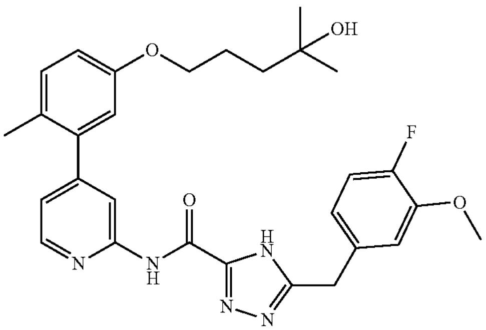
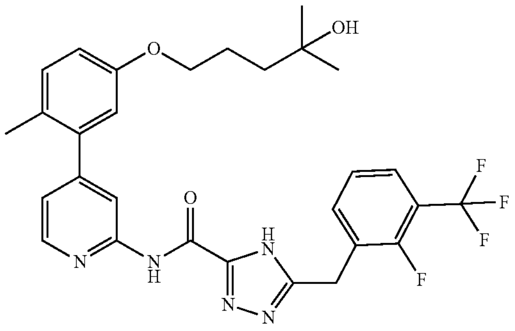
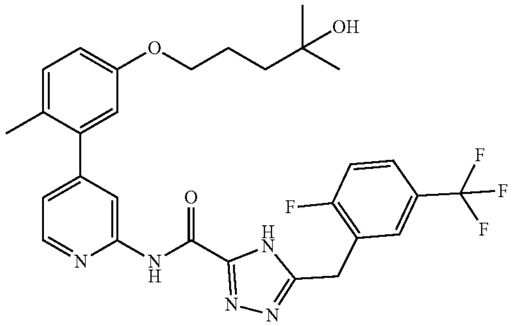
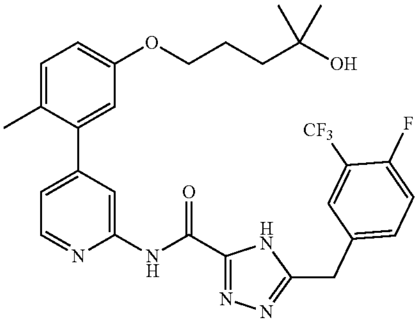
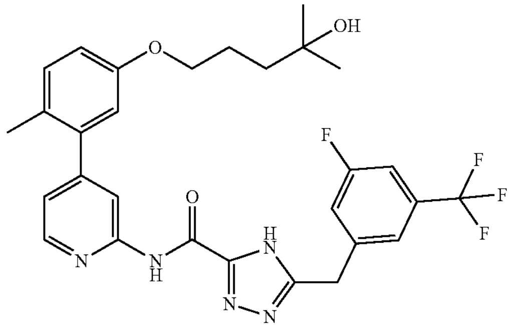

-continued
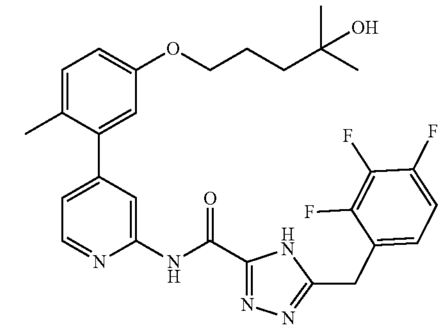
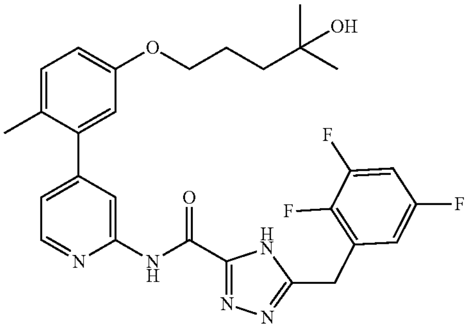
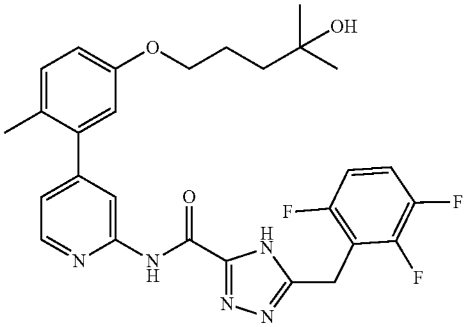
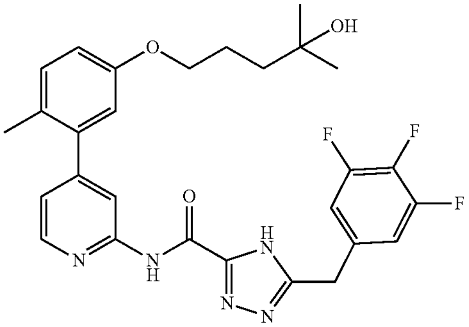
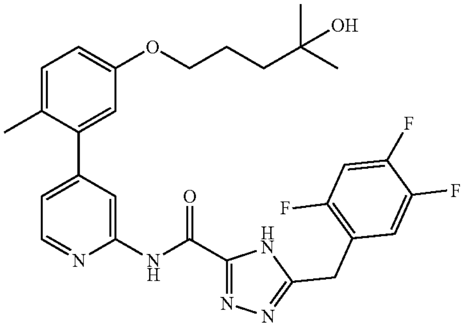
-continued
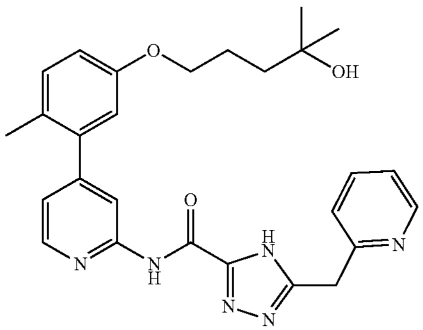
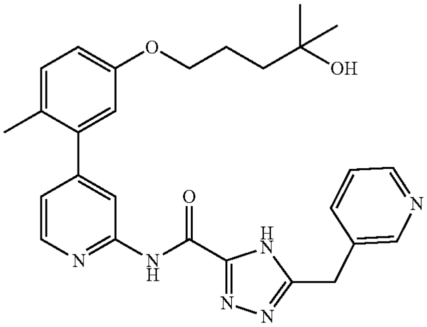
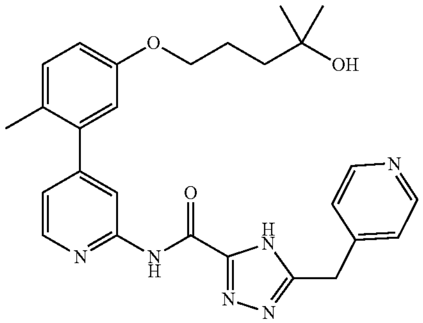
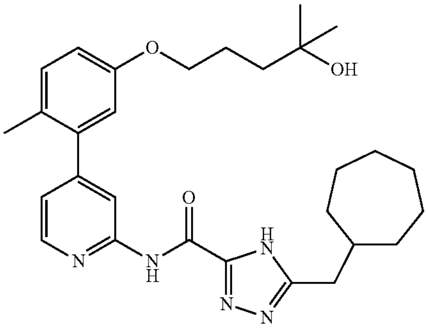
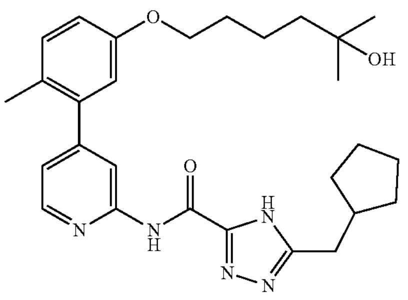

-continued
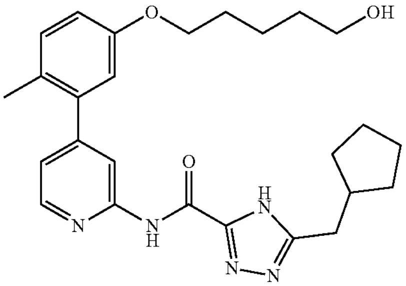
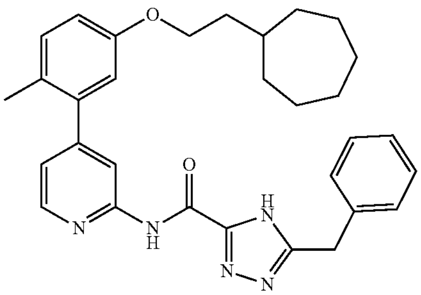
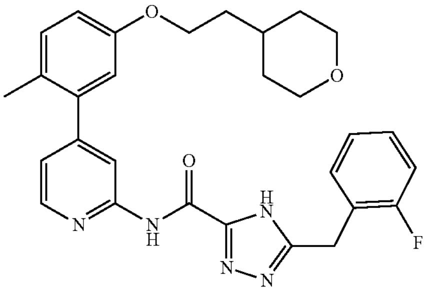
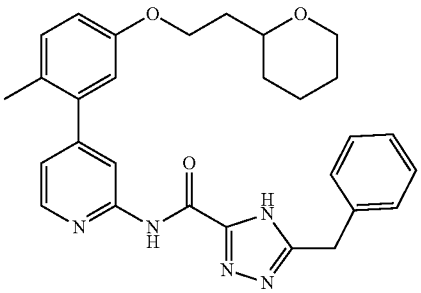
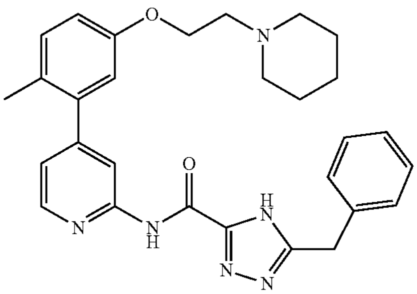
-continued
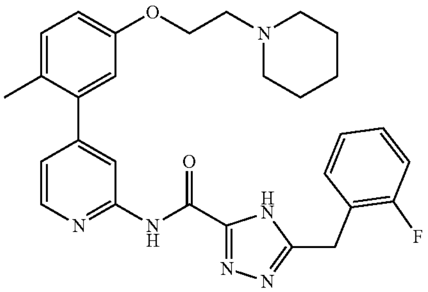
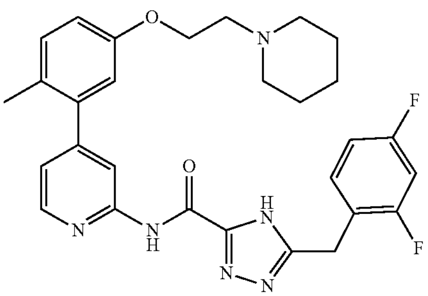
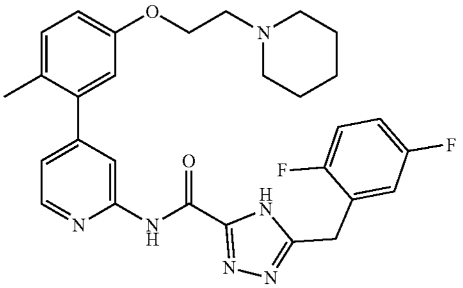
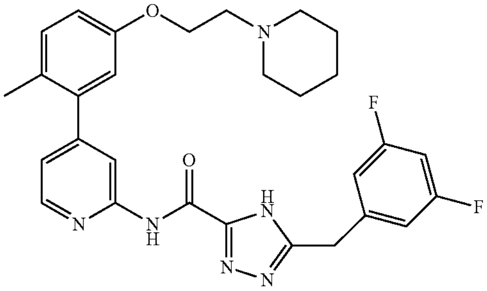
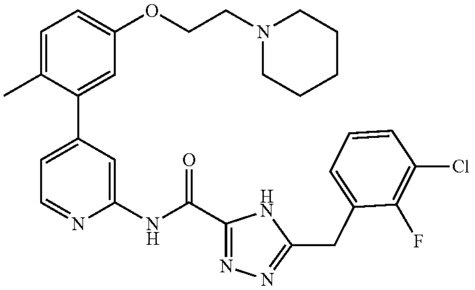

-continued
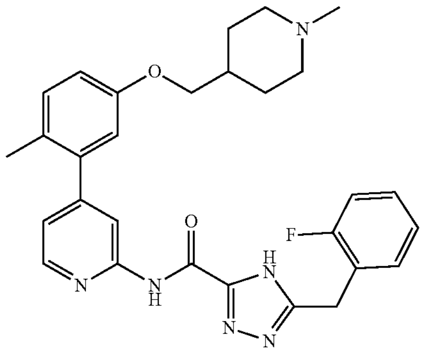
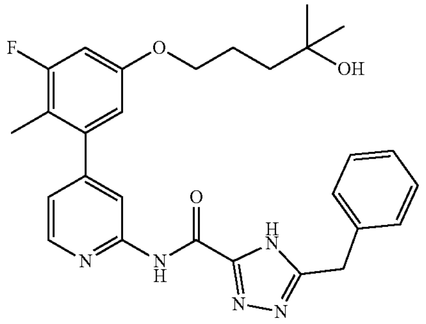
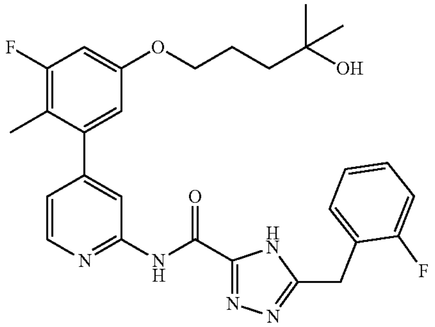
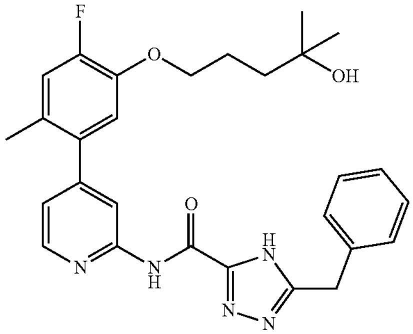
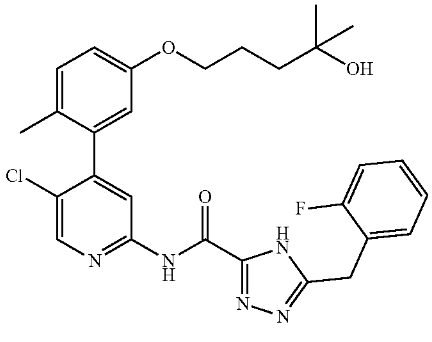
-continued
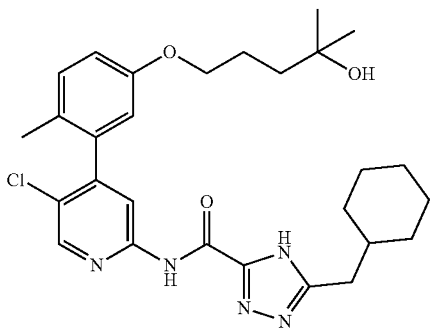
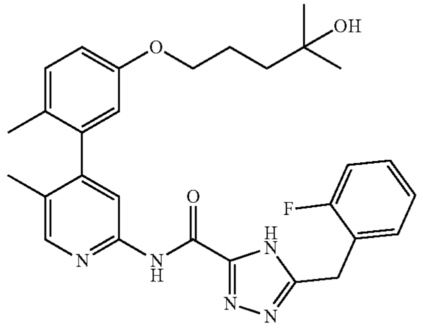
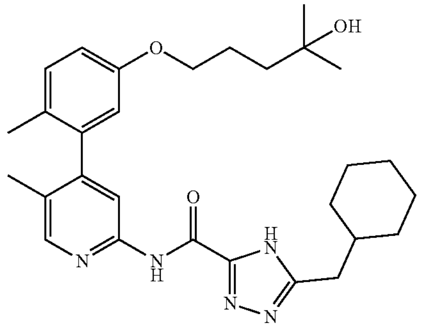
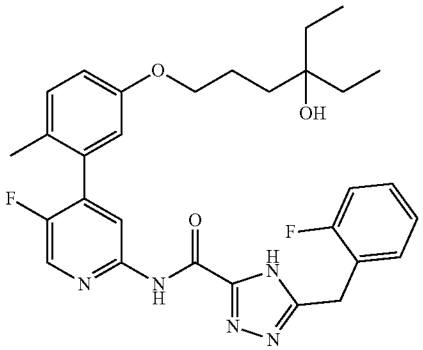
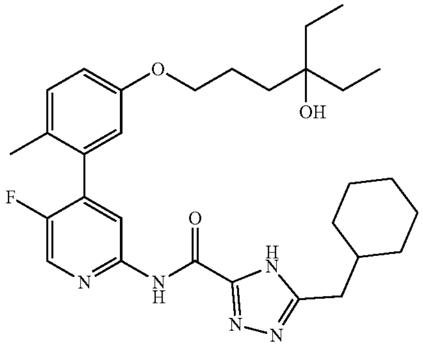

-continued
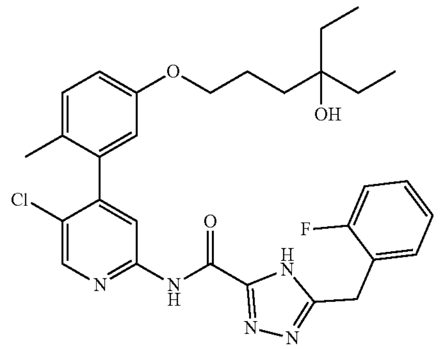
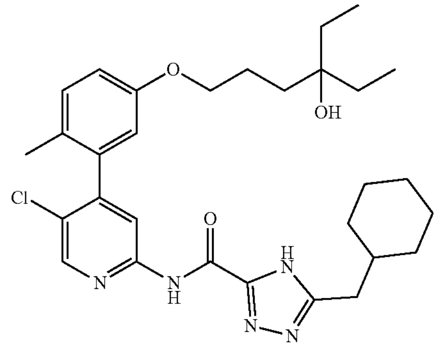
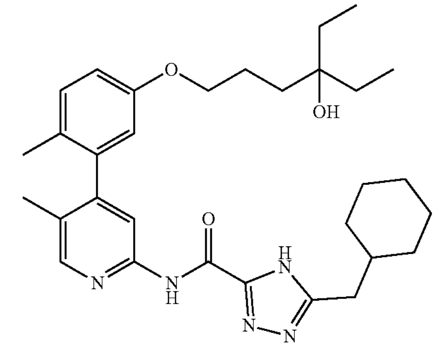
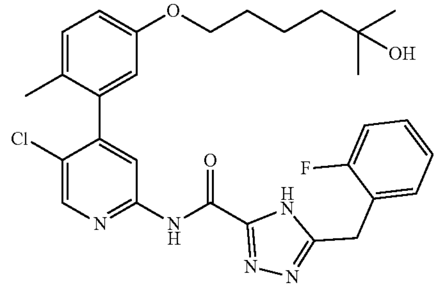
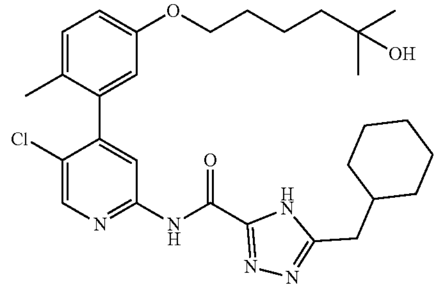
-continued
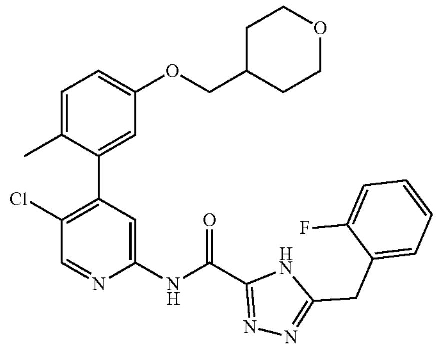
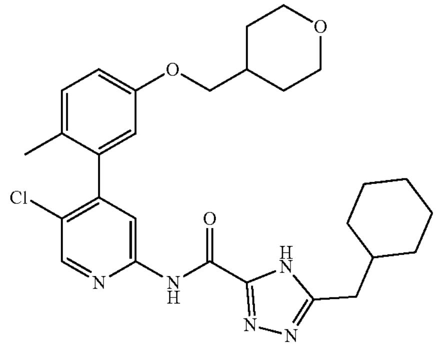
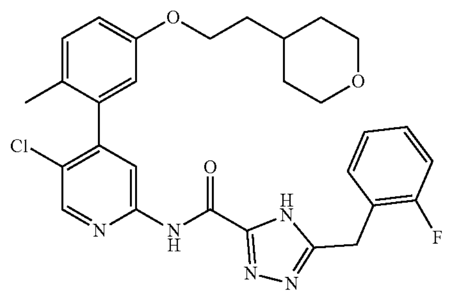
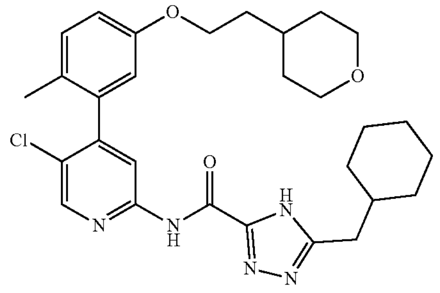
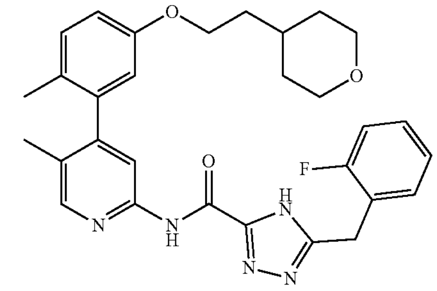

-continued
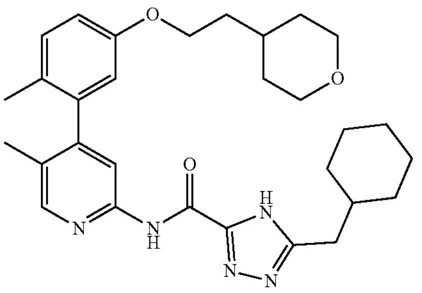
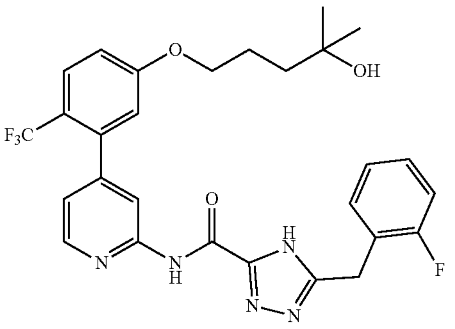
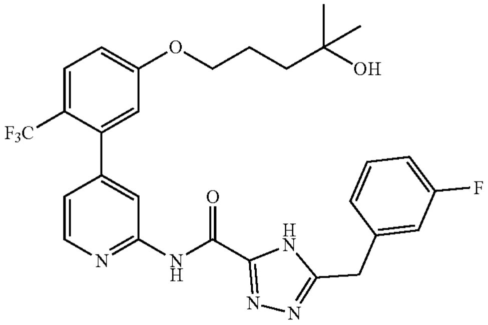
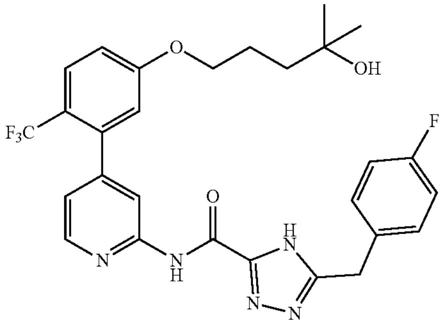
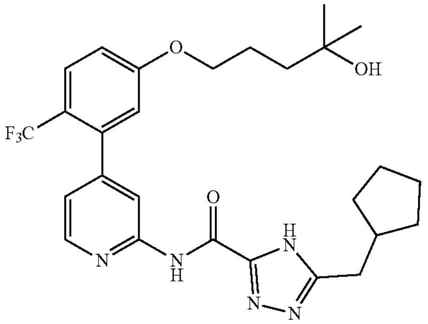
-continued
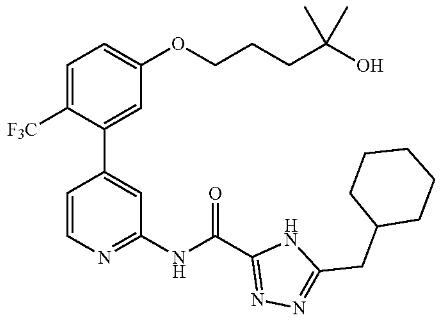
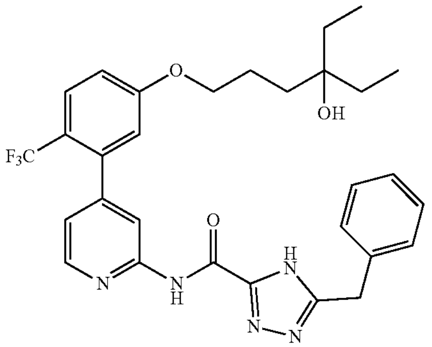
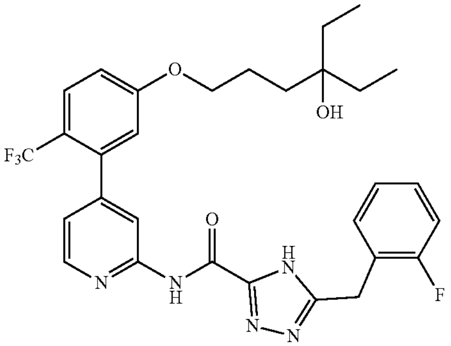
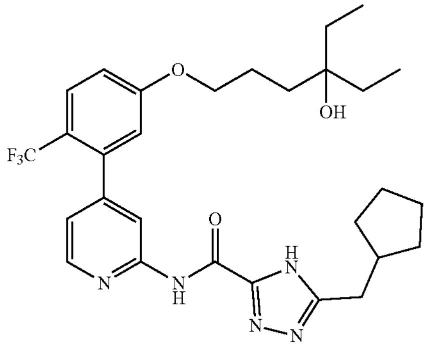
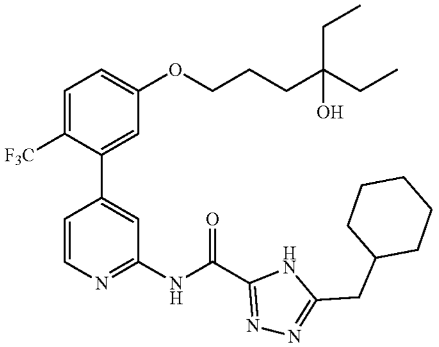

-continued
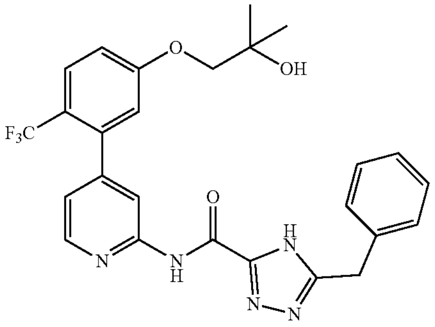
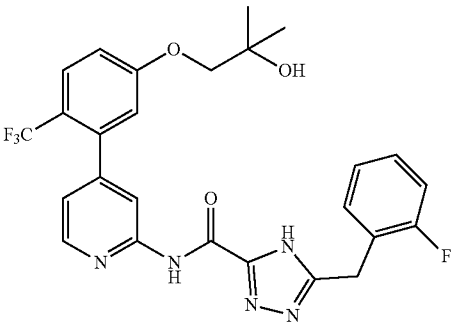
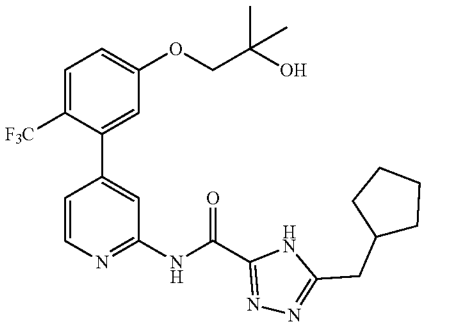
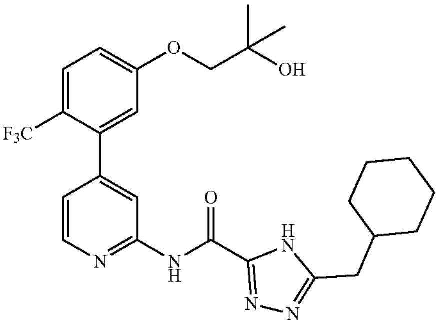
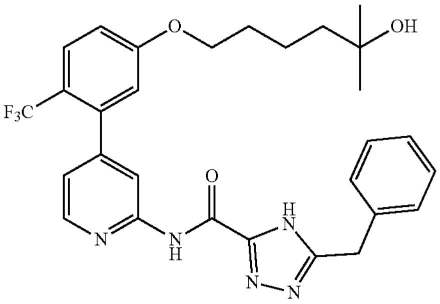 [SMILES: CC(C)(O)CCCCOc1ccc(C(F)(F)F)c(-c2ccnc(NC(=O)c3nnc(Cc4ccccc4)[nH]3)c2)c1]
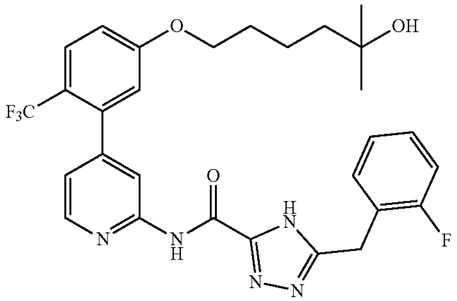
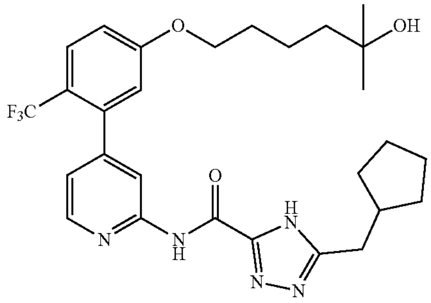
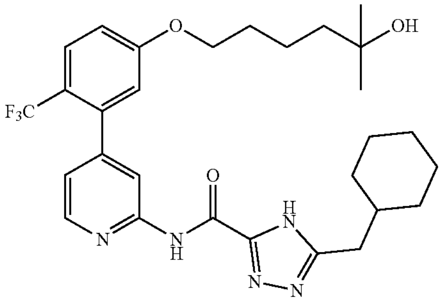
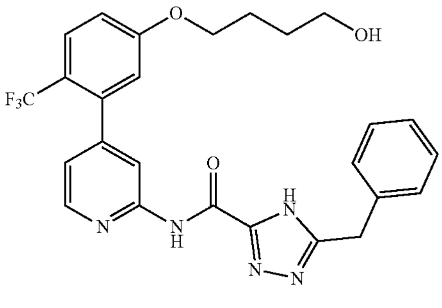
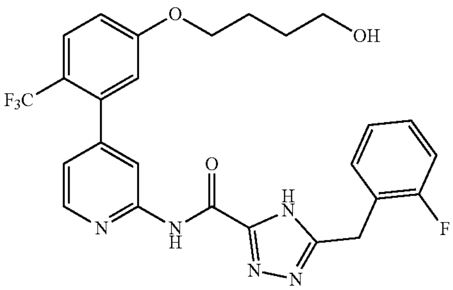

-continued
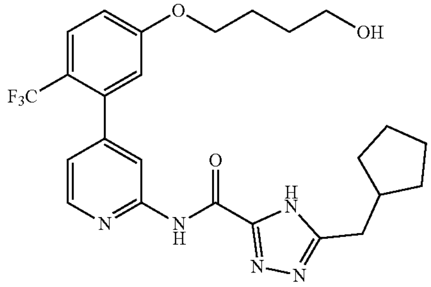
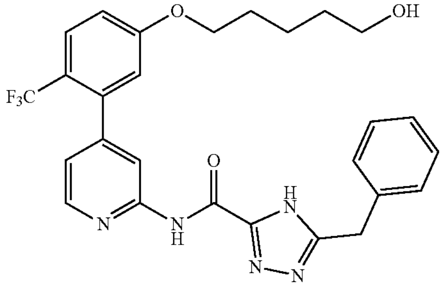
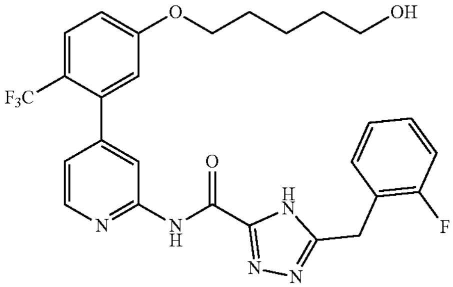
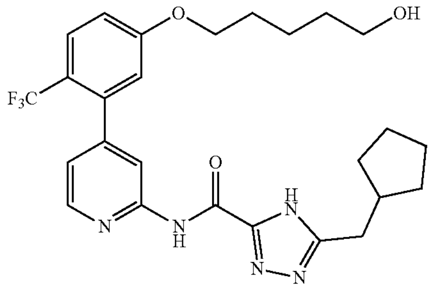
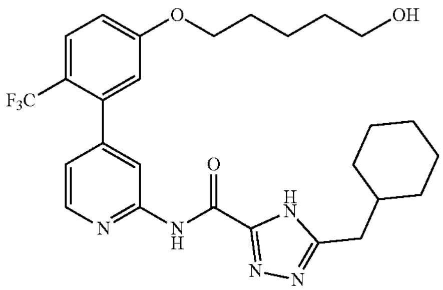
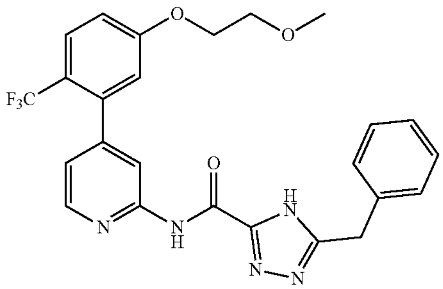
-continued
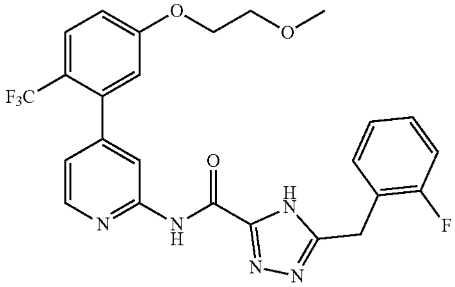
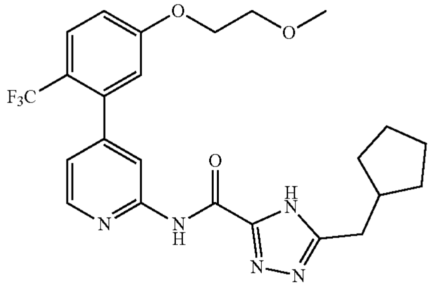
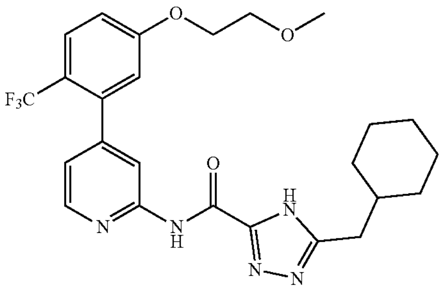
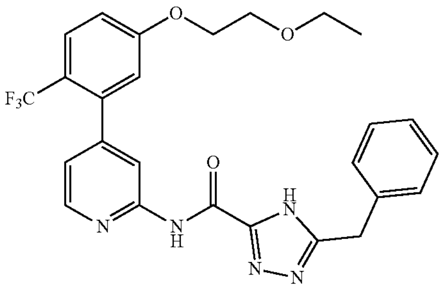
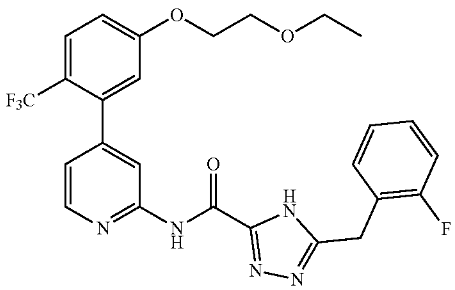
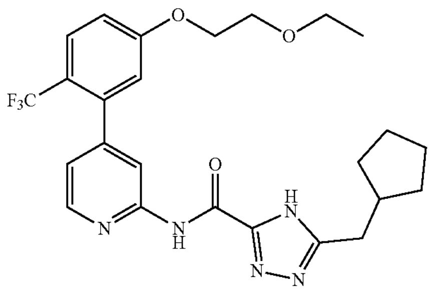

-continued
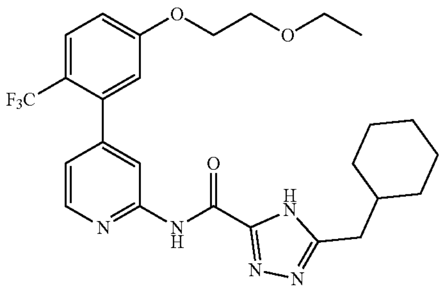
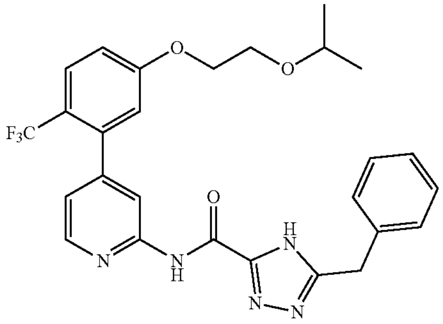
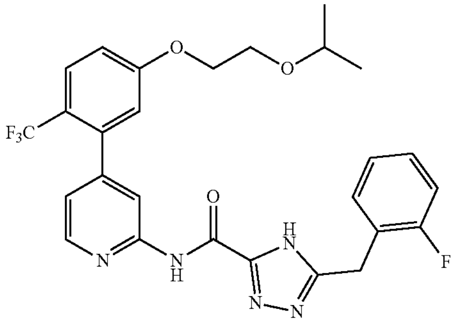
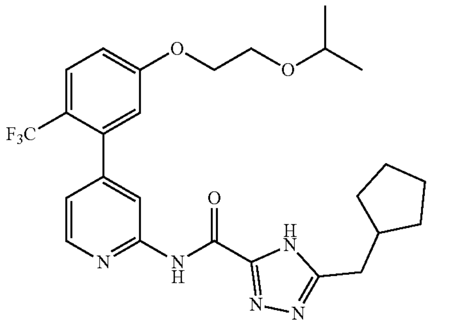
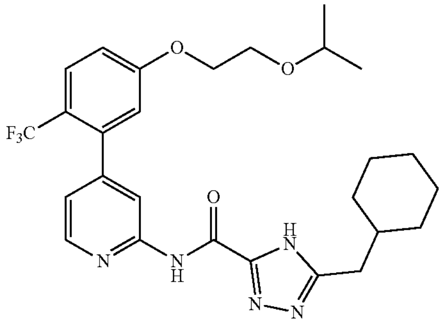
-continued
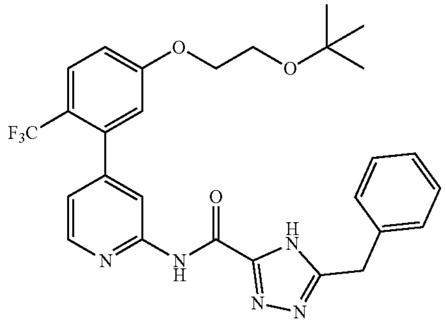
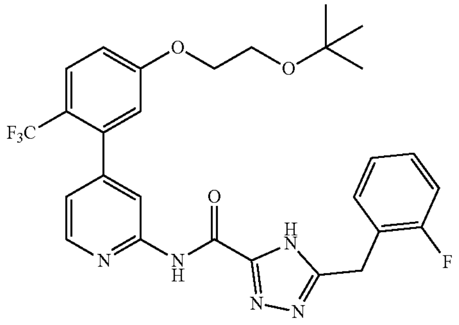
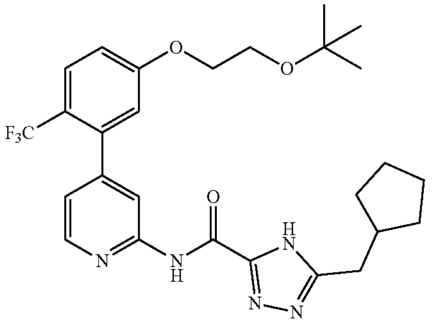
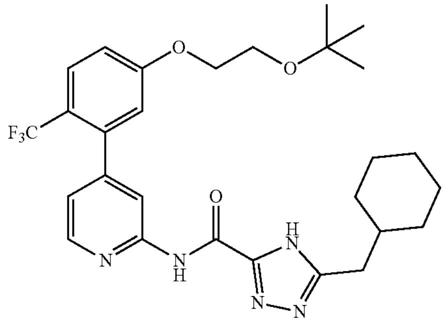
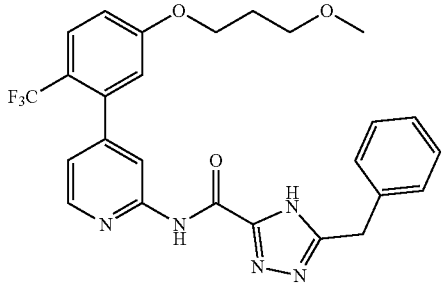

-continued
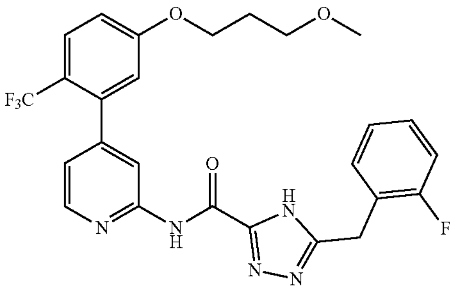
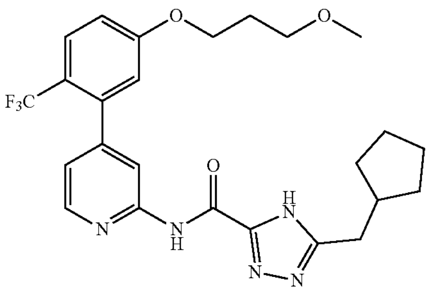
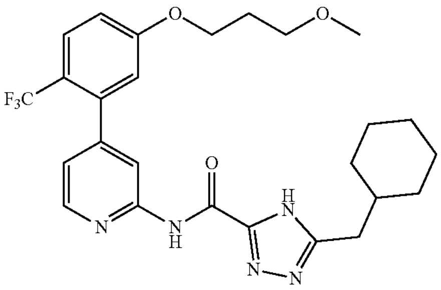
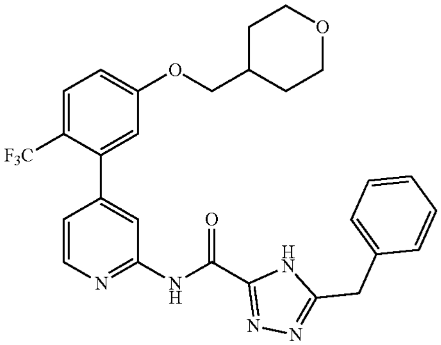
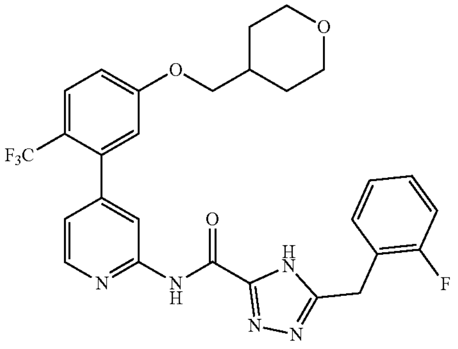
-continued
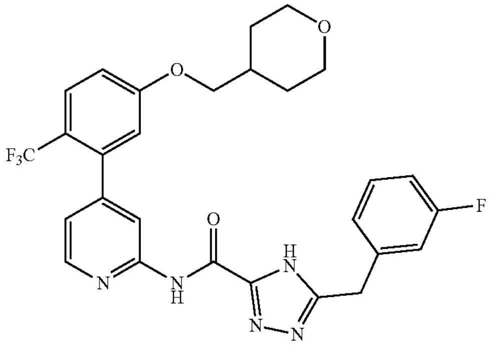
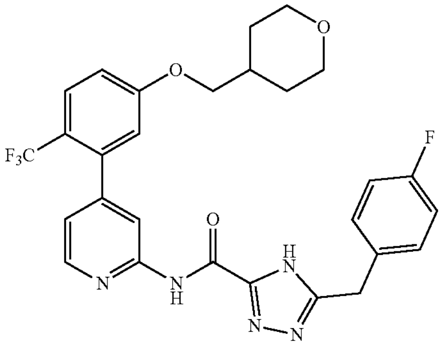
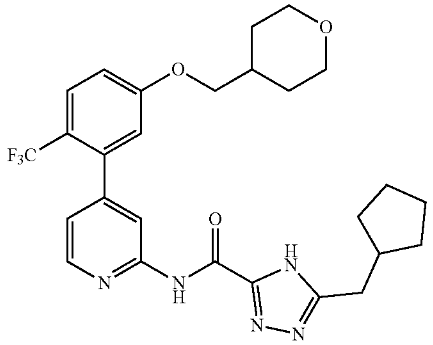
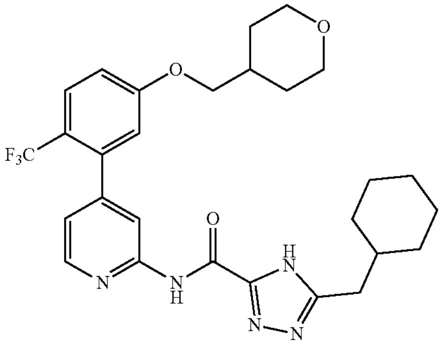
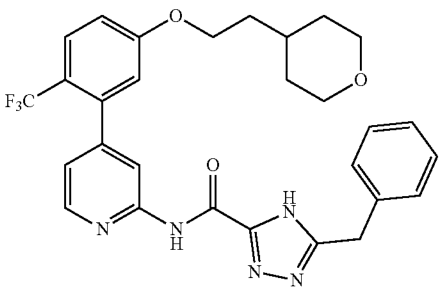

-continued
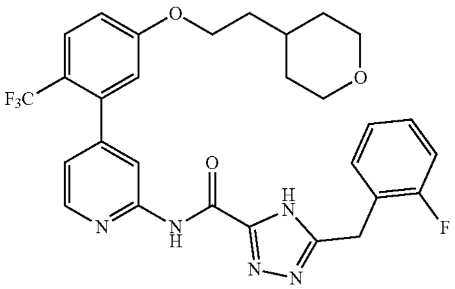
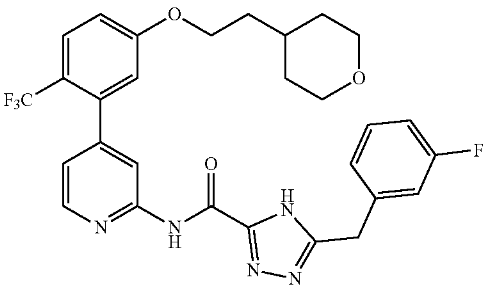
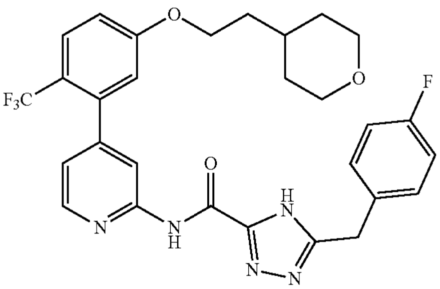
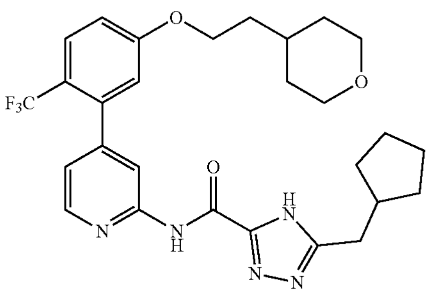
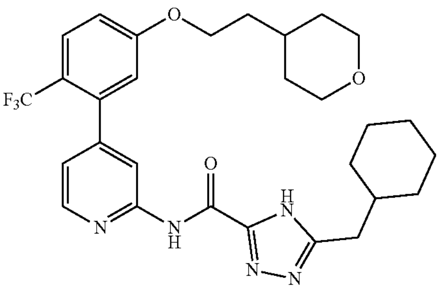
-continued
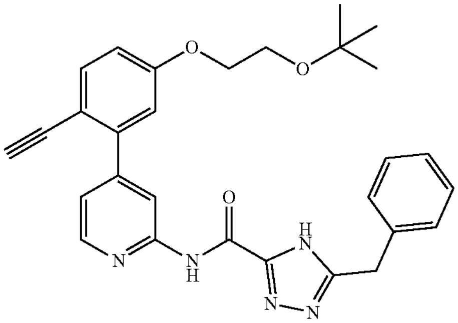
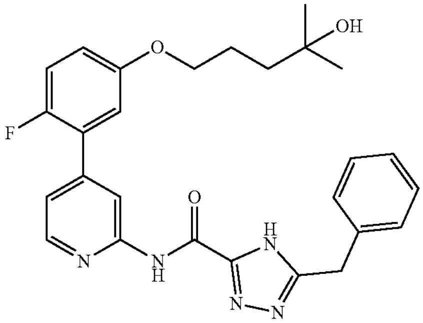
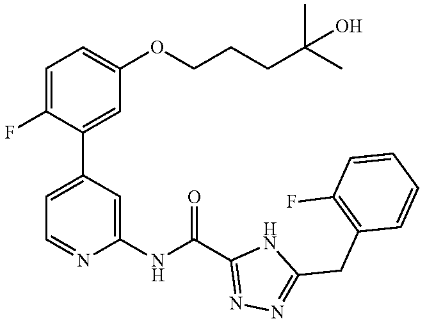
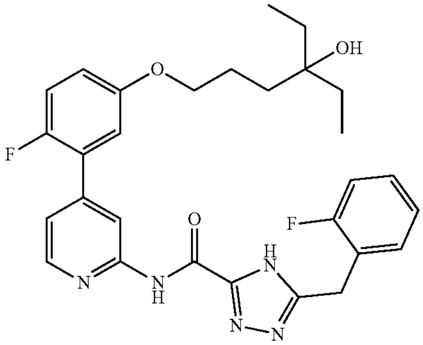
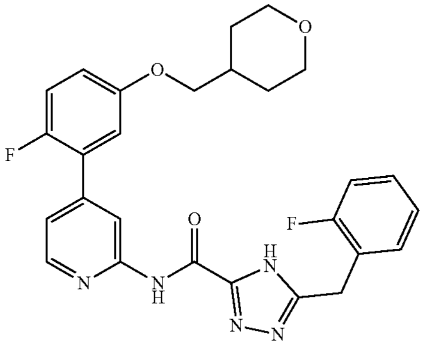

-continued
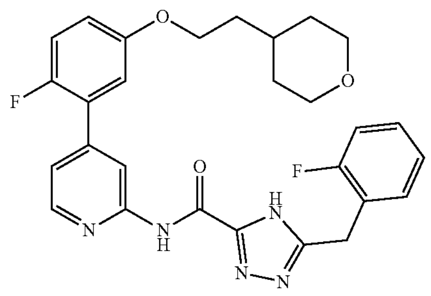
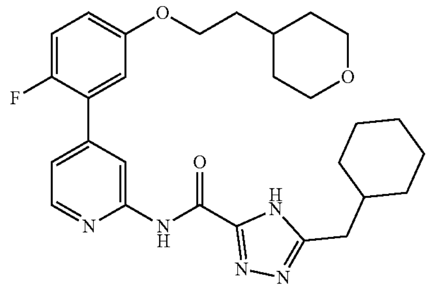
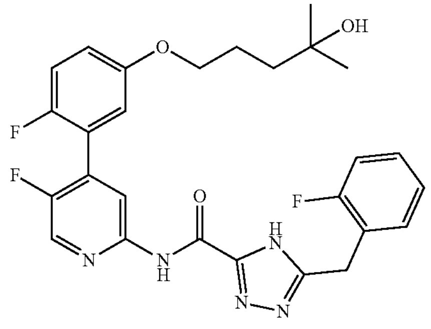
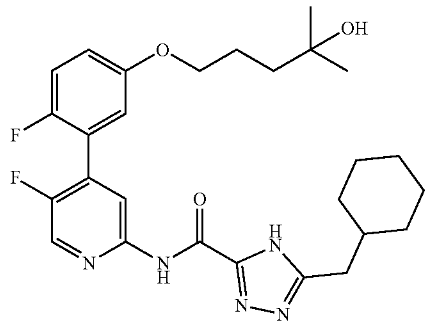
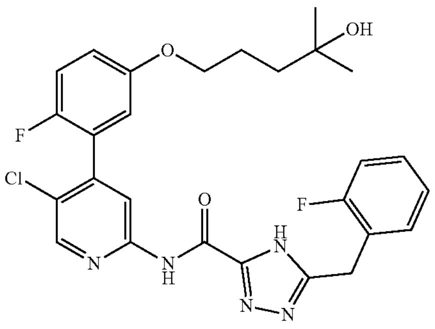
-continued
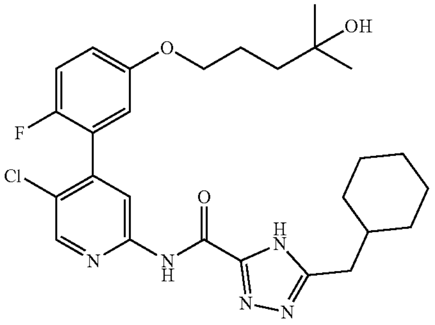
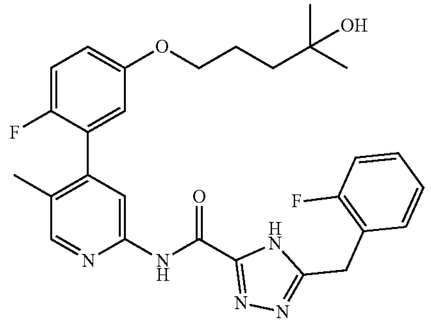
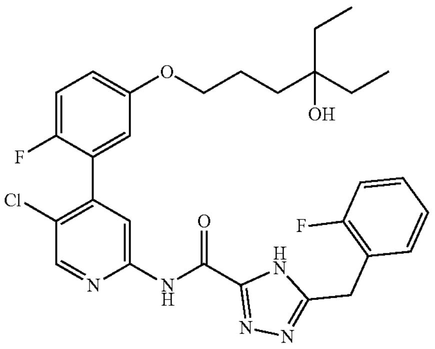
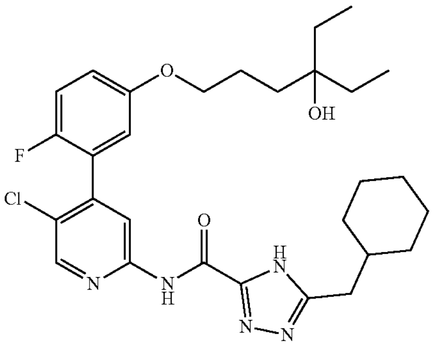
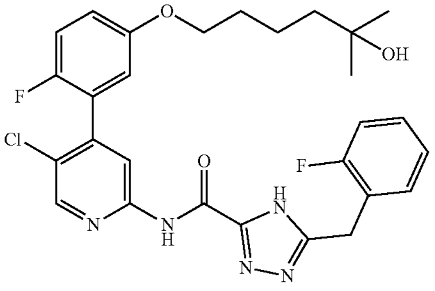

-continued
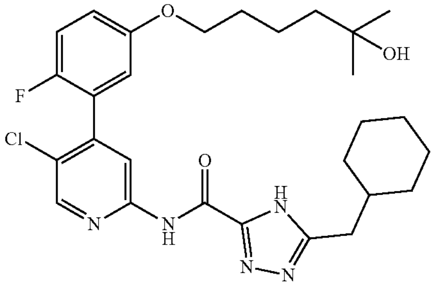
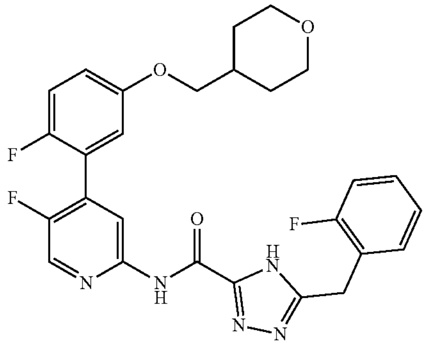
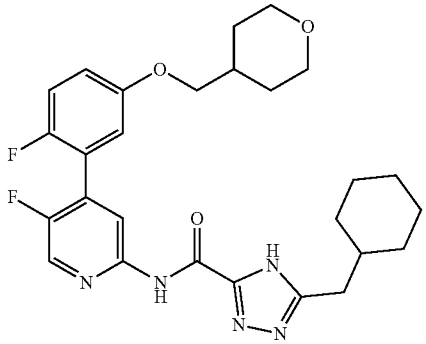
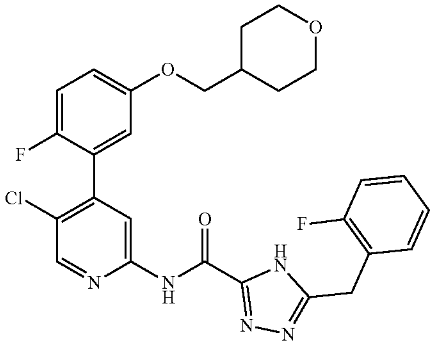
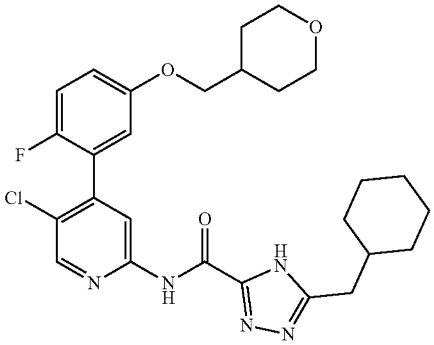
-continued
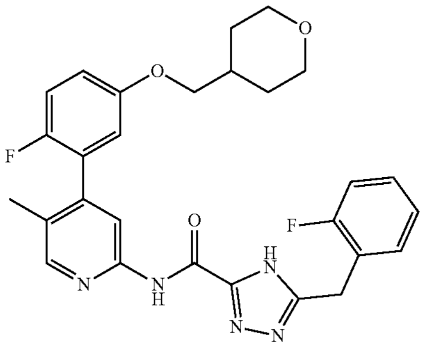
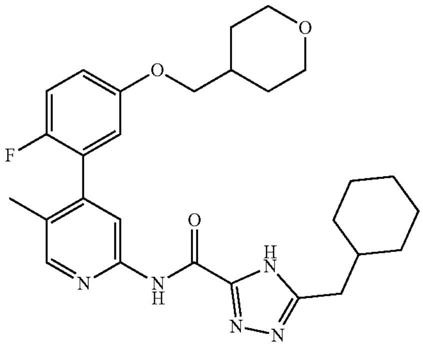
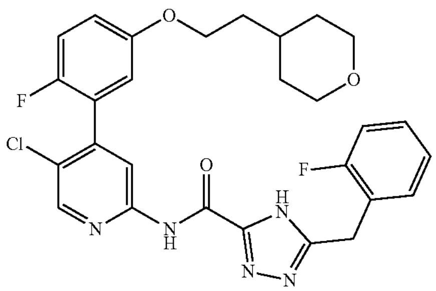
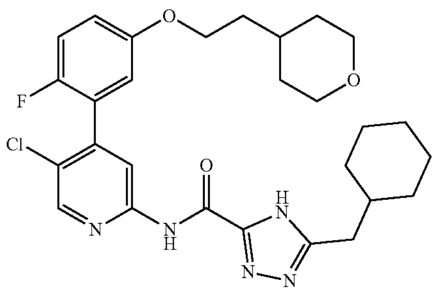
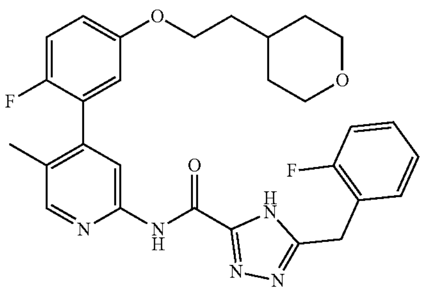

-continued
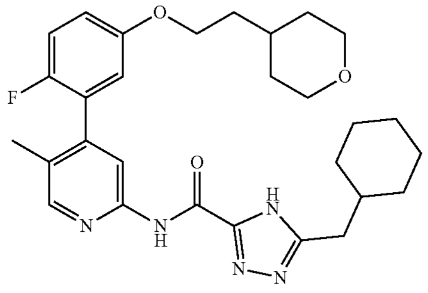
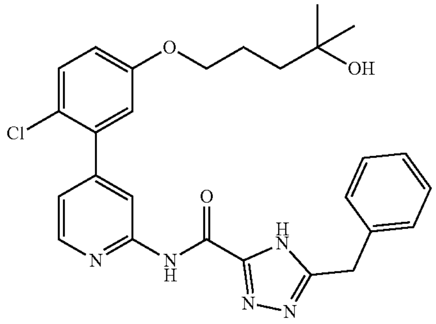
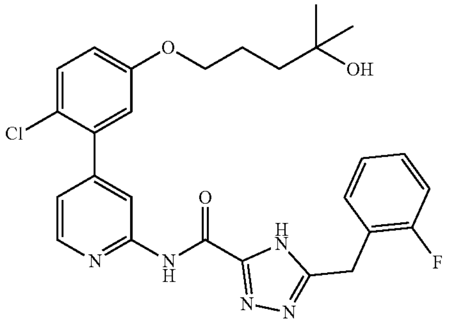
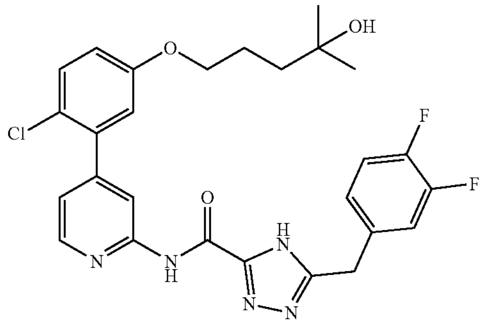
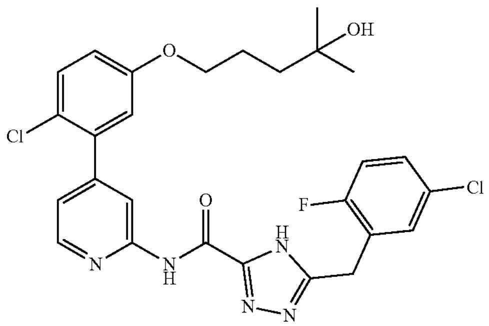
-continued
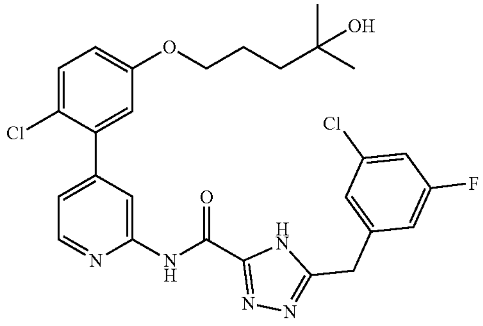
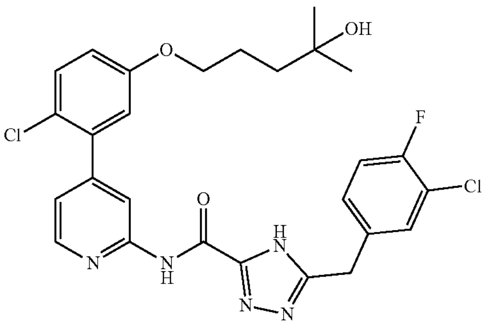
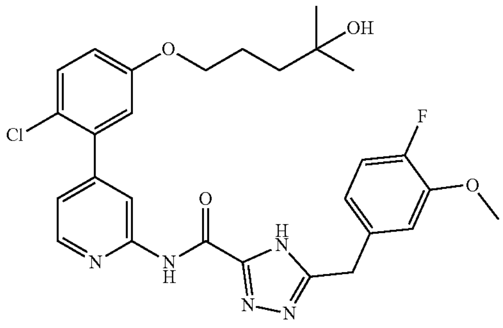
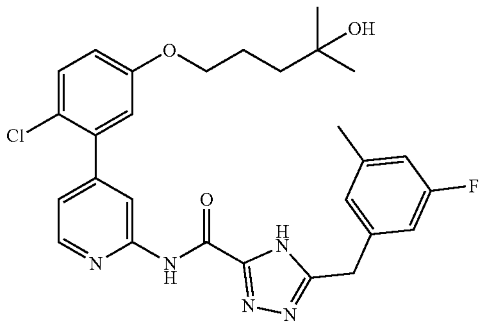
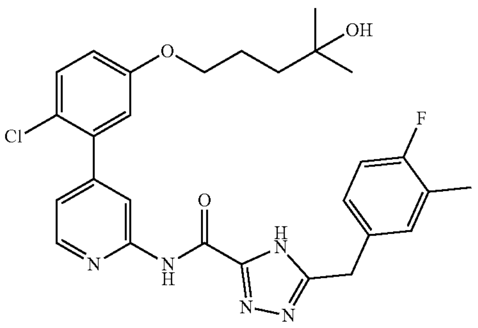

-continued
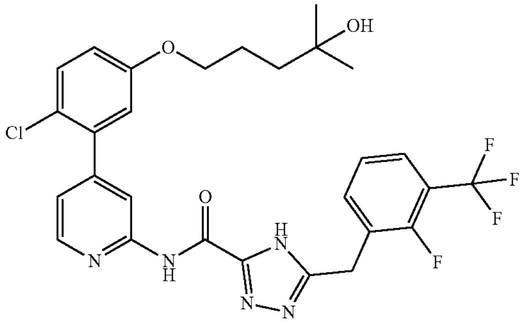
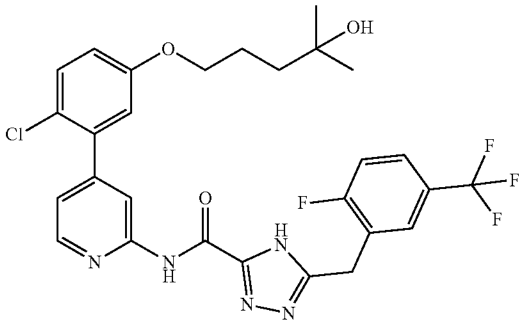
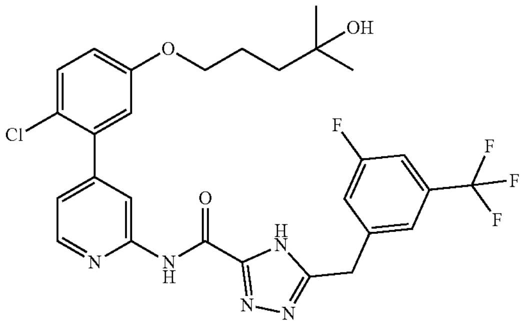
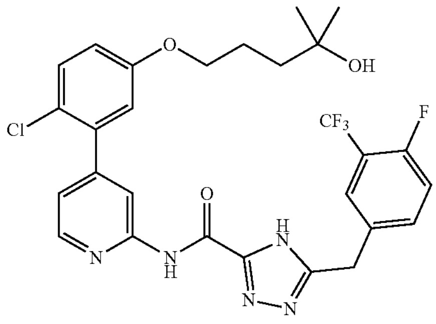
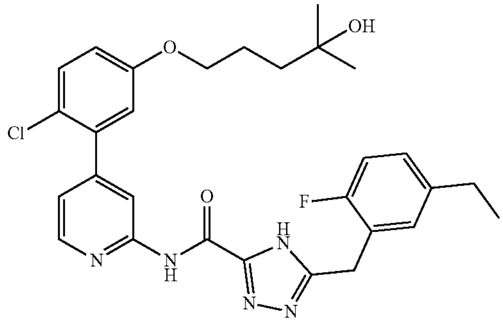
-continued
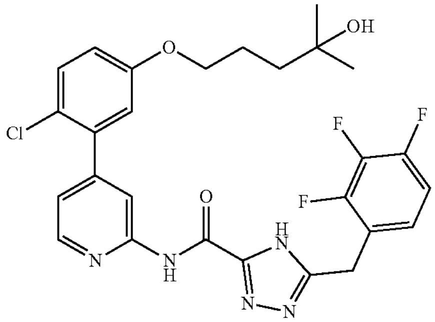
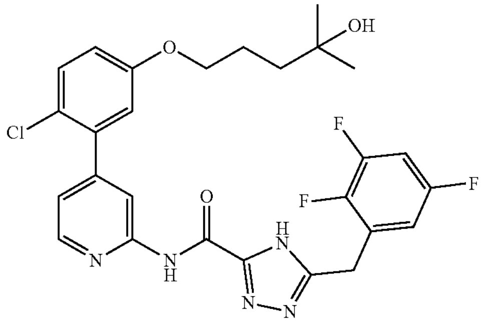
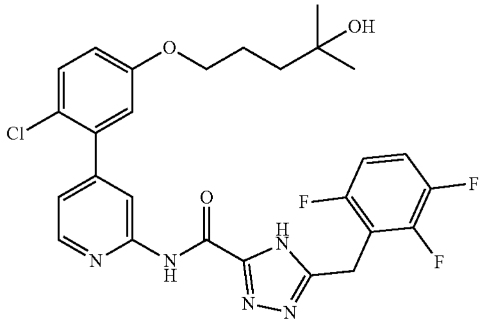
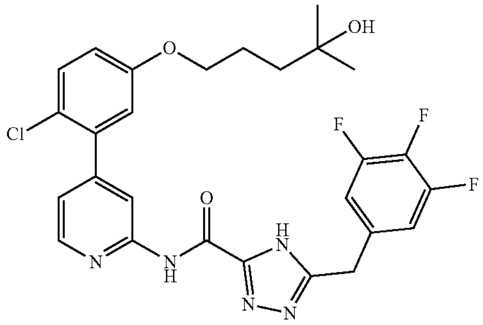
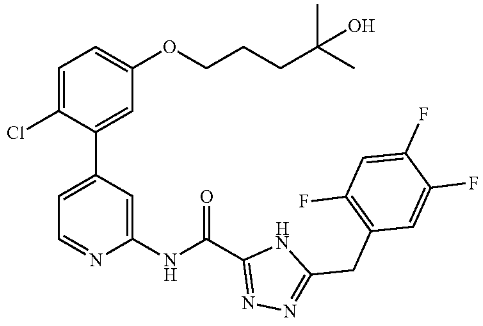

-continued
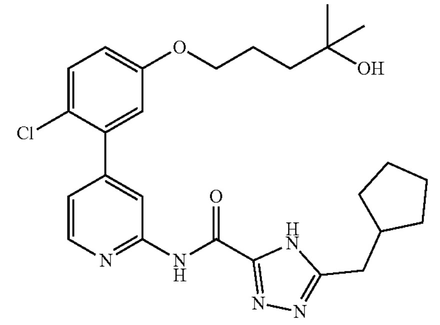
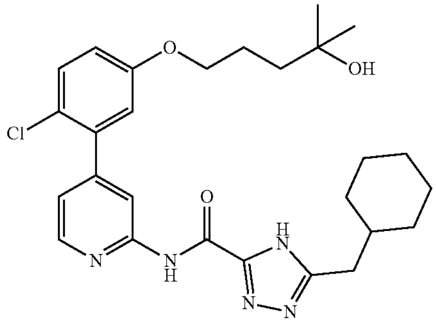
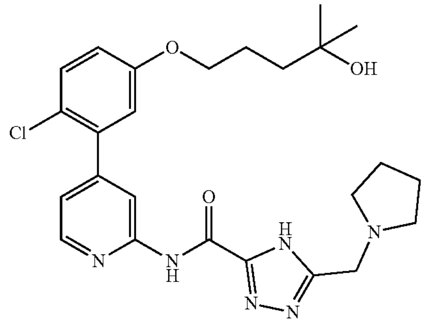
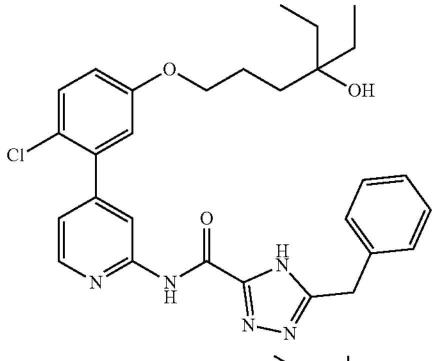
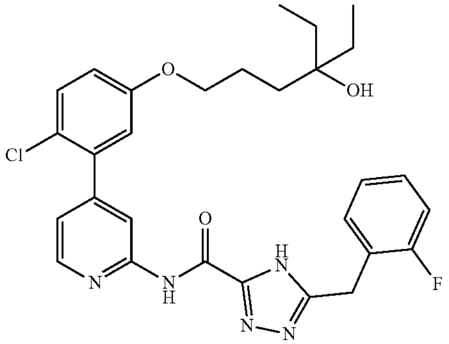
-continued
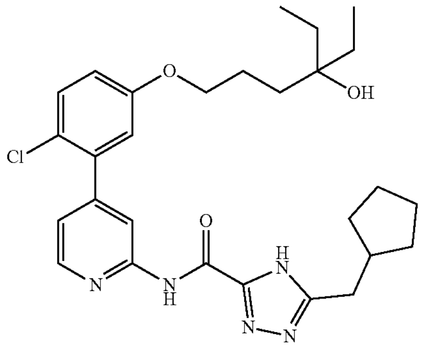
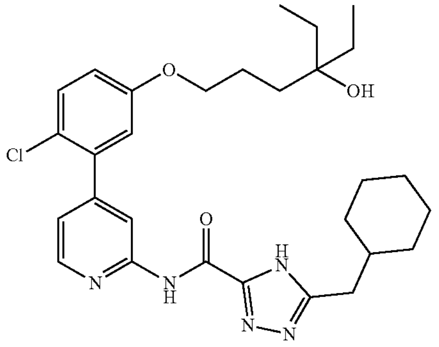
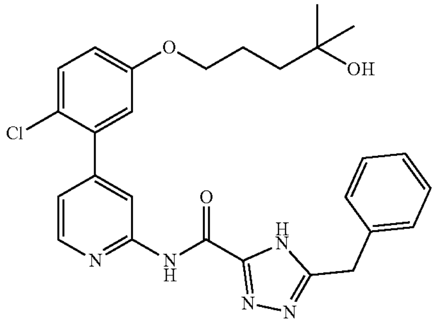
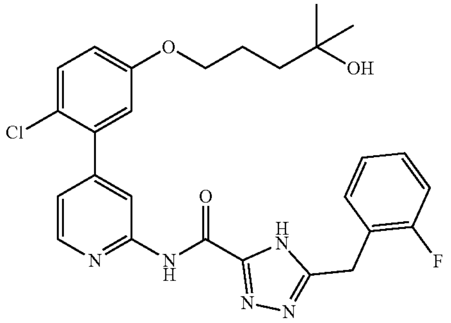
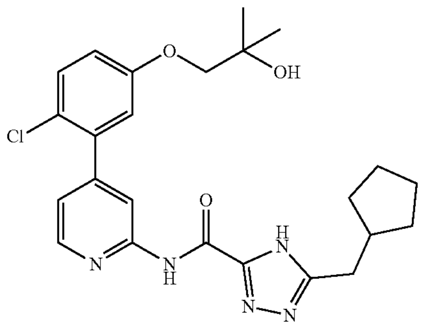

-continued
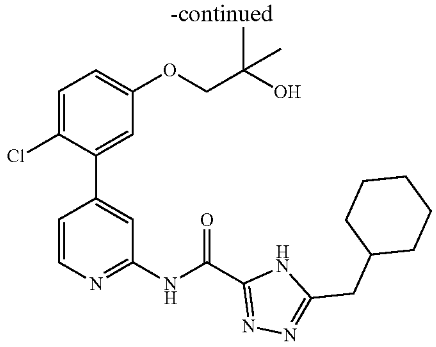
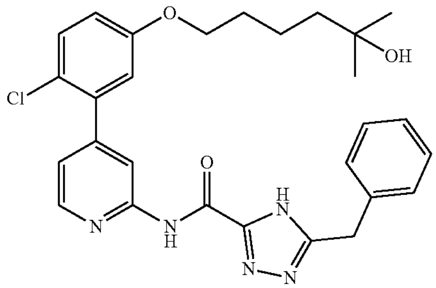
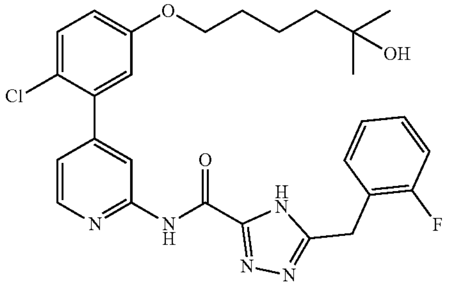
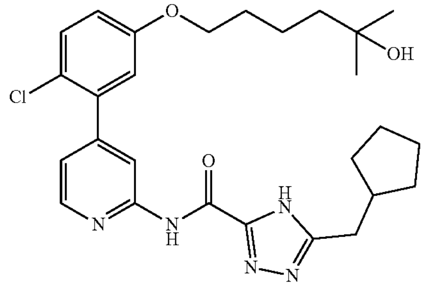
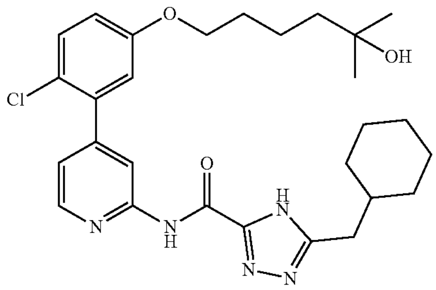
-continued
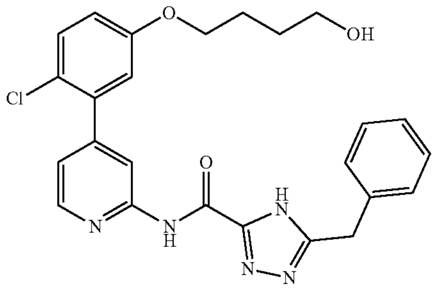
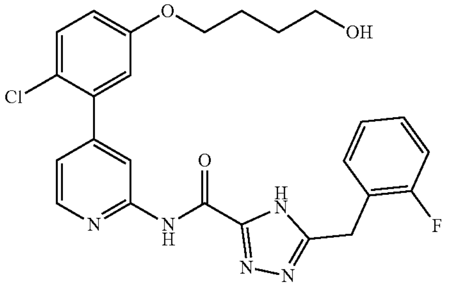
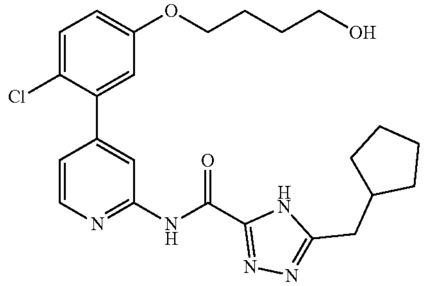
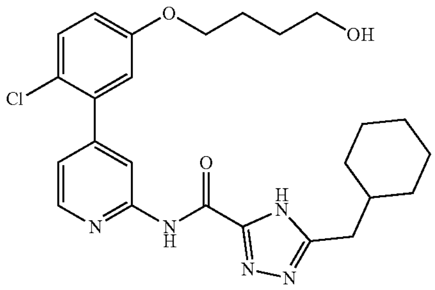
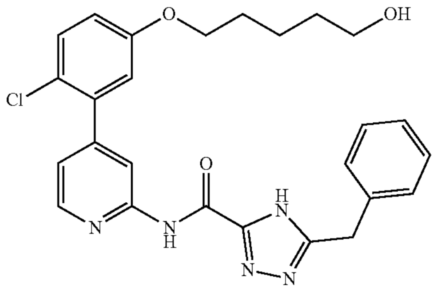
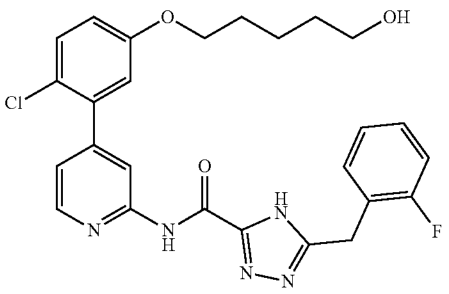

-continued
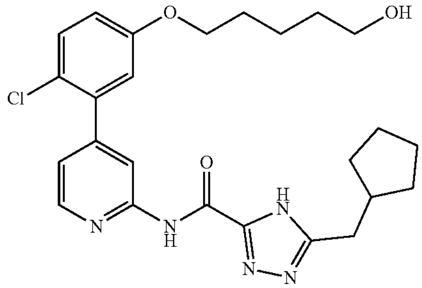
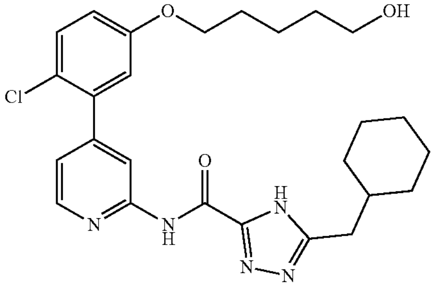
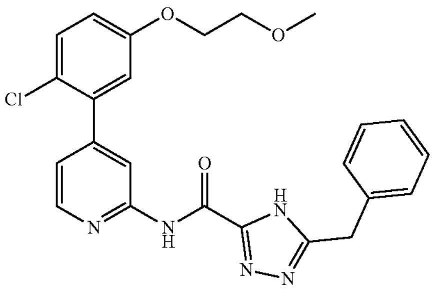
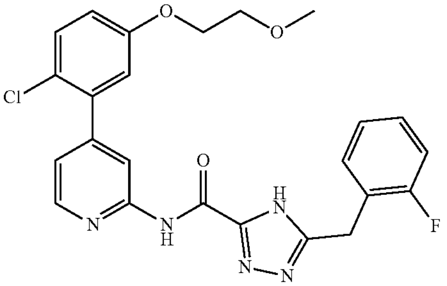
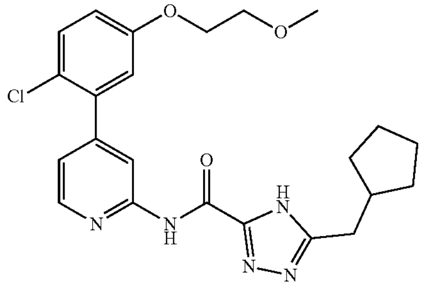
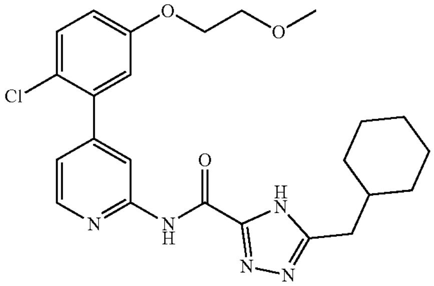
-continued
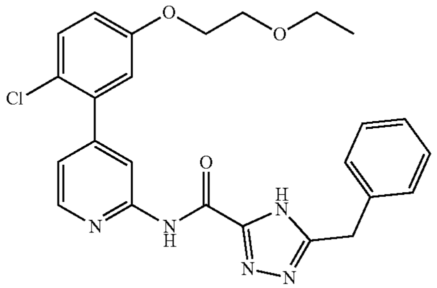
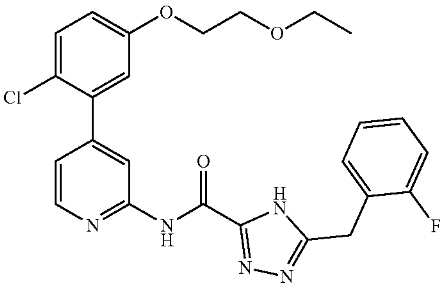
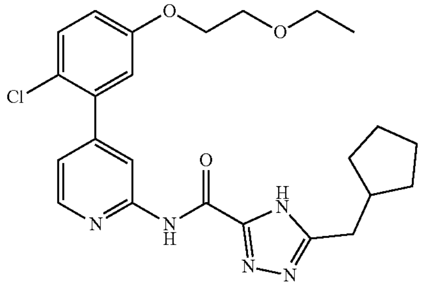
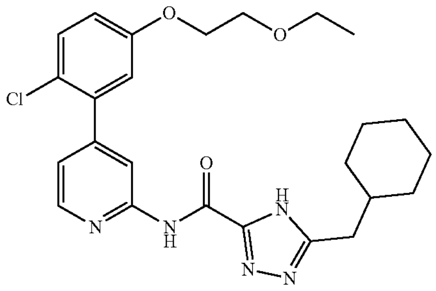
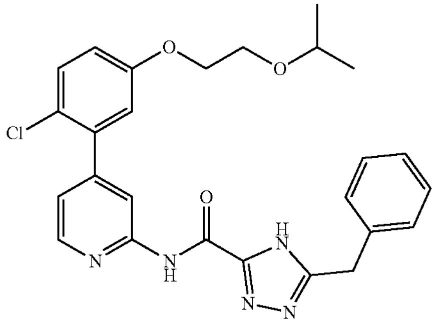

-continued
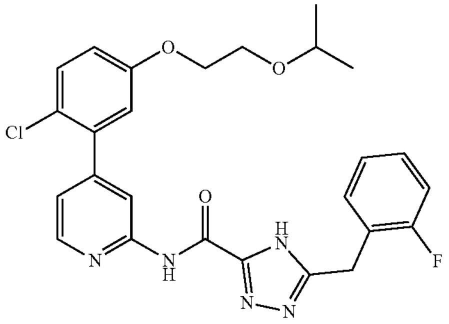
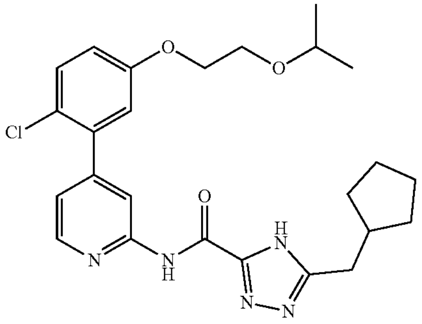
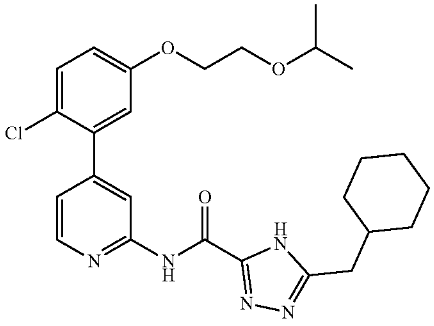
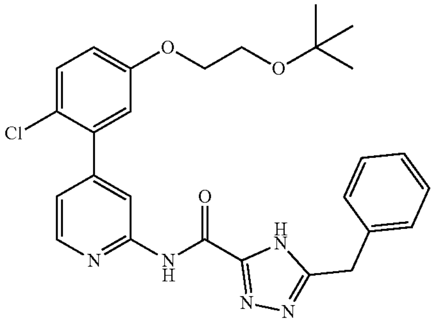
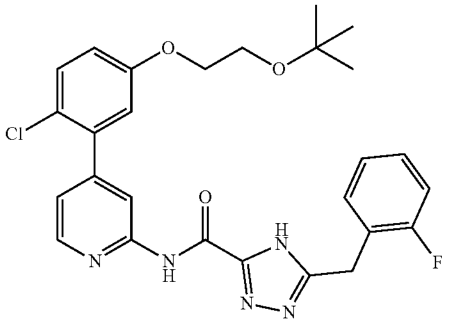
-continued
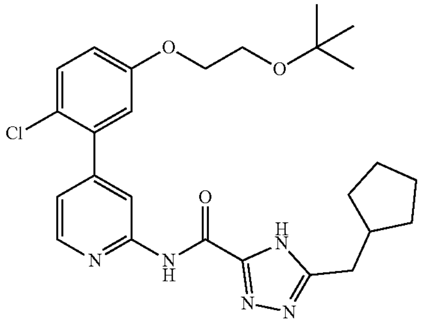
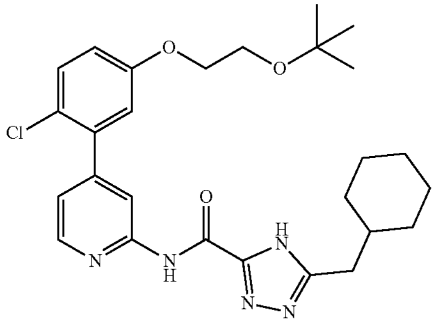
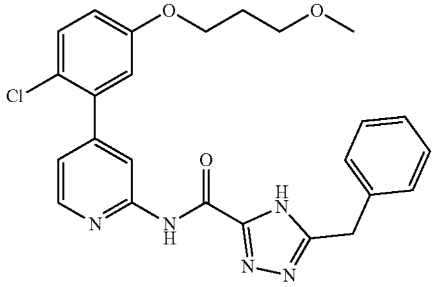
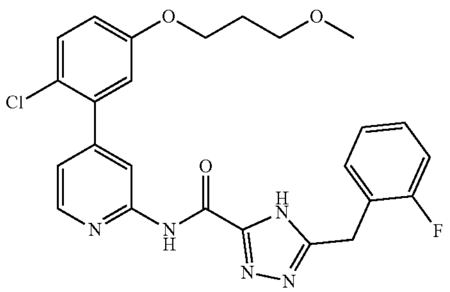
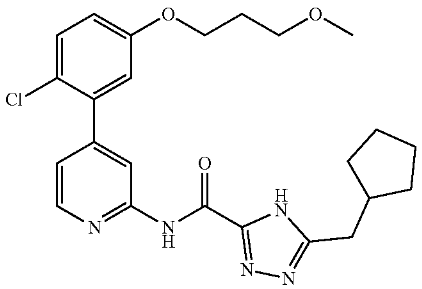

-continued
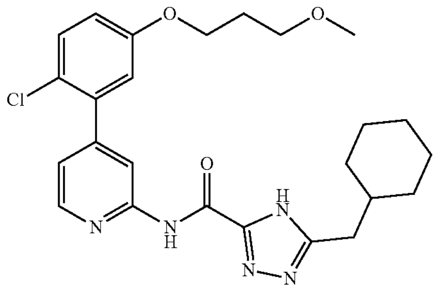
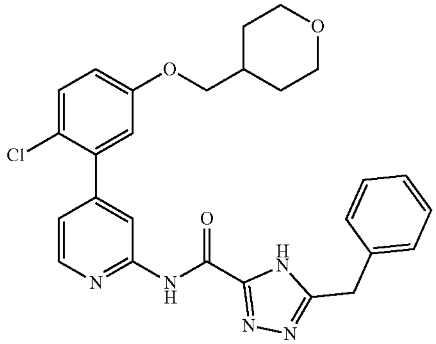
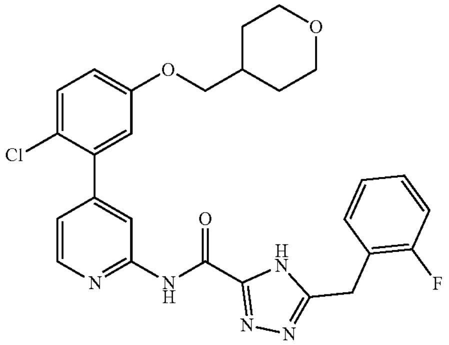
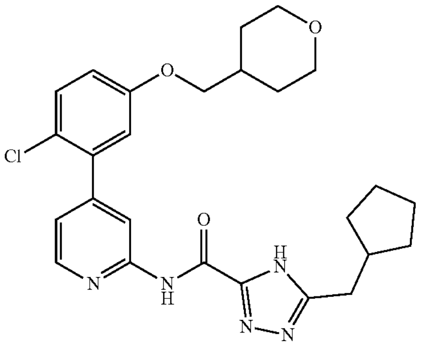
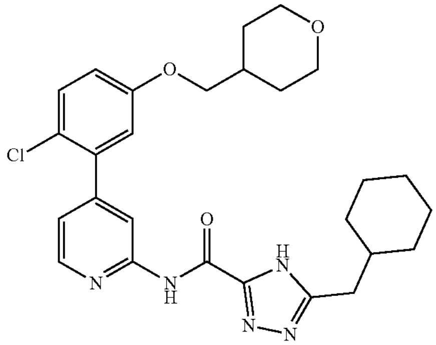
-continued
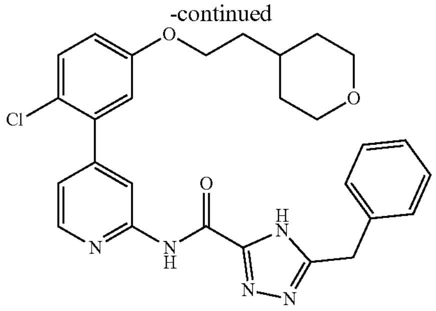
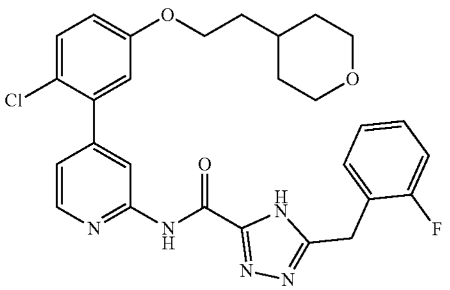
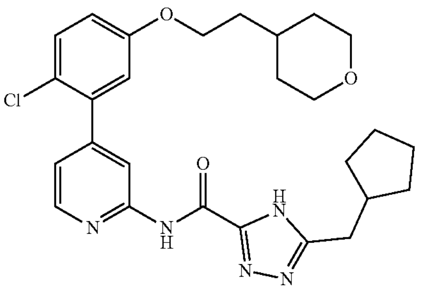
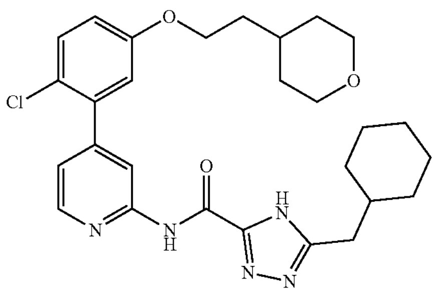
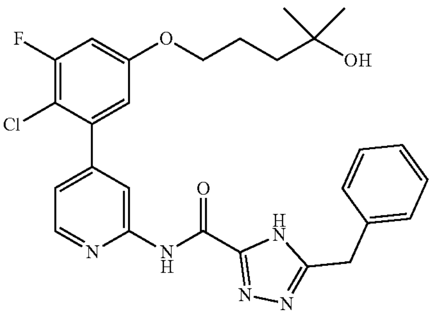

-continued
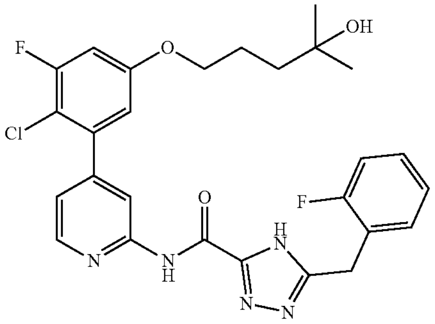
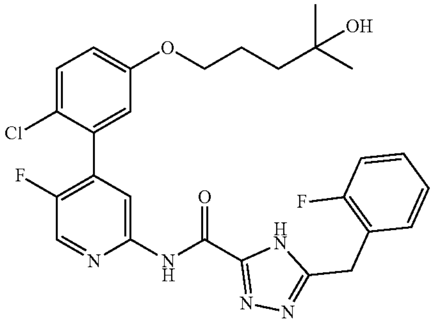
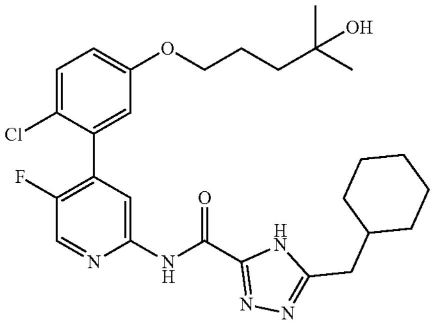
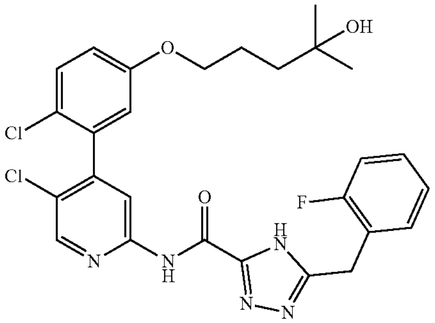
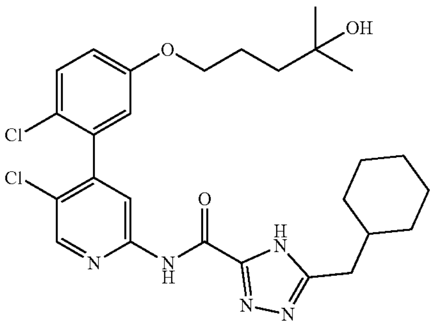
-continued
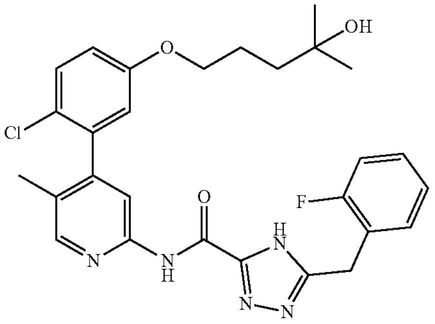
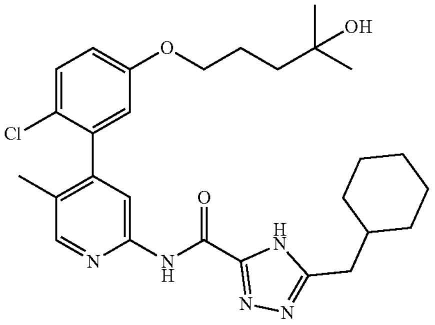
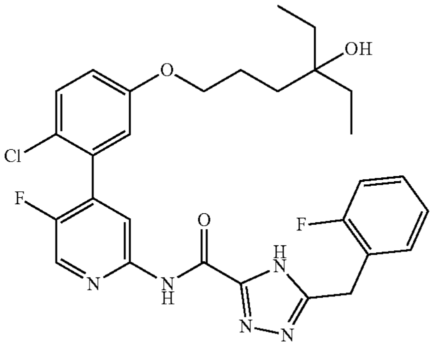
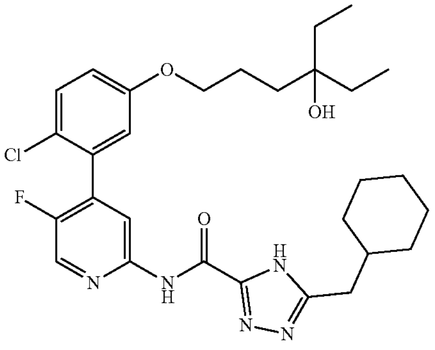
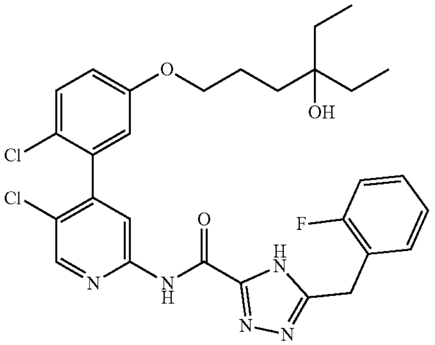

-continued
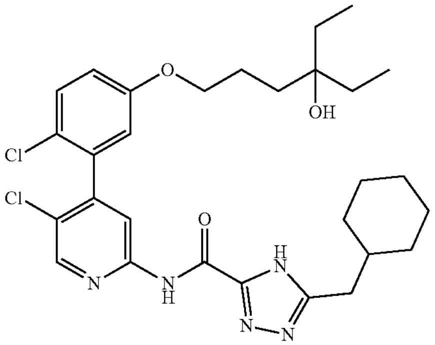
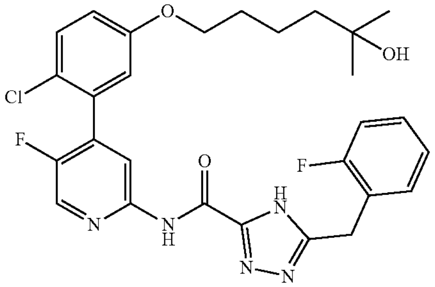
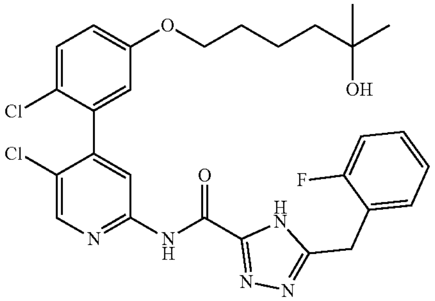
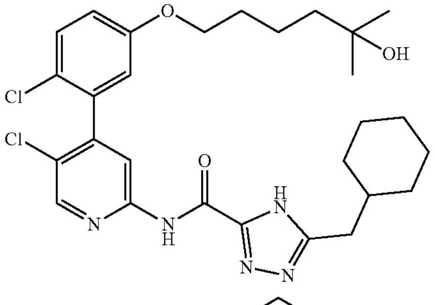
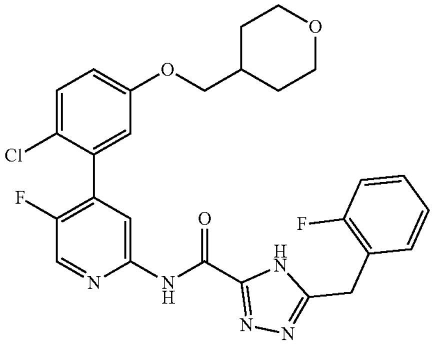
-continued
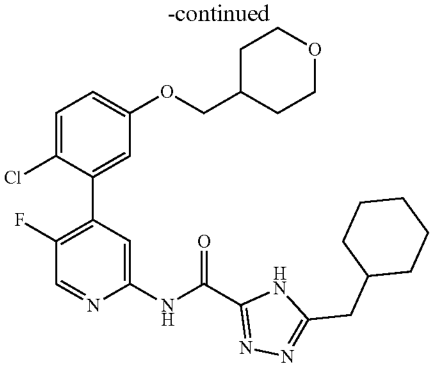
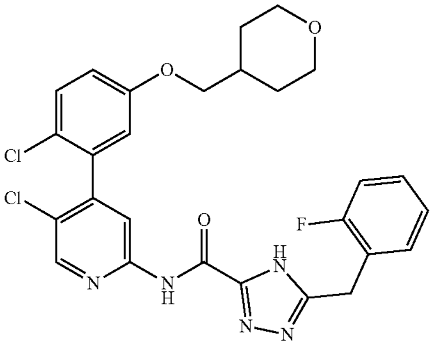
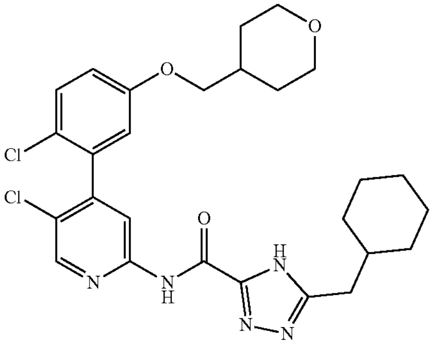
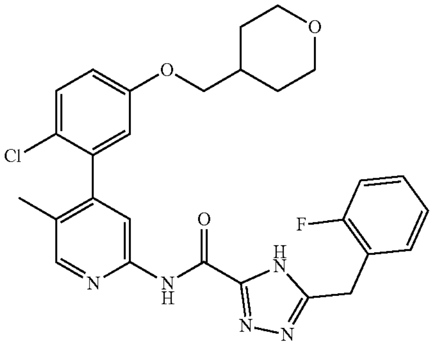
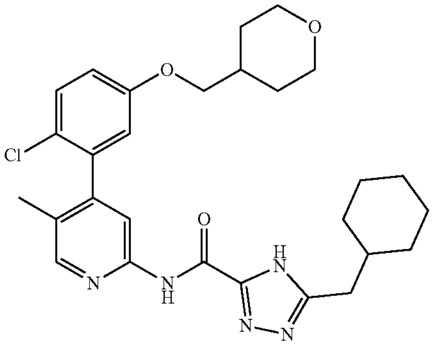

-continued
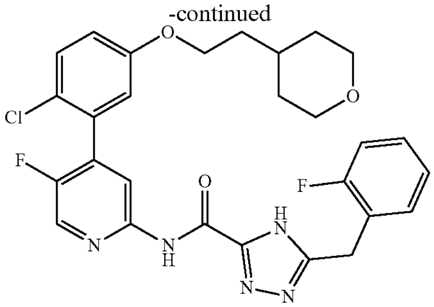
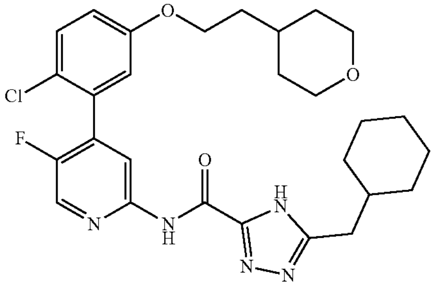
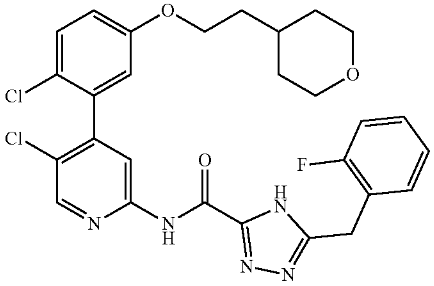
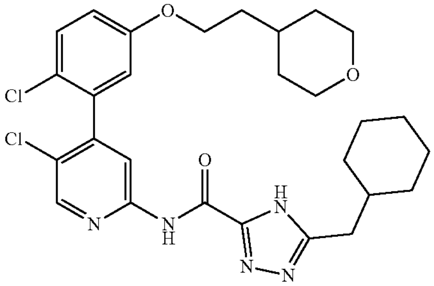
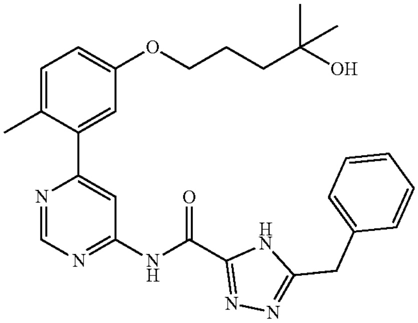
-continued
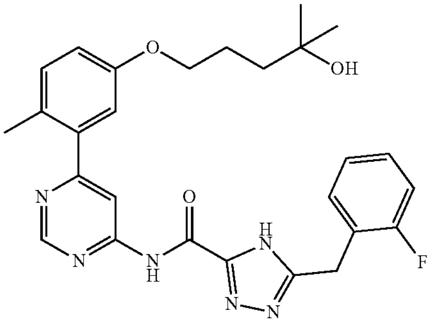
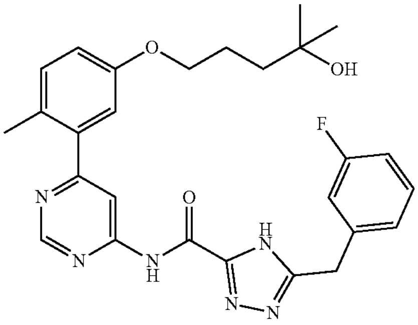
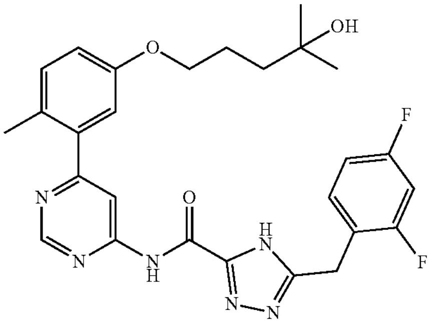
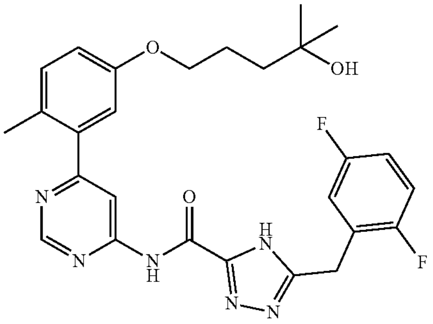
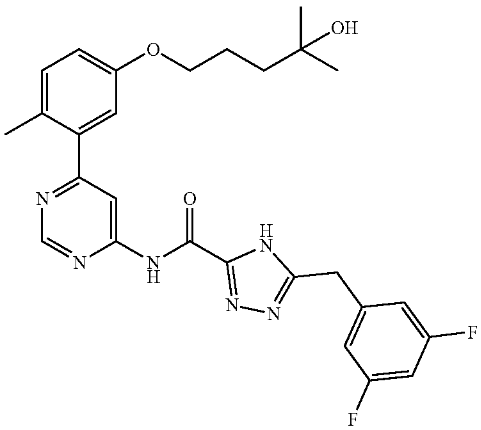

-continued
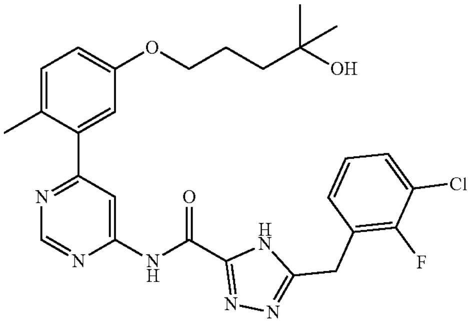
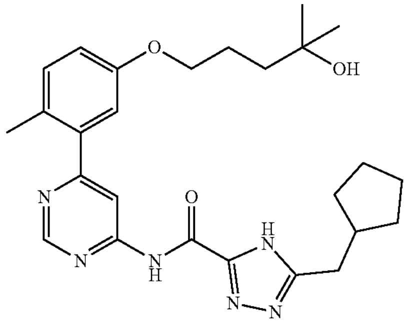
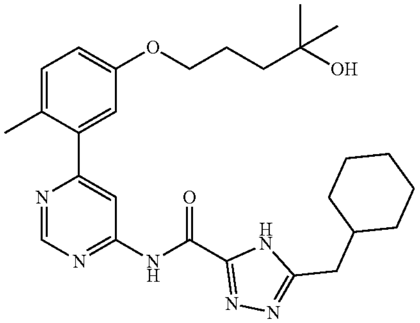
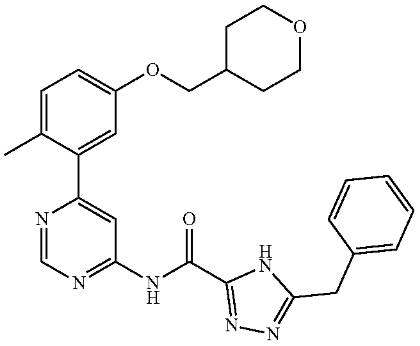
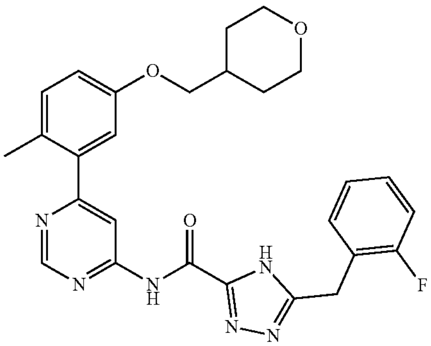
-continued
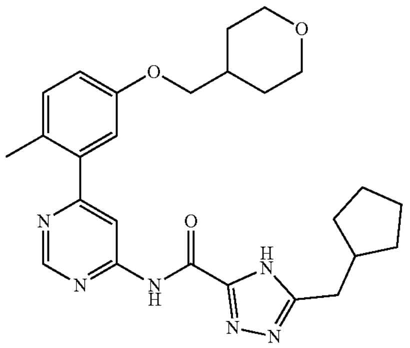
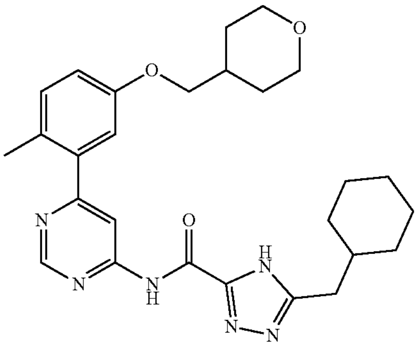
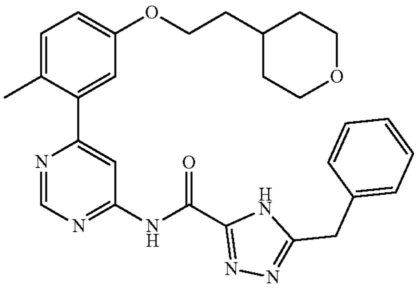
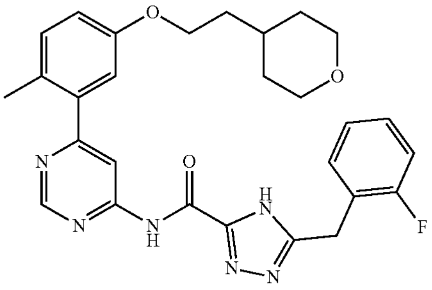
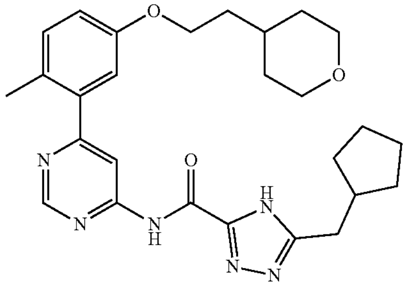

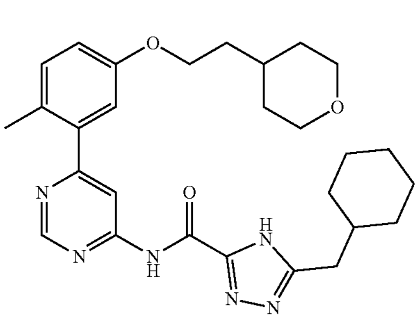
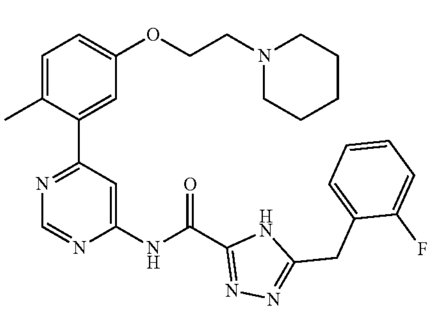
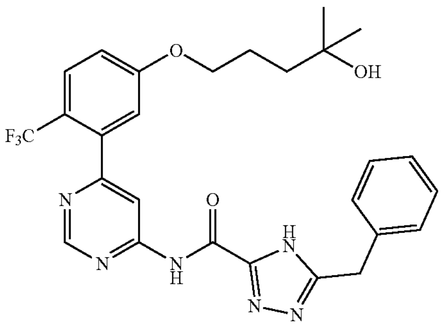
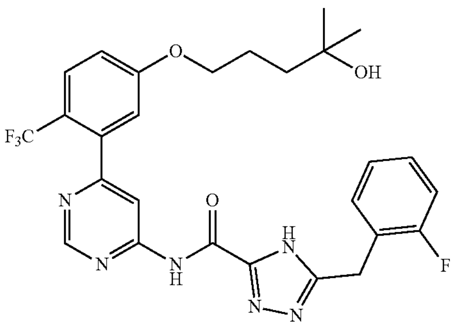
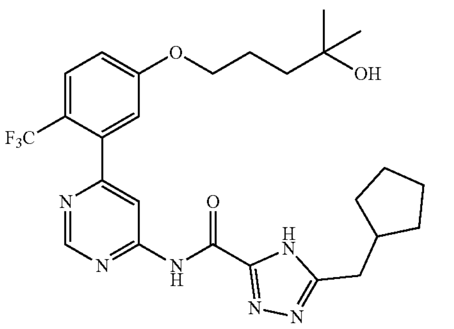
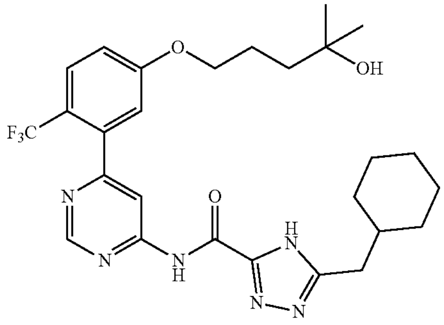
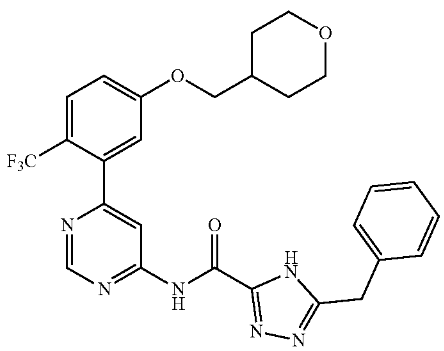
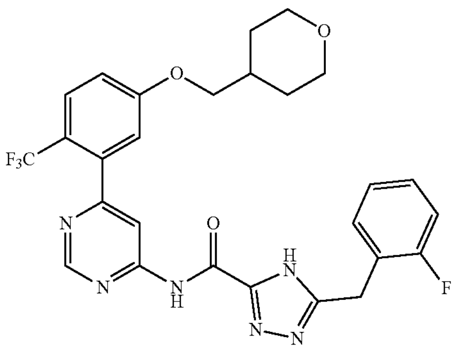
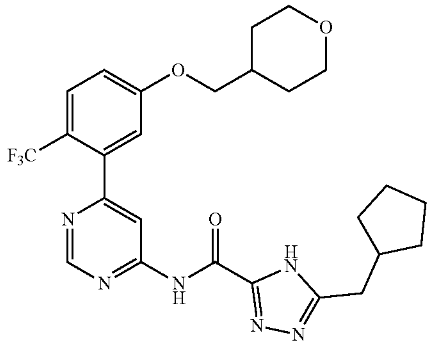
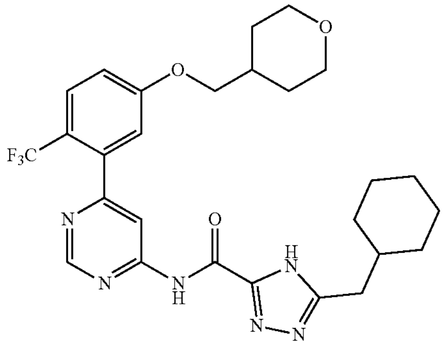

-continued
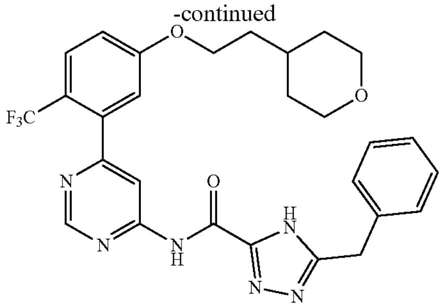
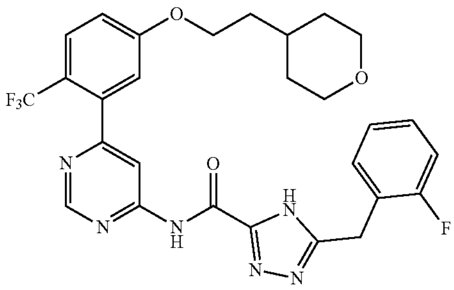
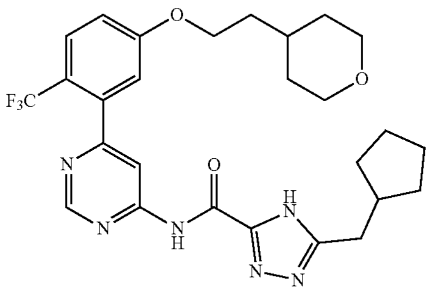
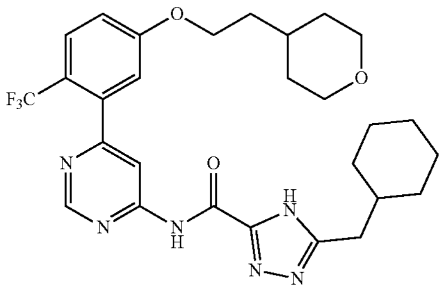
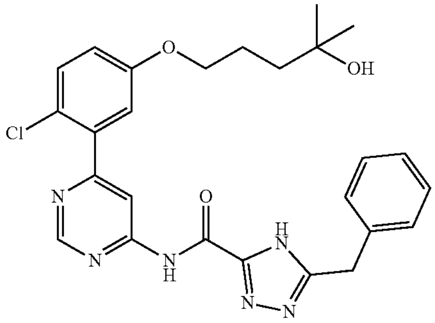
-continued
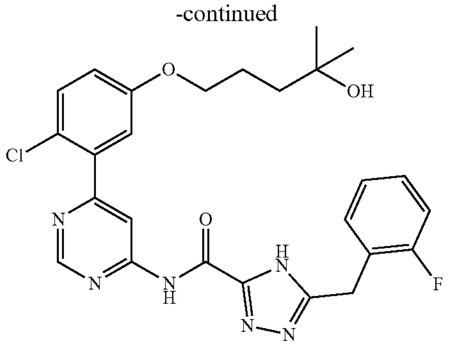
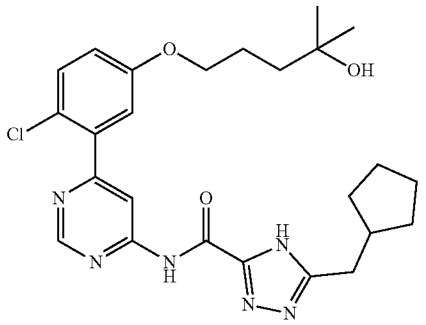
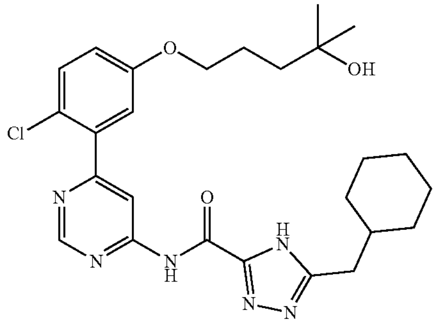
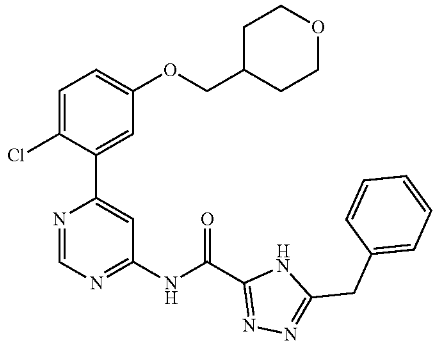
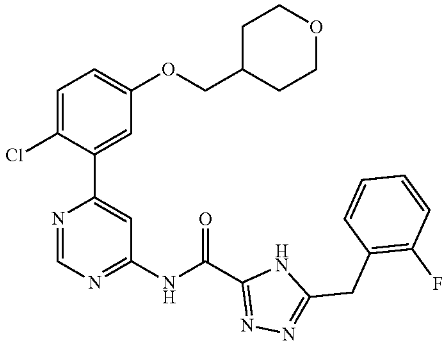

-continued
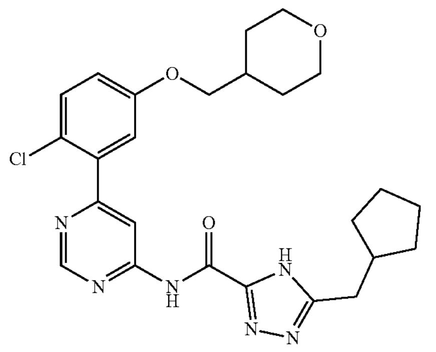
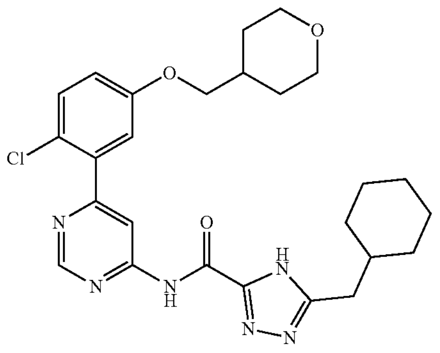
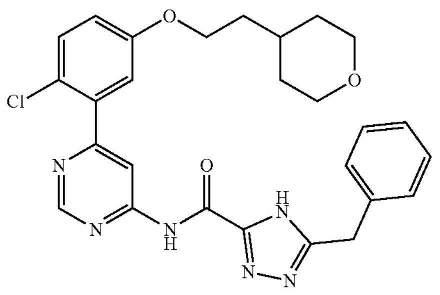
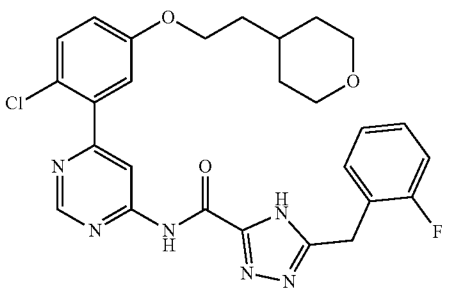
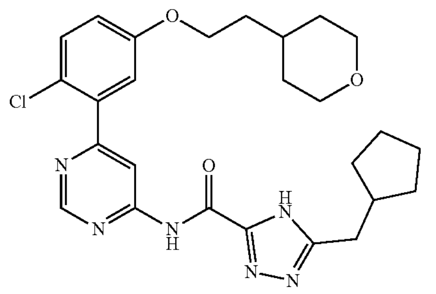
-continued
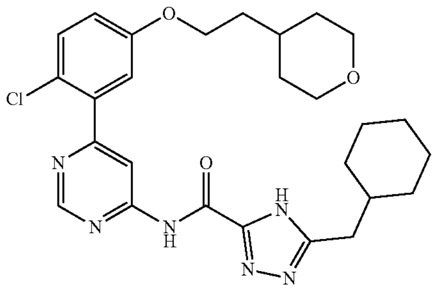
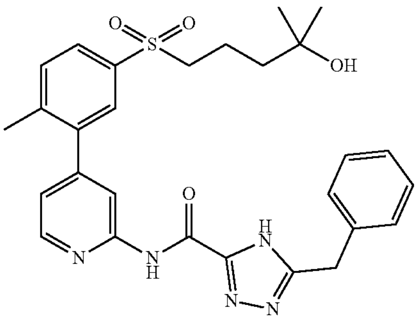
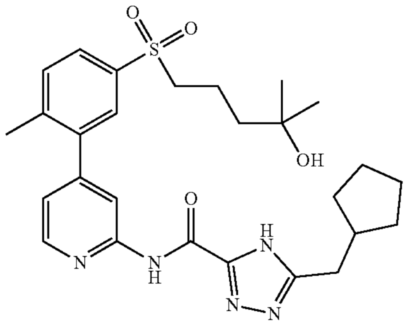
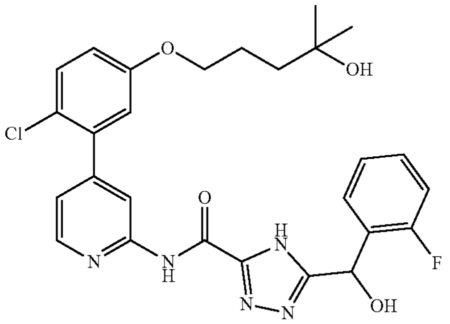
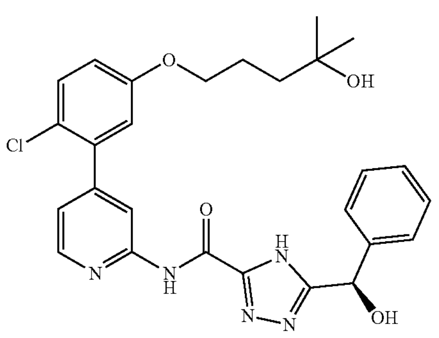

-continued
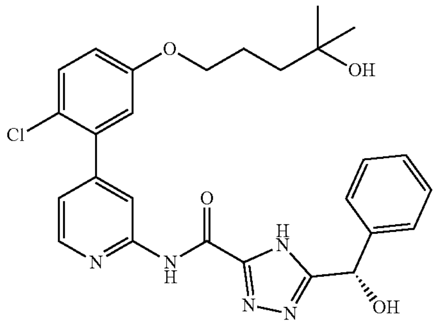
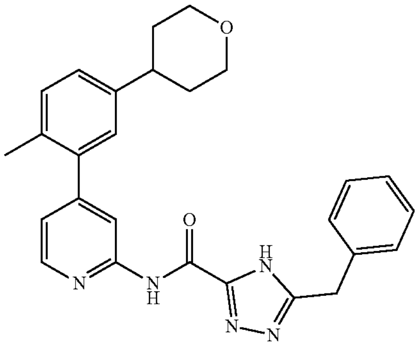
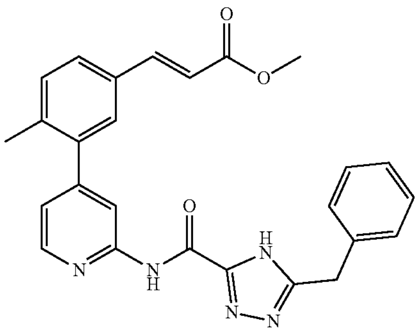
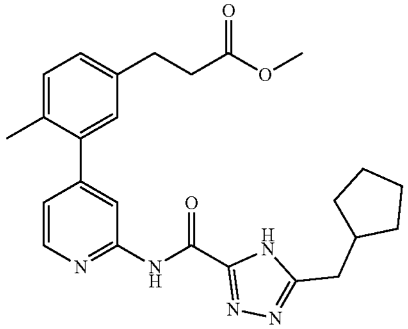
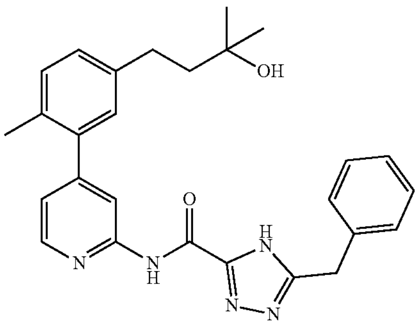
-continued
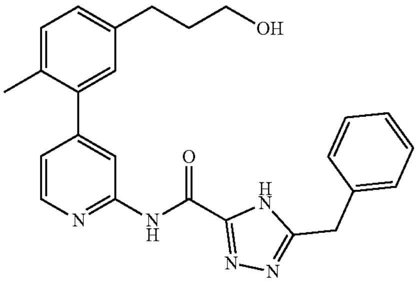
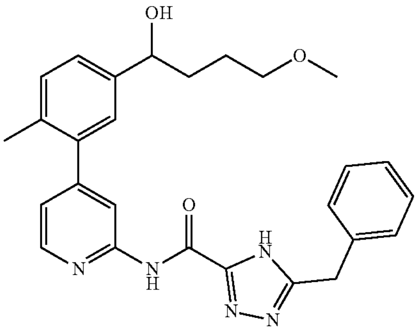
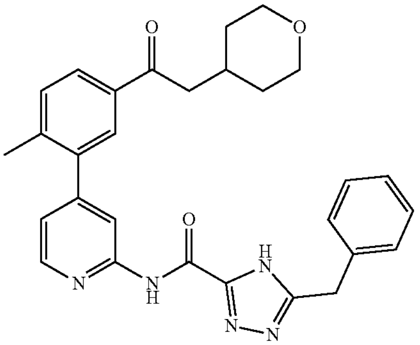
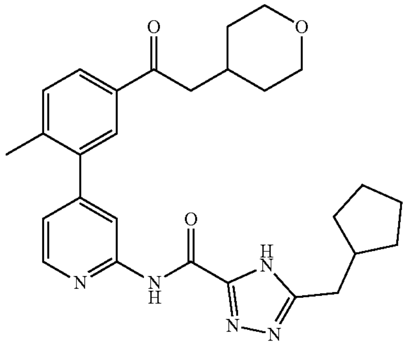
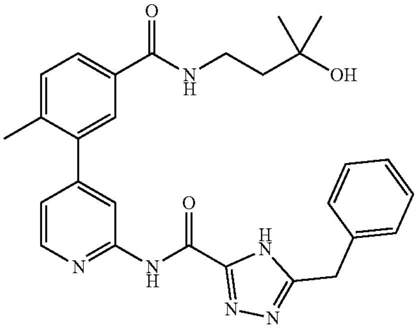

-continued
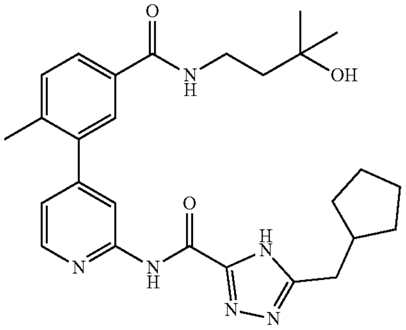
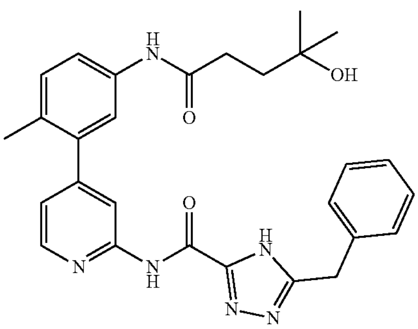
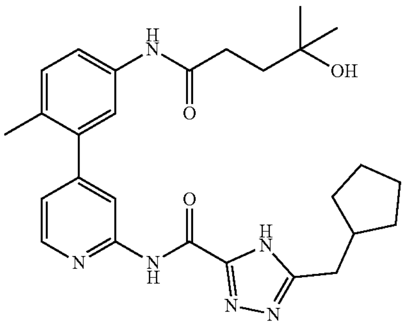
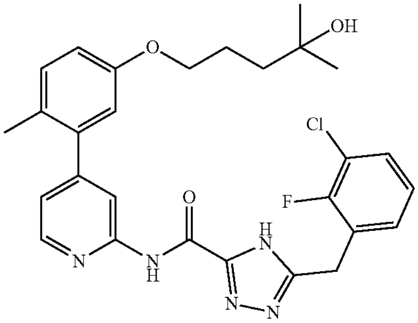
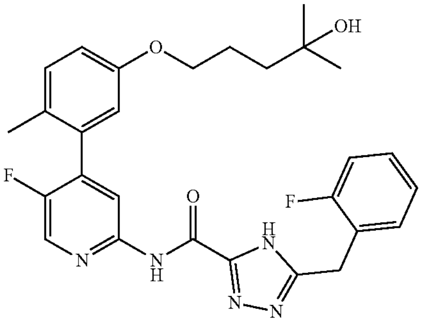
-continued
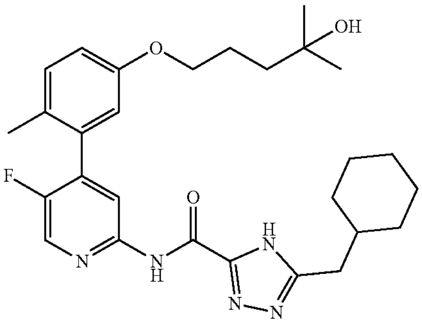
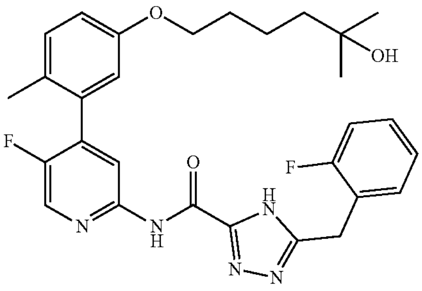
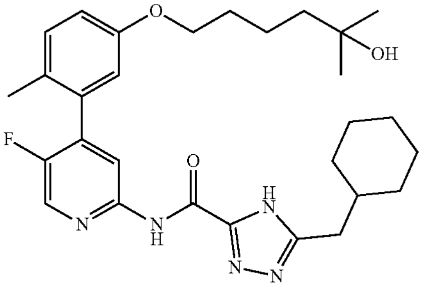
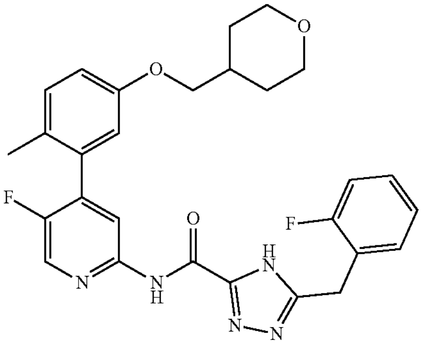
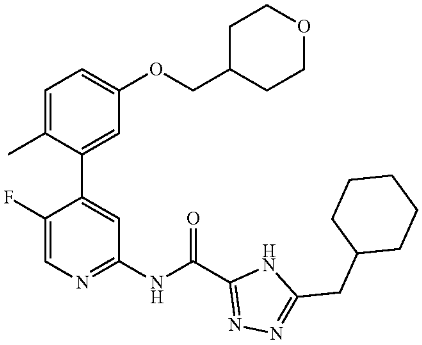

-continued

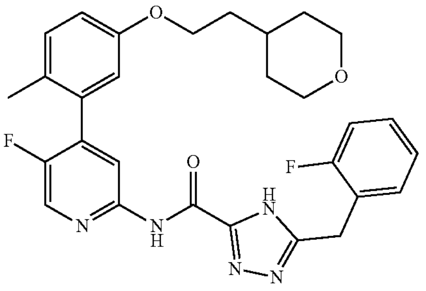

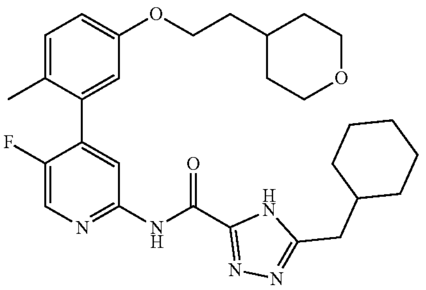

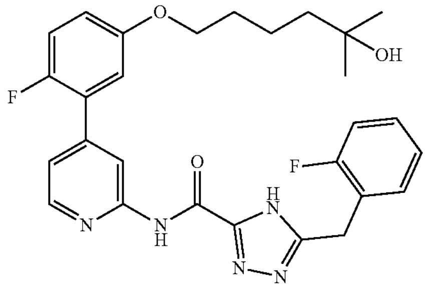

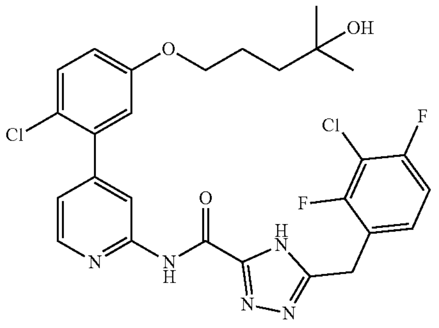

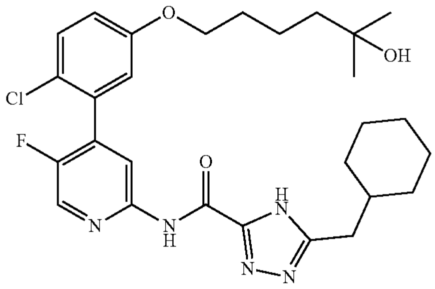

-continued

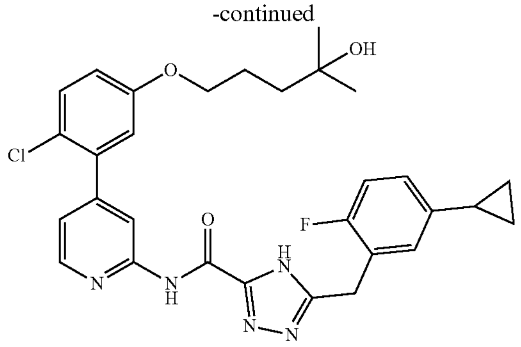

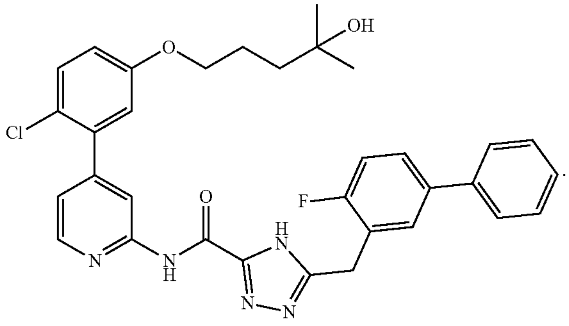

15. A method of treating RIP1-related diseases in a subject, comprising administering to the subject the compound, or the pharmaceutically acceptable salts, diastereomers, enantiomers, solvates or prodrugs thereof according to claim 1, wherein, the RIP1-related disease is selected from the group consisting of ocular fundus disease, xerophthalmia, psoriasis, leucoderma, dermatitis, alopecia areata, rheumatoid arthritis, colitis, multiple sclerosis, systemic lupus erythematosus, Crohn's disease, atherosclerosis, pulmonary fibrosis, liver fibrosis, myelofibrosis, non-small cell lung cancer, small cell lung cancer, breast cancer, pancreatic cancer, glioma, glioblastoma, ovarian cancer, cervical cancer, colorectal cancer, melanoma, endometrial cancer, prostate cancer, bladder cancer, leukemia, gastric cancer, liver cancer, gastrointestinal stromal tumor, thyroid cancer, chronic myeloid leukemia, acute myeloid leukemia, non-Hodgkin's lymphoma, nasopharyngeal cancer, esophageal cancer, brain tumor, B-cell and T-cell lymphoma, lymphoma, multiple myeloma, biliary cancer and sarcoma, cholangiocarcinoma, inflammatory bowel disease, ulcerative colitis, retinal detachment, retinitis pigmentosa, macular degeneration, pancreatitis, atopic dermatitis, spondyloarthritis, gout, SoJIA, Sjogren's syndrome, systemic scleroderma, antiphospholipid syndrome, vasculitis, osteoarthritis, non-alcoholic steatohepatitis, alcoholic steatohepatitis, autoimmune hepatitis, autoimmune hepatobiliary disease, primary sclerosing cholangitis, nephritis, celiac disease, autoimmune ITP, transplant rejection, ischemia-reperfusion injury of solid organs, sepsis, systemic inflammatory response syndrome, cerebrovascular accident, myocardial infarction, Huntington's disease, Alzheimer's disease, Parkinson's disease, allergic diseases, asthma, atopic dermatitis, multiple sclerosis, type I diabetes, Wegener's granulomatosis, pulmonary sarcoidosis, Behcet's disease, interleukin-1 converzyme-related fever syndrome, chronic obstructive pulmonary disease, tumor necrosis factor receptor related periodic syndrome and periodontitis.

16. A pharmaceutical composition, comprising a compound, or the pharmaceutically acceptable salts, diastereomers, enantiomers, solvates or prodrugs thereof according to claim 1, and one or more pharmaceutically acceptable carriers or excipients.

17. The compound, or the pharmaceutically acceptable salts, diastereomers, enantiomers, solvates or prodrugs thereof according to claim 1, formula (I)

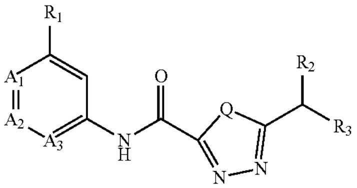

wherein, in formula (I),

Q is NH;

$A_1$, and $A_2$ are each CH;

$A_3$ is N;

$R_1$ is

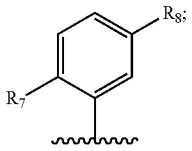

$R_7$ is methyl, ethyl, propyl, isopropyl, fluorine, chlorine, trifluoromethyl, vinyl, or propenyl;

$R_8$ is cyano, $C_1$-$C_3$ alkoxy $C_1$-$C_6$ alkylthio, or —O—$R_6$;

$R_5$ is $C_1$-$C_6$ alkyl;

$R_6$ is 4- to 8-membered heteroalicyclic group, or $C_1$-$C_{10}$ alkyl which is substituted with 1 to 3 substituents selected from the group consisting of hydroxyl, $C_1$-$C_6$ alkoxy, cyano, $C_3$-$C_8$ cycloalkyloxy, $C_3$-$C_8$ cycloalkyl, —$SO_2$—$R_5$, 4- to 8-membered heteroalicyclic group, and $C_1$-$C_6$ alkylthio;

$R_2$ is —$(CH_2)$n-$R^e$, wherein $R^e$ is aryl, which is unsubstituted or substituted with 1 substituent selected from the group consisting of halogen, and cyano, wherein n is an integer from 0 to 3;

the 4- to 8-membered heteroalicyclic group is a 4- to 8-membered heteroalicyclic group containing 1 to 2 atoms selected from N, O, or S as ring atoms;

the aryl group is a monocyclic or bicyclic group containing 6 to 12 carbon ring atoms and having at least one aromatic ring;

$R_3$ is hydrogen.

18. The compound, or the pharmaceutically acceptable salts, diastereomers, enantiomers, solvates or prodrugs thereof according to claim 17, wherein Q is NH;

$A_1$, and $A_2$ are each CH;

$A_3$ is N;

$R_1$ is

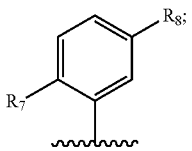

$R_7$ is methyl, chlorine, or trifluoromethyl;

$R_8$ is —O—$R_6$;

$R_6$ is $C_1$-$C_{10}$ alkyl which is substituted with 1 to 3 substituents selected from hydroxyl;

$R_2$ is —$(CH_2)$n-$R^e$, wherein $R^e$ is aryl, which is unsubstituted or substituted with 1 substituent selected from halogen, wherein n is an integer from 0;

the aryl group is a monocyclic or bicyclic group containing 6 to 12 carbon ring atoms and having at least one aromatic ring;

$R_3$ is hydrogen.

19. The compound, or the pharmaceutically acceptable salts thereof according to claim 1, wherein the compound is:

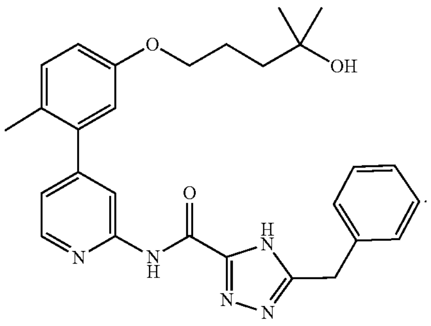 [SMILES: Cc1ccc(OCCCC(C)(C)O)cc1-c1ccnc(NC(=O)c2nnc(Cc3ccccc3)[nH]2)c1]

20. The compound, or the pharmaceutically acceptable salts thereof according to claim 1, wherein the compound is:

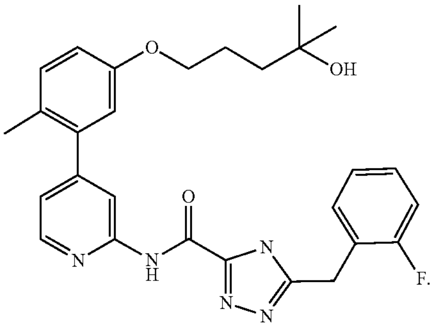 [SMILES: Cc1ccc(OCCCC(C)(C)O)cc1-c1ccnc(NC(=O)c2nnc(Cc3ccccc3F)[nH]2)c1]

21. The compound, or the pharmaceutically acceptable salts thereof according to claim 1, wherein the compound is:

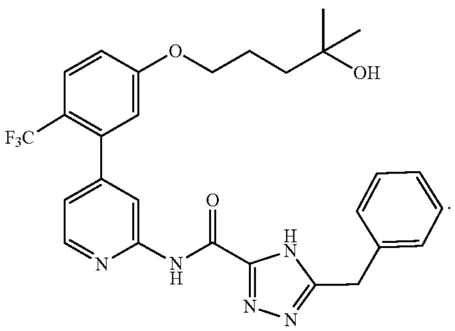 [SMILES: CC(C)(O)CCCOc1ccc(C(F)(F)F)c(-c2ccnc(NC(=O)c3nnc(Cc4ccccc4)[nH]3)c2)c1]

22. The compound, or the pharmaceutically acceptable salts thereof according to claim 1, wherein the compound is:

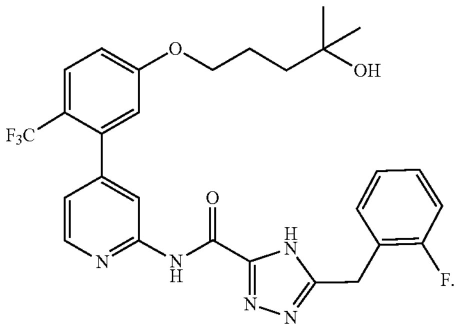 [SMILES: CC(C)(O)CCCOc1ccc(C(F)(F)F)c(-c2ccnc(NC(=O)c3nnc(Cc4ccccc4F)[nH]3)c2)c1]
23. The compound, or the pharmaceutically acceptable salts thereof according to claim 1, wherein the compound is:
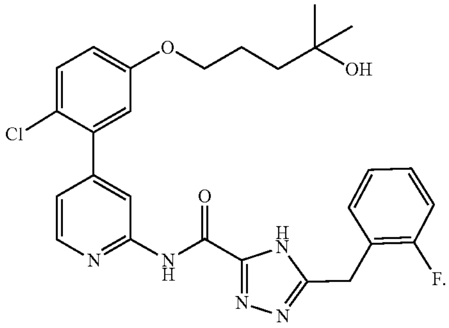 [SMILES: CC(C)(O)CCCOc1ccc(Cl)c(-c2ccnc(NC(=O)c3nnc(Cc4ccccc4F)[nH]3)c2)c1]
* * * * *